(12) United States Patent
Pinto et al.

(10) Patent No.: US 8,389,565 B2
(45) Date of Patent: *Mar. 5, 2013

(54) GLYCOSIDASE INHIBITORS AND METHODS OF SYNTHESIZING SAME

(75) Inventors: Brian Mario Pinto, Coquitlam (CA); Blair D. Johnston, Vancouver (CA); Ahmad Ghavami, Coquitlam (CA); Monica Gabriela Szczepina, Vancouver (CA); Hui Liu, Ottawa (CA); Kashinath Sadalapure, Vancouver (CA); Henrik H. Jensen, Burnaby (CA); Nag Sharwan Kumar, Coquitlam (CA); Ravindranath Nasi, Vancouver (CA)

(73) Assignee: Simon Fraser University, Burnaby, British Columbia (CA)

( * ) Notice: Subject to any disclaimer, the term of this patent is extended or adjusted under 35 U.S.C. 154(b) by 1192 days.

This patent is subject to a terminal disclaimer.

(21) Appl. No.: 11/368,014

(22) Filed: Mar. 2, 2006

(65) Prior Publication Data

US 2006/0247222 A1 Nov. 2, 2006

Related U.S. Application Data

(63) Continuation-in-part of application No. 10/877,490, filed on Jun. 25, 2004, now abandoned, and a continuation-in-part of application No. 10/226,657, filed on Aug. 22, 2002, now abandoned, which is a continuation of application No. 09/627,434, filed on Jul. 28, 2000, now Pat. No. 6,455,573.

(60) Provisional application No. 60/482,006, filed on Jun. 25, 2003, provisional application No. 60/174,837, filed on Jan. 7, 2000.

(51) Int. Cl.
*A61K 31/40* (2006.01)
*C07D 333/32* (2006.01)
*C07D 333/34* (2006.01)

(52) U.S. Cl. .............................. 514/425; 549/62; 549/66

(58) Field of Classification Search .................... 549/62, 549/66; 514/425

See application file for complete search history.

(56) References Cited

U.S. PATENT DOCUMENTS

| | | | |
|---|---|---|---|
| 6,143,932 A | 11/2000 | Dorner | |
| 6,376,682 B1 * | 4/2002 | Yamahara | ......................... 549/66 |
| 6,455,573 B1 * | 9/2002 | Pinto et al. | ..................... 514/425 |
| 7,534,811 B2 | 5/2009 | Muraoka | |
| 2002/0041904 A1 | 4/2002 | Yamahara | |
| 2003/0191104 A1 | 10/2003 | Pinto | |
| 2005/0065139 A1 | 3/2005 | Pinto | |
| 2006/0247222 A1 | 11/2006 | Pinto et al. | |
| 2007/0037870 A1 | 2/2007 | Asada | |

FOREIGN PATENT DOCUMENTS

| | | | |
|---|---|---|---|
| CA | 2522793 A1 | 11/2004 | |
| EP | 1645557 A1 | 4/2006 | |
| JP | 9301882 A | 11/1997 | |
| JP | 3030008 B2 | 2/1999 | |
| JP | 11029472 A | 2/1999 | |
| JP | 2000086653 A | 3/2000 | |
| JP | 2002179673 A | 6/2002 | |
| JP | 2004323420 A | 11/2004 | |
| JP | 2005002051 A | 1/2005 | |
| WO | WO0149674 A2 | 7/2001 | |
| WO | 2004094402 A1 | 11/2004 | |
| WO | WO2004113289 A2 | 12/2004 | |
| WO | 2008/082017 A1 | 7/2008 | |

(Continued)

OTHER PUBLICATIONS

Yoshikawa et al., Chem. Pharm. Bull. 46(8) 1339-1340 (1998), pp. 1339-1340.*

(Continued)

*Primary Examiner* — Rebecca Anderson
(74) *Attorney, Agent, or Firm* — Oyen, Wiggs, Green & Mutala LLP

(57) ABSTRACT

Methods for synthesizing Salacinol, its stereoisomers, and analogues, homologues and other derivatives thereof potentially useful as glycosidase inhibitors. In some embodiments the compounds of the invention may have the general formula (I) or (II):

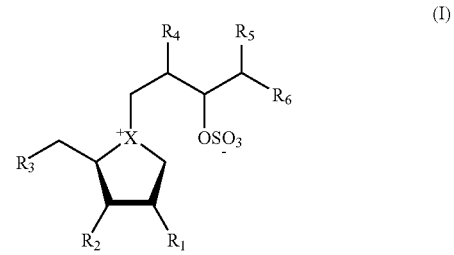

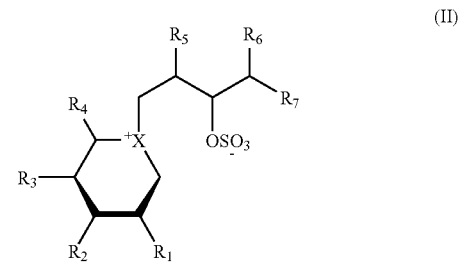

The synthetic schemes may comprise reacting a cyclic sulfate with a 5-membered ring sugar containing a heteroatom (X). The heteroatom preferably comprises sulfur, selenium, or nitrogen. The cyclic sulfate and ring sugar reagents may be readily prepared from carbohydrate precursors, such as D-glucose, L-glucose, D-xylose and L-xylose. The target compounds are prepared by opening of the cyclic sulfates by nucleophilic attack of the heteroatoms on the 5-membered ring sugars. The resulting heterocyclic compounds have a stable, inner salt structure comprising a heteroatom cation and a sulfate anion. The synthetic schemes yield various stereoisomers of the target compounds.

19 Claims, 7 Drawing Sheets

FOREIGN PATENT DOCUMENTS

WO 2009117829 A1 10/2009

OTHER PUBLICATIONS

Yoshikawa et al., Tetrahedron Letters, vol. 38, No. 48, pp. 8367-8370, 1997.*
Yuasa et al., Tetrahedron Letters 41 (2000) 6615-6618.*
Ghavami et al, J. Org. Chem. 2001, 66, 2312-2317.*
Shimoda, H. et al. "Safety profile of extractive from trunk of *Salacia reticulata* (Celastraceae)." Journal of the Food Hygienic Society of Japan. 1999, 40(3), 198-205.
Goss, P. E. et al. "Phase IB clinical trial of the oligosaccharide processing inhibitor swainsonine in patients with advanced malignancies." Clinical Cancer Res. 1997, 3, 1077-1086.
Goss, P. E. et al. "A phase I study of swainsonine in patients with advanced malignancies." Cancer. Res. 1994, 54, 1450-1457.
Eames, J. et al. "Scope and Limitation of [1,4]-Sbenzyl Participation and Debenzylation in the Stereochemically Controlled Synthesis of Substituted Thiolanes." Tetrahedron Lett. 1998, 39(10), 1247-1250.
Calvo-Flores, F. G. et al. "Application of cyclic sulfates of vic-diols: synthesis of episulfides, olefins, and thio sugars." J. Org. Chem. 1997, 62, 3944-3961.
Foster, A. B. et al. "Aspects of stereochemistry. Part VIII. Determination of the configuration at the benzylidene acetal carbon atoms in 4,6-O-benzylidene-D-glucose and 1,3-O-Benzylidene-L-arabinitol by nuclear magnetic resonance spectroscopy." J. Chem. Soc. 1961, 5005-5011.
MacDonald, D. L. et al. "The enantiomorphic erythritol 4-phosphates." J. Am. Chem. Soc. 1956, 78, 3720-3722.
Yoshimura, Y. et al. "A novel synthesis of 2'-modified 2'-deoxy-4'-thiocytidines from D-glucose." J. Org. Chem. 1997, 62, 3140-3152.
Satoh, H. et al. "Synthesis of L-enantiomers of 4'-thioarabinofuranosyl pyrimidine nucleosides." Bioorg. Med. Chem. Lett. 1998, 8(9), 989-992.
Fleet, G. et al. "The synthesis from D-xylose of the potent and specific enantiomeric glucosidase inhibitors, 1,4-dideoxy-1,4-imino-D-arabinitol and 1,4-dideoxy-1,4-imino-L-arabinitol." Tetrahedron, 1986, 42, 5685-5692.
Ghavami, A.; Johnston, B. D.; Jensen, M. T.; Svensson, B.; Pinto, B. M. "Synthesis of nitrogen analogues of salacinol and their evaluation as glycosidase inhibitors." J. Am. Chem. Soc. 2001, 123, 6268-6271.
Nichols, B. L. et al., "Human small intestinal maltase-glucoamylase cDNA cloning: homology to sucrase-isomaltase." J. Biol. Chem. 1998, 273, 3076-3081.
Braun, C. et al., "Mechanim-based inhibition of yeast alpha-glucosidase and human pancreatic alpha-amylase by a new class of inhibitors." J. Biol. Chem. 1995, 270, 26778-26781.
Stoffer, B. et al., "Production, purification and characterization of the catalytic domain of glycoamylase from *Aspergillus niger*." Biochem J. 1993, 292, 197-202.
Frandsen, et al., "Site-directed mutagenesis of the catalytic base glutamic acid 400 in glucoamylase from *Aspergillus niger* and of tyrosine 48 and glutamine 401, both hydrogen-bonded to the gamma-carboxylate group of glutamic acid 400." Biochemistry 1994, 33, 13808-13816.
Juge, N. "Overexpression, purification, and characterization of recombinant barley alpha-amylases 1 and 2 secreted by the methylotrophic yeast *Pichia pastoris*." Protein Expression Purif. 1996, 8, 204-214.
Fox, J. D. et al., "Miniaturization of three carbohydrate analyses using a microsample plate reader." Anal. Biochem. 1991, 195, 93-96.
Johnston, B. D. et al., "Synthesis of selenium analogues of the naturally occurring glycosidase inhibitor salacinol and their evaluation as glycosidase inhibitors." J. Am. Chem. Soc. 2002, 124, 8245-8250.
Yoshikawa, M. et al., "Absolute Stereostructure of potent alpha-glucosidase inhibitor, salacinol, with unique thiosugar sulfonium sulfate inner salt structure from *Salacia reticulata*." Bioorg. Med. Chem., 2002, 10, 1547-1554.
Svansson, L. et al., "Synthesis and conformational analysis of a sulfonium-ion analogue of the glycosidase inhibitor castanospermine." J. Am. Chem. Soc., 2000, 122, 10769-10775.

Wakabayashi, T. et al., "Total synthesis and structural elucidation of khafrefungin." J. Am. Chem. Soc. 2001, 123, 1372-1375.
Crivello, J.V. "Cationic polymerization—iodonium and sulfonium salt photoinitiators." Advances in Polymer Science 1984, 662, 1-48.
Izquierdo, I. et al., "Enatiospecific synthesis of 8-o-methylthioswainsonine from a derivative of D-glucose." Tetrahedron: Asymmetry 1996, 7, 2567-2575.
Ulgar, V. et al., "Synthesis and evaluation of sulfonium analogues of isofucofagomine as glycosidase inhibitors." J. Chem. Soc., Perkin Trans. 1 2002, 1242-1246.
Bazin, H. G. et al., "Regiospecific synthesis of new methyl sulfogluocopyranoside-based surfactants: nucleophilic displacement of a cyclic sulfate." Synthesis 1999, 621-624.
Calvo-Asin, J. A. et al., "Expeditious synthesis of monosulfated thio-linked disaccharides." J. Chem. Soc., Perkin Trans. 1 1997, 1079-1081.
Bozo, E. et al., "An economic synthesis of 1,2,3,4-tetra-O-acetyl-5-thio-D-xylopyranose and its transformation into 4-substituted-phenyl 1,5-dithio-D-xylopyranosides possessing antithrombotic activity." Carbohydr. Res. 1998, 308, 297-310.
Dagron, F. et al., "Ring opening of benzyl beta-D-galactoside cyclic sulfates into galactose monosulfates. New access to 6-deoxy-galacto-hex-5-enopyranoside and 4-deoxy-3-ketogalactopyranoside." J. Carbohydr. Chem. 2000, 19, 311-321.
Bazin, H. G. et al., "Regio- and stereoselective synthesis of beta-D-gluco-, alpha-L-ido-, and alpha-L-altropyranosiduronic acids from delta4-uronates." J. Org. Chem. 1999, 64, 144-152.
Yin, H. et al., "Arabinofuranosides from mycobacteria" synthesis of a highly branched hexasaccharides and related fragments containing beta-arabinofuranosyl residues. J Org Chem. 2002, 67, 892-903.
Ness, R. K. et al., "The anomeric 2,3,5-tri-O-benzoyl-D-arabinosyl bromides and other D-arabinofuranose derivatives." J. Am. Chem. Soc. 1958, 80, 2007-2010.
Fukuyama, Y. et al., "Matrix-assisted ultraviolet laser-desorption ionization and electrospray-ionization time-of-flight mass spectroscopy of sulfated neocarrabiose oligosaccharides." Carbohydr. Res. 2002, 337, 1553-1562.
Belleau, B. et al. "Synthesis and crystal structure of 17-deaza-17-methyl thionium isomorphinan (isosulforphanol) perchlorate, an isostere of the opiate isolevorphanol." Can. J. Chem. vol. 63, 1268-1274 (1985).
Belleau, B. et al., "Thionium analogs of the opiates levorphanol and isolevorphanol: synthesis of the 17-deaza-17-thia isosteres (sulforphanol and isofulforphanol."Can. J. Chem. 64, 110 (1986).
Lemaire, S. et al. "Alpha-sulfallorphan, a kappa opioid antagonist selective for endogenous Met-Enk-[Arg6, Phe7] and dynorphin B." Adv. Biosci. 75, 105 (1989).
Yuasa, H. et al., "Glycosidase inhibition by cyclic sulfonium compounds." Bioorg. Med. Chem. Lett. 11, 1137-1139 (2001).
Muraoka, O. et al., "Synthesis of a nitrogen analogue of salacinol and its alpha-glucosidase inhibitory activity." Chem. Pharm. Bull. 49, 1503 (2001).
P. A. M. van der Klein et al., "Synthesis of 2,3,5-tri-O-benzyl-D-arabinitol 1,4-cyclic sulfate and its conversion into potential precursors of shikimate substrate analogues." Synthesis 347, (1991).
Ghavami, A. et al., "Improved syntheses of the naturally occurring glycosidase inhibitor salacinol." Synlett 2003, 1259-1262.
Mootoo, D. R. et al., "An oxidative/reductive, non-hydrolytic procedure for "unraveling" complex acetals (glycosides): a possible chemical role for the exo-anomeric effect." J. Chem. Soc., Chem. Commun. 1987, 1462-1463.
Mootoo, D. R.; Date, V.; Fraser-Reid, B. "n-Pentenyl glycosides permit the chemospecific liberation of the anomeric center." J. Am. Chem. Soc. 1988, 110, 2662-2663.
Furneaux, R. H. et al., "The influence of boric acid on the acetylation of aldoses: "one-pot" syntheses of penta-O-acetyl-beta-D-glucofuranose and its crystalline propanoyl analogue." J. Chem. Soc., Perkin, Trans. 1, 2000, 2011-2014.
Gurjar, M. K. et al., "Synthesis of oligosaccharides of Motifs D and E of arabinogalactan present in *Mycobacterium tuberculosis*." J. Org. Chem. 2001, 66, 4657-4660.
Helenius, A. et al., "Intracellular functions of N-linked glycans." Science. 2001, 2364-2369.

Dwek, R. A. et al., "Targeting glycosylation as a therapeutic approach." Nature Rev. Drug Discovery, 2002, 1, 65-75.

Dwek, R. A., "Glycobiology: Toward understanding the function of sugars." Chem. Rev. 1996, 96, 683-720.

Asano, N, et al., "Sugar-mimic glycosidase inhibitors: natural occurrence, biological activity and prospects for therapeutic application." Tetrahedron: Asymmetry 2000, 11, 1645-1680.

McCarter, J.D., et al., "Mechanisms of enzymatic glycoside hydrolysis." Curr. Opin. Struct. Biol. 1994, 4, 885-892.

Ly, H. D. et al., "Mutagenesis of glycosidases." Annu. Rev. Biochem. 1999, 68, 487-522.

Jacob, G. S. "Glycosylation inhibitors in biology and medicine." Curr. Opin. Struct. Biol. 1995, 5, 605-611.

Sigurskjold, B. W. et al., "Thermodynamics of inhibitor binding to the catalytic site of glucoamylase from *Aspergillus niger* determined by displacement titration calorimetry." Biochemistry 1994, 33, 10191-10199.

Cox, T. et al., "Novel oral treatment of Gaucher's disease with N-butyldeoxynojirimycin (OGT 918) to decrease substrate biosynthesis." Lancet 2000, 355, 1481-1485.

Zechel, D. L. et al., "Dissection of nucleophilic and acid-base catalysis in glycosidases." Curr. Opin. Chem. Biol. 2001, 5, 643-649.

Lillelund, V. H. et al., "Recent developments of transition-state analogue glycosidase inhibitors of non-natural product origin." Chemical Reviews 2002, 102, 515-553.

Varrot, A. et al "Distortion of a cellobio-derived isofagomine highlights the potential conformational itinerary of inverting beta-glucosidases." Chem. Commun. 2003, 946-947.

Varrot, A. et al., "Direct observation of the protonation state of an imino sugar glycosidase inhibitor upon binding." J. Am. Chem. Soc. 2003, 125, 7496-7497.

Zechel, D. L. et al., "Iminosugar glycosidase inhibitors: structural and thermodynamic dissection of the binding of isofagomine and 1-deoxynojirimycin to beta-gluocsidases." J. Am. Chem. Soc. 2003, 125, 14313-14323.

Johnson, M. A. et al., "Selection of a high-energy bioactive conformation of a sulfonium-ion glycosidase inhibitor by the enzyme glucoamylase G2." J. Am. Chem. Soc. 2003, 125, 5663-5670.

Ghavami, A. et al., "Synthesis of a novel class of sulfonium ions as potential inhibitors of UDP-galactopyranose mutase." Carbohydr. Res. 2004, 339, 401-407.

Asano, N. et al., "N-alkylated nitrogen-in-the ring sugars: conformational basis of inhibition of glycosidases and HIV-1 replication." J. Med. Chem. 1995, 38, 2349-2356.

Hausler, H. et al., "N-Alkylated derivatives of 1,5-dideoxy-1,5-iminoxylitol as beta-xylosidase and beta-glucosidase inhibitors." Monatshefte fur Chem. 2002, 133, 555-560.

Halila, S. et al., "Short and efficient synthesis of polyhydroxylated tetrahydrothiophene, tetrahydrothiopyrane and thiepane from bielectrophilic erythro, threo, xylo, ribo, arabino, manno and gluco α, ω -dibromoalditol derivatives." Tetrahedron Lett. 2001, 42, 3307-3310.

Klayman, D. L. et al., "Reaction of selenium with sodium borohydride in protic solvents. A facile method for the introduction of selenium into organic molecules." J. Am. Chem. Soc. 1973, 95, 197-199.

Lucas, M. A. et al., "Preparation of 5-Selenopentopyranose Sugars from Pentose Starting Materials by Samarium(II) Iodide or (Phenylseleno) formate Mediated Ring Closures." Tetrahedron 2000, 56, 3995-4000.

Hashimoto, H. et al., "Novel conversion of aldopyranosides into 5-thioaldopyranosides via acyclic monothioacetals with inversion and retention of configuration at C-5." Carbohydr. Res. 1996, 282, 207-222.

Gao, Y. et al., "Vicinal diol cyclic sulfates: Like epoxides only more reactive." J. Am. Chem. Soc. 1988, 110, 7538-7539.

Wolf, B. W. et al., "Safety evaluation of an extract from *Salacia oblonga*." Food Chem. Toxicol. 2003, 41, 867-874.

Serasinghe, S. et al., "Oral hypoglycemic effect of *Salacia reticulata* in the Streptozotocin induced diabetic rat." Phytotherapy Res. 1990, 4, 205-206.

Szczepina, M. G. et al., "Synthesis of alkylated deoxynojirimycin and 1,5-dideoxy-1,5-iminoxylitol analogues: Polar side-chain modification, sulfonium and selenonium heteroatom variants, conformational analysis, and evaluation as glycosidase inhibitors." J. Am. Chem. Soc 2004, 126, 12458-12469.

Wen, X. et al., "A combined STD-NMR/molecular modeling protocol for predicting the binding modes of the glycosidase inhibitors kifunensine and salacinol to Golgi alpha-mannosidase II." Biochemistry, 2005. 44, 6729-6737.

Kuntz, D. et al. "Crystallographic analysis of the interactions of *Drosophila melanogaster* Golgi a-mannosidase II with the naturally occurring glycomimetic salacinol and its analogues." Tetrahedron: Asymmetry 2005, 16, 25-32.

Liu, H. et al., "Efficient synthesis of the glucosidase inhibitor blintol, the selenium analogue of the naturally occurring glycosidase inhibitor salacinol." J. Org. Chem. 2005, 70, 753-755.

Garcia-Olmeda, F. et al., "Plant proteinaceous inhibitors of proteinases and alpha-amylases." Oxford Surveys of Plant Molecular and Cell Biology 1987, Oxford, 4, 275-334.

Bompard-Gilles, C. et al., "Substrate mimicry in the active center of a mammalian alpha-amylase: structural analysis of an enzyme-inhibitor complex." Structure 1996, 4, 1441.

Vallee, F. et al., "Barley alpha-amylase bound to its endogenous protein inhibitor BASI: crystal structure of the complex at 1.9 A resolution." Structure 1998, 6, 649.

Strobl, S. et al., "A novel strategy for inhibition of alpha-amylases: yellow meal worm alpha-amylase in complex with the Ragi bifunctional inhibitor at 2.5 A resolution." Structure 1998, 6, 911.

Van Der Klein, P.A.M. et al., "An efficient route to 3-deoxy-D-manno-2-octulosonic acid (KDO) derivatives via A 1,4-cyclic sulfate approach." Tetrahedron Lett. 1989, 30, 5477-5780.

Gelas, J. et al., "Kinetic acetonation of d-mannose: preparation of 4,6-mono- and 2,3:4,6-DI-O-isopropylidene-D-mannopyranose." Carbohydr. Res. 1978, 67, 371-387.

Kuszmann, J. et al., "Two approaches to the synthesis of 3-beta-D-glucopyranosyl-D-glucitol." Carbohydr. Res. 2004, 339, 2407-2414.

Postema, M. H. D. et al., "An Olefin Metathesis Route for the Preparation of (1→46)-Linked C-Disaccharide Glycals. A Convergent and Flexible Approach to C-Saccharide Synthesis" J. Org Chem. 2000, 65, 6061-6068.

Elie, C. J. J. et al., "Synthesis of a spacer-containing trimeric fragment of the capsular polysaccharide from *Escherichia coli* K100." Recueil des Travaux Chimiques des Pays-Bas 1990, 109, 467-473.

Barker, R. et al., "2,3,5-tri-O-benzyl-D-ribosyl and -L-arabinosyl bromides." J. Org. Chem. 1961, 26, 4605-4609.

Naka, T. et al., "The stereoselective synthesis of 4'-beta-thioribonucleosides via the Pummerer reaction." J. Am. Chem. Soc. 2000, 122, 7233-7243.

Minakawa, N. et al., "An improved large scale synthesis of 1,4-anhydro-4-thio-D-ribitol. " Tetrahedron, 2003, 59, 1699-1702.

Fleet, G. W. J. et al., "Practical synthesis of deoxymannojirimycin and mannonolactam from L-gulonolactone. Synthesis of L-deoxymannojirimycin and L-mannonolactam from D-gulonolactone." Tetrahedron, 1989, 45, 319-326.

Jeong, L. S. et al., "N6-Substituted D-4'-Thioadenosine-5'-methyluronamides: Potent and Selective Agonists at the Human A3 Adenosine Receptor." J. Med. Chem. 2003, 46, 3775-3777.

Andrews, G. C. et al., "Stereoselective, catalytic reduction of L-ascorbic acid; A convenient synthesis of L-gulono-1,4-lactone." J. Org. Chem. 1981, 46, 2976-2977.

Gallienne, E. et al., "Short synthesis of new salacinol analogues and their evaluation as glycosidase inhibitors." Tetrahedron, 2005, 61, 4557-4568.

Rama Rao, A.V., et al., "Chiral polyhydroxylated tetrahydrothiophene derivatives: novel synthesis and structural elucidation by X-ray crystallography, NMR spectroscopy and molecular mechanics calculations." J. Chem. Soc., Perkin Trans. 1, 1993, 1255-1257.

Masaki, Y. et al., "Short-step synthesis of chiral C2-symmetric 2,3,4,5-tetrasubstituted pyrrolidines from D-mannitol and their use as chiral ligands in the reaction of diethyizinc and benzaldehyde." Tetrahedron Lett., 1992, 35, 5089-5092.

Sinnot, M. L. "Catalytic mechanisms of enzymic glycosyl transfer." Chem. Rev. 1990, 90, 1171-1202.

Zechel, D. et al., "Glycosidase mechanisms: anatomy of a finely tuned catalyst." Acc. Chem. Res. 2000, 33, 11-18.

Baggert, N. et al., "Asymmetric reduction of ketones by using complexes of lithium tetrahydridoaluminate(III) with 1,4:3,6-dianhydro-D-mannitol and 1,3:4,6-di-O-benzylidene-D-mannitol." J. Chem. Soc., Perkin Trans 1,1977, 1, 1123-1126.

Ley, S. V. et al., "1,2-Diacetals: A new opportunity for organic synthesis." J. Chem. Rev. 2001, 101, 53-80.

Hense, A. et al., "Direct preparation of diacetals from 1,2-diketones and their use as 1,2-diol protecting groups." J. Chem. Soc., Perkin Trans. 1, 1997, 2023-2031.

Smits, E. et al., "Reliable method for the synthesis of aryl beta-D-glucopyranosides, using boron trifluoride-diethyl ether as catalyst." J. Chem. Soc., Perkin Trans. 1, 1996, 2873-2877.

Ghavami, A.; Johnston, B. D.; Maddess, M. D.; Chinapoo, S. M.; Jensen, M. T.; Svensson, B.; Pinto, B. M. Can. J. Chem., 2002, 80, 937-942.

Holman, R. R.; Cull, C. A.; Turner, R. C. Diabetes Care, 1999, 22, 960-964.

Koshland, D. E. Biol. Rev. 1953, 28, 416-436.

Matsuda, Hisashi et al., Database Chemabs, 'Online!, Chemical Abstracts Service, Columbus, Ohio, US, "Antidiabetic principles of natural medicines. IV. Aldose Reductase and alpha-glucosidase inhibitors from the roots of *Salacia oblonga* Wall (Celastraceae) structure of a new friedelane-type triterpene, kotalageni 16-Acetate". Database accession No. 132:163473 XP002168785, 1999.

Database Chemabs 'Online!, Chemical Abstracts Service, Columbus, Ohio, US; Yoshikawa, Masayuki et al., "Antidiabetic constituents of Sri Lankan natural medicine Kotala himbutu (*Salacia reticulata*): absolute stereostructures of alpha-glucosidase inhibitors, salacinol and kotalanol, with unique thiosugar sulfonium sulfate inner salt structure", Database accession No. 131:106694 XP002168786, 1998.

Muraoka, "On the structure of the bioactive constituent from ayurvedic medicine *Salacia reticulata*: revision of the literature". Tetrahedron Letters 49 (2008) 7315-7317.

Andreana, P. R. et al., "Chemo-enzymatic synthesis of polyhydroxyazepanes", Tetrahedron Lett. 2002, 43, 6525-6528.

Asano, N., "Glycosidase inhibitors: update and perspectives on practical use", Glycobiology, 2003, 13(10):93R-104R.

Bertozzi, C.R., et al., "Chemical glycobiology", Science, 2001, 291(5512):2357-2364.

Borges de Melo, E., et al., "Alpha- and Beta-glucosidase inhibitors: chemical structure and biology activity", Tetrahedron, 2006, 62(44):10277-10302.

Branchaud, B. P. et al., "A Novel Strategy for the Synthesis of Ammonium 3-Deoxy-D-manno-2-octulosonate (Ammonium KDO) from Lower Monosaccharides. C—C Bond Construction at C6 of D-Mannose via Cobaloxime-Mediated Radical Alkyl-Alkenyl Cross Coupling", J. Org. Chem. 1989, 54, 1320-1326.

Cahn, "Tentative Rules for Carbohydrate Nomenclature", Part 1, Biochemistry, 1969, 10(21):3983-4004.

Cha, J.K., "Acylic stereocontrol induced by allylic alkoxy groups. Synthetic applications of stereoselective dihydroxylation in natural product synthesis", Chem Rev, 1995, 95(6):1761-1795.

Cha, J.K., et al., "On stereochemistry of osmium tetraoxide oxidation of allylic alcohol systems. Empirical rule", Tetrahedron, 1984, 40(12):2247-2255.

Chehade, J.M. et al., "A Rational Approach to Drug Therapy of Type 2 Diabetes Mellitus", Drugs 2000. 60(1): 95-113.

Database Chemabs 'Online!, Chemical Abstracts Service, Columbus, Ohio, US; Yoshikawa, Masayuki et al. "Kotalanol, a potent alpha-glucosidase inhibitor with thiosugar sulfoniu sulfate structure, from antidiabetic ayurvedic medicine *Salacia reticulata*", Database accession No. 129:300080 XP002168787, 1998; Chem. Pharm. Bull. 46(8) 1339-1340 (1998).

De Praeter, C.M., et al., "A novel disorder caused by defective biosynthesis of n-linked oligosaccharides due to glucosidase I deficiency", Am J Hum Genet, 2000, 66(6):1744-1756.

Eskandari, R. et al., "Potent Glucosidase Inhibitors: De-O-sulfonated Ponkoranol and Its Stereoisomer", Organic Letters, 2010, 12(7), 1632-1635.

Eskandari, R. et al., "Selectivity of 3'-O-methylponkoranol for inhibition of N- and C-terminal maltase glucoamylase and sucrase isomaltase, potential therapeutics for digestive disorders or their sequelae", Bioorganic & Medicinal Chemistry Letters, 2011, 21, 6491-6494.

Eskandari, R. et al., "Synthesis of a biologically active isomer of kotalanol, a naturally occurring glucosidase inhibitor", Bioorganic & Medicinal Chemistry, 2010, 18, 2829-2835.

Eskandari, R. et al., "The effect of heteroatom substitution of sulfur for selenium in glucosidase inhibitors on intestinal α-glucosidase activities", Chem. Commun., 2011, 47, 9134-9136.

Eskandari, R., et al., "Probing the active-site requirements of human intestinal N-terminal maltase glucoamylase: The effect of replacing the sulfate moiety by a methyl ether in ponkoranol, a naturally occurring α-glucosidase inhibitor", Bioorganic & Medicinal Chemistry Letters, 2010, 20, 5686-5689.

Farnsworth, N. R. et al., "Medicinal plants in therapy", Bull. W. H. O. 1985, 63, 965-981.

Fernandes, B., et al., "Beta 1-6 branched oligosaccharides as a marker of tumor progression in human breast and colon neoplasia", Cancer Res, 1991, 51(2):718-723.

Fiaux, H., et al., "Functionalized pyrrolidines inhibit alpha-mannosidase activity and growth of human glioblastoma and melanoma cells", J Med Chem, 2005, 48(13):4237-4246.

Fox, D. J.; House, D.; Warren, S., "Mechanisms of Sulfanyl (RS) Migrations: Synthesis of Heterocycles", Angew. Chem., Int. Ed. 2002, 41, 2462-2482.

Gallienne, E. et al., "Synthesis of New Nitrogen Analogues of Salacinol and Deoxynojirimycin and Their Evaluation as Glycosidase Inhibitors", J. Org. Chem 2006, 71, 894-902.

Greimel, P., et al., "Iminosugars and relatives as antiviral and potential anti-infective agents", Curr Top Med Chem, 2003, 3(5):513-523.

Grindley, T.B., et al., "Conformational studies on 1,3-dioxepanes. Part IV. Applications of geminal coupling constants to conformation analysis of 1,3-dioxepanes", Can J Chem, 1974, 52(24):4062-4070.

Guofeng, G. et al., Corrigendum to Facile synthesis of sulfonium ion derivatives of 1,5-anhydro-5-thio-L-fucitol as potential α-L-fucosidase inhibitors, Carbohydrate Research 342 (2007) 139.

Guofeng, G. et al., "Facile synthesis of sulfonium ion derivatives of 1,5-anhydro-5-thio-L-fucitol as potential α-L-fucosidase inhibitors", Carbohydrate Research 341 (2006) 2478-2486.

Harris, S. L, L. Craig, J. S. Mehroke, M. Rashed, M. B. Zwick, K. Kenar, E. J. Toone, N. Greenspan, F.-I. Auzanneau, J.-R. Marino-Albernas, B. M. Pinto, and J. K. Scott., "Exploring the basis of peptide-carbohydrate crossreactivity: Evidence for discrimination by peptides between closely related anti-carbohydrate antibodies", Proc. Natl. Acad. Sci. USA, 94, 2454 (1997).

Harris, J.M., et al., "Syntheses of D- and L-mannose, gulose, and talose via diastereoselective and enantioselective dihydroxylation reactions", J Org Chem, 1999, 64(9)2982-2983.

Heightman, T.D., et al., "Recent insights into inhibition, structure, and mechanism of configuration-retaining glycosidases", Angew Chem Int Ed, 1999, 38(6):750-770.

Jacobsen, E.N., et al., "Asymmetric dihydroxylation via ligand-accelerated catalysis", J Am Chem Soc, 1988, 110 (6):1968-1970.

Jayakanthan, K. et al., "Structure Proof and Synthesis of Kotalanol and De-O-sulfonated Kotalanol, Glycosidase Inhibitors Isolated from an Herbal Remedy for the Treatment of Type-2 Diabetes", Am. Chem. Soc. 2009, 131, 5621-5626.

Jayawardena, M.H., et al., "A double blind randomised placebo controlled cross over study of a herbal preparation containing *Salacia reticulata* in the treatment of type 2 diabetes", J Ethnopharmacol, 2005, 97(2)215-218.

Johnston, B.D., et al., "Synthesis of sulfonium sulfate analogues of disaccharides and their conversion to chain-extended homologues of salacinol: new glycosidase inhibitors", J Org Chem, 2006, 71(3):1111-1118.

Jolicoeur, F.B. et al., "In Vivo Opioid Activity of S-Methyl and S-Allyl Morphinan Derivatives", Int. Narcotics Res. Conf. 89, 49 (1990).

Jones, J.K., et al., "Isolation of D-glycero-D-galacto-heptitol from the wound exudate of avocado trees", Nature, 1961, 189(4766):746.

Kim, K.S., et al, "Methylenation of carbohydrates using phase-transfer catalysis", Synthesis, 1978, 48-50.

Koehn, F. E. et al., "The Evolving Role of Natural Products in Drug Discovery", Nat. Rev. Drug Discov. 2005, 4, 206-220.

Koto, S. et al., "One-stage glycosylation using protected glycose: the synthesis of O-β-D-glucopyranosyl-(1→3)-O-[β-D-glucopyranosyl-(1→6)]-D-glucopyranose", Can. J. Chem. 1981, 59, 255-259.

Kumar, N. S. et al., "Synthesis of D-lyxitol and D-ribitol analogues of the naturally occurring glycosidase inhibitor salacinol", Carbohydrate Research 340 (2005) 2612-2619.

Li, Y.; C. R. Scott N. A. Chamoles, A. Ghavami, B. M. Pinto, F. Furecek, and M. H. Gelb., "Direct Multiplex Assay of Lysosomal Enzymes in Dried Blood Spots for Newborn Screening", Clin. Chem. 2004, 50, 1785.

Liu, H., et al, "A new class of glucosidase inhibitor: analogues of the naturally occurring glucosidase inhibitor salacinol with different ring heteroatom substituents and acyclic chain extension", J Org Chem, 2006, 71(8):3007-3013.

Liu, H., et al., "Design and synthesis of selenonium and sulfonium ions related to the naturally occurring glucosidase inhibitor salacinol", Can J Chem, 2006, 84(10):1351-1362.

Liu, H., et al., "New synthetic routes to chain-extended selenium, sulfur, and nitrogen analogues of the naturally occurring glucosidase inhibitor salacinol and their inhibitory activities against recombinant human maltase glucoamylase", J Org Chem, 2007, 72(17):6562-6572.

Lopez, O., et al., "Iminosugars: From Synthesis to Therapeutic Applications", Eds. Philippe Compain, Olivier R. Martin, John Wiley & Sons, 2007, 131-151.

Matsuda et al., "Antidiabetic Principes of Natural Medicines. IV.1) Aldose Reductase and α-Glucosidase Inhibitors from the Roots of *Salacia oblonga* Wall. (Celastraceae): Structure of a New Friedelane-Type Triterpene, Kotalagenin 16-Acetate", Chem. Pharm. Bull., 1999, 47, 1725-1729.

Matsuda, H. et al., "Antidiabetogenic constituents from *Salacia* species", Journal of Trad. Med. 2005, 22, 145-153.

Matsuda, Hisashi, et al., "Antidiabetogenic constituents from several natural medicines", Pure Appl Chem, 2002, 74 (7):1301-1308.

Matsumoto, K., et al., "Effects of voglibose on glycemic excursions, insulin secretion, and insulin sensitivity in non-insulin-treated NIDDM patients", Diabetes Care, 1998, 21(2):256-260.

Mehta, A., et al., "Alpha-glucosidase inhibitors as potential broad based anti-viral agents", FEBS Lett, 1998, 430 (1-2):17-22.

Minami, Y. et al., "Effect of five-membered sugar mimics on mammalian glycogen-degrading enzymes and various glucosidases", Bioorg. Med. Chem. 2008, 76, 2734-2740.

Mohan, S. et al., "Probing the active-site requirements of human intestinal N-terminal maltase-glucoamylase: Synthesis and enzyme inhibitory activities of a six-membered ring nitrogen analogue of kotalanol and its de-O-sulfonated derivative", Bioorganic & Medicinal Chemistry, 2010, 18, 7794-7798.

Mohan, S. et al., Synthesis and Biological Evaluation of Heteroanalogues of Kotalanol and D-O-Sulfonated Kotalanol, Organic Letters, 2010, 12(5), 1088-1091.

Mohan, S. et al., "Towards the elusive structure of kotalanol, a naturally occurring glucosidase inhibitor", Natural Product Reports, 2010, 27, 481-488.

Mohan, S., et al., "Sulfonium-ion glycosidase inhibitors isolated form *Salacia* species used in traditional medicine, and related compounds", Collect. Czech. Chem. Commun., 2009, 74:1117-1136.

Mohan, S., et al., "Zwitterionic glycosidase inhibitors: salacinol and related analogues", Carbohydrate Research, 2007, 342:1551-1580.

Mohan S. et al., "Synthesis of S-alkylated sulfonium-ions and their glucosidase inhibitory activities against recombinant human maltase glucoamylase", Carbohydr. Res. 2007, 342, 901-912.

Montgomery, E.M., et al., "The synthesis of D-mannoheptulose, and the preparation of some of its derivatives", J Am Chem Soc, 1939, 61(7):1654-1658.

Moremen, K. W., et al., "Glycosidases of the asparagine-linked oligosaccharide processing pathway", Glycobiology, 1994, 4(2):113-125.

Muraoka, O. et al., "Characteristic alakaline catalyzed degredation of kotalanol, a potent α-glucosidase inhibitor isolated from Ayurvedic traditional medicine *Salacia reticulata*, leading to anhydroheptitols: another structure proof", Tetrahedron, 2010, 66, 3717-3722.

Muraoka, O. et al., "Synthesis and biological evaluatino of deoxy salacinols, the role of polar substituents in the side chain on the α-glucosidase inhibitory activity", Bioorganic & Medicinal Chemistry 14 (2006) 500-509.

Nakamura, S. et al., "Docking and SAR studies of salacinol derivatives as α-glucosidase inhibitors", Bioorganic & Medicinal Chemistry Letters, 2010, 20, 4420-4423.

Nash, R.J., "Naturally occurring glycosidase inhibitors", Bioactive Natural Products: Detection, Isolation, and Structural Determination (2nd edition), Ed. Steven M. Colegate and Russell J. Molyneux, Summit Wales Limited, Plas Gogerddan, Aberystwyth, UK. Chapter 15), 2008.

Nasi, R. et al., "Synthesis and glycosidase inhibitory activities of chain-modified analogues of the glycosidase inhibitors salacinol and blintol", Carbohydrate Research 342 (2007) 1888-1894.

Nasi, Ravindrath, et al., "New chain-extended analogues of salacinol and blintol and their glycosidase inhibitory activities. Mapping the active-site requirements of human maltase glucoamylase", J Org Chem, 2007, 72(1):180-186.

Nasi, R., et al., "Studies directed toward the stereochemical structure determination of the naturally occurring glucosidase inhibitor, kotalanol: synthesis and inhibitory activities against human maltase glucoamylase of seven-carbon, chain-extended homologues of salacinol", J Org Chem, 2008, 73(16):6172-6181.

Ness, A., et al., "The 1,3:5,7-dibenzylidene and 1,3:5,7-dimethylene acetals of the-, L-and D,L-perseitols", J Am Chem Soc, 1948, 70:765-770.

Newman, D. J. et al., "Natural Products as Sources of New Drugs over the Last 25 Years", J. Nat. Prod. 2007, 70, 461-477.

Nishimura, Y., "gem-Diamine 1-N-iminosugars, a new family of glycosidase inhibitors: synthesis and biological activity", Heterocycles, 2006, 67(1):461-488.

Nordal, A., et al., "Isolation of mannoheptulose and identification of its phosphate in avocado leaves", J Am Chem Soc, 1954, 76(20):5054-5055.

Oe, H., et al., "Hypoglycemic effect of 13-membered ring thiocyclitol, a novel alpha-glucosidase inhibitor from kothalahimbutu (*Salacia reticulata*)", Biosci Biotechnol Biochem, 2008, 72(7):1962-1964.

Ozaki, S., et al., "Alpha-glucosidase inhibitor from Kothala-himbutu (*Salacia reticulata* WIGHT)", J Nat Prod, 2008, 71 (6):981-984.

Potterat, O. et al., "Drug discovery and development with plant-derived compounds", Progress in Drug Research; Birkhauser Basel: 2008; vol. 65, p. 45-118.

Reichardt, C. "Solvents and Solvent Effects in Organic Chemistry", 2nd Ed.; VCH: Weinheim, 1996; pp. 137-147, 359-384.

Rempel, B., et al., "Covalent inhibitors of glycosidases and their applications in biochemistry and biology", Glycobiology, 2008, 18:570-586.

Rossi, E.J., et al,. "Inhibition of recombinant human maltase glucoamylase by salacinol and derivatives", FEBS J., 2006, 273(12):2673-2683.

Rybka, J. et al., "European Comparative Study of 2 Alpha-Glucosidase Inhibitors Miglitol and Acarbose", Diabetes 1999, 48 (Suppl 1): A101.

Sim, L. et al., "New Glucosidase Inhibitors from an Ayurvedic Herbal Treatment for Type 2 Diabetes: Structures and Inhibition of Human Intestinal Maltase-Glucoamylase with Compounds from *Salacia reticulata*", Biochemistry, 2010, 49, 443-451.

Siriwardena, A., et al., "Potent and selective inhibition of class II alpha-D-mannosidase activity by a bicyclic sulfonium salt", ChemBioChem, 2005, 6(5):845-848.

Skaanderup, P. R. et al., "Regioselective Conversion of Primary Alcohols into Iodides in Unprotected Methyl Furanosides and Pyranosides", Synthesis 2002, 1721-1727.

Tanabe, G. et al., "Biological evaluation of 3'-O-alkylated analogs of salacinol, the role of hydrophobic alkyl group at 30 position in the side chain on the α-glucosidase inhibitory activity", Bioorganic & Medicinal Chemistry Letters, 2011, 21, 3159-3162.

Tanabe, G. et al., "Biological evaluation of de-O-sulfonated analogs of salacinol, the role of sulfate anion in the side chain on the α-glucosidase inhibitory activity", Bioorganic & Medicinal Chemistry 15 (2007) 3926-3937.

Tanabe, G. et al., "Facile synthesis of de-O-sulfated salacinols: Revision of the structure of neosalacinol, a potent α-glucosidase inhibitor", Bioorg. & Med. Chem. Lett. 2009, 7, 2195-2198.

Tanabe, G., et al., "Structure-activity relationships of salacinol and kotalanol against α-glucosidase inhibitory activity and evaluation of salacia extracts by LC-MS", J Pharm Soc Jpn, 2007, 127, Suppl. 4, 129-130.

Tatsuta, K., "Significance of total synthesis of bioactive compounds", Curr Org Chem, 2001, 5:207-231.

van den Broek, L. A. G. M.; Vermaas, D. J.; Heskamp, B. M.; van Boeckel, C. A. A.; Tan, M. C. A. A.; Bolscher, J. G. M.; Ploegh, H. L.; van Kemenade, F. J.; de Goede, R. E. Y.; Miedema, F., "Chemical modification of azasugars, inhibitors of N-glycoprotein processing glycosidases and of HIV-I infection", Recl. Tray. Chim. Pays-Bas 1993, 112, 82-94.

Watson, A., et al., "Polyhydroxylated alkaloids—natural occurrence and therapeutic applications", Phytochemistry, 2001,56:265-295.

Xia, J.; Alderfer, J. L.; Piskorz, C. F.; Matta, K. L., "The 2-Naphthylmethyl (NAP) Group in Carbohydrate Synthesis: First Total Synthesis of the GlyCAM-1 Oligosaccharide Structures", Chem. Eur. J. 2001, 7, 356-367.

Xie, W. et al., "Isolation, structure identification and SAR studies on thiosugar sulfonium salts, neosalaprinol and neoponkoranol, as potent α-glucosidase inhibitors", Bioorganic & Medicinal Chemistry, 2011, 19, 2015-2022.

Xie, W. et al., "Role of the side chain stereochemistry in the α-glucosidase inhibitory activity of kotalanol, a potent natural α-glucosidase inhibitor", Bioorganic & Medicinal Chemistry, 2011, 19, 2252-2262.

Yoshikawa et al., "Salaprinol and Ponkoranol with thiosugar sulfonium sulfate structure from *Salacia prinoides* and α-glucosidase inhibitory activity of ponkoranol and kotalanol desulfate", Heterocycles, 2008, 75, 1397-1405.

Yoshikawa, Masayuki et al., "*Salacia reticulata* and Its Plyphenolic Constituents with Lipase Inhibitory and Lipolytic Activities Have Mild Antiobesity Effects in Rats", J. Nutr. 132: 1819-1824, 2002.

* cited by examiner

GLYCOSIDASE INHIBITORS AND METHODS OF SYNTHESIZING SAME

RELATED APPLICATIONS

This application is a continuation-in-part of U.S. patent application Ser. No. 10/877,490 filed 25 Jun. 2004, abandoned, which claims the benefit of U.S. Provisional Patent Application No. 60/482,006 filed 25 Jun. 2003, and is a continuation-in-part of U.S. patent application Ser. No. 10/226,657 filed 22 Aug. 2002, abandoned, which is a continuation of U.S. patent application Ser. No. 09/627,434 filed 28 Jul. 2000, now issued as U.S. Pat. No. 6,455,573 which claims the benefit of U.S. Provisional Patent Application No. 60/174,837 filed 7 Jan. 2000 which is hereby incorporated by reference.

TECHNICAL FIELD

This application relates to methods for synthesizing Salacinol, its stereoisomers, and analogues, homologues and other derivatives thereof potentially useful as glycosidase inhibitors.

BACKGROUND

In treatment of non-insulin dependent diabetes (NIDD) management of blood glucose levels is critical. One strategy for treating NIDD is to delay digestion of ingested carbohydrates, thereby lowering post-prandial blood glucose concentration. This can be achieved by administering drugs which inhibit the activity of enzymes, such as glucosidases, which mediate the hydrolysis of complex starches to oligosaccharides in the small intestine. For example, carbohydrate analogues, such as Acarbose, reversibly inhibit the function of pancreatic α-amylase and membrane-bound intestinal α-glucoside hydrolase enzymes. In patients suffering from Type II diabetes, such enzyme inhibition results in delayed glucose absorption into the blood and a smoothing or lowering of postprandial hyperglycemia, resulting in improved glycemic control.

Some naturally-occurring glycosidase inhibitors have been isolated from *Salacia reticulata,* a plant native to submontane forests in Sri Lanka and parts of India (known as "Kotala himbutu" in Singhalese). *Salacia reticulata* is a woody climbing plant which has been used in the Ayurvedic system of Indian medicine in the treatment of diabetes. Traditionally, Ayurvedic medicine advised that a person suffering from diabetes should drink water left overnight in a mug carved from Kotala himbutu wood. In an article published in 1997, Yoshikawa et al. reported the isolation of the compound Salacinol from a water-soluble fraction derived from the dried roots and stems of *Salacia reticulata*.[1] Yoshikawa et al. determined the structure of Salacinol, shown below, and demonstrated its efficacy as an x-glucosidase inhibitor.

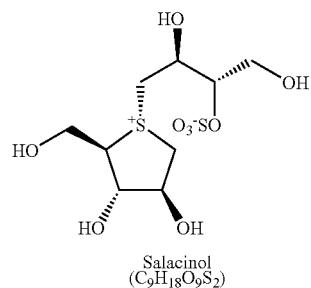

Salacinol
($C_9H_{18}O_9S_2$)

Yoshikawa et al. later reported the isolation from the roots and stems of *Salacia reticulata* of Kotalanol which was also shown to be effective as an α-glucosidase inhibitor.[2] Like Salicinol, Kotalanol contains a thiosugar sulfonium ion and an internal sulfate providing the counterion:

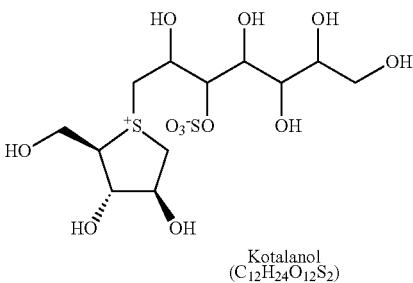

Kotalanol
($C_{12}H_{24}O_{12}S_2$)

Kotalanol has been found to show more potent inhibitory activity against sucrase than Salicinol and Acarbose.[2]

The exact mechanism of action of Salacinol and other glucosidase inhibitors has not yet been elucidated. Some known glycosidase inhibitors, such as the indolizidine alkaloids castanospermine and swainsonine, are known to carry a positive charge at physiological pH.

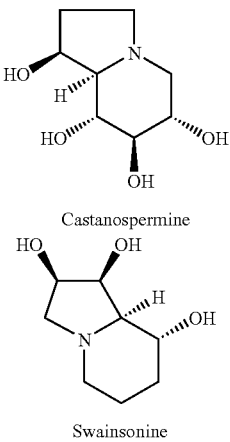

Castanospermine

Swainsonine

It is believed that the mechanism of action of some known inhibitors may be at least partially explained by the establishment of stabilizing electrostatic interactions between the inhibitor and the enzyme active site carboxylate residues. It is postulated that the compounds of the present invention, which comprise postively charged sulfonium, ammonium, and selenonium ions, could function in a similar manner. It is also possible that Salacinol and other compounds of the same class may act by alteration of a transport mechanism across the intestinal wall rather than by directly binding to glucosidase enzymes.

Salacinol and Kotalanol may potentially have fewer long-term side effects than other existing oral antidiabetic agents. For example, oral administration of Acarbose in the treatment of Type II diabetes results in undesirable gastrointestinal side effects in some patients, most notably increased flatulence, diarrhoea and abdominal pain. As mentioned above, Salacinol has been used as a therapy for diabetes in the Ayurvedic system of traditional medicine for many years with no notable side effects reported. Further, recent animal studies have shown that the oral ingestion of an extractive from a *Salacia reticulata* trunk at a dose of 5,000 mg/kg had no serious acute toxicity or mutagenicity in rats.[3]

The *Salacia reticulata* plant is, however, in relatively small supply and is not readily available outside of Sri Lanka and India. Accordingly, it would be desirable if Salicinol, Kotalanol and analogues thereof could be produced synthetically.

Carbohydrate processing inhibitors have also been shown to be effective in the treatment of some non-diabetic disorders, such as cancer. While normal cells display characteristic oligosaccharide structures, tumor cells display very complex structures that are usually found in embryonic tissues. It is believed that these complex structures provide signal stimuli for rapid proliferation and metastasis of tumor cells. A possible strategy for therapeutic use of glucosidase inhibitors is to take advantage of the differential rates of normal vs cancer cell growth to inhibit assembly of complex oligosaccharide structures. For example, the indolizidine alkaloid swainsonine, an inhibitor of Golgi α-mannosidase II, reportedly reduces tumor cell metastasis, enhances cellular immune responses, and reduces tumor cell growth in mice.[4] Swainsonine treatment has led to significant reduction of tumor mass in human patients with advanced malignancies, and is a promising drug therapy for patients suffering from breast, liver, lung and other malignancies.[5,6]

The compounds of the present invention may also find application in the treatment of Alzheimer's disease due to their stable, internal salt structure. Alzheimer's is characterized by plaque formation in the brain caused by aggregation of a peptide, β-amyloid, into fibrils. This is toxic to neuronal cells. One can inhibit this aggregation by using detergent-like molecules. It is believed that the compounds of the present invention, which are amphipathic, may demonstrate this activity.

The need has therefore arisen for a new class of glycosidase inhibitors which may be synthesized in high yields from readily available starting materials and which have potential use as therapeutics.

SUMMARY OF THE INVENTION

In accordance with the invention, a compound selected from the group consisting of non-naturally occurring compounds represented by the general formula (I), including stereoisomers and pharmaceutically acceptable salts thereof is disclosed,

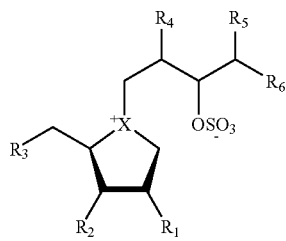

(I)

where X is selected from the group consisting of S, Se, and NH. Such compounds include stereoisomers of Salicinol. The target compounds have a stable, internal salt structure comprising heteroatom cation X and a sulfate anion; the substituents may vary without departing from the invention. Preferably, $R_1$, $R_2$, $R_3$, $R_4$ and $R_5$ are the same or different and are selected from the group consisting of H, OH, SH, $NH_2$, halogens and constituents of compounds selected from the group consisting of cyclopropanes, epoxides, aziridines and episulfides; and $R_6$ is selected from the group consisting of H and optionally substituted straight chain, branched, or cyclic, saturated or unsaturated hydrocarbon radicals, such as alkyl, alkenyl, alkynyl, aryl, and alkoxy substituents containing any suitable functionality. In one embodiment of the invention $R_6$ may be a polyhydroxylated, acyclic chain, such as an alditol chain of between 5 and 10 carbons.

In another embodiment of the invention, the heterocycle ring may comprise 6 rather 5 carbons and the compound may be represented by the general formula (II):

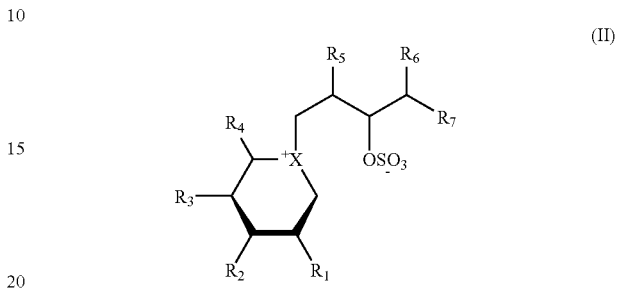

(II)

Processes for the production of compounds of the general formula (I) and (II) are also disclosed comprising reacting a cyclic sulfate having the general formula (III) with a 5-membered ring sugar having the general formula (IV) or (V)

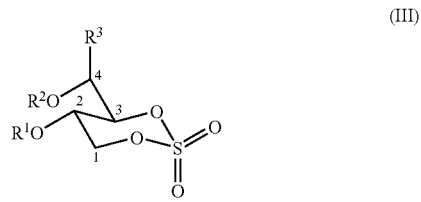

(III)

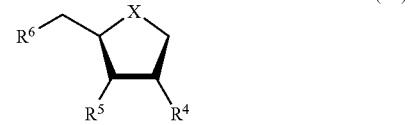

(IV)

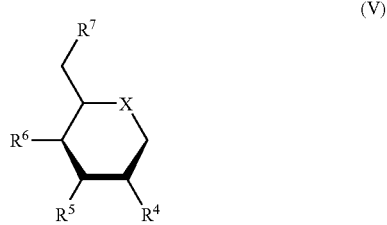

(V)

where X is selected from the group consisting of S, Se, and NH; $R^1$ and $R^2$ are selected from the group consisting of H and a protecting group; $R^3$ is selected from the group consisting of H and optionally substituted straight chain, branched, or cyclic, saturated or unsaturated hydrocarbon radicals and their protected derivatives; and $R^4$, $R^5$ and $R^6$ are the same or different and are selected from the group consisting of H, OH, SH, $NH_2$, halogens and constituents of compounds selected from the group consisting of cyclopropanes, epoxides, aziridines and episulfides and their protected derivatives. Preferably the cyclic sulfate is a 2,4-di-O-protected-D- or L-erythritol-1,3-cyclic sulfate, such as 2,4-O-Benzylidene-D- or L-erythritol-1,3-cyclic sulfate (i.e. $R_1$ and $R_2$ comprise a benzylidene protecting group); $R^3$ is H or a protected polyhydroxylated alkyl chain; and $R_4$, $R_5$ and $R^6$ are selected from the group consisting of OH and a protected OH group, such as $OCH_2C_6H_5$ or $OCH_2C_6H_4OCH_3$. The synthetic processes comprise the step of opening the cyclic sulfate (III) by nucleophilic attack of the heteroatom X on the sugar (IV) or (V).

The processes for the production of the target compounds may include the use of novel protecting and deprotecting agents, such as p-methoxybenzyl, and solvents, such as hexafluoroisopropanol.

The application also relates to the use of a compound according to formula (I) or (II) as a glycosidase inhibitor, and to pharmaceutical compositions comprising an effective amount of a compound according to formula (I) or (II), or combinations thereof, together with a pharmaceutically acceptable carrier, and to methods of treating carbohydrate metabolic disorders, such as non-insulin dependent diabetes by administering to a subject in need of such treatment an effective amount of such compounds.

BRIEF DESCRIPTION OF THE DRAWINGS

In drawings which are intended to illustrate embodiments of the invention and which are not intended to limit the scope of the invention.

DETAILED DESCRIPTION OF THE INVENTION

Figure 1:
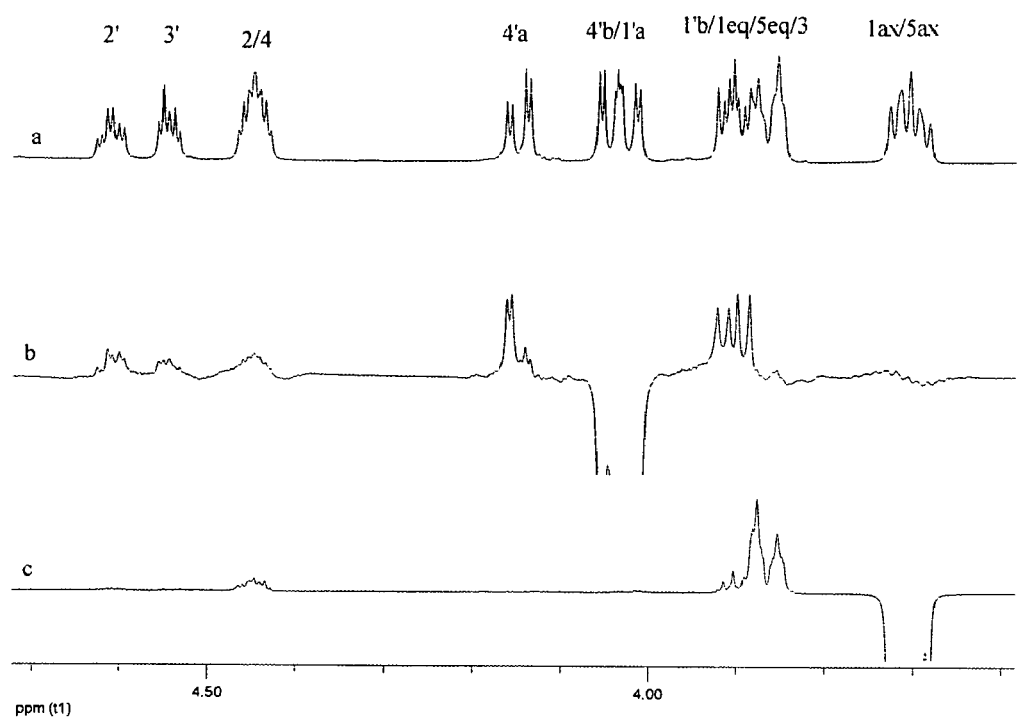
FIG. 1 depicts one dimensional transient NOE difference spectra of compound S-68b in $D_2O$. (a) $^1H$ NMR spectrum. (b) Spectrum with selective irradiation of the H-4'b/H-1'a multiplet. (c) Spectrum with selective irradiation of the H-1ax/H-5ax multiplet.

Salacinol is a naturally occurring compound which may be extracted from the roots and stems of *Salacia reticulata*, a plant native to Sri Lanka and India. This application relates to synthetic routes for preparing Salacinol (1), and its nitrogen (2) and selenium (3) analogues shown below.

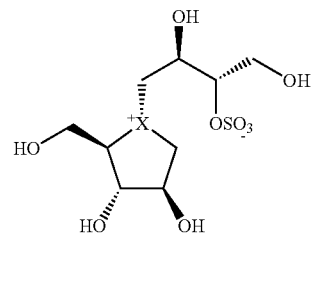

X = S (1)
X = NH (2)
X = Se (3)

This application also relates to synthetic routes for preparing compounds (1) to (3) and stereoisomers, analogues, homologues and other derivative thereof. As used in this patent application, stereoisomers includes enantiomers and diastereoisomers. The compounds of the invention (including stereoisomers of Salacinol) comprise a new class of compounds which are not naturally occurring and may find use as glycosidase inhibitors.

1.0 Summary of General Synthetic Scheme

Scheme 1(a) below, shows the general synthetic scheme developed by the inventors for arriving at some of the target compounds. To synthesize different stereoisomers of Salacinol and its nitrogen and selenium analogues (A)-(C), 5-membered-ring sugars are reacted with sulfate-containing compounds in accordance with the invention (in Scheme 1(a) the letters (A), (B), and (C) represent all stereoisomers of Salacinol and its nitrogen and selenium analogues (1), (2) and (3) respectively). The inventors followed a disconnection approach for determining the preferred synthetic route. A reasonable disconnection is one that gives the 5-membered-ring sugars (D) since they can be synthesized easily from readily available carbohydrate precursors. Nucleophilic substitution at $C_1$ of the sulfate fragment (E) can then yield the target molecules (Scheme 1(a)). A potential problem with this approach is that the leaving group (L) might act later as a base to abstract the acidic hydrogens of the sulfonium salt[7] and produce unwanted products. Therefore, the cyclic sulfate (F) may be used instead of (E) to obviate the problems associated with leaving group (L). Compound (G) may similarly be used as a cyclic sulfate reagent and is a protected version of (F).

Scheme 1(a). Disconnection approach for the synthesis of (A)-(C)

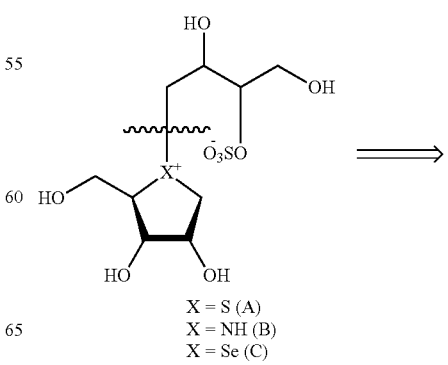

X = S (A)
X = NH (B)
X = Se (C)

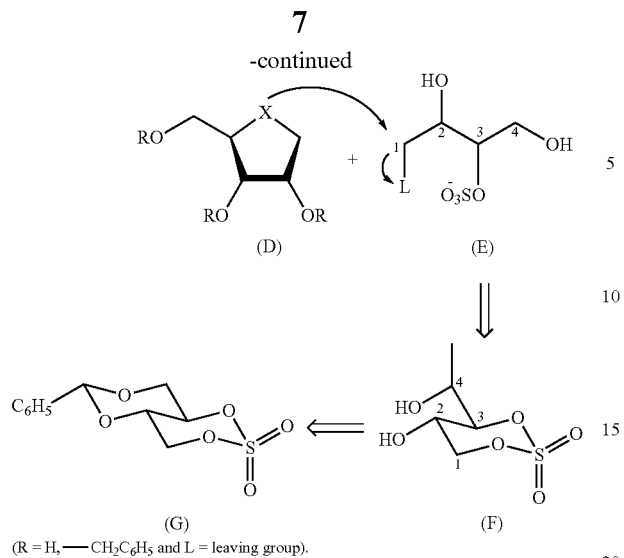

(R = H, —CH₂C₆H₅ and L = leaving group).

Scheme 1(b) below shows generally the coupling reactions for producing the target compounds (A)-(C).

Scheme 1(b). Typical coupling reaction for the synthesis of different steroisomers (A)-(C)

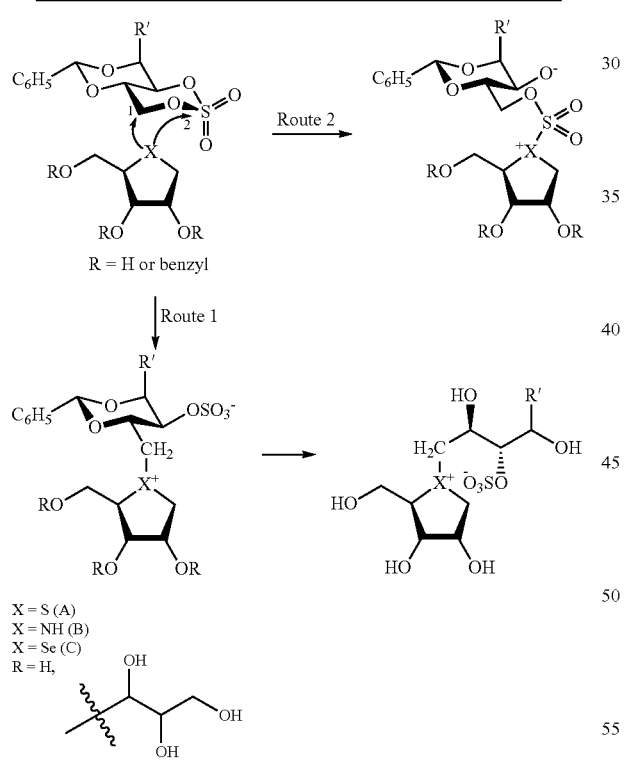

X = S (A)
X = NH (B)
X = Se (C)
R = H,

Route 1 of Scheme 1(b) shows the general strategy of reacting a cyclic sulfate with a 5-membered ring sugar to produce an intermediate compound, which may include benzyl or other protecting groups. As described in further detail below, the intermediate compound is then deprotected to yield the target compounds. The inventors have determined that Route 2 of Scheme 1(b), a possible side reaction, does not occur.

2.0 Synthesis of Reagents

Cyclic sulfates and 5-membered-ring sugars were prepared in accordance with the synthetic schemes described below. As will be apparent to a person skilled in the art, other equivalent schemes for producing the reagents of the invention could be substituted.

2.1 Cyclic Sulfates

Cyclic sulfates were prepared in analogous fashion to the ethylidene acetal.[8] The cyclic sulfate (7) was synthesized in 4 steps starting from D-glucose (Scheme 2). 2,4-O-Benzylidene-D-erythrithol (5) was synthesized from D-glucose in two steps,[9,10] and then treated with thionyl chloride to yield the cyclic sulfite (6) which was oxidized to the cyclic sulfate (7) as described by Calvo-Flores et al.[8]

Scheme 2. Synthesis of the cyclic sulfate (7).

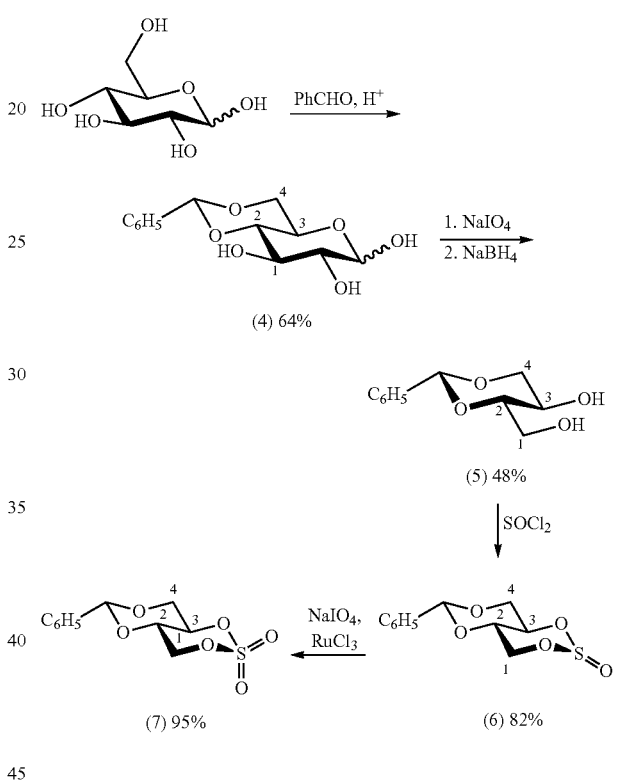

The enantiomer (10) was also synthesized using the same route but starting from L-glucose (Scheme 3).

Scheme 3. Synthesis of the cyclic sulfate (10).

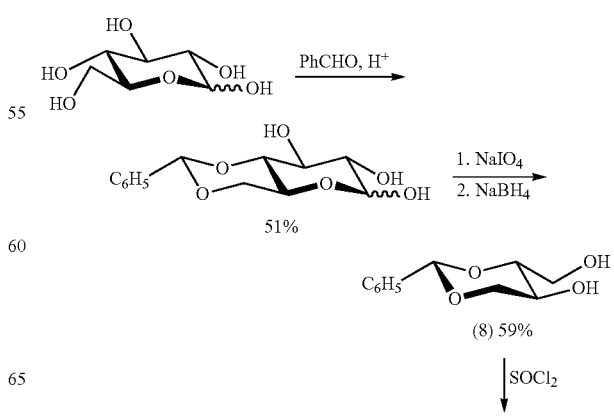

2.2 Synthesis of 5-Membered-ring Heterocycles

In order to synthesize one of the 5-membered-ring sugars (D, X=S), 1,4-anhydro-3-O-benzyl-4-thio-D-arabinitol (11), was synthesized in 9 steps starting from D-glucose (Scheme 4).[11] Benzylation of the compound (11), using benzyl bromide in DMF yielded 1,4-anhydro-2,3,5-tri-O-benzyl-4-thio-D-arabinitol (12) in 90% yield. Compound (11) was debenzylated to give 1,4-anhydro-4-thio-D-arabinitol (13) in 97% yield using a Birch reduction.

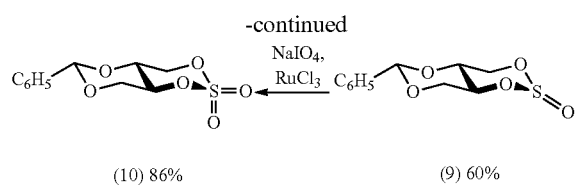

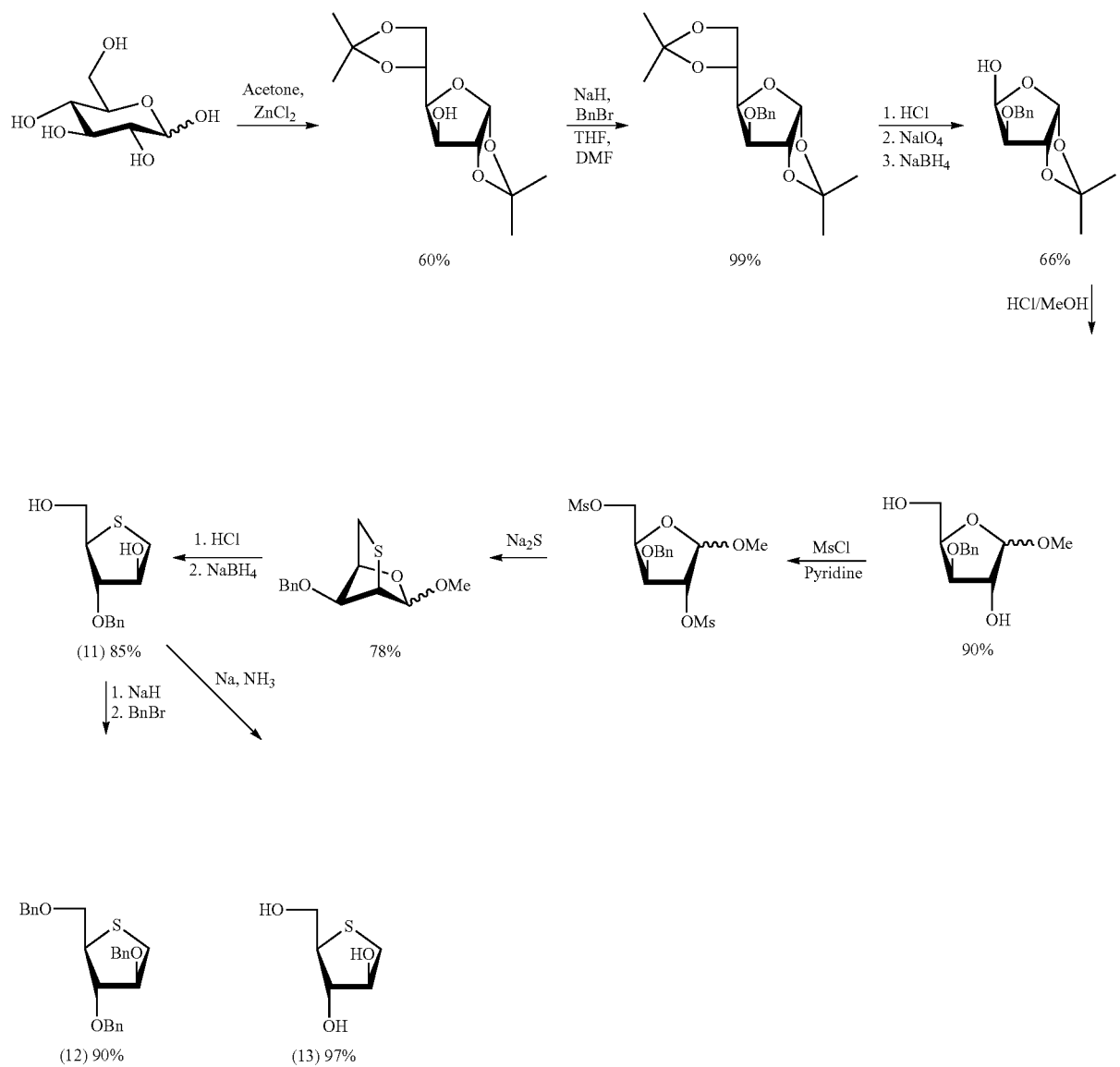

Scheme 4. Synthesis of compounds (11)-(13).

Bn = CH$_2$Ph
Ms = CH$_3$SO$_2$

The L-isomer, 1,4-anhydro-2,3,5-tri-O-benzyl-4-thio-L-arabinitol (14) was synthesized in 5 steps starting from D-xylose (Scheme 5).[12]

analogous way starting from L-xylose (Scheme 6). Compound (19) was also synthesized in 10 steps starting from D-xylose.[13] 1,4-Anhydro-2,3,5-tri-O-benzyl-4-seleno-D-

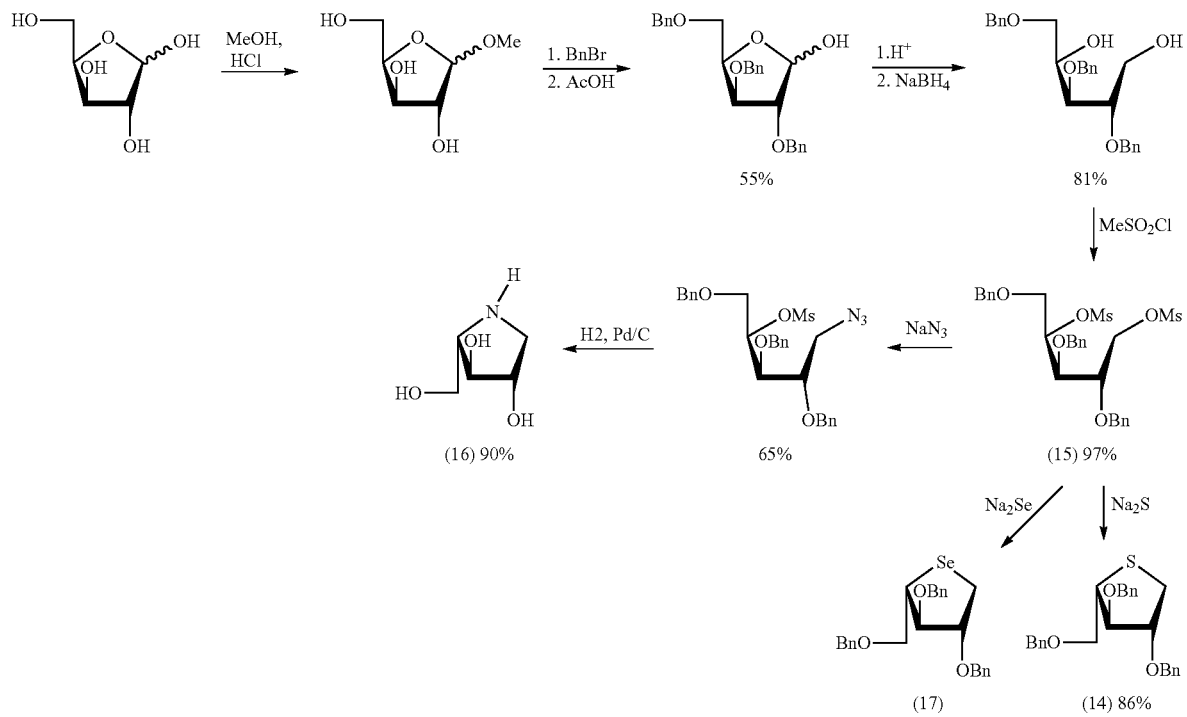

1,4-Di-O-methanesulfonyl-2,3,5-tri-O-benzyl-D-xylitol (15) is also a key intermediate for the synthesis of the aza and selena sugars (16) and (17). 1,4-Dideoxy-1,4-imino-L-arabinitol (16)[13] was synthesized in 7 steps starting from D-xylose (Scheme 5). The enantiomer (19)[13] was synthesized in an arabinitol (20) was synthesized in 5 steps starting from L-xylose (Scheme 6). To synthesize compound (20), Na$_2$Se was made in-situ by treatment of selenium metal with sodium in liquid ammonia.

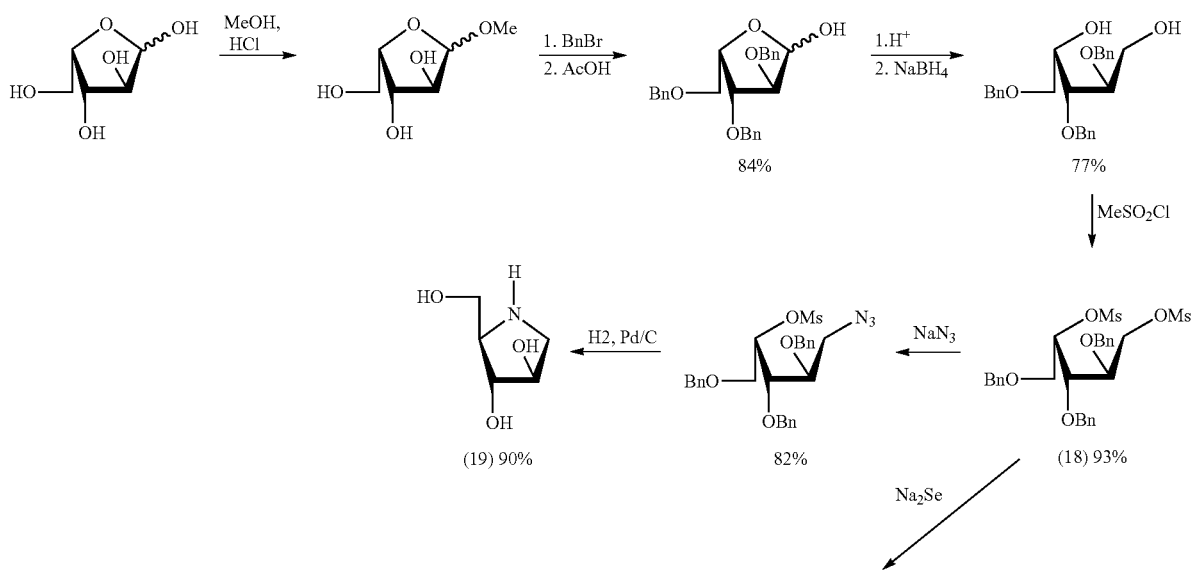

-continued

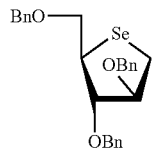

(20) 80%

Scheme 6(a) below shows a more generalized scheme for synthesizing compound (20) using other possible protecting groups (R=COR, $CH_2C_6H_4$—$OMe_p$).

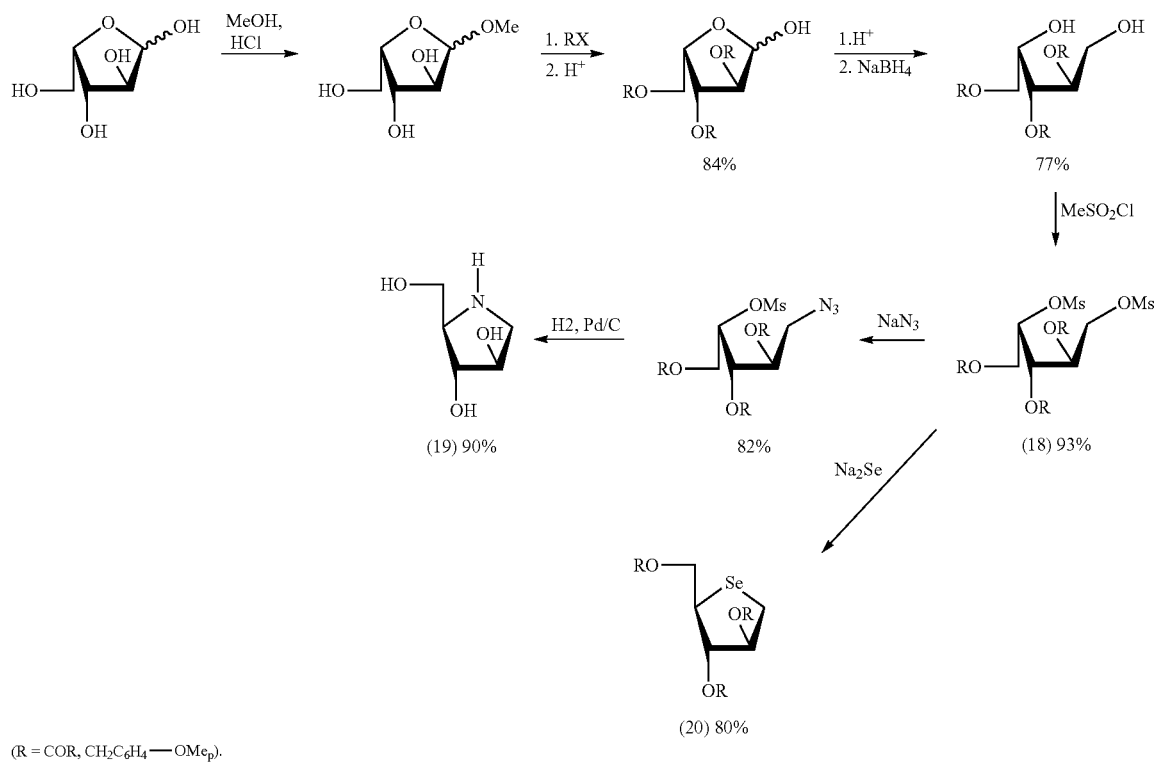

(R = COR, $CH_2C_6H_4$—$OMe_p$).

3.0 Synthesis of Target Compounds (1)-(3)

The target compounds (1)-(3) were prepared by opening of the cyclic sulfates by nucleophilic attack of the heteroatoms on the 5-membered rings (Scheme 1(b) above). The heteroatom gives rise to a positively charged cation and the cyclic sulfate gives rise to a negatively charged counterion. This internal salt structure may explain the stability of the target compounds toward decomposition by further nucleophilic attack.

3.1 Synthesis of Salacinol

Salacinol (1) was synthesized by nucleophilic substitution of the protected thio-arabinitol (12) with the cyclic sulfate (10) (1.2 equiv) in dry acetone containing $K_2CO_3$, to give the protected intermediate compound (21) in 33% yield. Hydrogenolysis of the benzyl and benzylidene groups in AcOH: $H_2O$, 4:1 afforded Salacinol (1) in 67% yield (Scheme 7).

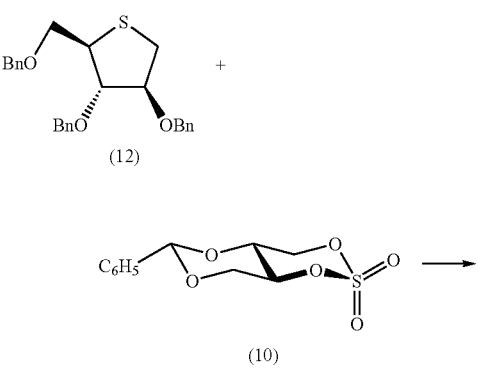

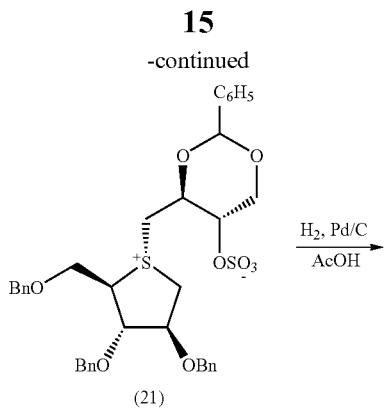

(21)

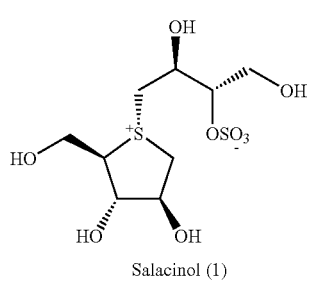

Salacinol (1)

The same procedure was used to prepare intermediate compound (22) in 79% yield from the enantiomeric cyclic sulfate (7). Deprotection as before gave compound (23) in 59% yield (Scheme 8). Compound (23) is a diastereomer of Salacinol (1).

Scheme 8. Synthesis of compound (23)

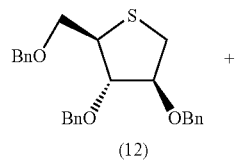

(12)

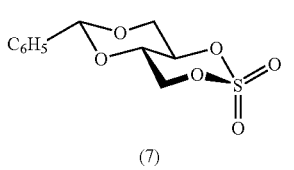

(7)

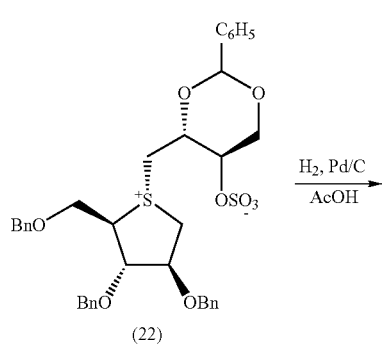

(22)

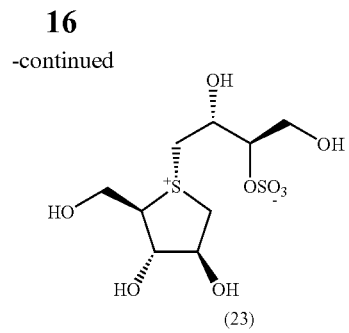

(23)

Compound (24) was prepared in 40% yield from (7) and the enantiomeric thio-ether (14) (Scheme 9). Deprotection in 80% yield gave the enantiomer of Salacinol (25).

Scheme 9. Synthesis of compound (25)

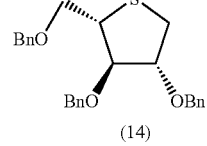

(14)

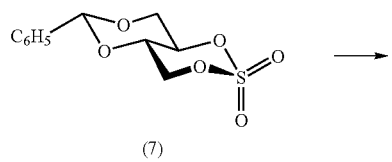

(7)

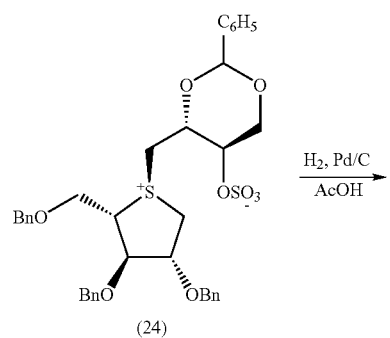

(24)

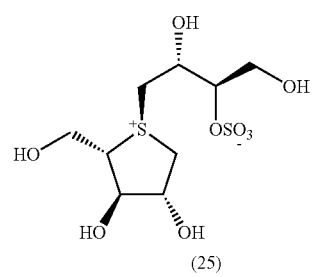

(25)

To reduce the number of synthetic steps, the inventors attempted the coupling reactions with the deprotected thio-arabinitols. Thus, the partially deprotected compound (11) was reacted with the cyclic sulfate (10) in acetone, to give compound (26) in 32% yield. Deprotection yielded Salacinol (1) in 36% yield (Scheme 10).

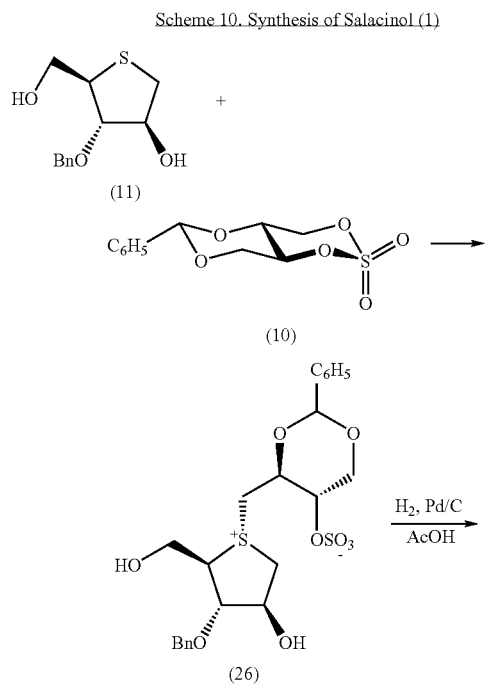
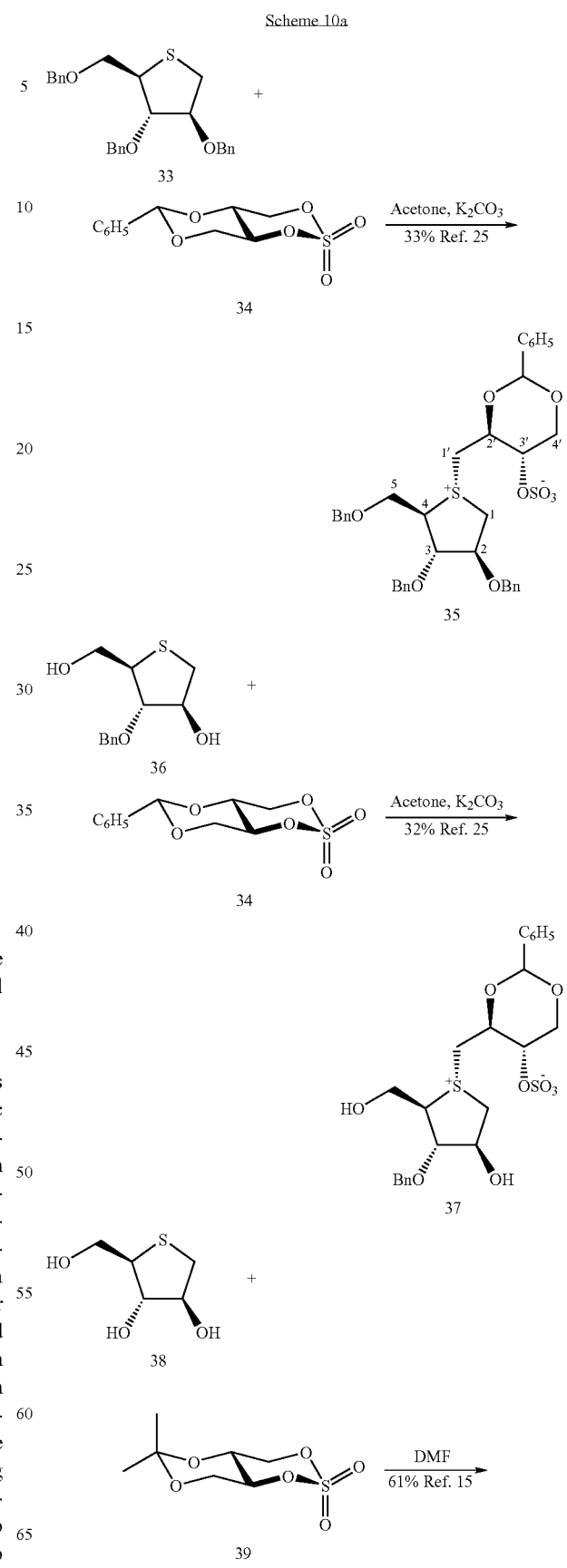

The fully-deprotected thio-arabinitol (13) was not soluble in acetone and the reaction in methanol produced several products.

3.1.1 Alternative Synthesis of Salacinol

As described above, a key step in the published syntheses of Salacinol (1)[15,25] is the ring opening reaction of a cyclic sulfate by nucleophilic attack of the ring sulfur atom of 1,4-anhydro-4-thio-D-pentitol (33) (Scheme 10a). The alkylation reaction involving these reagents is dependent on the protecting groups on the cyclic sulfate. Thus, the unoptimized reaction of the per-benzylated thioether 33 with the benzylidene-protected cyclic sulfate 34 in acetone, containing potassium carbonate, proceeded in 33% yield (Scheme 10a).[25] A similar yield was obtained in the reaction with the monobenzylated thioether 36.[25] Reaction of the unprotected thioether 38 with the isopropylidenated-cyclic sulfate 39 in DMF proceeded in 61% yield to give 40, although its reaction with the corresponding benzylated-cyclic sulfate 41 did not proceed.[15] The latter derivative 41 is clearly a much less reactive alkylating agent than 39. Significant decomposition of the cyclic sulfates 39 and 41 at temperatures of 60-70° C. in DMF was also observed.[15] Deprotection of 40 proceeded in 75% yield to afford Salacinol 1 in 46% overall yield.[15]

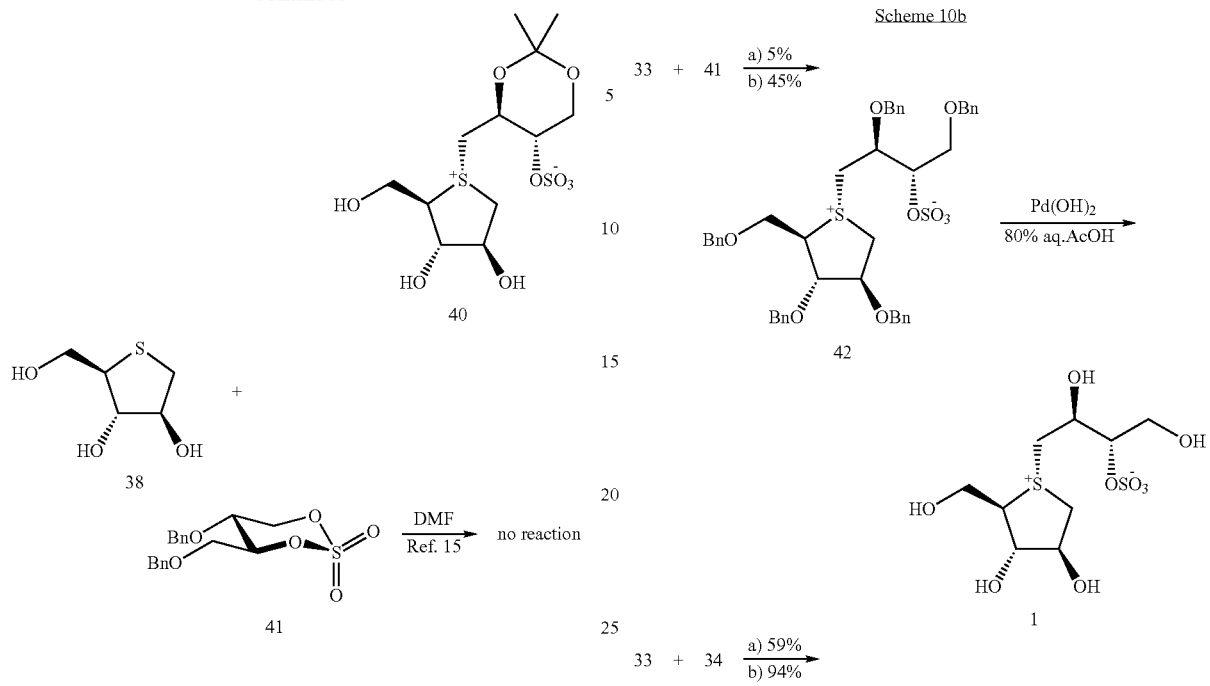

The biological importance of Salacinol (1)[1,2,27] prompted the inventors to investigate a more efficient method for its synthesis. The Hughes-Ingold rules indicate that the $S_N2$ reaction between a neutral nucleophile, such as 33 or 36, and a neutral electrophile, such as 34, 39 or 41, should show a large increase in rate on increasing solvent polarity. 1,1,1,3,3,3-Hexafluoroisopropanol (HFIP) has a higher normalized Dimnroth-Reichardt solvent polarity parameter, $E_T^N=1.068$, than water, $E_T^N=1.00$ In contrast, the $E_T^N$ values for acetone and DMF are only 0.355 and 0.404, respectively. Furthermore, HFIP, bp=59° C., is volatile, thus facilitating product purification. Preliminary studies indicated that tetrahydrothiophene reacted cleanly with 34 and 41 in HFIP at 45° C. for 2 days to give the desired alkylation products in >90% yield.

Therefore, a systematic evaluation of the role of solvent in the alkylation reactions of 33 with benzyl- or benzylidene-protected cyclic sulfates 41 or 34, respectively was undertaken. The reactions were carried out in acetone and hexafluoroisopropanol (HFIP) concurrently under identical conditions of concentration, temperature, and duration (Scheme 10b). Reaction of the thioether 33 (1 equiv) and the cyclic sulfate 41 (1.2 equiv) in acetone containing $K_2CO_3$ at 75-80° C. in a sealed tube proceeded very slowly and yielded the desired alkylated product 42 in only 5% yield; the remainder of the starting materials was recovered. Prolonged heating and use of excess cyclic sulfate did not improve the yields. In addition, when excess cyclic sulfate 39 was used, its slow decomposition complicated the purification of the product 42 formed. However, the analogous reaction between 33 and the cyclic sulfate 41 in HFIP yielded the adduct 42 in 45% yield, with recovery of the unreacted starting materials (Scheme 10b). It is noteworthy that the analogous reaction between 33 and the cyclic sulfate 41 in the polar, protic solvent 2-propanol at 83° C. for 26 h did not yield any desired product, the starting materials being recovered. It would appear, therefore, that it is the highly polar nature of HFIP that is important in facilitating this reaction.

Some studies[15] have indicated a far lesser reactivity of the benzylated cyclic sulfate relative to the cyclic sulfate containing an acetal protecting group (Scheme 10a). Thus, the reactions of the benzylidene-protected cyclic sulfate 34 in acetone and HFIP, containing potassium carbonate, under identical conditions of concentration, temperature, and duration were examined next (Scheme 10b). The alkylation reaction of 33 with 34 in acetone proceeded with a dramatic increase in the yield (59%) of the alkylated product 35 relative to the reaction with 41. The improvement from the unoptimized yield of 33%[25] is due to the use of a more concentrated reaction mixture.

More significantly, the desired product 35 was obtained in 94% yield when the reaction was performed in HFIP. Higher temperatures (>80° C.) and prolonged reaction times led to the decomposition of the cyclic sulfate, although the stability of the cyclic sulfate was greater in the presence of $K_2CO_3$. The increased yields in HFIP may be accounted for by better solvation of the transition states for the reactions and of the adducts. The increased reactivity of the cyclic sulfate with the benzylidene protecting group (34) may be accounted for by the relief of ring strain accompanying the reaction, unlike in the corresponding reaction of the benzyl-protected cyclic sulfate 41. Finally, the reaction of the thioether 38 (not containing protecting groups) with the benzylidene-protected cyclic sulfate 34 in HFIP was examined. At 60° C., decomposition of the cyclic sulfate was observed, with no significant formation of the desired coupled product. Hydrogenolysis of the protected derivatives 35[25] and 42 afforded Salacinol (1), although this step was problematic because of poisoning of the catalyst, and only afforded the product in 65% yield. The stereochemistry of Salacinol (1) shown in Scheme 10(b) is an equivalent representation to that shown on page 2 hereof.

In order to obviate the problematic hydrogenolysis step, the inventors next chose to examine the reaction of the thioether containing p-methoxybenzyl ether protecting groups with the benzylidene-protected L-erythritol-1,3-cyclic sulfate; the inventors reasoned that the removal of all protecting groups by acid hydrolysis would be facile. Thus, 2,3,5-tri-O-p-methoxybenzyl-1,4-anhydro-4-thio-D-arabinitol (43), synthesized in 87% yield from 38, was reacted with the cyclic sulfate 34 in HFIP to afford the sulfonium salt 44 in quantitative yield (Scheme 10c). Deprotection of 44 proceeded smoothly (86%) in aqueous trifluoroacetic acid to afford Salacinol 1 in 75% overall yield. The latter sequence represents, therefore, an efficient synthesis of the biologically important natural product Salacinol 1.

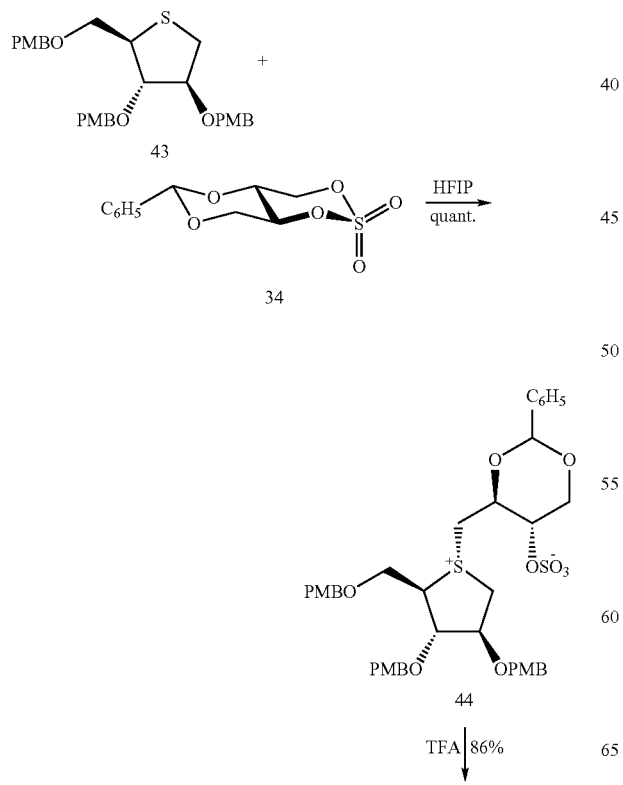

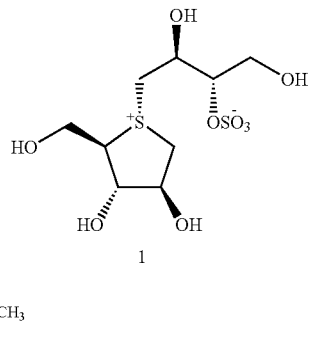

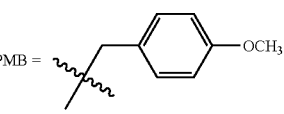

The inventors considered the stereochemistry at the stereogenic sulfonium center in 35, 42, and 13 and determined that these reactions proceeded stereoselectively irrespective of the solvent used in the reaction. The stereochemistry was confirmed by means of NOESY experiments that showed clear correlations between H-4 and H-1', thus indicating the presence of the isomer with a trans relationship between C-5 and C-1'. The barrier to inversion at the sulfonium ion center must be substantial since no evidence for isomerization in these and related derivatives[29] has been noted.

3.2 Synthesis of Selenium Analogues

The seleno-analogue intermediate (27) (R=$CH_2C_6H_5$) was made starting from the seleno-arabinitol (20) (R=$CH_2C_6H_5$) and the cyclic sulfate (10) in excellent yield 86% (Scheme 11), but NMR spectroscopy showed the presence of two isomers in a ratio of 7:1 that differed in stereochemistry at the stereogenic selenium center. The isomers were separable by analytical HPLC. The inventors have assigned the name "Blintol" to the new selenium analogue (3).

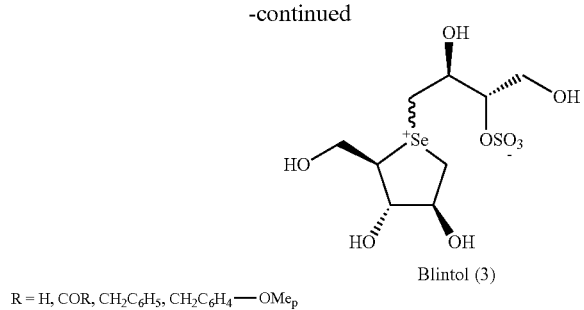

Blintol (3)

R = H, COR, CH$_2$C$_6$H$_5$, CH$_2$C$_6$H$_4$—OMe$_p$

The seleno-analogue intermediate (28) (R=CH$_2$C$_6$H$_5$) was made starting from the seleno-arabinitol (20) (R=CH$_2$C$_6$H$_5$) and the cyclic sulfate (7) in excellent yield 97% (Scheme 12); a mixture of two isomers in a ratio of 3:1 that differed in stereochemistry at the stereogenic selenium center was obtained. The isomers were separable by analytical HPLC.

Scheme 12. Synthesis of compound (29)

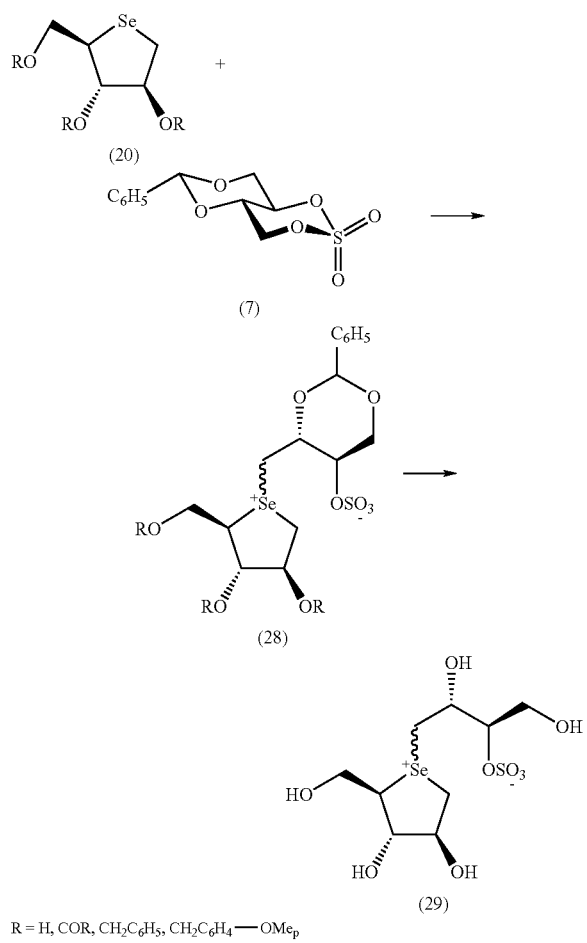

R = H, COR, CH$_2$C$_6$H$_5$, CH$_2$C$_6$H$_4$—OMe$_p$

Compound (29) is a diastereomer of Blintol (3).

3.2.1 Alternative Route to Synthesis of Blintol

Retrosynthetic analysis indicated that Blintol (3) could be obtained by alkylation of anhydroseleno-D-arabinitol (45) at the ring heteroatom using an appropriately protected cyclic sulfate (47) (Scheme 12a).[25]

Scheme 12a

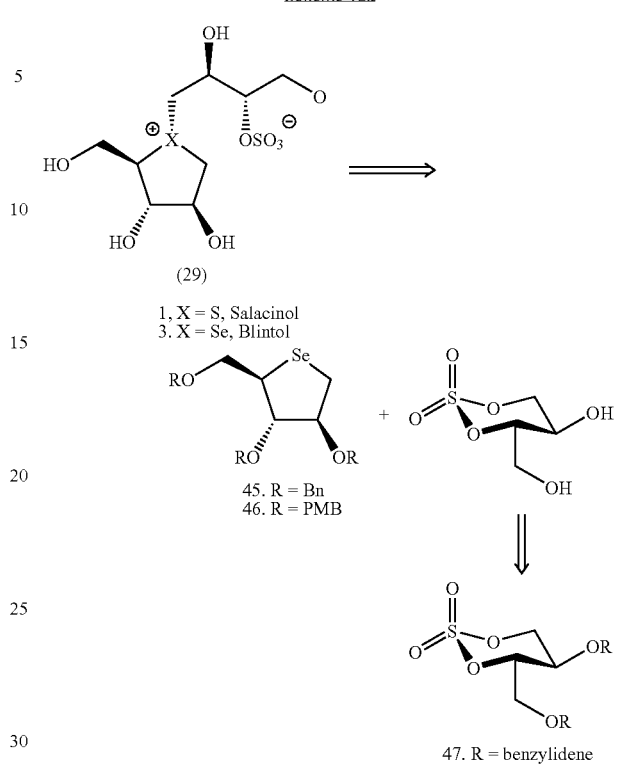

1, X = S, Salacinol
3, X = Se, Blintol

45. R = Bn
46. R = PMB

47. R = benzylidene

The previously discussed synthesis of Blintol (3) used benzyl ethers as the protecting groups for the hydroxyl groups on the anhydroseleno-D-arabinitol 45.[26] However, the deprotection of the benzyl-protected Blintol (3) by hydrogenolysis was problematic due to the poisoning of the palladium catalyst by small amounts of the selenoether 45 formed in the reaction mixture.

In order to eliminate the problematic hydrogenolysis step, the use of p-methoxybenzyl (PMB) protecting groups on the seleno-D-arabinitol, as in the inventors' optimized synthesis of Salacinol (1),[53] was considered. Thus, the reaction of the p-methoxybenzyl-protected selenoether 46 with the benzylidene-protected L-erythritol-1,3-cyclic sulfate (47; R=benzylidene) was examined. Since both PMB and benzylidene protecting groups are labile to acidic hydrolysis, the removal of all protecting groups by acid hydrolysis is facile.[53]

The synthesis of the PMB-protected anhydroseleno-D-arabinitol (45) from L-xylose (48) required the judicious choice of aglycon. Initial attempts to use the allyl glycosides yielded an inseparable mixture of the desired allyl xylofuranosides and undesired allyl xylopyranosides. Furthermore, the cleavage of the allyl group was judged to be too expensive a process for large-scale synthesis. Nevertheless, the mixture of furanosides and pyranosides was used in the successful synthesis of Blintol (3), their separation being effected at a later stage in the synthetic scheme.

These concerns led the inventors to explore the following strategy: 1) The use of n-pentenyl glycosides, first exploited by Fraser-Reid and coworkers;[54] this group was also reported to be cleaved by NBS without affecting the PMB groups,[55] and 2) The use of boric acid in the acid-catalyzed acetylation of L-xylose (48) to improve the furanoside to pyranoside ratio.[56] The latter procedure led to the conversion of L-xylose (48) to 1,2,3,5-tetra-O-acetyl-D-xylofuranose (49) in a two-step, one-pot procedure. Analysis of the $^1$H and $^{13}$C NMR spectra indicated that the furanosides 49 were formed exclusively without formation of the undesired pyranoside side products (Scheme 12b).

Scheme 12b

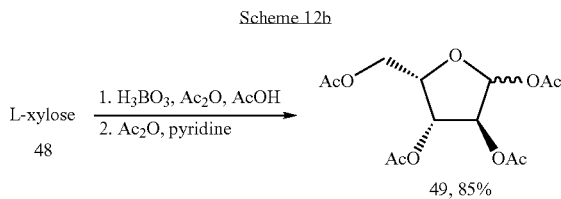 [SMILES: CC(=O)OC[C@@H]1OC(OC(C)=O)[C@@H](OC(C)=O)[C@@H]1OC(C)=O]

49, 85%

Compound 49 was then treated with 4-penten-1-ol and BF$_3$·OEt$_2$ to give the 4-pentenyl 2,3,5-tri-O-acetyl-L-xylo-furanosides (50).[57] This compound underwent acidic hydrolysis to cleave the acetyl groups, followed by the reprotection of the three hydroxyl groups with PMB groups, to afford the 4-pentenyl 2,3,5-tri-O-p-methoxybenzyl-L-xylo-furanosides (52). The anomeric hydroxyl group of 52 was then released using NBS in acetonitrile-water to yield the corresponding 2,3,5-tri-O-p-methoxybenzyl-L-xylofuranose (53) (Scheme 12c).

Scheme 12c

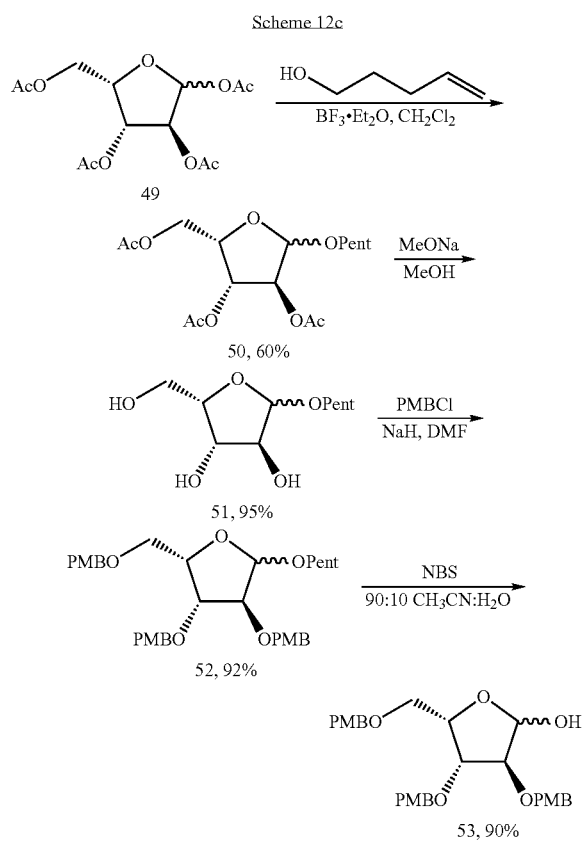

The 2,3,5-tri-O-p-methoxybenzyl-L-xylofuranose 53 was reduced to the corresponding xylitol 54 by NaBH$_4$; mesylation of the hydroxyl groups then gave the dimesylate 55. Compound 55 was then converted to the 1,4-anhydro-2,3,5-tri-O-p-methoxybenzyl-4-seleno-D-arabinitol (56) in 83% yield, using sodium selenide, generated in situ, from selenium metal and sodium borohydride in ethanol (Scheme 12d).

Scheme 12d

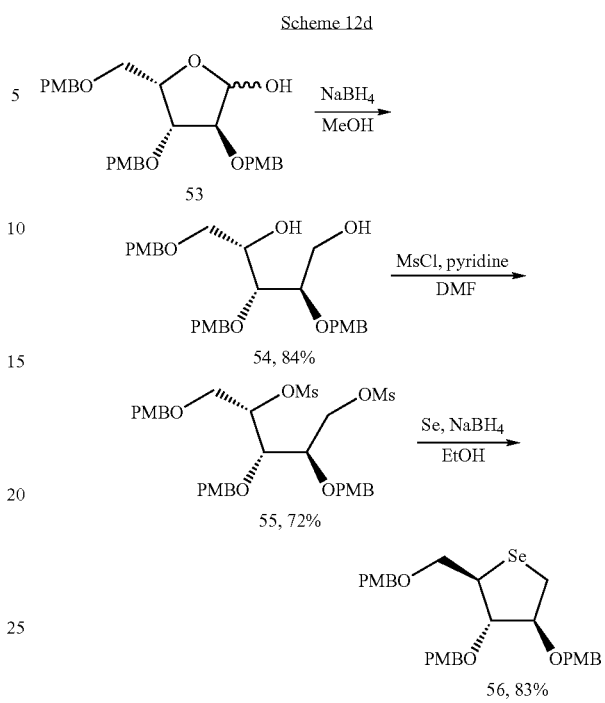

Another factor in the synthesis of Blintol (3) (and the optimized synthesis of Salacinol[53]) is the availability of 2,4-O-benzylidene-L-erythritol-1,3-cyclic sulfate (57). This compound was previously prepared from L-glucose.[25] However, due to the high cost of L-glucose and the fact that it was the starting material in a six-step synthetic route, it was desirable to prepare the cyclic sulfate (57) from a less expensive material. As described herein the inventors have successfully prepared the cyclic sulfate 57 from D-glucose (58).

Using the method developed by the inventors,[25,26] the benzyl-protected cyclic sulfate 62 was prepared from D-glucose (58). It is interesting to note that cleavage of the benzylidene protecting group in compound 59 was achieved with 60% TFA at room temperature for 30 min to afford the corresponding diol 60 in a comparable yield to that obtained with aqueous acetic acid. Since the original method involved refluxing compound 59 in 80% HOAc for 48 h, this modification proved to be more efficient. Compound 62 underwent hydrogenolysis to afford the unprotected cyclic sulfate 63. Installation of the benzylidene acetal using pyridinium p-toluenesulfonate (PPTS) as the catalyst was the important step since, under these conditions, the cyclic sulfate was not cleaved. The desired benzylidene-protected cyclic sulfate 57 was obtained in 71% yield (Scheme 12e).

Scheme 12e

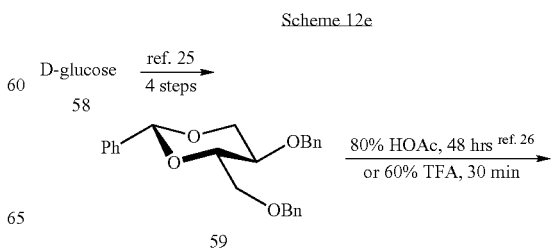

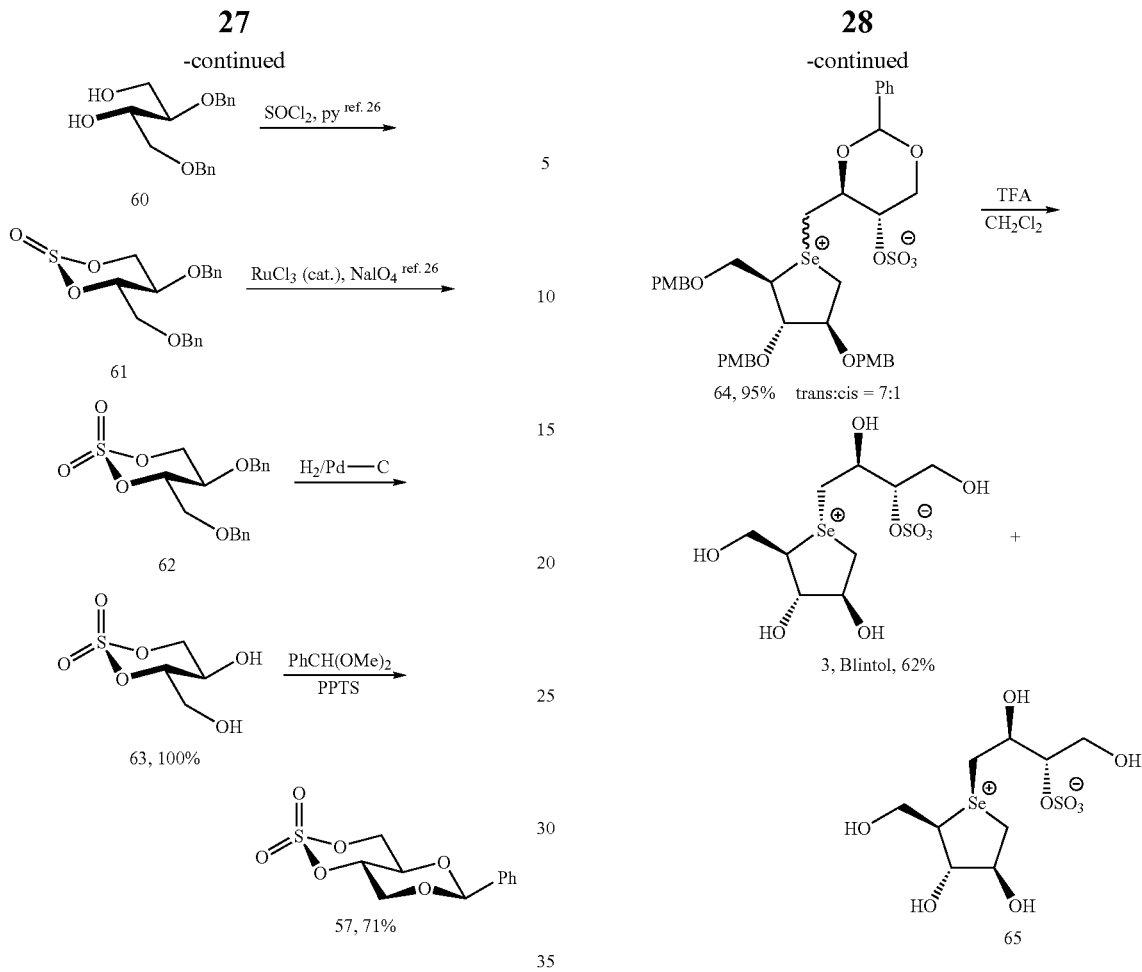

The coupling reaction of the anhydroseleno-D-arabinitol 56 with the cyclic sulfate 57 in 1,1,1,3,3,3-hexafluoro-2-propanol (HFIP) at 60-65° C. proceeded smoothly in 7 h, to give a mixture of the 2,3,5-tri-O-p-methoxybenzylselenonium salts 64 in 95% yield (Scheme 12f). Analysis of the $^1$H and $^{13}$C NMR spectra indicated that compound 64 was a 7:1 mixture of isomers at the stereogenic selenium center. The major isomer was assigned to that with a trans relationship between C-5 and C-1', by analogy with the results obtained previously.[26]

The selenonium salts 64 were subsequently deprotected by treatment with trifluoroacetic acid (TFA), and purified by recrystallization to afford pure Blintol (3) in 62% yield (Scheme 12f).

3.3 Synthesis of Nitrogen Analogues

The nitrogen analogue intermediate (30) was made by the reaction of the deprotected imino-arabinitol (19) with the cyclic sulfate (10) in a good yield 72% (Scheme 13). Compound (19) was not soluble in acetone so the reaction was performed in dry methanol. A side product (19%) which was identified to be the product of methanolysis of the cyclic sulfate was obtained. The inventors have assigned the name "Ghavamiol" to the new nitrogen analogue (2). Compound (30) was deprotected to give Ghavamiol (2) in 64% yield.

Scheme 13. Synthesis of Ghavamiol (2)

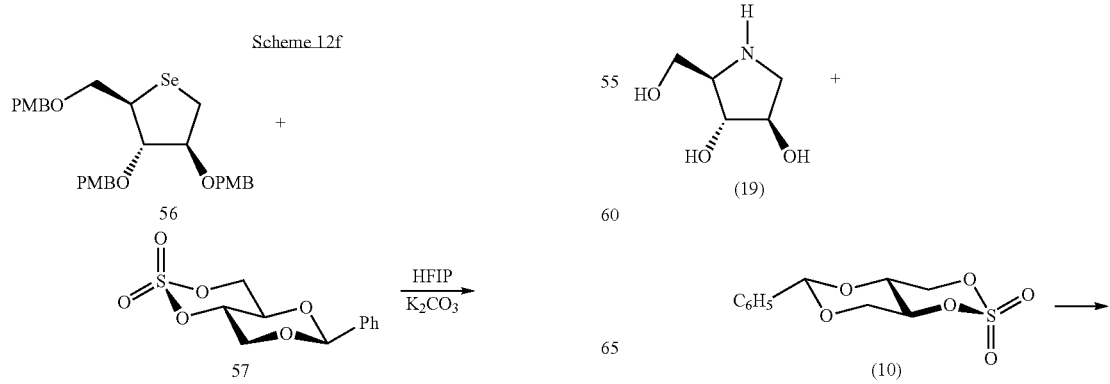

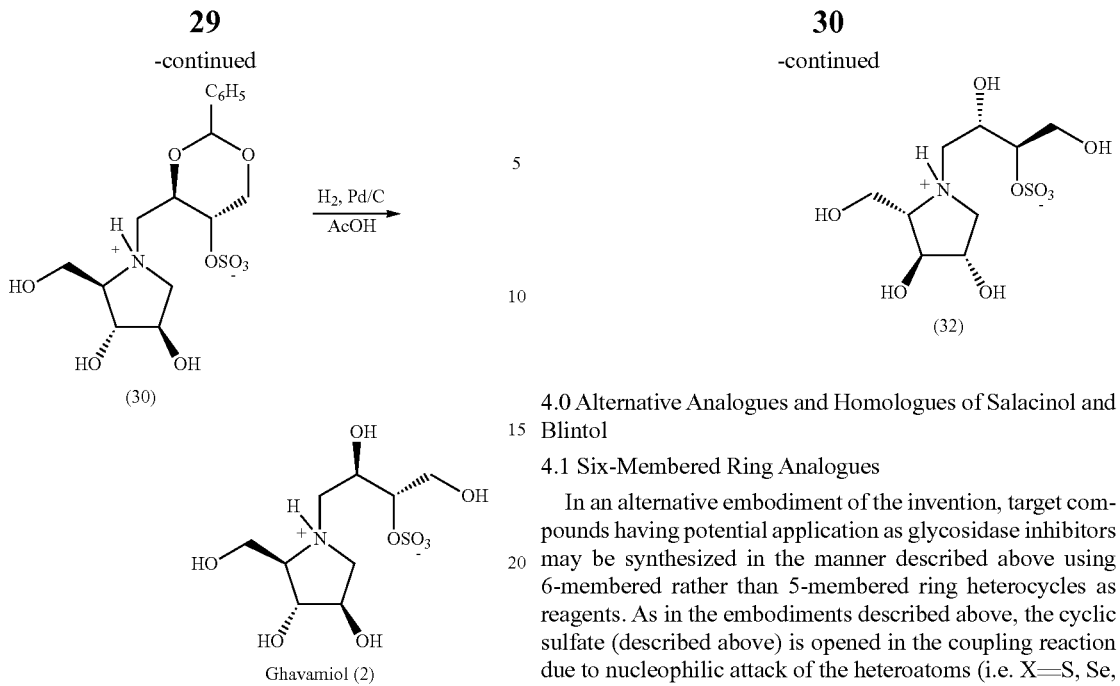

The enantiomer intermediate (31) was made by the reaction of the deprotected imino-arabinitol (16) with the cyclic sulfate (7) in a good yield 72% (Scheme 14). A side product (21%) which was identified to be the product of methanolysis of the cyclic sulfate was obtained. Compound (31) was deprotected to give compound (32) in 77% yield. Compound (32) is the enantiomer of Ghavamiol (2).

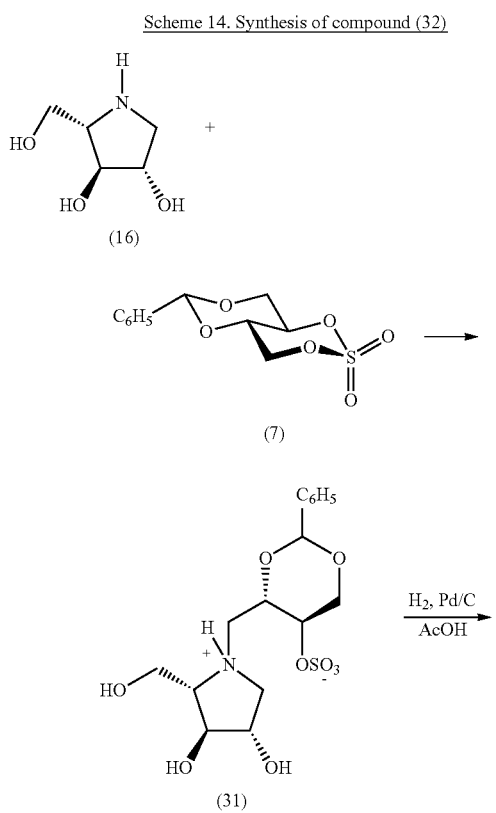

4.0 Alternative Analogues and Homologues of Salacinol and Blintol

4.1 Six-Membered Ring Analogues

In an alternative embodiment of the invention, target compounds having potential application as glycosidase inhibitors may be synthesized in the manner described above using 6-membered rather than 5-membered ring heterocycles as reagents. As in the embodiments described above, the cyclic sulfate (described above) is opened in the coupling reaction due to nucleophilic attack of the heteroatoms (i.e. X=S, Se, NH) on the ring sugars. As will be apparent to a person skilled in the art, the general formulas for the 6-membered sugar reagent and resulting target compound are as shown below.

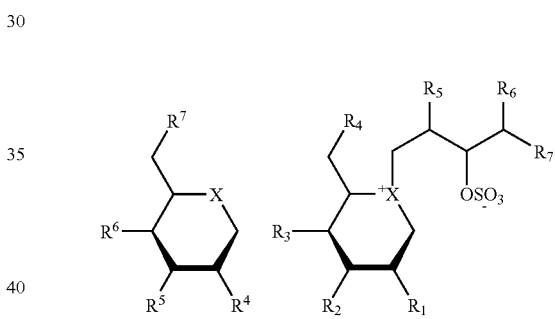

The 6-membered ring target compound shares the same internal salt structure as the 5-membered ring embodiment. The substituent groups may vary as described below without departing from the invention.

In particular, in order to expand the repertoire of molecules of this class that could serve as glycosidase inhibitors, the inventors proposed to synthesize N-alkylated 1,5-dideoxy-1,5-iminoxylitol (66a) and deoxynojirimycin (67a) having the same L-erythritol-derived, sulfated side-chain as Salacinol. The advantage of having an internal sulfate counterion for the ammonium salt was deemed to be worth pursuing in order to investigate whether such a structural modification would lead to increased in-vivo stability and/or membrane permeability. In addition, the internal sulfate salt and polar side-chain may provide cationic inhibitors that bind to glycosidase enzymes without deprotonating the catalytic active-site carboxylic acid and provide additional insight into the structural features that are important for inhibition. The inventors describe herein the syntheses of 66a and 67a as well as the corresponding sulfonium and selenonium analogues 68a, 69a and 70a. The inventors report also the syntheses of the corresponding enantiomers or diastereomers 66b-70b resulting from incorporation of a side chain derived from D-erythritol.

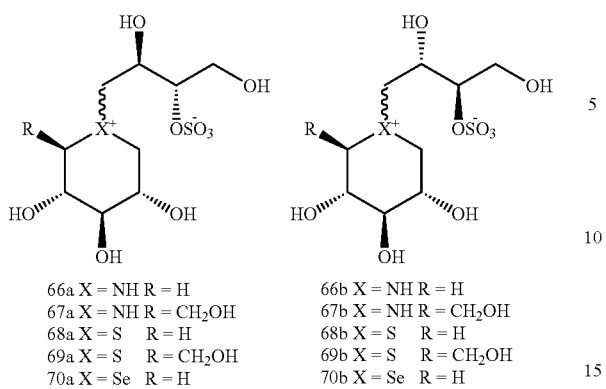

66a X = NH R = H
67a X = NH R = CH₂OH
68a X = S    R = H
69a X = S    R = CH₂OH
70a X = Se   R = H

66b X = NH R = H
67b X = NH R = CH₂OH
68b X = S    R = H
69b X = S    R = CH₂OH
70b X = Se   R = H

Each target six-membered ring compound was synthesized in two stereoisomeric forms (a or b) by using either of the enantiomeric forms of the cyclic sulfate 71a or 71b as the source of the sulfated alkyl side chain. In the case of compounds 66, 68, and 70 these stereoisomers are enantiomers while compounds 67 and 69 were prepared as either of two diastereomers. For the enantiomeric sulfonium salts 68a and 68b, R/S isomers at the stereogenic sulfonium-ion center were separated and characterized independently. Similar isomers for the sulfonium salts 69 and selenonium salt 70 were not separable by chromatography and the products were characterized as mixtures. In the case of the ammonium salts 66 and 67, inversion at the nitrogen center, via the free amine, was sufficiently fast in solution at room temperature that stereoisomers at the ammonium center were not observed.

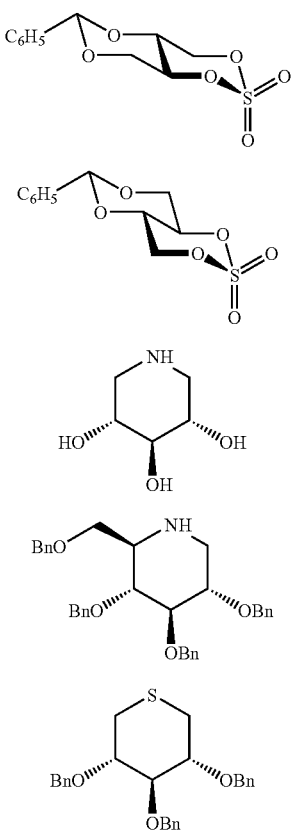

71a

71b

72

73

74

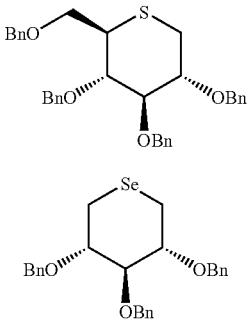

75

76

The general synthetic strategy (Scheme 15) involved alkylation of the piperidine (72 and 73), tetrahydrothiapyran (74 and 75), or tetrahydroselenapyran (76) heterocycles with either the 2,4-O-benzylidene-L-1,3-cyclic sulfate (71a),[16,53] derived from L-glucose, or its enantiomer (71b),[16,53] obtained from D-glucose. In general, the reactions with the less-expensive 71b were examined first. These methods are analogous to those described above used by the inventors to synthesize the five-membered ring analogues, Salacinol and its nitrogen or selenium congeners.[16,25,26,53,72]

Scheme 15

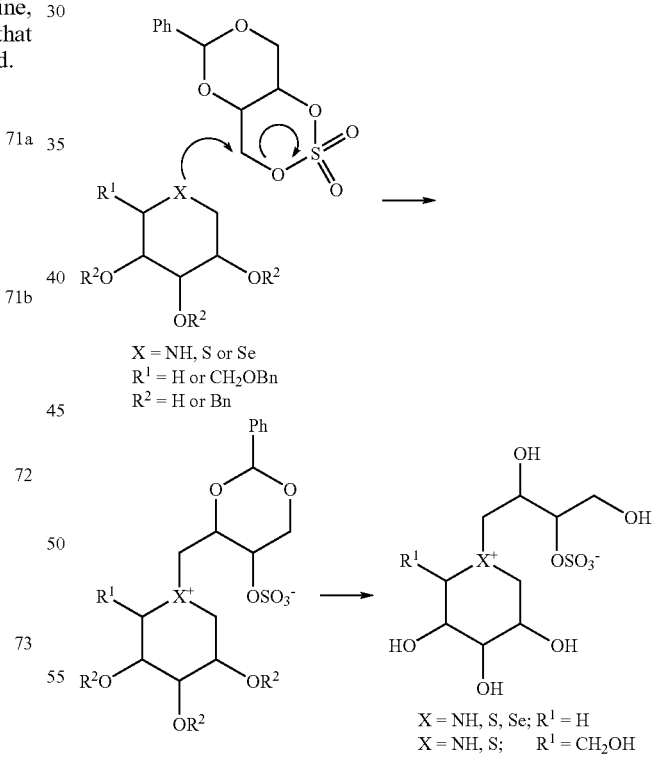

X = NH, S or Se
R¹ = H or CH₂OBn
R² = H or Bn

X = NH, S, Se; R¹ = H
X = NH, S;    R¹ = CH₂OH 4.1.1 Preparation of Starting Materials In preliminary experiments investigating the reactivity of the cyclic sulfate 71b, the inventors found that, for complex amine nucleophiles having only secondary alcohols as additional functional groups, protection of hydroxyl groups was unnecessary, but that any primary alcohol functional groups may be alkylated in competition with amines.

Scheme 16

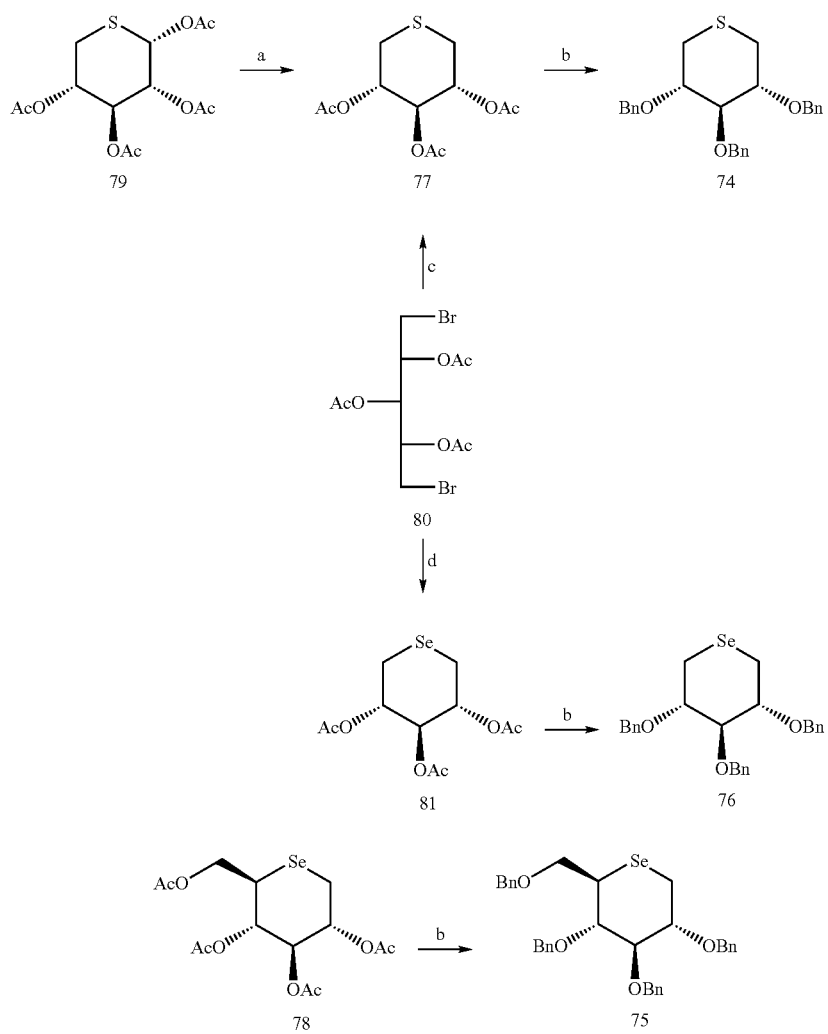

a. Et₃SiH, HOAc
b. i) NaOMe/MeOH; ii) BnBr/NaH/DMF
c. Na₂S/DMF
d. NaSeB(OEt)₃/EtOH

Accordingly, the unprotected anhydroxylitol imine (72) was prepared by the literature method[75] while deoxynojirimycin was prepared as its tetra-O-benzyl derivative (73).[73] The tetrahydrothiapyran derivative 74 was prepared (Scheme 16) by deacetylation and benzylation of the known tri-acetate 77.[75] The benzylated tetrahydrothiapyran 75 was similarly prepared from the known anhydro-5-thio-D-glucitol tetra-acetate (78)[28] by protecting group interchange. Compound 77 was obtained, in turn, either by reduction of tetra-O-acetyl-5-thio-D-xylopyranose (79)[39] or, more conveniently, from reaction of acetylated 1,5-dibromoxylitol (80) with sodium sulfide.[75] The selenium heterocyle 81 was prepared by substituting NaSeB(OEt)₃ (obtained in situ[77] by reduction of Se with NaBH₄/EtOH) for sodium sulfide in the reaction with acetylated 1,5-dibromoxylitol (80) (Scheme 16). Subsequent exchange of the acetates for benzyl protecting groups gave the desired tetrahydroselenapyran derivative 76, whose preparation has been reported by an unrelated method.[78]

4.1.2 Target Ammonium Compounds

Compound 72 was reacted with the D-cyclic sulfate 71b in MeOH containing K₂CO₃ (Scheme 17). Isolation of the more polar product gave the ammonium salt 84 in 43% yield. An abundant side-product (83) resulting from opening of the cyclic sulfate by the methanol solvent could be isolated from the early chromatographic fractions. A similar reaction with the L-cyclic sulfate 71a gave somewhat less of this side product and the desired coupled product 82 was obtained in slightly higher yield (56%). The $^1$H NMR spectra of compounds 82 and 84 exhibited sharp resonances for methylene groups a to the amine in D₂O (made basic with K₂CO₃), but neutral or acidic D₂O solutions gave downfield shifts and much broader resonances for these methylene resonances. The inventors attribute these observations to exchange, at an intermediate rate relative to the chemical-shift NMR time scale, of the conjugate-acid R/S ammonium salts, with nitrogen inversion taking place via the free amines that exist in equilibrium with their conjugate acids at acidic pH.

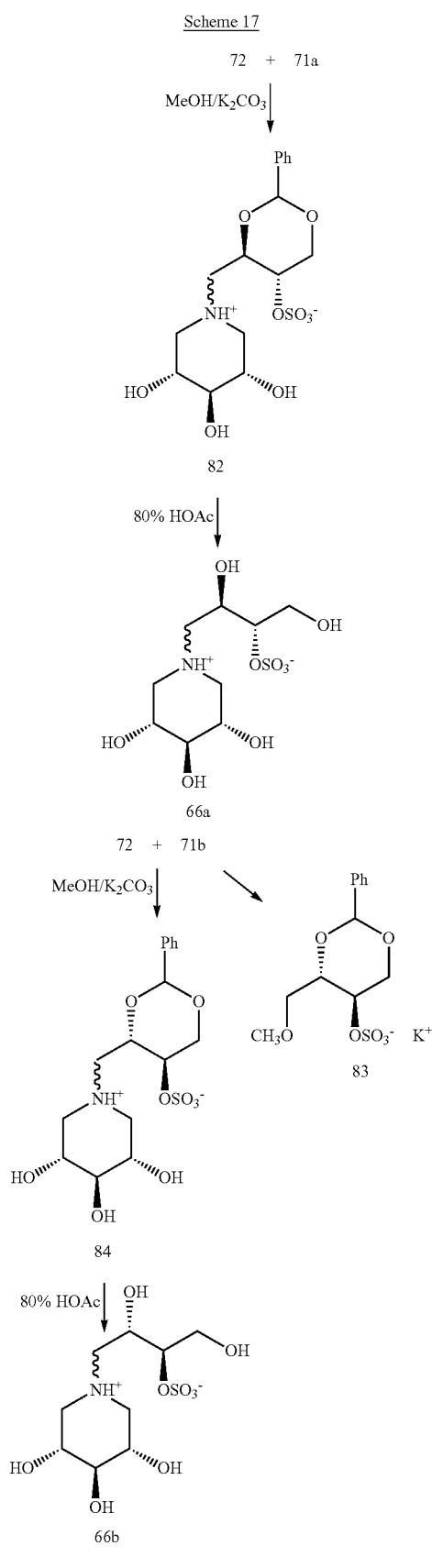

Scheme 17

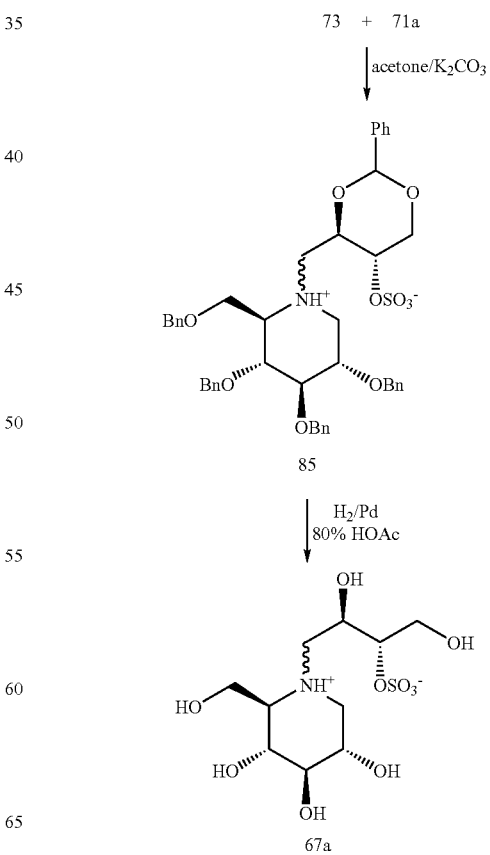

Scheme 18

Removal of the benzylidene protecting groups by hydrolysis in aqueous acetic acid gave the target compounds 66a (73%) and 66b (72%) after purification by chromatography on silica gel. These ammonium salts gave severely exchange-broadened NMR spectra and were more productively characterized by adding base to the NMR samples to produce the conjugate amine bases. Prolonged treatment with strong base should be avoided, however, due to the possibility of sulfate ester hydrolysis, as noted below. As expected for enantiomers, the NMR data for 66a and 66b were virtually identical although small differences in chemical shifts between different samples for both identical and enantiomeric compounds were noted. These differences were attributed to the concentration and temperature dependence of the NMR chemical shifts between samples. The tendency of zwitterionic compounds to exist as aggregates in solution is the likely origin of these effects.

The coupled products 85 and 86, derived from the benzyl-protected deoxynojirimycin, were obtained by reaction of compound 73 with the cyclic sulfates 71a and 71b in acetone/$K_2CO_3$ in yields of 80% and 65%, respectively (Scheme 18). The $^1$H NMR resonances for compounds 85 and 86 were extremely broad in $CDCl_3$ but sharpened in $CD_3OD$ (made basic with NaOD), thus indicating that the coupled products were obtained as an equilibrating mixture of the desired ammonium salts with the corresponding conjugate bases. Simultaneous removal of both the benzyl and benzylidene protecting groups was achieved by hydrogenolysis in aqueous acetic acid to give the target compounds 67a and 67b.

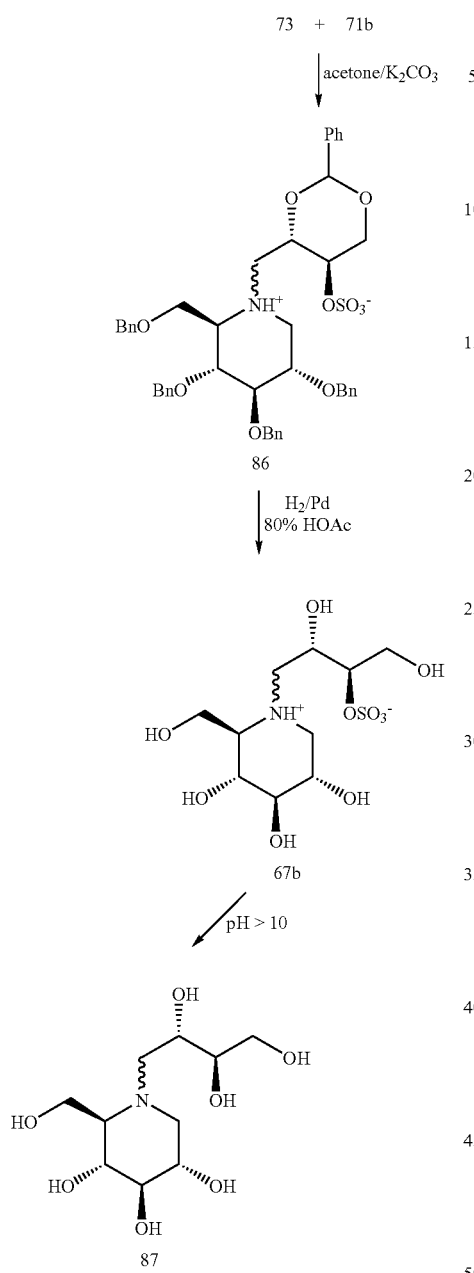

piperidine ring was $^4C_1$ (carbohydrate numbering) and that this conformational preference did not appear to change upon protonation (pH<3). Similar conclusions were reached in a previous conformational study of alkylated deoxynojirimycin derivatives.[74]

4.1.3 Target Sulfonium Compounds

The syntheses of sulfonium salts 68 and 69 (Schemes 19 and 20) were achieved in a similar fashion to those of the ammonium salts. Thus, compound 74 was initially reacted with the D-cyclic sulfate 71b in acetone at 65° C. Slow formation of two more polar products was observed by TLC analysis. Isolation of the mixture of products gave 88b and 89b in approximately 37% yield. On changing the solvent to 1,1,1,3,3,3-hexafluoro-2-propanol (HFIP), the yield improved to 87%. The dramatically beneficial effect of HFIP solvent on the yields for sulfonium salt formation has been noted above. The ratio of the major product 88b to the minor product 89b was 2:1. Pure samples of the two components were obtained by chromatography and characterized separately by NMR techniques.

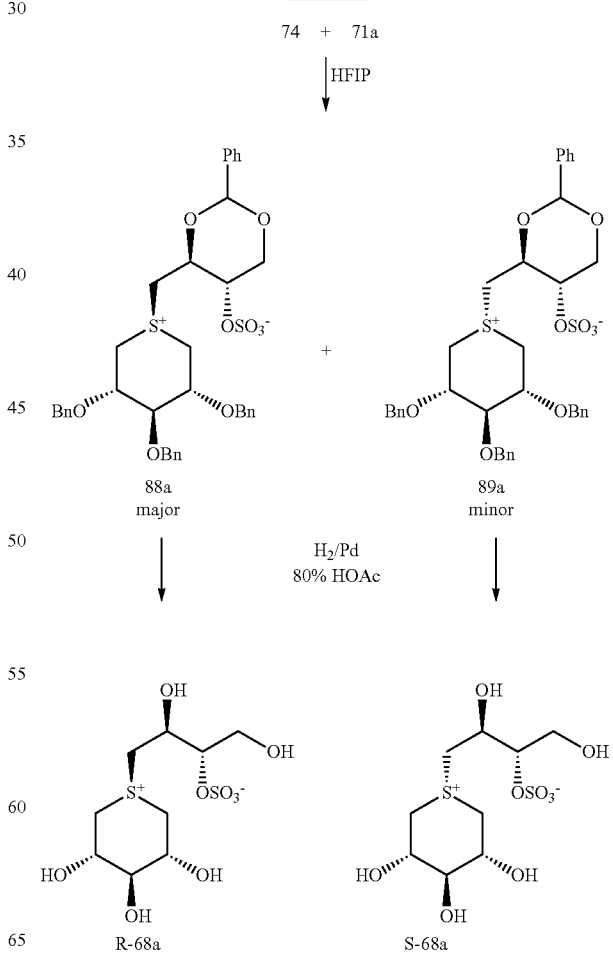

Analysis by $^1$H NMR spectroscopy indicated that these products were contaminated by KOAc. Nevertheless, other than a resonance at δ1.8 in the spectrum that was attributed to the acetate impurity, the target compounds were essentially pure and all resonances in both the $^1$H and $^{13}$C spectra were assigned by two-dimensional techniques. Prolonged storage of the NMR sample of compound 67b in $D_2O$/NaOD at pH>10 produced a slow loss of the 3'-sulfate group as evidenced by an upfield shift of the H-3' resonance. After 2 days at ambient temperature the sulfate ester had been completely hydrolyzed to yield cleanly the tertiary amine compound 87 and inorganic sulfate salts.

The $^1$H NMR data for all of the amine compounds in $D_2O$ (pH>8) indicated that the predominant conformation of the -continued 74 + 71b

↓ HFIP

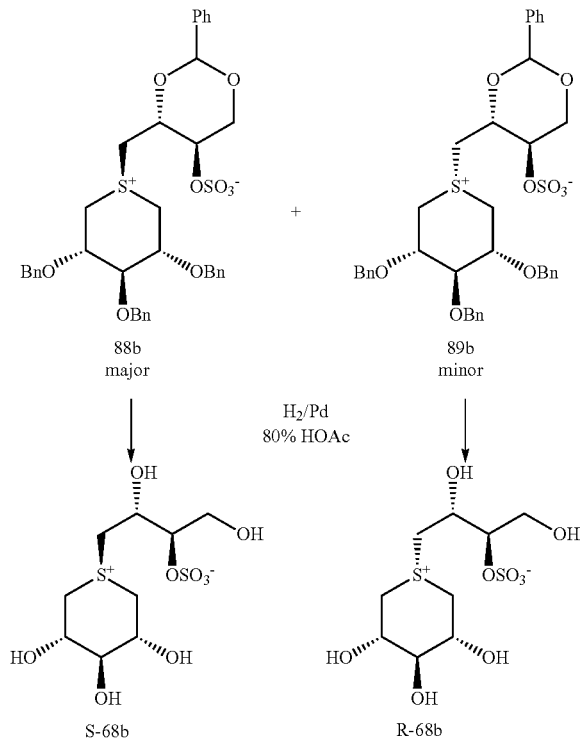

| 88b | 89b |
| major | minor |

↓ H₂/Pd
80% HOAc

S-68b          R-68b

Initially, 1D $^1$H NMR spectra were obtained which revealed that the two compounds were isomers, having the same number of hydrogen atoms. The similarity of the spectra of the two compounds suggested that the compounds differed in stereochemistry only at the stereogenic sulfur atom. COSY spectra permitted the assignment of the proton signals for the tetrahydrothiapyran ring and for the erythritol side chain in both compounds. Notably, it was found that all of the ring proton signals were shifted downfield relative to the parent tetrahydrothiapyran 17. This was anticipated since the positive sulfonium center is electron withdrawing. Furthermore, although it was initially expected that the three benzyloxy groups at C-2, C-3 and C-4 would favor the sterically less-hindered equatorial positions, analysis of vicinal coupling constants showed that $J_{2,3}$ and $J_{3,4}$=3.5-3.9 Hz. These values are much smaller than those ($J_{2,3} \approx J_{3,4} \neq 8.9$ Hz) observed for the axial-axial vicinal coupling constants in the precursor 17. Thus, the inventors reasoned that compounds 88b and 89b preferred a $^1C_4$ conformation, placing the three benzyloxy groups in axial positions and accounting for the small vicinal coupling constants. This conformational preference can be explained by the fact that the axial substituents at C-2 and C-4 provide stabilizing gauche electrostatic interactions of the polar benzyloxy groups with the sulfonium ion center; the group at C-3 can also provide stabilizing electrostatic interactions.[28] The results are reminiscent of the inventors' previous work with the sulfonium analogue of castanospermine.[28]

The configuration at the sulfonium center was next established by means of a NOESY experiment. The NOESY spectrum for the major diastereomer showed H-1b' correlations to H-1ax/H-1eq/H-5ax as well as H-1a' and correlations to H-5eq/H-5ax. This isomer was thus assigned to structure 88b with the erythritol side chain occupying the equatorial orientation. The absolute configuration at sulfur was thus established as being S.

The NOESY spectrum for the minor diastereomer showed a correlation between H-1a' and the isochronous signal assigned to H-1ax/H-1 eq, as well as a correlation between H-1b' and H-5eq. No correlation with H-5ax was observed. This isomer was thus assigned to structure 89b, the diastereomer with the erythritol side chain in an axial orientation. The absolute configuration at sulfur was thus established as being R. Each of the diastereomers 88b and 89b was deprotected by hydrogenolysis to give sulfonium salts S-68b and R-68b, which were obtained in 81 and 95% yields, respectively. Vicinal coupling constants indicated that deprotection was accompanied in both cases by a change in the preponderant ring conformation from $^1C_4$ to $^4C_1$ (S-68b $J_{2,3} \approx J_{3,4} \approx 7.2$ Hz, R-68b $J_{2,3} \approx J_{3,4} \approx 9.0$ Hz). Transient one-dimensional nuclear Overhauser enhancement (NOE) difference experiments confirmed that there was no configurational inversion at the sulfonium center upon removal of the benzyl and benzylidene protecting groups. Thus, the major isomer S-68b, upon irradiation of the H-4'b/H-1'a multiplet showed no NOE with the ring axial protons (FIG. 1). Irradiation of H-1ax/H-5ax showed NOEs on the H-1eq/H-5 eq/H-3 and H-2/H-4 multiplets only. No NOEs with the erythritol side chain protons were observed. These experiments provide evidence for the erythritol side chain occupying the axial position at sulfur, on the β-face and opposite to H-1ax., and confirm the S configuration at the sulfonium center for the major isomer S-68b, as was previously assigned for the protected precursor 88b.

Preferred conformations of 88b, 89b, S-68b and R-68b

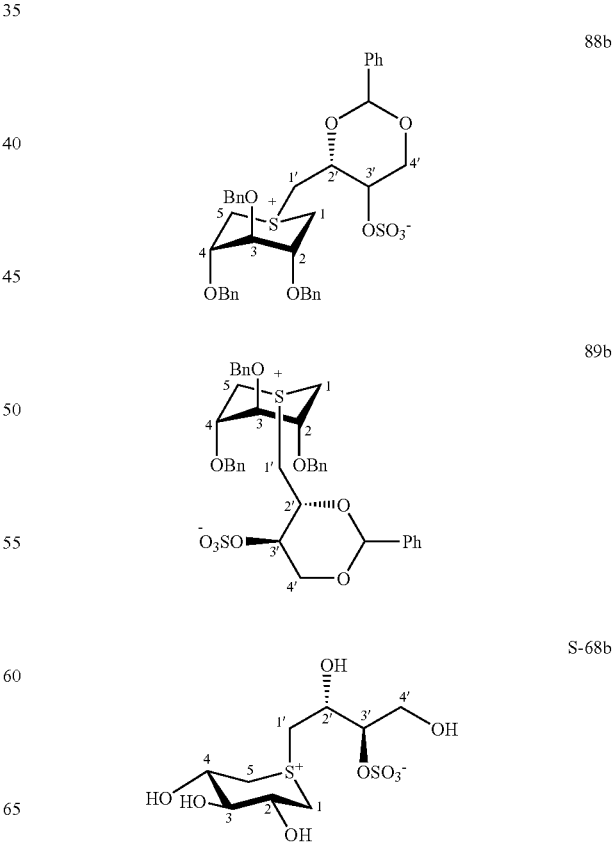

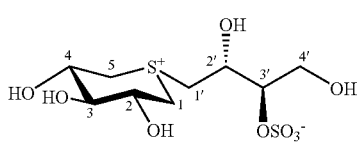

R-68b

Figure 2:
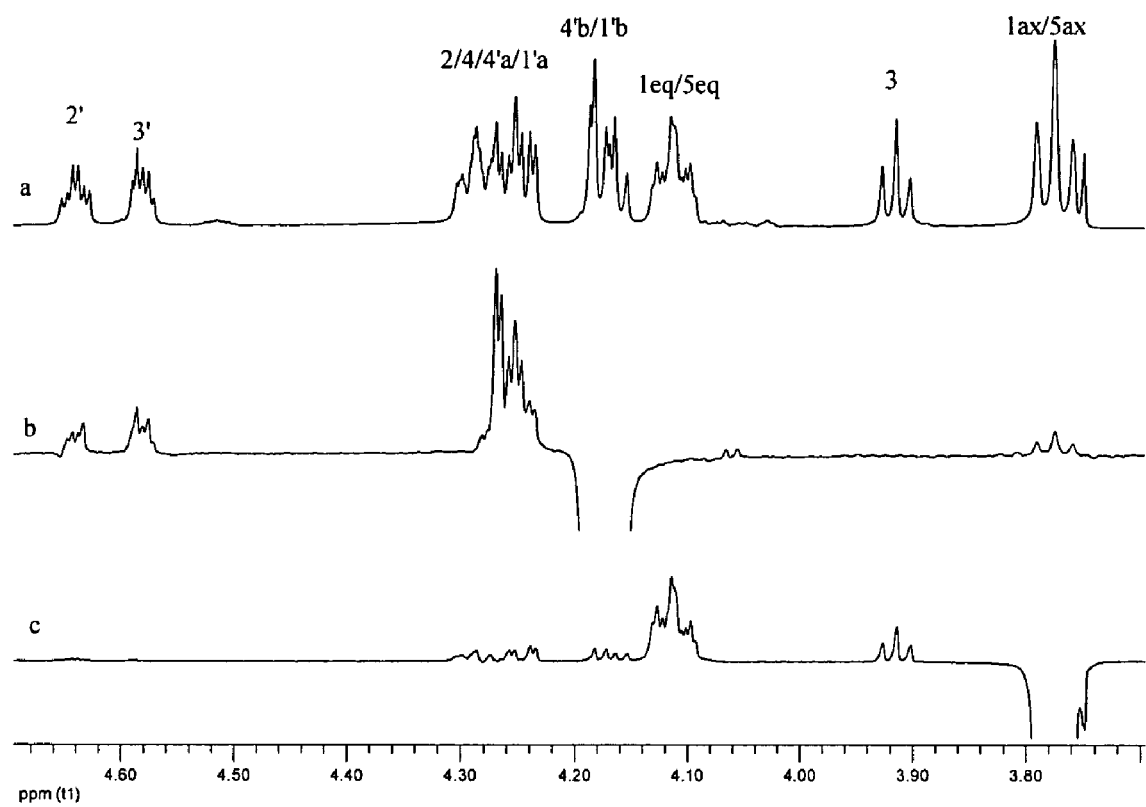
FIG. 2 depicts one dimensional transient NOE difference spectra of compound R-68b in $D_2O$. (a) $^1H$ NMR spectrum. (b) Spectrum with selective irradiation of the H-4'b/H-1'b multiplet. (c) Spectrum with selective irradiation of the H-1ax/H-5ax multiplet.

The minor isomer R-68b showed, upon irradiation of the H-4′b/H-1′b multiplet, NOE with the H-1ax/H-5ax protons (FIG. 2). Irradiation of the H-1ax/H-5ax multiplet showed NOEs with the H-4′b/H-1′b multiplet as well as to the H-2/H-4/H-4′a/H-1′a multiplet, in addition to NOEs to the ring protons. These experiments provide evidence for the erythritol side chain being present on the same face as H-1ax, occupying the α-equatorial position at sulfur, thus confirming the R configuration of the minor isomer R-68b at the sulfonium center, as was previously assigned for the protected precursor 89b.

The synthesis of the sulfonium salts from the L-cyclic sulfate 71a was examined next (Scheme 19). Compound 74 was reacted with 71a at 70° C. in HFIP solvent to give two products 88a and 89a in a 5:2 ratio (84% yield). The major diastereoisomer 88a, in which the erythritol side chain is cis to the C-3 benzyloxy group, was separated from the minor diastereoisomer 89a, with the erythritol side chain trans to the C-3 benzyloxy group. The $^1$H NMR spectra were virtually identical to those of the enantiomers 88b and 89b except for small variations due to concentration, as noted above. Each of the diastereomers 88a and 89a was deprotected via hydrogenolysis to give the target compounds R-68a and S-68a.

Entry into the 5-thio-D-glucitol analogues began by treatment of 1,5-anhydro-2,3,4,6-tetra-O-benzyl-5-thio-D-glucitol 75 with the D-cyclic sulfate 71b. The reaction afforded an inseparable mixture of compounds 90b and 91b with an approximate 2:1 isomer ratio in 70% yield (Scheme 20). As in the xylitol series, the protected glucitol derivative 90b displayed an unusual $^1C_4$ conformational preference, as indicated by the coupling constants. This places the three benzyloxy groups at C-2, C-3 and C-4 as well as the benzyloxymethyl group at C-5 in an axial orientation.

Scheme 20

75 + 71a

↓ HFIP

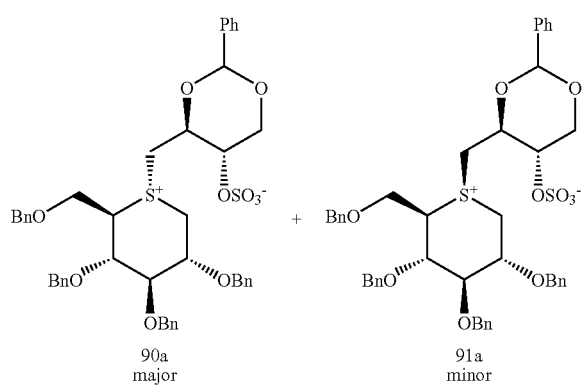

90a major + 91a minor

↓ H₂/Pd
80% HOAc

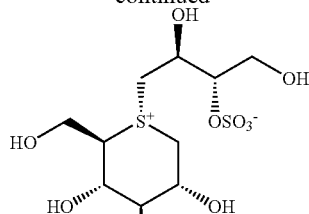

69a

75 + 71b

↓ HFIP

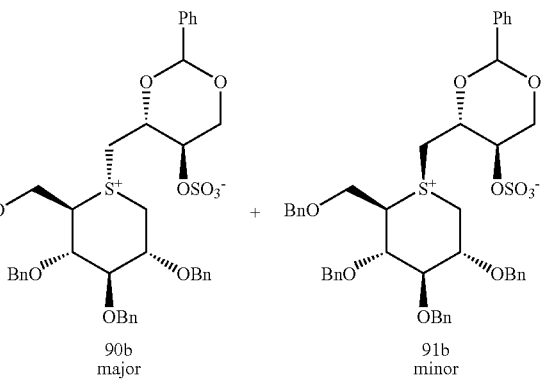

90b major + 91b minor

↓ H₂/Pd
80% HOAc

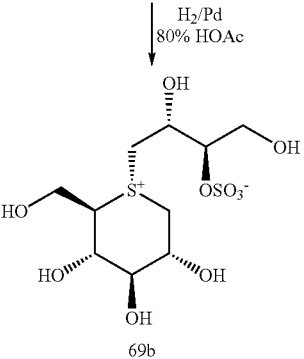

69b

The stereochemistry at the stereogenic sulfonium center for the major isomer 90b was established by means of a NOESY experiment. A strong NOESY correlation was observed between the H-1b′ proton and the H-5 proton, thus confirming that the benzylidene-protected erythritol side chain was cis to H-5. NOEs to H-1ax and to H-6a/H-6b were not observed. Thus, the absolute configuration at the sulfonium center in the major isomer was S. Alkylation of the sulfur must occur preferentially from the α-face of 1,5-anhydro-2,3,4,6-tetra-O-benzyl-5-thio-D-glucitol 75 due to shielding of the β-face by the adjacent C-5 benzyloxymethyl group.

The mixture consisting of compounds 90b and 91b was then subjected to hydrogenolysis to give primarily 1,5-dideoxy-1,5-[[(2R,3R)-2,4-dihydroxy-3-(sulfooxy)-butyl]-episulfoniumylidene]-D-glucitol inner salt S-69b in 81% yield (Scheme 20). Treatment of 1,5-anhydro-2,3,4,6-tetra-O-benzyl-5-thio-D-glucitol (75) with the L-cyclic sulfate 71a afforded an inseparable mixture of compounds 90a and 91a with an approximate 3:1 isomer ratio in 68% yield (Scheme 20). Whereas the achiral anhydroxylitol compound 74 generated enantiomers upon reaction with the enantiomeric D- and L-cyclic sulfates, this was not the case for the chiral compound 75. For this reaction, the products 90a and 90b are diastereomers rather than enantiomers.

The stereochemistry at the stereogenic sulfonium center for the major isomer 90a was again established by means of a NOESY experiment. A strong NOE correlation was observed between the H-1'a proton and H-5. In addition, there was also an NOE correlation between H-2' and H-5, confirming that the benzylidene protected erythritol side chain was on the same side as H-5. NOEs to H-1ax and to H-6a/H-6b were not observed. Thus, the absolute configuration at the sulfonium center for compound 90a was R; that is, the same stereochemistry at sulfur previously found for the diastereoisomer 90b. (Note: The change in R/S configuration between 90a and 90b due to sequence rules does not imply a change in stereochemistry at sulfur in this case). Therefore, independent of the configuration (71a or 71b) of the cyclic sulfate reagent, in both cases, alkylation at sulfur occurred preferentially from the least hindered β-face of compound 75.

The mixture containing 90a and 91a was then subjected to hydrogenolysis to give primarily 1,5-dideoxy-1,5-[[(2R,3R)-2,4-dihydroxy-3-(sulfooxy)-butyl]-R-episulfonium-ylidene]-D-glucitol inner salt R-69a in 67% yield (Scheme 20).

Upon removal of the protecting groups, compounds R-69a and S-69b adopted a $^4C_1$ conformation, as indicated by the vicinal proton coupling constants. This places all of the ring substituents in an equatorial orientation, as observed for the xylitol series.

4.1.4 Target Selenonium Compounds

The tetrahydroselenapyran 76 was coupled to the D-cyclic sulfate 71b in HFIP solvent and afforded an inseparable mixture of two compounds, 92b and 93b in a 1:4 ratio in 96% yield (Scheme 21). These two compounds are diastereoisomers at the stereogenic selenium center. Alkylation can occur on selenium to give, as with sulfur, the benzylidene protected erythritol side chain either cis to the C-3 benzyloxy group or trans to the C-3 benzyloxy group. It was found by comparison of the NMR data to those of the sulfonium analogues 88b/89b, and by analysis of the NOESY spectrum (see below), that the major product, 93b, was that in which the benzylidene-protected erythritol side chain was trans to the benzyloxy group at C-3. The minor product, 92b, was that in which the benzylidene protected erythritol side chain was cis to the C-3 benzyloxy group. Curiously, the ratio was opposite to the results obtained with the tetrahydrothiapyran products 88b and 89b for which the major isomer was the cis isomer. The predominant conformations observed in both compounds 92b and 93b were, as with the corresponding thio analogues, those which placed all three benzyloxy groups in an axial arrangement, thus favoring $^1C_4$ conformations, as evidenced by the coupling constants. The major isomer 93b in its preferred $^1C_4$ conformation places the selenonium alkyl group in the axial position. The longer C—Se bonds in compounds 92b/93b compared to the thio analogues must result in less severe gauche steric interactions between the selenonium alkyl group and C-2 and C-4.

The mixture consisting of compounds 92b and 93b was then deprotected via hydrogenolysis to give mostly one diastereoisomer of 70b, in 39% yield (Scheme 21). The low yield was due to catalyst poisoning by decomposition products and the reaction could not be brought to completion. This major compound was characterized by NMR techniques and found to be 1,5-dideoxy-1,5-[[(2R,3R)-2,4-dihydroxy-3-(sulfooxy)-butyl]-R-episelenoniumylidene]-xylitol inner salt R-70b.

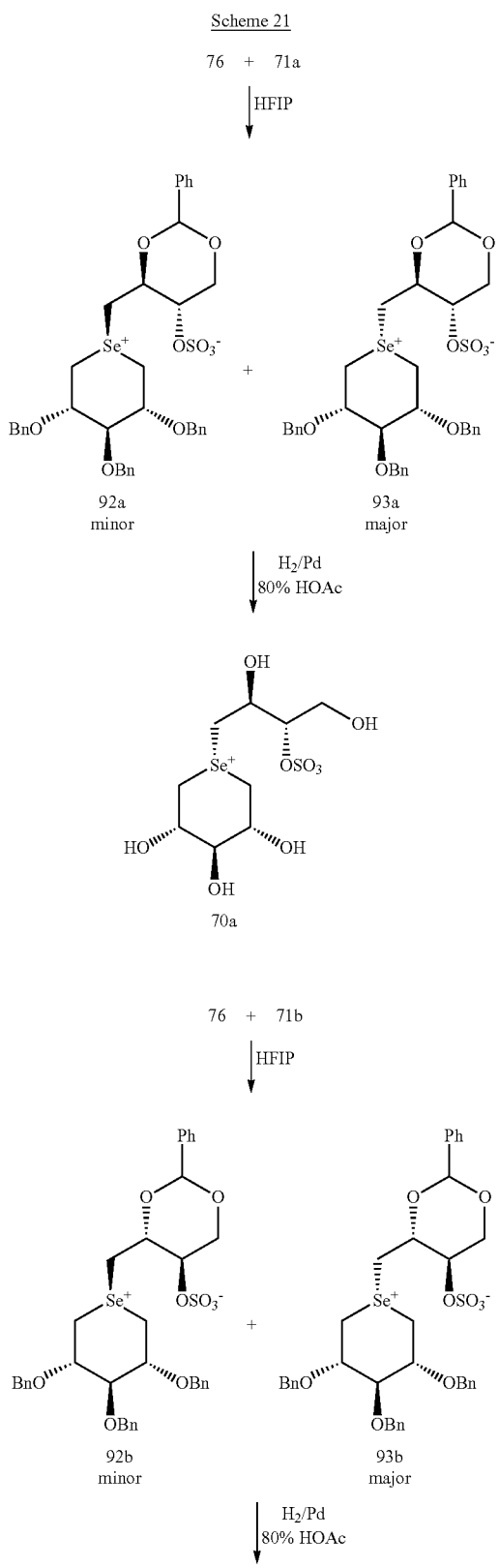

Scheme 21

-continued

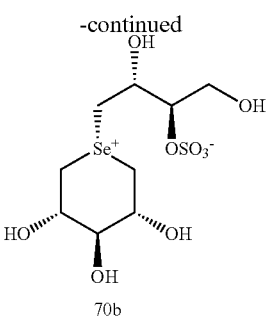

70b

Reaction of the selenoether 76 with the L-cyclic sulfate 71a was also performed. The product was an inseparable mixture of two diastereoisomers at the stereogenic selenium center, 92a and 93a, in a 1:3 ratio. (Scheme 21).

The configuration at the stereogenic selenonium centers for the enantiomers 93a and 93b was confirmed by means of NOESY experiments performed on the mixtures of the compounds containing their minor diastereomers. The major isomer in each case was found to be that in which the erythritol side chain occupied the axial position in the preferred $^1C_4$ conformation. This was evidenced by correlations between H-1b' and H-5 eq as well as correlations between H-1'a and H-1 eq. An axial preference would imply correlations between H-1'a/H-1'b and H-5 eq, and H-1'a/H-1'b and H-1eq only, since free rotation about the C-1'-Se bond would not permit the H-1'a and H-1'b protons to interact with the axial C-1 and C-5 protons as these are on the opposite side of the selenoether ring. Therefore, NOEs would not be expected between H-1'a/H-1'b and H-1ax/H-1eq. On the other hand, an equatorial preference would imply correlations between H-1'a/H-1'b to H-1ax and H-5ax as well as possibly to H-1eq and H-5 eq. Thus, for compound 93b the absolute configuration at the selenium center is R and that for the enantiomeric 93a is S. In both cases, the erythritol side chain is cis to the benzyloxy groups at C-2 and C-4 and trans to the C-3 benzyloxy group.

The mixture consisting of 92a and 93a was then deprotected by hydrogenolysis to afford mostly one diastereoisomer of 70a in 25% yield (Scheme 21). The major compound was characterized by NMR techniques and found to be the desired 1,5-dideoxy-1,5-[[(2S,3S)-2,4-dihydroxy-3-(sulfooxy)-butyl]-S-episelenoniumylidene]-xylitol inner salt S-70a, the enantiomer of compound R-70b.

4.2 Chain Extended Homologues of Salacinol

The synthesis of Salacinol and some of its enantio- and diastereoisomers is described above. In addition, the inventors have developed a strategy for synthesizing Salacinol homologues having an extended alditol side chain. In one embodiment, the side chain may have 5 or 6 carbons. Four salcinol homologues 94-97 are shown below.

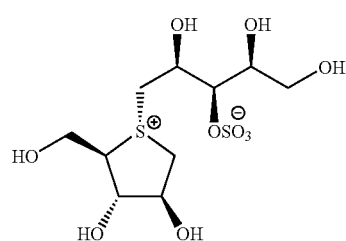

94

-continued

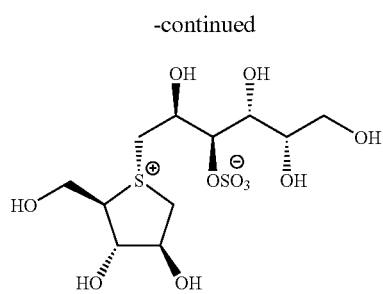

95

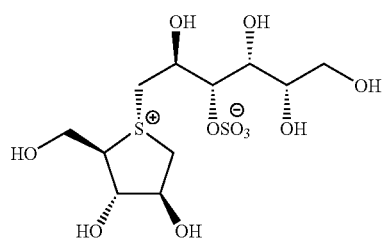

96

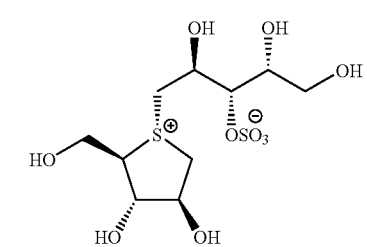

97

In principle, the desired compounds could be obtained from the sulfonium-sulfate disaccharide analogues 98-101; such analogues are representatives of a new class of carbohydrate derivatives and may have interesting properties in and of themselves. They are disaccharide analogues in which a permanent positive charge resides on the non-reducing ring and linkage heteroatom simultaneously. As such, they may be mimics of the partial positive charge that is generated on analogous atoms at the transition state stage of enzyme catalyzed glycoside hydrolysis.

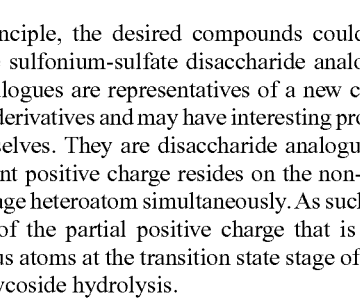

98

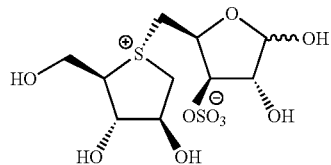

99

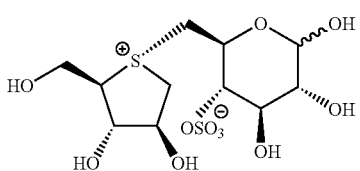

100

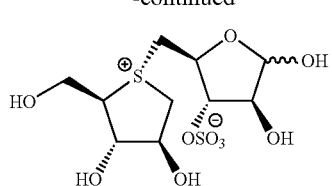

101

The inventors' synthetic strategy was similar to that used to the inventors' advantage for related structures as described above. This involves opening of a 1,3-cyclic sulfate ring by nucleophilic attack of a sulfide. In this case the target structures were chosen partly due to the availability of appropriate cyclic sulfate derivatives. A literature survey, searching for 1,3-cyclic sulfates of carbohydrate derivatives, returned the glucopyranoside 4,6-O-cyclic sulfates 102[37] and 103[38] as well as the xylose derivative 104[39] and the galactose derivative 105.[40]

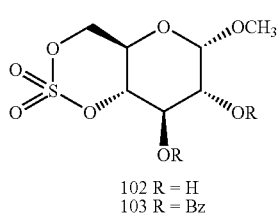

102 R = H
103 R = Bz

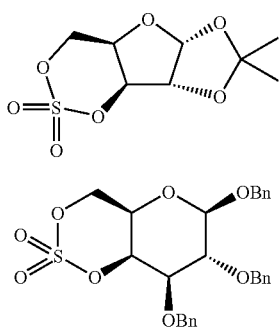

104

105

These derivatives have been shown to react with oxygen, nitrogen or sulfur nucleophiles selectively at the primary carbon. The methylpyranosides 102 and 103 were rejected due to the probable harsh conditions necessary for hydrolysis of the glycoside bond during the deprotection of the proposed, and possibly sensitive, sulfonium intermediates. Compounds 104 and 105 were deemed to be more suitable and could be prepared by the literature methods. Three other cyclic sulfates could be prepared by new methods. Benzyl glucopyranoside 4,6-cyclic sulfate 107 could be prepared by the Sharpless method[81] from known benzyl glucopyranoside 106[41] and similar treatment of the methyl or benzyl arabinofuranosides 108[42] and 109 would yield cyclic sulfates 110 and 111 (Scheme 22).

The cyclic sulfate derivatives 104 and 105 were prepared uneventfully. However, the trans fused [5.6] bicyclic systems in compounds 110 and 111 impart considerably more ring strain to these compounds than the cis fused [5.6] bicyclic compound 104 or the [6.6] cis or trans fused ring systems of compounds 105 or 107. This resulted in the formation of substantial amounts of disulfate dimers by intermolecular reactions during the synthesis of 110 and 111. The careful control of reactant concentration and temperature gave modest yields of monomeric cyclic sulfates 110 and 111, which were isolated as pure crystalline solids.

Scheme 22

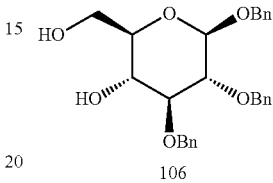

106

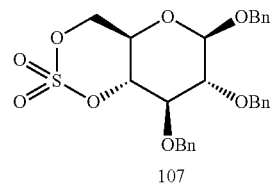

107

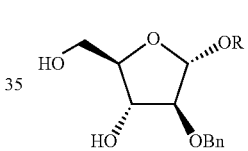

108 R = CH₃
109 R = Bn

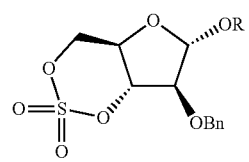

110 R = CH₃
111 R = Bn

The required diol 109 was prepared by analogy to the methods already reported for 108.42 Thus, benzyl arabinofuranoside 113[43] was prepared by glycosylation of benzyl alcohol with the glycosyl bromide 112[44] using the Helferich method. The benzoate protecting groups were removed to give 114 and the 3- and 5-positions were then blocked as the tetraisopropyldisiloxane derivative 115. The 2-hydroxyl group was protected as the benzyl ether 116 in a reaction that required careful monitoring to prevent premature silyl group cleavage and subsequent benzylation of the exposed hydroxyl groups. The silyl protecting group was finally removed by treatment of 116 with fluoride to give the diol 109 (Scheme 23).

Scheme 23

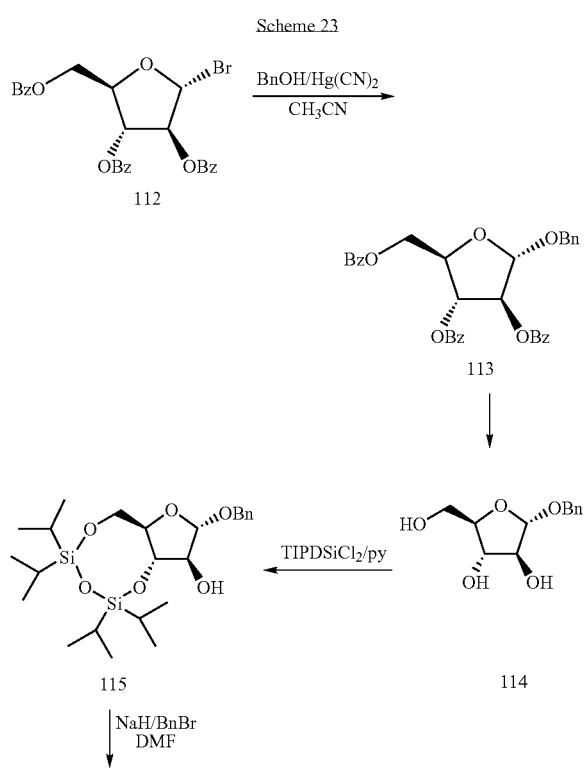

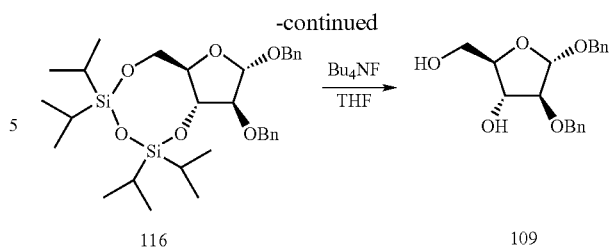

The thioether 117 was available from earlier work[25] and could be prepared more conveniently by a method analogous to that developed for the corresponding selenium derivative.[26,88,89] Compound 117 was reacted with each of the cyclic sulfates 104, 105, 107, 110 and 111 to give the protected sulfonium sulfate compounds 118-121 (Scheme 24). The solvent chosen for these reactions was 1,1,1,3,3,3-hexafluoroisopropanol (HFIP) which the inventors have found previously to offer significant advantages in reactions that yield sulfonium salts from neutral precursors.[53] Initial trials with the cyclic sulfate 104 showed that the addition of $K_2CO_3$, which the inventors had previously routinely included to ensure that the reaction mixture did not become acidic through hydrolysis of the cyclic sulfate by traces of water, was not necessary. In the present case, the presence of base led to decomposition of 104 and inferior yields of the desired coupled product 118. All subsequent reactions were therefore performed without base. In addition, use of the thioether 117 in slight excess over the cyclic sulfate gave superior yields in certain cases.

Scheme 24

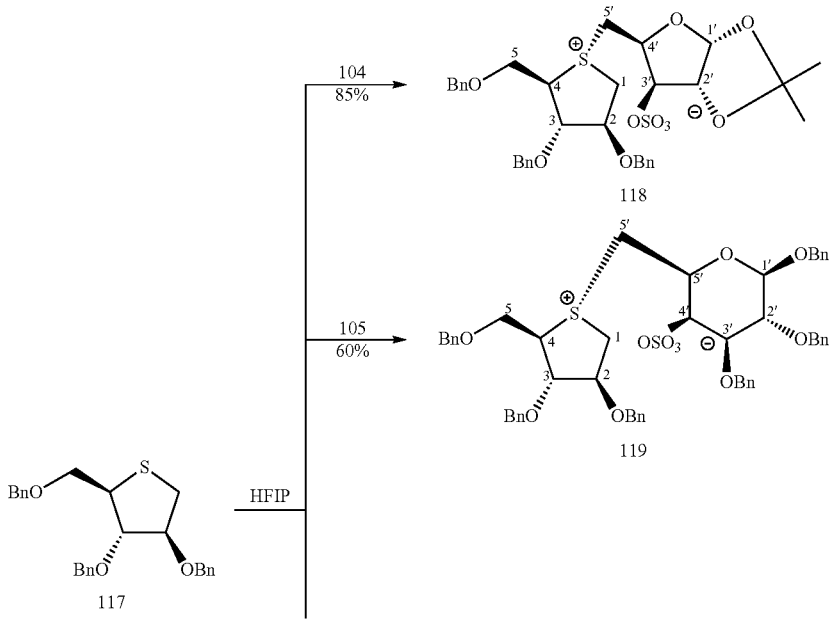

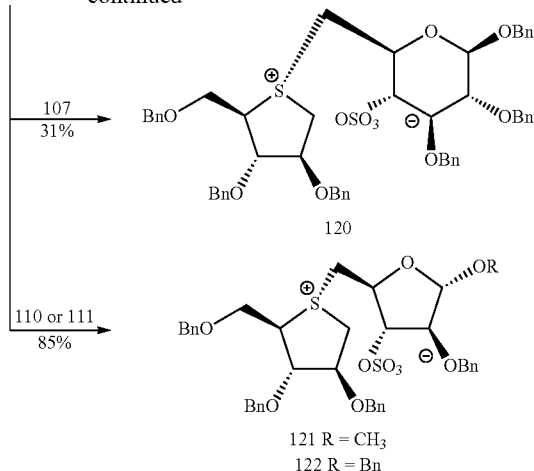

121 R = CH₃
122 R = Bn

Figure 5:
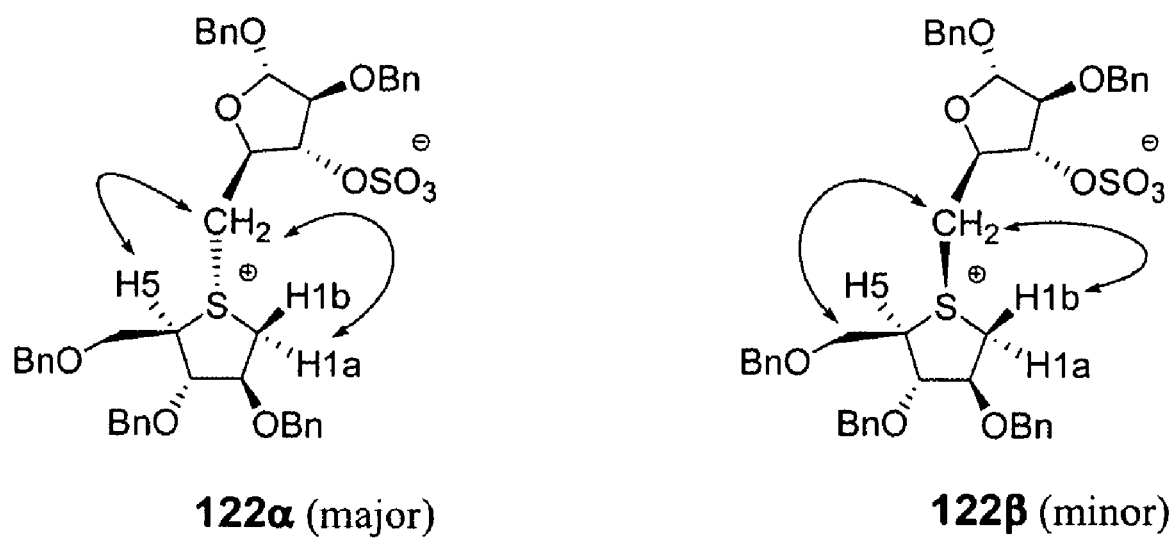
FIG. 5 depicts NOESY correlations of selected protons in isomers of Compound 122.

The reactivity of the cyclic sulfates varied widely, with the glucose derivative 107 being the least reactive and giving the desired product 120 in a yield of just 31% after 42 h at 70° C. In contrast, the strained cyclic sulfate 111 was most reactive and yielded the coupled product 122 in 85% yield after only 2.5 h at 40° C. The selectivity for attack of the thioether 117 at the primary over the secondary cyclic sulfate center was excellent, and in no case were isolable quantities of the regioisomeric products detected. There was evidence in the NMR spectra of the crude reaction mixtures for minor amounts of stereoisomers formed through electrophilic attack on the β-face of the thioether 117 to give products that were diastereomeric at the stereogenic sulfur center. These minor isomers were produced in variable proportion (up to 20% in the case of compound 120) but, due to the similarity in chromatographic mobilities, they could not be obtained free of the major isomers in most instances. However, in the case of the coupled product 122, almost pure fractions of the isomer 122β were obtained and the product was characterized by NMR spectroscopy. Its $^1$H and $^{13}$C NMR spectra were very similar to those of the major isomer 122α, but a NOESY spectrum showed clear H-5 to H-5' and H-1a to H-5' correlations, implying that these atoms are syn-facial on the sulfonium salt ring. In contrast, the major isomer 122α exhibited an H-1b to H-5' correlation, as expected for the isomer of the opposite configuration at the sulfonium center (FIG. 5). In all cases, the minor β-isomer was removed by chromatography, albeit in most instances only by sacrificing part of the major α-isomer. The final yields of the coupled products 118-122 in the Scheme 24 refer to the pure α-isomers isolated after one or two rounds of chromatography.

The inventors initially approached the deprotection steps with some apprehension of encountering problems in performing two or three successive reactions in the presence of a reactive sulfonium salt. This sense of unease was reinforced by the inventors' first attempts. Treatment of the sulfonium salt 118, first with aqueous trifluoroacetic acid to remove the isopropylidene group, and then with NaBH₄ to reduce the hemiacetal led only to an intractable mixture. Similarly, although hydrogenolysis of the benzyl groups in compound 121 seemed to be successful, giving eventually a single product according to TLC analysis of the reaction mixture; removal of the catalyst by filtration and concentration led to decomposition of this initial product to give extremely polar material. The inventors have been unable to develop an efficient deprotection protocol for compound 121.

In contrast, the corresponding benzyl glycoside 122 gave, upon hydrogenolysis, a virtually quantitative yield of the hemiacetal product 101 as a 1:1 α:β mixture. The crude product was stable after removal of solvent, and was even unchanged after storage in aqueous solution for several days at ambient temperature. Nevertheless, the crude product was generally immediately reduced with NaBH₄ to provide the desired alditol sulfonium sulfate compound 97, in a yield of 66% for the two steps (Scheme 25). Analogous treatment of the protected compounds 119 and 120 gave the target compounds 95 and 96 via the intermediate hemiacetal derivatives 99 and 100. The deprotection of compound 118 required a three-step procedure, which was eventually implemented as either of two possible sequences to give 94 (Scheme 25). Removal of the benzyl groups first (Procedure A) to yield the isopropylidene compound 123 was found to be advantageous since the alternative method (Procedure B), to give initially the 1,2-diol 124, was found to lead to partial conversion to a methylfuranoside mixture 125 during the subsequent hydrogenolysis reaction in MeOH solvent. The methyl glycoside could be hydroyzed by re-treatment with aqueous trifluoroacetic acid to give the intermediate hemiacetal 98 but this additional step resulted in a lower overall yield. Reduction of the hemiacetal with NaBH₄, as with the previous compounds, gave compound 94. The sulfonium sulfates 94-101 were obtained as hygroscopic gums that were unsuitable for combustion analysis. Despite intensive efforts they could not be induced to crystallize. They were, however, extensively characterized by spectroscopic methods. MALDI-TOF mass spectrometry for compounds 94-97 in the positive-ion mode typically showed base peaks for masses attributable to sodium adduct ions (M+Na), and lower-intensity peaks corresponding to M+H and M+H—SO₃H. The protected compounds 118-122 fragmented to give M+H—SO₃ base peaks and lower-intensity M+H and M+Na peaks. This behavior seems general for this class of compound and is similar to that of sulfated carbohydrates which show loss of sulfate ion in their MALDI mass spectra.[45] Both the protected and the deprotected sulfonium compounds also exhibit variable intensity dimer or trimer cluster-ion peaks at higher masses. The compounds 94-101 were also characterized by high resolution mass spectrometry. The NMR spectra for compounds 98-101 showed two sets of resonances corresponding to the mixture of α/, isomers at the hemiacetal center. In the ¹H NMR spectra, coupling constants between H-1 and H-2 allowed the assignment of these resonances to either the α- or the β-isomer and the assignment of the other resonances followed from analysis of the COSY spectra. The NMR spectra for compounds 94-97 were also in accord with the assigned structures, and were almost identical to those of salacinol for those portions of the sulfonium salts having similar structure (see Tables 5 and 6). As was the case with salacinol,[25] the stereochemical integrity at the stereogenic sulfur atom in each of 94-97 was maintained.

Scheme 25

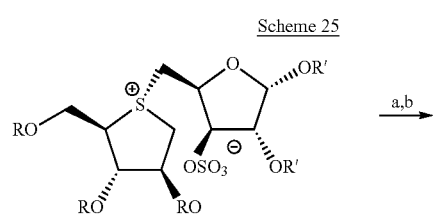

118 R = Bn, R' = C(CH₃)₂
123 R = H, R' = C(CH₃)₂
124 R = Bn, R' = H

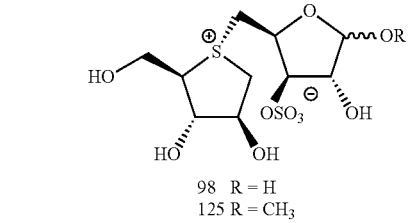

98 R = H
125 R = CH₃

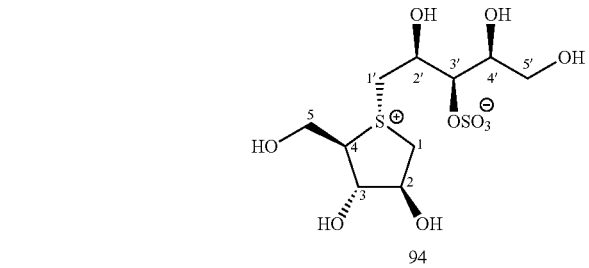

94

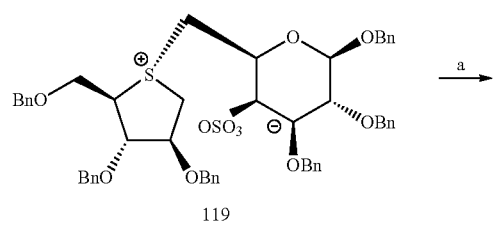

119

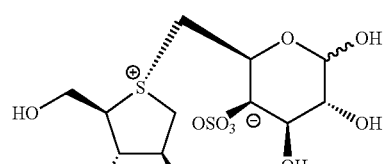

99

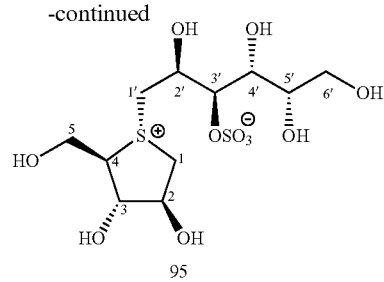

95

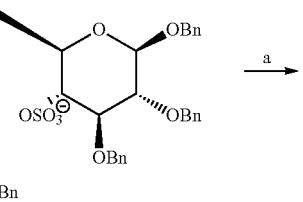

120

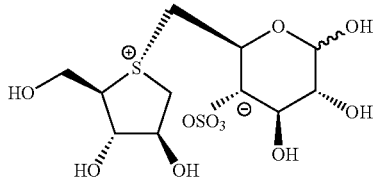

100

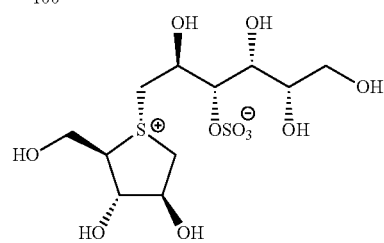

96

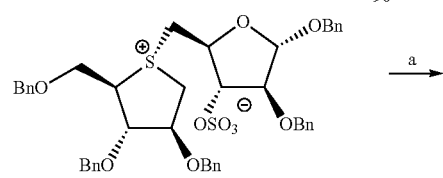

122

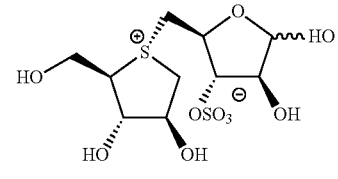

101

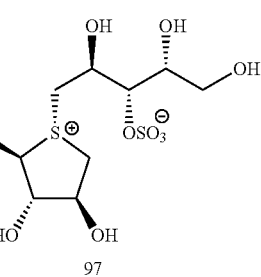

97 a H₂, Pd(C), b TFA/H₂O, c NaBH₄/H₂O

The inventors have also tested the glycosidase inhibitory properties of 94-101 against recombinant human maltase glucoamylase (MGA), a critical intestinal glucosidase involved in the processing of oligosaccharides of glucose into glucose itself, and of relevance to the control of Type 2 diabetes. Although compound 94 did not inhibit the activity of MGA, compounds 95-97 showed $K_i$ values of 0.25, 0.26, and 0.17 μM, respectively. For purposes of comparison, salacinol inhibits MGA with a Ki value of 0.19 μM. The stereochemistry of the C-4' stereogenic center appears to play a role in the inhibitory activity of the compounds. The disaccharide analogues 98-101 were not active against MGA.

4.3 D-Mannose Derived Chain-Extended Analogues of Salacinol

In another embodiment, the inventors disclose the synthesis of two series of selenonium and sulfonium sulfates 125-128 based on seleno- and thio-anhydroalditols derived from D-mannose. The analogues contain extended acyclic chains of six carbon atoms, as well as ring heteroatom substitutions (S, Se), and five- and six-membered heterocyclic rings. These syntheses utilized a 1,3-cyclic sulfate, also derived from D-mannose in four steps. The isopropylidene acetal, and benzylidene acetal protecting groups on the coupled products ensured facile deprotection with TFA to yield the final compounds 125-128.

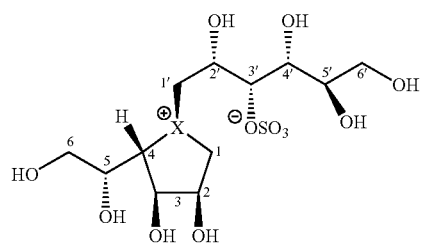

125 X = S
126 X = Se

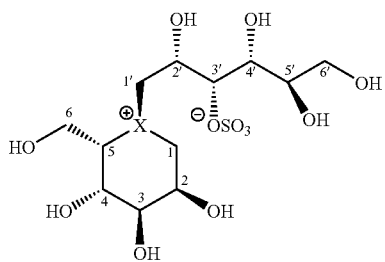

127 X = S
128 X = Se

Retrosynthetic analysis indicated that the analogues 125-128 could be synthesized by alkylation of the protected anhydro-heteroalditols at the ring heteroatom with a terminal 1,3-cyclic sulfate derived from D-mannose (Scheme 26).

Scheme 26

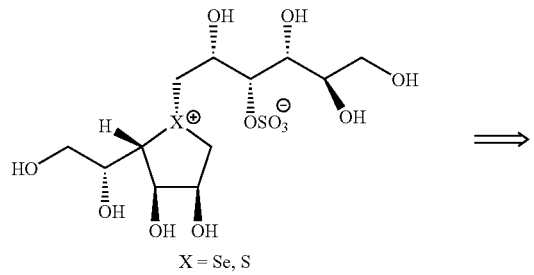

-continued

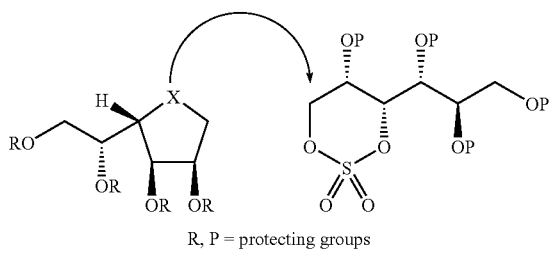

R, P = protecting groups

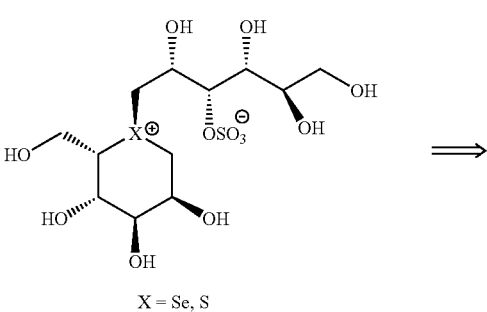

X = Se, S

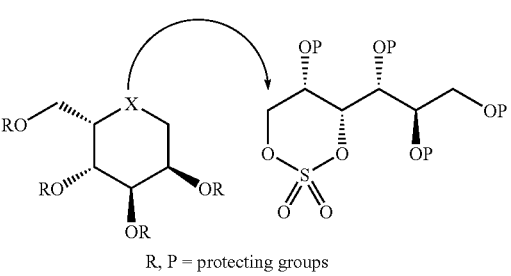

R, P = protecting groups

The choice of protecting groups for the seleno- and thio-anhydroalditols and the cyclic sulfate, however, merited careful consideration, especially in the case of the selenonium analogues. The inventors' previous work suggested that hydrogenolysis and strongly basic conditions as deprotection steps were problematic for the selenonium analogues.[26,88,16] Therefore, the inventors envisioned the use of only isopropylidene and benzylidene acetals as the protecting groups for the seleno- and thio-anhydroalditols 129-132 and the cyclic sulfate 133 since these acetals would be subject to acidic hydrolysis.

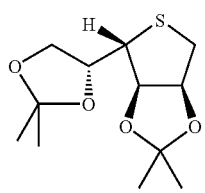

129

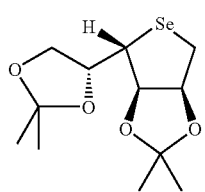

130

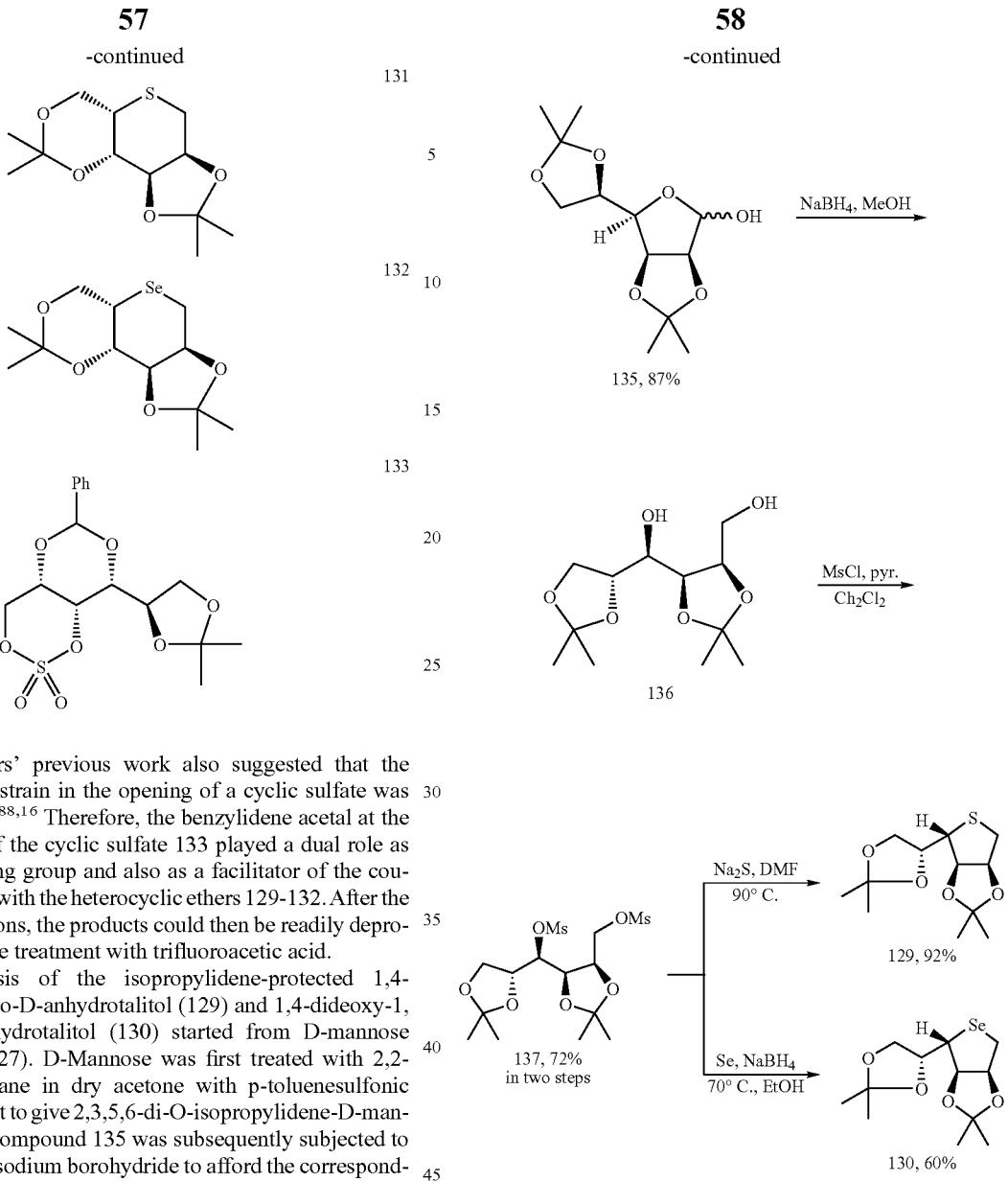

The inventors' previous work also suggested that the release of ring strain in the opening of a cyclic sulfate was beneficial.[29,26,88,16] Therefore, the benzylidene acetal at the 2,4-positions of the cyclic sulfate 133 played a dual role as both a protecting group and also as a facilitator of the coupling reactions with the heterocyclic ethers 129-132. After the coupling reactions, the products could then be readily deprotected by simple treatment with trifluoroacetic acid.

The synthesis of the isopropylidene-protected 1,4-dideoxy-1,4-thio-D-anhydrotalitol (129) and 1,4-dideoxy-1,4-seleno-D-anhydrotalitol (130) started from D-mannose (134, Scheme 27). D-Mannose was first treated with 2,2-dimethoxypropane in dry acetone with p-toluenesulfonic acid as a catalyst to give 2,3,5,6-di-O-isopropylidene-D-mannose (135).[95] Compound 135 was subsequently subjected to reduction with sodium borohydride to afford the corresponding diol 136. The diol was then converted to the corresponding dimesylate 137 in 80% yield by treatment with methanesulfonyl chloride and pyridine. The isopropylidene-protected 1,4-dideoxy-1,4-thio-D-anhydrotalitol 129 was prepared in 92% yield by treatment of the dimesylate 137 with sodium sulfide in DMF in 92% yield. When the dimesylate 137 was reacted with selenium and sodium borohydride in EtOH at 60-65° C., the isopropylidene-protected 1,4-dideoxy-1,4-seleno-D-anhydrotalitol 130 was obtained in a 60% yield (Scheme 27).

Scheme 27

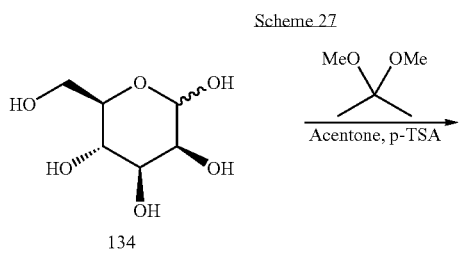

With D-mannose as a starting material, the isopropylidene-protected 1,5-dideoxy-1,5-thio-L-anhydrogulitol (131) and seleno-L-anhydrogulitol (132) were also synthesized (Scheme 28). D-Mannose 134 was first treated with 2-methoxypropene in dry DMF with p-toluenesulfonic acid as a catalyst to give the kinetically-controlled product, 2,3,4,6-di-O-isopropylidene-D-mannose (138).[96] Compound 138 was subsequently subjected to sodium borohydride reduction to afford the corresponding diol 139. The diol 139 was then converted to the corresponding dimesylate 140 in 90% yield by treatment with methanesulfonyl chloride and pyridine. The isopropylidene-protected 1,5-dideoxy-1,5-thio-L-anhydrogulitol (131) was prepared in 85% yield by treatment of the dimesylate 140 with sodium sulfide in DMF. Reaction of the dimesylate 140 with selenium and sodium borohydride in EtOH at 60-65° C. gave the isopropylidene-protected 1,5-dideoxy-1,5-seleno-L-anhydrogulitol (132) in 62% yield (Scheme 28).

Scheme 28

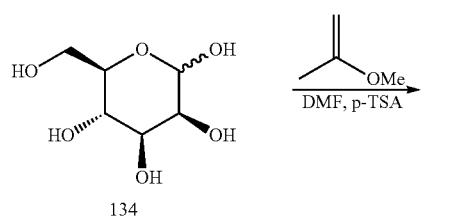

134

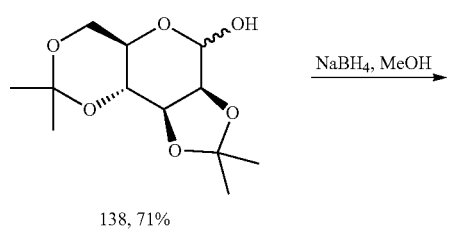

138, 71%

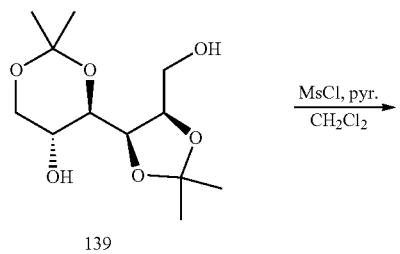

139

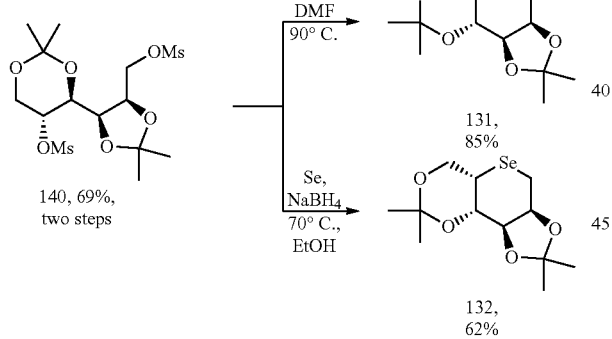

140, 69%, two steps 131, 85%

132, 62%

Scheme 29

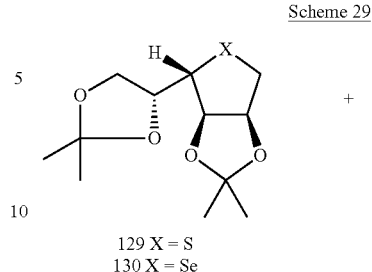

129 X = S
130 X = Se

+

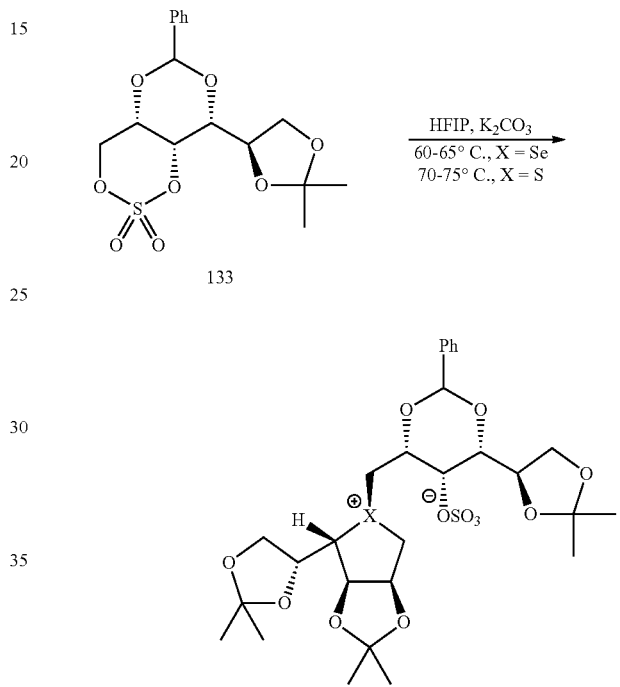

133

141 X = S, 85%
142 X = Se, 73%

The coupling reactions of the protected thio-D-anhydrotalitol 129 and seleno-D-anhydrotalitol 130 were then investigated (Scheme 29). The solvent chosen for the coupling reactions was the unusual solvent 1,1,1,3,3,3-hexafluoroisopropanol (HFIP) that was demonstrated in the inventors' earlier work to offer significant advantage in analogous reactions. The cyclic sulfate 133, prepared by a method developed in the inventors' earlier work, was used as the coupling partner. The cyclic sulfate 133 was reacted with isopropylidene-protected thio-D-anhydrotalitol 129 and seleno-D-anhydrotalitol 130, to give the corresponding protected sulfonium and selenonium compounds 141 and 142, respectively (Scheme 29).

In analogous fashion, the coupling reactions of the protected thio-L-anhydrogulitol 131 and seleno-L-anhydrogulitol 132 with the cyclic sulfate 133 afforded the protected sulfonium and selenonium compounds 143 and 144, respectively (Scheme 30).

Scheme 30

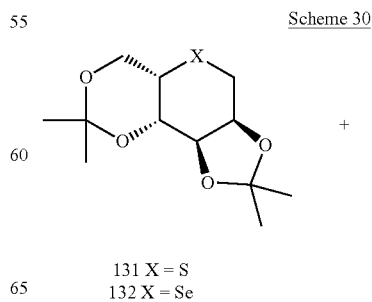

131 X = S
132 X = Se

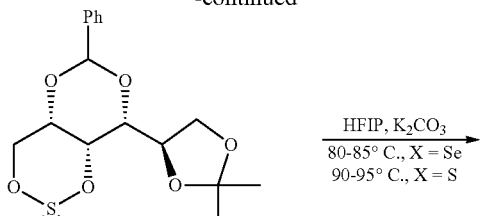

133

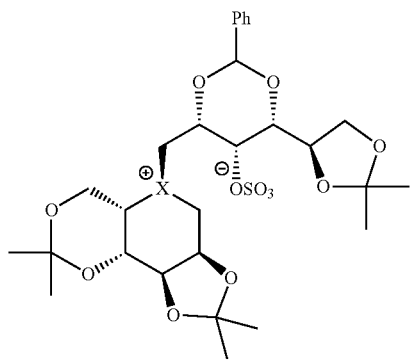

143 X = S, 90%
144 X = Se, 77%

The reactivities of the thio-D-anhydrotalitol 129, seleno-D-anhydrotalitol 130, thio-L-anhydrogulitol 131, and seleno-L-anhydrogulitol 132 with the cyclic sulfate 133 varied slightly. The five-membered thio-D-talitol 129 and seleno-D-anhydrotalitol 130 were more reactive than their six-membered counterparts, thio-L-anhydrogulitol 131 and seleno-L-anhydrogulitol 132, as illustrated by the higher temperatures required for the coupling reactions in the latter cases. The five-membered-ring compounds 129 and 130 reacted readily with the cyclic sulfate 133 at 70-75° C. and 60-65° C., respectively, while the six-membered-ring compounds 131 and 132 reacted very slowly and gave low yields of the coupling products at these temperatures. When the temperature was increased to 90-95° C. and 80-85° C. respectively, compounds 131 and 132 reacted readily with the cyclic sulfate 133. Within the same series, the selenoalditols were found to be slightly more reactive than their sulfur counterparts. Selectivity for the attack at the primary center of the cyclic sulfate 133 over possible alternative attack at the secondary center by compounds 129-132 was invariably excellent and in no case were isolable quantities of the regioisomers detected. In the case of the coupling reaction of seleno-D-anhydrotalitol 130 with the cyclic sulfate 133, there was a small amount (<10%) of the diastereomer formed resulting from electrophilic attack on the β-face of seleno-D-anhydrotalitol 130. However, diastereoisomers at the stereogenic heteroatom centers were not detected in all other cases.

Figure 6:
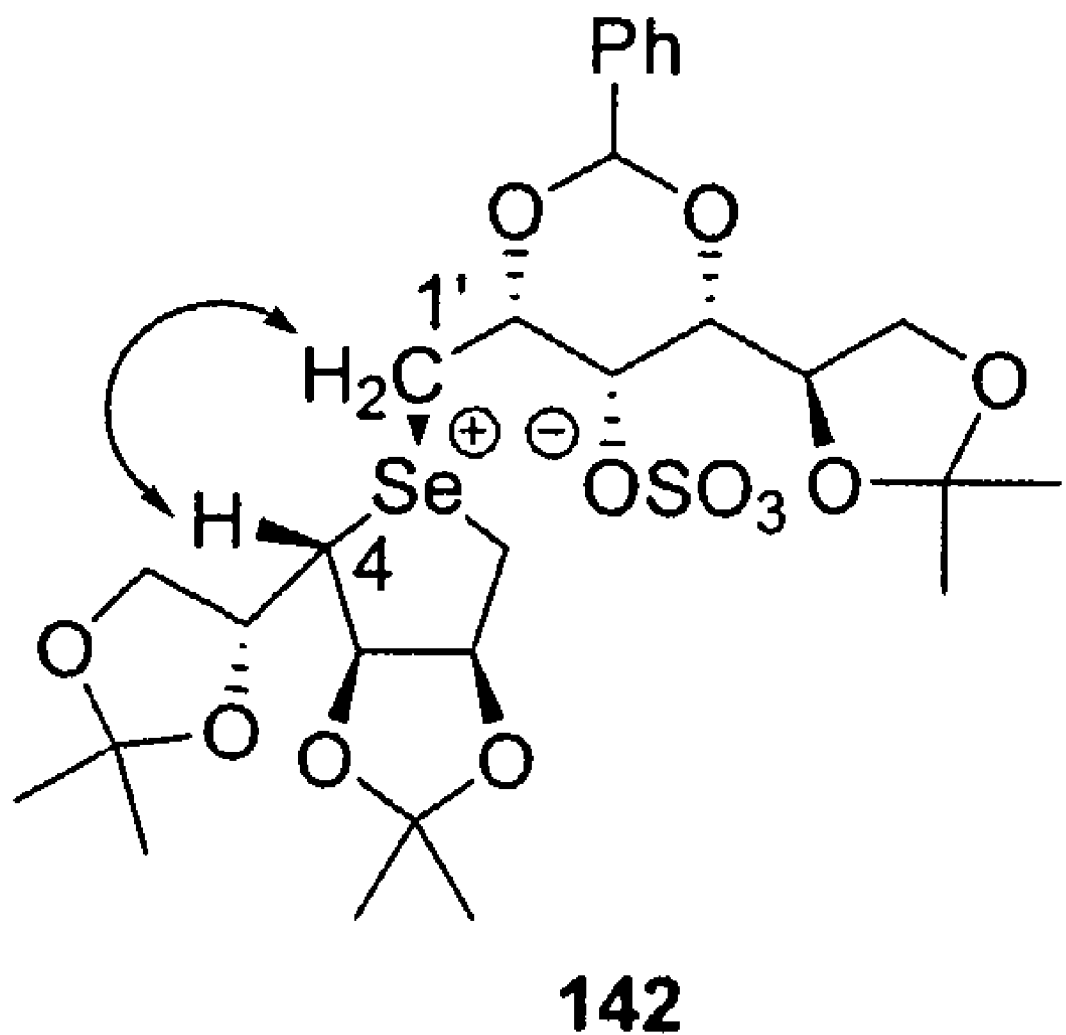
FIG. 6 depicts NOE correlations observed in the 1D-NOE spectrum of Compound 142.
Figure 7:
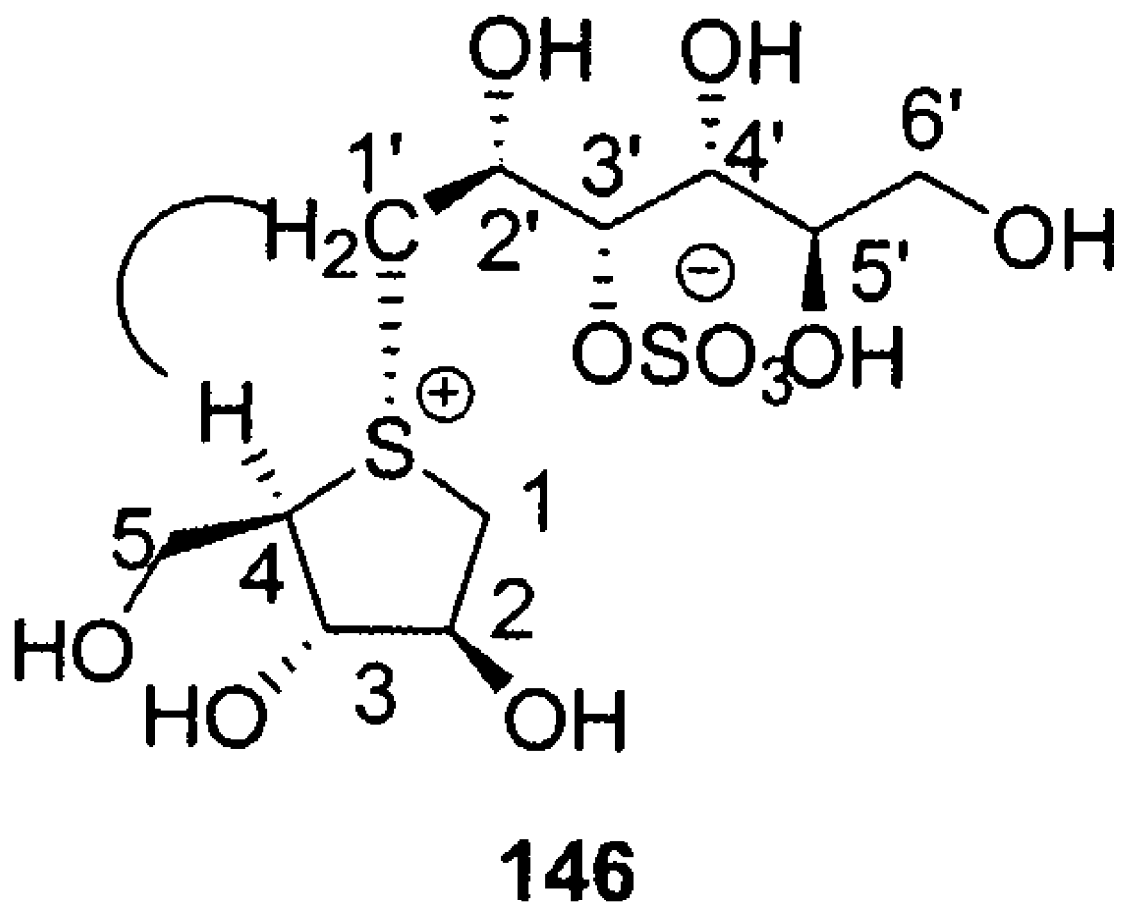
FIG. 7 depicts the NOESY spectrum of Compound 146.

The absolute stereochemistry at the heteroatom centre of compounds 141-144 was established by 1D-NOE NMR spectroscopy (FIG. 6). Thus, for example, the 1D NOE spectra of compound 142 indicated an H-4 to H-1'b correlation, implying that these hydrogens are syn-facial, and consequently, C-1' of the side chain must be anti to C-5 of the heterocyclic moiety.

Deprotection of the coupled products 141-144 was carried out by treatment with trifluoroacetic acid (Scheme 31). After rinsing away the cleaved protecting groups with dichloromethane, the resulting residues were purified by flash chromatography to yield compounds 125-128 as amorphous, hygroscopic solids.

These compounds were characterized by spectroscopic methods.

Scheme 31

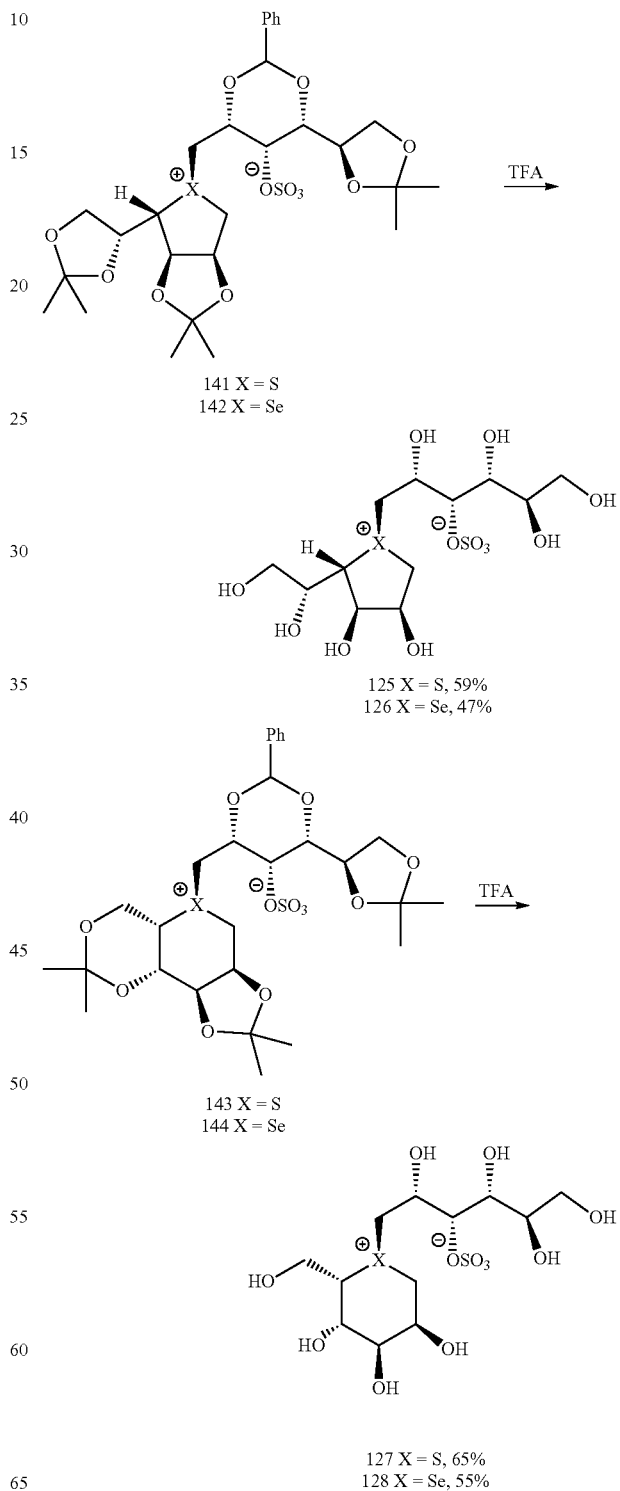

4.4 Salacinol Analogues Based on Selenoalditols and Thioalditols

In a further embodiment, a series of salacinol analogues 145-152 based on novel seleno- and thioalditols derived from D-gulonic-γ-lactone and L-ascorbic acid were synthesized. As indicated below, the target compounds were synthesized by means of nucleophilic attack at the least hindered carbon atom of 1,3-cyclic sulfates derived from D-glucose and D-mannose by the isopropylidene-protected 1,4-anhydro-4-thio- and seleno-D-allitols and 4-thio- and seleno-L-allitols. Deprotection of the coupled products afforded the novel sulfonium and selenonium ions containing polyhydroxylated, acyclic chains of 4- and 6-carbons, with different stereochemistry at the stereogenic centers, and with 1,4-anhydro-4-seleno or 4-thio-D- or L-alditol heterocyclic rings.

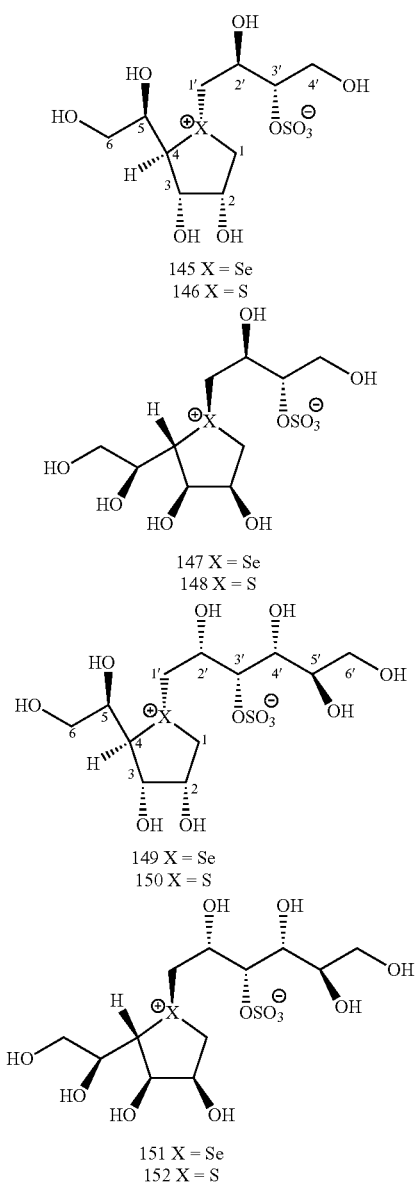

145 X = Se
146 X = S

147 X = Se
148 X = S

149 X = Se
150 X = S

151 X = Se
152 X = S

Retro synthetic analysis indicated that the analogues 145-152 could be synthesized by alkylation of a protected anhydro-alditol at the ring heteroatom with terminal 1,3-cyclic sulfates. The protected anhydro-alditols and the cyclic sulfates can be synthesized from the appropriate carbohydrate starting materials. (Scheme 32).

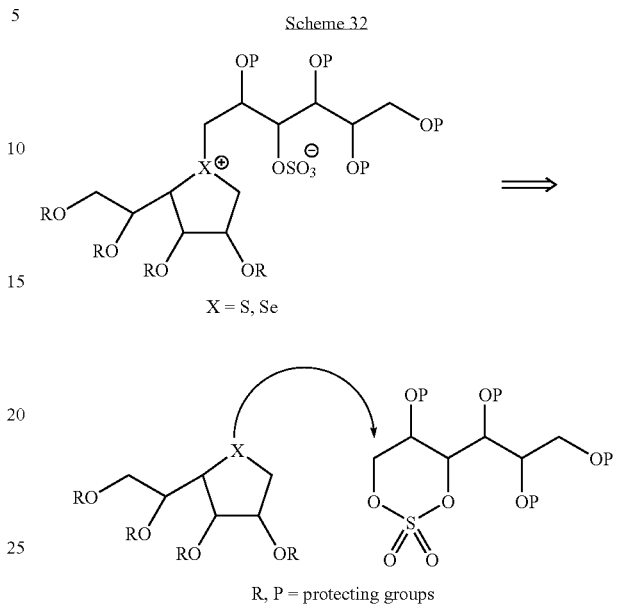

Scheme 32

X = S, Se

R, P = protecting groups

The choice of protecting groups for the thio- and seleno-anhydroalditols and the cyclic sulfates merited careful consideration, especially in the case of the selenonium analogues. Hydrogenolysis and strongly basic conditions as deprotection steps proved to be problematic for similar selenonium analogues; thus, these conditions needed to be avoided.[26,88,16] Therefore, the inventors envisioned the use of isopropylidene and benzylidene acetals as the protecting groups for the thio- and seleno-anhydroalditols 153-156 and the cyclic sulfates 157 and 158 since these acetals are both labile to acidic hydrolysis.

153 X = Se
154 X = S

155 X = Se
156 X = S

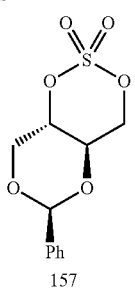

157

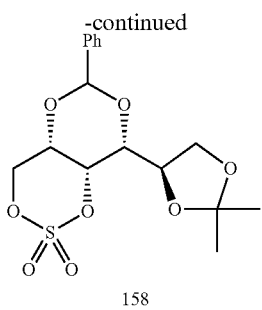

158

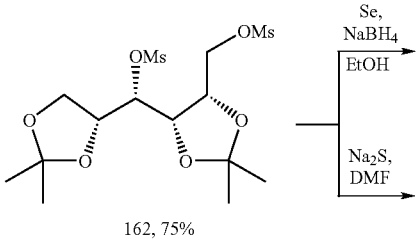

162, 75%

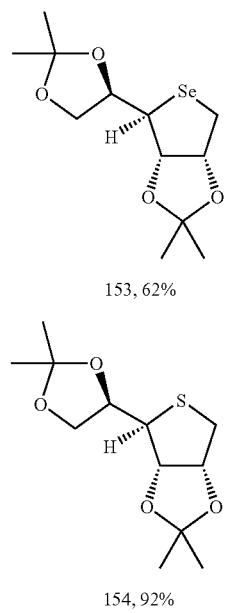

153, 62%

154, 92%

The inventors' previous work also suggested that the release of ring strain in the opening of a cyclic sulfate was beneficial.[29,26,88,16] Therefore, the benzylidene acetal at the 2,4-positions of the cyclic sulfates 157 and 158 played dual roles as protecting groups and reaction facilitators for the coupling reactions with compounds 153-156. After the coupling reactions, the products could then be readily deprotected by simple treatment with trifluoroacetic acid.

The synthesis of the isopropylidene-protected 1,4-anhydro-4-seleno-D-allitol (153 and 1,4-anhydro-4-thio-D-allitol (154) started from the commercially available D-gulonic-γ-lactone (159, Scheme 33). D-Gulonic-γ-lactone was first treated with 2,2-dimethoxypropane in dry acetone with p-toluenesulfonic acid as a catalyst to give 2,3,5,6-di-O-isopropylidene-D-gulonic-γ-lactone (160).[104] The lactone 160 was subsequently reduced with sodium borohydride to afford the corresponding diol 161 Compound 161 was then converted to the dimesylate 162 by treatment with methanesulfonyl chloride and pyridine in 80% yield.[105] When the dimesylate 162 was reacted with selenium metal and sodium borohydride in EtOH at 60-65° C., the isopropylidene-protected 1,4-anhydro-4-seleno-D-allitol 153 was obtained in 62% yield. The isopropylidene-protected 1,4-anhydro-4-thio-D-allitol 154 was prepared in 92% yield by treatment of the dimesylate 162 with sodium sulfide in DMF (Scheme 33).

Scheme 33

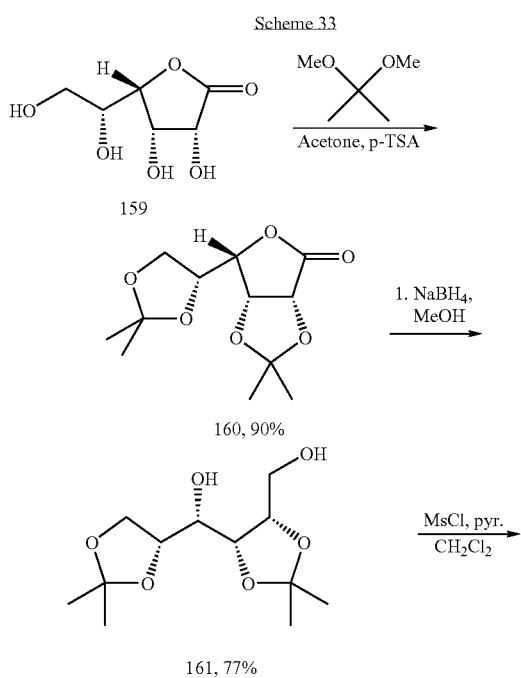

Although the enantiomeric isopropylidene-protected 1,4-anhydro-4-seleno-L-allitol (155) and 1,4-anhydro-4-thio-L-allitol (156) could, in principle, be prepared from L-gulonic-γ-lactone, the high cost of this starting material made these syntheses unrealistic. Thus, inexpensive and commercially available L-ascorbic acid (163) was used as the starting material in this synthesis (Scheme 34). L-Ascorbic acid 163 underwent hydrogenolysis to give the L-gulonic-γ-lactone (164) in 71% yield.[106] Compound 164 was first treated with 2,2-dimethoxypropane in dry acetone containing p-toluenesulfonic acid as a catalyst to give 2,3,5,6-di-O-isopropylidene-L-gulonic-γ-lactone (165).[104] The lactone 165 was subsequently reduced with sodium borohydride to afford the corresponding diol that was, in turn, converted to the dimesylate 166 by treatment with methanesulfonyl chloride and pyridine. When the dimesylate 166 was reacted with selenium metal and sodium borohydride in EtOH at 60-65° C., the isopropylidene-protected 1,4-anhydro-4-seleno-L-allitol 155 was obtained in 67% yield. The isopropylidene-protected 1,4-anhydro-4-thio-L-allitol 156 was prepared in 82% yield by treatment of the dimesylate 166 with sodium sulfide in DMF.

Scheme 34

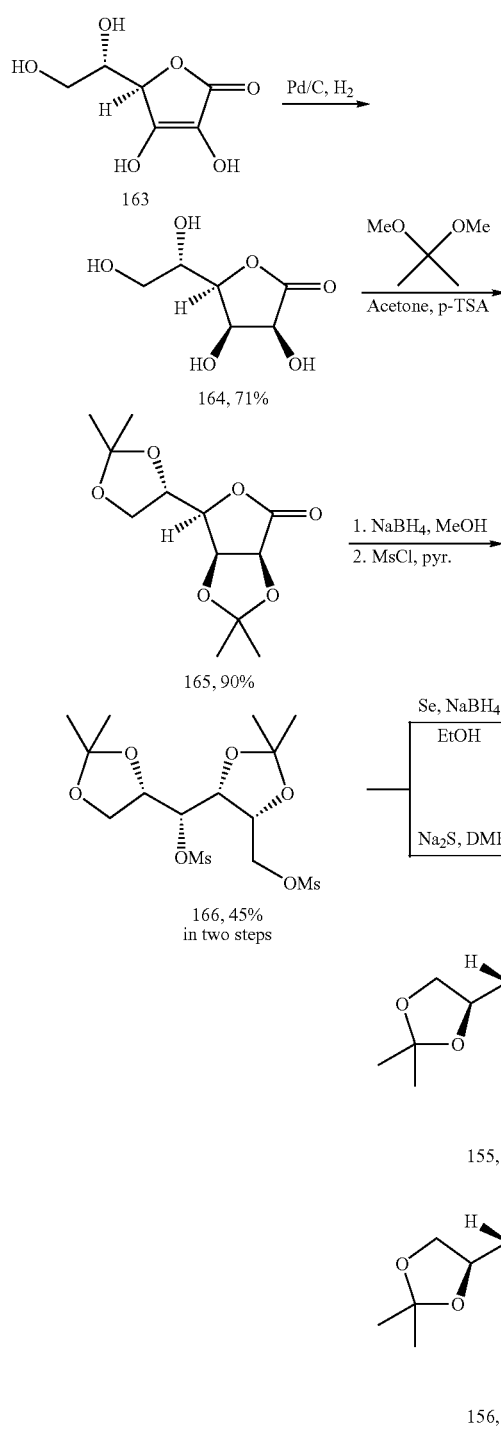

hexafluoroisopropanol (HFIP), which offers significant advantage in these types of coupling reactions compared with other solvents as indicated above.[26,88,16] The cyclic sulfate 157, prepared as described previously,[88] was reacted with isopropylidene-protected 1,4-anhydro-4-seleno-D-allitol (153) and 1,4-anhydro-4-thio-D-allitol (154), to give the corresponding protected selenonium and sulfonium sulfates 167 and 168, respectively (Scheme 35).

Scheme 35

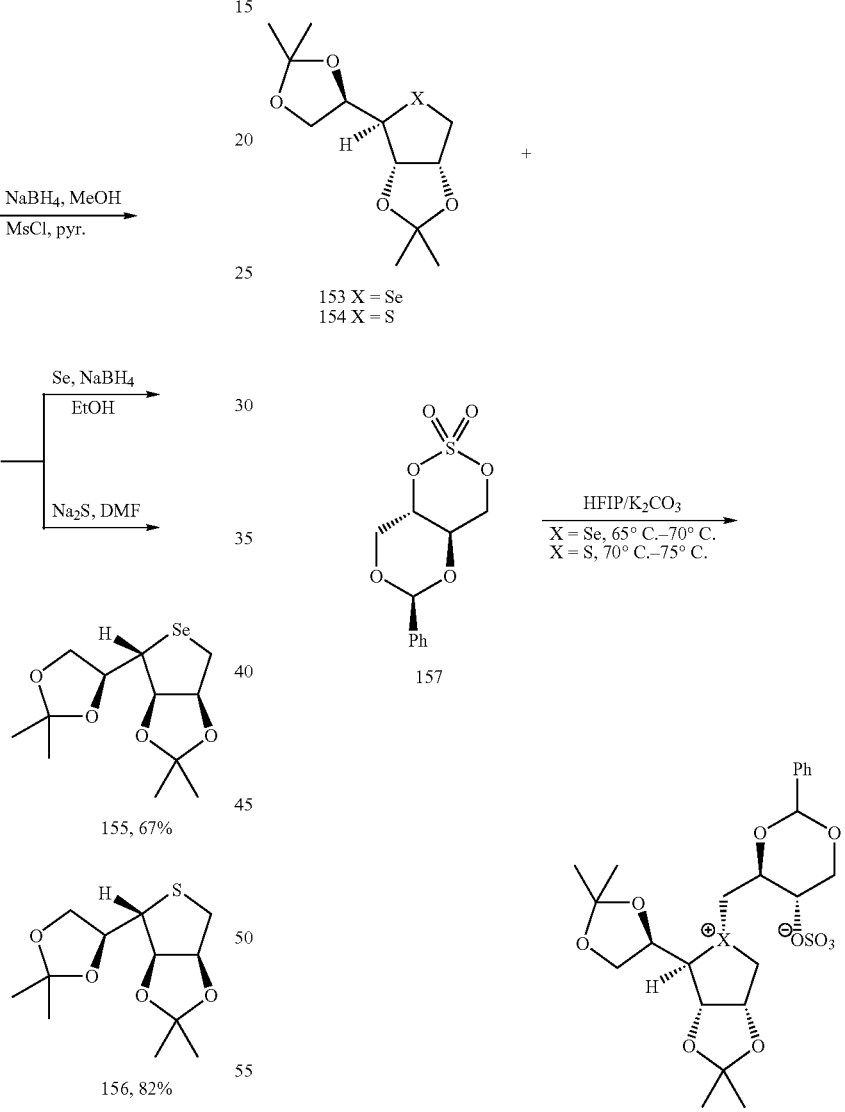

Since salacinol 1 and its selenonium analogue, blintol (3), are believed to be the most active so far of this class of glycosidase inhibitors against human maltase glucoamylase, the inventors first concentrated on the coupling reactions of the isopropylidene-protected 1,4-anhydro-4-seleno-D-allitol (153) and 1,4-anhydro-4-thio-D-allitol (154) with the cyclic sulfate 157 that would yield the identical side chain present in salacinol and blintol (Scheme 35). The solvent chosen for the coupling reactions was the unusual solvent 1,1,1,3,3,3-

The coupling reactions of the enantiomeric isopropylidene-protected 1,4-anhydro-4-seleno-L-allitol (155) and 1,4-anhydro-4-thio-L-allitol (156) with the cyclic sulfate 157 were carried out analogously, to give the corresponding protected selenonium and sulfonium sulfates 169 and 170, respectively (Scheme 36).

Scheme 36

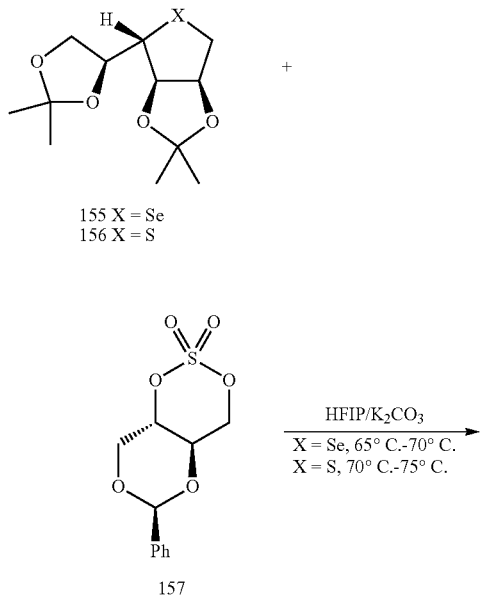

155 X = Se
156 X = S

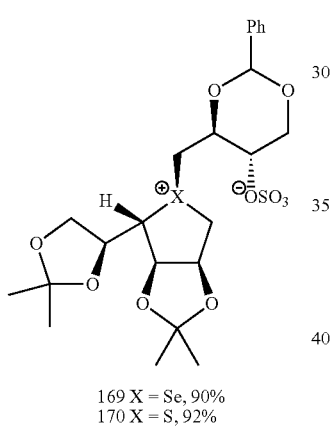

157

HFIP/K₂CO₃
X = Se, 65° C.-70° C.
X = S, 70° C.-75° C.

169 X = Se, 90%
170 X = S, 92%

Scheme 37

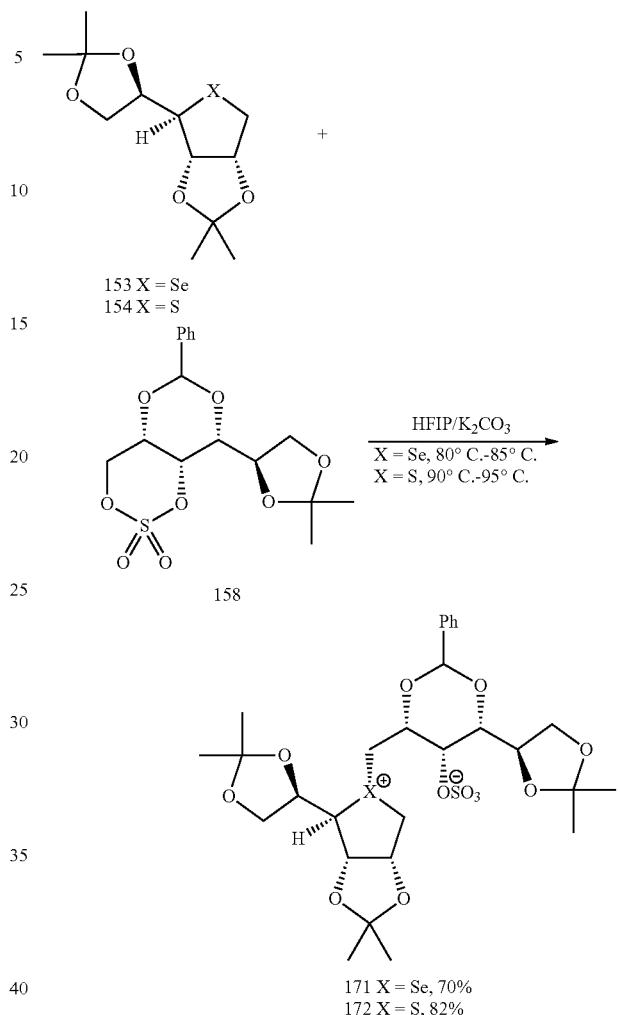

153 X = Se
154 X = S

158

HFIP/K₂CO₃
X = Se, 80° C.-85° C.
X = S, 90° C.-95° C.

171 X = Se, 70%
172 X = S, 82%

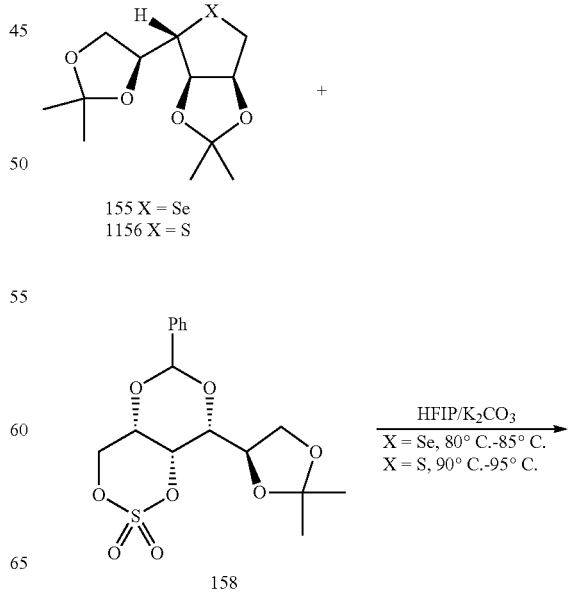

155 X = Se
1156 X = S

158

HFIP/K₂CO₃
X = Se, 80° C.-85° C.
X = S, 90° C.-95° C.

The inventors next turned their attention to the possibility of attaching longer side chains to the anhydroalditols 153-156. The inventors' interest in longer side chains stemmed from the fact that kotalanol, which has a seven-carbon side chain instead of salacinol's four-carbon side chain, exhibits stronger inhibitory activities toward certain glycosidase enzymes. Since the exact stereochemistry of kotalanol is not yet known, it is necessary and important to study the structure-activity relationships of these types of compounds systematically by attaching side chains with different chain lengths and different stereochemistry at the stereogenic centers to the heterocyclic rings of the anhydroheteroalditols. The cyclic sulfate 158, which consisted of a protected six-carbon, polyhydroxylated chain,[107] was chosen for this purpose. The cyclic sulfate 158 reacted with the isopropylidene-protected 1,4-anhydro-4-seleno-D-allitol (153) and 1,4-anhydro-4-thio-D-allitol (154), and their enantiomers 155 and 156 in HFIP, to give the corresponding protected selenonium and sulfonium compounds 171-174, respectively (Scheme 37).

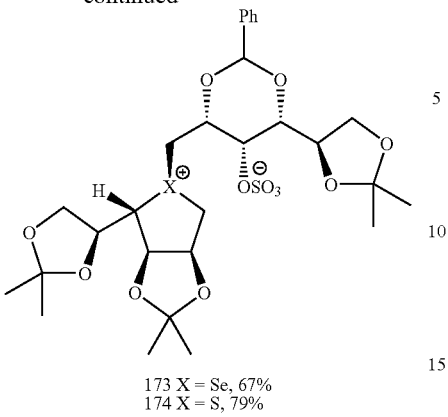

173 X = Se, 67%
174 X = S, 79%

The reactivity of the isopropylidene-protected 1,4-anhydro-4-seleno-D-allitol (153), 1,4-anhydro-4-thio-D-allitol (154), 1,4-anhydro-4-seleno-L-allitol (155), and 1,4-anhydro-4-thio-L-allitol (156) with the cyclic sulfates 157 and 158 varied slightly. With the same anhydroalditols, the cyclic sulfate 157 was more reactive than the cyclic sulfate 158, resulting also in higher yields of the coupling reactions. Thus, the coupling reactions with the cyclic sulfate 157 usually proceeded in yields of 90-95%, while the cyclic sulfate 158 typically gave yields of 70-80%, with the remainder consisting of starting materials and a small amount of decomposition products. With the same cyclic sulfate, the selenoalditols were slightly more reactive than their sulfur counterparts, as demonstrated by the different reaction temperatures required in the coupling reactions. The reactivity of the enantiomeric pairs, compounds 153/155 and 154/156, with the cyclic sulfates 157 and 158 were virtually the same. Selectivity for attack at the primary center of the cyclic sulfates 157 and 158 over possible alternative attack at the secondary center by compounds 153-156 was invariably excellent, and in no case were isolable quantities of the regioisomers detected. In the case of the coupling reaction of isopropylidene-protected 1,4-anhydro-4-seleno-D-allitol (153) and L-allitol (155) with the cyclic sulfates 157 and 158, there was a small amount (5-10%) of the stereoisomer formed through electrophilic attack on the E-face of the seleno-D-allitol 153 and the α-face of the seleno-L-allitol 155 to give products that were diastereomeric at the selenonium center, but could not be isolated in pure form. However, this type of minor product was not detected in the reactions of the corresponding thioallitols.

The deprotection of the coupled products 167-174 was carried out by treatment with trifluoroaceiic acid (Scheme 38). After rinsing away the cleaved protecting groups with dichloromethane, the resulting residues were purified by flash chromatography to yield compounds 145-148 as amorphous, hygroscopic solids. In the cases of compounds 171-174, however, some of the benzylidene acetal protecting group (up to 30% by NMR measurements) remained even after prolonged (up to 48 h) treatment with TFA. The remaining benzylidene acetal was eventually cleaved by hydrogenolysis in 80% acetic acid to give the corresponding deprotected products 149-152 as amorphous, hygroscopic solids. The yields of the compounds 149-152 were low, partly due to the adsorption of the products on the Pd/C catalyst. Compounds 145-152 were characterized by spectroscopic methods as indicated in the experimental section below. The MALDI-TOF mass spectra of compounds 145-152 showed major fragmentation peaks (M+Na$^+$—SO$_3$), together with the molecular ion peaks (M+Na$^+$) of much lower intensities.

Scheme 38

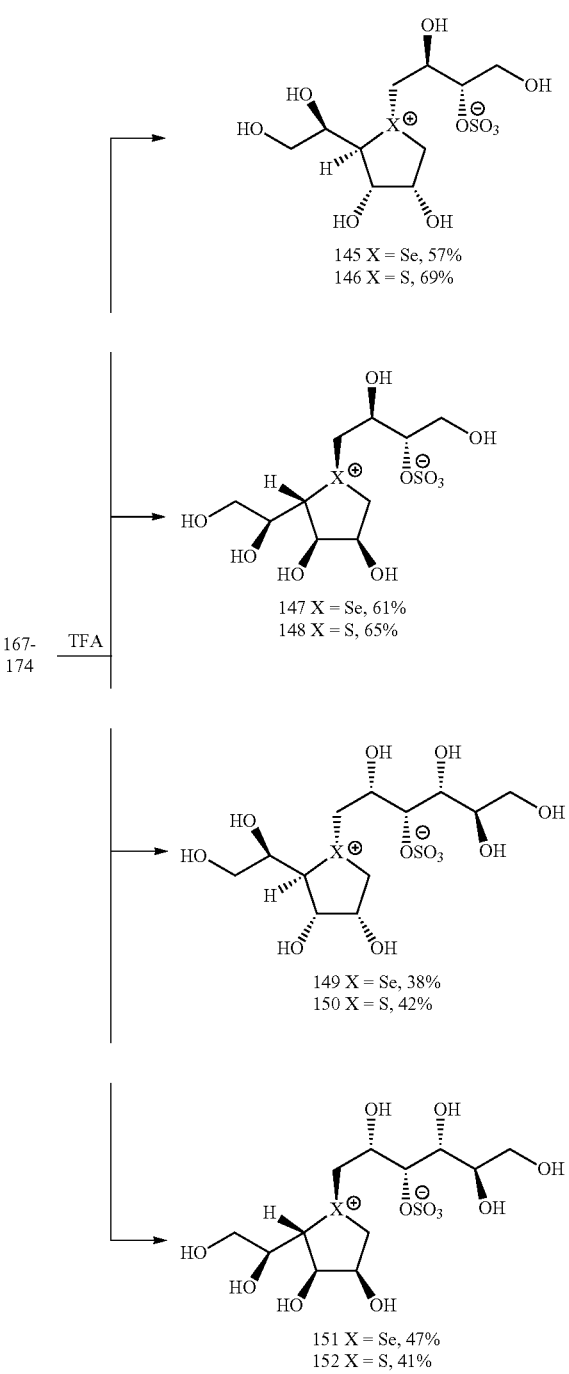

The absolute stereochemistry at the heteroatom center of compounds 145-152 was established by 1D-NOE NMR spectroscopy. For example, in the 1D NOE spectrum of compound 146 (shown below), the H-4 to H-1'b correlation was clearly exhibited, implying that these two hydrogens are syn-facial. Therefore, C-1' of the side chain must be anti to C-5 of the sulfonium salt ring.

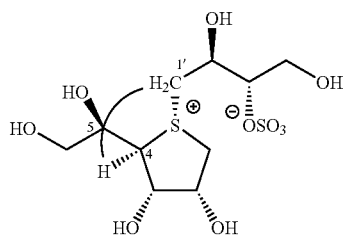

4.5 Synthesis of Salacinol Analogues Containing a Pendant Hydroxymethyl Group In a further embodiment of the invention analogues of salacinol, and its ammonium analogue, were synthesized. These analogues contain an additional hydroxymethyl group at C-1 that was intended to form additional polar contacts within the active site of glycosidase enzymes. The target zwitterionic compounds 175-178 were synthesized by means of nucleophilic attack at the least hindered carbon atom of 2,4-O-benzylidene-L (or D)-erythritol 1,3-cyclic sulfate by 2,5-anhydro-1,3:4,6-di-O-benzylidene-2,5-dideoxy-5-thio (or 1,5-imino)-L-iditol.

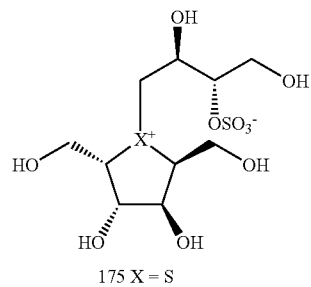

175 X = S
177 X = NH

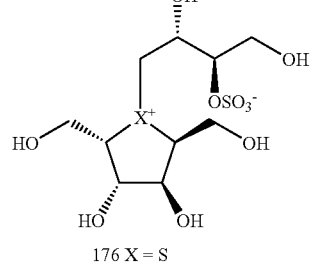

176 X = S
178 X = NH

The general synthetic strategy involved alkylation of the anhydro-alditol at the heteroatom by a cyclic sulfate derivative, whereby selective attack of the heteroatom at the least hindered primary centre would afford the desired target molecules.

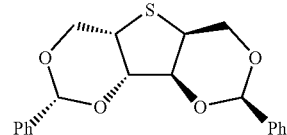

179

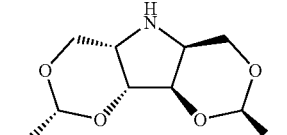

180

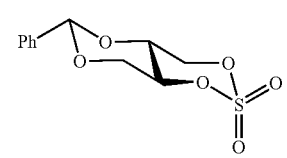

181

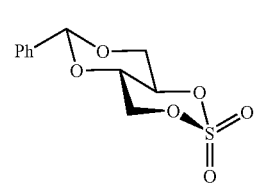

182

The thioether (179) was synthesized according to a reported method[108] by the radical-mediated cyclization of the corresponding 1,5-bis-dithiocarbonate derivative using tributyl tinhydride with α,α-diazoisobutyronitrile (AIBN) as a radical initiator (Scheme 39). The corresponding dithiocarbonate was synthesized, in turn, from 1,3:4,6-di-O-benzylidene-D-mannitol by sequential addition of sodium hydride, carbon disulfide and methyl iodide in THF (Scheme 39).

Scheme 39:

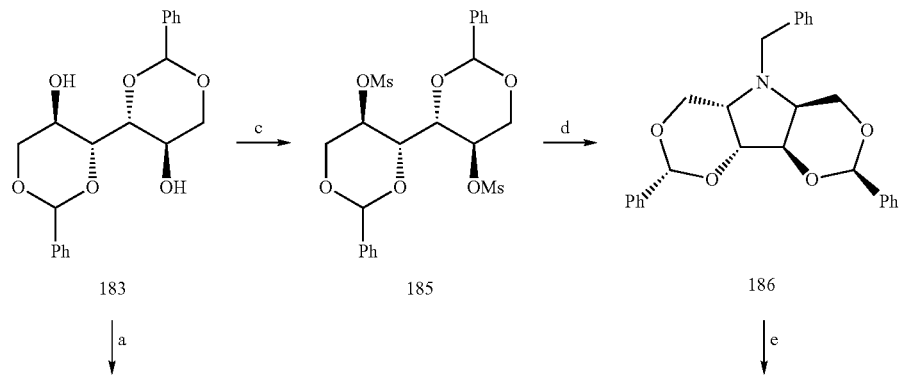

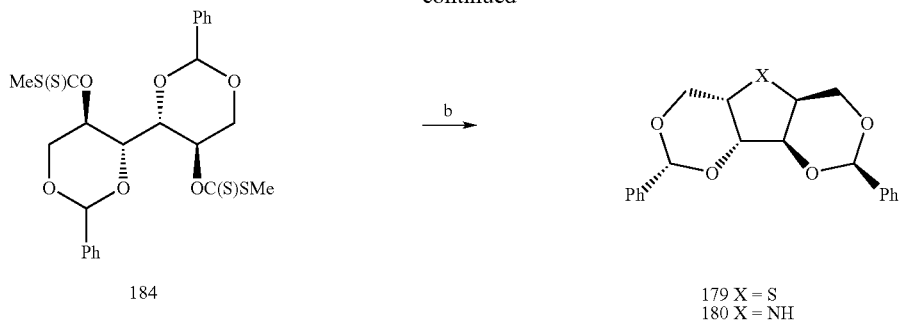

184 a) NaH, CS₂, THF and then MeI (82%)
b) Bu₃SnH, AIBN, toluene, 80° C. (77%)
c) MsCl/Py, CH₂Cl₂ (89%)
d) BnNH₂, 130° C. (84%)
e) Pd(OH)₂/C, H₂, EtOAc:MeOH (90%).

179 X = S
180 X = NH

The synthesis of the $C_2$-symmetric imino alditol (180) was patterned after that of Masaki and co-workers.[109] The C-2 and C-5 hydroxyl groups were activated by mesylation and pyrrolidine ring formation was effected by heating the dimesylate in benzylamine for 12 h at 130° C. Cyclization proceeded with complete inversion at both centers leading to 2,5-dideoxy-2,5-N-benzylimino-1,3;4,6-di-O-benzylidene-L-iditol in 87% yield. Unlike Masaki and co-workers, the inventors chose to use Pd(OH)₂/C and hydrogen for the removal of the N-benzyl group. The origin of this selectivity is unknown at present. The $^{13}$C NMR spectrum of compound 180 exhibited only three carbon resonances, thus confirming that the molecule possessed a $C_2$ axis of symmetry.

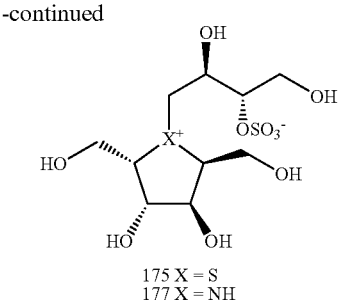

175 X = S
177 X = NH

Reagents and conditions:
a) HFIP, K₂CO₃, 70° C. for 187 (81%) and Acetone, 60° C. for 189 (88%).
b) TFA, for 175 (82%) and Pd/C, aq. acetic acid, H₂ for 177 (86%).

The inventors chose to alkylate compounds 179 and 180 with the protected D- and L-erythritol cyclic sulfates (181 and 182) as the source of the sulfated alkyl side chain, both of which were synthesized from D-glucose.[110,88] Alkylation of the thioether 179 with the cyclic sulfate 181 in 1,1,1,3,3,3-hexafluoroisopropanol (HFIP) proceeded smoothly in 24 h to give the sulfonium salt 187 as the sole product in 81% yield (Scheme 40). Subsequent removal of all three benzylidene groups by treatment with trifluoroacetic acid afforded the target compound 175. The $^1$H NMR and $^{13}$C NMR spectra of 175 were completely assigned with the help of $^1$H-$^1$H COSY, HMQC and HMBC experiments. In a similar manner, the reaction of 179 with the enantiomeric cyclic sulfate 182 yielded the corresponding sulfonium sulfate 188 in 78% yield, and deprotection with TFA produced the desired product 176 (Scheme 41). The $^1$H NMR and $^{13}$C NMR spectra for compound 176 were similar to those of 175. Each of the sulfonium salts (175 and 176) were obtained as a single isomer at the sulfur atom, correlated with the C2 axis of the starting thioether (179).

Scheme 40:

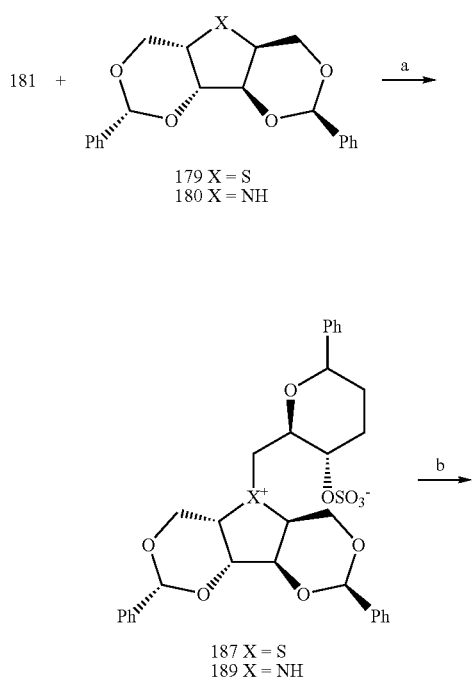

187 X = S
189 X = NH

Scheme 41:

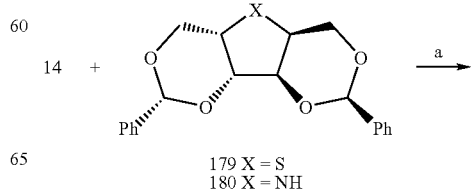

179 X = S
180 X = NH

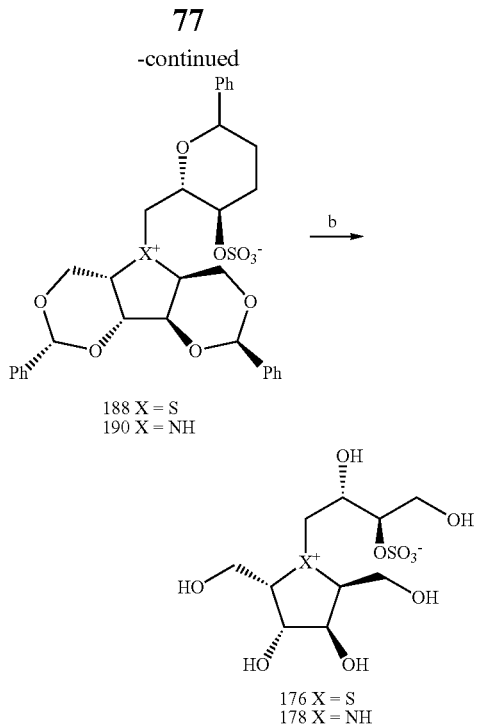

188 X = S
190 X = NH

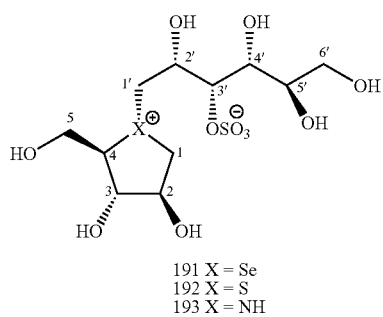

176 X = S
178 X = NH

Reagents and conditions:
a) HFIP, K$_2$CO$_3$, 70° C. for 188 (78%) and Acetone, 60° C. for 190 (80%).
b) TFA, for 176 (79%) and Pd/C, aq. acetic acid, H$_2$ for 178 (81%).

The amine 180 reacted with the L-cyclic sulfate 181 in dry acetone containing K$_2$CO$_3$ to give the ammonium salt 189 in 88% yield. Deprotection was accomplished with Pd/C/H$_2$ in aqueous acetic acid to effect the hydrogenolytic cleavage of the benzylidene groups, to give the target compound 177. The $^1$H NMR resonances for compounds were extremely broad in D$_2$O, but sharpened when the sample was made basic with K$_2$CO$_3$. Analogously, the reaction of amine 180 with the D-cyclic sulfate (182) produced the corresponding ammonium salt 190 in 80% yield; subsequent deprotection by hydrogenolysis, as before, gave the desired product, 178.

4.6 Chain-Extended Analogues of Salacinol Having Differing Stereochemistry at the Stereogenic Centers In a further embodiment, the inventors disclose synthetic routes to six-carbon chain homologues, their selenium and nitrogen congeners, and the corresponding diastereomers resulting from changes in stereochemistry at the stereogenic centers in the heterocyclic ring (191-196).

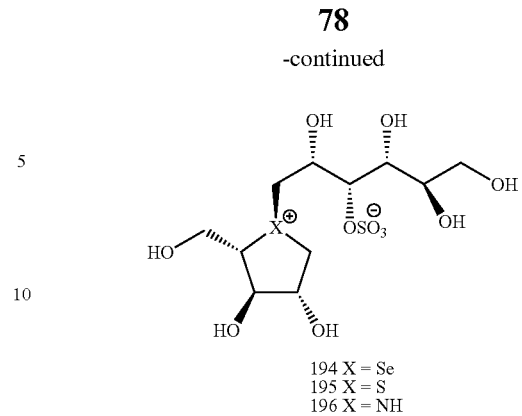

194 X = Se
195 X = S
196 X = NH

Retrosynthetic analysis indicated that the analogues 191-196 could be synthesized by alkylation of a protected anhydro-alditol at the ring heteroatom with a terminal 1,3-cyclic sulfate derived from D-sorbitol (Scheme 42).

Scheme 42

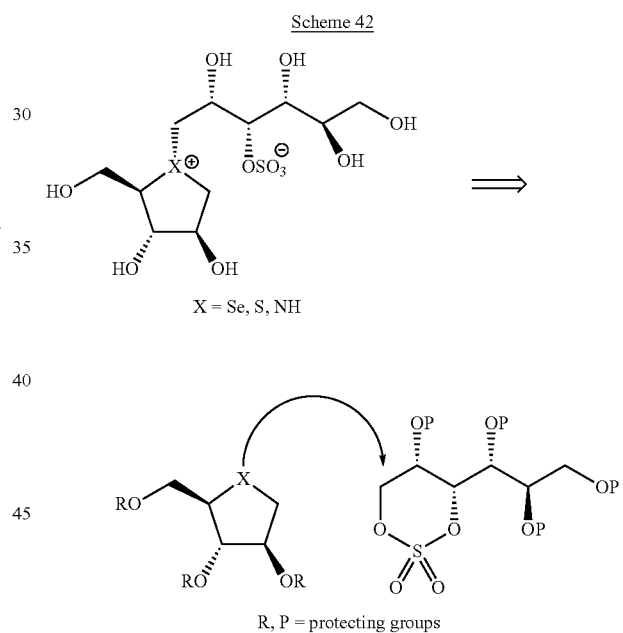

X = Se, S, NH

R, P = protecting groups

However, the choice of protecting groups for the cyclic sulfate merited careful consideration, especially in the case of the selenonium analogues. The inventors' previous studies[26,88,89] had suggested that the p-methoxybenzyl ether was the most appropriate protecting group for the anhydroalditol moiety. The inventors' previous work also suggested that the release of ring strain in the opening of a cyclic sulfate was beneficial. Accordingly, the inventors envisioned that the cyclic sulfate 197, in which the 2,4-positions were protected by a benzylidene acetal would serve this function. The 5,6-positions could be protected with an isopropylidene acetal. After the coupling reactions, the products could then be readily deprotected by simple treatment with trifluoroacetic acid.

191 X = Se
192 X = S
193 X = NH

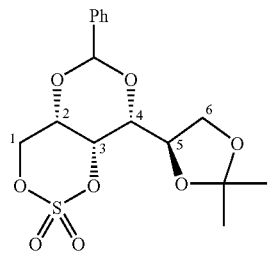

197

The synthesis of the cyclic sulfate 197, as depicted in Scheme 43, started from the commercially available D-sorbitol (198). Following the reported method by Kuszmann et al.,[98] D-sorbitol was first treated with benzaldehyde in hydrochloric acid and water to give 2,4-O-benzylidene-D-glucitol (199). Compound 199 was then reacted with 2,2-dimethoxypropene to afford the 2,4-O-benzylidene-5,6-O-isopropylidene-D-glucitol (200).[98] The glucitol derivative 200 was then converted to the cyclic sulfite by treatment with thionyl chloride and pyridine, and the sulfite was then oxidized with sodium periodate and ruthenium(III) chloride as a catalyst to yield the desired cyclic sulfate 197, as a crystalline solid in 75% yield.

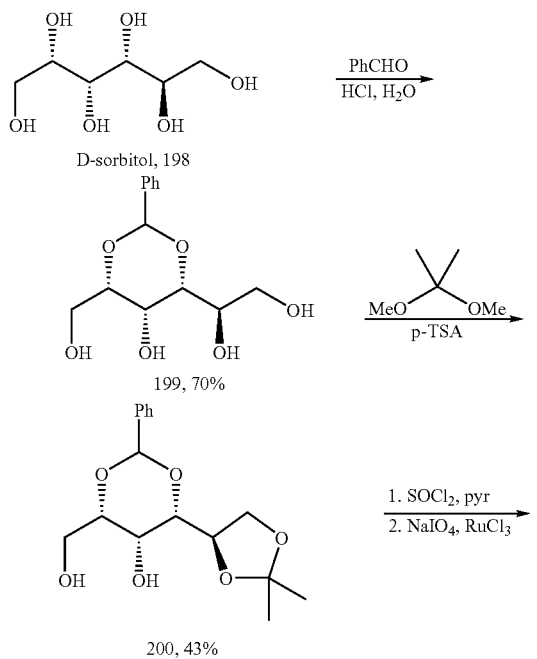

The coupling reactions of the cyclic sulfate 197 with the protected selenoarabinitols and thioarabinitols were investigated first. The PMB-protected D-selenoarabinitol 201 and D-thioarabinitol 202 were prepared by methods described in the inventors' earlier work.[53,88,89] The cyclic sulfate 197 was reacted with D-selenoarabinitol 201[88,89] and D-thioarabinitol 202[53], to give the protected selenonium and sulfonium compounds 203 and 204, respectively (Scheme 44). The solvent 1,1,1,3,3,3-hexafluoroisopropanol (HFIP) offered significant advantage, as observed in the inventors' previous work.[53,26,88,89] For example, while the coupling reaction of 201 with the cyclic sulfate 197 did not proceed in acetone at 100° C., it proceeded in HFIP at 65° C. within 12 hours to give 203 in 95% yield.

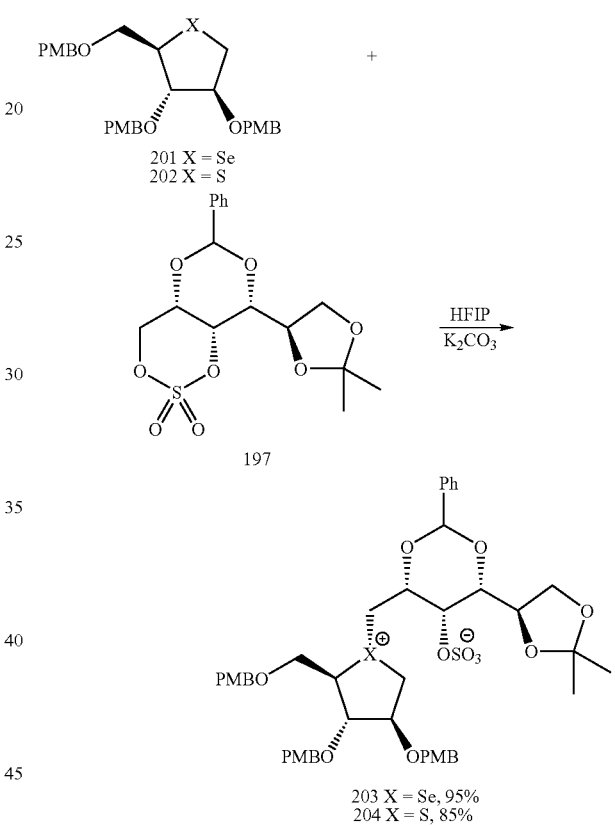

The PMB-protected L-selenoarabinitol 205 and L-thioarabinitol 206 were prepared as described for the corresponding D-isomers 201 and 202, respectively.[88,89] The cyclic sulfate 197 was reacted with L-selenoarabinitol 159 and L-thioarabinitol 206 in HFIP, to give the corresponding protected selenonium and sulfonium compounds 207 and 208, respectively (Scheme 45).

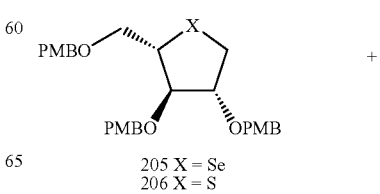

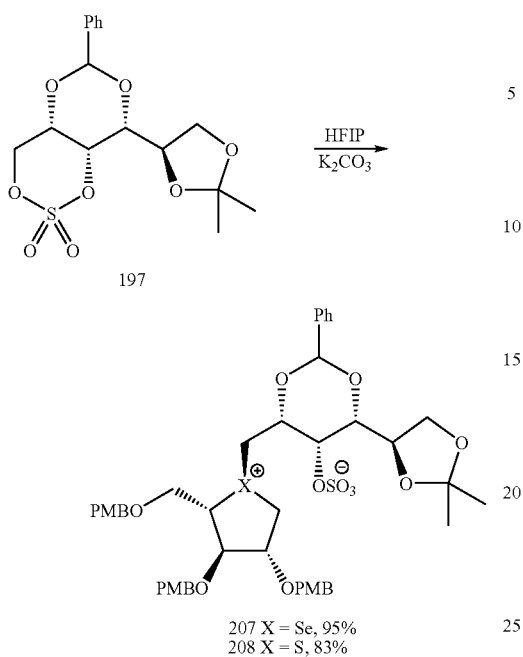

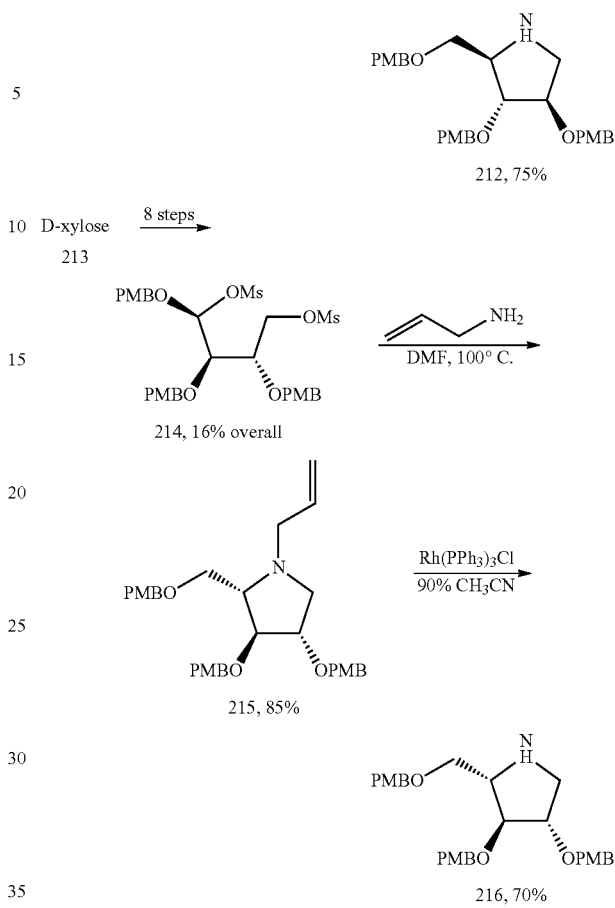

The inventors turned next to the synthesis of the corresponding chain-extended nitrogen analogues. The synthesis of the PMB protected D- and L-iminoarabinitols 212 and 216 took advantage of the inventors' established method for the synthesis of blintol (Scheme 46). Starting from L-xylose and D-xylose, respectively, the corresponding dimesylates 210 and 214[88,89] were prepared in overall yields of 21% and 16%, respectively. The dimesylates 210 and 214 were subsequently treated with allylamine and heated to 90° C. in DMF for 12 hours to yield the allylimino compounds 211 and 215, respectively. Compounds 211 and 215 were refluxed in 90% aqueous acetonitrile with Wilkinson's catalyst for 4 hours to afford the desired D-iminoarabinitol 212 and L-iminoarabinitol 216, respectively.

The coupling reactions of 212 and 216 with the cyclic sulfate 197 were then carried out in acetone, as described previously for the synthesis of ghavamiol.[16] The reactions proceeded smoothly at 55° C. to give the corresponding coupling products 217 and 219, respectively (Scheme 47).

Scheme 46

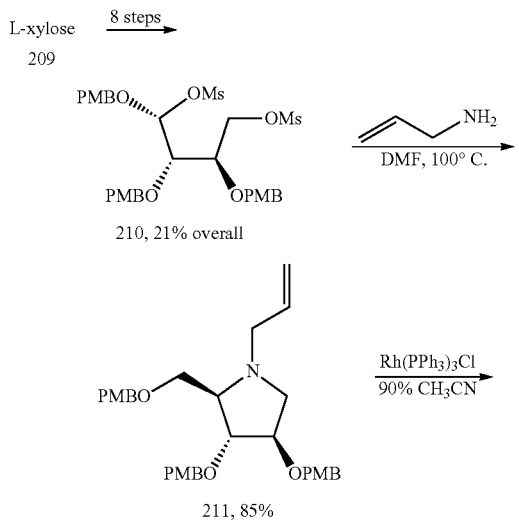

Scheme 47

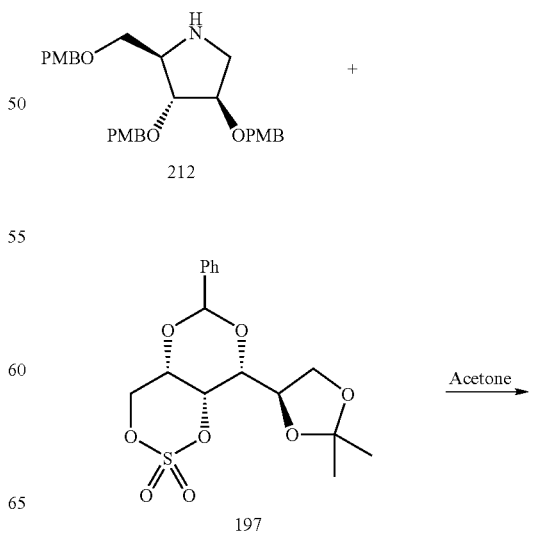

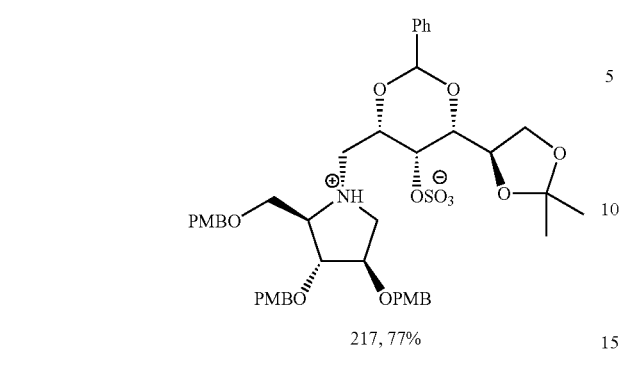

217, 77%

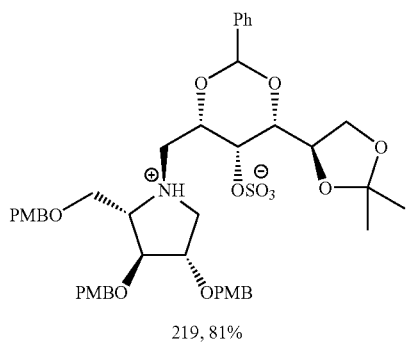

219, 81%

The reactivities of the seleno-, thio-, and iminoarabinitols with the cyclic sulfate 197 varied slightly. The iminoarabinitols were the most reactive, while the thioarabinitols were the least reactive of the three. Selectivity for attack of the seleno-, thio-, and iminoarabinitol derivatives at the primary carbon of the cyclic sulfate over possible alternative attack at the secondary carbon was invariably excellent and in no case were isolable quantities of the regioisomers detected. Of note, in the case of the coupling reactions of selenoarabinitols 201 and 205 with the cyclic sulfate 197, there was a small amount (less than 10%) of the stereoisomers formed through electrophilic attack on the β-face of the D-selenoarabinitol 201 and the α-face of the L-selenoarabinitol 205 to give products that were diastereomeric at the selenonium center.

The deprotection of the coupling products 203, 204, 207, 208, 217, and 219 was carried out by treatment with trifluoroacetic acid (Scheme 48). The resulting residues were purified by flash chromatography to yield compounds 191 to 196 as amorphous, hygroscopic solids.

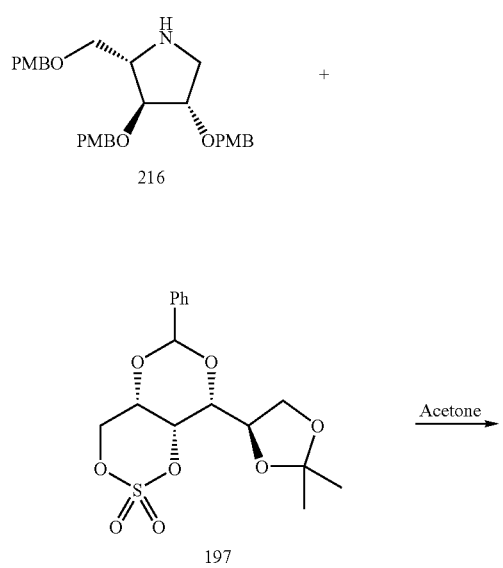

Scheme 48

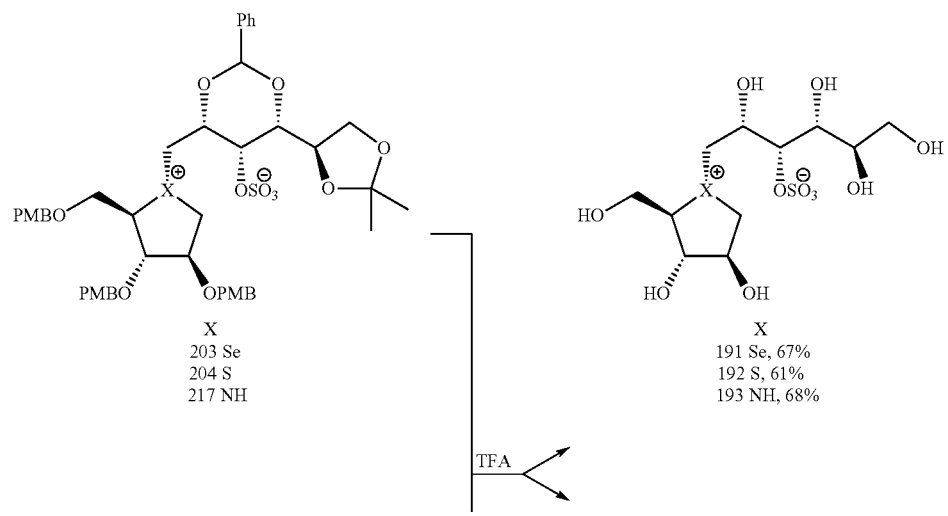

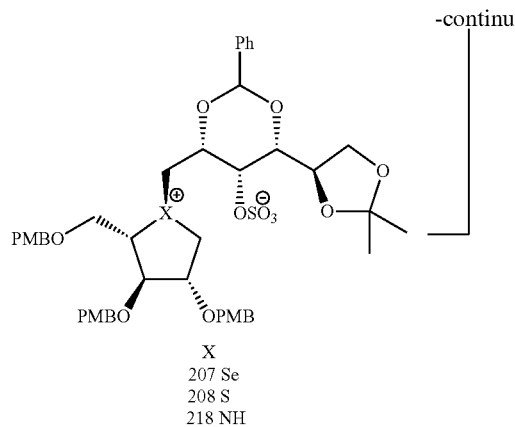

X
207 Se
208 S
218 NH

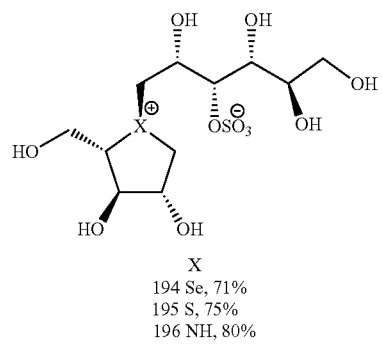

X
194 Se, 71%
195 S, 75%
196 NH, 80%

The absolute stereochemistry at the heteroatom center of compounds 191-196 was established by NOESY NMR spectroscopy (FIG. 8). For example, in the NOESY spectrum of compound 192, the H-4 to H-1'b correlation was clearly exhibited, implying that they are syn-facial. Therefore, C-1' of the side chain must be anti to C-5 of the sulfonium salt ring (FIG. 8). However, the correlation of H-1'a or H-1'b with H-1a, 1b could not be clearly established owing to overlap of signals.

As a final point of interest, we comment on the inhibitory activities of the compounds synthesized in this study against recombinant human maltase glucoamylase (MGA), a critical intestinal glucosidase involved in the processing of oligosaccharides of glucose into glucose itself. Compounds 191 and 193, with the D-arabinitol configuration in the heterocyclic ring displayed by salacinol, have Ki values of 41 and 26 μM, respectively. In contrast, the sulfur analogue 192 is not active. Of compounds 194-196, with the unnatural L-arabinitol configuration in the heterocyclic ring, the sulfur and nitrogen congeners 195 and 196 are active, with $K_i$ values of 25 and 5 μM, respectively.

4.7 Further Chain-Extended Analogues of Salacinol and Blintol

In a further embodiment of the invention, the synthesis of new chain-extended sulfonium and selenonium salts of 1,4-anhydro-4-thio-D-arabinitol, analogues of the salacinol are described. Nucleophilic attack at the least hindered carbon atom of 2,5-di-O-p-methoxybenzyl-4,6-O-benzylidene-D-mannitol-1,3-cyclic sulfate by 2,3,5-tri-O-p-methoxybenzyl-1,4-anhydro-4-thio-(or 4-seleno)-D-arabinitol gave the sulfonium and selenonium sulfates, respectively. Subsequent deprotection with trifluoroacetic acid yielded the target compounds. In these analogues, an extended polyhydroxylated aliphatic side chain has been incorporated while maintaining the stereochemistry of C-2' and C-3' of salacinol. These compounds were designed with the expectation that they would bind with higher affinity to glucosidases than salacinol because the extra hydroxyl groups in the acyclic chain would make favorable polar contacts within the active site. All three of the compounds inhibited recombinant human maltase glucoamylase, one of the key intestinal enzymes involved in the breakdown of glucose oligosaccharides in the small intestine, with Ki values in the micromolar range, thus providing lead candidates for the treatment of Type 2 diabetes.

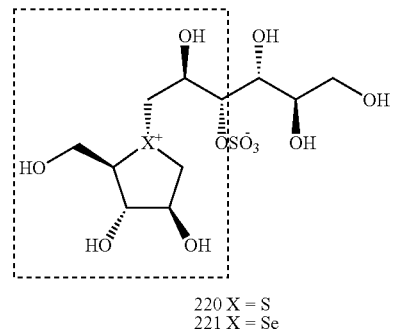

220 X = S
221 X = Se

Retrosynthetic analysis revealed that the target zwitterionic molecules 220 and 221 could be synthesized by alkylation at the sulfur or selenium atom of suitably protected anhydro-alditols. The alkylating agent could be a cyclic sulfate whereby selective attack of the heteroatom at the least hindered primary center would afford the desired compounds.

Scheme 49

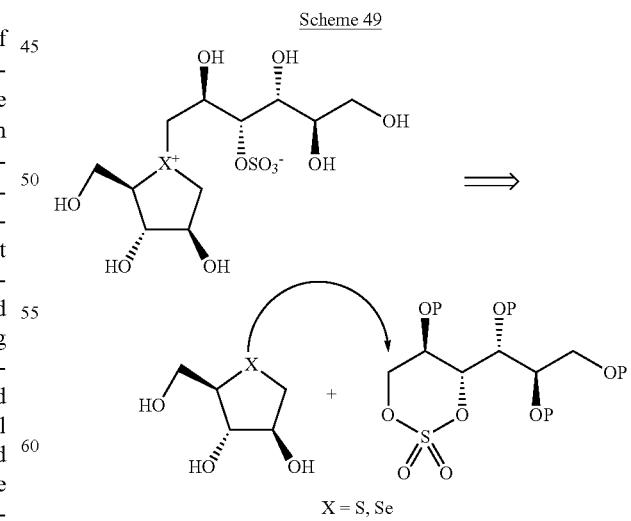

X = S, Se

Indeed, opening of 4,6-O-benzylidene-2,5-di-p-methoxybenzyl-D-mannitol-1,3-cyclic sulfate 222 by 2,3,5-tri-O-p-methoxybenzyl-1,4-anhydro-4-thio-(223) or 4-seleno-(224)-

D-arabinitol proceeded smoothly to give the corresponding coupled products. The reaction

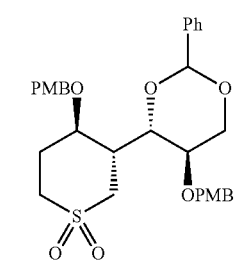

222

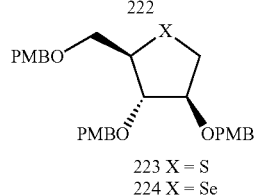

223 X = S
224 X = Se of the selenium compound, 224 afforded R/S isomers at the stereogenic selenium center that were separated and characterized independently.

The thioarabinitol, 223 and selenoarabinitol, 224 were synthesized from L-xylose according to the reported procedure.[53,88] The desired cyclic sulfate (222) was synthesized from D-mannitol in five steps, as depicted in Scheme 50. Due to the difficulties experienced before in hydrogenolysis of the benzyl ethers in sulfonium and selenonium salts, the inventors chose the acid labile protecting groups, p-methoxybenzyl and benzylidene groups instead of benzyl ethers. The reaction of 1,3:4,6-di-O-benzylidene D-mannitol Scheme 50: a) NaH, PMB-Cl, DMF (83%) b) PTSA, MeOH (73%) c) $SOCl_2$, $Et_3N$, $CH_2Cl_2$ (76%) d) $NaIO_4$, $RuCl_3 \cdot 3H_2O$, $CH_3CN:CCl_4$ (1:1) (86%).

(225)[111] with p-methoxybenzyl chloride (PMB-Cl) in the presence of NaH in DMF furnished the fully protected mannitol derivative, 226. One benzylidene group was then selectively removed using mild acetolysis with catalytic p-toluenesulfonic acid (PTSA) in methanol. The reaction proceeded smoothly to give the corresponding diol, 227 in 73% yield. The target compound was then obtained by treatment of the diol with thionyl chloride in the presence of triethylamine to give a mixture of distereomeric sufites (228), followed by their oxidation with $NaIO_4/RuCl_3$.

Scheme 51.

222 + 223 →ᵃ

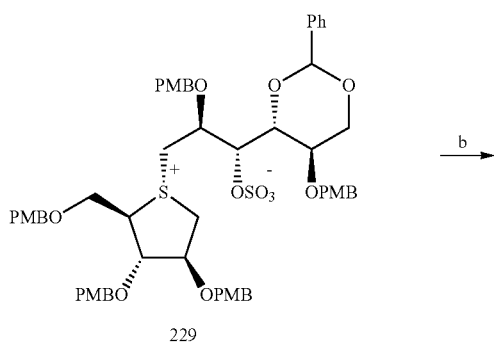

229

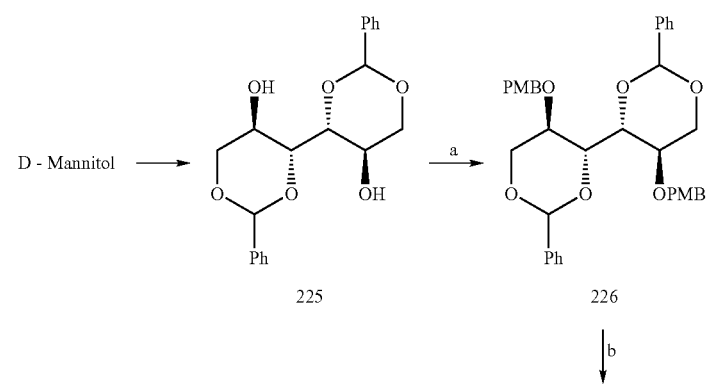

225 → 226

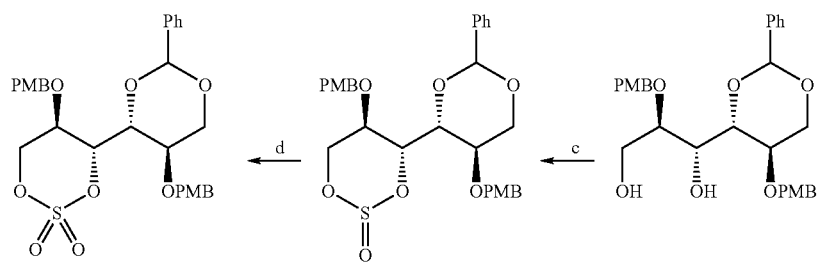

222    228    227

-continued

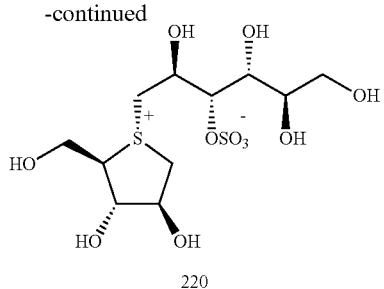

220 a) K₂CO₃, HFIP, 65-70° C. (77%) b) aq. TFA

The coupling reaction of 2,3,5-tri-O-p-methoxybenzyl-1,4-anhydro-4-thio-(223) and 4-seleno-D-arabinitol (224), with the cyclic sulfate 222 was then investigated. Thus, the mixture of the thioether (223) and the cyclic sulfate in 1,1,1,3,3,3-hexafluoroisopropanol (HFIP) was heated at 65-70° C. in the presence of anhydrous potassium carbonate for 36 h to give the sulfonium salt, 229 as the sole product in 77% yield. Deprotection of the coupled product using aqueous trifluoroacetic acid (TFA) gave the desired compound 220 in 82% yield. The zwitterionic compound was assigned to be the isomer with a trans relationship between C-5 and C-1' by analysis of transient one-dimensional nuclear overhauser enhancement (NOE) experiments which showed a correlation between H-1' and H-4.

The selenium congener 221 was synthesized in an analogous manner to that described for the sulfonium analogue. The coupling reaction of the selenoether, 224 with the cyclic sulfate 222 in HFIP at 70° C. afforded the selenonium salt as a mixture of diastereomers 230 and 231 in a 5:2 ratio, as judged by the ratio of benzylidene proton resonances in the ¹H NMR spectrum of the crude product. This is likely due to a longer

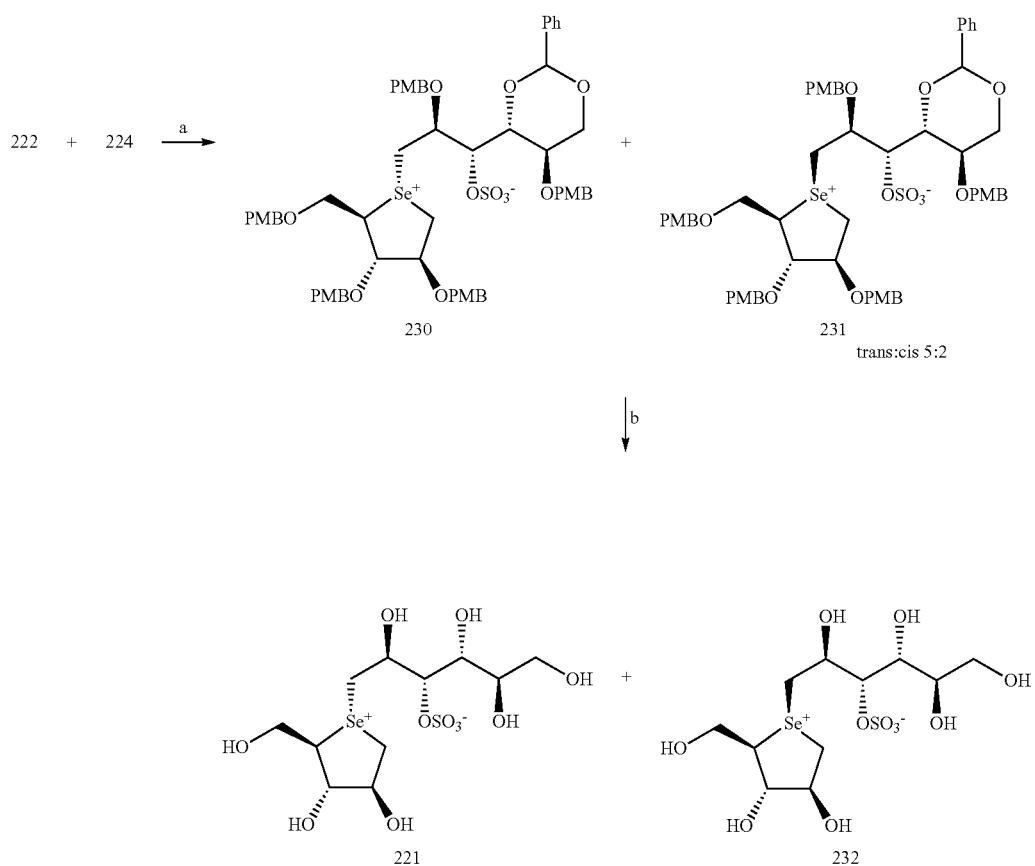

a) K₂CO₃, HFIP, 65-70° C. b) aq. TFA

C—Se than C—S bond that leads to less steric hindrance during C—Se bond formation. Both isomers were successfully separated by column chromatography and treated separately with TFA to give the desired selenonium salts 221 and 232 in quantitative yields. The major isomer, 221 was assigned to be that with a trans relationship between C-5 and C-1' by means of a 1D-transient NOE experiment.

As a final point of interest, the inhibitory activities of the compounds synthesized in this example against recombinant human maltase glucoamylase (MGA), a critical intestinal glucosidase involved in the processing of oligosaccharides of glucose into glucose itself, were examined. Compounds 220 and 221, with the same configuration at the stereogenic heteroatom center (and the same configuration as salacinol or blintol) have Ki values of 0.65±0.10 and 0.94±0.06 µM, respectively. The analogues 232, with the diastereomeric configuration at the selenium center is also active, with a $K_i$ value of 2.4±0.7 µM.

4.8 D-Lyxitol and D-Ribitol Derived Analogues of Salacinol

The inventors have also synthesized salacinol analogues in which the hetroalditol ring is D-lyxitol (233) and D-ribitol (234), and in which the stereochemistry at C-3 and C-2, respectively, are inverted. These compounds are useful for the study of structure-activity relationships with glycosidase enzymes.

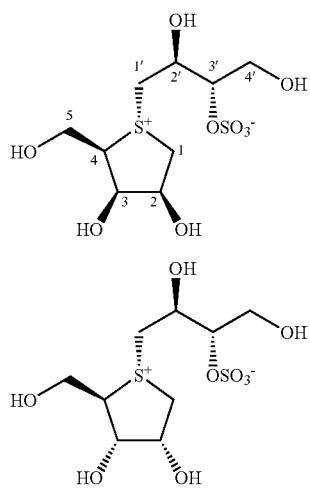

The target compounds 233 and 234 could be synthesized by alkylating the anhydro-alditol derivatives at the ring sulfur atom (Scheme 53). This route was chosen in order to provide flexibility in synthesizing compounds having different configurations of the sugar rings. The alkylation of 1,4-anhydro-2,3,5-tri-O-p-methoxybenzyl-4-thio-D-lyxitol (235) and 1,4-anhydro-2,3,5-tri-O-p-methoxybenzyl-4-thio-D-ribitol (236) with 2,4-O-benzylidene-L-erythritol-1,3-cyclic sulfate (237), previously synthesized in the inventors' laboratory,[25,88] should afford compounds 233 and 234, respectively.

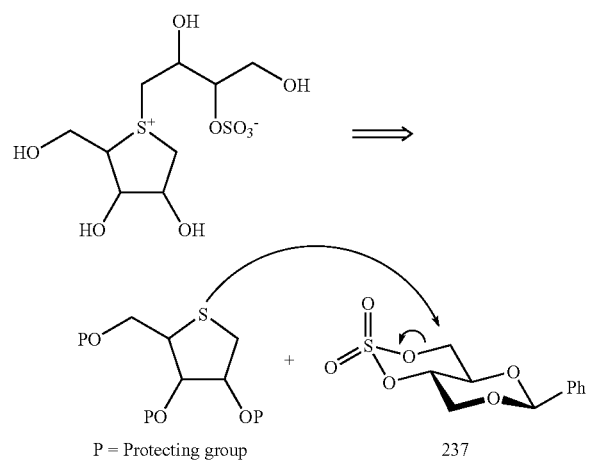

The required compound 235 was prepared from commercially available D-lyxose as shown in Scheme 54. 2,3,5-Tri-O-benzyl-D-lyxofuranoside (238) was prepared in three steps starting from D-lyxose, as described by Postema et al.[99] Reduction of 238 with sodium borohydride afforded the diol 239 in 91% yield. Selective protection of the primary hydroxyl group using tert-butyldimethylsilylchloride gave 240 in 93% yield. The D-lyxitol derivative 240 was converted to the L-ribitol derivative 241 by a Mitsunobu reaction using p-nitrobenzoic acid. Deprotection of the p-nitrobenzoyl and tert-butyldimethylsilyl groups using sodium methoxide and tetrabutylammonium fluoride, respectively, gave the diol 242. Although the preparation of 242 from L-ribose was reported by Elie et al,[100] the method was not practical for large scale synthesis since L-ribose is very expensive. Hence, the inventors started with less expensive D-lyxose to synthesize 242 by inverting the configuration at C-4 using a Mitsunobu reaction. Compound 242 was converted to the dimesylate using methanesulfonyl chloride in pyridine and the dimesylate was treated with sodium sulfide to give 243 in 87% yield. In order to eliminate the problematic hydrogenolysis step of removing the benzyl ether groups after the coupling reaction between benzyl-protected thio-D-lyxitol and 237, the inventors decided to use p-methoxybenzyl (PMB) protecting groups. The acid-sensitive PMB group is a suitable choice since the benzylidene group from the L-cyclic sulfate is also acid labile and both could be cleaved in one pot by acid hydrolysis after the coupling reaction between 237 and 235.53 Hence, the benzyl protecting group was cleaved using Birch reduction to give the triol 244 in 86% yield. Reprotection of the triol 244 with PMB groups afforded the required compound 235 in 94% yield.

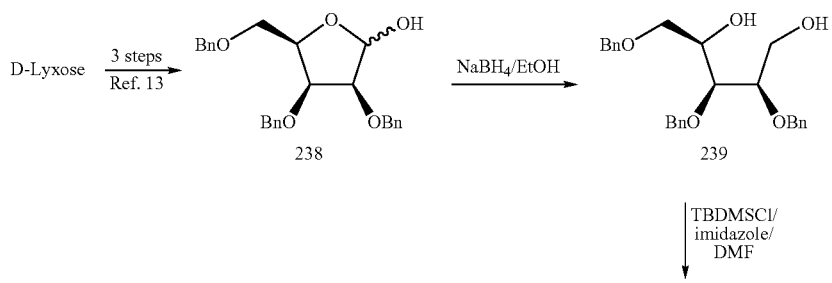

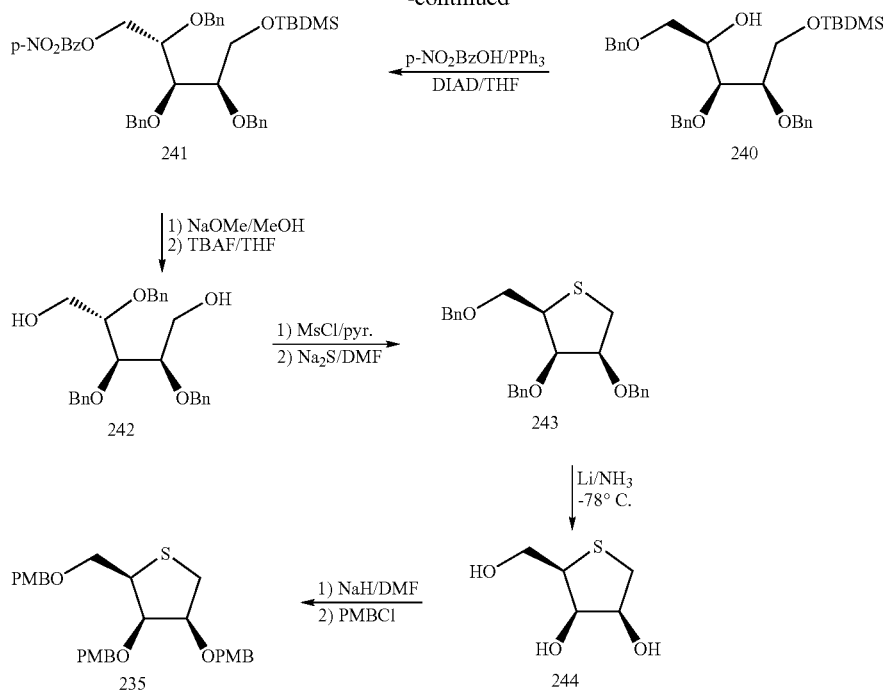

The required compound 236 was synthesized from commercially available D-ribose (Scheme 55). Methyl 2,3,5-tri-O-benzyl-D-ribofuranoside (245 was prepared in two steps starting from D-ribose, as described by Barker and Fletcher.[101] 1,4-Anhydro-4-thio-D-ribitol (246) was prepared from 245 in nine steps as described by Naka et al.[102] PMB protection of 246 afforded the desired compound 236 in 91% yield. Although the synthesis of 236 was reported earlier by Minakawa et al.,[103] the inventors employed an alternative route (Scheme 55) similar to that described above for the preparation of 235.

The inventors next turned the inventors' attention to the coupling reaction. Thus, compound 247 was prepared by alkylation of PMB-protected anhydro-4-thio-D-lyxitol 235 with the benzylidene-protected L-cyclic sulfate 237 in 1,1,1,3,3,3-hexafluoro-2-propanol (HFIP) containing $K_2CO_3$ at 70° C. in 90% yield (Scheme 56). The choice of HFIP as a solvent was based on the inventors' previous work where the yield of the coupling reaction was highest when HFIP was used as solvent.[53] $K_2CO_3$ was used to prevent the hydrolysis of the cyclic sulfate.[25] The stereochemistry at the sulfur centre was assigned with the aid of a NOESY experiment which showed a correlation between H-4 and H-1', suggesting that the L-erythritol side chain and the C-4 substituent were trans to each other. Deprotection of 247 proceeded smoothly in aqueous trifluroacetic acid (TFA) to give the final compound 233 in 78% yield.

Scheme 55

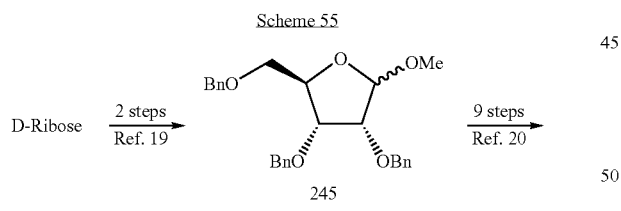

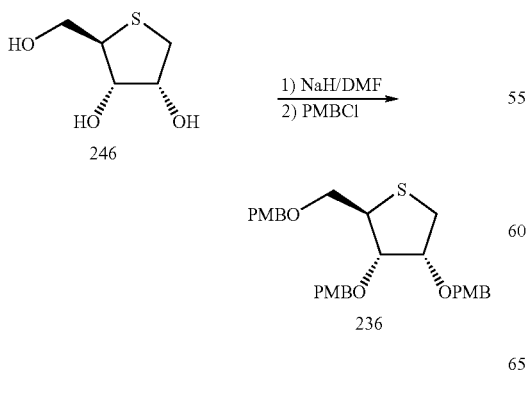

Scheme 56

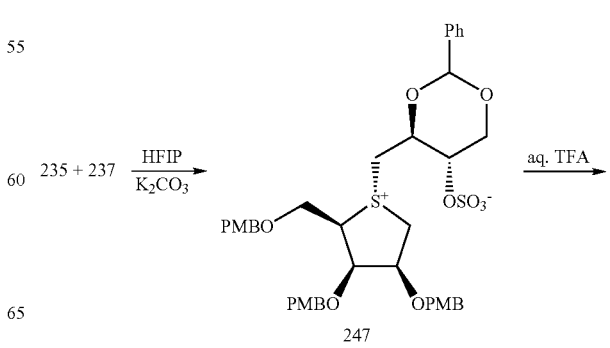

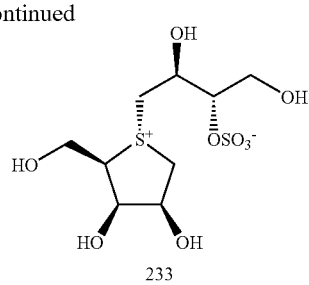

Compound 234 was obtained in a similar manner by coupling of 236 with the L-cyclic sulfate 237 to produce the sulfonium salt 248 in 92% yield (Scheme 57). Deprotection with aqueous TFA produced compound 234 in 81% yield. Proof of stereochemistry at the stereogenic sulfur atom was established as before with a NOESY experiment.

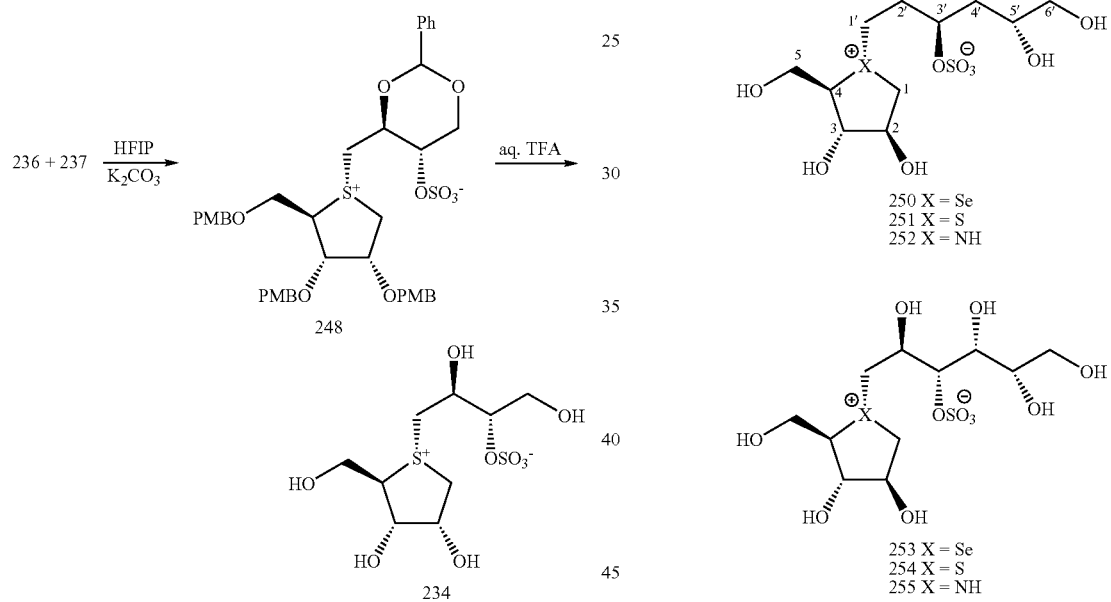

As a final point of interest, the inventors screened the compounds synthesized in this study against recombinant human maltase glucoamylase (MGA), a critical intestinal glucosidase involved in the processing of oligosaccharides of glucose into glucose itself. Compounds 233 and 234 were not effective inhibitors of MGA, whereas salacinol inhibited this enzyme with a Ki value of 0.19 μM. It would appear that the D-arabinitol configuration in the heterocyclic ring displayed by salacinol may be important for activity.

4.9 New Synthetic Route for Syntheis of Chain-Extended Selenium Sulfur and Nitrogen Analogues In a further embodiment of the invention a new synthetic route for syntheis of chain-extended selenium, sulfur and nitrogen analogues was designed. The inventors have postulated that that the stereochemistry at the stereogenic center at the 2' position of the alditol side chain, namely the S-configuration, may be critical for inhibitory activity. Thus, the chain-extended sulfonium ions 251 and 254 (see structures below), with the 2'-S-configuration were active against human maltase glucoamylase with $K_i$ values of similar magnitudes as salacinol. However, the synthetic route that afforded compounds 251 and 254 was not readily applicable to the syntheses of the corresponding selenium analogues, and did not afford these compounds. Since the selenium congener of salacinol, blintol, was shown to be a more potent glucosidase inhibitor than salacinol as shown above, the synthesis of chain-extended selenium analogues of salacinol was of particular interest. Accordingly, the inventors designed an alternative synthetic route and report herein its application to the synthesis of the selenium, sulfur, and nitrogen analogues 250-255.

The synthetic strategy was analogous to that used for the synthesis of salacinol (1) and related structures described above. It involved the opening of a 1,3-cyclic sulfate ring by nuclophilic attack of a protected heteroether (Scheme 58).

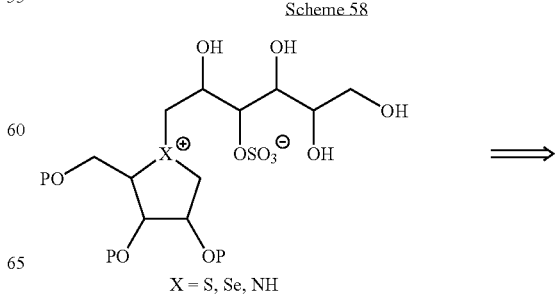

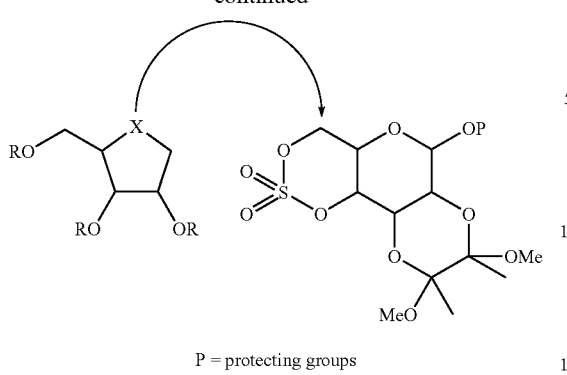

P = protecting groups

In other embodiments of the invention relating to synthesis of the sulfonium analogues 251 and 254, benzyl groups were used to protect both anhydroheteroalditols and cyclic sulfates. Hydrogenolysis was used to remove the benzyl protecting groups. However, the corresponding synthesis of the selenium analogues was expected to be difficult owing to poisoning of the catalyst, as shown in the inventors' previous work on the synthesis of the selenium analogues of salacinol.

In this embodiment of the invention p-Methoxybenzyl (PMB) groups were used to protect the 2, 3, and 5-positions in the heteroanhydroalditols. However, for the desired 1,3-cyclic sulfates derived from D-galactose and D-glucose, PMB groups were deemed to be unsuitable since they were susceptible to oxidation. Methods for selective protection of vicinal trans diequatorial diols are rare. In recent years, Ley and coworkers[112] have introduced dispiroketals as protecting groups for trans diequatorial 1,2-diols, the high selectivity in the protection of trans diequatorial 1,2-diols being attributed to the combination of two factors: the formation of the sterically less demanding trans ring junction and the control of configuration at the two acetal centers by the operation of anomeric effects.[112] Recently, Hense et al.[113] reported a convenient method to utilize butane diacetal (BDA) protecting groups for trans diequatorial 1,2-diols. The inventors envisioned the use of butane diacetal (BDA) protecting groups for the cyclic sulfates 259 and 260. The inventors' previous work also suggested that the release of additional ring strain in the opening of a cyclic sulfate was beneficial.[25,88,29] The BDA at the 2,3-positions of the cyclic sulfates 259 and 260 would thus play a dual role as a protecting groups and a reaction facilitator for the coupling reactions with the anhydro heteroalditols 256-258. After the coupling reactions, the BDA and PMB groups could be readily removed by treatment with trifluoroacetic acid.

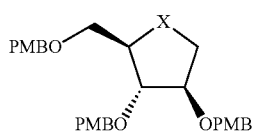

256. X = Se
257. X = S
258. X = NH

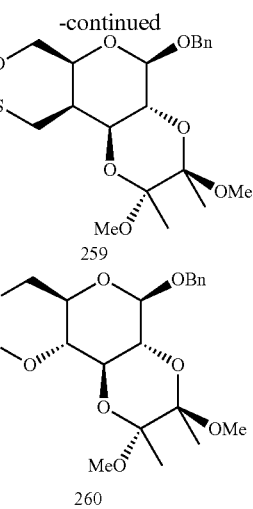

The synthesis of the BDA-protected cyclic sulfate (259) started from benzyl β-D-galactopyranoside (261)[114] (Scheme 2). Following the procedure described by Hense et al. for the preparation of similar compounds,[113] compound 261 was refluxed with 2,3-butanedione, trimethyl orthoformate, and methanol, with CSA as a catalyst for 12 h. The resulting benzyl 2,3-O-[(2R,3R)-2,3-dimethoxybutane-2,3-diyl]-β-D-galactopyranoside 262 was then reacted with thionyl chloride to afford the corresponding cyclic sulfites, which were subsequently oxidized with sodium periodate and RuCl₃ to afford the cyclic sulfate 259 in 67% yield (Scheme 59).

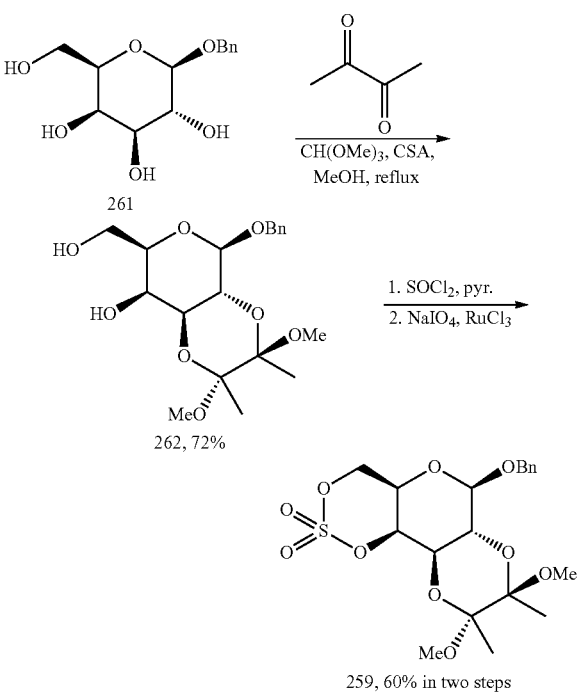

The synthesis of the BDA-protected cyclic sulfate (260) started from the benzyl β-D-glucopyranoside (263)[115] (Scheme 3). Compound 263 was refluxed with 2,3-butanedione, trimethyl orthoformate, and methanol, with CSA as a catalyst for 12 h, to give a mixture of the desired benzyl 2,3-O-[(2R,3R)-2,3-dimethoxybutane-2,3-diyl]-β-D-glucopyranoside (264) and benzyl 3,4-O-[(2R,3R)-2,3-dimethoxybutane-2,3-diyl]-β-D-glucoopyranoside (265). The ratio of products 264:265 was 1.8:1, which suggested that the reaction had not proceeded with any significant regioselectivity.[113] Fortunately, compound 264 could be readily separated from the reaction mixture by column chromatography. The purified compound 264 was treated with thionyl chloride to afford the cyclic sulfites, which were subsequently oxidized by sodium periodate and RuCl$_3$ to afford the corresponding cyclic sulfate 260 in 67% yield. (Scheme 60).

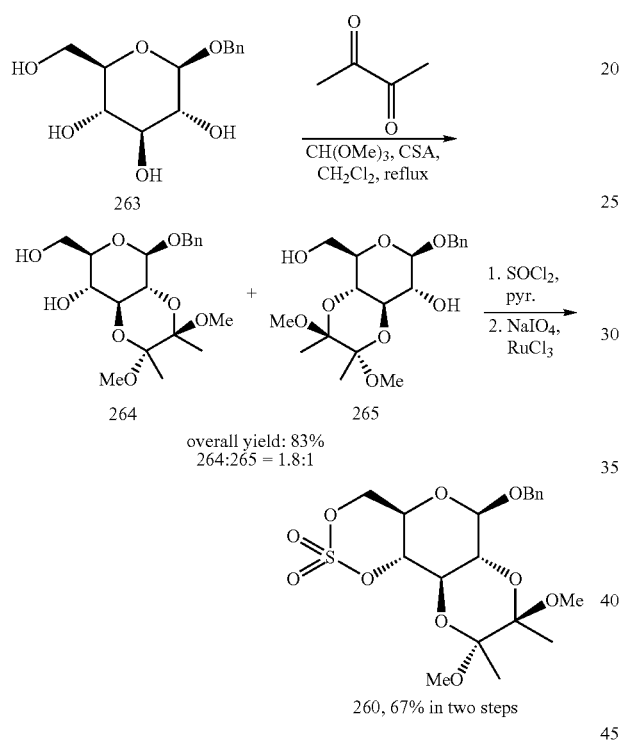

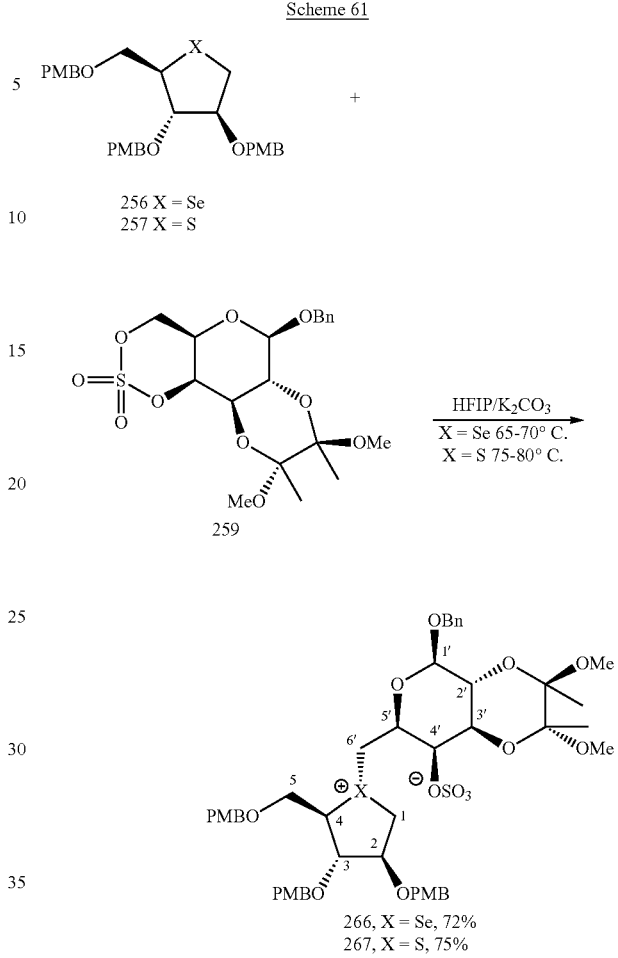

The coupling reactions of the PMB-protected 1,4-anhydro-4-seleno-D-arabinitol (256) and 1,4-anhydro-4-thio-D-arabinitol (257) with the cyclic sulfate 259 were carried out in 1,1,1,3,3,3-hexafluoroisopropanol (HFIP), which offers significant advantage compared with other solvents.[25,53,26,88,29] The cyclic sulfate 259 reacted with the PMB-protected 1,4-anhydro-4-seleno-D-arabinitol (256) and 1,4-anhydro-4-thio-D-arabinitol (257), to give the corresponding protected selenonium and sulfonium sulfates 266 and 267 in 72% and 75% yields, respectively (Scheme 61). Potassium carbonate was added to the reaction mixture to neutralize any acid generated by the possible decomposition of the cyclic sulfate 259 reacting with a trace amount of water. However, the presence of K$_2$CO$_3$ also led to a significant amount of by-product from the reaction of the cyclic sulfate 259 with HFIP anion. Based on this observation, the amount of K$_2$CO$_3$ added was greatly reduced in later trials, and no by-product was isolated. The presence of the cyclic sulfate 259 in slight excess over the seleno- and thioalditols 256 and 257 also resulted in improved yields.

The coupling reactions of the PMB-protected 1,4-anhydro-4-imino-D-arabinitol (258) with the cyclic sulfate 259 was carried out in dry acetone, and proceeded smoothly to give the corresponding protected ammonium sulfate 268 in 89% yield (Scheme 62).

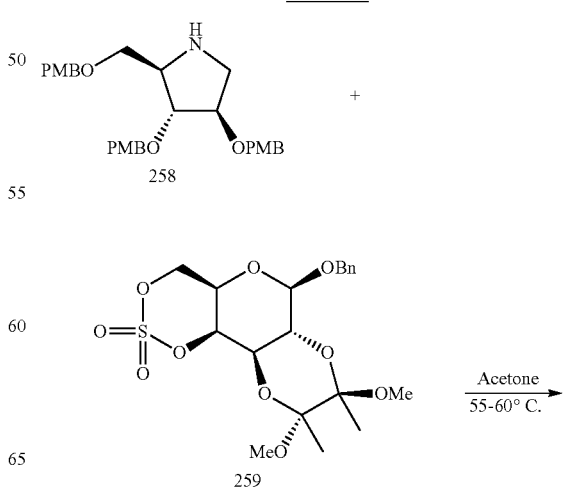

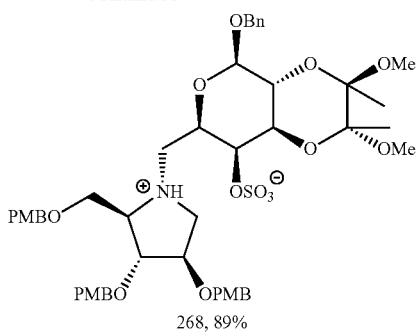

268, 89%

The coupling reactions of the cyclic sulfate 260 with the PMB-protected 1,4-anhydro-4-seleno-D-arabinitol (256) and 1,4-anhydro-4-thio-D-arabinitol (257) were carried out in HFIP, to give the corresponding protected selenonium and sulfonium sulfates 269 and 270 in 70% and 78% yields, respectively (Scheme 63). The PMB-protected 1,4-anhydro-4-imino-D-arabinitol (258) also reacted with the cyclic sulfate 260 in dry acetone to afford the ammonium sulfate 271 in 90% yield (Scheme 63).

Scheme 63

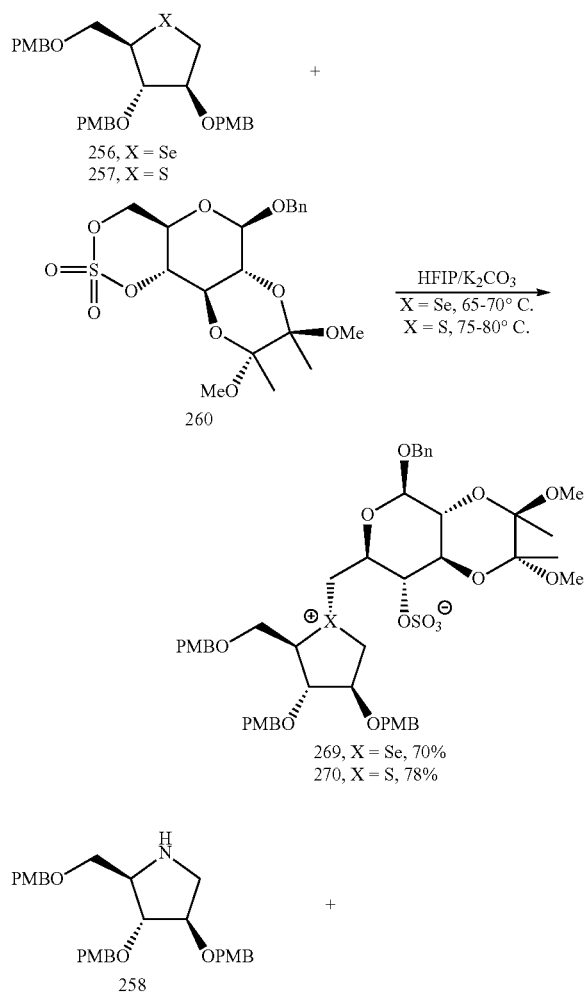

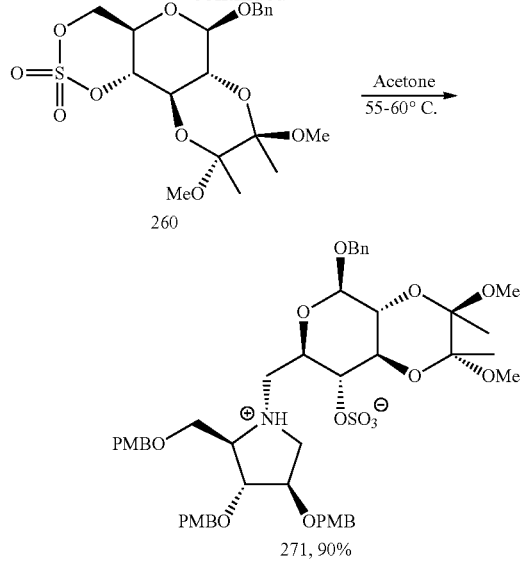

271, 90%

The reactivity of the PMB-protected 1,4-anhydroheteroalditols 256-258 with the cyclic sulfates 259 and 260 varied. The 1,4-anhydro-4-iminoarabinitol 258 was the most reactive of the three, and reacted with the cyclic sulfates 259 and 260 in good yields. The PMB-protected 1,4-anhydro-4-seleno- and thio-D-arabinitols 256 and 257 were less reactive with the cyclic sulfates 259 and 260, and the reactions proceeded very slowly in acetone. The polar solvent HFIP, which was believed to facilitate the reactions by stabilizing the late transition states, had to be used instead. The PMB-protected 1,4-anhydro-4-seleno-D-arabinitol 256 was slightly more reactive than its sulfur counterpart 257, as demonstrated by the different reaction temperatures required in the coupling reactions. The coupling reaction of compound 256 with 259 and 260 proceeded smoothly at 60-65° C. to give the desired products in moderate yields. However, attempts to improve the yields further by raising the reaction temperatures caused decomposition of the products. On the other hand, reaction of the PMB-protected 1,4-anhydro-4-thio-D-arabinitol 257 with the cyclic sulfates 259 and 260 proceeded slowly at 65-70° C. for 12 h, with about 30% starting material 257 still remaining. Raising the temperature to 75-80° C. resulted in completion of the reactions in high yields.

The selectivity for attack at the primary center of the cyclic sulfates 259 and 260 over possible alternative attack of compounds 256-258 at the primary over the secondary cyclic sulfate center was invariably excellent, and in no case were isolable quantities of the regioisomers detected. In the case of the coupling reaction of the selenoarabinitol 256 with the cyclic sulfates 259 and 260, there was a detectable amount (5-10%) of the stereoisomers that were diastereomeric at the selenonium center. However, due to the similarity in chromatographic mobilities, these minor products could not be isolated free from the major isomers. However, this type of minor product was not detected in the reactions of the corresponding thioarabinitol 257.

Deprotection of the coupled products 266-271 was carried out by a three-step procedure. Since PMB and BDA groups were both sensitive to acidic conditions, they were readily cleaved by treatment with TFA (Scheme 64). After rinsing away the cleaved PMB and BDA groups, the residue was purified by column chromatography to afford the corresponding compounds 272-277 as amorphous, hygroscopic solids.

The benzyl protecting groups at the anomeric positions in compounds 272-277 were not cleaved after prolonged treatment with TFA at elevated temperatures, only trace amounts of cleavage products being observed.

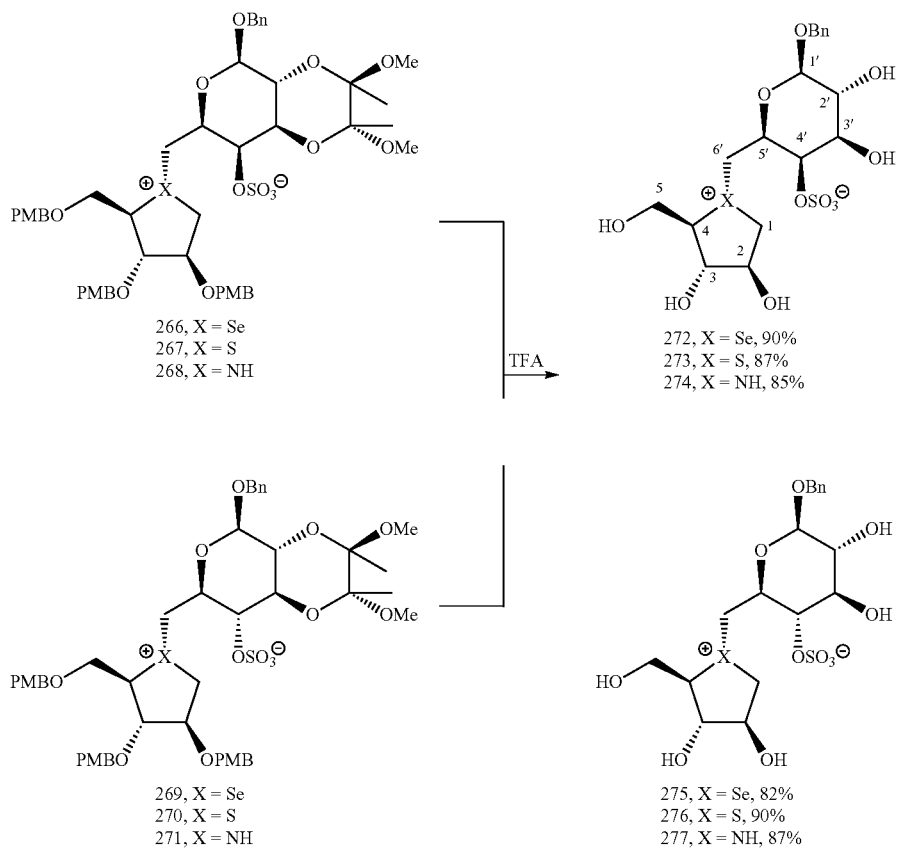

Scheme 64

The absolute stereochemistry at the heteroatom center of compounds 272-277 was established by NOESY experiments. For example, the NOESY spectrum of compound 272 (shown below), clearly exhibited the H-4 to H-1'b correlation, implying that these two hydrogens are syn-facial. Therefore, C-1' of the side chain must be anti to C-5 of the sulfonium salt ring.

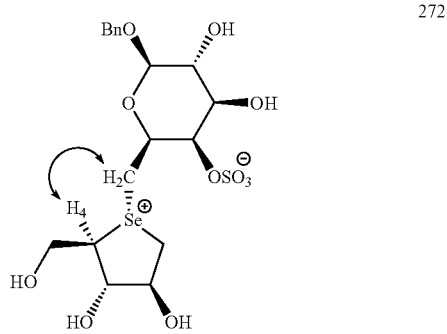

272

Compounds 272-277 were subjected to hydrogenolysis in 90% acetic acid using $Pd(OH)_2/C$ as the catalyst. After 24 hours, the anomeric benzyl groups of 272-277 were completely removed to yield the corresponding hemiacetals. The crude hemiacetals were subsequently reduced with $NaBH_4$ in water to provide the desired final products 250-255 (Scheme 65). The moderate yields for the three-step deprotection sequence were due in part to the difficulty in separation of the final products from contaminating borate salts. Compounds 250-255 were obtained as hydroscopic gums that were unsuitable for combustion analysis, but were characterized by spectroscopic methods. The $^1H$ and $^{13}C$ NMR spectra of compounds 251 and 254 matched the data for such compounds when synthesized by other means. MALDI mass spectrometry for compounds 250-255 in the positive-ion mode typically showed base peaks for masses attributable to sodium adduct ions (M+Na), and lower intensity peaks corresponding to M+H and M+H—$SO_3$ ions.

Scheme 65

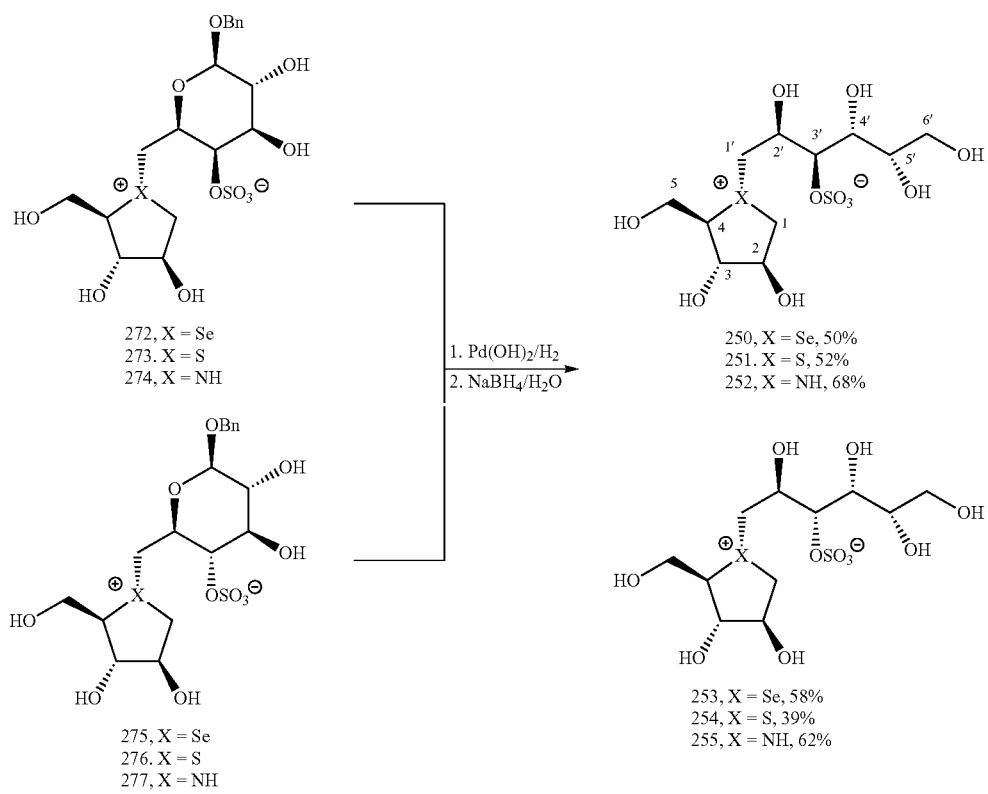

250, X = Se, 50%
251. X = S, 52%
252, X = NH, 68%

253, X = Se, 58%
254, X = S, 39%
255, X = NH, 62%

272, X = Se
273. X = S
274, X = NH

275, X = Se
276. X = S
277, X = NH

1. Pd(OH)$_2$/H$_2$
2. NaBH$_4$/H$_2$O

Finally, the inventors investigated the inhibitory activities of the compounds synthesized in this alternative synthetic embodiment against recombinant human maltase glucoamylase (MGA), a critical intestinal glucosidase involved in the processing of oligosaccharides of glucose into glucose itself. The selenium derivatives, 250 and 253, each have IC50 values of 1 µM. One of the nitrogen analogues 255 is slightly less active, with an IC50 value of 30 µM, and the other, 252, has an IC50 value of 100 µM. The sulfur analogues 251 and 254 have been shown to be active, with $K_i$ values of 0.25 and 0.26 µM, respectively.

5.0 EXAMPLES

The following examples will further illustrate the invention in greater detail although it will be appreciated that the invention is not limited to the specific examples.

5.1 Experimental Methods

Optical rotations were measured at 20° C. $^1$H and $^{13}$C NMR spectra were recorded at 400.13 and 100.6 MHz for proton and carbon respectively. All assignments were confirmed with the aid of two-dimensional $^1$H,$^1$H(COSYDFTP) or $^1$H,$^{13}$C (INVBTP) experiments using standard Bruker pulse programs. MALDI-TOF mass spectra were obtained for samples dispersed in a 2,5-dihydroxybenzoic acid matrix using a Perseptive Biosystems Voyager-DE instrument. Silica gel for chromatography was Merck kieselgel 60. High resolution mass spectra were LSIMS (Fab), run on a Kratos Concept H double focussing mass spectrometer at 10000 RP.

5.2 Preparation of Intermediates 5.2.1 Example 1

Preparation of Cyclic Sulfate (7) (Scheme 2)

Step 1-2,4-O-Benzylidene-D-erythritol (5)

Compound (5) was prepared from 4,6-O-benzylidene-D-glucose (4) according to standard procedures.[9,10] Compound (5) has been mentioned by MacDonald et al.,[10] without characterization, which is therefore dealt with here. Mp 138-139° C.; [α]$_D$ −44° (c 1.0, MeOH); $^1$H NMR (CD$_3$OD): δ 7.53-7.28 (5H, m, Ar), 5.53 (1H, s, H-5), 4.2 (1H, dd, J=10.1, 3.6 Hz, H-4a), 3.92 (1H, dd, J=12.1, 1.7 Hz, H-1a), 3.74 (1H, dd, J=12.1, 5.7 Hz, H-1b), 3.67-3.55 (3H, m, H-3, H-2, H-4b); $^{13}$C NMR (100.6 MHz, CD$_3$OD): δ 139.52 ($C_{ipso}$), 129.77 ($C_{para}$), 128.99, 127.49 (4$C_{ortho+meta}$), 102.36 (C-5), 84.22 (C-3), 72.21 (C-4), 62.76 (C-1), 62.59 (C-2); MALDI-TOF MS: m/e 211 (M$^+$+H), 233 (M$^+$+Na). Anal. Calcd for C$_{11}$H$_{14}$O$_4$: C, 62.83; H, 6.72. Found: C, 62.96; H, 6.55.

Step 2-2,4-O-Benzylidene-D-erythritol-1,3-cyclic sulfite (6)

A solution of the diol (5) (4.5 g, 21 mmol) and Et$_3$N (11 mL, 4 equiv) in dry CH$_2$Cl$_2$ (90 mL) was added dropwise to a solution of SOCl$_2$ (2.4 mL, 1.5 equiv) in dry CH$_2$Cl$_2$ (60 mL), with stirring in an ice-bath under an N$_2$ atmosphere. Stirring was continued at 0° C., until TLC (hex:EtOAc, 4:1) showed complete disappearance of the starting material. The mixture was diluted with CH$_2$Cl$_2$ (150 mL) and washed with H$_2$O (150 mL) and brine (150 mL). The organic solution was dried (Na$_2$SO$_4$) and concentrated on a rotary evaporator. The product was purified by flash chromatography [hex:EtOAc, 4:1+0.1% Et$_3$N] to give a mixture of two diastereomers (4.5 g, 82%). One of the isomers was selectively recrystallized from EtOAc:hex. Mp 137-139° C.; [α]$_D$ +32° (c 1.0, CH$_2$Cl$_2$); $^1$H NMR (CD$_2$Cl$_2$): δ 7.48-7.36 (5H, m, Ar), 5.68 (1H, s, H-5), 5.04 (1H, ddd, J=10.4, 9.5, 5.0 Hz, H-3), 4.80 (1H, dd, J=10.4, 10.4 Hz, H-1a), 4.24 (1H, dd, J=10.5, 5.0 Hz, H-4e), 4.18 (1H, ddd, J=10.4, 9.5, 4.8 Hz, H-2), 4.06 (1H, dd, J=10.4, 4.8 Hz, H-1e), 3.89 (1H, dd, J=10.5, 10.4 Hz, H-4a); $^{13}$C NMR (100.6 MHz, CD$_2$Cl$_2$): δ 137.14 (C$_{ipso}$), 129.74 (C$_{para}$), 128.65, 126.50 (4C$_{otho+meta}$), 102.72 (C-5), 73.56 (C-2), 68.16 (C-4), 63.90 (C-3), 60.18 (C-1). Anal. Calcd for C$_{11}$H$_{12}$O$_5$S: C, 51.55; H, 4.72. Found: C, 51.80; H, 4.66.

Step 3-2,4-O-Benzylidene-D-erythritol-1,3-cyclic sulfate (7)

The cyclic sulfite (6) (3.5 g, 14 mmol) was dissolved in a mixture of MeCN (50 mL) and CCl$_4$ (50 mL), and NaIO$_4$ (4.1 g, 1.5 equiv) and RuCl$_3$.H$_2$O (50 mg) were added followed by H$_2$O (50 mL). The mixture was stirred vigorously at rt until TLC (hex:EtOAc, 4:1) showed complete disappearance of the starting material. The mixture was diluted with Et$_2$O (200 mL) and washed with H$_2$O (200 mL) and brine (200 mL). The organic solution was dried (Na$_2$SO$_4$) and concentrated on a rotary evaporator. The product was purified by flash chromatography [hex:EtOAc, 4:1+0.1% Et$_3$N] to yield a white solid (3.5 g, 95%). A portion of the product was recrystallized from EtOAc:hex. Mp 115-125° C. (dec); [α]$_D$ +4° (c 1.0, CHCl$_3$); $^1$H NMR (CD$_2$Cl$_2$): δ 7.48-7.37 (5H, m, Ar), 5.65 (1H, s, H-5), 4.86 (1H, ddd, J=10.2, 9.8, 5.0 Hz, H-3), 4.76 (1H, dd, J=10.7, 10.5 Hz, H-1a), 4.65 (1H, dd, J=10.5, 5.0 Hz, H-1e), 4.44 (1H, dd, J=10.5, 5.0 Hz, H-4e), 4.25 (1H, ddd, J=10.7, 9.8, 5.0 Hz, H-2), 3.97 (1H, dd, J=10.5, 10.2 Hz, H-4a); $^{13}$C NMR (100.6 MHz, CD$_2$Cl$_2$): δ 136.32 (C$_{ipso}$), 130.03 (C$_{para}$), 128.74, 126.52 (4C$_{ortho+meta}$), 102.98 (C-5), 75.74 (C-3), 73.19 (C-1), 71.68 (C-2), 67.64 (C-4); MALDI-TOF MS: m/e 273 (M$^+$+H), Anal. Calcd for C$_{11}$H$_{12}$O$_6$S: C, 48.52; H, 4.45. Found: C, 48.43; H, 4.39.

5.2.2 Example 2

Preparation of thio-arabinitol (Scheme 4)

1,4-Anhydro-2,3,5-tri-O-benzyl-4-thio-D-arabinitol (12)

A mixture of 1,4-anhydro-3-O-benzyl-4-thio-D-arabinitol (1.0 g, 4.2 mmol) and 60% NaH (0.85 g, 5 equiv) in DMF (20 mL) was stirred in an ice-bath for 1 h. A solution of benzyl bromide (1.9 mL, 3.8 equiv) in DMF (5 mL) was added and the solution was stirred at rt for 3 h. The mixture was added to ice-water (150 mL) and extracted with Et$_2$O (150 mL). The organic solution was dried (Na$_2$SO$_4$) and concentrated. The product was purified by flash chromatography [hex:EtOAc, 4:1] to give a syrup (1.6 g, 90%). [α]$_D$ +5° (c 1.6, CHCl$_3$); $^1$H NMR (CDCl$_3$): δ 7.38-7.23 (15H, m, Ar), 4.64-4.45 (6H, m, CH$_2$Ph), 4.19 (1H, dd, J=8.9, 4.6 Hz, H-2), 4.11 (1H, dd, J=7.2, 3.8 Hz, H-3), 3.69 (1H, dd, J=8.8, 7.6 Hz, H-5a), 3.57 (1H, ddd, J=7.5, 6.4, 3.6 Hz, H-4), 3.50 (1H, dd, J=8.9, 6.3 Hz, H-5b), 3.08 (1H, dd, J=11.4, 5.1 Hz, H-1a), 2.91 (1H, dd, J=11.4, 4.6 Hz, H-1b). $^{13}$C NMR (100.6 MHz, CDCl$_3$): δ 138.16, 138.06, 137.88 (3C$_{ipso}$), 128.40-127.59 (15C$_{Ar}$), 85.08 (C-3), 85.04 (C-2), 73.01 (CH$_2$Ph), 72.34 (C-5), 71.85, 71.50 (2CH$_2$Ph), 48.99 (C-4), 33.10 (C-1). Anal. Calcd for C$_{26}$H$_{28}$O$_3$S: C, 74.25; H, 6.72. Found: C, 74.18; H, 6.53.

5.2.3 Example 3

Preparation of seleno-arabinitol (Scheme 6)

1,4-Anhydro-2,3,5-tri-O-benzyl-4-seleno-D-arabinitol (20)

Selenium metal (1.1 g, 14 mmol) was added to liquid NH$_3$ (60 mL) in a –50° C. bath and small pieces of Na (0.71 g) were added until a blue color appeared. A small portion of selenium (20 mg) was added to remove the blue color. NH$_3$ was removed by warming on a water bath and DMF was added and removed under high vacuum to remove the rest of NH$_3$. A solution of the mesylated compound (18) (7.4 g, 12.7 mmol) in DMF (100 mL) was added and the mixture was stirred under N$_2$ in a 70° C. bath for 3 h. The mixture was cooled and the solvent was removed on high vacuum. The product was partitioned between CH$_2$Cl$_2$ (150 mL) and water (50 mL), and the organic solution was washed with water (50 mL) and brine (50 mL) and dried (MgSO$_4$). The product was purified by flash chromatography (hex:EtOAc, 3:1) to give a yellow oil (4.74 g, 80%).

[α]$_D$ +22° (c 1.3, CHCl$_3$); $^1$H NMR (CDCl$_3$): δ 7.22-7.48 (15H, m, Ar), 4.67, 4.61 (2H, 2d, J=11.8 Hz, CH$_2$Ph), 4.56, 4.48 (2H, 2d, J=12.1 Hz, CH$_2$Ph), 4.53, 4.50 (2H, 2d, CH$_2$Ph), 4.22 (1H, dd, J=10.1, 5.1 Hz, H-2), 4.07 (1H, dd, J=4.6, 4.6 Hz, H-3), 3.85 (1H, dd, J=9.2, 7.6 Hz, H-5a), 3.77 (1H, ddd, J=7.5, 6.9, 4.5 Hz, H-4), 3.53 (1H, dd, J=9.1, 6.8 Hz, H-5b), 3.11 (1H, dd, J=10.4, 5.1 Hz, H-1a), 2.96 (1H, dd, J=10.4, 5.3 Hz, H-1b). $^{13}$C NMR (100.6 MHz, CDCl$_3$): δ 138.24, 138.21, 138.06 (3C$_{ipso}$), 128.40-127.60 (15C$_{Ar}$), 85.93 (C-2), 85.63 (C-3), 72.96 (C-5, CH$_2$Ph), 72.14, 71.50 (2CH$_2$Ph), 42.59 (C-4), 23.96 (C-1). Anal. Calcd for C$_{26}$H$_{28}$O$_3$Se: C, 66.65; H, 6.03. Found: C, 66.49; H, 6.05.

5.2.4 Example 4

General Procedure for the Synthesis of the Protected Sulfonium, Selenonium and Ammonium Sulfates (21), (22), (24), (26), (27), (28), (30), (31) (Schemes 7-14).

The thio, aza or selenosugar (3 mmol) and the cyclic sulfate (1.2 equiv) were dissolved in dry acetone (in the case of (21), (22), (24), (26), (27) and (28)) or dry methanol (in the case of (30) and (31)) (0.5 mL) and anhydrous K$_2$CO$_3$ (7 mg) was added. The mixture was stirred in a Caries tube in an oil-bath (75° C.) overnight. The solvent was removed under reduced pressure and the product was purified by column chromatography.

1-((1',4'-Anhydro-2',3',5'-tri-O-benzyl-4'-thio-D-arabinitol)-4'-S-yl)-2,4-O-benzylidene-1-deoxy-L-erythritol-3-sulfate (21)

Column chromatography [CHCl$_3$:MeOH, 10:1+0.1% Et$_3$N] of the crude product gave an amorphous solid (33%). [α]$_D$ –11.9° (c 1.7, CH$_2$Cl$_2$); $^1$H NMR (CD$_2$Cl$_2$): δ 7.49-7.12 (20H, m, Ar), 5.54 (1H, s, H-5), 4.59 (1H, ddd, J=9.9, 5.4, 4.5 Hz, H-3), 4.55-4.33 (8H, m, 4CH$_2$Ph, H-2', H-4a, H-1a, H-3'), 4.29 (1H, dt, J=9.5, 3.0 Hz, H-2), 4.25 and 4.15 (2H, 2d, J=11.9 Hz, CH$_2$Ph), 4.04 (1H, m, H-1'a) 4.02-3.95 (2H, m, H-4', H-1b), 3.78 (1H, dd, J=10.7, 10.7 Hz, H-4b), 3.74 (1H, dd, J=13.6, 3.8 Hz, H-1'b), 3.62 (1H, dd, J=9.9, 8.6 Hz, H-5'a), 3.54 (1H, dd, J=9.9, 7.2 Hz, H-5'b); $^{13}$C NMR (100.6 MHz, CD$_2$Cl$_2$): δ 137.34, 137.24, 136.56, 136.39 (4C$_{ipso}$), 129.73-126.62 (20C$_{Ar}$), 101.95 (C-5), 83.75 (C-3'), 82.82 (C-2'), 76.80 (C-2), 73.73, 72.84, 72.52 (3CH$_2$Ph), 69.54.(C-4), 67.01 (C-5'), 66.48 (C-3), 65.27 (C-4'), 49.67 (C-1), 48.28 (C-1'); MALDI-TOF MS: m/e 693 (M$^+$+H). Anal. Calcd for C$_{37}$H$_{40}$O$_9$S$_2$: C, 64.14; H, 5.82. Found: C, 63.88; H, 5.83.

1-((1',4'-Anhydro-2',3',5'-tri-O-benzyl-4'-thio-D-arabinitol)-4'-S-yl)-2,4-O-benzylidene-1-deoxy-D-erythritol-3-sulfate (22)

Column chromatography [CHCl$_3$:MeOH, 10:1+0.1% Et$_3$N] of the crude product gave an amorphous solid (79%). [α]$_D$ −46.9° (c 0.65, CH$_2$Cl$_2$); $^1$H NMR (CD$_2$Cl$_2$): δ 7.43-7.10 (20H, m, Ar), 5.49 (1H, s, H-5), 4.62-4.34 (11H, m, CH$_2$Ph, H-3, H-4a, H-2', H-1a, H-3'), 4.30-4.21 (2H, m, H-2, H-4'), 3.96 (1H, dd, J=9.7, 6.2 Hz, H-5'a), 3.90 (1H, dd, J=13.3, 3.4 Hz, H-1b), 3.82 (1H, dd, J=9.8, 9.8 Hz, H-5'b), 3.79-3.71 (2H, m, H-1'a, H-4b), 3.51 (1H, dd, J=13.2, 3.9 Hz, H-1'b); $^{13}$C NMR (100.6 MHz, CD$_2$Cl$_2$): δ 137.62, 137.27, 136.48, 136.29 (4C$_{ipso}$), 129.80-126.56 (20C$_{Ar}$), 102.16 (C-5), 84.25 (C-3'), 82.56 (C-2'), 77.07 (C-2), 74.02, 72.74 (3CH$_2$Ph), 69.75 (C-4), 67.19 (C-5'), 66.82 (C-3), 65.76 (C-4'), 50.41 (C-1), 49.60 (C-1'); MALDI-TOF MS: m/e 693 (M$^+$+H). Anal. Calcd for C$_{37}$H$_{40}$O$_9$S$_2$: C, 64.14; H, 5.82. Found: C, 64.16; H, 5.73.

1-((1',4'-Anhydro-2',3',5'-tri-O-benzyl-4'-thio-L-arabinitol)-4'-S-yl)-2,4-O-benzylidene-1-deoxy-D-erythritol-3-sulfate (24)

Column chromatography [CHCl$_3$:MeOH, 10:1+0.1% Et$_3$N] of the crude product gave an amorphous solid (40%). [α]$_D$ +14.3° (c 1.4, CH$_2$Cl$_2$); $^1$H NMR (CD$_2$Cl$_2$): δ 7.49-7.12 (20H, m, Ar), 5.55 (1H, s, H-5), 4.60 (1H, ddd, J=9.8, 5.5, 4.5 Hz, H-3), 4.55-4.44 (5H, m, 3CH$_2$Ph, H-2', H-4a), 4.42 (1H, dd, J=13.3, 2.3 Hz, H-1a), 4.39-4.34 (2H, m, CH$_2$Ph, H-3'), 4.28 (1H, dt, J=9.8, 2.9 Hz, H-2), 4.24 and 4.14 (2H, 2d, J=11.9 Hz, CH$_2$Ph), 4.10 (1H, d, J=13.4 Hz H-1'a), 3.98-3.90 (2H, m, H-4', H-1b), 3.78 (1H, dd, J=10.5, 10.5 Hz, H-4b), 3.67 (1H, dd, J=13.4, 3.8 Hz, H-1'b), 3.62 (1H, dd, J=9.9, 8.7 Hz, H-5'a), 3.53 (1H, dd, J=9.9, 7.2 Hz, H-5'b); $^{13}$C NMR (100.6 MHz, CD$_2$Cl$_2$): δ 137.32, 137.26, 136.48, 136.25 (4C$_{ipso}$), 129.79-126.64 (20C$_{Ar}$), 102.06 (C-5), 83.96 (C-3'), 82.74 (C-2'), 76.93 (C-2), 73.81, 72.97, 72.57 (3CH$_2$Ph), 69.59.(C-4), 67.07 (C-5'), 66.36 (C-3), 66.31 (C-4'), 49.96 (C-1), 48.52 (C-1'). Anal. Calcd for C$_{37}$H$_{40}$O$_9$S$_2$: C, 64.14; H, 5.82. Found: C, 64.13; H, 5.74.

1-((1',4'-Anhydro-3'-O-benzyl-4'-thio-D-arabinitol)-4'-S-yl)-2,4-O-benzylidene-1-deoxy-L-erythritol-3-sulfate (26)

Column chromatography [CHCl$_3$:MeOH, 10:1+0.1% Et$_3$N] of the crude product gave an amorphous solid (32%).; $^1$H NMR (CD$_2$Cl$_2$): δ 7.49-7.26 (10H, m, Ar), 6.22 (1H, d, J=4.4 Hz, 2'-OH), 5.54 (1H, s, H-5), 4.96 (1H, br-s, H-2'), 4.64 (1H, d, J=11.6 Hz, CH$_2$Ph), 4.64-4.62 (1H, m, 5'-OH), 4.56 (1H, d, J=11.6 Hz, CH$_2$Ph), 4.54-4.48 (1H, m, H-3), 4.46 (1H, dd, J=10.5, 5.4 Hz, H-4a), 4.33-4.25 (3H, m, H-3', H-2, H-1'a), 4.12 (1H, dd, J=13.5, 2.6 Hz, H-1a), 4.12-4.09 (1H, m, H-4'), 4.01 (1H, dd, J=13.5, 3.4 Hz, H-1b), 3.92-3.82 (2H, m, H-5'a, H-5'b), 3.78 (1H, dd, J=10.5, 10.1 Hz, H-4b), 3.67 (1H, dd, J=13.5, 3.9 Hz, H-1'b); $^{13}$C NMR (100.6 MHz, CD$_2$Cl$_2$): δ 136.92, 136.73 (2C$_{ipso}$), 129.97-126.61 (10C$_{Ar}$), 102.32 (C-5), 88.45 (C-3'), 76.61 (C-2), 76.22 (C-2'), 72.96 (CH$_2$Ph), 71.24 (C-4'), 69.27 (C-4), 66.96 (C-3), 60.51 (C-5'), 52.43 (C-1'), 48.30 (C-1); MALDI-TOF MS: m/e 513 (M$^+$+H). Anal. Calcd for C$_{23}$H$_{28}$O$_9$S$_2$: C, 53.89; H, 5.51. Found: C, 53.64; H, 5.34.

1-((1',4'-Anhydro-2',3',5'-tri-O-benzyl-4'-seleno-D-arabinitol)-4'-Se-yl)-2,4-O-benzylidene-1-deoxy-L-erythritol-3-sulfate (27)

Column chromatography [CHCl$_3$:MeOH, 15:1] of the crude product gave an amorphous solid (86%). NMR showed the presence of two isomers (7:1) at the stereogenic selenium center which were separated on analytical HPLC [acetonitrile/H$_2$O]. Anal. Calcd for C$_{37}$H$_{40}$O$_9$SSe: C, 59.99; H, 5.45. Found: C, 59.91; H, 5.44.

1-((1',4'-Anhydro-2',3',5'-tri-O-benzyl-4'-seleno-D-arabinitol)-4'-Se-yl)-2,4-O-benzylidene-1-deoxy-D-erythritol-3-sulfate (28)

Column chromatography [CHCl$_3$:MeOH, 15:1] of the crude product gave an amorphous solid (96%). NMR showed the presence of two isomers (3:1) at the stereogenic selenium center which were separated on analytical HPLC [acetonitrile/H$_2$O]. Anal. Calcd for C$_{37}$H$_{40}$O$_9$SSe: C, 59.99; H, 5.45. Found: C, 59.91; H, 5.37.

1-((1',4'-Dideoxy-1',4'-imino-D-arabinitol)-4'-N-yl)-2,4-O-benzylidene-1-deoxy-L-erythritol-3-sulfate (30)

A mixture of 1,4-Dideoxy-1,4-imino-D-arabinitol (19) (100 mg, 0.7 mmol) and 2,4-O-benzylidene-L-erythritol-1,3-cyclic sulfate (10) (235 mg, 1.2 equiv) were dissolved in dry MeOH (0.5 mL) and anhydrous K$_2$CO$_3$ (15 mg) was added. The mixture was stirred in a Caries tube in an oil-bath (75° C.) overnight. The solvent was removed under reduced pressure and column chromatography [CH$_2$Cl$_2$:MeOH, 4.5:1] of the crude product gave an amorphous solid (219 mg, 72%). $^1$H NMR (CD$_3$OD): δ 7.53-7.30 (5H, m, Ar), 5.61 (1H, s, H-5), 4.53 (1H, dd, J=11.1, 5.2 Hz, H-4a), 4.25 (1H, m, H-2), 4.20 (1H, ddd, J=9.8, 5.2, 4.4 Hz, H-3), 4.11 (1H, br-s, H-2'), 3.99-3.84 (4H, m, H-1a, H-3', H-5'a, H-5'b), 3.82 (1H, dd, J=10.7, 9.8 Hz H-4b) 3.58 (1H, m, H-1'a), 3.55-3.42 (2H, m, H-1'b, H-4'), 3.38 (1H, m, H-1b); $^{13}$C NMR (100.6 MHz, CD$_3$OD): δ 138.72 (C$_{ipso}$), 130.12 (C$_{para}$), 129.21, 127.39 (4C$_{otho+meta}$), 102.33 (C-5), 78.01 (C-4', C-3', C-2), 76.31 (C-2'), 70.29 (C-4), 69.02 (C-3), 62.64 (C-1'), 60.51 (C-5'), 58.46 (C-1); MALDI-TOF MS: m/e 428 (M$^+$+Na),406 (M$^+$+H); HRMS. Calcd for C$_{16}$H$_{23}$O$_9$SN (M+H): 406.1179. Found: 406.1192.

1-((1',4'-Dideoxy-1',4'-imino-L-arabinitol)-4'-N-yl)-2,4-O-benzylidene-1-deoxy-D-erythritol-3-sulfate (31)

A mixture of 1,4-Dideoxy-1,4-imino-L-arabinitol (16) (80 mg, 0.6 mmol) and 2,4-O-benzylidene-D-erythritol-1,3-cyclic sulfate (7) (190 mg, 1.2 equiv) were dissolved in dry MeOH (0.5 mL) and anhydrous K$_2$CO$_3$ (10 mg) was added. The mixture was stirred in a Caries tube in an oil-bath (75° C.) overnight. The solvent was removed under reduced pressure and column chromatography [CH$_2$Cl$_2$:MeOH, 5:1] of the crude product gave an amorphous solid (175 mg, 72%). $^1$H NMR (CD$_3$OD): δ 7.52-7.31 (5H, m, Ar), 5.62 (1H, s, H-5), 4.53 (1H, dd, J=10.9, 5.2 Hz, H-4a), 4.28 (1H, m, H-2), 4.20 (1H, ddd, J=9.7, 5.1, 4.6 Hz, H-3), 4.14 (1H, br-s, H-2'), 4.03

(1H, m, H-1a), 3.98-3.84 (3H, m, H-3', H-5'a, H-5'b), 3.81 (1H, dd, J=10.9, 10 Hz H-4b) 3.63 (1H, m, H-1'a), 3.55-3.42 (2H, m, H-1'b, H-4'), 3.38 (1H, m, H-1b); $^{13}$C NMR (100.6 MHz, CD$_3$OD): δ 138.66 (C$_{ipso}$), 130.15 (C$_{para}$), 129.23, 127.40 (4C$_{ortho+meta}$), 102.34 (C-5), 77.81 (C-4'), 77.52 (C-3', C-2), 76.19 (C-2'), 70.27 (C-4), 68.92 (C-3), 62.68 (C-1'), 60.41 (C-5'), 58.61 (C-1); MALDI-TOF MS: m/e 428 (M$^+$+Na),406 (M$^+$+H).

5.2.4.1 Example 4.1

General procedure for the Alternative Synthesis of Salacinol (1) (Schemes 10(a) to 10(c)).

2,3,5-Tri-O-benzyl-1,4-dideoxy-1,4-[[(2S,3S)-2,4-di-(benzyloxy)-3-sulfoxy)butyl]-episulfoniumylidene]-D-arabinitol Inner Salt (42)

A mixture of the thioether 33$^{25}$ (270 mg, 0.64 mmol) and 2,4-Di-O-benzyl-1,3-cyclic sulfate (41)$^{15,26}$ (280 mg, 0.77 mmol) in either acetone or HFIP (0.5 mL), containing anhydrous K$_2$CO$_3$ (16 mg, 0.10 mmol) was stirred in a sealed tube in an oil-bath (75-80° C.) for 14 h. The solvent was removed under reduced pressure and the residue was purified by column chromatography using (CH$_2$Cl$_2$:MeOH, 10:1) as eluant to give the title compound 42, as an amorphous solid (29 mg, 5%) in acetone and (229 mg, 45%) in HFIP. R$_f$ 0.40 (CH$_2$Cl$_2$: MeOH, 10:1); [α]$_D$ –26° (c 1.3, CHCl$_3$); $^1$H NMR (CDCl$_3$): δ 7.38-7.05 (25H, m, Ar), 4.67 and 4.45 (2H, 2d, J$_{A,B}$=11.8 Hz, CH$_2$Ph), 4.60 and 4.45 (2H, 2d, J$_{AB}$=9.5 Hz, CH$_2$Ph), 4.59 and 4.44 (2H, 2d, J$_{A,B}$=11.2 Hz, CH$_2$Ph), 4.58 (1H, dt, J$_{2,3}$=5.0 Hz, H-3'), 4.42 and 4.28 (2H, 2d, J$_{A,B}$=11.0 Hz, CH$_2$Ph), 4.36 (1H, m, H-2), 4.32 (1H, ddd, J=1.7, 4.1, 6.3 Hz, H-2'), 4.30 and 4.20 (2H, 2d, J$_{A,B}$=11.7 Hz, CH$_2$Ph), 4.23 (1H, m, H-3), 4.13 (1H, dd, J$_{1'a,1'b}$=13.4, J$_{1'a,2}$=2.0 Hz, H-1'a), 4.05 (1H, d, J$_{2,3}$=13.3 Hz, H-1a), 4.00 (1H, dd, J$_{4a',4'b}$=11.1, J$_{3',4'a}$=2.7 Hz, H-4'a), 3.86 (1H, dd, J$_{3',4'b}$=2.4, J$_{4'a,4'b}$=11.3 Hz, H-4'b), 3.71 (1H, brt, J=9.2 Hz, H-4), 3.69 (1H, dd, J$_{1'b,2}$=3.8, J$_{1'b,1'a}$=9.2 Hz, H-1'b), 3.60 (1H, dd, J$_{1a,1b}$=13.5, J$_{1b,2}$=3.8 Hz, H-1b), 3.51 (1H, dd, J$_{5a,5b}$=13.6, J$_{4,5a}$=9.7 Hz, H-5a), 3.49 (1H, dd, J$_{4,5b}$=9.7 Hz, H-5b); $^{13}$C NMR (CDCl$_3$): δ 137.97, 136.77, 136.71, 136.05 and 135.77 (5×C$_{ipso}$ Ph), 128.81-127.66 (25C, Ph), 83.14 (C-3), 81.65 (C-2), 74.59 (C-3'), 73.81, 73.53, 3.39, 72.12, 71.84 (5×CH$_2$Ph), 73.10 (C-2'), 68.79 (C-4'), 66.62 (C-5), 65.53 (C-4), 50.89 (C-1'), 48.07 (C-1). MALDI-TOF MS: m/e 785.41 (M$^+$+H), 808.32 (M$^+$+Na). Anal. Calcd for C$_{44}$H$_{48}$O$_9$S$_2$: C, 67.32; H, 6.16. Found: C, 67.36; H, 6.10.

2,3,5-Tri-O-benzyl-1,4-dideoxy-1,4-[[(2S,3S)-2,4-O-benzylidene-3 (sulfooxy)butyl]-episulfoniumylidene]-D-arabinitol (35)

A mixture of the thioether 33$^{25}$ (260 mg, 0.62 mmol) and 2,4-Di-O-benzylidene-1,3-cyclic sulfate (34)$^{25}$ (200 mg, 0.74 mmol) in either acetone or HFIP (0.5 ml) containing K$_2$CO$_3$ (13 mg, 0.09 mmol) was treated as described above to yield the title compound 35$^{25}$ as an amorphous solid (252 mg, 59% in acetone) and (406 mg, 94% in HFIP).

1,4-Anhydro-2,3,5-tri-O-(p-methoxybenzyl)-4-thio-D-arabinitol (43)

To an ice cold mixture of 1,4-anhydro-4-thio-D-arabinitol 38$^{25}$ (0.98 g, 6.52 mmol) and 60% NaH (1.56 g, 39.15 mmol, 6 equiv.) in THF (15 mL), a solution of p-methoxybenzyl chloride (4.59 g, 29.34 mmol, 4.5 equiv.) in THF (10 mL) was added over 30 min. The reaction mixture was allowed to attain room temperature and further stirred for 1 h before heating to 55° C. for 12 h. The reaction mixture was cooled and poured in to ice-water (150 mL) and extracted with Et$_2$O (150 mL). The organic solution was dried (Na$_2$SO$_4$) and concentrated. The product was purified by column chromatography [hexanes:EtOAc, 7:3] to give a colorless syrup (2.96 g, 87%). [α]$_D$ +6° (c 1, CHCl$_3$); $^1$H NMR (CDCl$_3$): δ 7.20-6.80 (12H, m, Ar), 4.55 (2H, s, CH$_2$Ph), 4.48 and 4.45 (2H, 2d, J$_{A,B}$=11.7 Hz, CH$_2$Ph), 4.42 and 4.39 (2H, 2d, J$_{A,B}$=12.0 Hz, CH$_2$Ph), 4.13 (1H, dd, J$_{1a,2}$=4.6, J$_{2,3}$=9.1 Hz, H-2), 4.05 (1H, dd, J$_{2,3}$=J$_{3,4}$=3.7 Hz, H-3), 3.81 (3H, s, OCH$_3$), 3.79 (3H, s, OCH$_3$), 3.76 (3H, s, OCH$_3$), 3.64 (1H, dd, J$_{5a,5b}$=8.9, J$_{4,5a}$=7.5 Hz, H-5a), 3.50 (1H, ddd, J$_{4,5b}$=6.3 Hz, H-4), 3.45 (1H, dd, H-5b), 3.04 (1H, dd, J$_{1a,1b}$=11.4, J$_{1a,2}$=5.2 Hz, H-1a), 2.85 (1H, dd, H-1b). $^{13}$C NMR (CDCl$_3$): δ 159.24, 159.16 (3 C$_{para}$), 130.31, 130.19, 130.01 (3C$_{ipso}$), 129.48, 129.28, 129.22 (6 C$_{ortho}$), 113.80, 113.74 (6 C$_{meta}$), 84.77 (C-3), 84.70 (C-2), 72.66, 71.49, 71.20 (3×CH$_2$Ph), 72.15 (C-5), 55.24 (3×OCH$_3$), 48.96 (C-4), 33.07 (C-1). Anal. Calcd for C$_{29}$H$_{34}$O$_6$S: C, 68.21; H, 6.71. Found: C, 67.99; H, 6.69.

2,3,5-Tri-O-p-Methoxybenzyl-1,4-dideoxy-1,4-[[(2S,3S)-2,4-benzylidenedioxy-3-(sulfooxy)butyl]-episulfoniumylidene]-D-arabinitol Inner Salt (44)

A mixture of the thioether 43 (1.50 g, 2.94 mmol), and the cyclic sulfate 34 (0.96 g, 1.2 equiv) in HFIP (2.5 mL) containing anhydrous K$_2$CO$_3$ (30 mg) was stirred in a sealed tube in an oil-bath (55° C.) overnight. TLC analysis (CH$_2$Cl$_2$: MeOH, 10:1) showed that the thioether 43 was completely consumed. The solvent was removed under reduced pressure and the product was purified by column chromatography (gradient of CH$_2$Cl$_2$ to CH$_2$Cl$_2$:MeOH, 10:1) to give compound 13 (2.3 g, 100%) as a colorless foam. [α]$_D$ –10.5° (c 1.1, CH$_2$Cl$_2$); $^1$H NMR (CD$_2$Cl$_2$): δ 7.51-6.81 (17H, m, Ph), 5.53 (1H, s, C$_6$H$_5$CH), 4.57 (1H, ddd, J$_{2,3}$=J$_{3',4'ax}$=10.0, J$_{3',4'eq}$=5.5 Hz, H-3'), 4.49 (1H, dd, J$_{4'ax,4'eq}$=10.8 Hz, H-4'eq), 4.44 (2H, s, CH$_2$Ph), 4.42-4.39 (1H, m, H-2), 4.39 and 4.29 (2H, 2d, J$_{A,B}$=11.4 Hz, CH$_2$Ph), 4.33 (1H, dd, J$_{1'a,1'b}$=13.4, J$_{1'a,2}$=2.6 Hz, H-1'a), 4.29-4.26 (1H, m, H-3), 4.26 (1H, ddd, H-2'), 4.19 and 4.09 (2H, 2d, J$_{A,B}$=11.5 Hz, CH$_2$Ph), 4.03 (1H, br d, J$_{1a,2}$<1 Hz, H-1a), 3.96-3.89 (2H, m, H-4, H-1'b), 3.80 (3H, s, OCH$_3$), 3.79 (3H, s, OCH$_3$), 3.78 (3H, s, OCH$_3$), 3.77 (1H, dd, H-4'ax), 3.63 (1H, dd, J$_{1a,1b}$=13.3, J$_{1b,2}$=3.8 Hz, H-1b), 3.58 (1H, dd, J$_{5a,5b}$=9.9, J$_{4,5a}$=8.5 Hz, H-5a), 3.49 (1H, dd, J$_{4,5b}$=7.3 Hz, H-5b); $^{13}$C NMR (CD$_2$Cl$_2$): δ 160.30, 160.23, 159.97, 137.20 and 130.27-126.61 (21×C, Ph), 114.45, 114.36 and 114.18 (3×C$_{ipso}$, OMBn), 101.96 (PHCH), 83.29 (C-3), 82.37 (C-2), 76.76 (C-2'), 73.36, 72.43, and 72.14 (3×CH$_2$Ph), 69.50 (C-4'), 66.71 (C-5), 66.55 (C-4), 66.45 (C-3'), 55.61 (3C, 3×OCH$_3$), 49.55 (C-1'), 48.48 (C-1). Anal. Calcd for C$_{40}$H$_{46}$O$_{12}$S$_2$: C, 61.36; H, 5.92. Found: C, 61.13; H, 6.00.

1,4-Dideoxy-1,4-[[(2S,3S)-2,4-dihydroxy-3-(sulfooxy) butyl]-episulfoniumylidene]-D-arabinitol Inner Salt (1). Compound 13 (2.30 g, 2.94 mmol) was dissolved in trifluoroacetic acid (24 mL) and while stirring, water (2.4 mL) was added. The mixture was stirred at room temperature for 0.5 h. The solvent was removed under reduced pressure and the gummy residue was washed with CH$_2$Cl$_2$ (3×20 mL). Water (15 mL) was added to dissolve the crude product, and then evaporated under reduced pressure to remove the traces of acid left. Salacinol 1 (0.67 g, 68%) was crystallized from MeOH. The mother liquor was concentrated and purified by column chromatography (EtOAc:MeOH:H₂O, 7:3:1) to give more Salacinol 1 as a white solid (0.18 g, 18%).

5.2.5 Example 5

General Procedure for the Deprotection of the Protected Sulfonium Sulfates (Schemes 7-10) and Ammonium Sulfates (Schemes 13-14)

The protected compound was dissolved in AcOH:H₂O, 4:1 (3 mL) and stirred with Pd—C (80 mg) under H₂ (52 psi). After 60 h the reaction mixture was filtered through a pad of Celite, which was consequently washed with MeOH. The combined filtrates were concentrated and the residue was purified by column chromatography.

1-((1'1',4'-Anhydro-4'-thio-D-arabinitol)-4'-S-yl)-1-deoxy-L-erythritol-3-sulfate (1)

Column chromatography [CHCl₃:MeOH:H₂O, 7:3:1] of the crude product gave an amorphous solid (67%). $[\alpha]_D$ +2.1° (c 0.48, MeOH); $^1$H NMR (pyridine-d5): δ 5.25 (1H, ddd, J=7.4, 3.8, 3.6 Hz, H-3), 5.14-5.09 (2H, m, H-3', H-2'), 5.00 (1H, m, H-2), 4.78 (1H, dd, J=13.0, 4.9 Hz H-1a), 4.70 (1H, m, H-4'), 4.63 (1H, dd, J=13.0, 4.0 Hz H-1b), 4.61 (1H, dd, J=11.8, 3.7 Hz H-4a) 4.53 (2H, m, H-5'a, H-5'b), 4.38 (1H, dd, J=11.8, 3.8 Hz H-4b), 4.32 (2H, br-s, H-1'a, H-1'b); $^{13}$C NMR (100.6 MHz, pyridine-d5): δ 79.14 (C-3), 79.06 (C-3'), 78.18 (C-2'), 72.30 (C-4'), 67.44 (C-2), 62.05 (C-4), 59.98 (C-5'), 52.46 (C-1), 50.35 (C-1'). HRMS. Calcd for C₉H₁₈O₉S₂ (M+H): 335.0471. Found: 335.0481.

1-((1',4'-Anhydro-4'-thio-D-arabinitol)-4'-S-yl)-1-deoxy-D-erythritol-3-sulfate (23)

Column chromatography [CHCl₃:MeOH:H₂O, 7:3:1] of the crude product gave an amorphous solid (59%). $[\alpha]_D$ −35.6° (c 0.86, MeOH); $^1$H NMR (pyridine-d5): δ 5.19 (1H, ddd, J=8.0, 4.1, 3.6 Hz, H-3), 5.17-5.12 (2H, m, H-2', H-3'), 5.00 (1H, ddd, J=8.0, 5.3, 4.1 Hz, H-2), 4.83 (1H, dd, J=13.0, 5.1 Hz H-1a), 4.78 (1H, m, H-4'), 4.65 (1H, dd, J=11.9, 3.8 Hz H-4a), 4.64-4.57 (2H, m, H-5'a, H-5'b), 4.53 (1H, dd, J=13.0, 4.1 Hz H-1b), 4.40 (1H, dd, J=11.9, 3.8 Hz H-4b), 4.29 (1H, dd, J=12.7, 3.9 Hz H-1'a), 4.17 (1H, dd, J=12.7, 2.6 Hz H-1'b); $^{13}$C NMR (100.6 MHz, pyridine-d5): δ 79.46 (C-3), 79.38 (C-3'), 78.94 (C-2'), 71.94 (C-4'), 67.52 (C-2), 62.02 (C-4), 60.26 (C-5'), 52.64 (C-1), 51.01 (C-1'). HRMS. Calcd for C₉H₁₈O₉S₂ (M+H): 335.0471. Found: 335.0486.

1-((1',4'-Anhydro-4'-thio-L-arabinitol)-4'-S-yl(1-deoxy-D-erythritol-3-sulfate (25)

Column chromatography [CHCl₃:MeOH:H₂O, 7:3:1] of the crude product gave an amorphous solid (80%). $[\alpha]_D$ +1.1° (c 1.5, MeOH); $^1$H NMR (pyridine-d5): δ 5.23 (1H, ddd, J=7.4, 3.8, 3.7 Hz, H-3), 5.11(1H, m, H-3'), 5.10 (1H, m, H-2'), 4.98 (1H,m, H-2), 4.76 (1H, dd, J=11.7, 3.7 Hz H-1a), 4.70 (1H, m, H-4'), 4.63 (1H, dd, J=11.7, 3.8 Hz H-1b), 4.60 (1H, dd, J=11.8, 3.7 Hz H-4a) 4.51 (2H, m, H-5'a, H-5'b), 4.35 (1H, dd, J=11.8, 4.0 Hz H-4b), 4.31 (2H, m, H-1'a, H-1'b); $^{13}$C NMR (100.6 MHz, pyridine-d5): δ 79.38 (C-3, C-2'), 78.41 (C-3'), 72.51 (C-4'), 67.63 (C-2), 62.23 (C-4), 60.21 (C-5'), 52.60 (C-1), 50.57 (C-1'). HRMS. Calcd for C₉H₁₈O₉S₂ (M+H): 335.0471. Found: 335.0466.

1-((1',4'-Dideoxy-1',4'-imino-D-arabinitol)-4'-N-yl)-1-deoxy-L-erythritol-3-sulfate (2)

Column chromatography [CHCl₃:MeOH:H₂O, 7:3:1] of the crude product gave an amorphous solid (64%). $^1$H NMR (CD₃OD): δ 4.26-4.20 (2H, m H-2, H-3), 4.15 (1H, m, H-2'), 3.98 (1H,br-s, H-3'), 3.94-3.87 (3H,m, H-5'a, H-5b', H-4a), 3.81 (1H, dd, J=12.0, 3.5 Hz H-4b), 3.74-3.62 (2H, m, H-1a, H-1'a), 3.49-3.42 (1H, m, H-1'b),3.40-3.35 (1H, m, H-4'), 3.15 (1H, m, H-1b); $^{13}$C NMR (100.6 MHz, CD₃OD): δ 81.17 (C-3), 78.27 (C-3'),77.86 (C-4'), 76.19 (C-2'), 68.07 (C-2), 62.57 (C-1'), 61.67(C-4), 60.72 (C-1, C-5'). HRMS. Calcd for C₉H₁₈O₉SN (M+H): 318.0859. Found: 318.0863.

1-((1',4'-Dideoxy-1',4'-imino-L-arabinitol)-4'-N-yl)-1-deoxy-D-erythritol-3-sulfate (32)

Column chromatography [CHCl₃:MeOH:H₂O, 7:3:1] of the crude product gave an amorphous solid (77%). $^1$H NMR (CD₃OD): δ 4.25 (1H, m H-2), 4.23(1H, m, H-3), 4.16 (1H, br-s, H-2'), 3.99 (1H,br-s, H-3'), 3.94-3.87 (3H,m, H-5'a, H-5b', H-4a), 3.81 (1H, dd, J=12.1, 3.6 Hz H-4b), 3.77-3.64 (2H, m, H-1a, H-1'a), 3.55-3.39 (2H, m, H-1'b, H-4'), 3.22 (1H, m, H-1b); $^{13}$C NMR (100.6 MHz, CD₃OD): δ 81.18 (C-3), 78.23 (C-3', C-4'), 76.10 (C-2'), 68.05 (C-2), 62.66 (C-1'), 61.88(C-4), 60.49 (C-1, C-5'). HRMS. Calcd for C₉H₁₈O₉SN (M+H): 318.0859. Found: 318.0856.

5.2.6 Example 6

General Procedure for the Alternative Synthesis of Blintol (3) (Schemes 12a-12f)

1,2,3,5-Tetra-O-acetyl-L-xylofuranose (49)

L-Xylose (5.00 g, 33.3 mmol), boric acid (4.50 g, 73.2 mmol), and glacial acetic acid (100 mL) were added into a 250 mL round bottom flask. The mixture was stirred at 80° C. until L-xylose and boric acid were dissolved in acetic acid. Acetic anhydride (50 mL) was added and the reaction mixture was stirred at 75° C. for 4 h. Analysis by TLC (EtOAc: MeOH: H₂O, 10:3:1) showed that the L-xylose had been completely consumed. MeOH was then added to the reaction mixture, and the reaction mixture was concentrated to give a dark, orange-brown syrup. To this syrup, acetic anhydride (50 mL) and pyridine (50 mL) were added and the reaction mixture was stirred at room temperature for 4 h. The orange-brown mixture was pour into crushed ice and was extracted with Et₂O (100 mL). The organic layer was washed with saturated aqueous NaHCO₃ (50 mL), aqueous HCl, water, and saturated NaCl, dried over MgSO₄ and concentrated to a yellow syrup. Purification by column chromatography on silica gel (Hexane:EtOAc, 2:1) yielded the tetra-O-acetylxylofuranose 49 (9.01 g, 85%) as a colorless syrup (α:β ratio 1:23). Data for the β (major) isomer.

$^1$H NMR (CDCl₃): δ 6.08 (1H, s, H-1), 5.35 (1H, dd, $J_{2,3}$=1.7, $J_{3,4}$=5.6 Hz, H-3), 5.18 (1H, d, $J_{1,2}$<1 Hz, H-2), 4.62 (1H, dd, $J_{4,5a}$<1, $J_{4,5b}$=12.1 Hz, H-4), 4.22 (2H, m, H-5a, H-5b), 2.10, 2.09, 2.08, and 2.04 (12H, 4 s, COCH₃). $^{13}$C NMR (CDCl₃): d 170.71, 169.69, 169.52, 169.43 (4×C=O, OAc), 99.01 (C-1), 80.03 (C-2), 79.58 (C-3), 74.43 (C-4), 62.54 (C-5), 21,33, 20.97, 20.82, 20.68 (4×CH₃, OAc). Anal. Calcd for C₁₃H₁₈O₉: C, 49.06; H, 5.70. Found: C, 48.93; H, 5.84.

4-Pentenyl-2,3,5-tri-O-acetyl-L-xylofuranoside (50)

Tetra-O-acetylxylofuranose 49 (5.00 g, 17.7 mmol), CH₂Cl₂ (100 mL), 4-penten-1-ol (9.1 mL, 88 mmol), and crushed molecular sieves (4A, 2 g) were added to a 250 mL round bottom flask and cooled to 0° C. Boron trifluoride (11 mL, 88 mmol) was added to the reaction mixture and the mixture was stirred at 0° C. for 2 h. The temperature was raised to room temperature and the mixture was stirred for 1 h. Analysis by TLC (Hexane: EtOAc, 2:1) showed that the majority of the starting material had been consumed. The reaction mixture was poured into ice/NaHCO₃ mixture, extracted with Et₂O (100 mL), and dried over MgSO₄. The reaction mixture was concentrated to a dark, orange-brown syrup. Purification by column chromatography on silica gel (Hexane:EtOAc, 2:1) yielded the pentenyl glycosides 50 (3.28 g, 60%) as a colorless syrup (α:β ratio 1:23).

Data for the β (major) isomer. $^1$H NMR (CDCl₃): δ 5.78 (1H, dddd, $J_{4',5b}$=23.6, $J_{4',5a}$=17.1, $J_{3a',4'}$=3.6, $J_{3b',4'}$=13.3 Hz, H-4'), 5.30 (1H, dd, $J_{2,3}$=1.5, $J_{3,4}$=6.0 Hz, H-3), 5.07 (1H, s, $J_{1,2}$<1 Hz, H-2), 4.99 (1H, 2 ddd, $J_{3'a,5'a}$=1.7, $J_{3'b,5'a}$=1.7, $J_{5b,5a}$=3.5 Hz, H-5a'), 4.94 (1H, s, H-1), 4.93 (1H, m, H-5'b), 4.55 (1H, ddd, $J_{4,5a}$=5.3, $J_{4,5b}$=7.3 Hz, H-4), 4.24 (1H, dd, $J_{5a,5b}$=11.5, H-5a), 4.18 (1H, dd, H-5b), 3.69 (1H, ddd, $J_{1'a,2'a}$=6.7, $J_{1'a,2'b}$=6.7, $J_{1'a,1'b}$=13.3 Hz, H-1'a), 3.40 (1H, ddd, $J_{1'b,2'a}$=6.4, $J_{1'b,2'b}$=6.4 Hz, H-1'b), 2.07 (6H, s, 2×COCH₃), 2.04 (3H, s, COCH₃), 2.04 (2H, m, H-3'a, H-3'b), 1.65 (2H, m, H-2'a, H-2'b). $^{13}$C NMR (CDCl₃): δ 170.72, 170.11, and 169.74 (3×C═O, OAc), 138.22 (C-4'), 115.13 (C-5'), 106.08 (C-1), 80.92 (C-2), 78.17 (C-4), 75.11 (C-3), 67.77 (C-1'), 63.42 (C-5), 30.34 (C-3'), 28.78 (C-2'), 20.99, 20.93, and 20.81(3×CH₃, OAc). Anal. Calcd for C₁₆H₂₄O₈: C, 55.81; H, 7.02. Found: C, 55.99; H, 7.19.

4-Pentenyl-L-xylofuranoside (51)

The pentenyl glycoside 50 (3.28 g, 9.52 mmol) was dissolved into MeOH (50 mL) in a 250 mL round bottom flask. NaOMe in MeOH (0.02 M) was added to the reaction mixture and the mixture was stirred at room temperature for 1 h. Analysis by TLC (CH₂Cl₂: MeOH, 10:1) showed the starting material had been consumed. Rexyn® 101 (H) resin was added to the reaction mixture to adjust the PH to 7. The reaction mixture was then filtered and the filtrate was concentrated to give a light brown syrup. Purification by column chromatography on silica gel (CH₂Cl₂: MeOH, 10:1) yielded the pentenyl glycosides 51 (1.97 g, 95%) as a colorless syrup (α:β ratio 1:23).

Data for the β (major) isomer. $^1$H NMR (CD₃OD): δ 5.75 (1H, m, H-4'), 5.03 (1H, m, H-5'a), 4.96 (1H, m, H-5'b), 4.86 (1H, s, $J_{1,2}$<1 Hz, H-1), 4.24 (1H, ddd, $J_{4,5a}$=5.0, $J_{4,5b}$=6.6, $J_{3,4}$=5.1 Hz, H-4), 4.08 (1H, dd, $J_{2,3}$=2.0, H-3), 4.03 (1H, br.s, H-2), 3.83 (1H, dd, $J_{5a,5b}$=11.6, H-5a), 3.79 (1H, m, H-5a), 3.74 (1H, m, H-5b), 3.43 (1H, m, H-1'b), 2.17 (2H, m, H-3'a, H-3'b), 1.68 (2H, m, H-2'a, H-2'b). $^{13}$C NMR (CD₃OD): δ 138.23 (C-4'), 114.17 (C-5'), 109.62 (C-1), 82.71 (C-4), 81.01 (C-2), 76.31 (C-3), 67.42 (C-1'), 61.49 (C-5), 32.20 (C-3'), 28.78 (C-2'). Anal. Calcd for C₁₀H₁₈O₅: C, 55.03; H, 8.31. Found: C, 55.30; H, 8.44.

4-Pentenyl-2,3,5-tri-O-p-methoxybenzyl-L-xylofuranoside (52)

In a 250 mL flask NaH (4.38 g, 0.11 mol) and DMF (80 mL) were added and cooled to 0° C. The pentenyl glycoside 51 (3.00 g, 13.7 mmol) was dissolved in DMF (10 mL) and the solution was added dropwise to the NaH/DMF mixture. After the addition, the reaction mixture was stirred at 0° C. for 2 h. The temperature was then raised to room temperature and the mixture was stirred for 1 h. p-Methoxybenzyl chloride (15 mL, 0.11 mol) dissolved in DMF (10 mL) was then added dropwise to the reaction mixture. The mixture was stirred at room temperature for 2 h after the addition. The reaction mixture was quenched with ice water, extracted with Et₂O (100 mL), washed with H₂O (8×20 mL portions), and dried over MgSO₄. The mixture was concentrated to give a orange-brown syrup. Purification by column chromatography on silica gel (Hexane:EtOAc, 4:1) yielded the pentenyl glycosides 52 (7.30 g, 92%) as a colorless syrup (α:β ratio 1:23).

Data for the β (major) isomer. $^1$H NMR (CDCl₃): δ 7.25-6.85 (12H, m, Ar), 5.83 (1H, dddd, $J_{4',5b}$=6.6, $J_{4',5a}$=16.9, $J_{3'a,4}$=6.8, $J_{3'b,4'}$=10.4 Hz, H-4'), 5.03 (1H, dddd, $J_{3'a,5'a}$=1.7, $J_{3'b,5'a}$=5.5, $J_{5'b,5'a}$=3.5 Hz, H-5a'), 4.98 (1H, br.s, $J_{1,2}$=1.8 Hz, H-1), 4.97 (1H, m, H-5'b), 4.49 (6H, m, 3×CH₂Ph), 4.41 (1H, m, H-4), 4.02 (1H, dd, $J_{2,3}$=2.3, $J_{3,4}$=5.8 Hz, H-3), 3.97 (1H, br.t, H-2), 3.81 (6H, s, 2×OCH₃), 3.80 (3H, s, OCH₃), 3.76 (1H, m, H-1'a), 3.72 (1H, dd, $J_{4,5a}$=4.7, $J_{5a,5b}$=10.3 Hz, H-5a), 3.67 (1H, dd, $J_{4,5b}$=7.3 Hz, H-5b), 3.42 (1H, m, H-1'b), 2.12 (2H, m, H-3'a, H-3'b), 1.68 (2H, m, H-2'a, H-2'b). $^{13}$C NMR (CDCl₃): δ 159.60-113.91 (12 $C_{Ar}$),138.51 (C-4'), 114.03 (C-5'), 107.38 (C-1), 87.02 (C-2), 81.83 (C-3), 80.04 (C-4), 73.32, 71.93, 71.81 (3×CH₂Ph), 69.78 (C-5), 67.94 (C-1'), 55.52 (OCH₃), 30.61 (C-3'), 28.98 (C-2'). Anal. Calcd for C₃₄H₄₂O₈: C, 70.57; H, 7.32. Found: C, 70.44; H, 7.48.

2,3,5-Tri-O-p-methoxybenzyl-L-xylofuranose (53)

In a 500 mL round bottom flask pentenyl glycosides 52 (7.00 g, 12.1 mmol) were dissolved in CH₃CN (180 mL). H₂O (20 mL) was added and the mixture was cooled to 0° C. N-Bromosuccinimide (5.38 g, 30.2 mmol) was added to the reaction mixture and the reaction mixture was stirred at 0° C. for 1 h. Analysis by TLC (Hexane: EtOAc, 2:1) showed that the starting material had been completely consumed. Na₂S₂O₃.5H₂O (15 g, 60 mmol) dissolved in H₂O (60 mL) was then added and the mixture was stirred for 20 min. The mixture was then concentrated to give a dark orange syrup. The syrup was dissolved in EtOAc (150 mL), washed with H₂O, saturated NaCl, and dried over MgSO₄. The mixture was then concentrated to give a dark brown syrup. Purification by column chromatography on silica gel (Hexane:EtOAc, 1:1) yielded the p-methoxybenzyl xylofuranoses 53 (5.52 g, 90%) as a colorless syrup (α:β ratio 1:2).

Data for the β (major) isomer. $^1$H NMR (CDCl₃): δ 7.25-6.80 (12H, m, Ar), 5.20 (1H, br.s, $J_{1,2}$=1.8 Hz, H-1), 4.55-4.40 (6H, m, 3×CH₂Ph), 4.34(1H, ddd, $J_{4,5b}$=5.0, $J_{4,5a}$=4.1, $J_{3,4}$=5.4 Hz, H-4), 4.05 (1H, dd, $J_{2,3}$=2.8 Hz, H-3), 3.95 (1H, br.d, $J_{1,2}$<1 Hz H-2), 3.82, 3.81, 3.80 (9H, 3×s, 3×OCH₃), 3.68 (2H, m, H-5a, H-5b). $^{13}$C NMR (CDCl₃): δ 159.60-113.50 (12 $C_{Ar}$),101.68 (C-1), 86.24 (C-2), 80.91 (C-3), 79.83 (C-4), 73.32, 72.33, 71.48 (3×CH₂Ph), 68.31 (C-5), 55.22 (OCH₃). Anal. Calcd for C₂₉H₃₄O₈: C, 68.22; H, 6.71. Found: C, 68.17; H, 6.65.

2,3,5-Tri-O-p-methoxybenzyl-L-xylitol (54)

The p-methoxybenzyl xylofuranoses 53 (5.50 g, 10.8 mmol) were dissolved in THF (10 mL) and MeOH (50 mL) was then added. NaBH₄ was added portionwise to the reaction mixture at room temperature until the TLC analysis (Hexane:EtOAc, 1:1) showed that the starting material had been consumed. The mixture was concentrated to give a light yellow solid. This solid was dissolved in EtOAc (150 mL), washed with water, saturated aqueous NaCl, dried over MgSO₄, and concentrated to give a light yellow syrup. Purification by column chromatography on silica gel (Hexane: EtOAc, 1:1) yielded the p-methoxybenzyl xylitol 54 as a colorless syrup (4.62 g, 84%).

[α]$_D$ +7.25 (c 2.8, CHCl₃). $^1$H NMR (CDCl₃): δ 7.20-6.80 (12H, m, Ar), 4.58, 4.43 (2H, 2d, $J_{A,B}$=11.2 Hz, CH₂Ph), 4.54 (2H, 2d, $J_{A,B}$=11.2 Hz, CH₂Ph), 4.44, 4.39 (2H, 2d, $J_{AB}$=11.7

Hz, CH$_2$Ph), 4.02 (1H, ddd, J$_{2,3}$=1.9, J$_{1a,2}$=6.4, J$_{1b,2}$=6.2 Hz, H-2), 3.80 (9H, s, 3×OCH$_3$), 3.75 (2H, m, H-4, H-5a), 3.66 (1H, dd, J$_{3,4}$=6.4 Hz, H-3), 3.63 (1H, m, H-5b), 3.46 (1H, dd, J$_{1a,1b}$=9.4 Hz, H-1a), 3.37 (1H, dd, H-1b). $^{13}$C NMR (CDCl$_3$): δ 159.60-113.50 (12 C$_{Ar}$), 78.32 (C-3), 77.01 (C-5), 73.88, 73.08, 72.10 (3×CH$_2$Ph), 71.23 (C-1), 68.79 (C-2), 60.81 (C-4), 55.53 (OCH$_3$). Anal. Calcd for C$_{29}$H$_{36}$O$_8$: C, 67.95; H, 7.08. Found: C, 67.85; H, 7.12.

2,3,5-Tri-O-p-methoxybenzyl-1,4-di-O-methane-sulfonyl-L-xylitol (55)

In a 250 mL round bottom flask, methanesulfonyl chloride (5.3 mL, 68 mmol), pyridine (6 mL, 68 mmol), and CH$_2$Cl$_2$ (50 mL) were cooled to 0° C. The p-methoxybenzyl xylitol (54, 3.50 g, 6.84 mmol) in CH$_2$Cl$_2$ (50 mL) was then added dropwise to the methanesulfonyl chloride/pyridine mixture. After the addition was completed, the temperature was raised to room temperature and the mixture was stirred for 3 h. The reaction mixture was then poured onto crushed ice, extracted with EtOAc (150 mL), washed with water, saturated aqueous NaCl, dried over MgSO$_4$, and was concentrated to give a light yellow syrup. Purification by column chromatography on silica gel (Hexane:EtOAc, 1:1) yielded the methanesulfonyl xylitol 55 as a colorless syrup (3.28 g, 72%).

[α]$_D$ −16.2 (c 5.6, CHCl$_3$). $^1$H NMR (CDCl$_3$): δ 7.20-6.80 (12H, m, Ar), 4.92 (1H, ddd, J$_{2,3}$=9.2, J$_{1a,2}$=3.6, J$_{1b,2}$=6.1 Hz, H-2), 4.60, 4.43 (2H, 2d, J$_{A,B}$=11.3 Hz, CH$_2$Ph), 4.57 (2H, 2d, J$_{AB}$=11.3 Hz, CH$_2$Ph), 4.41, 4.33 (2H, 2d, J$_{A,B}$=11.1 Hz, CH$_2$Ph), 4.36 (1H, dd, J$_{4,5a}$=5.6, J$_{5a,5b}$=11.0 Hz, H-5a), 4.31 (1H, dd, J$_{4,5b}$=4.2 Hz, H-5b), 3.83 (1H, m, H-4), 3.80, 3.79, 3.78 (9H, 3s, 3×OCH$_3$), 3.78 (1H, m, H-3), 3.56 (1H, dd, J$_{1a,1b}$=11.2 Hz, H-1a), 3.54 (1H, dd, H-1b), 2.99, 2.92 (6H, 2 s, 2×OSO$_2$CH$_3$). $^{13}$C NMR (CDCl$_3$): δ 159.60-113.50 (12 C$_{Ar}$), 80.32 (C-2), 75.63 (C-3), 75.24 (C-4), 74.11, 72.83, 72.69 (3×CH$_2$Ph), 68.43 (C-5), 68.41 (C-1), 55.12 (OCH$_3$), 38.5, 37.1 (2×OSO$_2$CH$_3$). Anal. Calcd for C$_{31}$H$_{40}$O$_{12}$S$_2$: C, 55.67; H, 6.03. Found: C, 55.45; H, 6.13.

1,4-Anhydro-2,3,5-tri-O-p-methoxybenzyl-4-seleno-D-arabinitol (56)

In a 250 mL round bottom flask, selenium metal (0.61 g, 7.7 mmol) and 95% EtOH (50 mL) were added. NaBH$_4$ was then added portionwise at room temperature until the color of the reaction mixture changed from black to white. The dimesylate 55 (3.28 g, 4.91 mmol) dissolved into THF (10 mL) was then added to the reaction mixture and the mixture was heated and stirred at 60° C. for 12 h. The mixture was then concentrated to give a dark orange-red syrup. This solid was dissolved into Et$_2$O (100 mL), washed with water, saturated aqueous NaCl, dried over MgSO$_4$, and was concentrated to give a light yellow syrup. Purification by column chromatography on silica gel (Hexane:EtOAc, 4:1) yielded the selenoarabinitol 56 as a colorless syrup (2.27 g, 83%).

[α]$_D$ +17.83 (c 1.5, CHCl$_3$). $^1$H NMR (CDCl$_3$): δ 7.20-6.80 (12H, m, Ar), 4.58, 4.52 (2H, 2d, J$_{A,B}$=11.4 Hz, CH$_2$Ph), 4.48, 4.44 (2H, 2d, J$_{A,B}$=11.6 Hz, CH$_2$Ph), 4.45, 4.42 (2H, 2d, J$_{A,B}$=11.7 Hz, CH$_2$Ph), 4.16 (1H, ddd, J$_{2,3}$=5.2, J$_{1a,2}$=5.1, J$_{1b,2}$=5.4 Hz, H-2), 4.00 (1H, dd, J$_{3,4}$=4.8 Hz, H-3), 3.81 (1H, m, H-5a), 3.81 (6H, s, 2×OCH$_3$), 3.80 (3H, s, OCH$_3$), 3.72 (1H, m, H-4), 3.48 (1H, dd, J$_{4,5b}$=7.2, J$_{5a,5b}$=9.3 Hz, H-5b), 3.06 (1H, dd, H-1a), 2.92 (1H, dd, H-1b). $^{13}$C NMR (CDCl$_3$): δ 159.20-113.50 (12 C$_{Ar}$), 85.73 (C-2), 85.33 (C-3), 72.89 (C-5), 72.83, 72.01, 71.42 (3×CH$_2$Ph), 55.22 (OCH$_3$), 42.38 (C-4), 23.91 (C-1). Anal. Calcd for C$_{29}$H$_{34}$O$_6$Se: C, 62.47; H, 6.15. Found: C, 62.39; H, 6.25.

2,4-O-Benzylidene-L-erythritol-1,3-cyclic sulfate (57)

The cyclic sulfate 62, prepared according to literature procedures, (13.5 g, 37.0 mmol) was dissolved in EtOAc (120 mL) in a 500 mL round bottom flask. Pd on activated carbon (200 mg, 10% palladium) was added to the solution and H$_2$ was bubbled through the solution with stirring at room temperature for 48 h. Periodic analysis by TLC (Hexane: EtOAc, 1:1) showed that the reaction proceeded smoothly until the cyclic sulfate 62 had been consumed. The Pd was removed by filtration and the solvent was evaporated to yield the deprotected cyclic sulfate 63 as a white solid (6.82 g, quantitative yield). The cyclic sulfate 63 was used directly without further purification. The cyclic sulfate 63 and pyridinium p-toluenesulfonate (500 mg) were dissolved in CH$_2$Cl$_2$ (20 mL) in a 250 mL round bottom flask and PhCH(OMe)$_2$ (37 mL, 0.26 mol) was added. The solution was heated to 60° C. on a rotary evaporator under vacuum for 1 h. Analysis by TLC (Hexane: EtOAc, 1:1) showed that the cyclic sulfate 57 had been consumed. The mixture was dissolved in EtOAc (100 mL), washed with saturated aqueous NaCl (20 mL), dried over MgSO$_4$, and was concentrated to give a colorless syrup. Purification by column chromatography on silica gel (Hexane: EtOAc, 1:1) yielded the cyclic sulfate 57 as a white solid (7.14 g, 71%). This material was identical in all respects to that obtained previously[25] using L-glucose.

1,3-Di-O-benzyl-D-erythritol (60)—Alternative Procedure

In a 250 mL flask, 2,4-O-Benzylidene-1,3-di-O-benzyl-D-erythritol (59, 36.6 g, 93.7 mmol) and 50% aqueous TFA solution (100 mL) were added. The reaction mixture was stirred at room temperature for 0.5 h. Analysis by TLC (Hexane: EtOAc, 2:1) showed the starting material had been consumed. The reaction mixture was cooled to 0° C. and 50% aqueous KOH solution (50 mL) was added. The reaction mixture was stirred at 0° C. for additional 0.5 h, extracted with EtOAc (200 mL), and dried over Na$_2$SO$_4$. The mixture was concentrated to give a brown syrup. Purification by column chromatography on silica gel (Hexane: EtOAc, 1:1) yielded the erythritol 60 (17.6 g, 60%) as a colorless syrup. This material was identical in all respects to that obtained previously[26] using aqueous acetic acid.

2,3,5-Tri-O-p-Methoxybenzyl-1,4-dideoxy-1,4-[[(2S,3S)-2,4-benzylidenedioxy-3-(sulfooxy)butyl]-episelenoniumylidene]-D-arabinitol Inner Salt (64)

The seleno-D-arabinitol 56 (3.11 g, 5.59 mmol), the cyclic sulfate 57 (1.33 g, 4.88 mmol) and K$_2$CO$_3$ (160 mg, 1.16 mmol) were added to 1,1,1,3,3,3-hexafluoro-2-propanol (8.0 mL) and the mixture was stirred in a sealed tube with heating at 60-65° C. for 7 h. Periodic analysis by TLC (EtOAc: MeOH, 10:1) showed that the reaction proceeded smoothly until the selenoether had been consumed leaving some cyclic sulfate unreacted. The mixture was cooled and filtered through Celite with the aid of CH$_2$Cl$_2$. The solvents were removed and the residue was purified by column chromatography (gradient of EtOAc to EtOAc: MeOH, 10:1). The selenonium salt 64 (3.85 g, 95% based on selenoether 14) was obtained as a colorless foam. Analysis of the $^1$H and $^{13}$C NMR spectra indicated that compound 64 was produced as a 7:1 mixture of isomers at the stereogenic selenium center. The major isomer was assigned to be the isomer with a trans relationship between C-5 and C-1' by analogy to the results obtained previously for the corresponding benzyl-protected selenonium salt. For trans 64: $^1$H NMR (600 MHz, CD$_2$Cl$_2$) δ 7.45-6.80 (17H, m, Ar), 5.58 (1H, s, C$_6$H$_5$CH), 4.51 (1H, dd, $J_{2,3}$=$J_{3',4'ax}$=9.7, $J_{3',4'eq}$=5.3 Hz, H-3'), 4.48 (1H, br s, H-2), 4.46 (1H, dd, $J_{4'ax,4'eq}$=10.5 Hz, H-4'eq), 4.41, 4.33 (2H, 2d, $J_{A,B}$=11.1 Hz, CH$_2$Ph), 4.57 (2H, 2d, $J_{AB}$=11.3 Hz, CH$_2$Ph), 4.43 and 4.40 (2H, 2d, $J_{A,B}$=12.0 Hz, CH$_2$Ph), 4.39 and 4.26 (2H, 2d, $J_{A,B}$=11.4 Hz, CH$_2$Ph), 4.32 (1H, dd, $J_{1'a,2'}$=2.2 Hz, H-1'a), 4.27 (1H, br d, $J_{2,3}$=2.0 Hz, H-3), 4.25 and 4.19 (2H, 2d, $J_{A,B}$=10.8 Hz, CH$_2$Ph), 4.21 (1H, ddd, H-2'), 4.04 (1H, br d, $J_{1,2}$<1 Hz, H-1a), 4.03 (1H, br dd, $J_{3,4}$<1 Hz, H-4), 3.90 (1H, dd, $J_{1'a,1'b}$=12.2, $J_{1'b,2'}$=3.6 Hz, H-4), 3.78 (3H, s, OCH$_3$), 3.77 (1H, dd, H-4'ax), 3.77 (3H, s, OCH$_3$), 3.76 (3H, s, OCH$_3$), 3.55 (1H, dd, $J_{1a,1b}$=12.8, $J_{1b,2}$=2.9 Hz, H-1b), 3.54 (1H, dd, $J_{5a,5b}$=9.7, $J_{4,5a}$=6.7 Hz, H-5a), 3.48 (1H, dd, $J_{4,5b}$=9.4 Hz, H-5b); $^{13}$C NMR (150 MHz, CDCl$_2$): δ 160.34, 160.09, 136.58 and 130.14-126.51 (21 $C_{Ar}$), 114.56, 114.47 and 114.70 (3×$C_{ipso}$, OMBn), 102.17 (PHCH), 84.31 (C-3), 83.00 (C-2), 77.30 (C-2'), 73.37, 72.49, and 72.10 (3×CH$_2$Ph), 69.67 (C-4'), 67.75 (C-3'), 66.80 (2×C, C-4, C-5), 55.67 (3×C, 3×OCH$_3$), 48.73 (C-1'), 46.69 (C-1). Anal. Calcd for C$_{40}$H$_{46}$O$_{12}$SSe: C, 57.90; H, 5.59. Found: C, 57.87; H, 5.57.

1,4-Dideoxy-1,4-[[(2S,3S)-2,4-dihydroxy-3-(sulfooxy)butyl]episelenoniumylidene]-D-arabinitol Inner Salt (Blintol, 3)

The selenonium salts 64 (3.80 g, 4.58 mmol) were dissolved in cold trifluoroacetic acid (40 mL) to give a purple solution. Water (4.0 mL) was added and the reaction mixture was kept at room temperature for 0.5 h. The solvents were removed on a rotary evaporator and the residue was triturated with CH$_2$Cl$_2$ (4×50 mL), with each portion of solvent being decanted from the insoluble gummy product. The crude product was dissolved in water (50 mL) and filtered to remove a small amount of insoluble material. The aqueous filtrate was concentrated to a syrupy residue (1.84 g). Analysis by NMR spectroscopy indicated that the product was an isomeric mixture (7:1) of 3 with its stereoisomer at the selenium center. Recrystallization from MeOH gave pure 3 (1.09 g, 62%) in two crops. This material was identical in all respects to that obtained previously[26] using hydrogenolysis to remove the benzyl protecting groups. Purification of the mother liquor fractions by column chromatography (EtOAc: MeOH: H$_2$O, 6:3:1) gave a 3:2 mixture of 3 with its isomer (0.25 g, 14%) as a syrup.

5.2.7 Example 7

Synthesis of Six-Membered Ring Analogues (Schemes 15 to 21)

General.

Optical rotations were measured at 23° C. Analytical thin-layer chromatography (TLC) was performed on aluminum plates precoated with Merck silica gel 60F-254 as the adsorbent. The developed plates were air-dried, exposed to UV light and/or sprayed with a solution containing 1% Ce(SO$_4$)$_2$ and 1.5% molybdic acid in 10% aq H$_2$SO$_4$ and heated. Compounds were purified by flash chromatography on Kieselgel 60 (230-400 mesh). Rexyn 101 was obtained from Fischer. $^1$H and $^{13}$C NMR spectra were recorded on: Bruker AMX-400 NMR spectrometer at 400.13 MHz, Bruker AMX-600 NMR spectrometer at 600.13 MHz and Varian INOVA 500 NMR spectrometer at 499.97 MHz for $^1$H. Chemical shifts are given in ppm downfield from TMS for those measured in CDCl$_3$, CD$_3$OD and CD$_2$Cl$_2$ and from 2,2-dimethyl-2-silapentane-5-sulfonate (DSS) for those spectra measured in D$_2$O. Chemical shifts and coupling constants were obtained from a first-order analysis of the spectra. Assignments were fully supported by two-dimensional $^1$H,$^1$H(COSY), $^1$H,$^1$H (NOESY) and $^1$H,$^{13}$C (HMQC) experiments using standard Bruker or Varian pulse programs. Processing of the spectra was performed with standard UXNMR and WINNMR software (Bruker) or MestReC software (Varian).

The 1D-transient NOE experiments were performed by inverting the signal of interest with a 80 ms Gaussian selective pulse which was constructed from 1024 steps. Spectra were collected in difference mode by alternating the phase of the receiver gain during on- and off-resonance. The digitized signal was stored in a 32 K data set using a sweep width of 10 ppm, an acquisition time of 2.72 s, 128 scans, and 8 dummy scans. Processing of the spectra was accomplished by zero filling to 64 K followed by an exponential multiplication using a line width of 1 Hz. NOESY spectra were obtained with a mixing time of 500 or 800 ms.

MALDI mass spectra were obtained on a PerSeptive Biosystems, Voyager DE time-of-flight spectrometer for samples dispersed in a 2,5-dihydroxybenzoic acid matrix. High resolution mass spectra were liquid secondary ion mass spectrometry (LSIMS), run on a Kratos Concept double focussing mass spectrometer at 10 000 RP, using a glycerin matrix or, in the case of compound 88a, with meta-NO$_2$-benzyl alcohol as the matrix. Solvents were distilled before use and were dried, as necessary. Solvents were evaporated under reduced pressure and below 50° C.

1,5-Anhydro-2,3,4-tri-O-benzyl-5-thioxylitol (74)

(a) Acetate Methanolysis: A mixture of 1,5-anhydro-2,3,4-tri-O-acetyl-5-thioxylitol 77 (0.125 g, 0.453 mmol) and 1M NaOMe in MeOH (0.6 mL, 0.6 mmol) in dry MeOH (10 mL) was stirred under N$_2$ overnight. The mixture was neutralized with excess Rexyn 101. The resin was removed by filtration and the organic phase was concentrated to give 1,5-anhydro-5-thioxylitol as a solid (59.6 mg, 88%). Mp 137-140° C.; $^1$H NMR (D$_2$O): δ 3.65 (2H, m, $J_{1eq,2}$=$J_{4,5eq}$=4.5 Hz, $J_{1ax,2}$=$J_{4,5ax}$=10.9 Hz, H-2 and H-4), 3.15 (1H, t, $J_{2,3}$=$J_{3,4}$=9.1 Hz, H-3), 2.66 (2H, m, H-5 eq and H-1 eq), 2.56 (2H, dd, $J_{5ax,5eq}$=$J_{1ax,1eq}$=13.6 Hz, H-5ax and H-1ax); $^{13}$C NMR (D$_2$O): δ 81.20 (C-3), 75.75 (2C, C-2 and C-4), 34.86 (2C, C-1 and C-5). Anal. Calcd for C$_5$H$_{10}$O$_3$S: C, 39.99; H, 6.71. Found: C, 39.68; H, 6.91.

(b) Benzylation: A mixture of 1,5-anhydro-5-thioxylitol (0.520 g, 3.47 mmol) and 60% NaH (0.744 g, 5 equiv) in DMF (50 mL) was stirred in an ice-bath for 1 h. A solution of BnBr (1.4 mL, 4 equiv) was added and the solution was stirred at RT overnight. The mixture was quenched with MeOH (8 mL), 1420 (100 mL) was added, and the solution was extracted with Et$_2$O (3×150 mL). The organic solution was dried over Na$_2$SO$_4$, concentrated, and the residue was purified by flash chromatography [hexanes:EtOAc, 20:1] to give 74 as a white solid (0.928 g, 64%). Mp 46-49° C.; $^1$H NMR (CDCl$_3$): δ 7.36-7.24 (15H, m, Ar), 4.83 (2H, s, CH$_2$Ph), 4.69 (2H, d, $J_{A,B}$=11.4 Hz, CH$_2$Ph), 4.65 (2H, d, $J_{A,B}$=11.6 Hz, CH$_2$Ph), 3.63 (2H, m, $J_{1eq,2}$=$J_{4,5eq}$=4.2 Hz, $J_{1ax,2}$=$J_{4,5ax}$=11.0 Hz, H-4 and H-2), 3.31 (1H, t, $J_{2,3}$=$J_{3,4}$=8.9 Hz, H-3), 2.72 (2H, m, H-5 eq and H-1 eq), 2.47 (2H, dd, $J_{5ax,5eq}$=$J_{1ax,1eq}$=13.4 Hz, H-5ax and H-1ax); $^{13}$C NMR (CDCl$_3$): δ 138.9, 138.37 (3C$_{ipso}$), 128.42-127.51

(15C, Ar), 86.76 (C-3), 82.26 (2C, C-2 and C-4), 76.33 (CH$_2$Ph), 73.02 (2 CH$_2$Ph), 31.49 (2C, C-1 and C-5). Anal. Calcd for C$_{26}$H$_{28}$O$_3$S: C, 74.25; H, 6.71. Found: C, 74.16; H, 6.91.

1,5-Anhydro-2,3,4,6-tetra-O-benzyl-5-thio-D-glucitol (75)

(a) Acetate Methanolysis: To a solution of 1,5-anhydro-2,3,4,6-tetra-O-acetyl-5-thio-D-glucitol 78 (0.310 g, 0.89 mmol) in dry MeOH (20 mL) was added 1M NaOMe/MeOH (4 mL, 4 equiv), and the mixture was stirred under N$_2$ overnight. The mixture was neutralized with excess Rexyn 101 ion-exchange resin, the resin was removed by filtration, and the organic phase was concentrated. The residue was purified by flash chromatography [CHCl$_3$:MeOH, 5:2] to give 1,5-anhydro-5-thio-D-glucitol as a white solid (0.125 g, 78%). Mp 110-115° C.; [α]$_D$=+27.4 (c 1.2, MeOH); $^1$H NMR (D$_2$O): δ 3.90 (1H, dd, J$_{5,6}$a=3.2 Hz, J$_{6b,6a}$=11.9 Hz, H-6a), 3.75 (1H, dd, J$_{5,6b}$=6.4 Hz, H-6b), 3.64 (1H, m, H-2), 3.48 (1H, dd, J$_{4,5}$=10.2 Hz, H-4), 3.19 (1H, t, J$_{2,3}$=J$_{3,4}$=9.1 Hz, H-3), 2.88 (1H, m, H-5), 2.71 (1H, dd, J$_{1eq,2}$=4.6 Hz, J$_{1eq,1ax}$=13.3 Hz, H-1 eq), 2.62 (1H, dd, J$_{1ax,2}$=11.0 Hz, H-1ax).

(b) Benzylation: To a stirred solution of 1,5-anhydro-5-thio-D-glucitol (0.194 g, 1.08 mmol) in dry DMF (60 mL) was added NaH (0.5 g, 12.5 mmol) and then BnBr (0.7 mL, 5.9 mmol), and the mixture was stirred overnight. Excess NaH was destroyed by the addition of MeOH. The organic phase was concentrated under reduced pressure. To the residue was added H$_2$O (200 mL) and this was extracted with CH$_2$Cl$_2$ (5×100 mL). The organic phase was dried over Na$_2$SO$_4$ and concentrated. The product was purified by flash chromatography [hexanes:EtOAc, 20:1] to give a syrup that was recrystallized from EtOAc/hexanes to give compound 75 as a white solid (0.276 g, 58%). Mp 56-59° C.; [α]$_D$=+15.1 (c 1.1, CHCl$_3$). The $^1$H NMR spectrum was consistent with the literature data.[79]

1,5-Anhydro-2,3,4-tri-O-acetyl-5-selenoxylitol (81)

To a stirred suspension of selenium (1.48 g, 18.7 mmol) in anhydrous EtOH (40 mL) at 0° C. was added NaBH$_4$ (0.9 g, 23.8 mmol). An almost colorless solution resulted. The ice bath was removed and 2,3,5-tri-O-acetyl-1,5-dibromo-1,5-dideoxy-xylitol 80 (4.87 g, 12.0 mmol) was added, and the mixture was stirred at RT overnight. H$_2$O (200 mL) was added and the mixture was extracted with Et$_2$O (5×100 mL). The solids were removed by filtration, the solution was concentrated, and the residue was purified by flash chromatography [hexanes:EtOAc, 1:1] to give 81 as yellow crystals (2.22 g, 57%). Mp 106-111° C.; $^1$H NMR (CDCl$_3$): δ 5.11 (2H, ddd, J$_{1eq,2}$=J$_{4,5eq}$=4.5 Hz, J$_{1ax,2}$=J$_{4,5ax}$=10.8 Hz, H-2, H-4), 4.96 (1H, t, J$_{2,3}$=J$_{3,4}$=9.7 Hz, H-3), 2.74 (2H, dd, H-1 eq, H-5 eq), 2.67 (2H, t, J$_{5ax,5eq}$=J$_{1ax,1eq}$=12.0 Hz, H-1ax, H-5ax), 2.00 (3H, s, OAc), 1.99 (6H, s, OAc); $^{13}$C NMR (CDCl$_3$): δ 169.79 and 169.65 (3C=O), 73.98 (C-3), 73.78 (2C, C-2 and C-4), 21.02 (2 OAc), 20.80 (2C, C-1 and C-5), 20.56 (OAc). Anal. Calcd for C$_{11}$H$_{16}$O$_6$Se: C, 40.88; H, 4.99. Found: C, 40.76; H, 5.02.

1,5-Anhydro-2,3,4-tri-O-benzyl-5-selenoxylitol (76)

(a) Acetate Methanolysis: A mixture of 1,S-anhydro-2,3,4-tri-O-acetyl-S-selenoxylitol 81 (2.22 g, 6.87 mmol) and 1M NaOMe in MeOH (10 mL, 10 mmol) in dry MeOH (60 mL) was stirred under a N$_2$ atmosphere overnight. The mixture was netralized with excess Rexyn 101, the resin was removed by filtration, and the organic phase was concentrated to give 1,S-anhydro-selenoxylitol as tan crystals (1.19 g, 88%). Mp 98-105° C.; $^1$H NMR (D$_2$O): δ 3.75 (2H, m, J$_{1eq,2}$=J$_{4,5eq}$=4.6 Hz, J$_{1ax,2}$=J$_{4,5}$, =10.8 Hz, H-2, H-4), 3.11 (1H, t, J$_{2,3}$=J$_{3,4}$=9.2 Hz, H-3), 2.66 (2H, t, J$_{5ax,5eq}$=J$_{1ax,1eq}$=11.8 Hz, H-5ax, H-1ax), 2.60 (2H, dd, H-1 eq, H-5eq); $^{13}$C NMR (D$_2$O): δ 81.40 (C-3), 76.62 (2C, C-2 and C-4), 25.65 (2C, C-1 and C—S). Anal. Calcd for C$_5$H$_{10}$O$_3$Se: C, 30.47; H, 5.11. Found: C, 30.29; H, 5.21.

(b) Benzylation: To 1,5-anhydro-5-selenoxylitol 81 (0.289 g, 1.47 mmol) in dry DMF (20 mL) was added 60% NaH (0.516 g, 6 equiv) while stirring in an ice bath. The ice bath was removed and BnBr (0.9 mL, 4 equiv) was added. The mixture was stirred under N$_2$ overnight. The reaction was then quenched with MeOH(S mL), H$_2$O (100 mL) was added, and the mixture was extracted with Et$_2$O (3×50 mL). The organic solution was dried over Na$_2$SO$_4$ and concentrated. The product was purified by flash chromatography [hexanes:EtOAc, 20:1] to give the title compound 76 as a white solid (0.505 g, 74%). Mp 56-60° C.; $^1$H NMR (CDCl$_3$): δ 7.32-7.24 (15H, m, ArH), 4.81 (2H, s, CH$_2$Ph), 4.70 (2H, d, J$_{A,B}$=11.6 Hz, CH$_2$Ph), 4.66 (2H, d, J$_{A,B}$=11.5 Hz, CH$_2$Ph), 3.73 (2H, m, J$_{1eq,2}$=J$_{4,5eq}$=4.2 Hz, J$_{1ax,2}$=J$_{4,5a}$=11.2 Hz, H-2, H-4), 3.27 (1H, t, J$_{2,3}$=J$_{3,4}$=8.9 Hz, H-3), 2.69 (2H, dd, J$_{5ax,5eq}$=J$_{1ax,1eq}$=12.0 Hz, H-5eq, H-1 eq), 2.58 (2H, t, H-5ax, H-1ax); $^{13}$C NMR (CDCl$_3$): 138.89 (C$_{ipso}$), 138.44 (2C$_{ipso}$), 128.39-127.46 (15C, Ar), 86.98 (C-3), 83.17 (2C, C-2 and C-4), 76.34 (CH$_2$Ph), 72.97 (2 CH$_2$Ph), 22.11 (2C, C-1 and C-5). Anal. Calcd for C$_{26}$H$_{28}$O$_3$Se: C, 66.80; H, 6.04. Found: C, 66.88; H, 6.22.

1,5-Dideoxy-1,5-[[N-(2R,3R)-2,4-O-benzylidene-2,4-dihydroxy-3-(sulfooxy)-butyl]iminoonium]-xylitol (84)

1,5-Dideoxy-1,5-iminoxylitol 72 (0.161 g, 1.21 mmol) and 2,4-O-benzylidene-D-erythritol-1,3-cyclic sulfate 71b (0.360 g, 1.32 mmol) were dissolved in reagent grade MeOH (2 mL). Anhydrous K$_2$CO$_3$ (0.015 g, 0.11 mmol) was added and the mixture was stirred in a sealed tube at 65° C. for 3.5 h, at which point TLC showed that the cyclic sulfate had been consumed. The solvent was removed and the residue was purified by column chromatography (EtOAc:MeOH:H$_2$O, 8:2:1) to give the product 84 as a yellow oil (0.209 g, 43%): [α]$_D$ –5° (c 0.48, H$_2$O); NMR data in Tables 1 and 3.

1,5-Dideoxy-1,5-[[N-(2R,3R)-2,4-dihydroxy-3-(sulfooxy)-butyl]iminoonium]-xylitol (66b)

Aqueous 60% HOAc (25 mL) was added to compound 84 (0.209 g, 0.515 mmol) and the mixture was stirred while warming in an open flask for 20 h at 70° C. The mixture was cooled and concentrated and the crude product was purified by column chromatography (EtOAc:MeOH:H$_2$O, 6:4:1) to give compound 66b (0.118 g, 72%) as a colorless, hard foam: [α]$_D$ –9 (c 0.57, H$_2$O); NMR data in Tables 2 and 4; MALDI MS m/e 339.99 (M$^+$+Na), 238.12 (M$^+$+H–SO$_3$).

1,5-Dideoxy-1,5-[[N-(2S,3S)-2,4-O-benzylidene-2,4-dihydroxy-3-(sulfooxy)-butyl]iminoonium]-xylitol (82)

1,5-Didexy-1,5-iminoxylitol 72 (0.158 g, 1.19 mmol) and 2,4-O-benzylidene-L-erythritol-1,3-cyclic sulfate 71a (0.347 g, 1.27 mmol) were dissolved in reagent grade MeOH (2 mL). Anhydrous K$_2$CO$_3$ (0.018 g, 0.15 mmol) was added and the mixture was stirred in a sealed tube at 65° C. for 4 h. The solvent was removed and the residue was purified by column chromatography (EtOAc:MeOH:H$_2$O, 8:2:1) to give the product 82 as a yellow oil (0.273 g, 56%). [α]$_D$ +55 (c 0.65, H$_2$O); $^1$H and $^{13}$C NMR data were virtually identical with those of the enantiomer 84 (see Tables 1 and 3); MALDI MS m/e 428.09 (M$^+$+Na), 406.11 (M$^+$+H), 326.15 (M$^+$+H—SO$_3$).

1,5-Dideoxy-1,5-[[N-(2S,3S)-2,4-dihydroxy-3-(sulfooxy)-butyl]iminoonium]-xylitol (66a)

Aqueous 60% HOAc (25 mL) was added to compound 82 (0.273 g, 0.673 mmol) and the mixture was stirred while warming in an open flask for 14 h at 75° C. The mixture was cooled and concentrated and the crude product was purified by column chromatography (EtOAc:MeOH:H$_2$O, 6:4:1) to give compound 66a (0.156 g, 73%) as a colorless, hard foam. [α]$_D$ +1 (c 0.56, H$_2$O); $^1$H and $^{13}$C NMR data were virtually identical to those of the enantiomer 66b (see Tables 2 and 4); MALDI MS m/e 399.99 (M$^+$+Na), 318.28 (M$^+$+H), 238.12 (M$^+$+H–SO$_3$).

2,3,4,6-Tetra-O-benzyl-1,5-dideoxy-1,5-[[N-(2R,3R)-2,4-O-benzylidene-2,4-dihydroxy-3-(sulfooxy)-butyl]iminoonium]-D-glucitol (86)

Tri-O-benzyldeoxynojirimycin 73 (0.241 g, 0.460 mmol) and 2,4-O-benzylidene-D-erythritol-1,3-cyclic sulfate 71b (0.143 g, 0.525 mmol) were dissolved in reagent grade acetone (2 mL). Anhydrous K$_2$CO$_3$ (0.020 g, 0.15 mmol) was added and the mixture was stirred in a sealed tube at 70° C. for 20 h. The solvent was removed and the residue was purified by column chromatography (CHCl$_3$: MeOH, 5:1) to give the product 86 as a colorless gum (0.240 g, 65%). [α]$_D$ –5.4 (c 0.9, CHCl$_3$); NMR data in Tables 1 and 3.

1,5-Dideoxy-1,5-[[N-(2R,RS)-2,4-dihydroxy-3-(sulfooxy)-butyl]iminoonium]-D-glucitol (67b)

Compound 86 (0.209 g, 0.263 mmol) was dissolved in 80% aqueous acetic acid (20 mL) and the solution was stirred with 10% Pd/C catalyst (0.42 g) under 1 atm of H$_2$ for 20 h. The catalyst was removed by filtration through a small plug of silica gel, and washed with water (50 mL). The filtrate was evaporated and the gummy residue was freed of acetic acid by dissolving in water and re-concentrating (2×50 mL). The crude product was purified by column chromatography (EtOAc: MeOH: H$_2$O, 6:3:1) to give compound 67b (0.096 g, containing 0.56 equiv. or 13% by weight of KOAc by $^1$H NMR, 91% after correcting for acetate content). NMR data in Tables 2 and 4.

2,3,4,6-Tetra-O-benzyl-1,5-dideoxy-1,5-[[N-(2S,3S)-2,4-O-benzylidene-2,4-dihydroxy-3-(sulfooxy)-butyl]iminoonium]-D-glucitol (85)

Tri-O-benzyldeoxynojirimycin 73 (0.223 g, 0.426 mmol) and 2,4-O-benzylidene-L-erythritol-1,3-cyclic sulfate 71a (0.123 g, 0.4535 mmol) were dissolved in reagent grade acetone (2 mL). Anhydrous K$_2$CO$_3$ (0.020 g, 0.15 mmol) was added and the mixture was stirred in a sealed tube at 70° C. for 20 h. The solvent was removed and the residue was purified by column chromatography (CHCl$_3$: MeOH, 5:1) to give the product 85 as a colorless amorphous solid (0.271 g, 80%): [α]$_D$ +36 (c 0.8, CHCl$_3$); NMR data in Tables 1 and 3.

1,5-Dideoxy-1,5-[[N-(2R,3R)-2,4-dihydroxy-3-(sulfooxy)-butyl]iminoonium]-D-glucitol (67a)

Compound 85 (0.205 g, 0.263 mmol) was dissolved in 80% aqueous acetic acid (20 mL) and the solution was stirred with 10% Pd/C catalyst (0.41 g) under 1 atm of H$_2$ for 20 h. The catalyst was removed by filtration through a small plug of silica gel, and washed with water (50 mL). The filtrate was evaporated and the gummy residue was freed of acetic acid by dissolving in water and re-concentrating (2×50 mL). The crude product was purified by column chromatography (EtOAc: MeOH: H$_2$O, 6:3:1) to give compound 67a (0.094 g, containing 0.77 equiv. or 18% by weight of KOAc by $^1$H NMR, 89% after correcting for acetate content). See Tables 2 and 4 for $^1$H and $^{13}$C NMR data.

2,3,4-Tri-O-benzyl-1,5-dideoxy-1,5-[[(2R,3R)-2,4-O-benzylidene-2,4-dihydroxy-3-(sulfooxy)butyl]-(S)-episulfoniumylidene]-xylitol inner salt (88b) and 2,3,4-tri-O-benzyl-1,5-dideoxy-1,5-[[(2R,3R)-2,4-O-benzylidene-2,4-dihydroxy-3-(sulfooxy) butyl]-(R)-episulfoniumylidene]-xylitol inner salt (89b)

To 1,1,1,3,3,3-hexafluoro-2-propanol (0.5 mL) were added 2,4-O-benzylidene-D-erythritol-1,3-cyclic-sulfate 71b (0.565 g, 2.08 mmol), 1,5-anhydro-2,3,4-tri-O-benzyl-5-thioxylitol 7 (0.677 g, 1.61 mmol) and anhydrous K$_2$CO$_3$ (70 mg). The mixture was stirred in a sealed tube in a 70° C. oil bath overnight, after which an extra 40 mg of anhydrous K$_2$CO$_3$ was added. The solvents were removed and the residue was chromatographed [CHCl$_3$:MeOH, 10:1] to give 88b and 89b in a 2:1 ratio (0.975 g, 87%).

Major isomer 88b: mp 186-189° C.; [α]$_D$ +2.1 (c 1.2, CH$_2$Cl$_2$); NMR data in Tables 1 and 3; HRMS Calcd for C$_{37}$H$_{40}$O$_9$S$_2$ (M+H): 693.2192. Found: 693.2209. Anal. Calcd for C$_{37}$H$_{40}$O$_9$S$_2$: C, 64.14; H, 5.82. Found: C, 64.39; H, 5.94.

Minor isomer 89b: mp 169-172° C.; [α]$_D$ –49.1 (c 0.8, CH$_2$Cl$_2$); NMR data in Tables 1 and 3; Anal. Calcd for C$_{37}$H$_{40}$O$_9$S$_2$: C, 64.14; H, 5.82. Found: C, 63.84: H, 5.96.

1,5-Dideoxy-1,5-[[(2R,3R)-2,4-dihydroxy-3-(sulfooxy)butyl]-(S)-episulfoniumylidene]-xylitol inner salt (S-68b)

To compound 88b (0.33 g, 0.48 mmol) dissolved in 80% AcOH (12 mL) was added Pd(OH)$_2$ (0.2 g). The mixture was stirred under H$_2$ (110 psi) for 48 h and then filtered through Celite with MeOH. The solvent was evaporated and the residue was purified by column chromatography [EtOAc:MeOH: H$_2$O, 7:3:1]. Compound S-68b was obtained as a syrup (0.13 g, 81%); [α]$_D$ –21.8 (c 1.1, H$_2$O); NMR data in Tables 2 and 4; HRMS Calcd for C$_9$H$_{19}$O$_9$S$_2$ (M+H): 335.0470. Found: 335.0454. Anal. Calcd for C$_9$H$_{18}$O$_9$S$_2$: C, 32.33; H, 5.43. Found: C, 32.03; H, 5.59.

1,5-Dideoxy-1,5-[[(2R,3R)-2,4-dihydroxy-3-(sulfooxy)butyl]-(R)-episulfoniumylidene]-xylitol inner salt (R-68b)

Compound 89b (0.249 g, 0.36 mmol) was deprotected by hydrogenolysis using the procedure described above for S-68b to give the title compound as a syrup (0.13 g, 95%); [α]$_D$ –16.2 (c 0.9, H$_2$O); NMR data in Tables 2 and 4; HRMS Calcd for C$_9$H$_{19}$O$_9$S$_2$ (M+H): 335.0470. Found: 335.0478. Anal. Calcd for C$_9$H$_{18}$O$_9$S$_2$: C, 32.33; H, 5.43. Found: C, 31.88; H, 5.21.

2,3,4-Tri-O-benzyl-1,5-dideoxy-1,5-[[(2S,3S)-2,4-O-benzylidene-2,4-dihydroxy-3-(sulfooxy)butyl]-(R)-episulfoniumylidene]-xylitol inner salt (88a) and 2,3,4-tri-O-benzyl-1,5-dideoxy-1,5-[[(2S,3S)-2,4-O-benzylidene-2,4-dihydroxy-3-(sulfooxy) butyl]-(S)-episulfoniumylidene]-xylitol inner salt (89a)

To 1,1,1,3,3,3-hexafluoro-2-propanol (0.5 mL) were added 2,4-O-benzylidene-L-erythritol-1,3-cyclic-sulfate 71a (0.265 g, 0.97 mmol), 1,5-anhydro-2,3,4-tri-O-benzyl-5-thioxylitol 74 (0.328 g, 0.78 mmol) and anhydrous $K_2CO_3$ (24 mg). The mixture was stirred in a sealed tube in a 70° C. oil bath for 5 days. The solvent was evaporated and the residue was purified by column chromatography [$CHCl_3$:MeOH, 10:1] to give 88a and 89a in a 5:2 ratio as a white solid (0.465 g, 86%). Pure samples were obtained by rechromatography.

Major isomer 88a: Mp 175-180° C.; $[\alpha]_D$ −3.7 (c 0.9, $CH_2Cl_2$); $^1H$ and $^{13}C$ NMR data were virtually identical to those of the enantiomer 88b. Anal. Calcd for $C_{37}H_{40}O_9S_2$: C, 64.14; H, 5.82; Found: C, 63.81; H, 5.68.

Minor isomer 89a: Mp 163-170° C.; $[\alpha]_D$ +41.8 (c 1.1, $CH_2Cl_2$); $^1H$ and $^{13}C$ NMR data were virtually identical to those of the enantiomer 89b. Anal. Calcd for $C_{37}H_{40}O_9S_2$: C, 64.14; H, 5.82. Found: C, 64.42; H, 5.75.

1,5-Dideoxy-1,5-[[(2S,3S)-2,4-dihydroxy-3-(sulfooxy)butyl]-(R)-episulfoniumylidene]-xylitol inner salt (R-68a)

To compound 88a (0.304 g, 0.44 mmol) dissolved in 80% AcOH (10 mL) was added Pd/C (0.5 g). The mixture was stirred under 120 psi $H_2$ for 96 h. The mixture was filtered through Celite with MeOH, and the solvent removed. The residue was then redissolved in 80% AcOH (10 ml). To the solution was added $Pd(OH)_2$ (0.2 g) and the solution was stirred under 120 psi $H_2$ for 48 h. The mixture was filtered through Celite with MeOH, the solvent evaporated, and the residue was purified by column chromatography [EtOAc:MeOH:$H_2O$, 7:3:1] to give the title compound as a syrup (0.08 g, 55%); $[\alpha]_D$ +21.7 (c 0.8, $H_2O$). $^1H$ and $^{13}C$ NMR data were virtually identical to those of the enantiomer S-68b (see Tables 1 and 3). HRMS Calcd for $C_9H_{18}O_9S_2Na$ (M+Na): 357.0290. Found: 357.0284.

1,5-Dideoxy-1,5-[[(2S,3S)-2,4-dihydroxy-3-(sulfooxy)butyl]-(S)-episulfoniumylidene]-xylitol inner salt (S-68a)

Compound 89a (0.240 g, 0.35 mmol) was deprotected by hydrogenolysis using the procedure described above for S-68b to give the title compound as a syrup (0.08 g, 67%); $[\alpha]_D$ +19.5 (c 0.7, $H_2O$). $^1H$ and $^{13}C$ NMR data were virtually identical to the enantiomer R-68b (see Tables 2 and 4) HRMS Calcd for $C_9H_{19}O_9S_2$ (M+H): 335.0470. Found: 335.0477.

2,3,4,6-Tetra-O-benzyl-1,5-dideoxy-1,5-[[(2R,3R)-2,4-O-benzylidene-2,4-dihydroxy-3-(sulfooxy)butyl]-(S/R)-episulfoniumylidene]-D-glucitol inner salts (90b) and (91b)

To 1,1,1,3,3,3-hexafluoro-2-propanol (0.5 mL) were added 2,4-O-benzylidene-D-erythritol-1,3-cyclic-sulfate 71b (0.115 g, 0.42 mmol), 1,5-anhydro-2,3,4,6-tetra-O-benzyl-5-thio-D-glucitol 75 (0.174 g, 0.32 mmol) and anhydrous $K_2CO_3$ (30 mg). The mixture was stirred in a sealed tube in a 70° C. oil bath for 5 days. The solvent was removed and the residue was purified by column chromatography [$CHCl_3$:MeOH, 10:1] to give an inseparable mixture of 90b and 91b in a 2:1 ratio as a white solid (0.182 g, 70%); $[\alpha]_D$=+2.1 (c 1.3, $CH_2Cl_2$). Major isomer 90b: See Tables 1 and 2 for $^1H$ and $^{13}C$ NMR data. Anal. Calcd for $C_{45}H_{48}O_{10}S_2$: C, 66.48; H, 5.96. Found: C, 66.36; H, 6.08.

1,5-Dideoxy-1,5-[[(2R,3R)-2,4-dihydroxy-3-(sulfooxy)butyl]-(S)-episulfoniumylidene]-D-glucitol inner salt (69b)

To a mixture of compounds 90b and 91b (0.1639 g, 0.20 mmol) dissolved in 80% AcOH (10 mL) was added $Pd(OH)_2$ (0.17 g). The mixture was stirred under 120 psi $H_2$ for 48 h. The mixture was filtered through Celite with MeOH, the solvent was removed, and the residue was purified by column chromatography [EtOAc:MeOH:$H_2O$, 7:3:1]. Compound 69b was obtained as a syrup (0.06 g, 81%); $[\alpha]_D$=−20.4 (c 0.8, $H_2O$). See Tables 2 and 4 for $^1H$ and $^{13}C$ NMR data. HRMS. Calcd for $C_{10}H_{21}O_{10}S_2$ (M+H): 365.0576 Found: 365.0574.

2,3,4,6-Tetra-O-benzyl-1,5-dideoxy-1,5-[[(2S,3S)-2,4-O-benzylidene-2,4-dihydroxy-3-(sulfooxy)butyl]-(R/S)-episulfoniumylidene]-D-glucitol inner salts (90a) and (91a)

To 1,1,1,3,3,3-hexafluoro-2-propanol (0.5 mL) were added 2,4-O-benzylidene-L-erythritol-1,3-cyclic-sufate 71a (0.148 g, 0.54 mmol), 1,5-anhydro-2,3,4,6-tetra-O-benzyl-5-thio-D-glucitol 75 (0.240 g, 0.44 mmol) and anhydrous $K_2CO_3$ (33 mg). The mixture was stirred in a sealed tube in a 69-70° C. oil bath for 84 h. The solvent was evaporated and the residue was purified by column chromatography [$CHCl_3$:MeOH, 10:1] to give an inseparable 3:1 mixture of 90a and 91a as a white solid (0.25 g, 68%); $[\alpha]_D$=+48.8 (c 1.6, $CH_2Cl_2$). Major isomer 90a: See Tables 1 and 2 for $^1H$ and $^{13}C$ NMR data. Anal. Calcd for $C_{45}H_{48}O_{10}S_2$: C, 66.48; H, 5.95. Found: C, 66.19; H, 6.07.

1,5-Dideoxy-1,5-[[(2S,3S)-2,4-dihydroxy-3-(sulfooxy)butyl]-(R)-episulfoniumylidene]-D-glucitol inner salt (69a)

To a mixture of compounds 90a and 91a (0.180 g, 0.22 mmol) dissolved in 80% AcOH (10 mL) was added $Pd(OH)_2$ (0.20 g), and the mixture was stirred under 120 psi $H_2$ for 6 days. The mixture was filtered through Celite with MeOH, the solvent was removed and the residue was purified by column chromatography [EtOAc:MeOH:$H_2O$, 7:3:1]. Compound 69a was obtained as a syrup (0.05 g, 67%); $[\alpha]_D$=+10.3 (c 0.6, $H_2O$). See Tables 2 and 4 for $^1H$ and $^{13}C$ NMR data. HRMS Calcd for $C_{10}H_{21}O_{10}S_2$ (M+H): 365.0576. Found: 365.0577.

2,3,4-Tri-O-benzyl-1,5-dideoxy-1,5-[[(2R,3R)-2,4-O-benzylidene-2,4-dihydroxy-3-(sulfooxy)butyl]-(S/R)-episelenoniumylidene]-xylitol inner salt (92b and 93b)

To 1,1,1,3,3,3-hexafluoro-2-propanol (0.5 mL) were added 2,4-O-benzylidene-D-erythritol-1,3-cyclic-sufate 71b (0.272 g, 1.00 mmol), 1,5-anhydro-2,3,4-tri-O-benzyl-5-selenoxylitol 76 (0.362 g, 0.78 mmol) and anhydrous $K_2CO_3$ (50 mg). The mixture was stirred in a sealed tube in a 70° C. oil bath for 48 h. The solvent was concentrated and the residue was purified by column chromatography [$CHCl_3$:MeOH, 10:1] to give an inseparable mixture of 92b and 93b in a 1:4 ratio (0.20 g, 96%). $[\alpha]_D$ −45.7 (c 1.1, $CH_2Cl_2$). For the major isomer 36b: See Tables 1 and 2 for $^1H$ and $^{13}C$ NMR data.

Anal. Calcd for $C_{37}H_4O_9SSe$: C, 59.99; H, 5.45. Found: C, 59.73; H, 5.36.

1,5-Dideoxy-1,5-[[(2R,3R)-2,4-dihydroxy-3-(sulfooxy)butyl]-(R)-episelenoniumylidene]-xylitol inner salt (70b)

To the mixture of compounds 92b and 93b (0.295 g, 0.40 mmol) dissolved in 80% AcOH (10 mL) was added Pd(OH)$_2$ (0.29 g), and the mixture was stirred under 120 psi H$_2$ for 5 days. TLC revealed one major product and two minor products. The mixture was filtered through Celite, concentrated, and the residue was purified by column chromatography [EtOAc:MeOH:H$_2$O, 7:3:1] to give the major product, compound 70b as a syrup (0.06 g, 39%); [α]$_D$ −16.6 (c 0.9, H$_2$O). See Tables 2 and 4 for $^1$H and $^{13}$C NMR data. HRMS Calcd for $C_9H_{19}O_9SSe$ (M+H): 382.9915. Found: 382.9916. Anal. Calcd for $C_9H_{18}O_9SSe$: C, 28.35; H, 4.76. Found: C, 28.44; H, 4.71.

2,3,4-Tri-O-benzyl-1,5-dideoxy-1,5-[[(2S,3S)-2,4-O-benzylidene-2,4-dihydroxy-3-(sulfooxy)butyl]-(R/S)-episelenoniumylidene]-xylitol inner salts (92a and 93a)

To 1,1,1,3,3,3-hexafluoro-2-propanol (0.5 mL) were added 2,4-O-benzylidene-L-erythritol-1,3-cyclic-sufate 71a (0.226 g, 0.83 mmol), 1,5-anhydro-2,3,4-tri-O-benzyl-5-selenoxylitol 76 (0.308 g, 0.66 mmol) and anhydrous K$_2$CO$_3$ (20 mg). The mixture was stirred in a sealed tube in a 70° C. oil bath for 72 h. The solvent was removed and the residue was purified by column chromatography [CHCl$_3$:MeOH, 10:1] to give an inseparable 1:3 mixture of 92a and 93a as a white solid (0.42 g, 85%). [α]$_D$ −44.° (c 0.9, CH$_2$Cl$_2$). For the major isomer 93a, the $^1$H and $^{13}$C NMR data were virtually identical to those of the enantiomer (compound 93b, see Tables 1 and 2) except for small chemical shift differences due to concentation effects. Anal. Calcd for $C_{37}H_{40}O_9SSe$: C, 59.99; H, 5.45. Found: C, 59.85; H, 5.58.

1,5-Dideoxy-1,5-[[(2S,3S)-2,4-dihydroxy-3-(sulfooxy)butyl]-(S)-episelenoniumylidene]-xylitol inner salt (70a)

To a mixture of compounds 92a and 93a (0.406 g, 0.55 mmol) dissolved in 80% AcOH (10 mL) was added Pd(OH)$_2$ (0.50 g), and the mixture was stirred under 120 psi H$_2$ for 8 days. TLC revealed one major product and two minor products. The mixture was filtered through Celite with MeOH, the solvent was removed, and the residue was purified by column chromatography [EtOAc/MeOH/H$_2$O, 7:3:1]. Compound 70a was obtained as a syrup (0.05 g, 25%); [α]$_D$ +14.1 (c 0.4, H$_2$O). For compound 70a, the $^1$H and $^{13}$C NMR data were virtually identical to the enantiomer (compound 70b, see Tables 1 and 2) except for small chemical shift differences due to concentration effects. HRMS Calcd for $C_9H_{18}O_9SSeNa$ (M+Na): 404.9734. Found: 404.9735. Anal. Calcd for $C_9H_{18}O_9SSe$: C, 28.35; H, 4.76. Found: C, 28.56; H, 4.54.

TABLE 1

$^1$H NMR Data for Compounds 84, 85, 86, 88b, 89b, 90a, 90b and 93b.

| Compound | 84[a]* | 85[b] | 86[c] | 88b[d]* | 89b[e]* | 90a[f] | 90b[g] | 93b[h]* |
|---|---|---|---|---|---|---|---|---|
| H-1eq | 3.18-3.13(m) | 3.47(dd) | 3.33(dd) | 3.59(ddd) | 3.38(d) | 3.82(dd) | 3.40(dd) | 3.36(dd) |
| (J$_{1eq,2}$, J$_{1eq,5eq}$) | (nd, nd) | (4.9, ~0) | (4.8, ~0) | (4.4, 2.4) | (2.9, ~0) | (4.5, ~01) | (4.5, ~0) | (3.2, ~0) |
| H-1ax | 2.32(dd) | 2.34(dd) | 2.58(dd) | 3.38(dd) | 3.38(d) | 3.57(dd) | 3.31(dd) | 3.18(dd) |
| (J$_{1ax,1eq}$, J$_{1ax,2}$) | (9.1, 9.1) | (11.5, 11.0) | (11.1, 10.6) | (12.5, 2.1) | (nd, 2.9) | (14.9, 2.7) | (14.7, 3.2) | (13.3, 4.0) |
| H-2 | 3.61-3.53(m) | 3.62(ddd) | 3.58(ddd) | 3.89(dddd) | 3.84(ddd) | 4.20(ddd) | 3.92(ddd) | 3.86(ddd) |
| (J$_{2,3}$, J$_{2,4}$) | (10.9, nd) | (9.0, ~0) | (9.0, ~0) | (3.6, 1.8) | (~2, ~0) | (4.3, ~0) | (4.5, ~0) | (4.2, ~0) |
| H-3 | 3.22(dd) | 3.38 dd) | 3.39 dd) | 3.79(dd) | 3.92(dd) | 3.87(dd) | 3.85(dd) | 3.91(dd) |
| (J$_{3,4}$) | (10.9) | (9.0) | (9.0) | (3.6) | (<1) | (4.3) | (4.5) | (4.2) |
| H-4 | 3.61-3.53(m) | 3.55(ddd) | 3.54(dd) | 4.05(dddd) | 4.02(ddd) | 3.79(dd) | 4.02(dd) | 3.98(ddd) |
| (J$_{4,5eq}$, J$_{4,5ax}$) | (nd, 9.1) | (na, 9.5) | (na, 9.5) | (4.1, 1.9) | (3.5, 2.6) | (4.3, na) | (5.1, na) | (4.5, 2.9) |
| H-5eq | 3.18-3.13(m) | na | na | 3.93(ddd) | 3.76(ddd) | 3.90(ddd) | 4.09(ddd) | 3.56(ddd) |
| H-5ax | 2.32(dd) | 2.40(ddd) | 2.55(ddd) | 3.54(ddd) | 3.64(dd) | na | na | 3.66(ddd) |
| (J$_{5eq,5ax}$) | (9.1) | (na) | (na) | (12.6) | (15.1) | | | (13.4) |
| H-6a | na | 3.90(dd) | 3.85(dd) | na | na | 3.72(dd) | 4.03(dd) | na |
| (J$_{6a,6b}$, J$_{5,6a}$) | | (10.7, 2.2) | (10.2, 2.4) | | | (11.1, 7.3) | (10.5, 5.7) | |
| H-6b | na | 3.68(dd) | 3.78(dd) | na | na | 3.63(dd) | 3.95(dd) | na |
| (J$_{5,6b}$) | | (1.6) | (2.0) | | | (5.1) | (5.3) | |
| H-1'a | 3.12(d) | 3.56(d) | 3.67(d) | 4.28(dd) | 4.99(dd) | 4.67(dd) | 4.70(dd) | 4.82(dd) |
| (J$_{1'a,1'b}$, J$_{1'a,2'}$) | (14.2, <1) | (15.1, <1) | (15.6, <1) | (13.5, 3.1) | (14.2, 3.7) | (13.9, 3.7) | (13.9, 4.1) | (12.8, 4.0) |
| H-1'b | 2.83(dd) | 2.78(dd) | 2.93(dd) | 3.67(dd) | 4.27(dd) | 4.32(dd) | 4.32(dd) | 4.30(dd) |
| (J$_{1'b,2'}$) | (8.3) | (8.0) | (7.9) | (3.9) | (1.5) | (1.8) | (1.9) | (1.7) |
| H-2' | 4.14(dd) | 4.05(dd) | 4.07(dd) | 4.32(ddd) | 4.21(ddd) | 4.21(ddd) | 4.22(ddd) | 4.18(ddd) |
| (J$_{2',3'}$) | (9.7) | (10.0) | (9.7) | (10.0) | (10.1) | (9.7) | (9.6) | (9.6) |
| H-3' | 4.21(ddd) | 4.11(ddd) | 4.16(ddd) | 4.62(ddd) | 4.66(ddd) | 4.66(ddd) | 4.62(ddd) | 4.54(ddd) |
| (J$_{3',4'eq}$) | (5.2) | (5.4) | (5.3) | (5.4) | (5.5) | (5.5) | (5.5) | (5.3) |
| H-4'eq | 4.50(dd) | 4.55(dd) | 4.60(dd) | 4.49(dd) | 4.47(dd) | 4.50(dd) | 4.51(dd) | 4.45(dd) |
| (J$_{4'eq,4'ax}$) | (11.0) | (10.6) | (11.0) | (10.9) | (10.8) | (10.5) | (10.7) | (10.6) |
| H-4'ax | 3.89(dd) | 3.77(dd) | 3.82(dd) | 3.77(dd) | 3.74(dd) | 3.74(dd) | 3.74(dd) | 3.76(dd) |
| (J$_{3',4'ax}$) | (9.8) | (9.8) | (9.7) | (10.3) | (10.1) | (10.9) | (10.2) | (10.1) |

Footnotes for Table 1

[a]500MHz, pH=8, D$_2$O. Others: 7.51-7.43(5H, m, Ar), 5.72(1H, s, benzylidene CH).

[b]500MHz, pH=10, CD$_3$OD.Others: 7.44-7.03(25H, m, Ar), 5.55(1H, s, benzylidene CH), 4.89 and 4.73(2H, 2d, J$_{A,B}$=11.2Hz, CH$_2$Ar), 4.75 and 4.41(2H, 2d, J$_{A,B}$=11.0Hz, CH$_2$Ar), 4.62 and 4.55(2H, 2d, J$_{A,B}$=11.5Hz, CH$_2$Ar), 4.57 and 4.43(2H, 2d, J$_{A,B}$=12.2Hz, CH$_2$Ar).

[c]500MHz, pH=10, CD$_3$OD. Others: 7.50-7.00(25H, m, Ar), 5.61(1H, s, benzylidene CH), 4.88 and 4.74(2H, 2d, J$_{A,B}$=11.3Hz, CH$_2$Ar), 4.74 and 4.38(2H, 2d, J$_{A,B}$=10.8Hz, CH$_2$Ar), 4.70 and 4.46(2H, 2d, J$_{A,B}$=11.7Hz, CH$_2$Ar), 4.62 and 4.57(2H, 2d, J$_{A,B}$=11.9Hz, CH$_2$Ar).

TABLE 1-continued

$^1$H NMR Data for Compounds 84, 85, 86, 88b, 89b, 90a, 90b and 93b.

| Compound | 84[a]* | 85[b] | 86[c] | 88b[d]* | 89b[e]* | 90a[f] | 90b[g] | 93b[h]* |
|---|---|---|---|---|---|---|---|---|

[d]600MHz, CD$_2$Cl$_2$. Others: 7.45-7.10(20H, m, Ar), 5.55(1H, s, benzylidene CH), 4.69 and 4.49(2H, 2d, $J_{A,B}$=11.5Hz, CH$_2$Ar), 4.49 and 4.43(2H, 2d, $J_{A,B}$=11.8Hz, CH$_2$Ar), 4.46 and 4.44(2H, 2d, $J_{A,B}$=11.6Hz, CH$_2$Ar).
[e]600MHz, CD$_2$Cl$_2$. Others: 7.45-7.05(20H, m, Ar), 5.52(1H, s, benzylidene CH), 4.64 and 4.58(2H, 2d, $J_{A,B}$=11.4Hz, CH$_2$Ar), 4.49 and 4.46(2H, 2d, $J_{A,B}$=11.9Hz, CH$_2$Ar), 4.40(2H, s, CH$_2$Ar).
[f]500MHz, CD$_2$Cl$_2$. Others: 7.46-7.01(25H, m, Ar), 5.52(1H, s, benzylidene CH), 4.65 and 4.54(2H, 2d, $J_{A,B}$=11.5Hz, CH$_2$Ar), 446 and 4.41(2H, 2d, $J_{A,B}$=11.7Hz, CH$_2$Ar), 4.46 and 4.43(2H, 2d, $J_{A,B}$=11.4Hz, CH$_2$Ar), 4.32 and 4.29(2H, 2d, $J_{A,B}$=11.9Hz, CH$_2$Ar).
[g]400MHz, CD$_2$Cl$_2$. Others: 7.44-7.06(25H, m, Ar), 5.52(1H, s, benzylidene CH), 4.66 and 4.50(2H, 2d, $J_{A,B}$=11.6Hz, CH$_2$Ar), 4.61 and 4.55(2H, 2d, $J_{A,B}$=11.4Hz, CH$_2$Ar), 4.48 and 4.44(2H, 2d, $J_{A,B}$=11.7Hz, CH$_2$Ar), 4.40(2H, s, CH$_2$Ar).
[h]600MHz, CD$_2$Cl$_2$. Others: 7.40-7.10(20H, m, Ar), 5.55(1H, s, benzylidene CH), 4.63 and 4.57(2H, 2d, $J_{A,B}$=11.4Hz, CH$_2$Ar), 4.50 and 4.47(2H, 2d, $J_{A,B}$=11.8Hz, CH$_2$Ar), 4.47 and 4.42(2H, 2d, $J_{A,B}$=11.8Hz, CH$_2$Ar).
*Assignments for diastereotopic H-1/H-5 and H-2/H-4 pairs may be reversed.
na = not applicable,
n.d. = not determined

TABLE 2

$^{13}$C NMR Data for Compounds 84, 85, 86, 88b, 89b, 90a, 90b and 93b.

| Compound | 84[a]* | 85[b] | 86[c] | 88b[d]* | 89b[e]* | 90a[f] | 90b[g] | 93b[h]* |
|---|---|---|---|---|---|---|---|---|
| C-1 | 57.89 | 56.62 | 56.96 | 42.08 | 32.90 | 32.49 | 34.69 | 30.17 |
| C-2 | 69.92 | 79.27 | 79.48 | 71.61 | 70.99 | 72.52 | 73.49 | 72.16 |
| C-3 | 78.72 | 88.10 | 88.17 | 70.94 | 70.31 | 73.84 | 76.87 | 72.48 |
| C-4 | 69.92 | 79.71 | 79.70 | 71.72 | 70.72 | 73.16 | 73.66 | 72.08 |
| C-5 | 58.07 | 66.55 | 64.35 | 39.24 | 33.41 | 52.36 | 53.46 | 30.73 |
| C-6 | na | 66.16 | 66.05 | na | na | 65.89 | 65.33 | na |
| C-1' | 57.77 | 54.19 | 53.95 | 46.00 | 43.31 | 44.94 | 45.38 | 43.37 |
| C-2' | 77.78 | 79.81 | 77.28 | 76.75 | 77.44 | 77.10 | 77.23 | 77.47 |
| C-3' | 69.18 | 69.53 | 69.34 | 66.88 | 65.73 | 65.80 | 66.63 | 67.41 |
| C-4' | 69.06 | 70.56 | 70.61 | 69.51 | 69.51 | 69.50 | 69.59 | 69.51 |

Footnotes for Table 2
[a]125MHz, D$_2$O. Others: 136.85(C$_{ipso}$, Ar), 130.34, 129.28, 126.66(5C, Ar), 101.44(benzylidene CH)
[b]125MHz, CD$_3$OD. Others: 140.32, 139.82, 139.76and 139.36(2C) (5×C$_{ipso}$, Ar), 129.93-127.27(25C, Ar), 101.97(benzylidene CH), 76.19(2C), 74.34 and 73.23(4×CH$_2$Ar).
[c]125MHz, CD$_3$OD. Others: 140.35, 139.88, 139.71, 139.506 and 139.41(5×C$_{ipso}$, Ar), 130.12-127.27(25C, Ar), 101.69(benzylidene CH), 76.23(2C), 74.25 and 73.34(4×CH$_2$Ar).
[d]100MHz, CD$_2$Cl$_2$. Others: 137.35, 136.96, 136.92 and 136.85(4×C$_{ipso}$, Ar), 128.84-126.54 (20C, Ar), 102.07(benzylidene CH), 73.68, 72.17 and 72.00(3×CH$_2$Ar).
[e]100MHz, CD$_2$Cl$_2$. Others: 137.38, 137.11, 137.00 and 136.80(4×C$_{ipso}$, Ar), 129.80-126.48 (20C, Ar), 102.19(benzylidene CH), 73.59, 72.64 and 72.10(3×CH$_2$Ar).
[f]100MHz, CD$_2$Cl$_2$. Others: 137.18, 137.07, 137.00, 136.85 and 136.75(5×C$_{ipso}$,Ar), 129.71-126.65(25C, Ar), 102.11(benzylidene CH), 73.70, 73.51, 73.40 and 71.85(4×CH$_2$Ar).
[g]100MHz, CD$_2$Cl$_2$. Others: 137.54, 137.44, 137.35, 137.17 and 136.85(5×C$_{ipso}$ Ar), 129.40-126.54(25C, Ar), 101.95(benzylidene CH), 74.48, 74.13, 73.99 and 72.35(4× CH$_2$Ar).
[h]100MHz, CD$_2$Cl$_2$. Others: 137.39, 137.29, 137.13 and 137.09(4×C$_{ipso}$,Ar), 129.74-126.49 (25C, Ar), 102.04(benzylidene CH), 73.37, 72.83 and 72.255(3×CH$_2$Ar).
*Assignments for diastereotopic C-1/C-5 and C-2/C-4 pairs may be reversed.

TABLE 3

$^1$H NMR Data Compounds 66b, 67a, 67b, S-68b, R-68b, 69a, 69b and 70b.

| Compound | 66b[a]* | 67a[b] | 67b[c] | S-68b[d]* | R-68b[e]* | 69a[f] | 69b[g] | 70b[h]* |
|---|---|---|---|---|---|---|---|---|
| H-1eq | 3.08 dd) | 3.57(br d) | 3.16(dd) | 3.70(dd) | 3.38-3.72(m) | 3.85(dd) | 3.89(dd) | 3.36(dd) |
| ($J_{1eq,2}$) | (4.8) | (4.8) | (4.9) | (3.5) | (3.8) | (3.6) | (3.9) | (3.2, <1) |
| H-1ax | 2.18(dd) | 2.93(br dd) | 2.49(dd) | 3.54(dd) | 3.36(d) | 3.52(dd) | 3.45(dd) | 3.18(dd) |
| ($J_{1ax,1eq}$, $J_{1ax,2}$) | (11.0, 11.0) | (11.8, 10.8) | (11.7, 11.1) | (13.9, 7.2) | (11.8, 11.8) | (11.5, 11.5) | (11.5, 11.5) | (13.3, 4.0) |
| H-2 | 3.58(ddd) | 3.80(ddd) | 3.55(ddd) | 4.29(ddd) | 4.01-3.93(m) | 3.91(ddd) | 3.97(ddd) | 3.86(ddd) |
| ($J_{2,3}$) | (9.2) | (9.4) | (9.3) | (7.2) | (9.0) | (8.5) | (9.1) | (4.2, <1) |
| H-3 | 3.20(dd) | 3.47 dd) | 3.30 dd) | 3.75(dd) | 3.51(dd) | 3.51(dd) | 3.54(dd) | 3.91(dd) |
| ($J_{3,4}$) | (9.2) | (9.4) | (9.5) | (7.2) | (9.0) | (8.5) | (9.1) | (4.2) |
| H-4 | 3.55(ddd) | 3.62(dd) | 3.44(dd) | 4.28(ddd) | 4.01-3.93(m) | 3.80(dd) | 3.86(dd) | 3.98(dd) |
| ($J_{4,5eq}$, $J_{4,5ax}$) | (4.7, 11.0) | (na, 9.8) | (na, 9.5) | (3.5, 7.2) | (3.5, 11.8) | (na, 10.5) | (na, 10.8) | (2.9, 4.5) |
| H-5eq | 3.073(dd) | na | na | 3.71(dd) | 3.38-3.72(m) | na | na | 3.66(ddd) |
| ($J_{5eq,6a}$) | na | | | (na) | (na) | | | (na) |
| H-5ax | 2.13(dd) | 3.07(br m) | 2.37(ddd) | 3.55(dd) | 3.36(dd) | 3.75(ddd) | 3.76(ddd) | 3.56(dd) |
| ($J_{5eq,5ax}$) | (11.0) | (na,) | (na,) | (13.8) | (11.8) | (na) | (na) | (13.4) |
| H-6a | na | 4.08(dd) | 3.93(dd) | na | na | 4.21(dd) | 4.21(dd) | na |
| ($J_{6a,6b}$, $J_{5,6a}$)) | | (12.7, 2.9) | (12.6, 2.4) | | | (12.8, 3.7) | (13.2, 3.8) | |
| H-6b | na | 4.03(dd) | 3.86(dd) | na | na | 4.12(dd) | 4.11(dd) | na |
| ($J_{5,6b}$) | | (2.8) | (2.4) | | | (2.8) | (2.6) | |
| H-1'a | 2.78(dd) | 3.57(br d) | 2.92(d) | 3.86(dd) | 3.93(dd) | 4.15(dd) | 3.98(dd) | 4.82(dd) |
| ($J_{1'a,1'b}$, $J_{1'a,2'}$) | (13.7, 2.8) | (14.1, 2.2) | (13.5, 2.6) | (14.4, 3.6) | (12.8, 3.7) | (13.9, 3.4) | (13.3, 6.3) | (12.8, 4.0) |
| H-1'b | 2.57(dd) | 3.15(br dd) | 2.88(dd) | 3.74(dd) | 3.83(dd) | 3.70(dd) | 3.85(dd) | 4.30(dd) |
| ($J_{1'b,2'}$) | (8.8) | (9.3) | (8.7) | (7.6) | (7.5) | 8.5) | (3.2) | (1.7) |
| H-2' | 4.12(ddd) | 4.35(ddd) | 4.19(ddd) | 4.45(ddd) | 4.41(ddd) | 4.40(ddd) | 4.39(ddd) | 4.18(ddd) |
| ($J_{2',3'}$) | (5.7) | (6.8) | (6.0) | (7.5) | (7.5) | (7.1) | (6.3) | (9.6) |
| H-3' | 4.23(ddd) | 4.29(ddd) | 4.24(ddd) | 4.39(ddd) | 4.32(ddd) | 4.27(ddd) | 4.35(ddd) | 4.54(ddd) |
| ($J_{3',4'a}$) | (3.5) | (3.4) | (3.4) | (3.6) | (3.4) | (3.6) | (2.7) | (5.3) |
| H-4'a | 3.87(dd) | 3.97(dd) | 3.91(dd) | 3.99(dd) | 4.94(dd) | 3.96(dd) | 3.97(dd) | 4.45(dd) |
| ($J_{4'a,4'b}$) | (12.6) | (12.7) | (12.2) | (12.9) | (12.6) | (12.5) | (12.6) | (10.6) |
| H-4'b | 3.80(dd) | 3.88(dd) | 3.85(dd) | 3.88(dd) | 3.84(dd) | 3.84(dd) | 3.84(dd) | 3.76(dd) |
| ($J_{3',4'b}$) | (4.6) | (3.8) | (4.3) | (3.3) | (3.4) | (3.5) | (3.4) | (10.1) |

Footnotes for Table 3
[a]500 MHz, pH = 10, D$_2$O.
[b]500 MHz, pH = 8, Temp. = 25° C., D$_2$O.

TABLE 3-continued

¹H NMR Data Compounds 66b, 67a, 67b, S-68b, R-68b, 69a, 69b and 70b.

| Compound | 66b[a]* | 67a[b] | 67b[c] | S-68b[d]* | R-68b[e]* | 69a[f] | 69b[g] | 70b[h]* |
|---|---|---|---|---|---|---|---|---|

[c]500 MHz, pH = 8, Temp. = 40° C., $D_2O$.
[d]600 MHz, $D_2O$.
[e]600 MHz, $D_2O$.
[f]500 MHz, $D_2O$.
[g]400 MHz, $D_2O$.
[h]600 MHz, $D_2O$.
*Assignments for diastereotopic H-1/H-5 and H-2/H-4 pairs may be reversed.
na = not applicable,
n.d. = not determined

TABLE 4

¹³C NMR Data Compounds 66b, 67a, 67b,
S-68b, R-68b, 69a, 69b and 70b.

| Compound | 66b[a]* | 67a[b] | 67b[b] | S-68b[c]* | R-68b[c]* | 69a[c] | 69b[c] | 70b[c]* |
|---|---|---|---|---|---|---|---|---|
| C-1 | 58.19 | 55.85 | 56.48 | 41.25 | 43.24 | 43.62 | 41.76 | 39.29 |
| C-2 | 69.96 | 67.67 | 78.62 | 69.09 | 69.85 | 69.69 | 69.64 | 70.64 |
| C-3 | 78.77 | 77.60 | 78.14 | 74.05 | 78.10 | 78.57 | 78.58 | 78.42 |
| C-4 | 70.00 | 79.04 | 69.68 | 69.05 | 69.81 | 70.95 | 70.91 | 70.64 |
| C-5 | 57.64 | 66.90 | 66.29 | 41.01 | 43.13 | 61.19 | 60.88 | 39.10 |
| C-6 | na | 56.57 | 56.91 | na | na | 58.69 | 58.63 | na |
| C-1' | 59.38 | 54.65 | 54.98 | 45.44 | 50.39 | 49.41 | 49.01 | 50.20 |
| C-2' | 67.82 | 66.90 | 65.99 | 67.97 | 69.09 | 68.54 | 67.04 | 68.02 |
| C-3' | 81.92 | 81.15 | 81.55 | 82.29 | 62.33 | 83.15 | 83.03 | 83.03 |
| C-4' | 60.20 | 60.03 | 60.16 | 62.01 | 62.04 | 62.10 | 62.11 | 62.30 |

Footnotes for Table 4
[a]125 MHz, pH = 10, $D_2O$.
[b]125 MHz, pH = 8, $D_2O$.
[c]100 MHz $D_2O$.
*Assignments for diastereotopic C-1/C-5 and C-2/C-4 pairs may be reversed.
na = not applicable

5.2.8 Example 8

Synthesis of Chain-Extended Homologues of Salacinol (Schemes 22 to 25)

General procedure. Optical rotations were measured at 23-C. ¹H and ¹³C NMR spectra were recorded at 600.13 and 126.9 MHz, respectively on a Bruker AMX 600 spectrometer. All assignments were confirmed with the aid of two-dimensional ¹H, ¹H(COSYDFTP) or ¹H, ¹³C (INVBTP) experiments using standard Bruker pulse programs. Column chromatography was performed with Merck Silica gel 60 (230-400 mesh). MALDI-TOF mass spectra were obtained on a PerSeptive Biosystems, Voyager DE time-of-flight spectrometer for samples dispersed in a 2,5-dihydroxybenzoic acid matrix. High resolution mass spectra were obtained by the liquid secondary ionization fast atom bombardment (LSIMS (FAB)) technique, using a Kratos Concept H double focusing mass spectrometer at 10000 RP, using glycerol as the matrix.

Benzyl 2,3-Di-O-benzyl-β-D-glucopyranoside-4,6-cyclic sulfate (107)

Benzyl 2,3-di-O-benzyl-β-D-glucopyranoside[41] (1.63 g, 3.62 mmol) and triethylamine (2.5 mL) were dissolved in $CH_2Cl_2$ (60 mL) and the mixture was stirred at rt. Thionyl chloride (0.60 mL, 8.2 mmol) was added dropwise and allowed to react for 20 min. The mixture was diluted with $CH_2Cl_2$ and washed with cold water (2×50 mL). The organic phase was dried over $MgSO_4$ and concentrated to a dark orange-brown syrup that was filtered through a short column of silica gel with hexanes:EtOAc, 3:1, and again concentrated to give a pale orange syrup (1.57 g). Analysis by TLC (hexanes:EtOAc, 3:1) showed that two products of approximately equal proportion had been formed. The mixture of cyclic sulfites was dissolved in $CCl_4$:$CH_3CN$ (1:1, 60 mL) and the solution was stirred at rt. Sodium periodate (3.2 g, 15 mmol), $RuCl_3$:$H_2O$ (56 mg, 0.25 mmol) and water (30 mL) were added sequentially. The dark-colored mixture was stirred for 15 min at rt and transferred to a separatory funnel with the aid of additional $CH_2Cl_2$ (50 mL). Without shaking, the organic phase was separated and the aqueous phase was extracted with $CH_2Cl_2$ (50 mL). The combined organic phase was treated with ethylene glycol (0.2 mL) and concentrated to a black syrup. This was dissolved in EtOAc (150 mL) and filtered through Celite to remove black $RuO_2$. The filtrate was washed with saturated aqueous $NaHCO_3$ (50 mL), dried over $MgSO_4$, and concentrated to give a yellow syrup. Purification by column chromatography on silica gel (hexanes:EtOAc, 1:1) yielded the cylic sulfate 107 as a colorless syrup (1.48 g, 80%) which crystallized on standing, and was recrystallized from $Et_2O$/hexanes: Mp 73-81° C., $[\alpha]_D$ −28° (c 1.4, $CHCl_3$); ¹H NMR ($CDCl_3$): δ 7.4-7.2 (1SH, m, Ar), 4.89, 4.64 (2H, 2d, $J_{A,B}$=11.7 Hz, $CH_2Ph$), 4.85, 4.71 (2H, 2d, $J_{A,B}$=10.8 Hz, $CH_2Ph$), 4.79, 4.73 (2H, 2d, $J_{A,B}$=11.1 Hz, $CH_2Ph$), 4.66 (1H, ddd, $J_{4,5}$=10.4 Hz, H-4), 4.65 (1H, dd, $J_{5,6}$a=10.5, $J_{6a,6b}$=10.7 Hz, H-6a), 4.63 (1H, d, $J_{1,2}$=7.7 Hz, H-1), 4.56 (1H, dd, $J_{5a,6b}$=5.2 Hz, H-6b), 3.75 (1H, ddd, H-5), 3.73 (1H, dd, $J_{2,3}$=8.7, $J_{3,4}$=9.2 Hz, H-3), 3.52 (1H, dd, H-2). ¹³C NMR ($CDCl_3$): δ 137.68, 137.41 and 136.42 (3×C=O, OBz), 128.60-127.94 (18$C_{Ar}$), 103.05 (C-1), 84.18 (C-4), 81.42 (C-2), 79.39 (C-3), 75.49, 75.37 and 71.89 (3×$CH_2Ph$), 71.76 (C-6), 64.35 (C-5). MALDI MS m/e 551.13 ($M^+$+K), 535.12 ($M^+$+Na). Anal. Calcd for $C_{27}H_{28}O_8S$: C, 63.27; H, 5.51. Found: C, 63.58; H, 5.47.

Methyl 2-O-Benzyl-α-D-arabinofuranoside 3,5-cyclic sulfate (110)

Methyl 2-O-benzyl-α-D-arabinofurananoside 108[42] (1.47 g, 5.78 mmol) and triethylamine (3.0 mL) were dissolved in $CH_2Cl_2$ (75 mL) and the mixture was stirred at rt. A solution of thionyl chloride (0.70 mL, 9.6 mmol) in $CH_2Cl_2$ (20 mL) was added dropwise over 15 min and allowed to react for 30 min. The mixture was diluted with $CH_2Cl_2$ (100 mL) and washed with ice-water (50 mL), cold saturated $NaHCO_3$ solution (50 mL), and cold water (20 mL). The organic phase was dried over $MgSO_4$ and concentrated to a dark orange-brown syrup that was filtered through a short column of silica gel with hexanes:EtOAc (1:2), and again concentrated to give a clear red oil (1.59 g). Analysis by TLC (hexanes:EtOAc, 3:1) showed that two products of approximately equal proportion had been formed. The mixture of cyclic sulfites was dissolved in CCl$_4$:CH$_3$CN (1:1, 40 mL), water (30 mL) was added, and the two phase mixture was stirred rapidly at rt. RuCl$_3$:H$_2$O (18 mg, 0.08 mmol) was added followed by small portions of NaIO$_4$ (1.59 g, 7.43 mmol in total) added over 45 min, while monitoring the progress of the reaction by TLC. A slightly more-polar, major product was formed along with more polar by-products. The dark-colored mixture was stirred for an additional 15 min at rt and then processed to give crude 110 by the same procedure described above for the preparation of compound 107. Purification by column chromatography on silica gel (hexanes:EtOAc, 3:1 to 1:1) yielded the cyclic sulfate 110 as a colorless crystalline solid (1.01 g, 55%). Also isolated was a sample of the major by-product as a colorless solid (216 mg). A sample of compound 110 was recrystallized from EtOAc/hexanes to give large leaflets: Mp 97-98° C., [α]$_D$ +12° (c 1.1, CHCl$_3$); $^1$H NMR (CDCl$_3$): δ 7.40-7.30 (5H, m, Ar), 4.97 (1H, d, J$_{1,2}$=2.8 Hz, H-1), 4.79 (1H, dd, J$_{2,3}$=7.6, J$_{3,4}$=10.2 Hz, H-3), 4.72 (1H, dd, J$_{4,5a}$=11.0, J$_{5a,5b}$=9.8 Hz, H-5a), 4.66 (1H, dd, J$_{4,5b}$=4.9 Hz, H-5b), 4.65 and 4.57 (2H, 2d, J$_{A,B}$=11.7 Hz, CH$_2$Ph), 4.26 (1H, ddd, H-4), 4.18 (1H, dd, H-2), 3.39 (3H, s, OCH$_3$). $^{13}$C NMR (CDCl$_3$): δ 136.46 (C$_{ipso}$, Ar), 128.58 (2C), 128.279, and 127.97 (2C) (5C$_{Ar}$), 109.57 (C-1), 86.69 (C-3), 83.69 (C-2), 73.72(C-5), 72.89 (CH$_2$Ph), 67.93 (C-4), 56.34 (OCH$_3$). MALDI MS m/e 355.08 (M$^+$+K), 339.08 (M$^+$+Na). Anal. Calcd for C$_{13}$H$_{16}$O$_7$S: C, 49.36; H, 5.10. Found: C, 49.56; H, 5.12.

Benzyl 2-O-Benzyl-α-D-arabinofuranoside-3,5-cyclic sulfate (111)

The diol 109 (1.37 g, 4.15 mmol) was converted to the cyclic sulfate 111 in two steps (via the intermediate cyclic sulfite) using the same procedure detailed above for the preparation of the cyclic sulfate 110 from diol 108. The syrupy product (1.23 g) after column chromatography was found to contain approximately 15% of a sulfate-dimer impurity by $^1$H NMR analysis. Crystallization from EtOAc:hexanes gave pure 111 (838 mg, 48%) as small colorless needles: Mp 84-86° C., [α]$_D$ +84° (c 1.2, CHCl$_3$); $^1$H NMR (CDCl$_3$): δ 7.40-7.27 (10H, m, Ar), 5.18 (1H, d, J$_{1,2}$=2.8 Hz, H-1), 4.80 (1H, dd, J$_{2,3}$=7.6, J$_{3,4}$=10.2 Hz, H-3), 4.76 and 4.50 (2H, 2d, J$_{A,B}$=11.7 Hz, CH$_2$Ph), 4.74 (1H, dd, J$_{4,5a}$=11.0, J$_{5a,5b}$=9.8 Hz, H-5a), 4.67 (1H, dd, J$_{4,5b}$=4.9 Hz, H-5b), 4.62 and 4.53 (2H, 2d, J$_{AB}$=11.7 Hz, CH$_2$Ph), 4.33 (1H, ddd, H-4), 4.28 (1H, dd, H-2). $^{13}$C NMR (CDCl$_3$): δ 136.47(2C) (2×C$_{ipso}$, Ar), 128.59-127.92 (10C$_{Ar}$), 107.54 (C-1), 86.71 (C-3), 83.70 (C-2), 73.70 (C-5), 72.83 and 70.73 (2×CH$_2$Ph), 68.07 (C-4). MALDI MS m/e 415.00 (M$^+$+Na). Anal. Calcd for C$_{19}$H$_{120}$O$_7$S: C, 58;15; H, 5.14. Found: C, 58.06; H, 5.17.

Benzyl 2,3,5-Tri-O-benzoyl-α-D-arabinofuranoside (113).[43]

To a stirred mixture of mercuric cyanide (5.20 g, 20.6 mmol) in CH$_3$CN (50 mL) was added benzyl alcohol (2.0 mL, 19 mmol) and the glycosyl bromide 112[44] (5.25 g, 10.0 mmol). The mixture was stirred for 0.5 h at rt and then concentrated by rotary evaporation to remove most of the solvent. The residue was partitioned between Et$_2$O (150 mL) and water (50 mL). The organic phase was washed with saturated NaHCO$_3$ (30 mL), water (30 mL) and brine (30 mL) and dried over MgSO$_4$. Solvent removal gave the crude product contaminated with mercury salts and excess benzyl alcohol. Purification by colmn chromatography on silica gel (hexanes:EtOAc, 3:1) yielded the benzyl glycoside 113 as a colorless syrup which crystallized on standing. Recrystallization from EtOH gave the pure compound 113 (4.73 g, 86%): Mp 92-93° C.; lit.[81] mp 89-90° C.; [α]$_D$ +9.3° (c 1.1, CHCl$_3$); lit.[81] [α]$_D$ +10.1° (c 1.04, CHCl$_3$); $^1$H NMR data were identical to the literature data;[81] $^{13}$C NMR (CDCl$_3$): δ 166.21, 165.75 and 165.34 (3×C=O, 3×OBz), 137.36-126.94 (24C$_{Ar}$), 105.07 (C-1), 82.04 (C-2), 81.36 (C-4), 77.94 (C-3), 68.91 (CH$_2$Ph), 63.86 (C-5).

Benzyl 3,5-O-(1,1,3,3-Tetraisopropyldisiloxane-1,3-diyl)-α-D-arabinofuranoside (115)

The tribenzoate 113 (4.48 g, 8.11 mmol) was added to MeOH (150 mL) and the heterogeneous mixture was placed under a nitrogen atmosphere. A solution of NaOMe in MeOH (1.0 M, 4.0 mL) was added and the mixture was stirred at rt for 3 h. The starting material slowly dissolved during the first hour. Upon completion of the reaction, as judged by TLC analysis, the NaOMe was neutralized by addition of excess Rexyn 101H$^+$ ion-exchange resin, the resin was removed by filtration, and the solution was concentrated. The syrupy residue was shaken with hexanes (3×50 mL) to dissolve methyl benzoate, and the hexane extracts were decanted from the insoluble, crude, triol product 114 (2.02 g, after 3 h under high vacuum). The triol was dissolved in pyridine (30 mL) and a solution of 1,3-dichloro-1,1,3,3-tetraisopropyldisiloxane (4.0 mL, 12 mmol) in CH$_2$Cl$_2$ (30 mL) was added dropwise at rt. The mixture was stirred for 2 h, diluted with CH$_2$Cl$_2$ (100 mL), and washed with saturated NaHCO$_3$ (50 mL). The aqueous phase was extracted with CH$_2$Cl$_2$ (50 mL) and the combined extracts were dried over MgSO$_4$ and concentrated by rotary evaporation, first at water aspirator pressure and then under high vacuum to remove pyridine. Purification by column chromatography on silica gel (hexanes:EtOAc, 5:1) yielded compound 115 as a colorless syrup (3.58 g, 91% for 2 steps): [α]$_D$ +47° (c 1.0, CHCl$_3$); $^1$H NMR (CDCl$_3$): δ 7.44-7.25 (5H, m, Ar), 4.97 (1H, d, J$_{1,2}$=2.7 Hz, H-1), 4.78, 4.49 (2H, 2d, J$_{A,B}$=11.8 Hz, CH$_2$Ph), 4.25 (1H, dd, J$_{2,3}$=6.1 Hz, H-2), 4.19-4.15 (1H, 2$^{nd}$ order m, H-3), 4.02-3.91 (3H, m, H-4, H-5a, H-5b), 1.12-0.98 (24H, m, 4×CH(CH$_3$)$_2$). 13C NMR (CDCl$_3$): δ 137.80, (C$_{ipso}$, Ar), 128.38 (2C), 127.88 (2C) and 127.66 (5C$_{Ar}$), 106.27 (C-1), 82.90 (C-2), 81.11 (C-4), 77.55 (C-3), 69.59 (CH$_2$Ph), 61.81 (C-5), 17.46, 17.34 (3C), 17.16, 17.10, 17.05, 17.00, 13.53, 13.19, 12.87 and 12.64 (12C, 4×CH(CH$_3$)$_2$). MALDI MS m/e 505.19 (M$^+$+Na).

Anal. Calcd for C$_{24}$H$_{42}$O$_6$Si$_2$: C, 59.71; H, 8.77. Found: C, 59.37; H, 8.99.

Benzyl 2-O-Benzyl-α-D-arabinofuranoside (109)

The silyl protected compound 115 (3.50 g, 7.26 mmol) was dissolved in DMF (20 mL) and cooled by stirring in an ice-bath under N$_2$. Benzyl bromide (2.0 mL, 17 mmol) was added in a single portion followed by 60% NaH/oil (0.37 g, 9.2 mmol), added carefully in small portions over 10 min. The reaction mixture was stirred at 0° C. for 1.5 h. Cold Et$_2$O (150 mL) and ice-water (50 mL) were added and the organic phase was separated. The aqueous phase was extracted with more Et$_2$O (100 mL) and the combined extracts were washed with water (2×50 mL), then brine (30 mL), and dried over MgSO$_4$. The solvents were evaporated and the residue was warmed under high vacuum to remove the excess benzyl bromide by distillation. The crude benzylated product 116 (4.12 g) was found to be approximately 90% pure as judged by analysis of the $^1$H NMR spectrum, and was used directly in the following procedure.

The syrupy compound 116 was dissolved in dry THF (70 mL) and stirred while a 1.0 M solution of n-Bu$_4$NF in THF (16 mL, 16 mmol) was added. The reaction mixture was kept for 0.5 h at rt and concentrated to a brown residue. Non-polar material was removed by shaking with hexanes (3×50 mL) and decanting the hexanes solution from the crude, insoluble diol product. The crude product was dissolved in EtOAc (150 mL), washed with brine (20 mL), dried over MgSO$_4$, and concentrated. The residue was purified by flash chromatography (hexanes:EtOAc, 1:3) to give diol 109 (1.50 g, 66%) as a colorless syrup which crystallized on standing: Mp 73-74° C.; $[\alpha]_D$ +99° (c 1.1, CHCl$_3$). MALDI MS m/e 353.02 (M$^+$+Na). Anal. Calcd for C$_{19}$H$_{22}$O$_5$: C, 69.07; H, 6.71. Found: C, 68.90; H, 6.79. NMR data for compound 109: $^1$H NMR (CDCl$_3$): δ 7.4-7.2 (10H, m, Ar), 5.16 (1H, s, J$_{1,20}$ Hz, H-1), 4.77 and 4.51 (2H, 2d, J$_{A,B}$=11.7 Hz, CH$_2$Ph), 4.61 and 4.54 (2H, 2d, J$_{AB}$=11.7 Hz, CH$_2$Ph), 4.17 (1H, ddd, J$_{3,4}$=3.1, J$_{4,5a}$=3.1, J$_{4,5b}$=4.2, H-4), 4.15 (1H, ddd, J$_{3,OH}$=9.8, J$_{2,3}$=1.1 Hz, H-3), 3.96 (1H, d, H-2), 3.83 (1H, ddd, J$_{5a,5b}$=11.7, J$_{5a,OH}$=4.5 Hz, H-5a), 3.77 (1H, ddd, J$_{5b,OH}$=7.0 Hz H-5b), 2.51 (1H, d, OH-3), 2.14 (1H, dd, OH-5). $^{13}$C NMR (CDCl$_3$): δ 137.08, (2C, 2×C$_{ipso}$,Ar), 128.56 (4C), 128.06 (3C) 128.01, and 127.92 (2C), (10C$_{Ar}$), 104.92 (C-1), 87.60 (C-2), 86.42 (C-4), 75.60 (C-3), 71.94 and 69.10 (2×CH$_2$Ph), 62.58 (C-5). NMR data for intermediate compound 116: $^1$H NMR (CDCl$_3$): δ 7.4-7.2 (10H, m, Ar), 5.02 (1H, d, J$_{1,2}$=2.4 Hz, H-1), 4.76 and 4.49 (2H, 2d, J$_{A,B}$=11.9 Hz, CH$_2$Ph), 4.59 and 4.55 (2H, 2d, J$_{AB}$=11.9 Hz, CH$_2$Ph), 4.30-4.27 (1H, 2$^{nd}$ order m, H-3), 4.04 (1H, dd, J$_{2,3}$=5.9 Hz, H-2), 4.02-3.91 (3H, m, H-4, H-5a, H-5b), 1.12-0.90) (24H, m, 4×CH(CH$_3$)$_2$. $^{13}$C NMR (CDCl$_3$): δ 137.94 and 137.86, (2×C$_{ipso}$, Ar), 128.35 (2C), 128.28 (2C) 127.93 (2C), 127.63 (2C), 127.64 and 127.60 (10C$_{Ar}$), 104.81 (C-1), 89.77 (C-2), 80.80 (C-4), 76.55 (C-3), 72.50 and 69.34 (2×CH$_2$Ph), 61.82 (C-5), 17.48, 17.35 (3C), 17.11 (2C), 17.06, 17.02, 13.53, 13.19, 12.90 and 12.61 (12C, 4×CH(CH$_3$)$_2$).

General Procedure for the Preparation of Sulfonium Sulfates 118-122.

A mixture of the thioether 117 (1.00-1.15 equiv) and the cyclic sulate 104, 105, 106, 107 or 108 (0.79-1.00 equiv) in HFIP (1.0-3.0 mL/mmol of 117) were placed in a sealed reaction vessel and warmed with stirring for the indicated time at the temperatures given below. The progress of the reaction was followed by TLC analysis of aliquots (developing solvent CHCl$_3$:MeOH, 10:1). When the limiting starting compound had been essentially consumed, the mixture was cooled, then diluted with CH$_2$Cl$_2$ and evaporated to give a syrupy residue. Purification by column chromatography (CHCl$_3$ to CHCl$_3$:MeOH, 10:1) gave the purified sulfonium salts 118-122.

1,2-O-Isopropylidene-3-O-sulfoxy-5-deoxy-5-[2,3,5-tri-O-benzyl-1,4-dideoxy-1,4-episufoniumylidene-D-arabinitol]-α-D-xylofuranose Inner Salt (118)

Reaction of the thioether 117 (833 mg, 2.03 mmol) with the cyclic sulfate 104 (649 mg, 2.57 mmol) in HFIP (2.5 mL) for 44 h at 70° C. gave compound 118 as a colorless crystalline solid (1.16 g, 85%). A sample was recrystallized from MeOH: Mp 149-151° C.; $[\alpha]_D$ −10° (c 1.0, CHCl$_3$). See Tables 1 and 2 for NMR data. MALDI MS m/e 695.18 (M$^+$+Na), 673.13 (M$^+$+H), 593.20 (M$^+$+H−SO$_3$). Anal. Calcd for C$_{34}$H$_{40}$O$_{10}$S$_2$: C, 60.70; H, 5.99. Found: C, 60.81; H, 5.86.

Benzyl 2,3-Di-O-benzyl-4-O-sulfoxy-6-deoxy-6-[2,3,5-tri-O-benzyl-1,4-dideoxy-1,4-episufoniumylidene-D-arabinitol]-β-D-galactopyranose Inner Salt (119)

Reaction of the thioether 117 (431 mg, 1.02 mmol) with the cyclic sulfate 105 (588 mg, 1.15 mmol) in HFIP (3.0 mL) for 42 h at 70° C. gave compound 119 as a colorless gummy solid (571 mg, 60%). $[\alpha]_D$ −7.6° (c 1.1, CHCl$_3$). See Tables 1 and 2 for NMR data. MALDI MS m/e 955.39 (M$^+$+Na), 853.42 (M$^+$+H−SO$_3$). Anal. Calcd for C$_{53}$H$_{56}$O$_1$S$_2$: C, 68.22; H, 6.05. Found: C, 68.48; H, 6.09.

Benzyl 2,3-Di-O-benzyl-4-O-sulfoxy-6-deoxy-6-[2,3,5-tri-O-benzyl-1,4-dideoxy-1,4-episufoniumylidene-D-arabinitol]-β-D-glucopyranose Inner Salt (120)

Reaction of the thioether 117 (937 mg, 2.22 mmol) with the cyclic sulfate 107 (1.12 g, 2.17 mmol) in HFIP (4.0 mL) for 42 h at 70° C. gave, after chromatography, partially purified compound 120 as a colorless gummy solid (1.02 g, 50%), containing a minor amount of a more-polar isomer. Analysis of this material by $^1$H NMR showed it to be ~80% pure and that the minor isomer could be tentatively identified as the diastereomer at the sulfonium center. Repurification by chromatography (CHCl$_3$:MeOH, 20:1) keeping only those fractions which were pure by TLC yielded compound 120 (639 mg, 31%) as a gum: $[\alpha]_D$ −8.7° (c 1.2, CHCl$_3$). See Tables 1 and 2 for NMR data. MALDI MS m/e 955.53 (M$^+$+Na), 933.60 (M$^+$+H), 853.54 (M$^+$+H—SO$_3$). Anal. Calcd for C$_{53}$H$_{56}$O$_1$S$_2$: C, 68.22; H, 6.05. Found: C, 68.34; H, 6.02.

Methyl 2-O-Benzyl-3-O-sulfoxy-5-deoxy-5-[2,3,5-tri-O-benzyl-1,4-dideoxy-1,4-episufoniumylidene-D-arabinitol]-α-D-arabinofuranose Inner Salt (121)

Reaction of the thioether 117 (487 mg, 1.16 mmol) with the cyclic sulfate 110 (322 mg, 1.02 mmol) in HFIP (2.5 mL) for 3 h at 40° C. gave compound 121 as a colorless gummy solid (756 mg, quantitative). Analysis by NMR showed the presence of an 8:1 ratio of isomers at the sulfonium center. See Tables 1 and 2 for NMR data of the major isomer 121. MALDI MS m/e 759.13 (M$^+$+Na), 737.18 (M$^+$+H), 657.16 (M$^+$+H—SO$_3$). Anal. Calcd for C$_{39}$H$_{44,0}$S$_2$: C, 63.57; H, 6.02. Found: C, 63.36; H, 6.01.

Benzyl 2-O-Benzyl-3-O-sulfoxy-5-deoxy-5-[2,3,5-tri-O-benzyl-1,4-dideoxy-1,4-episufoniumylidene-D-arabinitol]-α-D-arabinofuranose Inner Salt (122)

Reaction of the thioether 117 (514 mg, 1.22 mmol) with the cyclic sulfate 111 (448 mg, 1.06 mmol) in HFIP (3.0 mL) for 2.5 h at 40° C. gave the major isomer 122a as a pale-yellow amorphous, hard foam (763 mg, 85%). A sample of the minor isomer 122p suitable for NMR analysis (see Tables 1 and 2) was obtained with a purity of >80% from the early chromatographic fractions. For the major isomer 122a: $[\alpha]_D$ +40° (c 1.6, CHCl$_3$). See Tables 1 and 2 for NMR data. MALDI MS m/e 813.25 (M$^+$+H), 733.24 (M$^+$+H−SO$_3$). Anal. Calcd for C$_{45}$H$_{48}$O$_{10}$S$_2$: 66.48; H, 5.95. Found: C, 66.64; H, 5.88.

1,4-Dideoxy-1,4-[[2S,3R,4S-2,4,5-trihydroxy-3-(sulfooxy)pentyl]episufonium-ylidene]-D-arabinitol (94.)

Procedure A: The protected sulfonium salt 118 (252 mg, 0.375 mmol) was dissolved in MeOH (20 mL) and stirred at rt with 10% Pd/C catalyst (227 mg) under 1 atm. of H$_2$ for 17 h. Analysis by TLC (CHCl$_3$:MeOH, 7:3) showed the formation of a single product (R$_f$ 0.3). The catalyst was removed by filtration through Celite with additional MeOH and the filtrate was evaporated to give the crude isopropylidene compound 123 as a gummy residue (137 mg). The residue was dissolved in 50% aq. trifluoroacetic acid (3.0 mL) and kept at rt for 4 h. Evaporation of the solvent gave the crude hemiacetal, 3-O-sulfoxy-5-deoxy-5-[1,4-dideoxy-1,4-episufoniumylidene-D-arabinitol]-α/β-D-xylofuranose inner salt (98, α:β=5:4) as a pale-yellow glass (121 mg, 89%). See Tables 3 and 4 for NMR data of 98. MALDI MS m/e 385.02 ($M^+$+Na), 363.04 ($M^+$+H), 283.08 ($M^+$+H—$SO_3$).

NMR data for the intermediate compound 123: $^1$H NMR ($D_2O$): δ 6.17 (1H, d, $J_{1,2}$=3.7 Hz, H-1'), 5.05 (1H, d, $J_{2,3}$~0 Hz, H-2'), 4.95 (1H, d, $J_{3',4'}$=2.9 Hz, H-3'), 4.87 (1H, ddd, $J_{4',5'a}$=3.3, $J_{4',5'b}$=7.8 Hz, H-4'), 4.79 (1H, ddd, H-2), 447 (1H, dd, $J_{2,3}$=3.3, $J_{3,4}$=2.9 Hz, H-3), 4.17 (1H, ddd, H-4), 4.16 (1H, dd, $J_{4,5a}$=4.7, $J_{5a,5b}$=14.0 Hz, H-5a), 4.05 (1H, dd, $J_{5'a,5'b}$=13.8 Hz, H-5'a), 3.98 (1H, dd, $J_{1a,1b}$=12.7 Hz, H-1a), 3.97 (1H, dd, $J_{4,5b}$=11.0 Hz, H-5b), 3.95 (1H, dd, $J_{1b,2}$=3.1 Hz, H-1b), 3.94 (1H, dd, $J_{4',5'b}$=7.8 Hz, H-5'b), 1.57 and 1.40 (6H, 2×s, each 3H, C($CH_3$)$_2$). $^{13}$C NMR ($D_2O$): δ 114.22 (C($CH_3$)$_2$), 105.39 (C-1'), 83.62 (C-2'), 81.30 (C-3'), 78.21 (C-3), 77.41 (C-2), 75.58 (C-4'), 71.30 (C-4), 59.78 (C-5), 48.27 (C-1), 44.82 (C-5'), 26.22 and 25.79 (C($CH_3$)$_2$).

Procedure B: The protected sulfonium salt 118 (254 mg, 0.378 mmol) was dissolved in TFA (3.0 mL) and stirred at rt until the solid dissolved. Water (3.0 mL) was added and the mixture was placed in a 45° C. bath for 2 h. Analysis by TLC ($CHCl_3$:MeOH, 7:3) showed formation of a single product (Rf 0.8). The solvents were evaporated to give the crude hemiacetal 124 as an anomeric mixture (α:β=5:4) The mixture was dissolved in MeOH (20 mL) and hydrogenolyzed over 10% Pd/C catalyst (200 mg) at rt for 18 h. Filtration through Celite with additional MeOH and evaporation of the solvent gave a colorless foam that was shown by NMR analysis to consist of four compounds which were tentatively identified to be an anomeric mixture of the hemiacetal 98 together with an anomeric mixture of the corresponding methyl glycoside 124. Re-treatment of the mixture with 50% aq TFA (6.0 mL, rt, 4 h) resulted in hydrolysis of most of the methyl glycoside. Filtration through silica gel (EtOAc:MeOH:$H_2O$) to remove polar impurities, followed by solvent removal gave the crude compound 98 (101 mg, 74%) that was identical by NMR to that obtained above by procedure A.

The hemiacetal 98 (101 mg, 0.279 mmol) was dissolved in water (8.0 mL). The solution was stirred at rt while $NaBH_4$ (44 mg, 1.2 mmol) was added in small portions over 30 min. Stirring was continued for another 20 min and the mixture was acidified to pH≦4 by dropwise addition of 2M HCl. The solution was evaporated to dryness and then co-evaporated with anhydrous MeOH (3×30 mL). The semisolid residue was purified by column chromatograhy on silica gel (EtOAc:MeOH:$H_2O$, 6:3:1) to give the product 94 as a colorless gum (86 mg, 85%). $[α]_D$ +19° (c 0.32, MeOH). See Tables 5 and 6 for NMR data of 94. MALDI MS m/e 386.89 ($M^+$+Na), 285.01 ($M^+$+H–$SO_3$); HRMS. Calcd for $C_{10}H_{20}O_{10}S_2Na$ (M+Na): 387.0396. Found: 387.0382.

1,4-Dideoxy-1,4-[[2S,3R,4R,5S-2,4,5,6-tetrahydroxy-3-(sulfooxy)hexyl]episufonium-ylidene]-D-arabinitol (95)

The protected sulfonium salt 119 (460 mg, 0.493 mmol) was dissolved in MeOH (50 mL) and stirred at rt with 10% Pd/C catalyst (580 mg) under 1 atm. of $H_2$ for 24 h. Analysis by TLC (EtOAc:MeOH:$H_2O$, 6:3:1) showed the formation of a single product (Rf 0.10). The catalyst was removed by filtration through Celite, using additional MeOH, and the filtrate was evaporated to give the crude hemiacetal, 4-O-sulfoxy-6-deoxy-6-[1,4-dideoxy-1,4-episufoniumylidene-D-arabinitol]-α/β-D-galactopyranose inner salt (99, α:β=1:1) as a colorless foam (184 mg, 95%). See Tables 3 and 4 for NMR data of 99. MALDI MS m/e 414.89 ($M^+$+Na), 392.93 ($M^+$+H), 312.93 ($M^+$+H–$SO_3$).

Reduction of the hemiacetal 99 (430 mg, 1.10 mmol) with $NaBH_4$, as described above for compound 98, gave the sulfonium sulfate 95 (232 mg, 54%) as a colorless glass.

$[α]_D$ +18° (c 0.72, MeOH). See Tables 5 and 6 for NMR data of 95. MALDI MS m/e 416.94 ($M^+$+Na), 315.03 ($M^+$+H–$SO_3$); HRMS. Calcd for $C_{11}H_{22}O_{11}S_2Na$ (M+Na): 417.0501. Found: 417.0498.

1,4-Dideoxy-1,4-[[2S,3S,4R,5S-2,4,5,6-tetrahydroxy-3-(sulfooxy)hexyl]episufonium-ylidene]-D-arabinitol (96)

The protected sulfonium salt 120 (602 mg, 0.645 mmol) was dissolved in HOAc (22 mL). Water (2.2 mL) was added and the mixture was stirred at rt with 10% Pd/C catalyst (520 mg) under 1 atm. of $H_2$ for 22 h. Analysis by TLC (EtOAc:MeOH:$H_2O$, 6:3:1) showed the formation of a single product ($R_f$ 0.15). The catalyst was removed by filtration through Celite with additional water and the filtrate was evaporated to a syrup. Water (3×30 mL) was added and evaporated to remove residual HOAc. The crude hemiacetal, 4-O-sulfoxy-6-deoxy-6-[1,4-dideoxy-1,4-episufoniumylidene-D-arabinitol]-α/β-D-glucopyranose inner salt (100, α:β=1:1) was obtained as a colorless foam (263 mg, quantitative). See Tables 3 and 4 for NMR data of 100. MALDI MS m/e 414.99 ($M^+$+Na), 313.05 ($M^+$+H–$SO_3$).

Reduction of the hemiacetal 100 (255 mg, 0.650 mmol) with $NaBH_4$, as described above for compound 98, gave the sulfonium sulfate 96 (165 mg, 64%) as a colorless glass. $[α]_D$ +13° (c 0.92, MeOH). See Tables 5 and 6 for NMR data of 96. MALDI MS m/e 416.94 ($M^+$+Na), 315.00 ($M^+$+H—$SO_3$).; HRMS. Calcd for $C_{11}H_{22}O_{11}S_2Na$ (M+Na): 417.0501. Found: 417.0499.

1,4-Dideoxy-1,4-[[2S,3S,4R-2,4,5-trihydroxy-3-(sulfooxy)pentyl]episufonium-ylidene]-D-arabinitol (97)

The protected sulfonium salt 122 (677 mg, 0.789 mmol) was dissolved in HOAc (20 mL). Water (2.0 mL) was added and the mixture was stirred at rt with 10% Pd/C catalyst (510 mg) under 1 atm. of $H_2$ for 6 h. Analysis by TLC (EtOAc:MeOH:$H_2O$, 6:3:1) showed formation of a single product ($R_f$ 0.25). The catalyst was removed by filtration through Celite with additional water and the filtrate was evaporated to a syrup. Water (3×20 mL) was added and evaporated to remove residual HOAc. The crude hemiacetal, 3-O-sulfoxy-5-deoxy-5-[1,4-dideoxy-1,4-episufoniumylidene-D-arabinitol]-α/β-D-arabinose inner salt (101, α:β=1:1) was obtained as a colorless foam (294 mg, quantitative). See Tables 3 and 4 for NMR data of 101. MALDI MS m/e 384.97 ($M^+$+Na), 363.02 ($M^+$+H), 283.07 ($M^+$+H—$SO_3$).

Reduction of the hemiacetal 101 (283 mg, 0.781 mmol) with $NaBH_4$, as described above for compound 98, gave the sulfonium sulfate 97 (194 mg, 66%) as a colorless glass. $[α]_D$ –4.7° (c 1.0, MeOH). See Tables 5 and 6 for NMR data of 97. MALDI MS m/e 386.95 ($M^+$+Na), 364.97 ($M^+$+H), 285.05 ($M^+$+H–$SO_3$); HRMS. Calcd for $C_{10}H_{20}O_1S_2Na$ (M+Na): 387.0396. Found: 387.0386.

TABLE 1

1H NMR Data for Compounds 118-122

| Compound | 118[a] | 119[b] | 120[c] | 121[d] | 122α[e] | 122β[f] |
|---|---|---|---|---|---|---|
| H-1a | 4.92(dd) | 4.07(br d) | 4.06(dd) | 4.19(dd) | 4.08(dd) | 3.78(br d) |
| ($J_{1a,1b}$, $J_{1a,2}$) | (12.5, 0.6) | (13.3, <1) | (13.5, 1.0) | (13.2, <1) | (13.1, <1) | (14.1, 1.8) |
| H-1b | 3.78(dd) | 3.59(dd) | 3.76(dd) | 3.80(dd) | 3.79(dd) | 3.68(dd) |
| ($J_{1b,2}$) | (3.8) | (3.7) | (3.9) | (3.6) | (3.7) | (4.3) |
| H-2 | 4.44(br s) | 4.27(br d) | 4.49(br s) | 4.46(br m) | 4.47(br m) | 4.38(ddd) |
| ($J_{2,3}$) | (<1) | (~2) | (nd) | (~2) | (~2) | (2.3) |
| H-3 | 4.25(br s) | 4.32(br s) | 4.32(br d) | 4.26(br s) | 4.22(br s) | 4.36(dd) |
| ($J_{3,4}$) | (~0) | (<1) | (nd) | (<1) | (<1) | (3.1) |
| H-4 | 4.04(br t) | 3.91(dd) | 3.87(m) | 4.22(t) | 4.19(br t) | 4.28(ddd) |
| ($J_{4,5a}$) | (7.8) | (6.3) | (6.5) | (7.8) | (8.0) | (7.1) |
| H-5a | 3.72(dd) | 3.80(dd) | 3.69(dd) | 3.61(dd) | 3.61(dd) | 3.93(dd) |
| ($J_{5a,5b}$) | (10.1) | (9.6) | (8.4) | (10.1) | (10.2) | (10.7) |
| H-5b | 3.70(dd) | 3.63(t) | 3.61(dd) | 3.51(dd) | 3.55(dd) | 3.86(dd) |
| ($J_{4,5b}$) | (7.7) | (9.8) | (9.9) | (7.8) | (7.4) | (5.9) |
| H-1' | 5.76(d) | 4.45(d) | 4.57(d) | 4.74(s) | 4.97(d) | 5.04(d) |
| ($J_{1',2'}$) | (3.5) | (7.6) | (7.9) | (~0) | (1.2) | (1.5) |
| H-2' | 4.86(d) | 3.80(dd) | 3.37(dd) | 4.16(d) | 4.27(dd) | 4.26(dd) |
| ($J_{2',3'}$) | (~0) | (9.6) | (9.2) | (3.0) | (3.5) | (3.9) |
| H-3' | 5.06(d) | 3.55(dd) | 3.66(dd) | 4.91(dd) | 4.92(dd) | 4.83(dd) |
| ($J_{3',4'}$) | (3.1) | (3.4) | (9.1) | (6.3) | (6.8) | (7.3) |
| H-4' | 4.68(ddd) | 5.00(dd) | 4.56(m) | 4.68(ddd) | 4.68(ddd) | 4.65(ddd) |
| ($J_{4',5'a}$) | (1.8) | (1.2) | (n.d) | (4.7) | (5.0) | (5.1) |
| H-5'a | 4.20(dd) | — | — | 4.27(dd) | 4.25(dd) | 4.14(dd) |
| ($J_{5'a,5'b}$) | (3.9) | | | (13.9) | (13.5) | (13.6) |
| H-5'b | 3.98(dd) | — | — | 4.15(dd) | 4.17(dd) | 4.10(dd) |
| ($J_{4',5'b}$) | (5.0) | | | (3.0) | (3.0) | (3.4) |
| H-5' | — | 3.99(br m) | 3.88(m) | — | — | — |
| ($J_{5',6'a}$) | | (2.3) | (n.d) | | | |
| H-6'a | — | 4.35(dd) | 4.56(m) | — | — | — |
| ($J_{6'a,6'b}$) | | (13.0) | (n.d) | | | |
| H-5'b | — | 3.94(dd) | 3.88(m) | — | — | — |
| ($J_{5',6'b}$) | | (5.6) | (nd) | | | |

Footnotes for Table 1

[a]Others: 7.36-7.08(15H, m, Ar), 4.56 and 4.53(2H, 2d, $J_{A,B}$=11.8Hz, CH$_2$Ar), 4.52 and 4.46(2H, 2d, $J_{A,B}$=11.8Hz, CH$_2$Ar), 4.47 and 4.34(2H, 2d, $J_{A,B}$=11.8Hz, CH$_2$Ar), 1.46(3H, s, CH$_3$), 1.25(3H, s, CH$_3$).
[b]Others: 7.45-7.02(30H, m, Ar), 5.03 and 4.56(2H, 2d, $J_{A,B}$=12.0Hz, CH$_2$Ar), 4.78 and 4.55(2H, 2d, $J_{A,B}$=12.2Hz, CH$_2$Ar), 4.76 and 4.71(2H, 2d, $J_{A,B}$=11.3Hz, CH$_2$Ar), 4.54 and 4.52(2H, 2d, $J_{A,B}$=12.2Hz, CH$_2$Ar), 4.33 and 4.20(2H, 2d, $J_{A,B}$=11.8Hz, CH$_2$Ar), 4.25 and 4.19(2H, 2d, $J_{A,B}$=12.0Hz, CH$_2$Ar).
[c]Others: 7.50-7.10(30H, m, Ar), 5.31 and 4.71(2H, 2d, $J_{A,B}$=10.7Hz, CH$_2$Ar), 4.76 and 4.64(2H, 2d, $J_{A,B}$=11.9Hz, CH$_2$Ar), 4.73 and 4.70(2H, 2d, $J_{A,B}$=10.7Hz, CH$_2$Ar), 4.58 and 4.53(2H, 2d, $J_{A,B}$=12.0Hz, CH$_2$Ar), 4.48 and 4.36(2H, 2d, $J_{A,B}$=11.8Hz, CH$_2$Ar), 4.43 and 4.33(2H, 2d, $J_{A,B}$=11.9Hz, CH$_2$Ar).
[d]Others: 7.37-7.10(20H, m, Ar), 4.83 and 4.50(2H, 2d, $J_{A,B}$=11.3Hz, CH$_2$Ar), 4.59 and 4.55(2H, 2d, $J_{A,B}$=11.9Hz, CH$_2$Ar), 4.49 and 4.36(2H, 2d, $J_{A,B}$=11.8Hz, CH$_2$Ar), 4.38(2H, s, CH$_2$Ar), 3.25(3H, s, CH$_3$).
[e]Others: 7.35-7.10(25H, m, Ar), 4.87 and 4.52(2H, 2d, $J_{A,B}$=11.4Hz, CH$_2$Ar), 4.62 and 4.43(2H, 2d, $J_{A,B}$=12.3Hz, CH$_2$Ar), 4.58 and 4.55(2H, 2d, $J_{A,B}$=12.1Hz, CH$_2$Ar), 4.47 and 4.37(2H, 2d, $J_{A,B}$=11.8Hz, CH$_2$Ar), 4.39 and 4.35(2H, 2d, $J_{A,B}$=12.1Hz, CH$_2$Ar).
[f]Others: 7.34-7.12(25H, m, Ar), 4.82 and 4.54(2H, 2d, $J_{A,B}$=12.1Hz, CH$_2$Ar), 4.62 and 4.47(2H, 2d, $J_{A,B}$=12.3Hz, CH$_2$Ar), 4.54 and 4.43(2H, 2d, $J_{A,B}$=12.0Hz, CH$_2$Ar), 4.47 and 4.44(2H, 2d, $J_{A,B}$=11.7Hz, CH$_2$Ar), 4.45(3H, s, CH$_2$Ar).

n.d. not determined

TABLE 2

13C NMR Data for Compounds 118-122

| Compound | 118[a] | 119[b] | 120[c] | 121[d] | 122α[e] | 122β[f] |
|---|---|---|---|---|---|---|
| C-1 | 48.03 | 47.65 | 47.34 | 47.30 | 47.31 | 45.69 |
| C-2 | 82.40 | 81.94 | 81.72 | 82.48 | 82.58 | 83.05 |
| C-3 | 82.85 | 83.16 | 83.52 | 82.90 | 82.84 | 83.54 |
| C-4 | 66.85 | 65.81 | 65.40 | 65.98 | 66.04 | 60.78 |
| C-5 | 66.70 | 66.72 | 66.52 | 66.47 | 66.59 | 64.53 |
| C-1' | 105.16 | 103.20 | 103.26 | 107.75 | 106.02 | 105.92 |
| C-2' | 83.82 | 77.52 | 81.16 | 88.78 | 87.04 | 87.33 |
| C-3' | 80.05 | 78.28 | 81.44 | 81.16 | 81.40 | 81.41 |
| C-4' | 75.15 | 72.98 | 74.59 | 77.89 | 77.74 | 77.21 |
| C-5' | 47.31 | 69.21 | 71.01 | 46.92 | 48.87 | 41.36 |
| C-6' | — | 50.09 | 49.74 | — | — | — |

Footnotes for Table 2

[a]Others: 136.76, 136.01 and 135.83(3×C$_{ipso}$, Ar), 128.82-127.98(15C, Ar), 73.56, 72.23 and 71.93(3×CH$_2$Ar), 112.55(C(CH$_3$)$_2$), 26.85 and 26.04(C(CH$_3$)$_2$).
[b]Others: 138.61, 138.55, 137.25, 136.86, 136.22 and 135.83(6×C$_{ipso}$, Ar), 128.87-127.15 (30C, Ar), 75.37, 73.51, 72.34, 71.68, 71.59 and 71.36(6×CH$_2$Ar).
[c]Others: 138.65, 138.30, 137.03, 136.70, 136.15 and 135.92(6×C$_{ipso}$, Ar), 129.04-127.36 (30C, Ar), 75.59, 75.49, 73.63, 72.55, 72.21 and 72.06(6×CH$_2$Ar).
[d]Others: 137.47, 136.75, 136.07 and 135.82(4×C$_{ipso}$, Ar), 128.84-27.72(20C, Ar), 73.49, 72.39, 72.11 and 71.75(4×CH$_2$Ar), 55.13(OCH$_3$).
[e]Others: 137.57, 137.42, 136.73, 136.04, and 135.88(5×C$_{ipso}$, Ar), 128.84-127.59(25C, Ar), 75.50, 72.37, 72.16, 71.78 and 69.54(5×CH$_2$Ar).
[f]Others: 137.54, 137.48, 136.56, 136.12, and 136.04(5×C$_{ipso}$, Ar), 128.80-127.64(25C, Ar), 73.54, 72.40(2C), 71.93 and 69.77(5×CH$_2$Ar).

TABLE 3

$^1$H NMR Data for Compounds 98-105

| Compound | 98α[a] | 98β[a] | 99α[b] | 99β[b] | 100α[a] | 100β[a] | 101α[a] | 101β[a] |
|---|---|---|---|---|---|---|---|---|
| H-1a | 3.95(m) | 3.94(m) | 3.87(m) | 3.87(m) | 3.85(m) | 3.85(m) | 3.92(m) | 3.92(m) |
| $(J_{1a,1b}, J_{1a,2})$ | (n.d., 4.0) | (n.d., 4.0) | (n.d., 3.9) | (n.d., 3.9) | (n.d., n.d.) | (n.d., n.d.) | (n.d., 3.5) | (n.d., 3.5) |
| H-1b | 3.95(m) | 3.94(m) | 3.87(m) | 3.87(m) | 3.85(m) | 3.85(m) | 3.92(m) | 3.92(m) |
| $(J_{1b,2})$ | (4.0) | (4.0) | (3.9) | (3.9) | (n.d.) | (n.d.) | (3.5) | (3.5) |
| H-2 | 4.76(ddd) | 4.76(ddd) | 4.73(ddd) | 4.73(ddd) | 4.74(m) | 4.74(m) | 4.77(ddd) | 4.47(ddd) |
| $(J_{2,3})$ | (4.0) | (4.0) | (3.9) | (3.7) | (3.1) | (3.1) | (3.5) | (3.5) |
| H-3 | 4.44(dd) | 4.44(dd) | 4.44(dd) | 4.44(dd) | 4.47(dd) | 4.47(dd) | 4.46(dd) | 4.45(dd) |
| $(J_{3,4})$ | (2.8) | (2.8) | (3.7) | (3.7) | (3.1) | (3.1) | (2.8) | (2.9) |
| H-4 | 4.13(m) | 4.13(m) | 4.06(m) | 4.08(dd) | 4.12(m) | 4.12(m) | 4.14(ddd) | 4.11(ddd) |
| $(J_{4,5a})$ | (4.9) | (5.0) | (5.0) | (5.0) | (n.d.) | (n.d.) | (n.d.) | (n.d.) |
| H-5a | 4.14(dd) | 4.12(dd) | 4.11(dd) | 4.13(dd) | 4.10(m) | 4.10(m) | 4.12(m) | 4.12(m) |
| $(J_{5a,5b})$ | (n.d.) | (13.7) | (11.8) | (12.2) | (n.d.) | (n.d.) | (n.d.) | (n.d.) |
| H-5b | 3.97(dd) | 3.95(dd) | 3.95(dd) | 3.96(dd) | 3.96(m) | 3.96(m) | 3.93(m) | 3.93(m) |
| $(J_{4,5b})$ | (n.d.) | (n.d.) | (n.d.) | (n.d.) | (n.d.) | (n.d.) | (n.d.) | (n.d.) |
| H-1' | 5.53(d) | 5.3(d) | 5.32(d) | 4.65(d) | 5.28(d) | 4.76(d) | 5.41(d) | 5.44(d) |
| $(J_{1',2'})$ | (4.1) | (1.2) | (3.9) | (7.9) | (3.8) | (8.0) | (1.0) | (4.4) |
| H-2' | 4.41(dd) | 4.38(dd) | 3.83(dd) | 3.52(dd) | 3.66(dd) | 3.37(dd) | 4.33(dd) | 4.34(dd) |
| $(J_{2',3'})$ | (3.8) | 1.8) | (10.4) | (10.1) | (9.9) | (9.6) | (2.3) | (6.0) |
| H-3' | 4.91(dd) | 4.83(dd) | 4.02(dd) | 3.81(dd) | 3.88(dd) | 3.71(dd) | 4.58(dd) | 4.69(dd) |
| $(J_{3',4'})$ | (5.3) | (5.1) | (3.3) | (3.3) | (9.1) | (9.0) | (3.5) | (4.9) |
| H-4' | 4.88(ddd) | 4.86(ddd) | 4.74(d) | 4.68(dd) | 4.22(dd) | 4.23(dd) | 4.76(ddd) | 4.53(ddd) |
| $(J_{4',5'a})$ | (3.9) | (3.8) | (<1) | (0.9) | (9.8) | (9.5) | (n.d.) | (2.9) |
| H-5'a | 3.98(dd) | 3.999(dd) | — | — | — | — | 4.12(dd) | 4.09(dd) |
| $(J_{5'a,5'b})$ | (13.8) | (13.7) | | | | | (n.d.) | (n.d) |
| H-5'b | 3.86(dd) | 3.93(dd) | — | — | — | — | 3.92(dd) | 3.96(dd) |
| $(J_{4',5'b})$ | (7.1) | (7.1) | | | | | (n.d.) | (10.0) |
| H-5' | — | — | 4.67(m) | 4.30(ddd) | 4.44(ddd) | 4.12(ddd) | — | — |
| $(J_{5',6'a})$ | | | (n.d.) | (7.6.) | (3.2) | (n.d.) | | |
| H-6'a | — | — | 3.95(dd) | 3.97(dd) | 4.11(dd) | 4.08(dd) | — | — |
| $(J_{6'a,6'b})$ | | | (n.d.) | (12.2.) | (10.0) | (n.d.) | | |
| H-5'b | — | — | 3.92(dd) | 3.94(dd) | 3.95(dd) | 3.88(dd) | — | — |
| $(J_{5',6'b})$ | | | (n.d.) | (4.0.) | (5.8) | (n.d.) | | |

Footnotes for Table 3
n.d. not determined,
[a]Temperature 308 K, $D_2O$,
[b]Temperature 313 K, D2O

TABLE 4

$^{13}$C NMR Data for Compounds 98-105

| Compound | 98α[a] | 98β[a] | 99α[b] | 99β[b] | 100α[a] | 100β[a] | 101α[a] | 101β[a] |
|---|---|---|---|---|---|---|---|---|
| C-1 | 48.41[e] | 48.29[e] | 49.27 | 49.27 | 48.38[j] | 48.29[j] | 48.22[n] | 48.17[n] |
| C-2 | 77.48 | 77.48 | 78.35[i] | 78.29[i] | 77.33[n] | 77.30[n] | 77.56 | 74.50 |
| C-3 | 78.29[f] | 78.17[f] | 79.26 | 79.06 | 78.54[k] | 78.45[k] | 78.17 | 78.32 |
| C-4 | 71.23[g] | 70.68[g] | 71.43 | 71.26 | 70.95[l] | 70.66[l] | 70.61 | 70.87 |
| C-5 | 59.59 | 59.58 | 60.62 | 60.62 | 59.65[m] | 59.52[m] | 59.67 | 59.67 |
| C-1' | 96.99 | 103.24 | 94.07 | 98.17 | 92.53 | 96.73 | 96.96 | 105.52 |
| C-2' | 74.97 | 79.54 | 69.35 | 72.85 | 71.59 | 74.22 | 79.90 | 75.18 |
| C-3' | 82.75 | 82.07 | 69.17 | 72.85 | 71.15 | 74.04 | 84.73 | 84.25 |
| C-4' | 73.35 | 76.10 | 79.63 | 78.65 | 78.37 | 78.22 | 78.60 | 76.46 |
| C-5' | 47.03[h] | 46.71[h] | 66.88 | 60.91 | 66.62 | 70.58[l] | 48.17[n] | 50.12 |
| C-6' | — | — | 48.73 | 48.30 | 47.77 | 48.25[j] | — | — |

Footnotes for Table 4
[a]Temperature 308 K, $D_2O$,
[b]Temperature 313 K, $D_2O$,
[efghijklmn]Assignments may be interchanged for resonances with the same superscript letter.

TABLE 5

$^1$H NMR Data for Compounds 1 and 94-97

| Compound | 1 | 94[a] | 95[b] | 96[c] | 97[c] |
|---|---|---|---|---|---|
| H-1a | 3.90(d) | 3.94(dd) | 3.92(d) | 3.89(d) | 3.89(d) |
| $(J_{1a,1b}, J_{1a,2})$ | (n.d., 3.8) | (13.2, 3.4) | (n.d., 3.6) | (n.d., 3.9) | (n.d., 3.8) |
| H-1b | 3.90(d) | 3.92(dd) | 3.92(d) | 3.89(d) | 3.89(d) |
| $(J_{1b,2})$ | (3.8) | (4.0) | (3.6) | (3.9) | (3.8) |
| H-2 | 4.74(ddd) | 4.79(ddd) | 4.78(dt) | 4.75(td) | 4.75(td) |
| $(J_{2,3})$ | (3.5) | (3.0) | (3.6) | (3.7) | (3.7) |
| H-3 | 4.46(dd) | 4.48(dd) | 4.47(dd) | 4.46(dd) | 4.47(dd) |
| $(J_{3,4})$ | (2.9) | (2.8) | (2.9) | (2.7) | (2.6) |
| H-4 | 4.10(ddd) | 4.11(br t) | 4.11(ddd) | 4.09(ddd) | 4.11(ddd) |
| $(J_{4,5a})$ | (4.8) | (4.8) | (4.8) | (5.0) | (5.0) |
| H-5a | 4.13(dd) | 4.17(dd) | 4.16(dd) | 4.12(dd) | 4.13(dd) |
| $(J_{5a,5b})$ | (11.5) | (12.2) | (11.2) | (11.5) | (11.7) |

TABLE 5-continued $^1$H NMR Data for Compounds 1 and 94-97

| Compound | 1 | 94$^a$ | 95$^b$ | 96$^c$ | 97$^c$ |
|---|---|---|---|---|---|
| H-5b<br>($J_{4,5b}$) | 3.96(dd)<br>7.9 | 3.97(dd)<br>(9.0) | 3.91(dd)<br>(8.1) | 3.96(dd)<br>(7.9) | 3.97(dd)<br>(7.9) |
| H-1a'<br>($J_{1'a,1'b}$, $J_{1'a,2'}$) | 4.10(dd)<br>(13.4, 3.2) | 3.98(dd)<br>(13.3, 9.3) | 3.99(dd)<br>(13.3, 9.8) | 4.06(dd)<br>(13.4, 3.1) | 4.08(dd)<br>(13.5, 3.2) |
| H-1'b<br>($J_{1'b,2'}$) | 3.84(ddd)<br>(8.3) | 3.94(dd)<br>(3.9) | 3.92(dd)<br>(3.6) | 3.89(dd)<br>(7.1) | 3.90(dd)<br>(7.3) |
| H-2'<br>($J_{2',3'}$) | 4.42(ddd)<br>(7.5) | 4.59(ddd)<br>(3.9) | 4.63(ddd)<br>(1.3) | 4.47(ddd)<br>(7.3) | 4.46(ddd)<br>(7.8) |
| H-3'<br>($J_{3',4'a}$) | 4.37(dd)<br>(3.2) | 4.47(dd)<br>(3.3) | 4.45(dd)<br>(9.2) | 4.46(dd)<br>(1.7) | 4.42(dd)<br>(7.4) |
| H-4'<br>($J_{4',5a'}$) | 3.97(dd) | 4.13(ddd)<br>(4.8) | 3.98(dd)<br>(1.0) | 3.95(dd)<br>(6.1) | 4.05(ddd)<br>(5.3) |
| H-4'b<br>($J_{4'a,4'b}$, $J_{3',4'b}$) | 3.87(dd)<br>(12.7, 3.1) | — | — | — | — |
| H-5'a<br>($J_{5'a,5'b}$) | — | 3.72(dd)<br>(11.8) | — | — | 3.75(dd)<br>(10.7) |
| H-5'b<br>($J_{4',5'b}$) | — | 3.77(dd)<br>(7.0) | — | — | 3.70(dd)<br>(7.6) |
| H-5'<br>($J_{5',6'a}$) | — | — | 4.03(t)<br>(6.6) | 3.92(ddd)<br>(3.5) | — |
| H-6'a<br>($J_{6'a,6'b}$) | — | — | 3.71(d)<br>(n.d.) | 3.77(dd)<br>(12.0) | — |
| H-6'b<br>($J_{5',6'b}$) | — | — | 3.71(d)<br>(6.6) | 3.67(dd)<br>(6.0) | — |

Footnotes for Table 5
n.d. not determined
$^a$Temperature 305 K, D$_2$O,
$^b$Temperature 318 K, D2O,
$^c$Temperature 308 K, D2O

TABLE 6

$^{13}$C NMR Data for Compounds 1 and 94-97

| Compound | 1 | 94$^a$ | 95$^b$ | 96$^c$ | 97$^c$ |
|---|---|---|---|---|---|
| C-1 | 48.30 | 48.33 | 48.49 | 48.36 | 48.33 |
| C-2 | 77.30 | 77.54 | 77.58 | 77.36 | 77.35 |
| C-3 | 78.14 | 78.25 | 78.32 | 78.37 | 78.40 |
| C-4 | 70.44 | 70.36 | 70.40 | 70.46 | 70.48 |
| C-5 | 59.57 | 59.77 | 59.85 | 59.72 | 59.72 |
| C-1' | 50.17 | 49.82 | 51.15 | 50.70 | 50.91 |
| C-2' | 66.19 | 67.04 | 66.58 | 67.30 | 66.92 |
| C-3' | 80.48 | 79.30 | 78.89 | 80.30 | 79.48 |
| C-4' | 60.09 | 70.57 | 769.36 | 69.57 | 70.36 |
| C-5' | — | 62.84 | 70.12 | 72.00 | 63.24 |
| C-6' | — | — | 63.40 | 62.90 | — |

Footnotes for Table 6
$^a$Temperature 305 K, D$_2$O,
$^b$Temperature 318 K, D2O,
$^c$Temperature 308 K, D2O

5.2.9 Example 9

Synthesis of Chain-Extended Homologues of Salacinol from D-Mannose (Schemes 26 to 31)

General. Optical rotations were measured at 23° C. $^1$H and $^{13}$C NMR spectra were recorded at 500 and 125 MHz respectively. All assignments were confirmed with the aid of two-dimensional $^1$H, $^1$H(COSYDFTP) or $^1$H, $^{13}$C (INVBTP) experiments using standard Bruker pulse programs. Column chromatography was performed with Merck Silica gel 60 (230-400 mesh). MALDI mass spectra were obtained on a PerSeptive Biosystems, Voyager DE time-of-flight spectrometer for samples dispersed in a 2,5-dihydroxybenzoic acid matrix. High resolution mass spectra were obtained by the electrospray ionization (ESI) technique, using a ZabSpec oaTOF mass spectrometer at 10000 RP.

2,3,5,6-Di-O-isopropylidene-1,4-di-O-methanesulfonyl-D-mannitol (137)

The 2,3,5,6-di-O-isopropylidene-D-mannose (135) was prepared by the literature method.[95] To a solution of 135 (20 g, 85 mmol) in MeOH (200 mL), NaBH$_4$ was added portionwise at 0° C. The progress of the reaction was followed by TLC analysis of aliquots (developing solvent Hexane:EtOAc, 1:1). When starting material 135 had been essentially consumed, the solvent was evaporated under reduced pressure. The residue was redissolved in EtOAc (150 mL), washed with saturated NH$_4$Cl solution (200 mL), brine (50 mL), and dried over Na$_2$SO$_4$. After evaporating the solvent, the crude diol (136) was used without further purification. The diol 136 was dissolved in CH$_2$Cl$_2$ (50 mL), and then added dropwise to a mixture of pyridine (100 mL) and methanesulfonyl chloride (26 mL, 0.34 mol) cooled to 0° C. The reaction mixture was stirred at 0° C. for 30 min, then allowed to raise to room temperature for 6 h. When TLC analysis of aliquots (developing solvent Hexane:EtOAc, 1:1) showed total consumption of the starting material, the reaction mixture was poured into ice water, extracted with CH$_2$Cl$_2$ (3×100 mL), washed with brine (50 mL), and dried over Na$_2$SO$_4$. Purification by column chromatography (Hexane:EtOAc, 2:1) yielded compound 137 as a colorless syrup (25 g, 72%). $[\alpha]^{22}{}_D$ +18.° (c 0.5, CH$_2$Cl$_2$); $^1$H NMR ((CD$_3$)$_2$O) δ: 4.86 (1H, dd, $J_{3,4}$=6.8, $J_{4,5}$=6.5, H-4), 4.55-4.50 (3H, m, H-2, H-3, H-1b), 4.47 (1H, dd, $J_{1a,1b}$=11.1, $J_{1a,2}$=7.6, H-1a), 4.29 (1H, ddd, $J_{4,5}$=6.5, H-5), 4.16 (1H, dd, $J_{5,6b}$=6.4, $J_{6a,6b}$=8.5, H-6b), 3.99 (1H, dd, $J_{5,6}$a=7.5, $J_{6a,6b}$=8.5, H-6a), 3.22 and 3.16 (6H, 2 s, 2 OSO$_2$CH$_3$), 1.53, 1.43, 1.38, and 1.33 (12H, 4 s, 4 CH$_3$). $^{13}$C NMR ((CD$_3$)$_2$O) δ: 109.97, 109.44 ((CH$_3$)$_2$C(OR)$_2$), 78.72 (C-4), 76.79 (C-3), 75.11 (C-5), 75.02 (C-2), 68.92 (C-1), 66.43 (C-6), 38.93, 36.75 (2 SO$_2$CH$_3$), 26.89, 25.68, 25.34, and 24.82 (4 CH$_3$). Anal. Calcd for C$_{14}$H$_{26}$O$_{10}$S$_2$: C, 40.18; H, 6.26. Found: C, 40.45; H, 6.14.

2,3,4,6-Di-O-isopropylidene-1,5-di-O-methanesulfonyl-D-mannitol (140)

The 2,3,4,6-di-O-isopropylidene-D-mannose (138) was prepared by the literature method.[96] To a solution of 138 (20 g, 85 mmol) in MeOH (200 mL), NaBH$_4$ was added portionwise at 0° C. The progress of the reaction was followed by TLC analysis of aliquots (developing solvent Hexane:EtOAc, 1:1). When starting material 135 had been essentially consumed, the solvent was evaporated under reduced pressure. The residue was redissolved in EtOAc (150 mL), washed with saturated NH$_4$Cl solution (200 mL), brine (50 mL), and dried over Na$_2$SO$_4$. After evaporating the solvent, the crude diol (139) was used without further purification. The diol 139 was dissolved in CH$_2$Cl$_2$ (50 mL), and then added dropwise to a mixture of pyridine (100 mL) and methanesulfonyl chloride (26 mL, 0.34 mol) cooled to 0° C. The reaction mixture was stirred at 0° C. for 30 min, then allowed to raise to room temperature for 6 h. When TLC analysis of aliquots (developing solvent Hexane:EtOAc, 1:1) showed total consumption of the starting material, the reaction mixture was poured into ice water, extracted with CH$_2$Cl$_2$ (3×100 mL), washed with brine (50 mL), and dried over Na$_2$SO$_4$. Purification by column chromatography (Hexane:EtOAc, 2:1) yielded compound 140 as a colorless syrup (24 g, 69%). $[\alpha]^{22}{}_D$+2.4 (c 0.5, CH$_2$Cl$_2$); $^1$H NMR (CDCl$_3$) δ: 4.82 (1H, ddd, $J_{5,6}$a=7.3, $J_{5,6b}$=5.1, $J_{4,5}$=8.8, H-5), 4.54 (1H, ddd, $J_{1a,2}$=4.1, $J_{1b,2}$=7.5, $J_{2,3}$=6.3, H-2), 4.50 (1H, dd, $J_{1a,1b}$=10.3, $J_{1b,2}$=7.5, H-1b), 4.40 (1H, dd, $J_{3,4}$=1.1, H-3), 4.38 (1H, dd, H-1a), 4.14 (1H, dd, $J_{6a,6b}$=12.0, H-6b), 3.89 (1H, dd, H-6a), 3.82 (1H, dd, H-4), 3.09 and 3.08 (6H, 2 s, two OSO$_2$CH$_3$), 1.52, 1.49, 1.41, and 1.37 (12H, 4 s, 4 CH$_3$). $^{13}$C NMR (CDCl$_3$) δ: 110.55, 100.03 ((CH$_3$)$_2$C(OR)$_2$), 74.94 (C-2), 73.85 (C-3), 72.22 (C-5), 69.58 (C-4), 68.13 (C-1), 62.64 (C-6), 38.11, 38.04 (2 SO$_2$CH$_3$), 27.45, 26.83 25.82, and 20.37 (four CH$_3$).

Anal. Calcd for C$_{14}$H$_{26}$O$_{10}$S$_2$: C, 40.18; H, 6.26. Found: C, 39.99; H, 6.02.

2,3,5,6-Di-O-isopropylidene-1,4-dideoxy-1,4-epi-thio-D-talitol (129)

To a solution of the dimesylate 137 (4.0 g, 9.6 mmol) in DMF (80 mL), Na$_2$S.9H$_2$O (2.8 g, 11.5 mmol) was added and the reaction mixture was heated at 90° C. for 12 h. The reaction mixture was poured into water (100 mL), extracted with Et$_2$O (4×50 mL), washed with water (10×20 mL), and dried over Na$_2$SO$_4$. After evaporating the solvent, the crude product was purified by column chromatography (Hexane: EtOAc, 3:1) to give 129 as a colorless oil (2.2 g, 90%). $[\alpha]^{22}_D$ −47 (c 0.5, CH$_2$Cl$_2$); $^1$H NMR ((CD$_3$)$_2$O) δ: 4.93 (1H, ddd, $J_{2,3}$=5.7, $J_{1a,2}$=1.3, $J_{1b,2}$=5.1, H-2), 4.75 (1H, dd, $J_{3,4}$=1.6, $J_{2,3}$=5.7, H-3), 4.06 (1H, dd, $J_{6a,6b}$=7.7, $J_{5,6b}$=6.2, H-6b), 3.72 (1H, dd, $J_{5,6a}$=7.4, H-6a), 3.34 (1H, dd, H-4), 3.17 (1H, dd, $J_{1a,1b}$=12.2, H-1b), 2.74 (1H, dd, H-1a), 1.43, 1.38, 1.29, and 1.28 (12H, 4 s, 4 CH$_3$). $^{13}$C NMR ((CD$_3$)$_2$O) δ: 110.85, 109.27 ((CH$_3$)$_2$C(OR)$_2$), 87.33 (C-3), 84.09 (C-2), 78.25 (C-5), 68.03 (C-6), 56.34 (C-4), 38.47 (C-1), 26.45, 25.93, 25.38, and 24.24 (4 CH$_3$). Anal. Calcd for C$_{12}$H$_{20}$O$_4$S: C, 55.36; H, 7.74. Found: C, 55.62; H, 7.73.

2,3,5,6-Di-O-isopropylidene-1,4-dideoxy-1,4-epise-leno-D-talitol (130)

To a suspension of Se (1.6 g, 20.2 mmol) and 95% EtOH (100 mL), NaBH$_4$ was added portionwise until the black Se color disappeared. To this mixture a solution of the dimesylate 137 (6.0 g, 14.3 mmol) in THF (10 mL) was added and the reaction mixture was heated at 70° C. for 12 h. The solvent of the reaction mixture was evaporated under reduced pressure, redissolved in EtOAc, washed with water (20 mL), brine (20 mL), and dried over Na$_2$SO$_4$. After evaporating the solvent, the crude product was purified by column chromatography (Hexane:EtOAc, 3:1) to give 130 as a colorless oil (3.1 g, 71%).

$[\alpha]^{22}_D$ −4° (c 1, CH$_2$Cl$_2$); $^1$H NMR ((CD$_3$)$_2$O) δ: 4.97 (1H, ddd, $J_{2,3}$=5.7, $J_{1a,2}$=2.4, $J_{1b,2}$=5.5, H-2), 4.71 (1H, dd, $J_{3,4}$=2.9, $J_{2,3}$=5.7, H-3), 4.28 (1H, dd, $J_{5,6a}$=7.4, $J_{5,6b}$=6.1, H-5), 4.09 (1H, dd, $J_{6a,6b}$=8.1, H-6b), 3.69 (1H, dd, $J_{5,6a}$=7.4, H-6a), 3.61 (1H, dd, $J_{4,5}$=5.1, H-4), 3.23 (1H, dd, $J_{1a,1b}$=11.3, H-1b), 2.87 (1H, dd, H-1a), 1.43, 1.38, 1.29, and 1.27 (12H, 4 s, 4 CH$_3$). $^{13}$C NMR ((CD$_3$)$_2$O) δ: 110.59, 109.16 ((CH$_3$)$_2$C(OR)$_2$), 88.44 (C-3), 85.37 (C-2), 78.42 (C-5), 68.97 (C-6), 51.34 (C-4), 29.17 (C-1), 26.73, 26.06, 25.37, and 24.31 (4 CH$_3$). Anal. Calcd for C$_{12}$H$_{20}$O$_4$Se: C, 46.91; H, 6.56. Found: C, 46.71; H, 6.62.

2,3,4,6-Di-O-isopropylidene-1,5-dideoxy-1,5-epi-thio-L-gulitol (131)

To a solution of the dimesylate 140 (6.0 g, 14.3 mmol) in DMF (100 mL), Na$_2$S.9H$_2$O (4.1 g, 18.2 mmol) was added and the reaction mixture was heated at 100° C. for 12 h. The reaction mixture was poured into water (100 mL), extracted with Et$_2$O (4×50 mL), washed with water (10×20 mL), and dried over Na$_2$SO$_4$. After evaporating the solvent, the crude product was purified by column chromatography (Hexane: EtOAc, 3:1) to give 131 as a colorless oil (3.5 g, 93%). $[\alpha]^{22}_D$ −41 (c 0.5, CH$_2$Cl$_2$); $^1$H NMR ((CD$_3$)$_2$O) δ: 4.51 (1H, ddd, $J_{2,3}$=2.9, $J_{1b,2}$=4.2, H-2), 4.30-4.24 (2H, m, H-4, H-6b), 4.06 (1H, dd, $J_{3,4}$=6.2, $J_{5,6b}$=6.2, H-3), 3.63 (1H, dd, $J_{5,6}$a=1.9, $J_{6a,6b}$=12.5, H-6a), 2.95 (1H, dd, $J_{1a,1b}$=13.5, H-1b), 2.92 (1H, m, H-5), 2.57 (1H, dd, $J_{1b,2}$=7.2, H-1a), 1.45, 1.39, 1.32, and 1.25 (12H, 4 s, 4 CH$_3$). $^{13}$C NMR ((CD$_3$)$_2$O) δ: 112.52, 103.61 ((CH$_3$)$_2$C(OR)$_2$), 79.65 (C-3), 75.26 (C-4), 71.63 (C-2), 68.40 (C-6), 39.94 (C-5), 33.77 (C-1), 31.53, 29.55, 29.49 and 23.22 (4 CH$_3$). Anal. Calcd for C$_{12}$H$_{20}$O$_4$S: C, 55.36; H, 7.74. Found: C, 55.43; H, 7.70.

2,3,4,6-Di-O-isopropylidene-1,5-dideoxy-1,5-epise-leno-L-gulitol (132)

To a suspension of Se powder (1.6 g, 20.2 mmol) and 95% EtOH (100 mL), NaBH$_4$ was added portionwise until the black color of selenium disappeared. To this mixture a solution of the dimesylate 140 (6.0 g, 14.3 mmol) in THF (10 mL) was added and the reaction mixture was heated at 70° C. for 12 h. The solvent of the reaction mixture was evaporated under reduced pressure, redissolved in EtOAc, washed with water (20 mL), brine (20 mL), and dried over Na$_2$SO$_4$. After evaporating the solvent, the crude product was purified by column chromatography (Hexane:EtOAc, 3:1) to give 132 as a colorless oil (2.7 g, 62%). $[\alpha]^{22}_D$ −32 (c 0.5, CH$_2$Cl$_2$); $^1$H NMR ((CD$_3$)$_2$O) δ: 4.97 (1H, ddd, $J_{2,3}$=5.8, $J_{1a,2}$=2.4, $J_{1b,2}$=5.4, H-2), 4.71 (1H, dd, $J_{3,4}$=2.9, H-3), 4.28 (1H, ddd, $J_{4,5}$=5.1, $J_{5,6}$a=7.9, $J_{5,6b}$=6.1, H-5), 4.09 (1H, dd, $J_{6a,6b}$=8.0, H-6b), 3.69 (1H, dd, H-6a), 3.61 (1H, dd, H-4), 3.23 (1H, dd, $J_{1a,1b}$=11.4, H-1b), 2.87 (1H, dd, H-1a), 1.45, 1.39, 1.28, and 1.26 (12H, 4 s, 4 CH$_3$). $^{13}$C NMR ((CD$_3$)$_2$O) δ: 110.64, 109.13 ((CH$_3$)$_2$C(OR)$_2$), 88.46 (C-3), 85.42 (C-4), 78.46 (C-5), 68.93 (C-6), 51.34 (C-4), 26.71 (C-1), 26.06, 25.38, 25.23 and 24.43 (4 CH$_3$). Anal. Calcd for C$_{12}$H$_{20}$O$_4$Se: C, 46.91; H, 6.56. Found: C, 46.67; H, 6.28.

General Procedure for the Preparation of Sulfonium and Selenium Sulfates 141-144.

A mixture of the 1,4-thio-D-talitol 129 or 1,5-thio-L-gulitol 131, or 1,4-seleno-D-talitol 130 or 1,5-seleno-L-gulitol 132, and the cyclic sulfate 133 in HFIP (1,1,1,3,3,3-hexafluoroisopropanol) were placed in a reaction vessel and K$_2$CO$_3$ (20 mg) was added. The stirred reaction mixture was heated in a sealed tube at the indicated temperature for the indicated time, as given below. The progress of the reaction was followed by TLC analysis of aliquots (developing solvent EtOAc:MeOH, 10:1). When the limiting reagent had been essentially consumed, the mixture was cooled, then diluted with CH$_2$Cl$_2$ and evaporated to give a syrupy residue. Purification by column chromatography (EtOAc to EtOAc:MeOH, 10:1) gave the purified and sulfonium salts 141, 143 and selenonium salts 142, 144.

2,3,5,6-Di-O-isopropylidene-1,4-dideoxy-1,4-[(S)-[(2'R,3S,4'R,5'R)-2',4'-benzylidenedioxy-5',6'-isopropylidenedioxy-3'-(sulfooxy)hexyl]-episulfoniumylidene]-D-talitol Inner Salt (141)

Reaction of the 1,4-thio-D-talitol 129 (400 mg, 1.53 mmol) with the cyclic sulfate 133 (740 mg, 1.84 mmol) in HFIP (2.0 mL) for 12 h at 70-75° C. gave compound 141 as a colorless, amorphous solid (820 mg, 85% based on 129). $[\alpha]^{22}_D$ −4° (c 0.5, CH$_2$Cl$_2$); $^1$H NMR (CD$_2$Cl$_2$) δ: 7.48-7.30 (5H, m, Ar), 5.68 (1H, s, CHPh), 5.15 (1H, ddd, $J_{2,3}$=5.6, $J_{1a,2}$=1.9, $J_{1b,2}$=5.6, H-2), 4.98 (1H, dd, H-3), 4.55-4.51(2H, m, H-4, H-2'), 4.46 (1H, ddd, $J_{4,5}$=4.1, $J_{5',6'a}$=6.3, $J_{5',6b'}$=6.3, H-5'), 4.40 (1H, dd, $J_{1'a,1'b}$=13.4, $J_{1'b,2}$=5.6, H-1'b), 4.18 (2H, dd, H-6'a, H-6'b), 4.16-4.04 (4H, m, H-1'a, H-3', H-4', H-5), 3.76 (2H, dd, H-1a, H-1b), 3.35 (1H, dd, $J_{6a,6b}$=9.5, $J_{5,6b}$=7.6, H-6b), 3.16 (1H, dd, $J_{5,6}$a=6.4, H-6a), 1.52, 1.33, 1.31, 1.28, 1.26, and 1.16 (18H, 6 s, 6 CH$_3$). $^{13}$C NMR (CD$_2$Cl$_2$) δ: 137.28, 129.65, 128.63, and 126.37 (4 C$_{Ar}$), 112.85, 111.37, and 108.64 (three (CH$_3$)$_2$C(OR)$_2$), 100.87 (CHPh), 89.77 (C-3), 84.24 (C-2), 79.32 (C-3'), 75.48 (C-5'), 75.33 (C-5), 74.36 (C-4), 70.47 (C-2'), 67.92 (C-4'), 67.05 (C-6), 65.18 (C-6'), 50.12 (C-1), 44.42 (C-1') 26.56, 26.15, 25.62, 25.57, 25.03 and 22.86 (6 CH$_3$).
Anal. Calcd for C$_{28}$H$_{40}$O$_{12}$S$_2$: C, 53.15; H, 6.37. Found: C, 52.92; H, 6.17.

2,3,5,6-Di-O-isopropylidene-1,4-dideoxy-1,4-[(S)-[(2'R,3'S,4'R,5'R)-2',4'-benzylidenedioxy-5' 6'-isopropylidenedioxy-3'-(sulfooxy)hexyl]-episelenoniumylidene]-D-talitol Inner Salt (142)

Reaction of the protected 1,4-seleno-D-talitol 130 (500 mg, 1.63 mmol) with the cyclic sulfate 133 (780 mg, 1.95 mmol) in HFIP (2.0 mL) for 12 h at 60-65° C. gave compound 142 and a minor product (<10%) as a colorless, amorphous solid (810 mg, 73% based on 130). The major product 142: $[α]^{22}_D$ –46 (c 0.5, CH$_2$Cl$_2$); $^1$H NMR ((CD$_3$)$_2$O) δ: 7.62-7.38 (5H, m, Ar), 5.92 (1H, s, CHPh), 5.47 (1H, ddd, $J_{2,3}$=5.6, $J_{1'a,2}$=1.3, $J_{1'b,2}$=5.9, H-2), 5.35 (1H, dd, H-3), 4.92 (1H, ddd, H-2'), 4.60 (1H, dd, $J_{1'b,2'}$=6.4, $J_{1'a,1'b}$=12.3, H-1'b), 4.57 (1H, m, H-4'), 4.55 (1H, ddd, $J_{5,6b}$=6.9, $J_{5,6a}$=6.6, $J_{4,5}$=1.5, H-5), 4.48 (1H, ddd, $J_{5',6'b}$=6.7, $J_{5',6'a}$=7.4, $J_{4',5}$=2.5, H-5'), 4.42-4.34 (3H, m, H-3', H-6'b, H-4), 4.24 (1H, dd, $J_{6a,6b}$=8.1, H-6'a), 4.09 (1H, dd, $J_{1'a,2}$=1.5, H-1'a), 3.89 (1H, dd, $J_{1a,1b}$=14.1, H-1b), 3.84 (1H, dd, H-1a), 3.70 (1H, dd, $J_{6a,6b}$=9.4, H-6b), 3.34 (1H, dd, H-6a),1.59, 1.38, 1.35, 1.30, 1.29 and 1.24 (18H, 6 s, 6 CH$_3$). $^{13}$C NMR ((CD$_3$)$_2$O) δ: 138.21, 129.24, 128.42, and 126.48 (4 C$_{Ar}$), 111.32, 107.67, and 100.47 (three (CH$_3$)$_2$C(OR)$_2$), 100.41 (CHPh), 91.54 (C-3), 85.82 (C-2), 78.92 (C-3'), 76.67 (C-5'), 75.54 (C-5), 74.18 (C-2'), 70.82 (C-4'), 67.97 (C-6), 67.45 (C-4), 64.74 (C-6'), 46.24 (C-1), 41.78 (C-1') 26.02, 25.85, 25.67, 25.44, 24.02 and 22.75 (6 CH$_3$). Anal. Calcd for C$_{28}$H$_{40}$O$_2$SSe: C, 49.48; H, 5.93. Found: C, 49.16; H, 6.09.

2,3,4,6-Di-O-isopropylidene-1,5-dideoxy-1,5-[(S)-[(2'R,3S,4'R,5'R)-2',4'-benzylidenedioxy-5' 6'-isopropylidenedioxy-3'-(sulfooxy)hexyl]-episulfoniumylidene]-L-gulitol Inner Salt (143)

Reaction of the protected 1,5-thio-L-gulitol 131 (500 mg, 1.92 mmol) with the cyclic sulfate 143 (860 mg, 2.30 mmol) in HFIP (2.0 mL) for 12 h at 90-95° C. gave compound 143 as a colorless, amorphous solid (1.12 g, 90% based on 131). $[α]^{22}_D$ –52 (c 0.5, CH$_2$Cl$_2$); $^1$H NMR ((CD$_3$)$_2$O) δ: 7.62-7.38 (5H, m, Ar), 5.88 (1H, s, CHPh), 4.94 (1H, ddd, $J_{2,3}$=3.0, $J_{1a,2}$=2.4, $J_{1b,2}$=3.0, H-2), 4.85 (1H, ddd, $J_{2',3}$=1.8, $J_{1'a,2'}$=6.1, $J_{1'b,2'}$=3.1, H-2'), 4.60(1H, dd, $J_{3,4}$=3.0, H-4), 4.55 (1H, ddd, $J_{4,5}$=2.0, $J_{5',6'a}$=7.7, $J_{5',6'b}$=6.7, H-5'), 4.52 (1H, dd, $J_{3',4}$=1.9, H-3'), 4.44 (1H, dd, $J_{1'a,1'b}$=14.2, H-1'b), 4.43 (1H, m, H-4'), 4.39 (1H, dd, $J_{6'a,6'b}$=8.5, H-6'b), 4.35 (1H, dd, H-3), 4.33 (1H, dd, H-1'a), 4.26 (1H, dd, H-6'a), 4.18 (1H, dd, $J_{1a,1b}$=13.6, H-1b), 4.14 (1H, m, H-6b), 3.93 (1H, dd, $J_{6a,6b}$=13.3, $J_{5,6}$a=1.6, H-6a), 3.80 (1H, dd, H-1a), 3.68 (1H, m, H-5), 1.62, 1.48, 1.40, 1.36, 1.35, and 1.29 (18H, 6 s, 6 CH$_3$). $^{13}$C NMR ((CD$_3$)$_2$O) δ: 138.12, 129.26, 128.46, and 126.52 (4 C$_{Ar}$), 109.73, 107.42, and 100.73 (three (CH$_3$)$_2$C(OR)$_2$), 100.46 (CHPh), 79.03 (C-4'), 76.84 (C-5') 74.24 (C-2'), 71.66 (C-3), 69.95 (C-3'), 67.16 (C-4), 65.71 (C-4), 64.66 (C-6'), 61.52 (C-6), 49.18 (C-1'), 48.93 (C-5), 33.77 (C-1), 28.73, 25.92, 25.74, 25.67, 22.72 and 18.23 (6 CH$_3$).
Anal. Calcd for C$_{28}$H$_{40}$O$_{12}$S$_2$: C, 53.15; H, 6.37. Found: C, 52.95; H, 6.14.

2,3,4,6-Di-O-isopropylidene-1,5-dideoxy-1,5-[(S)-[(2'R,3S,4'R,5'R)-2',4'-benzylidenedioxy-5' 6'-isopropylidenedioxy-3'-(sulfooxy)hexyl]-episelenoniumylidene]-L-gulitol Inner Salt (144)

Reaction of the protected 1,5-seleno-L-gulitol 132 (500 mg, 1.63 mmol) with the cyclic sulfate 133 (780 mg, 1.95 mmol) in HFIP (2.0 mL) for 12 h at 80-85° C. gave compound 144 as a colorless, amorphous solid (850 mg, 77% based on 132). $[α]^{22}_D$ –31 (c 0.5, CH$_2$Cl$_2$); $^1$H NMR ((CD$_3$)$_2$O) δ: 7.62-7.40 (5H, m, Ar), 5.92 (1H, s, CHPh), 5.46 (1H, ddd, $J_{2,3}$=5.6, $J_{1a,2'}$=1.2, $J_{1b,2}$=5.9, H-2), 5.37 (1H, dd, H-3), 4.85 (1H, m, H-2'), 4.62(1H, dd, $J_{1'b,2'}$=6.5, $J_{1'a,1'b}$=11.3, H-1'b), 4.60 (1H, m, H-3'), 4.55 (1H, ddd, $J_{4,5}$=1.3, $J_{5,6}$a=6.6, $J_{5,6b}$=6.8, H-5), 4.47 (1H, ddd, $J_{4,5'}$=2.4, $J_{5',6'a}$=7.4, $J_{5',6'b}$=6.6, H-5'), 4.39 (2H, m, H-4, H-4')), 4.35 (1H, dd, $J_{6'a,6'b}$=8.5, H-6'b), 4.24 (1H, dd, H-6'a), 4.09 (1H, dd, $J_{1'a,2}$=1.4, H-1'a), 3.90 (1H, dd, $J_{1a,1b}$=14.2, H-1b), 3.84 (1H, dd, H-1a), 3.70 (1H, dd, $J_{6a,6b}$=9.4, H-6b), 3.32 (1H, dd, H-6a), 1.59, 1.38, 1.35, 1.31, 1.30, and 1.24 (18H, 6 s, 6 CH$_3$). $^{13}$C NMR ((CD$_3$)$_2$O) δ: 138.23, 129.22, 128.47, and 126.45 (4 C$_{Ar}$), 110.43, 110.75, and 107.67 (three (CH$_3$)$_2$C(OR)$_2$), 100.45 (CHPh), 91.58 (C-3), 85.89 (C-2), 78.93 (C-4'), 76.55 (C-5'), 75.42 (C-5), 74.16 (C-2'), 70.95 (C-3'), 68.03 (C-6), 67.56 (C-4), 64.86 (C-6'), 46.23 (C-1), 41.60 (C-1'), 26.03, 25.85, 25.62, 25.34, 23.99 and 22.72 (6 CH$_3$). Anal. Calcd for C$_{28}$H$_4$O$_{12}$SSe: C, 49.48; H, 5.93. Found: C, 49.71; H, 6.10.
General Procedure for the Deprotection of the Coupling Products to Yield the Final Compounds 125-128.

The protected coupling products 141-144 were dissolved in CH$_2$Cl$_2$ (2 mL), TFA (10 mL) was then added, and the mixture was stirred for 6-8 h at room temperature. The progress of the reaction was followed by TLC analysis of aliquots (developing solvent EtOAc:MeOH:H$_2$O, 7:3:1). When the starting material had been consumed, the TFA and CH$_2$Cl$_2$ were removed under reduced pressure. The residue was rinsed with CH$_2$Cl$_2$ (4×2 mL) and the CH$_2$Cl$_2$ was decanted to remove the cleaved protecting groups. The remaining gum was dissolved in MeOH and purified by column chromatography (EtOAc and EtOAc:MeOH, 2:1) to give the purified compounds 125-128 as colorless, amorphous, and hygroscopic solids.

1,4-Dideoxy-1,4-[(S)-[(2'R,3'S,4'R,5R)-2',4',5',6'-tetrahydroxy-3'-(sulfooxy)hexyl]-episulfoniumylidene]-D-talitol Inner Salt (125)

To a solution of 141 (400 mg, 0.63 mmol) in CH$_2$Cl$_2$ (2 mL) was added TFA (10 mL) to yield the compound 125 as a colorless, amorphous, and hygroscopic solid (150 mg, 59%). $[α]^{22}_D$ –29 (c 0.1, H$_2$O); $^1$H NMR (D$_2$O) δ: 4.60 (1H, m, H-2), 4.56 (1H, dd, $J_{3,4}$=1.1, $J_{2,3}$=5.0, H-3'), 4.50 (1H, ddd, $J_{1'b,2'}$=10.5, $J_{1'a,2'}$=2.8, H-2'), 4.32 (1H, dd, $J_{2,3}$=9.6, $J_{3,4}$=2.8, H-3), 4.17 (1H, ddd, H-5), 4.00 (1H, dd, $J_{1'a,1'b}$=13.2, H-1'b), 3.92 (1H, dd, $J_{4,5}$=9.5, H-4), 3.91 (1H, dd, H-1'a), 3.80 (1H, dd, $J_{4',5}$=9.0, H-4'), 3.78 (1H, dd, $J_{6a,6b}$=12.2, $J_{5,6b}$=3.5, H-6b), 3.73 (1H, dd, $J_{5',6'b}$=2.7, $J_{6'a,6'b}$=11.8, H-6'b), 3.69 (1H, ddd, $J_{5',6'a}$=6.1, H-5'), 3.66 (1H, dd, $J_{5,6}$a=4.1, H-6a), 3.56 (1H, dd, $J_{1b,2}$=7.6, $J_{1a,1b}$=11.4, H-1b), 3.55 (1H, dd, $J_{1a,2}$=5.8, H-1a), 3.54 (1H, m, H-6'a). $^{13}$C NMR (D$_2$O) δ: 77.81 (C-3'), 76.26 (C-3), 72.93 (C-2), 70.52 (C-5'), 68.98

(C-4'), 67.91 (C-2'), 67.55 (C-5), 64.62 (C-6), 64.53 (C-4), 62.85 (C-6'), 49.41 (C-1'), 44.57 (C-1). HRMS. Calcd for $C_{12}H_{24}O_{12}S_2Na$ (M+Na): 447.0601; Found: 447.0604.

1,4-Dideoxy-1,4-[(S)-[(2'R,3S,4R,5M-2',4',5',6'-tetrahydroxy-3'-(sulfooxy)hexyl]-episelenoniumylidene]-D-talitol Inner Salt (126)

To a solution of 142 (400 mg, 0.59 mmol) in $CH_2Cl_2$ (2 mL) was added TFA (10 mL) to yield the compound 126 as a colorless, amorphous, and hygroscopic solid (132 mg, 47%). $[\alpha]^{22}_D$ −5° (c 0.1, $H_2O$); $^1H$ NMR ($D_2O$) δ: 4.74 (1H, m, H-2), 4.54 (1H, dd, $J_{3,4}$=1.1, $J_{2,3}$=5.0, H-3'), 4.47 (1H, ddd, H-2'), 4.22 (1H, dd, $J_{2,3}$=10.0, $J_{3,4}$=2.9, H-3), 4.14 (1H, m, H-5), 3.96 (1H, dd, $J_{1'b,2}$=10.3, H-1'b), 3.92 (1H, dd, $J_{1'a,2}$=3.7, $J_{1'a,1'b}$=12.3, H-1'a), 3.85 (1H, dd, $J_{4,5}$=1.9, H-4), 3.77 (1H, dd, $J_{5,6b}$=2.6, $J_{6a,6b}$=12.2, H-6b), 3.71 (1H, dd, $J_{6'a,6'b}$=11.8, $J_{5',6'b}$=2.4, H-6'b), 3.70-3.63 (2H, m, H-4', H-5'), 3.60 (1H, dd, $J_{5,6}$a=3.5, H-6a), 3.55 (1H, dd, $J_{5',6'a}$=9.1, H-6'a), 3.41 (1H, dd, $J_{1b,2}$=3.2, $J_{1a,1b}$=13.2, H-1b), 3.36 (1H, dd, H-1a). $^{13}C$ NMR ($D_2O$) δ: 78.44 (C-3'), 77.28 (C-3), 73.62 (C-2), 70.50 (C-5'), 69.13 (C-4'), 67.96 (C-2'), 67.22 (C-5), 65.06 (C-6), 63.69 (C-4), 62.73 (C-6'), 46.84 (C-1'), 40.99 (C-1). HRMS. Calcd for $C_{12}H_{24}O_{12}SSeNa$ (M+Na): 495.0046; Found: 495.0044.

1,5-Dideoxy-1,5-[(S)-[(2'R,3'S,4R,5R)-2',4',5',6'tetrahydroxy-3'-(sulfooxy)hexyl]-episulfoniumylidene]-L-gulitol Inner Salt (127)

To a solution of 143 (400 mg, 0.63 mmol) in $CH_2Cl_2$ (2 mL) was added TFA (10 mL) to yield the compound 127 as a colorless, amorphous, and hygroscopic solid (172 mg, 65%). $[\alpha]^{22}_D$ −54 (c 0.2, $H_2O$); $^1H$ NMR ($D_2O$) δ: 4.61 (1H, m, H-2), 4.57 (1H, dd, $J_{3',4}$=3.0, $J_{2,3}$=6.5, H-3'), 4.54 (1H, m, H-2'), 4.33 (1H, dd, $J_{2,3}$=5.5, $J_{3,4}$=2.4, H-3), 4.30 (1H, ddd, $J_{4,5}$=4.5, $J_{5,6b}$=6.3, H-5), 4.07 (1H, dd, $J_{1'b,2}$=3.3, $J_{1'a,1'b}$=10.8, H-1'b), 4.06-4.02 (2H, m, H-4', H-6'b), 3.98 (1H, dd, $J_{6'a,6'b}$=11.9, $J_{5',6}$a=7.4, H-6'a), 3.94 (1H, dd, $J_{3,4}$=2.4, $J_{4,5}$=4.5, H-4), 3.86-3.83 (1H, m, H-5), 3.73 (1H, dd, $J_{5,6b}$=2.6, $J_{6a,6b}$=11.8, H-6b), 3.69 (1H, dd, $J_{1'a,2}$=4.4, H-1'a), 3.58 (1H, dd, $J_{1b,2}$=5.5, $J_{1a,1b}$=11.4, H-1b), 3.56 (1H, dd, $J_{5,6}$a=5.8, H-6a), 3.46 (1H, dd, H-1a). $^{13}C$ NMR ($D_2O$) δ: 77.63 (C-2'), 70.53 (C-2), 69.57 (C-3), 69.04 (C-4), 68.84 (C-5'), 67.42 (C-3'), 63.55 (C-5), 62.73 (C-6), 59.60 (C-6'), 54.03 (C-4'), 45.56 (C-1'), 37.34 (C-1). HRMS. Calcd for $C_{12}H_{24}O_{12}S_2Na$ (M+Na): 447.0601; Found: 447.0601.

1,5-Dideoxy-1,5-[(S)-[(2R,3'S,4'R,5'R)-2',4' 5',6'-tetrahydroxy-3'-(sulfooxy)hexyl]-episelenoniumylidene]-L-gulitol Inner Salt (128)

To a solution of 144 (400 mg, 0.59 mmol) in $CH_2Cl_2$ (2 mL) was added TFA (10 mL) to yield the compound 128 as a colorless, amorphous, and hygroscopic solid (150 mg, 55%). $[\alpha]^{22}_D$ −68 (c 0.1, $H_2O$); $^1H$ NMR ($D_2O$) δ: 4.74 (1H, m, H-2), 4.55 (1H, dd, $J_{3',4}$=1.1, $J_{2',3}$=5.0, H-3'), 4.49 (1H, ddd, $J_{1'b,2}$=10.3, H-2'), 4.23 (1H, dd, $J_{2,3}$=3.1, $J_{3,4}$=10.2, H-3), 4.15 (1H, m, H-5), 3.98 (1H, dd, $J_{1'a,1'b}$=12.3, H-1'b), 3.94 (1H, dd, $J_{1'a,2}$=3.7, H-1'a), 3.86 (1H, dd, $J_{4,5}$=1.7, H-4), 3.81-3.75 (2H, m, H-4', H-6b), 3.73 (1H, dd, $J_{5',6'b}$=2.8, $J_{6'a,6'b}$=11.7, H-6'b), 3.69 (1H, ddd, H-5'), 3.61 (1H, dd, $J_{5,6}$a=3.3, $J_{6a,6b}$=8.7, H-6a), 3.55 (1H, dd, $J_{5',6'a}$=11.7, H-6'a), 3.41 (1H, dd, $J_{1b,2}$=3.2, $J_{1a,1b}$=13.4, H-1b), 3.37 (1H, dd, H-1a). $^{13}C$ NMR ($D_2O$) δ: 78.35 (C-3'), 77.22 (C-3), 73.54 (C-2), 70.54 (C-5'), 69.28 (C-4'), 67.92 (C-2'), 67.15 (C-5), 65.04 (C-6), 63.78 (C-4), 62.74 (C-6'), 46.63 (C-1'), 40.68 (C-1). HRMS. Calcd for $C_{12}H_{24}O_{12}SSeNa$ (M+Na): 495.0046; Found: 495.0045.

5.2.10 Example 10

Synthesis of Salacinol Analogues based on Selenoalditols and Thioalditols (Schemes 32 to 38)

General. Optical rotations were measured at 23° C. $^1H$ and $^{13}C$ NMR spectra were recorded at 500 and 125 MHz, respectively. All assignments were confirmed with the aid of two-dimensional $^1H$, $^1H$(COSYDFTP) or $^1H$, $^{13}C$ (INVBTP) experiments using standard Bruker pulse programs. Column chromatography was performed with Merck silica gel 60 (230-400 mesh). MALDI mass spectra were obtained on a PerSeptive Biosystems, Voyager DE time-of-flight spectrometer for samples dispersed in a 2,5-dihydroxybenzoic acid matrix. High resolution mass spectra were obtained by the electrospray ionization (ESI) technique, using a ZabSpec oaTOF mass spectrometer at 10000 RP.

2,3,5,6-di-O-Isopropylidene-1,4-di-O-methanesulfonyl-D-gulitol (162)

2,3,5,6-Di-O-isopropylidene-1,4-di-O-methanesulfonyl-D-gulitol (162) was prepared by the literature method[105] with slight variations. To a solution of commercially available D-gulonic-γ-lactone 159 (10.0 g, 56.1 mmol) in dry acetone (200 mL), 2,2-dimethoxypropane (40 mL, 0.32 mmol) was added at RT. To this solution p-toluenesulfonic acid (200 mg) was added as a catalyst. The progress of the reaction was followed by TLC analysis of aliquots (Hexane:EtOAc, 1:1). When the starting material 159 had been essentially consumed, the reaction was stopped by addition of triethylamine (1 mL) to the reaction mixture. The solvent was then evaporated under reduced pressure, and the residue was purified by column chromatography (Hexane:EtOAc, 1:1) to give compound 160 as a white solid (13.1 g, 90%). The NMR spectrum of compound 160 matched that of the published.[104] The lactone 160 (5.0 g, 19.3 mmol) was dissolved in THF (20 mL), and MeOH (50 mL) was then added. To this solution, $NaBH_4$ was added portionwise at 0° C. The progress of the reaction was followed by TLC analysis of aliquots (Hexane:EtOAc, 1:1). When the starting material 160 had been consumed, the solvent was evaporated under reduced pressure. The residue was redissolved in EtOAc (50 mL), washed with aqueous tartaric acid solution (2×10 mL), brine (50 mL), and dried over $Na_2SO_4$. Purification by column chromatography (Hexane:EtOAc, 2:1) yielded compound 161 as a colorless syrup (3.9 g, 77%). The NMR spectrum of compound 161 matched that of the published.[105] The diol 161 (5.0 g, 19.1 mmol) was dissolved in $CH_2Cl_2$ (50 mL), and the solution was added dropwise to a mixture of pyridine (100 mL) and methanesulfonyl chloride (6 mL, 77.5 mmol), cooled to 0° C. The reaction mixture was stirred at 0° C. for 30 min, and then allowed to warm to room temperature for 6 h. When TLC analysis of aliquots (Hexane:EtOAc, 1:1) showed total consumption of the starting material, the reaction mixture was poured into ice water, extracted with $CH_2Cl_2$ (3×100 mL), washed with brine (50 mL), and dried over $Na_2SO_4$. Purification by column chromatography (Hexane:EtOAc, 2:1) yielded compound 162 as a colorless syrup (5.9 g, 75%). $[\alpha]^{22}_D$ −46 (c 1, $CH_2Cl_2$); $^1H$ NMR (($CD_3$)$_2$O) δ: 4.87 (dd, 1H, $J_{3,4}$=5.8, $J_{4,5}$=4.7, H-4), 4.56 (ddd, 1H, $J_{1b,2}$=6.0, $J_{1a,1b}$=12.0, H-1b), 4.56-4.48 (m, 2H, H-2, H-3, H-1a), 4.48 (dd, 1H, H-1a), 4.46 (ddd, 1H, H-5), 4.14 (dd, 1H, $J_{5,6b}$=6.8, $J_{6a,6b}$=8.7, H-6b), 4.02 (dd, 1H, $J_{5,6}$a=6.7, H-6a), 3.23, and 3.14 (2 s, 6H, 2×OSO$_2$CH$_3$), 1.51, 1.41, 1.38, and 1.34 (4 s, 12H, 4×CH$_3$). $^{13}$C NMR ((CD$_3$)$_2$O) δ: 110.1, 109.6 ((CH$_3$)$_2$C(OR)$_2$), 79.1 (C-4), 75.6 (C-3), 75.0 (C-2), 74.9 (C-1), 68.7 (C-5), 65.4 (C-6), 38.8, 36.7 (2×OSO$_2$CH$_3$), 26.9, 25.6, 25.1, and 25.0 (4×CH$_3$). Anal. Calcd. for C$_{14}$H$_{26}$O$_{10}$S$_2$: C, 40.18; H, 6.26. Found: C, 40.35; H, 6.14.

2,3,5,6-di-O-Isopropylidene-1,4-di-O-methanesulfonyl-L-gulitol (166)

To a solution of commercially available L-ascorbic acid 163 (30.0 g, 0.17 mmol) in distilled water (200 mL), palladium on activated carbon (10%, 1.0 g) was added as a catalyst at RT. The reaction mixture was placed in a steel reaction vessel and underwent hydrogenation (100 psi) at 60° C. for 48 h. The progress of the reaction was followed by TLC analysis of aliquots (EtOAc: MeOH: H$_2$O=10:3:1). When the starting material 163 had been essentially consumed, the reaction was stopped and the reaction mixture was filtered under vacuum, and washed with water (2×50 mL). The filtrate and the wash were combined and the water was then evaporated under reduced pressure. The residue was recrystallized from methanol-ethyl acetate to give compound 164 as a white solid (21.5 g, 71%). The NMR spectrum of compound 164 matched that of the published.[105] To a suspension of the lactone 164 (10.0 g, 56.1 mmol) in dry acetone (200 mL), 2,2-dimethoxypropane (40 mL, 0.32 mmol) was added at RT. To this mixture, p-toluenesulfonic acid (200 mg) was added as a catalyst. The progress of the reaction was followed by TLC analysis of aliquots (Hexane:EtOAc, 1:1). When the starting material 164 had been essentially consumed, the reaction was stopped by addition of triethylamine (1 mL). The solvent was then evaporated under reduced pressure, and the residue was purified by column chromatography (Hexane:EtOAc, 1:1) to give compound 165 as a white solid. The NMR spectrum of compound 164 matched that of the published data.[105] The lactone 165 (5.0 g, 19.3 mmol) was dissolved in THF (20 mL), and MeOH (50 mL) was then added. To this solution, NaBH$_4$ was added portionwise at 0° C. The progress of the reaction was followed by TLC analysis of aliquots (Hexane:EtOAc, 1:1). When the starting material 165 had been consumed, the solvent was evaporated under reduced pressure. The residue was redissolved in EtOAc (50 mL), washed with aqueous tartaric acid solution (2×10 mL), brine (50 mL), and dried over Na$_2$SO$_4$. After evaporating the solvent, the crude diol was used directly in the next step. The crude diol was dissolved in CH$_2$Cl$_2$ (50 mL), and the solution was added dropwise to a mixture of pyridine (100 mL) and methanesulfonyl chloride (6 mL, 77.5 mmol) cooled to 0° C. The reaction mixture was stirred at 0° C. for 30 min, then allowed to warm to room temperature for 6 h. When TLC analysis of aliquots (Hexane: EtOAc, 1:1) showed total consumption of the starting material, the reaction mixture was poured into ice water, extracted with CH$_2$Cl$_2$ (3×100 mL), washed with brine (50 mL), and dried over Na$_2$SO$_4$. Purification by column chromatography (Hexane:EtOAc, 2:1) yielded compound 166 as a colorless syrup (3.6 g, 45% o for two steps). [α]$^{22}_D$ +54 (c 4, CH$_2$Cl$_2$); $^1$H NMR ((CD$_3$)$_2$O) δ: 4.87 (dd, 1H, J$_{3,4}$=6.1, J$_{4,5}$=4.8, H-4), 4.57 (ddd, 1H, J$_{1b,2}$=6.0, J$_{1a,1b}$=12.0, H-1b), 4.56-4.48 (m, 3H, H-2, H-3, H-1a), 4.45 (ddd, 1H, H-5), 4.13 (dd, 1H, J$_{5,6b}$=6.7, J$_{6a,6b}$=8.6, H-6b), 4.03 (dd, 1H, J$_{5,6}$a=6.6, H-6a), 3.24, and 3.15 (2 s, 6H, 2×OSO$_2$CH$_3$), 1.52, 1.41, 1.38, and 1.34 (4 s, 12H, 4×CH$_3$). $^{13}$C NMR ((CD$_3$)$_2$O) δ: 114.3, 113.8 ((CH$_3$)$_2$C(OR)$_2$), 83.3 (C-4), 79.7 (C-3), 79.0 (C-2), 78.9 (C-1), 72.9 (C-5), 69.6 (C-6), 43.0, 40.9 (2×OSO$_2$CH$_3$), 31.3, 29.9, 29.3, and 29.2 (4×CH$_3$). Anal. Calcd. for C$_{14}$H$_{26}$O$_{10}$S$_2$: C, 40.18; H, 6.26. Found: C, 39.89; H, 6.02.

1,4-Anhydro-2,3,5,6-di-O-isopropylidene-4-seleno-D-allitol (153)

To a suspension of grey selenium metal (1.6 g, 20.2 mmol) and 95% EtOH (100 mL), NaBH$_4$ was added portionwise until the black Se color disappeared. To this mixture, a solution of the dimesylate 162 (7.0 g, 16.8 mmol) in THF (10 mL) was added and the reaction mixture was heated at 70° C. for 12 h. The solvent was evaporated under reduced pressure, the residue was redissolved in EtOAc, and washed with water (20 mL), brine (20 mL), and dried over Na$_2$SO$_4$. After evaporating the solvent, the crude product was purified by column chromatography (Hexane:EtOAc, 3:1) to give 153 as a colorless oil (3.2 g, 62%).

[α]$^{22}_D$+152 (c 1, CH$_2$Cl$_2$); $^1$H NMR ((CD$_3$)$_2$O) δ: 4.98 (ddd, 1H, J$_{1b,2}$=4.5, H-2), 4.91 (dd, 1H, J$_{2,3}$=5.6, H-3), 4.12 (dd, 1H, J$_{6a,6b}$=8.4, J$_{5,6b}$=6.4, H-6b), 4.04 (ddd, 1H, J$_{5,6}$a=5.9, J$_{4,5}$=5.8, H-5), 3.71 (dd, 1H, H-6a), 3.18(m, 1H, H-4), 3.16 (dd, 1H, J$_{1a,1b}$=12.8, H-1b), 2.78 (dd, 1H, H-1a), 1.42, 1.38, 1.29, and 1.28 (4 s, 12H, 4×CH$_3$). $^{13}$C NMR ((CD$_3$)$_2$O) δ: 110.3, 109.8 ((CH$_3$)$_2$C(OR)$_2$), 85.6 (C-3), 83.9 (C-2), 76.4 (C-5), 69.0 (C-6), 57.7 (C-4), 37.4 (C-1), 26.5, 26.0, 25.1, and 24.1 (4×CH$_3$).

Anal. Calcd. for C$_{12}$H$_{20}$O$_4$Se: C, 46.91; H, 6.56. Found: C, 46.67; H, 6.37.

1,4-Anhydro-2,3,5,6-di-O-isopropylidene-4-thio-D-allitol (154)

To a solution of the dimesylate 162 (5.0 g, 11.9 mmol) in DMF (80 mL), Na$_2$S.9H$_2$O (4.0 g, 16.7 mmol) was added, and the reaction mixture was heated at 90° C. for 12 h. The reaction mixture was poured into water (100 mL), extracted with Et$_2$O (4×50 mL), washed with water (10×20 mL), and dried over Na$_2$SO$_4$. After evaporating the solvent, the crude product was purified by column chromatography (Hexane: EtOAc, 3:1) to give 154 as a colorless oil (2.9 g, 92%). [α]$^{22}_D$ +127 (c 1, CH$_2$Cl$_2$); $^1$H NMR ((CD$_3$)$_2$O) δ: 5.04 (ddd, 1H, J$_{1b,2}$=4.7, H-2), 4.91 (dd, 1H, J$_{2,3}$=5.6, H-3), 4.15-4.12 (m, 1H, H-4), 4.13 (dd, 1H, H-6b), 3.68 (ddd, 1H, J$_{5,6}$a=6.7, J$_{4,5}$=9.2, J$_{5,6b}$=8.2, H-5), 3.45 (dd, 1H, J$_{6a,6b}$=8.5, H-6a), 3.29 (dd, 1H, J$_{1a,1b}$=11.2, H-1b), 2.92 (dd, 1H, H-1a), 1.42, 1.38, 1.29, and 1.27 (4 s, 12H, 4×CH$_3$). $^{13}$C NMR ((CD$_3$)$_2$O) δ: 109.9, 109.8 ((CH$_3$)$_2$C(OR)$_2$), 87.1 (C-3), 85.3 (C-2), 77.1 (C-5), 69.6 (C-6), 52.6 (C-4), 29.7 (C-1), 26.6, 26.2, 25.2, and 24.1 (4×CH$_3$). Anal. Calcd. for C$_{12}$H$_{20}$O$_4$S: C, 55.36; H, 7.74. Found: C, 55.64; H, 7.72.

1,4-Anhydro-2,3,5,6-di-O-isopropylidene-4-seleno-L-allitol (155)

To a suspension of grey selenium metal (1.4 g, 18.7 mmol) and 95% EtOH (100 mL), NaBH$_4$ was added portionwise until the black Se color disappeared. To this mixture, a solution of the dimesylate 166 (6.0 g, 14.3 mmol) in THF (10 mL) was added and the reaction mixture was heated at 65-70° C. for 12 h. The solvent was evaporated under reduced pressure, the residue was redissolved in EtOAc, washed with water (20 mL), brine (20 mL), and dried over Na$_2$SO$_4$. After evaporating the solvent, the crude product was purified by column chromatography (Hexane:EtOAc, 3:1) to give 155 as a colorless oil (2.9 g, 67%). [α]$^{22}_D$ −143 (c 1, CH$_2$Cl$_2$); $^1$H NMR ((CD$_3$)$_2$O) δ: 5.03 (ddd, 1H, H-2), 4.91 (dd, 1H, J$_{2,3}$=5.6, H-3), 4.15-4.10 (m, 2H, H-5, H-6b), 3.68 (dd, 1H, J$_{5,6}$a=8.9, $J_{6a,6b}$=11.4, H-6a), 3.45 (dd, 1H, H-4), 3.27 (dd, 1H, $J_{1b,2}$=4.7, $J_{1a,1b}$=12.0, H-1b), 2.92 (dd, 1H, $J_{1b,2}$=0.7, H-1a), 1.42, 1.37, 1.29, and 1.27 (4 s, 12H, 4×CH$_3$). $^{13}$C NMR ((CD$_3$)$_2$O) δ: 110.0, 109.8 ((CH$_3$)$_2$C(OR)$_2$), 87.1 (C-3), 85.3 (C-2), 77.1 (C-5), 69.6 (C-6), 52.6 (C-4), 29.8 (C-1), 26.6, 26.2, 25.3, and 24.1 (4×CH$_3$). Anal. Calcd. for C$_{12}$H$_{20}$O$_4$Se: C, 46.91; H, 6.56. Found: C, 46.76; H, 6.66.

1,4-Anhydro-2,3,5,6-di-O-isopropylidene-4-thio-L-allitol (156)

To a solution of the dimesylate 166 (5.0 g, 11.9 mmol) in DMF (80 mL), Na$_2$S.9H$_2$O (4.0 g, 16.7 mmol) was added, and the reaction mixture was heated at 90° C. for 12 h. The reaction mixture was poured into water (100 mL), extracted with Et$_2$O (4×50 mL), washed with water (10×20 mL), and dried over Na$_2$SO$_4$. After evaporating the solvent, the crude product was purified by column chromatography (Hexane:EtOAc, 3:1) to give 156 as a colorless oil (2.5 g, 82%). [α]$^{22}_D$ −139 (c 1, CH$_2$Cl$_2$); $^1$H NMR ((CD$_3$)$_2$O) δ: 4.99 (ddd, 1H, H-2), 4.92 (dd, 1H, $J_{2,3}$=5.6, H-3), 4.12 (dd, 1H, $J_{6a,6b}$=8.2, $J_{5,6b}$=6.4, H-6b), 4.04 (ddd, 1H, H-5), 3.71 (dd, 1H, $J_{5,6a}$=5.9, H-6a), 3.19-3.15 (m, 1H, H-4), 3.17 (dd, 1H, H-1b), 2.80 (dd, 1H, $J_{1a,1b}$=12.9, H-1a), 1.42, 1.38, 1.29, and 1.28 (4 s, 12H, 4×CH$_3$). $^{13}$C NMR ((CD$_3$)$_2$O) δ: 110.3, 109.8 ((CH$_3$)$_2$C(OR)$_2$), 85.6 (C-3), 83.9 (C-2), 76.3 (C-5), 69.0 (C-6), 57.7 (C-4), 37.4 (C-1), 26.5, 26.0, 25.1, and 24.1 (4×CH$_3$). Anal. Calcd for C$_{12}$H$_{20}$O$_4$S: C, 55.36; H, 7.74. Found: C, 55.16; H, 7.58.

General procedure for the preparation of sulfonium and selenonium sulfates 167-174.

A mixture of the isopropylidene-protected 1,4-anhydro-4-seleno-D-allitol 153, or 1,4-anhydro-4-thio-D-allitol 154, or 1,4-anhydro-4-seleno-L-allitol 155, or 1,4-anhydro-4-thio-L-allitol 156, and the cyclic sulfate 157 or 158, in HFIP (1,1,1,3,3,3-hexafluoroisopropanol) was placed in a reaction vessel and K$_2$CO$_3$ (20 mg) was added. The stirred reaction mixture was heated in a sealed tube at the indicated temperature for the indicated time, as given below. The progress of the reaction was followed by TLC analysis of aliquots (EtOAc:MeOH, 10:1). When the limiting reagent had been essentially consumed, the mixture was cooled, then diluted with CH$_2$Cl$_2$, and evaporated to give a syrupy residue. Purification by column chromatography (EtOAc to EtOAc:MeOH, 10:1) gave the purified sulfonium salts and selenonium salts 167-174.

1,4-Anhydro-2,3,5,6-di-O-isopropylidene-1-[(S)-[(2S',3S')-2',4'-benzylidenedioxy-3'-(sulfooxy)butyl]selenonio]-D-allitol Inner Salt (167)

Reaction of compound 153 (500 mg, 1.63 mmol) with the cyclic sulfate 157 (530 mg, 1.94 mmol) in HFIP (2.0 mL) for 12 h at 80-85° C. gave compound 167 as a colorless, amorphous solid (850 mg, 90% based on 153). [α]$^{22}_D$ +12 (c 0.5, CH$_2$Cl$_2$); $^1$H NMR ((CD$_3$)$_2$O) δ: 7.56-7.38 (m, 5H, H-Arom.), 5.74 (s, 1H, CHPh), 5.52 (ddd, 1H, $J_{1b,2}$=5.2, $J_{2,3}$=5.7, H-2), 5.27 (dd, 1H, H-3), 4.78 (ddd, 1H, $J_{5,6b}$=7.3, $J_{5,6a}$=5.2, $J_{4,5}$=3.8, H-5), 4.62 (dd, 1H, H-4), 4.46-4.37 (m, 4H, H-1'b, H-2', H-3', H-4'b), 4.28 (dd, 1H, $J_{1'a,1'b}$=13.4, $J_{1'a,2}$=3.8, H-1'a), 4.25 (dd, 1H, $J_{6a,6b}$=9.5, $J_{5,6b}$=7.3, H-6b), 4.10 (dd, 1H, $J_{1b,2}$=5.2, $J_{1a,1b}$=15.4, H-1b), 3.97 (dd, 1H, H-1a), 3.96 (dd, 1H, $J_{5,6}$a=5.2, H-6a), 3.78 (m, 1H, H-4'a), 1.64, 1.42, 1.38, and 1.32 (4 s, 18H, 4×CH$_3$). $^{13}$C NMR ((CD$_3$)$_2$O) δ: 142.3, 133.9, 133.0, and 131.1 (C—Ar), 116.9, 115.7 (2 (CH$_3$)$_2$C(OR)$_2$), 106.1 (CHPh), 89.9 (C-3), 89.8 (C-2), 81.3 (C-2'), 79.0 (C-5), 73.9 (C-4), 73.5 (C-4'), 71.8 (C-6), 71.5 (C-3'), 52.8 (C-1), 50.4 (C-1'), 30.3, 30.1, 28.2, and 27.1 (4×CH$_3$). HRMS. Calcd. for C$_{23}$H$_{33}$O$_{10}$SSe (M+H$^+$): 581.0594; Found: 581.0597.

4-Anhydro-2,3,5,6-di-O-isopropylidene-1-[(S)-[(2S',3S')-2',4'-benzylidenedioxy-3'-(sulfooxy)butyl]sulfonio]-D-allitol Inner Salt (168)

Reaction of compound 154 (500 mg, 1.92 mmol) with the cyclic sulfate 157 (630 mg, 2.31 mmol) in HFIP (2.0 mL) for 12 h at 70-75° C. gave compound 168 as a colorless, amorphous solid (960 mg, 94% based on 154). [α]$^{22}_D$ +1.2 (c 0.1, CH$_2$Cl$_2$); $^1$H NMR ((CD$_3$)$_2$O) δ: 7.56-7.38 (m, 5H, H-Arom.), 5.74 (s, 1H, CHPh), 5.52 (ddd, 1H, $J_{1b,2}$=5.2, $J_{2,3}$=5.7, H-2), 5.26 (dd, 1H, H-3), 4.79 (ddd, 1H, ddd, 1H, $J_{5,6b}$=7.4, $J_{5,6}$a=5.1, $J_{4,5}$=3.9, H-5), 4.63 (dd, 1H, H-4), 4.49-4.36 (m, 4H, H-1'b, H-2', H-3', H-4'b), 4.28 (dd, 1H, $J_{1'a,1'b}$=13.4, $J_{1'a,2}$=3.7, H-1'a), 4.25 (dd, 1H, $J_{6a,6b}$=9.4, H-6b), 4.10 (dd, 1H, $J_{1b,2}$=5.2, $J_{1a,1b}$=14.4, H-1b), 3.97 (dd, 1H, H-1a), 3.97 (dd, 1H, $J_{5,6}$a=5.1, H-6a), 3.78 (m, 1H, H-4'a), 1.64, 1.42, 1.38, and 1.32 (4 s, 18H, 4×CH$_3$). $^{13}$C NMR ((CD$_3$)$_2$O) δ: 138.5, 129.3, 128.4 and 126.5 (C—Ar), 112.3, 111.1(2 (CH$_3$)$_2$C(OR)$_2$), 101.4 (CHPh), 85.3 (C-3), 85.2 (C-2), 76.7 (C-2'), 74.4 (C-5), 69.2 (C-4'), 68.8 (C-4), 67.1 (C-6), 67.0 (C-3'), 48.2 (C-1), 45.8 (C-1'), 25.7, 25.5, 23.6, and 22.5 (4×CH$_3$). Anal. Calcd for C$_{23}$H$_{32}$O$_{10}$S$_2$: C, 51.86; H, 6.06. Found: C, 52.06; H, 5.87. HRMS. Calcd. for C$_{23}$H$_{33}$O$_{10}$S$_2$ (M+H$^+$): 533.1510; Found: 533.1512.

1,4-Anhydro-2,3,5,6-di-O-isopropylidene-1-[(S)-[(2S',3S')-2',4'-benzylidenedioxy-3'-(sulfooxy)butyl]selenonio]-L-allitol Inner Salt (169)

Reaction of compound 155 (500 mg, 1.63 mmol) with the cyclic sulfate 157 (530 mg, 1.94 mmol) in HFIP (2.0 mL) for 12 h at 65-70° C. gave compound 169 as a colorless, amorphous solid (850 mg, 90% based on 155). [α]$^{22}_D$ +18 (c 1.0, CH$_2$Cl$_2$); $^1$H NMR (CD$_2$Cl$_2$) δ: 7.48-7.38 (m, 5H, H-Arom.), 5.61 (s, 1H, CHPh), 5.41 (ddd, 1H, H-2), 5.15 (dd, 1H, $J_{2,3}$=5.3, H-3), 4.81 (ddd, 1H, $J_{4,5}$=2.0, $J_{5,6}$a=4.6, $J_{5,6b}$=7.8, H-5), 4.60 (m, 1H, H-4), 4.55 (ddd, 1H, H-3'), 4.52 (dd, 1H, H-4'b), 4.42 (d, 2H, H-1'b, H-1'a), 4.38-4.32 (m, 1H, H-2'), 4.20 (dd, 1H, $J_{5,6b}$=7.8, $J_{6a,6b}$=9.6, H-6b), 3.95 (dd, 1H, $J_{5,6}$a=4.6, H-6a), 3.85 (dd, 1H, $J_{4'a,4'b}$=10.0, H-4'a), 3.63 (dd, 1H, H-1b), 3.60 (dd, 1H, $J_{1a,2}$=5.1, $J_{1a,1b}$=13.9, H-1a), 1.60, 1.44, 1.36, and 1.32 (4 s, 12H, 4×CH$_3$). $^{13}$C NMR (CD$_2$Cl$_2$) δ: 137.0, 129.5, 128.6, and 126.3 (C—Ar), 112.1, 111.2 (2 (CH$_3$)$_2$C(OR)$_2$), 101.8 (CHPh), 87.8 (C-2), 85.7 (C-3), 76.9 (C-3'), 74.7 (C-5), 70.5 (C-4), 69.3 (C-4'), 67.7 (C-2'), 67.2 (C-6), 44.5 (C-1'), 43.2 (C-1), 26.2, 26.0, 23.3, and 22.9 (4×CH$_3$). Anal. Calcd. for C$_{23}$H$_{32}$O$_{10}$SSe: C, 47.67; H, 5.57. Found: C, 47.89; H, 5.67.

1,4-Anhydro-2,3,5,6-di-O-isopropylidene-1-[(S)-[(2S',3S')-2',4'-benzylidenedioxy-3'-(sulfooxy)butyl]sulfonio]-L-allitol Inner Salt (170)

Reaction of compound 156 (500 mg, 1.92 mmol) with the cyclic sulfate 157 (630 mg, 2.31 mmol) in HFIP (2.0 mL) for 12 h at 80-85° C. gave compound 170 as a colorless, amorphous solid (940 mg, 92% based on 156). [α]$^{22}_D$ +1° (c 0.5, CH$_2$Cl$_2$); $^1$H NMR ((CD$_3$)$_2$O) δ: 7.48-7.39 (m, 5H, H-Arom.), 5.59 (s, 1H, CHPh), 5.26 (ddd, 1H, H-2), 5.10 (dd, 1H, $J_{2,3}$=5.8, H-3), 4.88 (ddd, 1H, $J_{4,5}$=7.6, H-5), 4.68 (ddd, 1H, H-3'), 4.54 (m, 1H, H-4), 4.50 (dd, 1H, $J_{3,4}$=1.8, H-4'), 4.40 (d, 2H, H-1'b, H-1'a), 4.34 (dd, 1H, H-2'), 4.32 (dd, 1H, $J_{6a,6b}$=7.9, $J_{6a,6b}$=9.8, H-6b), 4.01 (dd, 1H, $J_{5,6a}$=4.6, H-6a), 3.82 (dd, 1H, H-4'a), 3.68 (dd, 1H, $J_{1b,2}$=5.3, $J_{1a,1b}$=15.0, H-1b), 3.62 (dd, 1H, H-1a), 1.60, 1.44, 1.36, and 1.34 (4 s, 12H, 4×CH$_3$). $^{13}$C NMR ((CD$_3$)$_2$O) δ: 136.9, 129.6, 128.6 and 126.3 (C—Ar), 112.8, 111.5 (2 (CH$_3$)$_2$C(OR)$_2$), 101.9 (CHPh), 86.2 (C-2), 84.1 (C-3), 76.9 (C-3'), 74.8 (C-5), 71.4 (C-4), 69.2 (C-2'), 67.3 (C-6), 65.7 (C-4'), 47.7 (C-1), 45.9 (C-1'), 26.0, 25.9, 23.3, and 22.6 (4×CH$_3$). HRMS. Calcd. for C$_{23}$H$_{33}$O$_{10}$S$_2$ (M+H$^+$): 533.1510; Found: 533.1515.

4-Anhydro-2,3,5,6-di-O-isopropylidene-1-[(S)-[(2R',3S',4R',5R')-2',4'-benzylidenedioxy-5',6'-isopropylidenedioxy-3'-(sulfooxy)hexyl]selenonio]-D-allitol Inner Salt (171)

Reaction of compound 153 (500 mg, 1.63 mmol) with the cyclic sulfate 158 (730 mg, 1.96 mmol) in HFIP (2.0 mL) for 12 h at 80-85° C. gave compound 171 as a colorless, amorphous solid (770 mg, 70% based on 153). [α]$^{22}_D$ +8 (c 0.5, CH$_2$Cl$_2$); $^1$H NMR ((CD$_3$)$_2$O) δ: 7.58-7.32 (m, 5H, H-Arom.), 5.90 (s, 1H, CHPh), 5.63 (ddd, 1H, J$_{2,3}$=5.4, H-2), 5.26 (dd, 1H, H-3), 4.92(m, 1H, H-2'), 4.82 (ddd, 1H, J$_{5,6b}$=7.7, J$_{5,6}$a=4.9, J$_{4,5}$=3.2, H-5), 4.62 (dd, 1H, J$_{1'a,1'b}$=12.2, J$_{1'b,2}$=5.9, H-1'b), 4.59-4.57 (m, 2H, H-3', H-4), 4.46 (ddd, 1H, J$_{4,5}$=2.3, J$_{5',6'a}$=8.1, J$_{5',6'b}$=6.8, H-5'), 4.40 (m, 1H, H-4'), 4.29 (dd, 1H, J$_{6'a,6'b}$=8.5, H-6'b), 4.28 (dd, 1H, H-6b), 4.18 (dd, 1H, H-1'a), 4.16 (dd, 1H, H-6'a), 4.08 (dd, 1H, J$_{6a,6b}$=9.5, H-6a), 3.76 (dd, 1H, J$_{1a,1b}$=14.1, J$_{1b,2}$=5.4, H-1b), 3.60 (dd, 1H, H-1a), 1.59, 1.43, 1.36, 1.33, 1.31, 1.29, and 1.28 (6 s, 18H, 6×CH$_3$). $^{13}$C NMR ((CD$_3$)$_2$O) δ: 138.2, 129.1, 128.4 and 126.3 (C—Ar), 111.3, 110.6, and 107.5 (3×(CH$_3$)$_2$C(OR)$_2$), 100.6 (CHPh), 88.1 (C-2), 85.9 (C-3), 78.9 (C-4'), 76.5 (C-5'), 74.8 (C-5), 74.0 (C-2'), 71.1 (C-3'), 69.1 (C-4), 67.1 (C-6), 64.6 (C-6'), 43.9 (C-1'), 43.6 (C-1), 26.0, 25.7, 25.6, 25.5, 23.4, and 22.5 (6×CH$_3$). Anal. Calcd. for C$_{28}$H$_4$O$_{12}$SSe: C, 49.48; H, 5.93. Found: C, 49.16; H, 6.09.

1,4-Anhydro-2,3,5,6-di-O-isopropylidene-1-[(S)-[(2R',3S',4R',5R')-2',4'-benzylidenedioxy-5',6'-isopropylidenedioxy-3'-(sulfooxy)hexyl]sulfonio]-D-allitol Inner Salt (172)

Reaction of compound 154 (500 mg, 1.92 mmol) with the cyclic sulfate 158 (860 mg, 2.30 mmol) in HFIP (2.0 mL) for 12 h at 90-95° C. gave compound 172 as a colorless, amorphous solid (1.0 g, 82% based on 154). [α]$^{22}_D$ +5.4 (c 0.1, CH$_2$Cl$_2$); $^1$H NMR ((CD$_3$)$_2$O) δ: 7.60-7.38 (m, 5H, H-Arom.), 5.89 (s, 1H, CHPh), 5.50 (ddd, 1H, H-2), 5.26 (dd, 1H, J$_{2,3}$=5.8, H-3), 4.88 (ddd, 1H, J$_{2,3}$=5.0, J$_{1'b,2}$=5.0, J$_{1'a,2}$=2.1, H-2'), 4.83 (ddd, 1H, J$_{5,6b}$=2.8, J$_{5,6}$a=5.1, J$_{4,5}$=7.6, H-5), 4.59 (dd, 1H, J$_{3,4}$=2.4, H-4), 4.57-4.52 (m, 2H, H-1'b, H-3'), 4.50 (ddd, 1H, J$_{4,5}$=2.1, J$_{5',6'a}$=9.1, J$_{5',6'b}$=7.1, H-5'), 4.42 (dd, 1H, J$_{3',4}$=1.8, H-4'), 4.33 (dd, 1H, H-6'b), 4.30 (dd, 1H, J$_{5,6b}$=2.8, H-6b), 4.28 (m, 1H, H-1'a), 4.18 (dd, 1H, J$_{6'a,6'b}$=8.4, H-6'a), 4.11 (dd, 1H, J$_{6a,6b}$=9.6, H-6a), 3.90 (dd, 1H, J$_{1b,2}$=5.4, H-1b), 3.75 (dd, 1H, J$_{1a,1b}$=14.3, H-1a), 1.61, 1.43, 1.37, 1.30, 1.29, and 1.28 (6 s, 18H, 6×CH$_3$). $^{13}$C NMR ((CD$_3$)$_2$O) δ: 138.2, 129.1, 128.4 and 126.3 (C—Ar), 112.1, 110.9, and 107.5 (3×(CH$_3$)$_2$C(OR)$_2$), 100.7 (CHPh), 86.2 (C-2), 84.5 (C-3), 79.0 (C-4), 76.7 (C-5'), 74.7 (C-5), 74.1 (C-2'), 70.3 (C-3'), 70.0 (C-4'), 67.1 (C-6), 64.6 (C-6'), 47.9 (C-1), 46.1 (C-1'), 23.9, 25.6, 25.5, 25.4, 23.4, and 22.4 (6×CH$_3$). Anal. Calcd. for C$_{28}$H$_{40}$O$_{12}$S$_2$: C, 53.15; H, 6.37. Found: C, 52.92; H, 6.17.

1,4-Anhydro-2,3,5,6-di-O-isopropylidene-1-[(S)-[(2R',3S',4R',5R)-2',4'-benzylidenedioxy-5',6'-isopropylidenedioxy-3'-(sulfooxy)hexyl]selenonio]-L-allitol Inner Salt (173)

Reaction of compound 155 (500 mg, 1.63 mmol) with the cyclic sulfate 158 (730 mg, 1.96 mmol) in HFIP (2.0 mL) for 12 h at 80-85° C. gave compound 173 as a colorless, amorphous solid (740 mg, 67% based on 155). [α]$^{22}_D$ −12 (c 1, CH$_2$Cl$_2$); $^1$H NMR ((CD$_3$)$_2$O) δ: 7.60-7.38 (m, 5H, H-Arom.), 5.92 (s, 1H, CHPh), 5.55 (ddd, 1H, H-2), 5.21 (dd, 1H, J$_{2,3}$=5.4, J$_{3,4}$=1.8, H-3), 4.96-4.92 (m, 1H, H-2'), 4.60 (dd, 1H, H-3'), 4.53 (dd, 1H, J$_{1'b,2'}$=6.4, J$_{1'b,1'a}$=12.2, H-1'b), 4.45 (ddd, 1H, J$_{4,5}$=2.3, J$_{5,6'a}$=9.2, J$_{5,6b}$=6.9, H-5'), 4.41 (dd, 1H, H-4'), 4.40-4.36 (m, 1H, H-5), 4.34 (dd, 1H, J$_{6',6'b}$=8.6, H-6'b), 4.24-4.18 (m, 3H, H-4, H-1'a, H-6a), 3.99 (dd, 1H, J$_{5,6b}$=7.3, J$_{6a,6b}$=9.3, H-6b), 3.96 (dd, 1H, J$_{1b,2}$=5.2, H-1b), 3.90 (dd, 1H, J$_{1a,1b}$=14.2, H-1a), 3.76 (dd, 1H, J$_{5,6}$a=5.2, H-6a), 1.59, 1.39, 1.35, 1.30, 1.29, and 1.25 (6 s, 18H, 6×CH$_3$). $^{13}$C NMR ((CD$_3$)$_2$O) δ: 142.9, 133.9, 133.1, and 131.0 (C—Ar), 116.1, 115.3, and 112.1 (3×(CH$_3$)$_2$C(OR)$_2$), 105.0 (CHPh), 91.5 (C-3), 91.0 (C-2), 83.4 (C-4'), 81.2 (C-5'), 78.7 (C-5), 78.5 (C-2'), 75.5 (C-3'), 72.3 (C-4), 71.6 (C-6), 69.3 (C-6'), 49.3 (C-1), 48.0 (C-1'), 30.7, 30.6, 30.3, 30.2, 28.1, and 27.5 (6×CH$_3$). Anal. Calcd. for C$_{28}$H$_{40}$O$_{12}$SSe: C, 49.48; H, 5.93. Found: C, 49.31; H, 5.90.

1,4-Anhydro-2,3,5,6-di-O-isopropylidene-1-[(S)-[(2R',3S',4R',5R')-2',4'-benzylidenedioxy-5',6'-isopropylidenedioxy-3'-(sulfooxy)hexyl]sulfonio]-L-allitol Inner Salt (174)

Reaction of compound 156 (500 mg, 1.92 mmol) with the cyclic sulfate 158 (860 mg, 2.30 mmol) in HFIP (2.0 mL) for 12 h at 90-95° C. gave compound 174 as a colorless, amorphous solid (960 mg, 77% based on 156). [α]$^{22}_D$ −15 (c 0.5, CH$_2$Cl$_2$);
$^1$H NMR (CD$_2$Cl$_2$) δ: 7.56-7.40 (m, 5H, H-Arom.), 5.76 (s, 1H, CHPh), 5.19 (ddd, 1H, H-2), 4.98 (dd, 1H, J$_{2,3}$=5.7, H-3), 4.68-4.62 (m, 2H, H-2', H-3'), 4.51 (ddd, 1H, H-5'), 4.42 (dd, 1H, J$_{1'b,2'}$=5-7, J$_{1'b,1'a}$=13.5, H-1'b), 4.28 (dd, 1H, J$_{1'a,2'}$=2.3, H-1'a), 4.28-4.25 (m, 1H, H-5), 4.25-4.18 (m, 3H, H-6'a, H-6'b, H-4'), 4.14 (m, 1H, H-4), 3.90 (dd, 1H, J$_{1a,1b}$=15.4, H-1b), 3.86 (dd, 1H, J$_{1a,2}$=4.6, H-1a), 3.86 (dd, 1H, J$_{5,6b}$=7.8, H-6b), 3.71 (dd, 1H, J$_{5,6}$a=5.1, J$_{6a,6b}$=9.5, H-6a), 1.62, 1.39, 1.38, 1.37, 1.34, and 1.24 (6 s, 18H, 6×CH$_3$). $^{13}$C NMR (CD$_2$Cl$_2$) δ: 137.4, 129.7, 128.6, and 126.3 (C—Ar), 112.7, 111.5, and 108.5 (3×(CH$_3$)$_2$C(OR)$_2$), 100.9 (CHPh), 85.2 (C-2), 84.8 (C-3), 79.1 (C-4'), 75.5 (C-5'), 74.3 (C-5), 74.0 (C-3'), 70.5 (C-2'), 69.8 (C-4), 67.0 (C-6), 65.0 (C-6'), 47.8 (C-1), 45.9 (C-1'), 26.4, 26.1, 25.9, 25.5, 23.3, and 22.8 (6×CH$_3$). Anal. Calcd. for C$_{28}$H$_{40}$O$_{12}$S$_2$: C, 53.15; H, 6.37. Found: C, 53.36; H, 6.41.

General Procedure for the Deprotection of the Coupled Products to Yield the Final Compounds 145-152.

The protected coupled products 167-174 were dissolved in CH$_2$Cl$_2$ (2 mL), TFA (10 mL) was then added, and the mixture was stirred for 6-8 h at room temperature. The progress of the reaction was followed by TLC analysis of aliquots (EtOAc:MeOH:H$_2$O, 7:3:1). When the starting material had been consumed, the TFA and CH$_2$Cl$_2$ were removed under reduced pressure. The residue was rinsed with CH$_2$Cl$_2$ (4×2 mL) and the CH$_2$Cl$_2$ was decanted to remove the cleaved protecting groups. The remaining gum was dissolved in water and purified by column chromatography (EtOAc and EtOAc:MeOH, 2:1) to give the purified compounds 145-148 as colorless, amorphous, and hygroscopic solids. In the cases of 171-174, the benzylidene groups were not completely cleaved. The residue was then dissolved in 80% AcOH (10 mL), and Pd/C (10%, 200 mg, in two portions) was added and the reaction mixture was subjected to hydrogenolysis for 48 h at room temperature. After filtering the Pd/C, the filtrate was mixed with water (100 mL), and the solvents were removed under reduced pressure. The remaining gum was dissolved in water and purified by column chromatography (EtOAc and EtOAc:MeOH, 2:1) to give the purified compounds 149-152 as colorless, amorphous, and hygroscopic solids.

1,4-Anhydro-1-[(S)-[(2S',3S)-2',4'-dihydroxy-3'-(sufooxy)butyl]selenonio]-D-allitol Inner Salt (145)

To a solution of 167 (500 mg, 0.86 mmol) in CH$_2$Cl$_2$ (2 mL) was added TFA (10 mL) to yield the compound 145 as a colorless, amorphous, and hygroscopic solid (202 mg, 57%). $[\alpha]^{22}_D$ +54 (c 2, H$_2$O); $^1$H NMR (D$_2$O) δ: 4.74 (m, 1H, H-2), 4.34 (dd, 1H, $J_{2,3}$=9.1, $J_{3,4}$=3.1, H-3), 4.28 (ddd, 1H, H-3'), 4.25-4.18 (m, 2H, H-2', H-5), 4.05 (dd, 1H, $J_{4,5}$=4.3, H-4), 3.97 (dd, 1H, $J_{1'b,2'}$=3.6, $J_{1'a,1'b}$=12.6, H-1'b), 3.82 (dd, 1H, $J_{3',4'b}$=6.4, H-4'b), 3.80 (dd, 1H, $J_{1'a,2'}$=3.2, H-1'a), 3.73 (dd, 1H, $J_{3',4'a}$=3.3, 1H, $J_{4'a,4'b}$=12.8, H-4'a), 3.68 (m, 2H, H-6a, H-6b), 3.55 (dd, 1H, $J_{1b,2}$=3.7, H-1b), 3.33 (dd, 1H, $J_{1a,2}$=2.1, $J_{1a,1b}$=13.1, H-1a). $^{13}$C NMR (D$_2$O) δ: 80.8 (C-3'), 76.0 (C-2), 75.9 (C-3), 68.4 (C-5), 66.0 (C-2'), 65.1 (C-4), 63.4 (C-6), 60.1 (C-4'), 48.5 (C-1'), 40.5 (C-1). Calcd. for C$_{10}$H$_{19}$O$_{10}$SSe (M-H): 410.9859; Found: 410.9861.

1,4-Anhydro-1-[(S)-[(2S',3S')-2',4'-dihydroxy-3'-(sufooxy)butyl]sulfonio]-D-allitol Inner Salt (146)

To a solution of 168 (500 mg, 0.94 mmol) in CH$_2$Cl$_2$ (2 mL) was added TFA (10 mL) to yield the compound 146 as a colorless, amorphous, and hygroscopic solid (240 mg, 69%). $[\alpha]^{22}_D$ +39 (c 2, H$_2$O); $^1$H NMR (D$_2$O) δ: 4.63 (m, 1H, H-2), 4.48 (dd, 1H, $J_{2,3}$=8.7, $J_{3,4}$=3.3, H-3), 4.36-4.30 (m, 2H, H-2', H-5), 4.27 (ddd, 1H, H-3'), 4.12 (dd, 1H, $J_{1'b,2'}$=3.4, $J_{1'a,1'b}$=13.6, H-1'b), 4.05 (dd, 1H, $J_{3,4}$=3.3, $J_{4,5}$=8.6, H-4), 3.86 (dd, 1H, $J_{3',4'b}$=2.8, H-4'b), 3.85 (dd, 1H, $J_{1a,2}$=8.3, H-1'a), 3.78 (dd, 1H, $J_{3',4'a}$=3.2, 1H, $J_{4'a,4'b}$=12.8, H-4'a), 3.70 (m, 2H, H-6a, H-6b), 3.69 (dd, 1H, $J_{1b,2}$=3.3, H-1b), 3.46 (dd, 1H, $J_{1a,2}$=1.6, $J_{1a,1b}$=14.4, H-1a). $^{13}$C NMR (D$_2$O) δ: 79.8 (C-3'), 74.7 (C-2), 74.4 (C-3), 68.3 (C-2'), 65.6 (C-4), 65.5 (C-5), 63.0 (C-6), 59.9 (C-4'), 51.1 (C-1'), 44.2 (C-1). HRMS. Calcd. for C$_{10}$H$_{20}$O$_{10}$S$_2$Na (M+Na): 387.0390; Found: 387.0391.

1,4-Anhydro-1-[(S)-[(2S',3S')-2',4'-dihydroxy-3'-(sufooxy)butyl]selenonio]-L-allitol Inner Salt (147)

To a solution of 169 (500 mg, 0.86 mmol) in CH$_2$Cl$_2$ (2 mL) was added TFA (10 mL) to yield the compound 147 as a colorless, amorphous, and hygroscopic solid (216 mg, 61%). $[\alpha]^{22}_D$ −17 (c 0.5, H$_2$O); $^1$H NMR (D$_2$O) δ: 4.77 (ddd, 1H, H-2), 4.42 (dd, 1H, $J_{2,3}$=8.8, $J_{3,4}$=3.0, H-3), 4.33-4.25 (m, 2H, H-5, H-2'), 4.25-4.30 (ddd, 1H, H-3'), 4.13 (dd, 1H, $J_{4,5}$=8.7, H-4), 3.97 (dd, 1H, $J_{1'b,2'}$=4.0, $J_{1'a,1'b}$=12.4, H-1'b), 3.94 (dd, 1H, $J_{1'a,2}$=8.7, H-1'a), 3.83 (dd, 1H, $J_{3',4'b}$=3.2, H-4'b), 3.75 (dd, 1H, $J_{3',4'a}$=3.2, 1H, $J_{4'a,4'b}$=12.8, H-4'a), 3.68 (d, 2H, H-6a, H-6b), 3.58 (dd, 1H, $J_{1b,2}$=8.5, H-1b), 3.36 (dd, 1H, $J_{1a,2}$=2.2, $J_{1a,1b}$=13.3, H-1a). $^{13}$C NMR (D$_2$O) δ: 81.0 (C-3'), 75.8 (C-2), 75.5 (C-3), 68.7 (C-2'), 66.5 (C-5), 65.5 (C-4), 63.4 (C-6), 60.0 (C-4'), 48.4 (C-1'), 40.4 (C-1). HRMS. Calcd. for C$_{10}$H$_{19}$O$_{10}$SSe (M-H): 410.9859; Found: 410.9857.

1,4-Anhydro-1-[(S)-[(2S',3S')-2',4'-dihydroxy-3'-(sufooxy)butyl]sulfonio]-L-allitol Inner Salt (148)

To a solution of 170 (500 mg, 0.94 mmol) in CH$_2$Cl$_2$ (2 mL) was added TFA (10 mL) to yield the compound 148 as a colorless, amorphous, and hygroscopic solid (223 mg, 65%). $[\alpha]^{22}_D$ +6 (c 0.5, H$_2$O); $^1$H NMR (D$_2$O) δ: 4.60 (m, 1H, H-2), 4.47 (dd, 1H, $J_{2,3}$=8.3, $J_{3,4}$=3.3, H-3), 4.32 (ddd, 1H, H-5), 4.28-4.24 (m, 1H, H-2'), 4.22 (ddd, 1H, H-3'), 4.07 (dd, 1H, $J_{4,5}$=8.5, H-4), 3.98 (dd, 1H, $J_{1'b,2'}$=3.5, H-1'b), 3.92 (dd, 1H, $J_{1a,2}$=8.8, $J_{1'a,1'b}$=13.6, H-1'a), 3.86 (dd, 1H, $J_{3',4'b}$=9.5, H-4'b), 3.74 (dd, 1H, $J_{3',4'a}$=3.2, 1H, $J_{4'a,4'b}$=12.8, H-4'a), 3.66 (d, 2H, H-6a, H-6b), 3.64-3.61 (m, 1H, H-1b), 3.44 (dd, 1H, $J_{1a,2}$=9.7, $J_{1a,1b}$=14.3, H-1a). $^{13}$C NMR (D$_2$O) δ: 80.5 (C-3'), 74.6 (C-2), 74.5 (C-3), 68.8 (C-5), 66.6 (C-2'), 66.2 (C-4), 63.1 (C-6), 59.9 (C-4'), 50.9 (C-1'), 44.1 (C-1). HRMS. Calcd. for C$_{10}$H$_{20}$O$_{10}$S$_2$Na (M+Na): 387.0390; Found: 387.0389.

1,4-Anhydro-1-[(S)-[(2R',3S',4R',5R')-2',4',5',6'-tetrahydroxy-3'-(sufooxy)hexyl]selenonio]-D-allitol Inner Salt (149)

To a solution of 171 (600 mg, 0.88 mmol) in CH$_2$Cl$_2$ (2 mL) was added TFA (10 mL). After removing the cleaved protecting groups, the remaining gum was then dissolved in AcOH (10 mL), Pd/C (10%, 100 mg) was added, and the reaction mixture was subjected to hydrogenolysis to give compound 149 as a colorless, amorphous, and hygroscopic solid (157 mg, 38%). $[\alpha]^{22}_D$ −8 (c 0.5, H$_2$O); $^1$H NMR (D$_2$O) δ: 4.80 (m, 1H, H-2), 4.59 (dd, 1H, H-3'), 4.48 (ddd, 1H, H-2'), 4.43 (dd, 1H, $J_{2,3}$=8.9, $J_{3,4}$=2.8, H-3), 4.31 (ddd, 1H, H-5), 4.14 (dd, 1H, $J_{4,5}$=8.9, H-4), 4.08 (dd, 1H, $J_{1'b,2'}$=9.9, $J_{1'a,1'b}$=12.2, H-1'b), 3.95 (dd, 1H, $J_{1a,2}$=3.5, H-1'a), 3.84-3.74 (m, 3H, H-4', H-5', H-6'b), 3.72 (d, 2H, H-6a, H-6b), 3.62-3.57 (m, 2H, H-6'a, H-1b), 3.38 (dd, 1H, $J_{1a,2}$=1.9, $J_{1a,1b}$=13.0, H-1a). $^{13}$C NMR (D$_2$O) δ: 78.5 (C-3'), 75.8 (C-2), 75.7 (C-3), 70.7 (C-5'), 69.6 (C-4'), 68.8 (C-5), 68.1 (C-2'), 65.5 (C-4), 63.4 (C-6'), 62.8 (C-6), 47.7 (C-1'), 40.2 (C-1).). HRMS. Calcd. for C$_{12}$H$_{25}$O$_9$Se (M+H—SO$_3$): 393.0658; Found: 393.0656.

1,4-Anhydro-1-[(S)-[(2R',3S',4R',5R')-2',4',5',6'-tetrahydroxy-3'-(sufooxy)hexyl]sulfonio]-D-allitol Inner Salt (150)

To a solution of 172 (500 mg, 0.79 mmol) in CH$_2$Cl$_2$ (2 mL) was added TFA (10 mL). After removing the cleaved protecting groups, the remaining gum was then dissolved in AcOH (10 mL), Pd/C (10%, 100 mg) was added, and the reaction mixture was subjected to hydrogenolysis to give compound 150 as a colorless, amorphous, and hygroscopic solid (140 mg, 42%). $[\alpha]^{22}_D$ −32 (c 2, H$_2$O); $^1$H NMR (D$_2$O) δ: 4.53 (m, 1H, H-2), 4.51 (dd, 1H, $J_{2,3}$=5.1, $J_{3,4}$=1.1, H-3'), 4.44 (ddd, 1H, H-2'), 4.26 (dd, 1H, $J_{2,3}$=9.6, $J_{3,4}$=3.1, H-3), 4.12 (ddd, 1H, H-5), 3.95 (dd, 1H, $J_{1'b,2'}$=10.8, $J_{1'a,1'b}$=13.4, H-1'b), 3.88 (dd, 1H, $J_{1'a,2'}$=2.8, H-1'a), 3.86 (dd, 1H, $J_{4,5}$=8.2, H-4), 3.74 (dd, 1H, $J_{4,5'}$=9.2, H-4'), 3.72 (dd, 1H, $J_{5,6b}$=3.1, $J_{6a,6b}$=11.9, H-6b), 3.67 (dd, 1H, $J_{5',6'b}$=2.5, $J_{6'a,6'b}$=11.8, H-6'b), 3.66-3.63 (m, 1H, H-5'), 3.59 (dd, 1H, $J_{5,6a}$=3.9, H-6a), 3.52-3.46 (m, 3H, H-1a, H-1b, H-6'a). $^{13}$C NMR (D$_2$O) δ: 77.7 (C-3'), 76.1 (C-3), 72.8 (C-2), 70.4 (C-5'), 68.9 (C-4'), 67.8 (C-2'), 67.4 (C-5), 64.6 (C-6), 64.3 (C-4), 62.7 (C-6'), 49.3 (C-1'), 44.4 (C-1 HRMS. Calcd. for C$_{12}$H$_{25}$O$_9$S (M+H—SO$_3$): 345.1214; Found: 345.1214.

1,4-Anhydro-1-[(S)-[(2R',3S',4R',5R)-2',4',5',6'-tetrahydroxy-3'-(sufooxy)hexyl]selenonio]-L-allitol Inner Salt (151)

To a solution of 173 (600 mg, 0.88 mmol) in CH$_2$Cl$_2$ (2 mL) was added TFA (10 mL). After removing the cleaved protecting groups, the remaining gum was then dissolved in AcOH (10 mL), Pd/C (10%, 100 mg) was added, and the reaction mixture was subjected to hydrogenolysis to give compound 151 as a colorless, amorphous, and hygroscopic solid (197 mg, 47%). $[\alpha]^{22}_D$ −22 (c 1, $H_2O$); $^1H$ NMR ($D_2O$) δ: 4.76 (ddd, 1H, H-2), 4.57 (dd, 1H, $J_{2,3}$=5.2, H-3'), 4.50 (ddd, 1H, H-2'), 4.37 (dd, 1H, $J_{2,3}$=9.1, $J_{3,4}$=3.0, H-3), 4.25 (ddd, 1H, H-5), 4.06 (dd, 1H, $J_{4,5}$=7.9, H-4), 4.00 (dd, 1H, $J_{1'b,2}$=4.0, $J_{1'a,1'b}$=12.4, H-1'b), 3.89 (dd, 1H, $J_{1'a,2}$=9.0, H-1'a), 3.84-3.79 (m, 1H, H-5'), 3.72 (d, 2H, H-6a, H-6b), 3.63 (dd, 1H, H-4'), 3.60-3.50 (m, 3H, H-6'b, H-6'a, H-1b), 3.34 (dd, 1H, $J_{1a,2}$=2.7, $J_{1a,1b}$=13.0, H-1a). $^{13}C$ NMR ($D_2O$) δ: 78.3 (C-3'), 76.0 (C-3), 75.4 (C-2), 73.1 (C-5'), 69.8 (C-4'), 68.2 (C-5), 67.1 (C-2'), 64.7 (C-4), 62.8 (C-6), 62.6 (C-6'), 47.4 (C-1'), 40.2 (C-1). HRMS. Calcd. for $C_{12}H_{25}O_9Se$ (M+H—$SO_3$): 393.0658; Found: 393.0656.

1,4-Anhydro-1-[(S)-[(2R',3S',4R',5R)-2',4',5',6'-tetrahydroxy-3'-(sufooxy)hexyl]sulfonio]-L-allitol Inner Salt (152)

To a solution of 174 (600 mg, 0.95 mmol) in $CH_2Cl_2$ (2 mL) was added TFA (10 mL). After removing the cleaved protecting groups, the remaining gum was then dissolved in AcOH (10 mL), Pd/C (10%, 100 mg) was added, and the reaction mixture was subjected to hydrogenolysis to give compound 152 as a colorless, amorphous, and hygroscopic solid (165 mg, 41%). $[\alpha]^{22}_D$ −32 (c 1, $H_2O$); $^1H$ NMR ($D_2O$) δ: 4.58 (ddd, 1H, H-2), 4.55 (dd, 1H, $J_{2,3}$=4.6, $J_{3,4}$=0.7, H-3'), 4.49 (ddd, 1H, H-2'), 4.42 (dd, 1H, $J_{2,3}$=8.7, $J_{3,4}$=3.2, H-3), 4.25 (ddd, 1H, H-5), 4.03 (dd, 1H, $J_{1'b,2}$=3.8, H-1'b), 4.04-3.99 (m, 1H, H-4), 3.92 (dd, 1H, $J_{1'a,2}$=9.1, $J_{1'a,1'b}$=13.5, H-1'a), 3.79 (dd, 1H, $J_{4,5}$=8.0, H-4'), 3.68 (dd, 1H, $J_{5',6'b}$=2.4, H-6'b), 3.68-3.64 (m, 1H, H-5'), 3.67 (d, 2H, H-6a, H-6b), 3.61 (dd, 1H, $J_{1b,2}$=3.2, $J_{1a,1b}$=14.2, H-1b), 3.52 (dd, 1H, $J_{5',6'a}$=5.6, $J_{6a,6b}$=11.5, H-6'a), 3.44 (dd, 1H, $J_{1a,2}$=8.0, H-1a). $^{13}C$ NMR ($D_2O$) δ: 77.7 (C-3'), 74.8 (C-3), 74.4 (C-2), 70.5 (C-5'), 69.1 (C-4'), 68.3 (C-5), 67.0 (C-2'), 65.0 (C-4), 62.8 (C-6'), 62.7 (C-6), 49.9 (C-1'), 43.9 (C-1). HRMS. Calcd. for $C_{12}H_{25}O_9S$ (M+H—$SO_3$): 345.1214; Found: 345.1211.

5.2.11 Example 11

Synthesis of Salacinol Analogues containing a Pendant Hydroxymethyl Group (Schemes 39 to 41)

General: Optical rotations were measured at 23° C. $^1H$ and $^{13}C$-NMR spectra were recorded at 500 and 125 MHz, respectively. All assignments were confirmed with the aid of two dimensional experiments ($^1H$-$^1H$ COSY, HMQC, HMBC) using standard Varian pulse programs. Processing of the spectra was performed at Mestrac software. Column chromatography was performed with Merck silica gel 60 (230-400 mesh) and thin layer chromatography (TLC) was performed on aluminium plates precoated with E. Merck Silica Gel 60F-254 as the absorbent. MALDI-TOF mass spectra were recorded on a perSeptive Biosystems Voyager-DE spectrometer, using 2,5-dihydroxybenzoic acid as a matrix.

2,5-Dideoxy-2,5-N-benzylimino-1,3; 4,6-di-O-benzylidene-L-iditol (186)

The compound 185 (3.2 g, 5.89 mmol) in benzylamine (10 ml) was stirred at 130° C. for 12 h. The excess benzylamine was removed under high vacuum and the residue was purified by flash column chromatography to yield compound 186 (2.14 g, 84%) as a white solid. mp 118-120° C. (lit. 120° C.); $[\alpha]_D$ +9° (c 1.60, $CHCl_3$; lit[10]. $[\alpha]_D$ +90.6 (c 0.32, $CHCl_3$)). The spectral data were in with those reported.

2,5-Dideoxy-2,5-imino-1,3:4,6-di-O-benzylidene-L-iditol (180)

2,5-Dideoxy-2,5-N-benzylimino-1,3:4,6-di-O-benzylidene-L-iditol (186, 1.98 g, 4.6 mmol) was dissolved in 100 ml EtOAc:MeOH (1:1), and 20% Pd(OH)$_2$/C (200 mg) was added. The solution was stirred under an atmosphere of $H_2$ for 3 h. The catalyst was removed by filtration, the solvents were removed under vacuum, and the residue was purified by flash chromatography (EtOAc:MeOH, 20:1) to afford 180 (1.42 g, 90%) as a white solid. mp 130-131° C. (lit. 130° C.); $[\alpha]_D$ +15.2 (c 1.00, $CHCl_3$; lit[10]. $[\alpha]_D$=+7.7 (c 0.5, $CHCl_3$)). The spectral data were in with those reported.

1,3:4,6-Di-O-benzylidine-2,5-dideoxy-1,5-[[(2S,3S)-2,4-O-benzylidene-2,4-dihydroxy-3-(sulfooxy)butyl]sulfoniumylidene]-L-iditol Inner salt (187)

To 1,1,1,3,3,3-hexafluoro propanol (2 ml) were added 1,3;4,6-di-O-benzylidene-2,5-dideoxy-1,5-thio-L-iditol (179) (282 mg, 0.79 mmol), 2,4-O-benzylidine-L-erythritol-1,3-cyclic-sulfate (181) (260 mg. 0.94 mmol), and $K_2CO_3$ (45 mg) in a sealed tube and the reaction mixture was stirred for 48 h at 75° C. The solvent was removed and the crude product was purified by column chromatography (EtOAc:MeOH, 15:1) to afford the coupled product 187 as a colorless foam (405 mg, 81%) $^1H$-NMR ($CDCl_3$): δ 5.54, 5.52, 5.42 (3H, 3×Ph-CH—), 4.94 (2H, d, $J_{1a,1b}$=14.0, $J_{1'a,1'b}$=14.0 Hz, H-1a, H-1a'), 4.80 (1H, brs, H-3), 4.79 (1H, brs, H-4), 4.66 (1H, d, $J_{6a,6b}$=14.0 Hz, H-6a), 4.56 (1H, dd, $J_{4a',4}b'$=10.3, $J_{3',4a}$=5.6 Hz, H-4a'), 4.48 (1H, ddd, $J_{3',4a}$=5.6, $J_{3',4b}$=10.7, $J_{3,2}$=9.7 Hz, H-3'), 4.37 (1H, ddd, $J_{2',1a'}$=3.0, $J_{2',1b}$=6.1 Hz, H-2'), 4.32 (1H, brs, H-5), 4.30 (1H, dd, $J_{1b,2}$=3.2 Hz, H-1b), 4.21 (1H, brs, H-2), 4.13 (1H, dd, H-1b'), 3.97 (1H, dd, $J_{6b,5}$=1.8 Hz, H-6b), 3.75 (1H, dd, H-4b'). $^{13}C$-NMR ($CD_2Cl_2$): δ 136.2-126.3 (18C), 101.5, 100.8, 100.4 (3H, Ph-CH—), 83.0 (C-3), 80.6 (C-4), 76.8 (C-2'), 69.0 (C-4'), 65.6 (C-3'), 64.0 (C-5), 63.9 (C-6), 63.4 (C-1), 54.3 (C-2), 47.4 (C-1'). MALDI-MS: m/e 651.20 (M$^+$+Na), 629.48 (M$^+$+H), 549.37 (M$^+$+H–$SO_3$). HRMS Calcd. for $C_{31}H_{32}O_{10}S_2Na$ (M+Na): 651.1329. Found: 651.13263.

2,5-Dideoxy-1,5-[[(2S,3S)-2,4-dihydroxy-3-(sulfooxy)butyl]sulfoniumylidene]-L-iditol Inner salt (175)

Compound 187 (220 mg, 0.35 mmol) was dissolved in a $CH_2Cl_2$ (1 ml) and 50% aqueous TFA (15 ml) was added and the mixture was stirred at room temperature for 2 h. The solvents were removed by high vacuum to give a brown gummy product. Purification by column chromatography (EtOAc:MeOH, 10:1) gave 175 as an amorphous solid (109 mg, 85%). $^1H$-NMR ($D_2O$): δ 4.58 (1H, dd, $J_{3,2}$=2.4, $J_{3,4}$=2.2 Hz, H-3), 4.50 (1H, dd, $J_{4,5}$=2.3 Hz, H-4), 4.44 (1H, ddd, $J_{5,6}a$=5.0, $J_{5,6b}$=9.0 Hz, H-5), 4.41 (1H, dd, $J_{2,1a}$=6.2, $J_{2,1b}$=9.6 Hz, H-2), 4.27 (1H, ddd, $J_{2',1b}$=7.6, $J_{2',1a}$=10.5, $J_{2',3}$=2.2 Hz, H-2'), 4.16 (1H, dd, $J_{6a,6b}$=12.4 Hz, H-6a), 4.14 (1H, ddd, $J_{3',4a}$=3.2, $J_{3',4b}$=3.2 Hz, H-3'), 4.07 (1H, dd, $J_{1a,1b}$=14.0 Hz, H-1b'), 4.04 (1H, dd, $J_{1a,1b}$=12.4 Hz, H-1a), 4.02 (1H, dd, H-1b), 4.00 (1H, dd, H-6b), 3.82 (1H, dd, $J_{4a',4b}$=12.8 Hz, H-4a'), 3.72 (1H, dd, H-4b'), 3.39 (1H, H-1b'). $^{13}C$-NMR ($D_2O$): δ 80.9 (C-3'), 78.4 (C-4), 76.9 (C-3), 70.0 (C-2), 66.6 (C-2'), 63.1 (C-5), 59.7 (C-4'), 57.7 (C-1), 55.5 (C-6), 44.8 (C-1'). MALDI-MS: m/e 387.15 (M$^+$+

1,3:4,6-Di-O-benzylidene-2,5-dideoxy-1,5-[[(2R, 3R)-2,4-O-benzylidene-2,4-dihydroxy-3-(sulfoxy) butyl]sulfoniumylidene]-L-iditol Inner salt (188)

The thio-L-iditol (179) (240 mg, 0.67 mmol) was coupled to 2,4-O-benzylidene-D-erythritol-1,3-cyclic-sulfate (182) (214 mg, 0.78 mmol) in HFIP (2 ml) following the same procedure that was used for the synthesis of 187. Column chromatography (EtOAc: MeOH, 15:1) of the crude product gave 188 as an amorphous solid (338 mg, 79%). $^1$H-NMR (CD$_2$Cl$_2$): δ 5.74 (1H, Ph-CH—), 5.62, 5.46 (2H, Ph-CH—), 5.20 (1H, d, $J_{1a,1b}$=14.8 Hz, H-1a), 4.98 (1H, brs, H-3), 4.87 (1H, brs, H-4), 4.78 (1H, d, $J_{1a',1b}$=13.9 Hz, H-1a'), 4.72 (1H, ddd, $J_{3',2'}$=9-5, $J_{3',4a'}$=10.5 Hz, H-3'), 4.62 (1H, dd, $J_{1b,2}$=3.1 Hz, H-1b), 4.58 (1H, dd, $J_{4a',4b'}$=10.5 Hz, H-4a'), 4.56 (1H, brs, H-2), 4.45 (1H, dd, $J_{2',1b}$=3.0 Hz, H-2'), 4.30 (1H, d, $J_{6a,6b}$=14.0 Hz, H-6a), 4.06 (1H, brs, H-5), 3.89 (1H, dd, H-1b'), 3.83 (1H, d, H-4b'), 3.79 (1H, dd, H-6b). $^{13}$C NMR (CD$_2$Cl$_2$): δ 136.2-126.3 (18C), 101.5, 100.8, 100.4 (3H, Ph-CH—), 83.0 (C-3), 80.6 (C-4), 76.8 (C-2'), 69.0 (C-4'), 65.6 (C-3'), 64.0 (C-5), 63.9 (C-6), 63.4 (C-1), 54.3 (C-2), 47.4 (C-1'). MALDI-MS: m/e 651.20 (M$^+$+Na), 629.48 (M$^+$+1), 549.37 (M$^+$−SO$_3$). HRMS Calcd. for C$_{31}$H$_{32}$O$_{10}$S$_2$Na (M+Na): 651.13291. Found: 651.13289.

2,5-Dideoxy-1,5-[[(2R,3R)-2,4-dihydroxy-3-(sulfooxy)butyl]sulfoniumylidene]-L-iditol Inner salt (176)

Compound 188 (190 mg, 0.30 mmol) was dissolved in CH$_2$Cl$_2$ (1 ml) and 50% aqueous TFA (15 ml) was added and stirred at room temperature for 2.5 h. The solvents were removed by high vacuum to give a brown residue which was purified by column chromatography (EtOAc:MeOH, 10:1) to give 176 as an amorphous solid (83 mg, 76%). $^1$H NMR (D$_2$O): δ 4.60 (1H, dd, $J_{3,2}$=2.4, $J_{3,4}$=3.4 Hz, H-3), 4.50 (1H, $J_{4,5}$=2.1 Hz, H-4), 4.47 (1H, dd, $J_{5,6}$a=5.3, $J_{5,6b}$=9.8 Hz, H-5), 4.34 (1H, ddd, $J_{2,1a}$=4.8, $J_{2,1b}$=9.6 Hz, H-2), 4.30 (1H, ddd, $J_{2,1b}$=10.5, $J_{2',1a'}$=2.0, $J_{2',3'}$=3.6 Hz H-2'), 4.18 (1H, ddd, $J_{3',4a'}$=3.4, $J_{3',4b'}$=3.3 Hz, H-3'), 4.11 (1H, dd, $J_{1a',1b'}$=12.6 Hz, H-1a'), 4.04 (1H, d, $J_{1a,1b}$=12.5 Hz, 12.5 Hz, H-1a), 3.98 (1H, dd, H-6b), 3.88 (1H, dd, H-1b), 3.83 (1H, dd, $J_{1a',1b'}$=13.0 Hz, H-1a'), 3.82 (1H, dd, $J_{4a',4b'}$=12.8 Hz, H-4a'), 3.73 (1H, dd, H-4b'), 3.38 (1H, dd, H-1b'). $^{13}$C NMR (D$_2$O): δ 80.6 (C-3'), 78.1 (C-4), 77.1 (C-3), 70.2 (C-2), 64.5 (C-2'), 62.5 (C-5), 59.7 (C-4'), 57.8 (C-6), 55.5 (C-1), 44.0 (C-1'). MALDI-MS: m/e 651.20 (M$^+$+Na), 629.48 (M$^+$+H), 549.37 (M$^+$+H−SO$_3$). HRMS Calcd. for C$_{31}$H$_{32}$O$_{10}$S$_2$Na (M+Na): 387.03901. Found: 387.03904.

1,3:4,6-Di-O-benzylidene-2,5-dideoxy-1,5-[[(2S, 3S)-2,4-O-benzylidene-2,4-dihydroxy-3-(sulfooxy) butyl]iminonium]-L-iditol Inner salt (189)

The imino alditol 180 (260 mg, 0.76 mmol) and the cyclic sulfate 181 (228 mg, 0.83 mmol) were added to anhydrous acetone (2 ml) containing K$_2$CO$_3$ (50 mg) and the mixture was stirred in a sealed tube for 12 h at 65° C. The solvent was removed and the mixture was purified by column chromatography. The coupled product 189 was obtained as a colorless foam (398 mg, 85%). $^1$H NMR (d6-Acetone, pH>8): δ 7.40-7.20 (15H), 5.57 (2H, 2×Ph-CH—), 5.48 (1H, Ph-CH—), 4.69 (2H, d, $J_{1a,1b\ (6a,6b)}$=12.8 Hz, H-1a, H-6a), 4.60 (1H, m, H-4a'), 4.35 (2H, brs, H-3, H-4), 4.20 (1H, m, H-3'), 4.02 (2H, d, H-1b, H-6b), 3.98 (1H, d, $J_{1a',1b}$=12.5 Hz, H-1a'), 3.91 (1H, m, H-2'), 3.68 (1H, m, H-4b'), 3.44 (2H, brs, H-2, H-5), 2.98 (1H, m, H-1b'). MALDI-MS: m/e 633.58 (M$^+$+Na), 611.66 (M$^+$+H), 531.76 (M$^+$+H—SO$_3$).

2,5-Dideoxy-1,5-[[(2S,3S)-2,4-dihydroxy-3-(sulfooxy)butyl]iminonium]-L-iditol Inner salt (177)

Compound 189 (230 mg, 0.37 mmol) was dissolved in a 4:1 mixture of CH$_3$COOH:H$_2$O (20 ml) and the solution was stirred with 10% Pd/C (180 mg) under 1 atm of H$_2$ for 30 h. The catalyst was removed by filtration through a silica bed, and washed with water (25 ml). The filtrate was evaporated, and the mixture was purified by column chromatography (EtOAc:MeOH:H$_2$O, 10:3:1) to give an amorphous solid (177) (112 mg, 86%). $^1$H NMR (D$_2$O, pH>8): δ 4.20 (3H, m, H-3, H-4, H-3'), 4.00 (1H, ddd, $J_{2',3}$=2.2, $J_{2',1a}$=5.6, $J_{2',1b}$=10.2 Hz, H-2'), 3.81 (1H, dd, $J_{4a',3}$=3.5, $J_{4a',4b}$=12.6 Hz, H-4a'), 3.75 (1H, dd, $J_{4b',3}$=4.7 Hz, H-4b'), 3.70 (2H, dd, $J_{1a,1b\ (6a,6b)}$=12.1, $J_{1a,2\ (6a,5)}$=4.3 Hz, H-1a, H-6a), 3.59 (2H, dd, $J_{1b,2\ (6b,5)}$=3.0 Hz, H-1b, H-6b), 3.16 (3H, m, H-2, H-5, H-1a'), 2.59 (1H, dd, $J_{1b',1a}$=13.9 Hz, H-1b'). $^{13}$C NMR: δ 81.6 (C-3'), 76.3 (C-3, C-4), 67.3 (C-2'), 62.4 (C-2, C-5), 60.0 (C-4'), 58.1 (C-1, C-6), 50.9 (C-1'). MALDI-MS: m/e 371.28 (M$^+$+Na), 348.43 M$^+$+H), 268.32 (M$^+$+H—SO$_3$). Anal. Calcd for C$_{10}$H$_{21}$NO$_{10}$S: C, 34.58; H, 6.09; N, 4.03. Found: C, 34.82; H, 5.89; N, 3.94.

4,6-Di-O-benzylidene-2,5-dideoxy-1,5-[[(2R,3R)-2, 4-O-benzylidene-2,4-dihydroxy-3-(sulfooxy)butyl] iminonium]-L-iditol Inner salt (190)

The imino alditol (180) (210 mg, 0.61 mmol) was reacted with 2,4-O-benzylidene-L-erythritol-1,3-cyclicsulfate (192 mg, 0.70 mmol) in acetone (2 ml) following the same procedure that was used for the synthesis of 189. Column chromatography (EtOAc: MeOH, 15:1) of the crude product gave 190 as an amorphous solid (338 mg, 89%). $^1$H NMR (d6-Acetone, pH>8): δ 7.38-7.20 (1SH), 5.60, 5.55 (3H, 3×Ph—CH—), 4.68 (2H, d, $J_{1a,1b\ (6a,6b)}$=12.7 Hz, H-1a, H-6a), 4.57 (1H, dd, $J_{4a',4b}$=10.7, $J_{4a',3}$=5.4 Hz, H-4a'), 4.34 (2H, brs, H-3, H-4), 4.24 (1H, m, H-3'), 4.00 (2H, d, H-1b, H-6b), 3.94 (2H, m, H-1a', H-2'), 3.66 (1H, dd, $J_{4b',3}$=10.4 Hz, H-4b'), 3.52 (2H, brs, H-2, H-5), 3.46 (1H, brs, H-1b'). MALDI-MS: m/e 633.85 (M$^+$+Na), 611.91 (M$^+$+H), 531.99 (M$^+$+H−SO$_3$).

2,5-Dideoxy-1,5-[[(2R,3R)-2,4-dihydroxy-3-(sulfooxy)butyl]iminonium]-L-iditol Inner salt (178)

Compound 190 (216 mg, 0.35 mmol) was dissolved in a 4:1 mixture of CH$_3$COOH:H$_2$O (20 ml) and the solution was stirred with 10% Pd/C (160 mg) under 1 atm of H$_2$ for 44 h. The catalyst was removed by filtration through a silica bed, and washed with water (30 ml). The filtrate was evaporated, and the micture was purified by column chromatography (EtOAc:MeOH:H$_2$O, 10:3:1) to give an amorphous solid (178) (103 mg, 83%). $^1$H NMR (D$_2$O, pH>8): δ 4.29 (1H, ddd, $J_{3,2}$=2.1, $J_{3',4a'}$=3.4, $J_{3',4b}$=5.1 Hz, H-3'), 4.19 (2H, m, H-3, H-4), 4.03 (1H, ddd, $J_{2',1a}$=7.7, $J_{2',1b}$=5.6 Hz, H-2'), 3.82 (1H, dd, $J_{4a',4b}$=12.7 Hz, H-4a'), 3.74 (1H, dd, H-4b'), 3.73 (2H, dd, $J_{1a,1b\ (6a,6b)}$=12.0, $J_{1a,2}$ (6a,5)=6.2 Hz, H-1a, H-6a), 3.61 (2H, dd, H-1b, H-6b), 3.17 (2H, m, H-2, H-5), 2.94 (1H, dd, $J_{1a',1b}$=3.9 Hz, H-1a'), 2.85 (1H, dd, H-1b'). $^{13}$C NMR: δ 81.5 (C-3'), 76.2 (C-3, C-4), 69.9 (C-2'), 63.8 (C-2, C-5), 59.8 (C-4'), 58.4 (C-1, C-6), 51.0 (C-1'). MALDI-MS: m/e 371.52 (M$^+$+Na), 348.2 (M+), 268.18 (M+−SO$_3$). Anal. Calcd for C$_{10}$H$_{21}$NO$_{10}$S: C, 34.58; H, 6.09; N, 4.03. Found: C, 34.27; H, 6.27; N, 3.81.

5.2.12 Example 12

Synthesis of Chain-Extended Analogues of Salacinol Having Differing Stereochemistry at the Stereogenic Centers (Schemes 42 to 48)

General. Optical rotations were measured at 23° C. $^1$H and $^{13}$C NMR spectra were recorded at 500 and 125 MHz respectively. All assignments were confirmed with the aid of two-dimensional $^1$H, $^1$H(COSYDFTP) or $^1$H, $^{13}$C (INVBTP) experiments using standard Bruker pulse programs. Column chromatography was performed with Merck Silica gel 60 (230-400 mesh). MALDI mass spectra were obtained on a PerSeptive Biosystems, Voyager DE time-of-flight spectrometer for samples dispersed in a 2,5-dihydroxybenzoic acid matrix. High resolution mass spectra were obtained by the electrospray ionization (ESI) technique, using a ZabSpec oaTOF mass spectrometer at 10000 RP.

2,4-O-benzylidene-5,6-O-isopropylidene-D-glucitol-1,3-cyclic sulfate (197)

The 2,4-O-benzylidene-5,6-O-isopropylidene-D-glucitol (200) was prepared by the literature method.[94] To a solution of 200 (4.7 g, 15 mmol) in $CH_2Cl_2$ (80 mL) was added pyridine (10 mL) at room temperature. Thionyl chloride (1.65 mL, 22 mmol) dissolved in $CH_2Cl_2$ (20 mL) was then added and the mixture was heated at 40-50° C. for 4 h. The progress of the reaction was followed by TLC analysis of aliquots (developing solvent Hexane:EtOAc, 2:1). When starting material 200 had been essentially consumed, the reaction mixture was cooled, then poured into ice water, extracted with $CH_2Cl_2$ (100 mL), washed with brine (20 mL), and dried over $Na_2SO_4$. After evaporating the solvent, the crude sulfite was passed through a short silica gel column. The resulting sulfite was redissolved in a mixture of $CH_3CN$, $CCl_4$, and water ($CH_3CN$:$CCl_4$:$H_2O$, 3:3:0.5, 65 mL). Ruthenium(III) chloride (50 mg) was then added to the solution. At room temperature, $NaIO_4$ (4.26 g, 20 mmol) was added to the mixture and the mixture was stirred for 2 h. When TLC analysis of aliquots (developing solvent Hexane:EtOAc, 1:1) showed total consumption of the starting material, the reaction mixture was filtered through a short column of silica gel and the silical gel was washed with $CH_2Cl_2$ (100 mL). The filtrate was combined and evaporated to dryness. It was then redissolved in EtOAc (100 mL), washed with water (50 mL), and dried over $Na_2SO_4$. Purification by column chromatography (Hexane:EtOAc, 1:1), followed by recrystallization with Hexane/EtOAc yielded 197 as a colorless, crystalline solid (3.9 g, 70%). Mp 126-128° C. (decomp.); $[\alpha]_D$ +12.3 (c 1.1, $CH_2Cl_2$); $^1$H NMR ($CD_2Cl_2$) δ: 7.50-7.30 (m, 5H, Ar.), 5.73 (s, 1H, Cl/Ph), 5.07 (br.t, 1H, $J_{3,4}$=1.4, H-4), 4.98 (dd, 1H, $J_{5,6b}$=1.8, $J_{6a,6b}$=12.6, H-6b), 4.72 (dd, 1H, $J_{5,6a}$=1.3, H-6a), 4.36 (ddd, 1H, $J_{1a,2}$=3.6, $J_{1b,2}$=6.0, $J_{2,3}$=8.9, H-2), 4.13 (dd, 1H, $J_{1a,1b}$=9.0, H-1b), 4.09 (m, 1H, H-5), 4.08 (dd, 1H, H-1a), 3.94 (dd, 1H, H-3). $^{13}$C NMR ($CD_2Cl_2$) δ: 136.7, 129.8, 128.6, and 126.4 (4C, Ar.), 110.2 (($CH_3$)$_2$C), 101.0 (CHPh), 78.0 (C-3), 77.2 (C-4), 75.4 (C-6), 71.7 (C-2), 67.9 (C-5), 66.7 (C-1), 27.1, and 24.8 (2 $CH_3$). Anal. Calcd for $C_{16}H_{20}O_8S$: C, 51.60; H, 5.41. Found: C, 51.56; H, 5.41.

N-Allyl-2,3,5-O-p-methoxybenzyl-1,4-dideoxy-1,4-imino-D-arabinitol (211)

The dimesylate (210) was prepared by a literature method.[88,89] To a solution of the dimesylate 210 (8.0 g, 12.0 mmol) in DMF (30 mL), allylamine (10 mL, 0.13 mol) was added and the reaction mixture was heated at 90° C. for 12 h. The reaction mixture was poured into water (100 mL), extracted with $Et_2O$ (4×50 mL), washed with water (10×20 mL), and dried over $Na_2SO_4$. After evaporating the solvent, the crude product was purified by column chromatography (Hexane:EtOAc, 1:1) to give 211 as a colorless oil (5.4 g, 85%). $[\alpha]_D$ −8.6 (c 2.2, $CH_2Cl_2$); $^1$H NMR (CDCl$_3$) δ: 7.20-6.70 (m, 12H, Ar.), 5.85 (dddd, 1H, $J_{1a',2'}$=7.4, $J_{1b',2'}$=5.8, $J_{2',3a'}$=9.9, $J_{2',3b'}$=17.1, H-2'), 5.10 (d, 1H, H-3b'), 5.02 (d, 1H, H-3a'), 4.34 (s, 2H, $CH_2Ph$), 4.38 and 4.28 (two d, 2H, $J_{AB}$=12.0, $CH_2Ph$), 3.82 (m, 2H, $CH_2Ph$), 3.80 (dd, 1H, $J_{2,3}$=4.0, $J_{1a,2}$=4.8, H-2), 3.76 (dd, 1H, $J_{3,4}$=5.1, H-3), 3.72, 3.71, and 3.70 (three s, 9H, 3 OCH$_3$), 3.48 (dd, 1H, $J_{4,5b}$=5.2, $J_{5a,5b}$=9.8, H-5b), 3.44 (dd, 1H, H-1b'), 3.40 (dd, 1H, $J_{4,5a}$=6.6, H-5a), 3.05 (d, 1H, $J_{1a,1b}$=10.4, H-1b), 2.92 (dd, 1H, $J_{1a',2'}$=7.4, $J_{1a',1b'}$=12.8, H-1a'), 2.64 (m, 1H, H-4), 2.50 (dd, 1H, H-1a). $^{13}$C NMR ($CD_2Cl_2$) δ: 159.4, 159.3, 159.2, 133.2, 133.1, 132.9, 130.8, 130.7, 130.6, 128.3, 112.0, and 111.9 (12 C, Ar.), 135.9 (C-2'), 114.0 (C-3'), 85.5 (C-3), 81.2 (C-2), 73.0, 71.2 (2 $CH_2Ph$), 70.8 (C-5), 68.6 (C-4), 58.3 (C-1'), 57.3 (C-1), 56.5 ($CH_2Ph$), 55.5 (3 OCH$_3$). Anal. Calcd for $C_{32}H_{39}NO_6$: C, 72.02; H, 7.37; N, 2.62. Found: C, 71.74; H, 7.16; N, 2.84.

N-Allyl-2,3,5-O-p-methoxybenzyl-1,4-dideoxy-1,4-imino-L-arabinitol (215)

The dimesylate (214) was prepared by a literature method.[88,89] To a solution of the dimesylate 214 (3.6 g, 5.4 mmol) in DMF (30 mL), allylamine (10 mL, 0.13 mol) was added and the reaction mixture was heated at 90° C. for 12 h. The reaction mixture was poured into water (100 mL), extracted with $Et_2O$ (4×50 mL), washed with water (10×20 mL), and dried over $Na_2SO_4$. After evaporating the solvent, the crude product was purified by column chromatography (Hexane:EtOAc, 1:1) to give 215 as a colorless oil (2.5 g, 85%). $[\alpha]_D$ +15.7 (c 3.0, $CH_2Cl_2$); $^1$H NMR (CDCl$_3$) δ: 7.30-6.80 (m, 12H, Ar.), 5.93 (dddd, 1H, $J_{1a',2'}$=7.3, $J_{1b',2'}$=5.6, $J_{2',3a'}$=9.9, $J_{2',3b'}$=17.1, H-2'), 5.18 (d, 1H, H-3b'), 5.10 (d, 1H, H-3a'), 4.46 and 4.43 (two d, 2H, $J_{AB}$=12.1, $CH_2Ph$), 4.41 (s, 2H, $CH_2Ph$), 4.41 and 4.36 (two d, 2H, $J_{AB}$=11.9, $CH_2Ph$), 3.85 (m, 1H, H-2), 3.83 (m, 1H, H-3), 3.80, 3.79, and 3.78 (three s, 9H, 3 OCH$_3$), 3.56 (dd, 1H, $J_{4,5b}$=5.5, $J_{5a,5b}$=10.9, H-5b), 3.52 (m, 1H, H-1b'), 3.48 (dd, 1H, $J_{4,5a}$=6.3, H-5a), 3.12 (d, 1H, H-1b), 3.00 (dd, 1H, $J_{1a',1b'}$=12.9, H-1a'), 2.72 (m, 1H, H-4), 2.56 (dd, 1H, $J_{1a,2}$=4.8, H-1a). $^{13}$C NMR ($CD_2Cl_2$) δ: 159.4, 159.3, 159.2, 130.9, 130.8, 130.7, 130.6, 130.5, 129.6, 129.5, 112.0, and 111.9 (12C, Ar.), 135.9 (C-2'), 114.0 (C-3'), 85.5 (C-3), 81.2 (C-2), 73.0, 71.2 (2 $CH_2Ph$), 70.8 (C-5), 68.6 (C-4), 58.4 (C-1'), 57.4 (C-1), 55.5 ($CH_2Ph$), 55.4 (3 OCH$_3$). Anal. Calcd for $C_{32}H_{39}NO_6$: C, 72.02; H, 7.37; N, 2.62. Found: C, 71.89; H, 7.04; N, 2.63.

2,3,5-O-p-Methoxybenzyl-1,4-dideoxy-1,4-imino-D-arabinitol (212)

To a solution of the N-allyl compound 211 (5.0 g, 9.3 mmol) in 90% $CH_3CN$ (50 mL), Wilkinson's catalyst (Rh (PPh)$_3$Cl, 100 mg) was added and the reaction mixture was refluxed for 4 h. The solvent was removed under reduced pressure and the crude product was purified by column chromatography (Hexane:EtOAc, 1:1) to afford 212 as a colorless oil (3.5 g, 75%). $[\alpha]_D$ +0.8 (c 4.0, $CH_2Cl_2$); $^1$H NMR (CDCl$_3$) δ: 7.50-6.80 (m, 12H, Ar.), 4.46 (m, 2H, $CH_2Ph$), 4.47 and 4.43 (two d, 2H, $J_{AB}$=10.9, $CH_2Ph$), 4.49 and 4.41 (two d, 2H, $J_{AB}$=11.4, $CH_2Ph$), 3.97 (m, 1H, H-2), 3.82 (dd, 1H, $J_{2,3}$=4.3, $J_{3,4}$=3.0, H-3), 3.81, 3.80, 3.79 (three s, 3 OCH$_3$), 3.58 (dd, 1H, J$_{4,5b}$=5.0, J$_{5a,5b}$=9.5, H-5b), 3.53 (dd, 1H, J$_{4,5a}$=3.6, H-5a), 3.25 (dd, 1H, H-4), 3.09 (d, 2H, H-1a, H-1b). $^{13}$C NMR (CD$_2$Cl$_2$) δ: 159.5, 159.4, 159.3, 133.2, 133.1, 133.0, 130.5, 130.4, 130.3, 130.2, 114.0, and 111.9 (12C, Ar.), 85.3 (C-3), 84.1 (C-2), 73.1, 71.8, 70.9 (3 CH$_2$Ph), 70.1 (C-5), 64.2 (C-4), 55.5, 55.4, and 55.3 (3 OCH$_3$), 51.1 (C-1). Anal. Calcd for C$_{29}$H$_{35}$NO$_6$: C, 70.57; H, 7.15; N, 2.84. Found: C, 70.90; H, 7.21; N, 2.99.

2,3,5-O-p-methoxybenzyl-1,4-dideoxy-1,4-imino-L-arabinitol (216)

To a solution of the N-allyl compound 215 (3.0 g, 5.6 mmol) in 90% CH$_3$CN (50 mL), Wilkinson's catalyst (Rh (PPh)$_3$Cl, 100 mg) was added and the reaction mixture was refluxed for 4 h. The solvent was removed under reduced pressure and the crude product was purified by column chromatography (Hexane:EtOAc, 1:1) to give 216 as a colorless oil (1.9 g, 70%). [α]$_D$ −0.34 (c 0.6, CH$_2$Cl$_2$); $^1$H NMR (CDCl$_3$) δ: 7.24-6.84 (m, 12H, Ar.), 4.46 (m, 2H, CH$_2$Ph), 4.48 and 4.45 (two d, 2H, J$_{AB}$=11.5, CH$_2$Ph), 4.44 and 4.40 (two d, 2H, J$_{AB}$=11.5, CH$_2$Ph), 3.98 (m, 1H, H-2), 3.84 (dd, 1H, J$_{2,3}$=4.6, J$_{3,4}$=1.6, H-3), 3.82, 3.81, 3.80 (three s, 3 OCH$_3$), 3.58 (dd, 1H, J$_{4,5b}$=5.1, J$_{5a,5b}$=10.2, H-5b), 3.52 (dd, 1H, J$_{4,5a}$=5.7, H-5a), 3.20 (ddd, 1H, H-4), 3.06 (dd, 1H, J$_{1b,2}$=4.6, J$_{1a,1b}$=12.3, H-1b), 3.05 (dd, 1H, J$_{1a,2}$=3.0, H-1a). $^{13}$C NMR (CD$_2$Cl$_2$) δ: 159.5, 159.4, 159.3, 130.6, 130.5, 130.4, 129.6, 129.5, 129.4, 114.1, 114.0, and 113.9 (12C, Ar.), 85.5 (C-3), 84.4 (C-2), 73.1, 71.7, 70.9 (3 CH$_2$Ph), 70.2 (C-5), 64.3 (C-4), 55.5, 55.4, and 55.3 (3 OCH$_3$), 51.2 (C-1). Anal. Calcd for C$_{29}$H$_{35}$NO$_6$: C, 70.57; H, 7.15; N, 2.84. Found: C, 70.70; H, 6.95; N, 3.02.

General Procedure for the Preparation of Selenonium and Sulfonium Sulfates 203, 207, 204, and 208.

A mixture of the selenoarabinitol 201 or 205, or the thioarabinitol 202 or 206 and the cyclic sulfate 197 in HFIP (1,1,1,3,3,3-hexafluoroisopropanol) were placed in a reaction vessel and K$_2$CO$_3$ (20 mg) was added. The stirred reaction mixture was heated in a sealed tube at the indicated temperature for the indicated time, as given below. The progress of the reaction was followed by TLC analysis of aliquots (developing solvent EtOAc:MeOH, 10:1). When the limiting reagent had been essentially consumed, the mixture was cooled, then diluted with CH$_2$Cl$_2$ and evaporated to give a syrupy residue. Purification by column chromatography (EtOAc to EtOAc: MeOH, 10:1) gave the purified selenonium salts 203, 207 and sulfonium salts 204, 208.

2,3,5-Tri-O-p-methoxybenzyl-1,4-dideoxy-1,4-[[(2R,3S,4R,5R)-2,4-benzylidenedioxy-5,6-isopropylidenedioxy-3-(sulfooxy)hexyl]-episelenoniumylidene]-D-arabinitol Inner Salt (203)

Reaction of the selenoarabinitol 201 (500 mg, 0.89 mmol) with the cyclic sulfate 197 (430 mg, 1.1 mmol) in HFIP (2 mL) for 12 h at 65° C. gave compound 203 as a colorless, amorphous solid (790 mg, 95% based on 201). [α]$_D$ −39 (c 1.0, CH$_2$Cl$_2$); $^1$H NMR (CD$_2$Cl$_2$) δ: 7.50-6.80 (m, 17H, Ar.), 5.70 (s, 1H, CHPh), 4.60 (m, 1H, H-4'), 4.55 (dd, 1H, J$_{2,3}$=8.2, H-2'), 4.53-4.48 (m, 5H, H-3', 2CH$_2$Ph), 4.44 (m, 1H, H-2), 4.43 and 4.38 (two d, 2H, J$_{AB}$=11.4, CH$_2$Ph), 4.28 (m, 2H, H-3, H-6a), 4.25 (dd, 1H, J$_{1'a,1'b}$=11.8, J$_{1'b,2'}$=1.9, H-1'b), 4.23-4.17 (m, 3H, H-5', H-4, H-6'b), 4.00 (dd, 1H, J$_{4,5a}$=5.9, J$_{5a,5b}$=9.8, H-5a), 3.92 (dd, 1H, J$_{1'a,2'}$=5.9, J$_{1'a,1'b}$=11.8, H-1'a), 3.80 (m, 1H, H-5b), 3.81, 3.80, and 3.79 (three s, 9H, 3 OCH$_3$), 3.52 (dd, 1H, J$_{1b,2}$=1.1, J$_{1a,1b}$=12.3, H-1b), 3.30 (dd, J$_{1a,2}$=3.3, 1H, H-1a), 1.36 and 1.38 (two s, 6H, 2 CH$_3$). $^{13}$C NMR (CD$_2$Cl$_2$) δ: 160.0, 159.9, 159.7, 137.4, 130.2, 129.8, 129.7, 129.6, 129.5, 128.6, 128.5, 128.3, 114.3, 114.2, 114.1, 114.0 (16C, Ar.), 108.3 ((CH$_3$)$_2$C), 101.0 (CHPh), 84.5 (C-2), 82.2 (C-3'), 79.3 (C-5'), 75.8 (CH$_2$Ph), 74.0 (C-2'), 73.3 and 71.8 (2 CH$_2$Ph), 71.6 (C-3), 70.8 (C-4'), 67.0 (C-5), 65.0 (C-6'), 64.2 (C-4), 55.5, 55.4, and 55.3 (3 OCH$_3$), 48.6 (C-1'), 47.4 (C-1), 26.4, 25.5 (2 CH$_3$). HRMS. Calcd for C$_{45}$H$_{55}$O$_{14}$SSe: 931.2477. Found: 931.2471.

2,3,5-Tri-O-p-methoxybenzyl-1,4-dideoxy-1,4-[[(2R,3S,4R,5R)-2,4-benzylidenedioxy-5,6-isopropylidenedioxy-3-(sulfooxy)hexyl]-episelenoniumylidene]-L-arabinitol Inner Salt (207)

Reaction of the selenoarabinitol 205 (400 mg, 0.72 mmol) with the cyclic sulfate 197 (350 mg, 0.93 mmol) in HFIP (2 ml) for 12 h at 65° C. gave compound 207 as a colorless, amorphous solid (630 mg, 95% based on 205). [α]$_D$ −14 (c 2.8, CH$_2$Cl$_2$); $^1$H NMR (CD$_2$Cl$_2$) δ: 7.50-6.80 (m, 17H, Ar.), 5.73 (s, 1H, CHPh), 4.69 (br. s, 1H, H-4'), 4.64 (dd, 1H, J$_{1'a,2'}$=6.9, J$_{1'b,2'}$=5.5, H-2'), 4.54 (ddd, 1H, J$_{5',6'a}$=9.9, J$_{5',6b}$=3.5, J$_{4',5}$=6.5, H-5'), 4.48 (d, 2H, CH$_2$Ph), 4.44 (m, 1H, H-2), 4.37 (m, 1H, H-3), 4.32-4.24 (m, 3H, H-3', H-6'a, H-6'b), 4.32 and 4.25 (two d, 2H, J$_{AB}$=11.5, CH$_2$Ph), 4.16 (br.d, 1H, J$_{1'a,1'b}$=11.9, H-1'b), 4.03 (dd, 1H, J$_{1a,2}$=6.9, H-1'a), 4.00 (m, 1H, H-1b), 4.10 and 3.95 (two d, 2H, J$_{AB}$=11.6, CH$_2$Ph), 3.88 (m, 1H, H-4), 3.81, 3.80, and 3.79 (three s, 9H, 3 OCH$_3$), 3.56 (dd, 1H, J$_{1a,2}$=2.7, J$_{1a,1b}$=12.2, H-1a), 3.44 (dd, 1H, J$_{4,5b}$=9.6, J$_{5a,5b}$=9.7, H-5b), 3.24 (dd, 1H, J$_{4,5a}$=6.7, H-5a), 1.38 and 1.42 (two s, 6H, 2 CH$_3$). $^{13}$C NMR (CD$_2$Cl$_2$) δ: 160.0, 159.9, 159.7, 137.6, 130.1, 130.0, 129.8, 129.7, 129.6, 129.5, 128.8, 128.7, 128.5, 114.2, 114.1, 113.9 (16C, Ar.), 108.5 ((CH$_3$)$_2$C), 101.2 (CHPh), 83.1 (C-3'), 82.9 (C-2), 79.1 (C-5'), 75.8 (C-2'), 73.9 72.8, and 71.9 (3 CH$_2$Ph), 71.4 (C-3), 71.3 (C-4'), 66.7 (C-5), 65.3 (C-4), 65.0 (C-6'), 55.5, 55.4, and 55.3 (3 OCH$_3$), 47.4 (C-1'), 45.2 (C-1), 26.5, 25.6 (2 CH$_3$). HRMS. Calcd for C$_{45}$H$_{55}$O$_{14}$SSe: 931.2477. Found: 931.2479.

2,3,5-Tri-O-p-methoxybenzyl-1,4-dideoxy-1,4-[[(2R,3S,4R,5R)-2,4-benzylidenedioxy-5,6-isopropylidenedioxy-3-(sulfooxy)hexyl]-episulfoniumylidene]-D-arabinitol Inner Salt (204)

Reaction of the thioarabinitol 202 (500 mg, 0.98 mmol) with the cyclic sulfate 197 (470 mg, 1.27 mmol) in HFIP (1.5 mL) for 12 h at 75° C. gave compound 204 as a colorless, amorphous solid (731 mg, 85% based on 202). [α]$_D$ −26 (c 1.0, CH$_2$Cl$_2$); $^1$H NMR (CD$_2$Cl$_2$) δ: 7.50-6.82 (m, 17H, Ar.), 5.56 (s, 1H, CHPh), 4.53-4.50 (m, 2H, H-4', H-5'), 4.49 and 4.41 (two d, 2H, J$_{AB}$=11.7, CH$_2$Ph), 4.42 (m, 1H, H-2'), 4.42 and 4.32 (two d, 2H, J$_{AB}$=11.2, CH$_2$Ph), 4.36 and 4.32 (two d, 2H, J$_{AB}$=11.5, CH$_2$Ph), 4.34-4.28 (m, 2H, H-2, H-3), 4.26 (dd, 1H, J$_{5',6'b}$=6.4, J$_{6'a,6'b}$=8.6, H-6'b), 4.20 (dd, 1H, J$_{5',6'a}$=6.6, H-6'a), 4.09 (dd, 1H, J$_{1'b,2'}$=7.1, J$_{1'a,1'b}$=13.3, H-1'b), 4.08-4.04 (m, 2H, H-3', H-4), 4.04 (dd, 1H, J$_{1'a,2'}$=4.0, H-1'a), 3.86-3.81 (m, 2H, H-1b, H-5b), 3.81, 3.80, 3.79 (3s, 9H, 3 OCH$_3$), 3.76 (dd, 1H, J$_{5a,5b}$=9.4, J$_{4,5a}$=8.8, H-5a), 3.58 (dd, 1H, J$_{1a,2}$=3.5, J$_{1a,1b}$=13.2, H-1a), 1.37 (s, 6H, two CH$_3$). $^{13}$C NMR (CD$_2$Cl$_2$) δ: 160.1, 160.0, 159.8, 137.5, 133.4, 133.2, 133.1, 130.2, 129.9, 129.8, 129.5, 128.5, 126.3, 114.3, 114.2, and 114.1 (16C, Ar.), 101.3 (CHPh), 82.7 (C-2), 82.1 (C-3), 79.3 (C-3'), 75.9 (C-5'), 74.6 (C-2'), 73.5, 72.0, 71.8 (3 CH$_2$Ph), 69.5 (C-4'), 67.0 (C-5), 66.0 (C-4), 64.8 (C-6'), 55.4, 55.3, and 55.2 (3 OCH$_3$), 49.2 (C-1'), 48.9 (C-1), 26.4, and 25.6 (2 CH$_3$). HRMS. Calcd for C$_{45}$H$_{55}$O$_{14}$S$_2$: 883.3033. Found: 883.3031.

2,3,5-Tri-O-p-methoxybenzyl-1,4-dideoxy-1,4-[[(2R,3S,4R,5R)-2,4-benzylidenedioxy-5,6-isopropylidenedioxy-3-(sulfooxy)hexyl]-episulfoniumylidene]-L-arabinitol Inner Salt (208)

Reaction of the thioarabinitol 206 (400 mg, 0.78 mmol) with the cyclic sulfate 197 (372 mg, 1.0 mmol) in HFIP (1.5 mL) for 12 h at 75° C. gave compound 208 as a colorless, amorphous solid (570 mg, 83% based on 206). [α]$_D$ +21 (c 4.4, CH$_2$Cl$_2$); $^1$H NMR (CD$_2$Cl$_2$) δ: 7.50-6.70 (m, 17H, Ar.), 5.58 (s, 1H, CHPh), 4.50-4.46 (m, 2H, H-4', H-5'), 4.42 (ddd, 1H, J$_{1'a,2'}$=5.7, J$_{1'b,2'}$=3.2, J$_{2',3}$=9.8, H-2'), 4.37 (s, 2H, CH$_2$Ph), 4.22-4.10 (m, 8H, H-6'b, H-1'b, H-2, H-3, H-3', CH$_2$Ph), 3.87 (dd, 1H, J$_{1b,2}$=1, H-1b), 3.85 (dd, 1H, J$_{1'a,2}$=5.7, J$_{1'a,1'b}$=12.5, H-1'a), 3.96 and 3.83 (two d, 2H, J$_{AB}$=11.3, CH$_2$Ph), 3.74 (dd, 1H, J$_{3,4}$=7.9, H-4), 3.72, 3.70, 3.68 (three s, 9H, three OCH$_3$), 3.49 (dd, 1H, J$_{1a,1b}$=13.1, J$_{1a,2}$=3.2, H-1a), 3.40 (dd, 1H, J$_{4,5b}$=9.4, H-5b), 3.20 (dd, 1H, J$_{4,5a}$=6.7, J$_{5a,5b}$=9.5, H-5a), 1.27 and 1.29 (two s, 6H, two CH$_3$). $^{13}$C NMR (CD$_2$Cl$_2$) δ: 160.1, 160.0, 159.7, 137.5, 130.2, 129.8, 129.7, 129.6, 129.5, 128.6, 128.5, 128.2, 126.5, 114.2, 114.1, and 113.9 (16C, Ar.), 108.3 (CHPh), 101.1 ((CH$_3$)$_2$C), 82.5 (C-2), 82.1 (C-3'), 79.2 (C-3), 75.9 (C-5'), 73.8 (C-2'), 72.9, 72.0, 71.6 (3 CH$_2$Ph), 70.6 (C-4'), 66.6 (C-5), 66.4 (C-4), 64.9 (C-6'), 55.5, 55.4, and 55.3 (3 OCH$_3$), 49.7 (C-1'), 48.2 (C-1), 26.4 and 25.6 (2 CH$_3$). Anal. Calcd for C$_{45}$H$_{54}$O$_{14}$S$_2$: C, 61.21; H, 6.16. Found: C, 61.25; H, 6.13.

2,3,5-Tri-O-p-methoxybenzyl-1,4-dideoxy-1,4-[[(2R,3S,4R,5R)-2,4-benzylidenedioxy-5,6-isopropylidenedioxy-3-(sulfooxy)hexyl]-iminoniumlidene]-D-arabinitol Inner Salt (217)

A mixture of the iminoarabinitol 212 (450 mg, 0.9 mmol) and the cyclic sulfate 197 (470 mg, 1.2 mmol) in acetone (2 mL) containing K$_2$CO$_3$ (20 mg) was warmed at 55° C. in a sealed reaction vessel with stirring for 12 h. The progress of the reaction was followed by TLC analysis of aliquots (developing solvent EtOAc:MeOH, 10:1). When the iminoarabinitol 212 had been completely consumed, the mixture was cooled, then diluted with CH$_2$Cl$_2$, and evaporated to give a syrupy residue. Purification by column chromatography (EtOAc to EtOAc:MeOH, 10:1) gave the iminium salt 217 as an amorphous solid (600 mg, 77% based on 212). [α]$_D$ +10 (c 0.5, CH$_2$Cl$_2$); $^1$H NMR (CD$_2$Cl$_2$) δ: 7.50-6.73 (m, 17H, Ar.), 5.54 (s, 1H, CHPh), 4.56-4.53 (m, 2H, H-3', H-5'), 4.52 and 4.38 (two d, 2H, J$_{AB}$=12.4, CH$_2$Ph), 4.46 and 4.36 (two d, 2H, J$_{AB}$=12.0, CH$_2$Ph), 4.20 and 4.14 (two d, 2H, J$_{AB}$=11.5, CH$_2$Ph), 4.15 (m, 1H, H-2'), 4.11 (dd, 1H, J$_{5',6'b}$=4.2, J$_{6'a,6'b}$=8.6, H-6'b), 4.09 (dd, 1H, J$_{5',6'a}$=6.1, H-6'a), 3.89 (br.d, 1H, J$_{3,4}$=6.7, H-4'), 3.74 (m, 1H, H-3), 3.77, 3.75, 3.73 (three s, 9H, 3 OCH$_3$), 3.65 (d, 1H, J$_{1b,2}$=3.5, H-2), 3.58 (dd, 1H, J$_{4,5b}$=4.1, J$_{5a,5b}$=10.0, H-5b), 3.43 (dd, 1H, J$_{4,5a}$<1, H-5a), 3.30 (m, 2H, H-1'b, H-1b), 3.14 (dd, 1H, J$_{1'a,1'b}$=12.1, J$_{1'a,2}$=6.1, H-1'a), 2.96 (dd, 1H, J$_{1a,2}$<1, J$_{1a,1b}$=10.1, H-1a), 2.80 (m, 1H, H-4), 1.18 and 1.21 (two s, 6H, 2 CH$_3$). $^{13}$C NMR (CD$_2$Cl$_2$) δ: 159.6, 159.5, 159.4, 138.1, 130.3, 130.2, 130.1, 129.9, 129.8, 129.4, 128.9, 128.3, 126.3, 113.9, 113.8, 113.7 (16C, Ar.), 109.2 (CHPh), 100.8 ((CH$_3$)$_2$C), 79.8 (C-2), 79.7 (C-3), 77.1 (C-4'), 74.6 (C-3'), 73.0 (C-2'), 71.6, 71.1, 71.0 (3 CH$_2$Ph, C-5'), 68.4 (C-4), 65.6 (C-5), 59.2 (C-6'), 56.4 (C-1), 55.4, 55.3, 55.2 (3 OCH$_3$), 55.2 (C-1'), 27.0 and 25.6 (2 CH$_3$). Anal. Calcd for C$_{45}$H$_{54}$KNO$_{14}$S: C, 59.78; H, 6.02; N, 1.55. Found: C, 60.01; H, 6.07; N, 1.55.

2,3,5-Tri-O-p-methoxybenzyl-1,4-dideoxy-1,4-[[(2R,3S,4R,5R)-2,4-benzylidenedioxy-5,6-isopropylidenedioxy-3-(sulfooxy)hexyl]-iminoniumlidene]-L-arabinitol Inner Salt (219)

A mixture of the iminoarabinitol 216 (450 mg, 0.9 mmol) and the cyclic sulfate 197 (470 mg, 1.2 mmol) in acetone (2 mL) containing K$_2$CO$_3$ (20 mg) was warmed at 55° C. in a sealed reaction vessel with stirring for 12 h. The progress of the reaction was followed by TLC analysis of aliquots (developing solvent EtOAc:MeOH, 10:1). When the iminoarabinitol 216 had been completely consumed, the mixture was cooled, then diluted with CH$_2$Cl$_2$, and evaporated to give a syrupy residue. Purification by column chromatography (EtOAc to EtOAc:MeOH, 10:1) gave the iminium salt 219 as an amorphous solid (620 mg, 81% based on 216). [α]$_D$ +15 (c 1.0, CH$_2$Cl$_2$); $^1$H NMR (CD$_2$Cl$_2$) δ: 7.38-6.68 (m, 17H, Ar.), 5.57 (s, 1H, CHPh), 4.51-4.47 (m, 2H, H-3', H-5'), 4.36 and 4.31 (two d, 2H, J$_{AB}$=11.8, CH$_2$Ph), 4.54 and 4.17 (two d, 2H, J$_{AB}$=11.8, CH$_2$Ph), 4.15 and 4.06 (two d, 2H, J$_{AB}$=11.6, CH$_2$Ph), 4.04-4.01 (m, 3H, H-6'a, H-6'b, H-2'), 3.86 (dd, 1H, J$_{3',4}$=6.3, H-4'), 3.69 (m, 2H, H-2, H-3), 3.68, 3.66, and 3.65 (three s, 9H, 3 OCH$_3$), 3.57 (dd, 1H, J$_{4,5b}$=3.3, J$_{5a,5b}$=10.0, H-5b), 3.38 (dd, 1H, J$_{1'a,1'b}$=13.3, J$_{1'b,2}$=5.6, H-1'b), 3.28 (dd, 1H, J$_{4,5a}$=2.9, H-5a), 3.16 (dd, 1H, J$_{1a,1b}$=10.3, H-1b), 2.58 (m, 2H, H-4, H-1'a), 2.53 (dd, 1H, J$_{1a,2}$=3.9, H-1a), 1.27 and 1.34 (two s, 6H, 2 CH$_3$). $^{13}$C NMR (CD$_2$Cl$_2$) δ: 159.7, 159.5, 159.4, 138.1, 130.2, 130.1, 130.0, 129.9, 129.7, 129.4, 128.9, 128.3, 126.2, 114.0, 113.9, and 113.8 (16C, Ar.), 109.3 (CHPh), 100.9 ((CH$_3$)$_2$C), 83.5 (C-2), 80.4 (C-3), 79.6 (C-4'), 77.6 (C-2'), 74.7 (C-3'), 72.7 (CH$_2$Ph), 71.2 (two CH$_2$Ph, C-5', C-4), 66.9 (C-5), 65.6 (C-6'), 58.1 (C-1), 55.4 (3 OCH$_3$, C-1'), 26.9, and 25.7 (two CH$_3$). Anal. Calcd for C$_{45}$H$_{54}$KNO$_{14}$S: C, 59.78; H, 6.02; N, 1.55. Found: C, 60.12; H, 6.17; N, 1.60.

General Procedure for the Deprotection of the Coupling Products to Yield the Final Compounds 191-196.

The protected coupling products 203, 204, 207, 208, 217, or 218 were dissolved in CH$_2$Cl$_2$ (2 mL), TFA (10 mL) was then added, and the mixture was stirred for 6-8 h at room temperature. The progress of the reaction was followed by TLC analysis of aliquots (developing solvent EtOAc:MeOH:H$_2$O, 7:3:1). When the starting material had been consumed, the TFA and CH$_2$Cl$_2$ were removed under reduced pressure. The residue was rinsed with CH$_2$Cl$_2$ (4×2 mL) and the CH$_2$Cl$_2$ was decanted to remove the cleaved protecting groups. The remaining gum was dissolved in MeOH and purified by column chromatography (EtOAc and EtOAc:MeOH, 2:1) to give the purified compounds 191-196 as colorless, amorphous, and hygroscopic solids.

1,4-Dideoxy-1,4-[[(2R,3S,4R,5R)-2,4,5,6-tetrahydroxy-3-(sulfooxy)hexyl]-episelenoniumylidene]-D-arabinitol Inner Salt (191)

To a solution of 203 (500 mg) in CH$_2$Cl$_2$ (2 mL) was added TFA (10 mL) to yield the compound 191 as a colorless, amorphous, and hygroscopic solid (160 mg, 67%). [α]$_D$ −21 (c 0.1, H$_2$O); $^1$H NMR (D$_2$O) δ: 4.70 (m, 1H, H-2), 4.55 (dd, 1H, J$_{2,3}$=4.9, J$_{3',4}$=1.3, H-3'), 4.49 (ddd, 1H, J$_{1'b,2'}$=9.7, J$_{1'a,2'}$=3.9, H-2'), 4.39 (dd, 1H, J$_{3,4}$=3.1, J$_{2,3}$=3.7, H-3), 4.14 (ddd, 1H, J$_{4,5a}$=8.3, J$_{4,5b}$=5.2, J$_{3,4}$=3.1, H-4), 3.96 (dd, 1H, J$_{5a,5b}$=12.6, H-5b), 3.91 (dd, 1H, J$_{1'a,1'b}$=12.1, H-1'b), 3.87 (dd, 1H, H-5a), 3.81 (dd, 1H, H-1'a), 3.78 (dd, 1H, J$_{4,5}$=9.2, H-4'), 3.71 (dd, 1H, $J_{6'a,6'b}$=2.8, $J_{6'a,6'b}$=11.6, H-6'b), 3.69 (m, 1H, H-5'), 3.67 (br.d, 2H, H-1a, H-1b), 3.54 (dd, 1H, $J_{6'a,6'a}$=5.6, H-6'a). $^{13}$C NMR (D$_2$O) δ: 78.6 (C-3), 78.2 (C-3'), 77.8 (C-2), 70.5 (C-5'), 70.1 (C-4), 69.2 (C-4'), 67.7 (C-2'), 62.7 (C-6'), 59.4 (C-5), 46.5 (C-1'), 44.4 (C-1). HRMS. Calcd for C$_{11}$H$_{22}$O$_{11}$SSeNa (M+Na): 464.9946. Found: 464.9945.

1,4-Dideoxy-1,4-[[(2R,3S,4R,5R)-2,4,5,6-tetrahydroxy-3-(sulfooxy)hexyl]-episelenoniumylidene]-L-arabinitol Inner Salt (194)

To a solution of 207 (500 mg) in CH$_2$Cl$_2$ (2 mL) was added TFA (10 mL) to yield the compound 194 as a colorless, amorphous, and hygroscopic solid (210 mg, 71%). [α]$_D$ −45 (c 0.1, H$_2$O); $^1$H NMR (D$_2$O) δ: 4.69 (m, 1H, H-2), 4.57 (dd, $J_{3',4'}$=1.3, $J_{2,3}$=4.9, 1H, H-3'), 4.48 (ddd, 1H, $J_{1'a,2}$=9.2, $J_{1'b,2}$=4.6, H-2'), 4.37 (t, $J_{2,3}$=$J_{3,4}$=3.2, 1H, H-3), 4.05 (ddd, 1H, $J_{4,5a}$=8.6, $J_{3,4}$=3.2, $J_{4,5b}$=5.1, H-4), 3.98 (dd, 1H, $J_{5a,5b}$=12.5, $J_{4,5b}$=5.1, H-5b), 3.86 (dd, 1H, H-5a), 3.85 (dd, 1H, H-1'b), 3.82 (dd, 1H, $J_{1'a,1'b}$=12.3, H-1'a), 3.77 (dd, 1H, $J_{4,5}$=4.9, H-4'), 3.72 (dd, 1H, $J_{5',6'a}$=5.3, $J_{5',6'b}$=1.8, H-5'), 3.68 (br.d, 2H, H-1a, H-1b), 3.67 (dd, 1H, $J_{6'a,6'b}$=11.2, H-6'b), 3.53 (dd, 1H, H-6'a). $^{13}$C NMR (D$_2$O) δ: 78.4 (C-3), 78.1 (C-3'), 77.8 (C-2), 70.5 (C-5'), 69.7 (C-4), 69.2 (C-4'), 67.2 (C-2'), 62.7 (C-6'), 59.4 (C-5), 46.4 (C-1'), 44.9 (C-1). HRMS. Calcd for C$_{11}$H$_{22}$O$_{11}$SSeNa (M+Na): 464.9946. Found: 464.9944.

1,4-Dideoxy-1,4-[[(2R,3S,4R,5R)-2,4,5,6-tetrahydroxy-3-(sulfooxy)hexyl]-episulfoniumylidene]-D-arabinitol Inner Salt (192)

To a solution of 204 (500 mg) in CH$_2$Cl$_2$ (2 mL) was added TFA (10 mL) to yield the compound 192 as a colorless, amorphous, and hygroscopic solid (136 mg, 61%). [α]$_D$ −19 (c 0.2, MeOH); $^1$H NMR (D$_2$O) δ: 4.62 (ddd, 1H, $J_{2,3}$=3.4, $J_{1a,2}$=3.4, $J_{1b,2}$=6.7, H-2), 4.57 (dd, 1H, $J_{3',4'}$=1.4, $J_{2',3}$=5.0, H-3'), 4.49 (ddd, 1H, $J_{1'a,2}$=3.9, $J_{1'b,2'}$=8.9, $J_{2',3'}$=5.0, H-2'), 4.35 (dd, 1H, $J_{3,4}$=2.7, H-3), 4.06 (ddd, 1H, $J_{4,5a}$=8.4, $J_{4,5b}$=4.8, H-4), 3.99 (dd, 1H, $J_{5a,5b}$=12.4, H-5b), 3.87 (dd, 1H, H-5a), 3.85 (dd, 1H, $J_{1'b,2'}$=8.9, $J_{1'a,1'b}$=13.5, H-1'b), 3.83 (dd, 1H, H-1'a), 3.80 (dd, 1H, $J_{4,5}$=8.8, H-4'), 3.75 (d, 2H, H-1a, H-1b), 3.71 (dd, 1H, $J_{5',6'b}$=2.6, $J_{6'a,6'b}$=11.6, H-6'b), 3.68 (ddd, 1H, $J_{5',6'a}$=5.7, H-5'), 3.54 (dd, 1H, H-6'a). $^{13}$C NMR (D$_2$O) δ: 78.0 (C-3), 77.6 (C-3'), 76.9 (C-2), 70.4 (C-5'), 69.9 (C-4), 68.9 (C-4'), 67.6 (C-2'), 62.7 (C-6'), 59.3 (C-5), 48.6 (C-1'), 46.9 (C-1). HRMS. Calcd for C$_{11}$H$_{22}$O$_{11}$S$_2$Na (M+Na): 417.0501. Found: 417.0500.

1,4-Dideoxy-1,4-[[(2R,3S,4R,5R)-2,4,5,6-tetrahydroxy-3-(sulfooxy)hexyl]-episulfoniumylidene]-L-arabinitol Inner Salt (195)

To a solution of 208 (400 mg) in CH$_2$Cl$_2$ (2 mL) was added TFA (10 mL) to yield the compound 195 as a colorless, amorphous, and hygroscopic solid (165 mg, 75%). [α]$_D$ −9.6 (c 0.5, MeOH); $^1$H NMR (D$_2$O) δ: 4.63 (dd, 1H, $J_{1a,2}$=4.0, $J_{1b,2}$=4.0, $J_{2,3}$=3.3, H-2), 4.57 (dd, 1H, $J_{2',3'}$=5.0, $J_{3',4'}$=1.2, H-3'), 4.50 (ddd, $J_{2',3'}$=5.0, H-2'), 4.35 (br. t., 1H, $J_{2,3}$=3.3, H-3), 4.07 (ddd, 1H, $J_{3,4}$=2.7, $J_{4,5a}$=1.9, $J_{4,5b}$=5.1, H-4), 3.99 (dd, 1H, $J_{5a,5b}$=12.4, H-5b), 3.87 (dd, 1H, H-5a), 3.85 (dd, 1H, $J_{1'b,2}$=4.0, $J_{1'a,1'b}$=9.6, H-1'b), 3.83 (dd, 1H, $J_{1'a,2}$=3.9, H-1'a), 3.80 (dd, 1H, $J_{4,5}$=8.8, H-4'), 3.75 (d, 2H, H-1a, H-1b), 3.71 (dd, 1H, $J_{5',6'b}$=2.7, $J_{6'a,6'b}$=11.6, H-6'b), 3.68 (ddd, 1H, $J_{5',6'a}$=5.6, H-5'), 3.54 (1H, dd, H-6'a). $^{13}$C NMR (D$_2$O) δ: 77.9 (C-3), 77.6 (C-3'), 76.9 (C-2), 70.4 (C-5'), 69.9 (C-4), 68.9 (C-4'), 67.5 (C-2'), 62.7 (C-6'), 59.3 (C-5), 48.6 (C-1'), 46.9 (C-1). HRMS. Calcd for C$_{11}$H$_{22}$O$_{11}$S$_2$Na (M+Na): 417.0501. Found: 417.0501.

1,4-Dideoxy-1,4-[[(2R,3S,4R,5R)-2,4,5,6-tetrahydroxy-3-(sulfooxy)hexyl]-iminoniumylidene]-D-arabinitol Inner Salt (193)

To a solution of 217 (800 mg) in CH$_2$Cl$_2$ (2 mL) was added TFA (10 mL) to yield the compound 193 as a colorless, amorphous, and hygroscopic solid (236 mg, 68%). [α]$_D$ −11 (c 0.5, MeOH); $^1$H NMR (D$_2$O) δ: 4.56 (dd, 1H, $J_{2',3'}$=5.3, $J_{3',4'}$=1.2, H-3'), 4.40 (ddd, 1H, $J_{1'a,2'}$=7.0, $J_{1'b,2'}$=1.8, $J_{2,3}$=5.3, H-2'), 4.27 (ddd, 1H, $J_{1a,2}$=5.1, $J_{1b,2}$=2.5, $J_{2,3}$=2.9, H-2), 4.01 (dd, 1H, $J_{3,4}$=3.6, H-3), 3.90 (dd, 1H, $J_{5a,5b}$=12.7, $J_{4,5b}$=4.6, H-5b), 3.87 (dd, 1H, $J_{4,5a}$=6.7, H-5a), 3.77 (dd, 1H, $J_{4',5}$=9.1, $J_{3',4'}$=1.2, H-4'), 3.71 (dd, 1H, $J_{1'a,1'b}$=11.8, H-1'b), 3.68 (dd, 1H, $J_{1a,1b}$=12.8, H-1b), 3.67 (m, 1H, H-5'), 3.64 (d, $J_{6'a,6'b}$=13.2, H-6'b), 3.53 (dd, 1H, H-1'a), 3.52 (m, 2H, H-1a, H-4), 3.45 (d, 1H, H-6'a). $^{13}$C NMR (D$_2$O) δ: 77.1 (C-3'), 75.8 (C-3), 75.1 (C-4), 73.6 (C-2), 70.4 (C-5'), 68.5 (C-4'), 66.2 (C-2'), 62.7 (C-1), 58.6 (C-1'), 58.1 (C-6'), 57.9 (C-5). HRMS. Calcd for C$_{11}$H$_{23}$NO$_{11}$SNa (M+Na): 400.0889. Found: 400.0887.

1,4-Dideoxy-1,4-[[(2R,3S,4R,5R)-2,4,5,6-tetrahydroxy-3-(sulfooxy)hexyl]-iminoniumylidene]-L-arabinitol Inner Salt (196)

To a solution of 218 (600 mg) in CH$_2$Cl$_2$ (2 mL) was added TFA (10 mL) to yield the compound 196 as a colorless, amorphous, and hygroscopic solid (265 mg, 80%). [α]$_D$ −35 (c 0.1, MeOH); $^1$H NMR (D$_2$O) δ: 4.53 (dd, $J_{3',4'}$=1.2, $J_{2,3}$=5.2, 1H, H-3'), 4.49 (m, 1H, H-2'), 4.24 (m, 1H, H-2), 4.00 (m, 1H, H-3), 3.88 (dd, 1H, $J_{5a,5b}$=12.5, $J_{4,5b}$=4.9, H-5b), 3.85 (dd, 1H, $J_{4,5a}$=7.3, H-5a), 3.77 (dd, 1H, $J_{4',5}$=9.0, $J_{3',4'}$=1.2, H-4'), 3.73 (dd, 1H, $J_{1'a,1'b}$=11.8, H-1'b), 3.71 (dd, 1H, H-1'a), 3.66 (dd, 1H, $J_{1a,1b}$=12.8, H-1b), 3.65 (m, 1H, H-5'), 3.54-3.49 (m, 4H, H-1a, H-4, H-6'a, H-6'b). $^{13}$C NMR (D$_2$O) δ: 77.2 (C-3'), 75.9 (C-3), 75.8 (C-4), 74.1 (C-2), 70.4 (C-5'), 68.5 (C-4'), 66.9 (C-2'), 62.8 (C-1), 60.9 (C-1'), 58.8 (C-6'), 58.6 (C-5). HRMS. Calcd for C$_{11}$H$_{23}$NO$_{11}$SNa (M+Na): 400.0889. Found: 400.0887.

5.2.13 Example 13

Synthesis of Further Chain-Extended Analogues of Salacinol and Blintol (Schemes 49 to 52)

General. Optical rotations were measured at 23° C. $^1$H and $^{13}$C-NMR spectra were recorded at 500 and 125 MHz, respectively. All assignments were confirmed with the aid of two dimensional experiments ($^1$H-$^1$H COSY, HMQC and HMBC). Column chromatography was performed with Merck silica gel 60 (230-400 mesh). MALDI-TOF mass spectra were recorded on a perSeptive Biosystems Voyager-DE spectrometer, using 2,5-dihydroxybenzoic acid as a matrix.

1,3:4,6-Di-O-benzylidene-2,5-di-O-p-methoxybenzyl-D-mannitol (226)

To a suspension of NaH (44.7 mmol) in DMF (100 ml) at 0° C., 1,3:4,6-di-O-benzylidene-D-mannitol (6.4 g, 17.1 mmol) was added dropwise and the reaction mixture was stirred for 1 h under N$_2$ atmosphere. p-Methoxybenzyl chloride (7.0 g, 44.7 mmol) in DMF (30 ml) was then added to the reaction mixture and the latter was stirred for an additional 3 h at RT.

The mixture was poured into ice-cold water and extracted with EtOAc (3×100 ml). The combined organic layers were washed with water (2×50 ml) and dried over anhydrous $NaSO_4$. The solvent was then removed and the residue was purified by column chromatography to the product (226) as pale yellow oil (8.7 g, 81%).

4,6-O-Benzylidene-2,5-di-O-p-methoxybenzyl-D-mannitol (227)

To a solution of 1,3:4,6-di-O-benzylidene-2,5-di-O-p-methoxybenzyl-D-mannitol (5.8 g) in MeOH (150 ml) was added PTSA (160 mg) and the reaction mixture was stirred for 4 h at RT. The reaction was then quenched by addition of $Et_3N$ and the solvents were removed under vacuum to give a pale yellow syrup that was purified by flash column chromatography to give 227 as a white solid (3.62 g, 73%). $^1H$ NMR ($CDCl_3$): δ 7.27-6.80 (13H, Ar—H), 5.31 (1H, s, Ph-CH—), 4.60 (2H, dd, MeO-Ph-$CH_2$—), 4.50 (2H, dd, MeO-Ph-$CH_2$—), 4.25 (1H, dd, $J_{6a,6b}$=10.6, $J_{6a,5}$=4.9 Hz, H-6a), 4.01 (1H, dd, $J_{3,2}$=9.6, $J_{3,3\text{-}OH}$=10.2 Hz, H-3), 3.93-3.78 (4H, m, $H_2$-1, H-4, H-5), 3.80, 3.72 (2×-OMe), 3.58 (2H, m, H-2, H-6b), 2.17 (1H, dd, OH-1), 2.09 (1H, d, OH-3). $^{13}C$ NMR ($CDCl_3$): δ 159.7-114.1 (18C, Ar), 100.6 (Ph-CH—), 78.5 (C-4), 76.6 (C-2), 72.8, 71.8 (2×MeO-Ph-$CH_2$—), 69.8 (C-6), 68.9 (C-3), 67.6 (C-5), 61.8 (C-1), 55.5, 55.4 (2×-OMe). MALDI: m/e 532.48 ($M^+$+Na). Anal. Calcd for $C_{29}H_{34}O_8$: C, 68.22; H, 6.71. Found: C, 68.02; H, 6.82.

5-Di-O-p-methoxybenzyl-4,6-O-benzylidene-D-mannitol-1,3-cyclic sulfite (228)

A mixture of 227 (11.2 g, 21.9 mmol) and $Et_3N$ (84.0 mmol) in $CH_2Cl_2$ (100 ml) was stirred in ice bath. Thionyl chloride (31.0 mmol) in $CH_2Cl_2$ (10 ml) was then added drop wise over 20 min and the mixture was stirred for an additional 30 min. The mixture was poured into ice-cold water and extracted with $CH_2Cl_2$ (2×100 ml). The combined organic layers were washed with brine solution, dried over $NaSO_4$, and concentrated. Column chromatography (8:1, 5:1, 3:1 hexane:EtOAc) gave the diastereomeric mixture of cyclic sulfites, 228 (2.74 g, 76%). Data for major isomer: $^1$H-NMR ($CDCl_3$): δ 7.48-6.84 (Ar—H), 6.02 (1H, Ph-CH—), 4.83 (1H, d, H-1a), 4.80 (1H, br t, H-3), 4.72-4.56 (4H, 2×MeO-Ph-$CH_2$—), 4.22 (1H, dd, $J_{6a,6b}$=12.8, $J_{6a,5}$=3.7 Hz, H-6a), 4.16 (1H, m, H-5), 4.03 (1H, d, H-6b), 4.02 (1H, m, H-2), 3.96 (1H, br t, H-4), 3.81, 3.79 (6H, 2×-OMe), 3.61 (1H, dd, $J_{1a,1b}$=12.9, $J_{1b,2}$=3.2 Hz, H-1b). $^{13}C$ NMR ($CDCl_3$): δ 80.1 (C-5), 78.6 (C-3), 77.1 (C-4), 76.7 (C-2), 72.2, 72.0 (2×Ph-$CH_2$—), 61.3 (C-6), 58.2 (C-1). MALDI: m/e 579.6 ($M^+$+ Na).

4,6-O-Benzylidene-2,5-di-O-p-methoxybenzyl-D-mannitol-1,3-cyclic sulfate (222)

To a solution of compound, 228 (2.58 g, 4.63 mmol) in a mixture of $CH_3CN$:$CCl_4$ (100 ml), were added sodium periodate (1.48 g, 6.95 mmol) and $RuCl_3$ (100 mg) followed by $H_2O$ (20 ml). The mixture was then stirred for 2 h at RT. The reaction mixture was filtered through a silica bed and washed successively with EtOAc. The volatile solvents were removed, and the aqueous solution was extracted with EtOAc (2×100 ml). The combined organic layer was washed with saturated NaCl, dried over $NaSO_4$, and evaporated under diminished pressure. The residue was purified by flash column chromatography to give 222 as a white solid (2.30 g, 86%). $^1H$ NMR ($CDCl_3$): δ 7.39-6.77 (13H, Ar—H), 5.32 (1H, s, Ph-CH—), 5.08 (1H, d, $J_{3,2}$=9.8 Hz, H-3), 4.50 (4H, 2×MeO—Ph—$CH_2$—), 4.46 (1H, dd, $J_{1a,2}$=4.8 Hz, H-1a), 4.32 (1H, dd, $J_{1b,1a}$=10.1, $J_{1b,2}$=9.6 Hz, H-1b), 4.29 (1H, dd, $J_{6a,5}$=5.6 Hz, H-6a), 4.21 (1H, ddd, H-2), 3.98 (1H, d, $J_{4,5}$=9.6 Hz, H-4), 3.81, 3.72 (2×-OMe), 3.80 (1H, m, H-5), 3.60 (1H, dd, $J_{6a,6b}$=10.4, $J_{6b,5}$=10.2 Hz, H-6b). $^{13}C$ NMR ($CDCl_3$): δ 160.0-114.0 (18C, Ar), 101.5 (Ph-CH—), 82.2 (C-3), 76.3 (C-4), 73.3, 72.8 (2×MeO-Ph-$CH_2$—), 71.9 (C-1), 69.6 (C-6), 66.0 (C-5), 64.8 (C-2). 55.5, 55.4 (2×-OMe). MALDI: m/e 595.6 ($M^+$+Na). Anal. Calcd for $C_{29}H_{32}O_{10}S$: C, 60.83; H, 5.63. Found: C, 60.81; H, 5.66.

2,3,5-Tri-O-p-methoxybenzyl-1,4-dideoxy-1,4-[[(2S, 3S,4R,5R)-4,6-O-benzylidene 2,5-di-O-p-methoxy-benzyl-3-(sulfooxy)hexyl]-(R)-epi-sulfo-niumylidene]-D-arabinitol Inner salt (229)

The thio-sugar 223 (212 mg, 0.42 mmol) and the cyclic sulfates 222 (296 mg, 0.52 mmol) were added to 1,1,1,3,3,3-hexafluoroisopropanol (HFIP) (3 ml) containing anhydrous $K_2CO_3$ (40 mg). The mixture stirred in a sealed tube at 65-70° C. for 42 h. The solvent was removed under reduced pressure and the residue was purified by flash column chromatography (3:1 hexane/EtOAc and then 20:1, 15:1 EtOAc/MeOH). The coupled product, 229 was obtained as a white amorphous solid (350 mg, 77%). $^1H$ NMR ($d_6$-Acetone): δ 5.37 (1H, s, Ph-CH—), 4.92 (1H, d, $J_{3',2'}$=9.1 Hz, H-3'), 4.83-4.54 (10H, 5×MeO-Ph-$CH_2$—), 4.50 (1H, m, H-3), 4.32 (3H, m, H-1a', H-2', H-6a'), 4.23 (1H, dd, $J_{1b',1a'}$=13.6, $J_{1b',2'}$=4.5 Hz, H-1b'), 4.16 (1H, m, H-5'), 4.06 (1H, m, H-1a), 3.97-3.81 (3H, m, H-4, H-4', H-1b), 3.80-3.66 (15H, 5×-OMe), 3.70 (2H, m, $H_2$-5), 3.51 (1H, m, H-6b'). $^{13}C$ NMR ($d_6$-Acetone): δ 159.9-113.5 (36C, Ar), 100.6 (Ph—CH—), 83.6 (C-3), 81.9 (C-2), 77.9 (C-4'), 72.9 (C-2'), 72.4 (C-3'), 72.7, 72.6, 71.7, 71.4, 71.3 (5×MeO-Ph-$CH_2$—), 69.9(C-6'), 67.2 (C-5'), 66.7 (C-5), 65.2 (C-4). 54.8, 55.7 (5×-OMe), 50.9 (C-1'), 48.0 (C-1).

1,4-Dideoxy-1,4 [[2S,3S,4R,5R]-2,4,5,6-tetrahydroxy-3-(sulfooxy)hexyl](R)-epi-sulfoniumylidine]-D-arabinitol Inner salt (220)

To a solution of compound 229 (240 mg) in $CH_2Cl_2$ (3 ml) was added trifluoroacetic acid (10 ml), followed by $H_2O$ (4 ml). The mixture was stirred at room temperature for 2 h. The solvents were then evaporated under diminished pressure and the residue was purified by flash column chromatography to give 220 as a white amorphous solid (72 mg, 82%). $^1H$ NMR ($D_2O$): δ 4.60 (1H, dd, $J_{2,1}$=4.0, $J_{2,3}$=3.7 Hz, H-2), 4.50 (1H, d, $J_{3',2'}$=8.1 Hz, H-3'), 4.32 (1H, dd, $J_{3,4}$=3.2 Hz, H-3), 4.29 (1H, ddd, $J_{2',1a'}$=3.3, $J_{2',1b'}$=7.7 Hz, H-2'), 3.99 (1H, dd, $J_{5a,4}$=5.0 Hz, $J_{5a,5b}$=10.8, H-5a), 3.94 (2H, m, H-1a', H-4), 3.84 (1H, dd, $J_{5b,4}$=7.1 Hz, H-5b), 3.77 (1H, dd, $J_{1b',1a'}$=13.6 Hz, H-1a'), 3.75-3.71 (5H, m, H2-1, H-4', H-5', H-6a'), 3.54 (1H, m, H-6b'). $^{13}C$ NMR ($D_2O$): δ 78.3 (C-3'), 77.8 (C-3), 76.8 (C-2), 70.1 (C-4', C-4), 68.8 (C-5'), 66.1 (C-2'), 62.9 (C-6'), 59.2 (C-5), 50.8 (C-1'), 47.9 (C-1). MALDI: m/e 395.36 ($M^+$+H), 417.58 ($M^+$+Na). HRMS Calcd for $C_{11}H_{21}O_{11}S_2$ (M–H): 393.05119. Found: 393.05215.

2,3,5-Tri-O-p-methoxybenzyl-1,4-dideoxy-1,4 [[2S,3S, 4R,5R]-4,6-O-benzylidene-2,5-di-O-p-methoxybenzyl-3-(sulfooxy)hexyl](R/S)-epi-seleniumylidine]-D-arabinitol Inner salt (230 and 231)

To HFIP (3 ml) were added 1,4-dideoxy-2,3,5-tri-O-p-methoxybenzyl-1,4-anhydro-4-thio-D-arabinitol 224 (254 mg, 0.45 mmol), 4,6-O-benzylidene-2,5-O-di-p-methoxybenzyl-1,3-O-sulfonyl-D-mannitol 222 (318 mg, 0.55 mmol), and, anhydrous K$_2$CO$_3$ (40 mg). The mixture was stirred in a sealed tube at 65-70° C. for 36 h. The solvent was removed under reduced pressure and the residue was purified by flash column chromatography (3:1 hexane:EtOAc and then 15:1 EtOAc:MeOH) to give 230 (286 mg, 56%) and 231 (122 mg, 23%) in a 5:2 ratio as white amorphous solids. Data for trans isomer (230): $^1$H NMR (d$_6$-Acetone): δ 7.45-6.79 (25H, Ar—H), 5.21 (1H, s, Ph-CH—), 4.83 (1H, br d, $J_{3',2'}$=8.9 Hz, H-3'), 4.81-4.39 (10H, 5×MeO-Ph-CH$_2$—), 4.73 (1H, br dd, H-2), 4.55 (1H, br dd, H-3), 4.30-4.19 (4H, m, H2-1', H-2', H-6a'), 4.13 (1H, m, H-5'), 4.09 (1H, br d, $J_{1a,1b}$=13.1, H-1a), 4.04 (1H, m, H-4), 3.84-3.63 (1SH, 5×-OMe), 3.81 (1H, m, H-4'), 3.79 (1H, m, H-5a), 3.72 (1H, m, H-1b), 3.71 (1H, dd, H-5b), 3.46 (1H, dd, H-6b'). $^{13}$C NMR (d$_6$-Acetone): δ 159.6-113.2 (36C, Ar), 100.2 (Ph—CH—), 84.4 (C-3), 82.4 (C-2), 77.9 (C-4'), 73.0 (C-3'), 72.4 (C-2'), 72.8, 72.6, 71.5, 71.4, 71.3 (5×MeO—Ph—CH$_2$—), 69.8 (C-6'), 67.4 (C-5'), 67.3 (C-5), 64.8 (C-4). 54.7 (5×-OMe), 50.0 (C-1'), 45.8 (C-1). MALDI: m/e 1130.51 (M+), 1050.74 (M$^+$—SO$_3$). Anal. Calcd for C$_{58}$H$_{65}$O$_{16}$SSe: C, 61.64; H, 5.89. Found: C, 61.31; H, 5.66. Data for cis isomer (231): $^1$H NMR (d$_6$-Acetone): δ 7.31-6.81 (25H, Ar—H), 5.30 (1H, s, Ph-CH—), 4.86 (1H, br d, $J_{3',2'}$=9.0 Hz, H-3'), 4.82-4.45 (10H, 5×MeO—Ph—CH$_2$—), 4.74 (1H, br s, H-2), 4.68 (1H, br s, H-3), 4.41 (1H, m, H-4), 4.29 (2H, m, H-2', H-6a'), 4.21 (1H, dd, $J_{5a,5b}$=9-9, $J_{5a,4}$=5.4 Hz, H-5a), 4.18 (1H, m, H-5'), 4.06 (2H, m, H$_2$-1), 4.00 (1H, dd, $J_{5b,4}$=9.4 Hz, H-5b), 3.83 (1H, m, H-4'), 3.80-3.65 (15H, 5×-OMe), 3.63 (1H, m, H-1a), 3.56 (1H, br d, $J_{1b,1a}$=12.9, H-1b), 3.48 (1H, dd, $J_{6b',6a'}$=10.4, $J_{6b',5'}$=10.2 Hz, H-6b'). $^{13}$C NMR (d$_6$-Acetone): δ 159.8-114.0 (36C, Ar), 100.6 (Ph—CH—), 83.2 (C-2), 82.6 (C-3), 77.8 (C-4'), 73.1 (C-3'), 72.8 (C-2'), 72.7, 72.1, 71.6, 71.2, 71.2 (5×MeO-Ph-CH$_2$—), 69.8 (C-6'), 67.2 (C-5'), 65.6 (C-5), 58.4 (C-4). 54.8, 54.7 (5×-OMe), 42.3 (C-1), 41.0 (C-1'). MALDI: m/e 1130.81 (M+), 1050.92 (M$^+$—SO$_3$). Anal. Calcd for C$_{58}$H$_{65}$O$_{16}$SSe: C, 61.64; H, 5.89. Found: C, 61.30; H, 5.97.

1,4-Dideoxy-1,4-[[2S,3S,4R,5R]-2,4,5,6-tetrahydroxy-3-(sulfooxy)hexyl]-(R/S)-epi-seleniumylidine]-D-arabinitol Inner salts (221 and 232)

The selenonium salts 230 and 231 were deprotected separately using aq. TFA following the same procedure that was used for compound 220, to give compounds 221 (85%) and 232 (81%), respectively. Data for the trans isomer, 221: $^1$H NMR (D$_2$O): δ 4.68 (1H, dd, $J_{2,1}$=3.8, $J_{2,3}$=3.7 Hz, H-2), 4.49 (1H, d, $J_{3,2}$=7.7 Hz, H-3'), 4.37 (1H, dd, $J_{3,4}$=3.2 Hz, H-3), 4.29 (1H, ddd, $J_{2',1a}$=4.0, $J_{2',1b}$=7.2 Hz, H-2'), 4.05 (1H, ddd, $J_{4,5a}$=5.1 Hz, $J_{4,5b}$=8.9, H-4), 3.99 (1H, dd, $J_{1a',1b}$=12.3 Hz H-1a'), 3.94 (1H, dd, $J_{5a,5b}$=12.6 Hz, H-5a), 3.83 (1H, dd, H-5b), 3.81 (1H, dd, H-1b'), 3.70 (3H, m, H-4', H-5', H-6a'), 3.67 (2H, d, H$_2$-1), 3.54 (1H, dd, $J_{6b',6a'}$=12.3, $J_{6b',5'}$=5.7 Hz, H-6b'). $^{13}$C NMR (D$_2$O): δ 78.6 (C-3'), 77.6 (C-3), 77.6 (C-2), 70.1 (C-5'), 70.0 (C-4), 68.9 (C-4'), 66.1 (C-2'), 62.9 (C-6'), 59.4 (C-5), 49.1 (C-1'), 44.9 (C-1). MALDI: m/e 464.72 (M$^+$+Na), 362.75 (M$^+$+H—SO$_3$). Data for the cis isomer, 232: $^1$H NMR (D$_2$O): δ 4.61 (1H, ddd, $J_{2,1b}$=3.4, $J_{2,3}$=3.8 Hz, H-2), 4.51 (1H, d, $J_{3,2}$=8.0 Hz, H-3'), 4.43 (1H, t, $J_{3,4}$=3.8 Hz, H-3), 4.28 (1H, ddd, $J_{2',1a}$=3.8, $J_{2',1b}$=7.8 Hz, H-2'), 4.13 (1H, ddd, $J_{4,5a}$=5.5 Hz, $J_{4,5b}$=9.0, H-4), 4.08 (1H, dd, $J_{5a,5b}$=12.2 Hz H-5a), 3.97 (2H, m, H-5b, H-1a'), 3.97 (1H, dd, H-b'), 3.71 (4H, m, H-1a, H-4', H-5', H-6a'), 3.54 (1H, dd, $J_{6b',6a'}$=12.3, $J_{6b',5'}$=4.9, H-6b'), 3.49 (1H, dd, $J_{1b,1a}$=12.7 Hz, H-1b). $^{13}$C NMR (D$_2$O): δ 79.0 (C-3'), 78.6 (C-2), 78.2 (C-3), 70.1 (C-5'), 69.0 (C-4'), 66.0 (C-2'), 64.1 (C-4), 62.9 (C-6'), 58.2 (C-5), 42.6 (C-1), 41.5 (C-1'). MALDI: m/e 464.69 (M$^+$+Na), 362.56 (M$^+$+H—SO$_3$). HRMS Calcd for C$_{11}$H$_{21}$O$_{11}$SSe (M–H): 440.9964. Found: 440.9961.

5.2.14 Example 14

Synthesis of D-Lyxitol and D-Ribitol Derived Analogues of Salacinol (Schemes 53 to 57)

General. Optical rotations were measured at 23° C. using a Rudolph Research Autopol II polarimeter. $^1$H and $^{13}$C NMR spectra were recorded on a Varian Inova spectrometer with frequencies of 500 and 125 MHz, respectively. All assignments were confirmed with the aid of two-dimensional $^1$H, $^1$H (gCOSY) or $^1$H, $^{13}$C (gHMQC) experiments using standard Varian pulse programs. Processing of the spectra was performed with MesRec software. Matrix-assisted laser desorption ionization time-of-flight (MALDI-TOF) mass spectra were obtained using 2,5-dihydroxybenzoic acid as a matrix on a PerSeptive Biosystems Voyager-DE spectrometer. Column chromatography was performed with Merck Silica gel 60 (230-400 mesh).

2,3,5-Tri-O-benzyl-D-lyxitol (239)

To a stirred solution of 2,3,5-tri-O-benzyl-D-lyxofuranoside 238 (5.64 g, 13.4 mmol) in EtOH (150 mL) at 0° C. was added sodium borohydride (0.215 g, 6.72 mmol) gradually. After stirring for 1.5 h at 0° C., the reaction was quenched with AcOH and the reaction mixture was concentrated. The residue was diluted with EtOAc (200 mL) and washed with H$_2$O (2×100 mL) and brine (100 mL). The organic phase was dried over anhydrous Na$_2$SO$_4$ and concentrated. The crude product was purified by flash chromatography (Hexanes:EtOAc, 1:3→1:1) to give a colorless oil 239 (5.50 g, 97%): $[α]_D$ –200.5 (c 0.54, CHCl$_3$); $^1$H NMR (CDCl$_3$) δ 7.38-7.25 (m, 15H, Ar), 4.74 and 4.54 (2H, 2d, $J_{a,b}$=11.5 Hz, CH$_2$Ph), 4.63 (s, 2H, CH$_2$Ph), 4.53 and 4.48 (2d, each 1H, $J_{a,b}$=12.5 Hz, CH$_2$Ph), 4.01 (1H, ddd, $J_{3,4}$=1.8 Hz, $J_{4,5a}$=$J_{4,5b}$=6.1 Hz, H-4), 3.88 (1H, dd, $J_{1a,1b}$=11.7 Hz, $J_{1a,2}$=4.1 Hz, H-1a), 3.81 (1H, dd, $J_{2,3}$=5.9 Hz, H-3), 3.75 (1H, dd, $J_{1b,2}$=3.7 Hz, H-1b), 3.72 (1H, ddd, H-2), 3.55 (1H, dd, $J_{5a,5b}$=9.9 Hz, H-5a), 3.47 (1H, dd, H-5b); $^{13}$C NMR (CDCl$_3$) δ 137.84, 137.80, 137.75 (3C$_{ipso}$), 128.52-127.79 (15C, Ar), 79.48 (C-2), 77.00 (C-3), 74.37, 73.44, 72.38 (3CH$_2$Ph), 71.22 (C-5), 69.67 (C-4), 60.47 (C-1); MALDI-TOF MS: m/e 423.07 (M$^+$+H), 445.12 (M$^+$+Na), 4.61.11 (M$^+$+K). Anal. Calcd for C$_{26}$H$_{30}$O$_5$: C, 73.91; H, 7.16. Found: C, 74.05; H, 7.21.

2,3,5-Tri-O-benzyl-1-O-tert-butyldimethylsilyl-D-lyxitol (240)

A mixture of 239 (5.24 g, 12.4 mmol), imidazole (3.72 g, 54.6 mmol), and TBDMSCl (2.07 g, 13.6 mmol) in dry DMF (50 mL) was stirred at 0° C. under N$_2$ for 30 min. The reaction was quenched with ice (20 mL), and the reaction mixture was partitioned between Et$_2$O (200 mL) and H$_2$O (100 mL). The separated organic phase was washed with H$_2$O (100 mL) and brine (100 mL). The organic layer was dried over anhydrous Na$_2$SO$_4$ and concentrated. The residue was purified by flash chromatography (hexanes:EtOAc, 3:1) to give a colorless oil 240 (6.164 g, 93%): $[α]_D$ –140.4° (c 0.87, CHCl$_3$); $^1$H NMR (CDCl$_3$) δ 7.35-7.25 (15H, m, Ar), 4.74 and 4.60 (2H, 2d, $J_{a,b}$=11.7 Hz, CH$_2$Ph), 4.69 and 4.51 (2H, 2d, $J_{a,b}$=11.9 Hz, CH$_2$Ph), 4.51 and 4.45 (2H, 2d, $J_{a,b}$=11.6 Hz, CH$_2$Ph), 4.05 (1H, dddd, $J_{3,4}$=2.3 Hz, $J_{4,5a}$=$J_{4,5b}$=5.9 H,$J_{4,OH}$=5.9 Hz, H-4), 3.88 (1H, dd, $J_{1a,1b}$=11.0 Hz, $J_{1a,2}$=4.2 Hz, H-1a), 3.78 (1H, dd, $J_{1b,2}$=4.9 Hz, H-1b), 3.77 (1H, dd, $J_{2,3}$=4.1 Hz, H-3), 3.73 (1H, ddd, H-2), 3.54(1H, dd, H-5a), 3.49 (1H, dd, H-5b), 3.02 (1H, d, OH), 0.891 (9H, s, $(CH_3)_3CSi$), 0.05 (6H, s, $(CH_3)_2Si$); $^{13}C$ NMR ($CDCl_3$) δ 149.11, 145.62, 140.95 ($3C_{ipso}$), 128.35-127.60 (15C, Ar), 80.25 (C-2), 77.25 (C-3), 73.65, 73.26, 72.84 ($3CH_2Ph$), 71.16 (C-5), 69.75 (C-4), 62.04 (C-1), 25.88 (3C, $(CH_3)_3CSi$) 18.23 (1C, CSi), −5.40, −5.44 (2C, $(CH_3)_2Si$); MALDI-TOF MS: m/e 537.89 ($M^+$+H), 559.33 ($M^+$+Na). Anal. Calcd for $C_{32}H_{44}O_5Si$: C, 71.60; H, 8.26. Found: C, 71.44; H, 8.34.

2,3,5-Tri-O-benzyl-D-ribitol (242)

A solution of 240 (6.50 g, 12.1 mmol) in THF (60 mL) containing p-nitrobenzoic acid (4.06 g, 24.2 mmol) and triphenylphosphine (6.36 g, 24.2 mmol) was cooled to 0° C. A solution of diisopropylazodicarboxylate (4.8 mL, 24.2 mmol) in THF (30 mL) was added to the mixture over 2 h. After stirring for 20 h at ambient temperature, the reaction mixture was concentrated and then partitioned between $Et_2O$ (200 mL) and $H_2O$ (100 mL). The organic phase was washed with saturated aqueous $NaHCO_3$ (3×50 mL), followed by brine (50 mL). The organic layer was dried over anhydrous $Na_2SO_4$ and concentrated under vacuum. The residue was dissolved in MeOH (50 mL) and 1N NaOMe/MeOH (1.0 mL) was added. The mixture was stirred at room temperature for 1 h and concentrated. The residue was partitioned between $Et_2O$ (150 mL) and $H_2O$ (100 mL). The organic layer was washed with brine (50 mL), dried over anhydrous $Na_2SO_4$, and concentrated. The residue was re-dissolved in THF (50 mL) and a solution of tetrabutylammonium fluoride (1M in THF, 13.0 mL, 13.0 mmol) was added. The mixture was stirred at room temperature for 1.5 h and partitioned between $Et_2O$ (150 mL) and $H_2O$ (50 mL). The organic layer was washed with brine (50 mL), dried over anhydrous $Na_2SO_4$, and concentrated. The crude product was purified by flash chromatography (hexanes:EtOAc, 4:1→1:1) to give a colorless oil 242 (2.80 g, 57%). See Ref. 100 for experimental data.

1,4-Anhydro-2,3,5-tri-O-benzyl-4-thio-D-lyxitol (243)

To a stirred solution of 242 (6.01 g, 14.2 mmol) in pyridine (60 mL) at 0° C. under $N_2$ was added methanesulfonyl chloride (2.70 mL, 2.5 equiv.) dropwise. The mixture was stirred at 0° C. for 2 h and concentrated under high vacuum. The residue was diluted with EtOAc (200 mL) and the organic phase was washed with $H_2O$ (100 mL), 1M HCl (100 mL), saturated aqueous $NaHCO_3$ (2×100 mL), and brine (100 mL). The organic layer was dried over anhydrous $Na_2SO_4$ and concentrated. The residue was dissolved in dry DMF (60 mL) together with $Na_2S.9H_2O$ (4.61 g, 1.3 equiv.). The mixture was stirred at 105° C. for 2 h. After cooling to room temperature, the mixture was diluted with $Et_2O$ (200 mL) and washed with $H_2O$ (3×100 mL), followed by brine (100 mL). The organic layer was dried over anhydrous $Na_2SO_4$ and concentrated. The crude product was purified by a flash chromatography (hexanes:EtOAc, 5:1) to give a colorless oil 243 (5.20 g, 87%): $[α]_D$ +94.0° (c 0.93, $CHCl_3$); $^1H$ NMR ($CDCl_3$) δ 7.38-7.22 (15H, m, Ar), 4.88 and 4.78 (2H, 2d, $J_{a,b}$=11.6 Hz, $CH_2Ph$), 4.68 (2H, s, $CH_2Ph$) 4.49 (2H, s, $CH_2Ph$), 4.20 (1H, dd, $J_{2,3}$=3.1 Hz, $J_{3,4}$=3.8 Hz, H-3), 4.04 (1H, ddd, $J_{1a,2}$=9.2 Hz, $J_{1b,2}$=6.3 Hz, H-2), 3.89 (1H, dd, $J_{4,5a}$=7.3 Hz, $J_{5a,5b}$=8.7 Hz, H-5a), 3.58 (1H, m, H-4), 3.54 (1H, dd, $J_{4,5b}$=6.6 Hz, H-5b), 3.07 (1H, dd, $J_{1a,1b}$=9.2 Hz, H-1a), 2.92 (1H, dd, H-1b); $^{13}C$ NMR ($CDCl_3$) δ 138.85, 138.33, 138.27 ($3C_{ipso}$), 128.68-127.64 (15C, Ar), 83.71 (C-2), 78.99 (C-3), 73.81, 73.56, 72.37 ($3CH_2Ph$), 70.42 (C-5), 40.92 (C-4), 30.56 (C-1); MALDI-TOF MS: m/e 421.29 ($M^+$+H), 443.29 ($M^+$+Na), 459.29 ($M^+$+K), 511.32 ($M^+$+Bn), 313.28 ($M^+$−OBn). Anal. Calcd for $C_{26}H_{28}O_3S$: C, 74.25; H, 6.71. Found: C, 74.02; H, 6.73.

1,4-Anhydro-4-thio-D-lyxitol (244)

To condensed $NH_3$ (~30 mL) at −78° C. was added lithium metal (4 small pieces) gradually. A solution of 243 (0.70 g, 1.7 mmol) in $Et_2O$ (5 mL) was then added to the mixture dropwise. The mixture was stirred at −78° C.→ambient temperature for 5 h. The reaction was quenched with MeOH (5 mL) and concentrated. The crude product was purified by flash chromatography ($CH_2Cl_2$:MeOH, 1:10→1:8) to give a colorless oil 244 (0.215 g, 86%): $[α]_D$ +3.96° (c 0.21, $CHCl_3$); $^1H$ NMR ($CDCl_3$) δ 4.38 (1H, dd, $J_{2,3}$=4.3 Hz, $J_{3,4}$ 6.7 Hz, H-3), 4.26 (1H, ddd, $J_{1a,2}$=5.9 Hz, $J_{1b,2}$=5.2 Hz, H-2), 4.01 (1H, dd, $J_{4,5a}$=2.6 Hz, $J_{5a,5b}$=11.9 Hz, H-5a), 3.69 (1H, dd, $J_{4,5b}$=5.0 Hz, H-5b), 3.56 (1H, ddd, H-4), 3.04 (1H, dd, $J_{1a,1b}$=11.5 Hz, H-1a), 2.89 (1H, dd, H-1b); $^{13}C$ NMR ($CDCl_3$) δ 76.62 (C-2), 74.23 (C-3), 60.16 (C-5), 55.70 (C-4), 37.43 (C-1). Anal. Calcd for $C_5H_{10}O_3S$: C, 39.98; H, 6.71. Found: C, 39.62; H, 6.65.

1,4-Anhydro-2,3,5-tri-O-p-methoxybenzyl-4-thio-D-lyxitol (235)

A solution of 244 (0.201 g, 1.33 mmol) in DMF (20 mL) was added to a suspension of NaH (60% in oil, 175 mg, 3.3 equiv.) in DMF (30 mL) at 0° C. under $N_2$. After stirring at 0° C. for 45 min, p-methoxybenzyl chloride (0.687 g, 3.3 equiv.) was added dropwise. The reaction mixture was stirred at room temperature for 2 h and then quenched with ice (20 mL). The mixture was diluted with $H_2O$ (50 mL) and extracted with $Et_2O$ (3×100 mL). The organic phase was dried over anhydrous $Na_2SO_4$ and concentrated. The crude product was purified by flash chromatography (hexanes:EtOAc, 8:1→5:1) to give a colorless oil 235 (0.640 g, 94%): $[α]_D$ −2.08° (c 0.25, $CHCl_3$); $^1H$ NMR ($CDCl_3$) δ 7.28-7.19 (6H, m, Ar), 6.90-6.79 (6H, m, Ar), 4.76 and 4.59 (2H, 2d, $J_{a,b}$=11.4 Hz, $CH_2Ar$), 4.48 (2H, s, $CH_2Ar$), 4.43 and 4.42 (2H, 2d, $J_{a,b}$=11.4 Hz $CH_2Ar$), 4.14 (1H, dd, $J_{2,3}$=3.1 Hz, $J_{3,4}$=4.0, H-3), 3.98 (1H, ddd, $J_{1a,2}$=9.2 Hz, $J_{1b,2}$=6.1 Hz, H-2), 3.82 (1H, dd, $J_{4,5a}$=7.2 Hz, $J_{5a,5b}$=8.7 Hz, H-5a), 3.81 (3H, s, $CH_3OAr$), 3.80 (3H, s, $CH_3OAr$), 3.79 (3H, s, $CH_3OAr$), 3.53 (1H, ddd, $J_{4,5b}$=6.6 Hz H-4), 3.47 (1H, dd, H-5b), 3.01 (1H, dd, $J_{1a,1b}$=9.3 Hz, H-1a), 2.86 (1H, dd, H-1b); $^{13}C$ NMR ($CDCl_3$) δ 159.45, 159.42, 159.32, ($3C_{ipso}$), 131.01-113.84 (15C, Ar), 83.41 (C-2), 78.38 (C-3), 73.34, 73.20, 72.03 ($3CH_2Ar$), 70.08 (C-5), 55.52, 55.49, 55.47 ($3CH_3OAr$), 45.98 (C-4), 30.59 (C-1); MALDI-TOF MS: m/e 511.28 ($M^+$+H), 533.26 ($M^+$+Na), 549.21 ($M^+$+K). Anal. Calcd for $C_{29}H_{34}O_6S$: C, 68.21; H, 6.71. Found: C, 67.90; H, 7.09.

1,4-Anhydro-2,3,5-tri-O-p-methoxybenzyl-4-thio-D-ribitol (236)

A solution of 246 (0.510 g, 3.4 mmol) in DMF (30 mL) was added to a suspension of NaH (60% in oil, 0.449 g, 3.3 equiv.) in DMF (50 mL) at 0° C. under $N_2$. After stirring at 0° C. for 45 min, p-methoxybenzyl bromide (1.74 g, 3.3 equiv.) was added dropwise. The reaction mixture was stirred at room temperature for 2 h and then quenched with ice (20 mL). The mixture was diluted with $H_2O$ (100 mL) and extracted with $Et_2O$ (3×100 mL). The organic phase was dried over anhydrous $Na_2SO_4$ and concentrated. The crude product was purified by flash chromatography (hexanes:EtOAc, 8:1-5:1) to give a white solid 236 (1.58 g, 91%). See Ref. 103 for experimental data.

2,3,5-Tri-O-p-methoxybenzyl-1,4-dideoxy-1,4-[[(2S,3S)-2,4-O-benzylidene-3-(sulfooxy)butyl]-(S)-episulfoniumylidene]-D-lyxitol Inner Salt (247)

To a mixture of 235 (90 mg, 0.176 mmol) and the L-cyclic sulfate 237 (57 mg, 1.2 equiv.) in HFIP (0.5 mL) was added $K_2CO_3$ (5 mg). The mixture was stirred in a sealed tube at 70° C. for 16 h. The reaction mixture was concentrated and the crude product was purified by flash chromatography ($CH_2Cl_2$:MeOH, 1:0→15:1) to give an amorphous solid 247 (124 mg, 90%): $[\alpha]_D$ −11.58° (c 0.53, $CHCl_3$); $^1$H NMR ($CDCl_3$) δ 7.46-6.84 (17H, m, Ar), 5.36 (1H, s, $CH_2Ph$), 4.85 (1H, ddd, $J_{1a,2}$=6.1 Hz, $J_{1b,2}$=8.6 Hz, $J_{2,3}$=2.5 Hz, H-2), 4.70 and 4.45 (2H, 2d, $J_{a,b}$=11.0 Hz, $CH_2Ar$), 4.60 (2H, s, $CH_2Ar$), 4.57 (1H, dd, $J_{3',4a}$=5.5 Hz, $J_{4a',4b}$=11.0 Hz, H-4a'), 4.53 (1H, dd, $J_{3,4}$=3.9 Hz, H-3), 4.44 (1H, m, H-3'), 4.33 (1H, m, H-4), 4.30 and 4.26 (2H, 2d, $J_{a,b}$=11.7 Hz, $CH_2Ar$), 4.26-4.21 (2H, m, H-2', H-1a'), 4.19 (1H, dd, $J_{1a',1b'}$=13.6 Hz, H-1b'), 3.91 (1H, dd, $J_{1a,1b}$=12.9 Hz, H-1a), 3.81 (1H, dd, $J_{4,5a}$=4.6 Hz, $J_{5a,5b}$=9.8 Hz, H-5a), 3.80 (3H, s, $CH_3OAr$), 3.79 (3H, s, $CH_3OAr$), 3.76 (3H, s, $CH_3OAr$), 3.74 (1H, dd, $J_{3',4b}$=3.9 Hz, H-4b'), 3.71 (1H, dd, $J_{4,5b}$=4.6 Hz, H-5b), 3.54 (1H, dd, H-1b'); $^{13}$C NMR ($CDCl_3$) δ 159.86, 159.81, 159.77 (3$C_{ipso}$, PMB), 137.04 (1$C_{ipso}$, Ph), 130.32-113.98 (20C, Ar), 101.50 (1C, $CH_2Ph$), 81.51 (C-2), 78.33 (C-3), 76.01 (C-2'), 74.24, 73.38 and 73.29 (3$CH_2Ar$), 69.54 (C-4'), 67.72 (C-3'), 65.41 (C-5), 62.55 (C-4), 54.15-53.29 (3C, $CH_3OAr$), 47.63 (C-1'), 41.40 (C-1); MALDI-TOF MS: m/e 783.45 ($M^++H$), 805.21 ($M^++Na$), 821.84 ($M^++K$). Anal. Calcd for $C_{40}H_{46}O_{12}S_2$: C, 61.36; H, 5.92. Found: C, 61.61; H, 6.04.

2,3,5-Tri-O-p-methoxybenzyl-1,4-dideoxy-1,4-[[(2S,3S)-2,4-O-benzylidene-3-(sulfooxy)butyl]-(R)-episulfoniumylidene]-D-ribitol Inner Salt (248)

To a solution of 1,4-anhydro-2,3,5-tri-O-p-methoxybenzyl-4-thio-D-ribitol (236) (300 mg, 588 mmol) and the L-cyclic sulfate 237 (192 mg, 1.2 equiv.) in HFIP (1.5 mL) was added $K_2CO_3$ (20 mg). The mixture was stirred in a sealed tube at 70° C. for 16 h. The reaction mixture was concentrated and the crude product was purified by flash chromatography ($CH_2Cl_2$:MeOH, 1:0→20:1) to give a white foam 248 (425 mg, 92%): $[\alpha]_D$ +64.2° (c 0.26, $CHCl_3$); $^1$H NMR ($CDCl_3$) δ 7.42-6.84 (17H, m, Ar), 5.53 (1H, s, $CH_2Ph$), 4.66 and 4.54 (2H, 2d, $J_{a,b}$=11.3 Hz, $CH_2Ar$), 4.53 (1H, ddd, $J_{23}$=$J_{3',4a'}$=9.8 Hz, $J_{3',4b'}$=5.3 Hz, H-3'), 4.48 (1H, dd, $J_{4a',4b'}$=10.8 Hz, H-4a'), 4.45 (1H, d, $J_{1a',1b'}$=13.9 Hz, H-1a'), 4.85 (1H, dd, $J_{1a,2}$=$J_{2,3}$=2.6 Hz, H-2), 4.44 and 4.27 (2H, 2d, $J_{a,b}$=11.2 Hz, $CH_2Ar$), 4.34 and 4.19 (2H, 2d, $J_{a,b}$=11.9 Hz, $CH_2Ar$), 4.23 (1H, dd, $J_{1b',2b'}$=2.9 Hz, H-2'), 4.15 (1H, dd, $J_{3,4}$=9.5 Hz, H-3), 4.01 (1H, dd, H-1b'), 3.82 (3H, s, $CH_3OAr$), 3.81 (3H, s, $CH_3OAr$), 3.80 (3H, s, $CH_3OAr$), 3.76 (1H, dd, H-4b'), 3.68 (1H, ddd, $J_{4,5a}$=$J_{4,5b}$=2.0 Hz, H-4), 3.58 (2H, br s, H-1a, H-1b), 3.34 (1H, dd, $J_{5a,5b}$=10.9 Hz, H-5a), 3.29 (1H, dd, H-5b); $^{13}$C NMR ($CDCl_3$) δ 160.08, 160.05, 159.95 (3$C_{ipso}$, PMB), 136.82 (1$C_{ipso}$, Ph), 136.82-114.09 (20C, Ar), 101.44 (1C, $CH_2Ph$), 81.66 (C-3), 76.64 (C-2'), 76.34 (C-2), 73.64, 73.10, 72.51 (3$CH_2Ar$), 69.16 (C-4'), 65.68 (C-3'), 64.09 (C-4), 62.17 (C-5), 55.50-55.46 (3$CH_3OAr$), 51.34 (C-1'), 43.68 (C-1). MALDI-TOF MS: m/e 783.31 ($M^++H$), 805.34 ($M^++Na$), 821.87 ($M^++K$). Anal. Calcd for $C_{40}H_{46}O_{12}S_2$: C, 61.36; H, 5.92. Found: C, 61.19; H, 5.98.

1,4-Dideoxy-1,4-[[(2S,3S)-2,4-dihydroxy-3-(sulfooxy)butyl]-(S)-episulfoniumylidene]-D-lyxitol Inner Salt (233)

To a stirred solution of 247 (120 mg, 0.153 mmol) in TFA (10 mL) was added $H_2O$ (1 mL) and the reaction mixture was stirred at ambient temperature for 2 h. The reaction mixture was concentrated and the crude product was purified by flash chromatography ($CH_2Cl_2$:MeOH, 3:1→EtOAc:MeOH: $H_2O$, 6:3:1) to give an amorphous solid 233 (30 mg, 78%): $[\alpha]_D$ +8.23° (c 0.21, $D_2O$); $^1$H NMR ($D_2O$) δ 4.85 (1H, ddd, $J_{1a,2}$=6.8 Hz, $J_{1b,2}$=9.6 Hz, $J_{2,3}$=3.0 Hz, H-2), 4.61 (1H, dd, $J_{3,4}$=3.2 Hz, H-3), 4.38 (1H, ddd, $J_{2',3'}$=7.4 Hz, $J_{3',4a'}$=2.9 Hz, $J_{3',4b'}$=9.6 Hz, H-3'), 4.34-4.26 (2H, m, H-2', H-4), 4.18 (1H, dd, $J_{4,5a}$=5.1 Hz, $J_{5a,5b}$=12.3 Hz, H-5a), 4.02 (1H, dd, $J_{4,5b}$=9.4 Hz, H-5b), 3.94 (1H, dd, $J_{1a',1b'}$=12.6 Hz, $J_{1a',2'}$=3.3 Hz, H-1a'), 3.84 (1H, dd, $J_{1b',2'}$=3.5 Hz, H-1b'), 3.83 (1H, dd, $J_{4',4b'}$=13.6 Hz, H-4a'), 3.73 (1H, dd, $J_{1a,1b}$=13.3 Hz, H-1a), 3.72 (1H, dd, H-4b'), 3.62 (1H, dd, H-1b); $^{13}$C NMR ($D_2O$) δ 82.91 (C-3'), 76.08 (C-2), 75.34 (C-3), 68.79 (C-4), 68.01 (C-2'), 62.06 (C-1'), 60.32 (C-5), 50.91 (C-4'), 43.84 (C-1); MALDI-TOF MS: m/e 335.04 ($M^++H$), 357.11 ($M^++Na$). Anal. Calcd for $C_9H_{18}O_9S_2$: C, 32.33; H, 5.43. Found: C, 32.02; —H, 5.45.

1,4-Dideoxy-1,4-[[(2S,3S)-2,4-dihydroxy-3-(sulfooxy)butyl]-(R)-episulfoniumylidene]-D-ribitol Inner Salt (234)

To a stirred solution of 248 (202 mg, 0.258 mmol) in TFA (20 mL) was added $H_2O$ (2 mL) and the reaction mixture was stirred at ambient temperature for 2 h. The reaction mixture was concentrated and the crude product was purified by flash chromatography ($CH_2Cl_2$:MeOH, 3:1→EtOAc:MeOH: $H_2O$, 6:3:1) to give an amorphous solid 234 (69 mg, 81%): $[\alpha]_D$ +40.9° (c 0.31, $D_2O$); $^1$H NMR ($D_2O$) δ 4.57 (1H, ddd, $J_{1a,2}$=$J_{2,3}$=3.3 Hz, $J_{1b,2}$=2.0 Hz, H-2), 4.28 (1H, ddd, $J_{1a',2'}$=$J_{2',3'}$=3.6 Hz, $J_{1b',2'}$=7.1 Hz, H-2'), 4.26 (1H, dd, $J_{3,4}$=8.4 Hz, H-3), 4.22 (1H, ddd, $J_{2',3'}$=$J_{3',4b'}$=3.3 Hz, $J_{3',4a'}$=7.5 Hz, H-3'), 4.06 (1H, dd, $J_{4,5a}$=3.2 Hz, $J_{5a,5b}$=12.4 Hz, H-5a), 4.03 (1H, dd, $J_{1a',1b'}$=13.2 Hz, H-1a'), 3.93 (1H, ddd, $J_{4,5b}$=5.4 Hz, H-4), 3.84 (1H, dd, H-5b), 3.83 (1H, dd, $J_{4a',4b'}$=12.9 Hz, H-4a'), 3.80 (1H, dd, H-1b), 3.72 (1H, dd, H-4b'), 3.65 (1H, dd, $J_{1a,1b}$=14.5 Hz, H-1a), 3.40 (1H, dd, H-1b); $^{13}$C NMR ($D_2O$) δ 79.80 (C-3'), 75.19 (C-3), 73.33 (C-2), 65.41 (C-2'), 65.13 (C-4), 59.74 (C-4'), 57.35 (C-5), 51.06 (C-1'), 44.3 (C-1); MALDI-TOF MS: m/e 335.07 ($M^++H$), 357.01 ($M^++Na$). Anal. Calcd for $C_9H_{18}O_9S_2$: C, 32.33; H, 5.43. Found: C, 32.12; H, 5.67.

5.2.15 Example 15

New Synthetic Route for synthesis of chain-extended selenium, sulfur and nitrogen analogues (Schemes 58-65)

Enzyme Activity Assay. Analysis of MGA inhibition was performed using maltose as the substrate, and measuring the release of glucose. Reactions were carried out in 100 mM MES buffer pH 6.5 at 37° C. for 15 min. The reaction was stopped by boiling for 3 min. 20 μL aliquots were taken and added to 100 mL of glucose oxidase assay reagent (Sigma) in a 96-well plate. Reactions were developed for 1 hour and absorbance was measured at 450 nm to determine the amount of glucose produced by MGA activity in the reaction. One unit of activity is defined as the hydrolysis of one mole of maltose per minute. All reactions were performed in triplicate and absorbance measurements were averaged to give a final result.

Enzyme Kinetics: Kinetic parameters of recombinant MGA were determined using the glucose oxidase assay to follow the production of glucose upon addition of enzyme (15 nM) at increasing maltose concentrations (from 1 mM-3.5 mM) with a reaction time of 15 minutes. The program GraFit 4.0.14 was used to fit the data to the Michaelis-Menten equation and estimate the kinetic parameters, $K_m$ and $V_{max}$, of the enzyme. $K_i$ values for each inhibitor were determined by measuring the rate of maltose hydrolysis by MGA at varying inhibitor concentrations. Data were plotted in Lineweaver-Burk plots (1/rate vs. 1/[substrate]) and $K_i$ values were determined by the equation $K_i = K_m[I]/(V_{max})m - K_m$, where "m" is the the slope of the line. The $K_i$ reported for each inhibitor was estimated by averaging the $K_i$ values obtained from each of the different inhibitor concentrations.

Benzyl 2,3-O-[(2R,3R)-2,3-dimethoxybutane-2,3-diyl]-β-D-galactopyranoside (262)

To a solution of benzyl β-D-galactopyranoside (261)[114] (10.0 g, 37.0 mmol) in dry MeOH (200 mL), 2,3-butanedione (4.0 mL, 45.6 mmol), trimethyl orthoformate (25 mL, 0.23 mol) was added. CSA (300 mg) was added as a catalyst at R.T., and the reaction mixture was then refluxed for 24 h. When TLC analysis of aliquots (Hexane:EtOAc, 1:1) showed total consumption of the starting material, the reaction was stopped by the addition of triethylamine (1 mL). Purification by column chromatography (Hexane:EtOAc, 2:1) yielded compound 262 as a colorless solid (10.2 g, 72%). $[\alpha]^{22}_D$ −58.7 (c 1.0, $CH_2Cl_2$); $^1H$ NMR ($CDCl_3$): δ 7.40-7.24 (m, 5H, Ar), 4.90 and 4.74 (2 d, 2H, $J_{AB}$=12.3, $CH_2Ph$), 4.60 (d, 1H, $J_{1,2}$=8.0, H-1), 3.98 (dd, 1H, $J_{2,3}$=10.3, H-2), 3.95 (m, 1H, H-4), 3.94 (dd, 1H, $J_{5,6}a$=6.7, H-6a), 3.81 (dd, 1H, $J_{5,6b}$=4.6, $J_{6a,6b}$=11.7, H-6b), 3.74 (dd, 1H, $J_{3,4}$=3.0, H-3), 3.57 (m, 1H, H-5), 3.28 and 3.25 (2 s, 6H, 2×$OCH_3$), 1.33 and 1.32 (2 s, 6H, 2×$CH_3$). $^{13}C$ NMR ($CDCl_3$): δ 138.0, 128.4, 127.7, 127.6 ($C_{Ar}$), 100.9 (C-1), 100.5, 100.0 (2×C(OMe)(OR)), 75.2 (C-5), 71.3 ($CH_2Ph$), 70.4 (C-3), 68.4 (C-4), 67.1 (C-2), 62.7 (C-6), 48.3, 48.2 (2×$OCH_3$), 17.9, 17.8 (2×$CH_3$). Anal. Calcd. for $C_{19}H_{28}O_8$: C, 59.36; H, 7.34. Found: C, 59.33; H, 7.30.

Benzyl 2,3-O-[(2R,3R)-2,3-dimethoxybutane-2,3-diyl]-β-D-glucopyranoside (264) and benzyl 3,4-O-[(2R,3R)-2,3-dimethoxybutane-2,3-diyl]-β-D-glucopyranoside (20)

To a solution of benzyl β-D-glucopyranoside (263)[115] (15.0 g, 55.5 mmol) in dry MeOH (200 mL), 2,3-butanedione (6.0 mL, 68.4 mmol), and methyl orthoformate (37.5 mL, 0.34 mol) was added. CSA (300 mg) was added as a catalyst at R.T., and the reaction mixture was then refluxed for 24 h. When TLC analysis of aliquots (Hexane:EtOAc, 1:1) showed total consumption of the starting material and the formation of two main products 264 and 265. The reaction was stopped by the addition of triethylamine (1 mL). Purification by column chromatography (Hexane:EtOAc, 2:1) yielded compound 264 and 265 (264:265=1.8:1) as colorless solids (11.4 g, 53% for 264, 6.3 g, 30% for 265, yields based on 263). For compound 264: $[\alpha]^{22}_D$ −48.3 (c 1.0, $CH_2Cl_2$); $^1H$ NMR ($CDCl_3$): δ 7.41-7.20 (m, 5H, Ar), 4.86 and 4.67 (2 d, 2H, $J_{AB}$=12.3, $CH_2Ph$), 4.62 (d, 1H, $J_{1,2}$=7.9, H-1), 3.84 (dd, 1H, $J_{5,6}a$=3.0, $J_{6a,6b}$=12.0, H-6a), 3.79 (dd, 1H, $J_{5,6b}$=4.4, H-6b), 3.73 (t, 1H, $J_{3,4}$=$J_{4,5}$=9.5, H-4), 3.67 (t, 1H, $J_{2,3}$=$J_{3,4}$=9.5, H-3), 3.55 (dd, 1H, H-2), 3.34 (ddd, 1H, H-5), 3.26 and 3.25 (2 s, 6H, 2×$OCH_3$), 1.31 and 1.30 (2 s, 6H, 2×$CH_3$). $^{13}C$ NMR ($CDCl_3$): δ 137.8, 128.5, 127.9, 127.6 ($C_{Ar}$), 100.7 (C-1), 99.8, 99.7 (2×C(OMe)(OR)), 76.2 (C-5), 72.8 (C-3), 71.7 ($CH_2Ph$), 69.5 (C-2), 68.2 (C-4), 62.6 (C-6), 48.2, 48.1 (2×$OCH_3$), 17.8 (2×$CH_3$). Anal. Calcd. for $C_{19}H_{28}O_8$: C, 59.36; H, 7.34. Found: C, 59.18; H, 7.22.

For compound 265: $[\alpha]^{22}_D$ +8.2 (c 1.0, $CH_2Cl_2$); $^1H$ NMR ($CDCl_3$): δ 7.40-7.25 (m, 5H, Ar), 4.90 and 4.68 (2 d, 2H, $J_{AB}$=11.7, $CH_2Ph$), 4.47 (d, 1H, $J_{1,2}$=7.4, H-1), 3.88 (dd, 1H, $J_{5,6}a$=3.0, $J_{6a,6b}$=12.0, H-6a), 3.75 (dd, 1H, $J_{5,6b}$=4.8, H-6b), 3.74-3.68 (m, 2H, H-3, H-4), 3.62 (dd, 1H, $J_{2,3}$=8.6, H-2), 3.54 (ddd, 1H, H-5), 3.30 and 3.26 (2 s, 6H, 2×$OCH_3$), 1.34 and 1.30 (2 s, 6H, 2×$CH_3$). $^{13}C$ NMR ($CDCl_3$): δ 137.1, 128.8, 128.4, 128.3 ($C_{Ar}$), 102.9 (C-1), 99.9, 99.8 (2×C(OMe)(OR)), 74.3 (C-5), 72.0 ($CH_2Ph$), 71.9 (C-4), 71.5 (C-2), 66.0 (C-3), 61.6 (C-6), 48.3, 48.2 (2×$OCH_3$), 17.9, 17.8 (2×$CH_3$). Anal. Calcd. for $C_{19}H_{28}O_8$: C, 59.36; H, 7.34. Found: C, 59.08; H, 7.26.

Benzyl 2,3-O-[(2R,3R)-2,3-dimethoxybutane-2,3-diyl]-β-D-galactopyranoside-4,6-cyclic sulfate (259)

To a solution of benzyl 2,3-O-[(2R,3R)-2,3-dimethoxybutane-2,3-diyl]-β-D-galactopyranoside (262) (10.0 g, 26.0 mmol) in $CH_2Cl_2$ (50 mL) and pyridine (50 mL) cooled at 0° C., thionyl chloride (4.7 mL, 64.4 mmol) in $CH_2Cl_2$ (20 mL) was added dropwise. After the addition, the reaction mixture was warmed to R.T. and stirred for 2 h. The progress of the reaction was followed by TLC (Hexane:EtOAc, 1:1). When the starting material 267 had been essentially consumed, the reaction mixture was poured into crushed ice (100 mL), extracted with $CH_2Cl_2$ (2×100 mL), washed with brine (50 mL), and dried over $Na_2SO_4$. After removal of the solvent and excess pyridine under reduced pressure, the crude product was passed through a short silica gel column. The cyclic sulfites were subsequently dissolved in $CH_3CN$—$CCl_4$-$H_2O$ mixture (10:10:1, 84 mL) and sodium periodiate (7.2 g, 33.8 mmol) was added. To this reaction mixture $RuCl_3.3H_2O$ (100 mg) was added as a catalyst. The reaction mixture was stirred at R.T. for 3 h. The progress of the reaction was followed by TLC (Hexane:EtOAc, 2:1). When the cyclic sulfites had been consumed, a single slightly less polar spot was observed. The reaction mixture was filtered through a short column of Celite, and the Celite was washed with $CH_2Cl_2$ (2×20 mL). The filtrate was combined and the solvents evaporated. The residue was redissolved in $CH_2Cl_2$ (200 mL), washed with $H_2O$ (2×20 mL), brine (2×10 mL), and dried over $Na_2SO_4$. Purification by column chromatography (Hexane: EtOAc, 1:1) gave compound 259 as a colorless solid (7.1 g, 60% for two steps). $[\alpha]^{22}_D$ −165.3 (c 1.0, $CH_2Cl_2$); $^1H$ NMR ($CDCl_3$): δ 7.40-7.22 (m, 5H, Ar), 5.08 (d, 1H, $J_{1,2}$=3.0, H-1), 4.95 and 4.70 (2 d, 2H, $J_{AB}$=12.1, $CH_2Ph$), 4.78 (dd, 1H, $J_{5,6}a$=1.7, $J_{6a,6b}$=12.3, H-6a), 4.68 (d, 1H, H-4), 4.63 (dd, 1H, $J_{5,6b}$=0.9, H-6b), 4.00 (dd, 1H, $J_{2,3}$=10.4, $J_{3,4}$=7.8, H-3), 3.92 (dd, 1H, H-2), 3.66 (br.s., 1H, H-5), 3.30 and 3.26 (2 s, 6H, 2×$OCH_3$), 1.34 and 1.31 (2 s, 6H, 2×$CH_3$). $^{13}C$ NMR ($CDCl_3$): δ 138.1, 128.6, 128.0, 127.6 ($C_{Ar}$), 100.9, 100.0 (2×C(OMe)(OR)), 100.4 (C-4), 81.1 (C-1), 74.6 (C-6), 71.2 ($CH_2Ph$), 67.6 (C-2), 66.1 (C-3), 64.8 (C-5), 48.5, 48.3 (2×$OCH_3$), 17.9, 17.6 (2×$CH_3$). Anal. Calcd. for $C_{19}H_{26}O_{10}S$: C, 51.11; H, 5.87. Found: C, 51.30; H, 5.79.

Benzyl 2,3-O-[(2R,3R)-2,3-dimethoxybutane-2,3-diyl]-β-D-glucopyranoside-4,6-cyclic sulfate (260)

To a solution of benzyl 2,3-O-[(2R,3R)-2,3-dimethoxybutane-2,3-diyl]-β-D-glucopyranoside (264) (14.0 g, 36.4 mmol) in $CH_2Cl_2$ (50 mL) and pyridine (50 mL) cooled to 0° C., thionyl chloride (6.6 mL, 90.4 mmol) dissolved in $CH_2Cl_2$ (20 mL) was added dropwise. After the addition, the reaction mixture was warmed to R.T. and stirred for 2 h. The progress of the reaction was followed by TLC (Hexane:EtOAc, 1:1). When the starting material 264 had been essentially consumed, the reaction mixture was poured into crushed ice (100 mL), extracted with $CH_2Cl_2$ (2×100 mL), washed with brine (50 mL), and dried with $Na_2SO_4$. After removal of the solvent and excess pyridine under reduced pressure, the crude product was passed through a short silica gel column to give a mixture of cyclic sulfites. The cyclic sulfites were subsequently dissolved in $CH_3CN$—$CCl_4$-$H_2O$ mixture (10:10:1, 105 mL), and sodium periodate (9.3 g, 43.6 mmol) was added. To this reaction mixture $RuCl_3.3H_2O$ (100 mg) was added as a catalyst and the reaction mixture was stirred at R.T. for 3 h. The progress of the reaction was followed by TLC (Hexane:EtOAc, 2:1). When the cyclic sulfite had been consumed, a single slightly less polar spot was observed. The reaction mixture was filtered through a short column of Celite, and the Celite was washed with $CH_2Cl_2$ (2×20 mL). The filtrates were combined and the solvents evaporated. The residue was dissolved in $CH_2Cl_2$ (200 mL), washed with $H_2O$ (2×50 mL), brine (2×50 mL), and dried over $Na_2SO_4$. Purification by column chromatography (Hexane: EtOAc, 1:1) gave compound 260 as a colorless solid (10.9 g, 67% for two steps). $[\alpha]^{22}_D$ −169.° (c 1.0, $CH_2Cl_2$); $^1H$ NMR ($CDCl_3$): δ 7.40-7.23 (m, 5H, Ar), 4.90 and 4.71 (2 d, 2H, $J_{AB}$=12.1, $CH_2Ph$), 4.74 (d, 1H, H-1), 4.70-4.68 (d, 1H, H-4), 4.67 (dd, 1H, $J_{5,6}a$=10.4, H-6a), 4.53 (dd, 1H, $J_{5,6b}$=5.0, $J_{6a,6b}$=10.6, H-6b), 4.02 (dd, 1H, $J_{3,4}$=9.9, H-3), 3.80 (ddd, 1H, $J_{4,5}$=10.3, H-5), 3.70 (dd, 1H, $J_{2,3}$=9.2, $J_{1,2}$=8.5, H-2), 3.28 and 3.26 (2 s, 6H, 2×$OCH_3$), 1.38 and 1.35 (2 s, 6H, 2×$CH_3$). $^{13}C$ NMR ($CDCl_3$): δ 138.3, 128.6, 128.2, 127.6 ($C_{Ar}$), 101.1 (C-1), 100.3, 100.2 (2×C(OMe)(OR)), 80.7 (C-4), 72.0 (C-6), 71.8 ($CH_2Ph$), 69.7 (C-2), 68.5 (C-3), 65.8 (C-5), 48.5, 48.3 (2×$OCH_3$), 17.7, 17.6 (2×$CH_3$). Anal. Calcd. for $C_{19}H_{26}O_{10}S$: C, 51.11; H, 5.87. Found: C, 51.15; H, 6.09.

General Procedure for the Preparation of Selenonium, Sulfonium, and Iminonium Sulfates 266-271.

A mixture of the 1,4-anhydro-2,3,5-O-p-methoxybenzyl-4-seleno-D-arabinitol 250, or 1,4-anhydro-2,3,5-O-p-methoxybenzyl-4-thio-D-arabinitol 257, and the cyclic sulfate 259 or 260, in HFIP (1,1,1,3,3,3-hexafluoroisopropanol) was placed in a sealed tube and $K_2CO_3$ (10 mg) was added. In the case of the reaction of 1,4-anhydro-2,3,5-O-p-methoxybenzyl-4-imino-D-arabinitol 258 with the cyclic sulfates 259 and 260, dry acetone was used instead of HFIP. The stirred reaction mixture was heated at the indicated temperature for the indicated time as given below. The progress of the reaction was followed by TLC (EtOAc:MeOH, 10:1). When the limiting reagent had been essentially consumed, the mixture was cooled to R.T., then diluted with $CH_2Cl_2$, and evaporated to give a syrupy residue. Purification by column chromatography (EtOAc to EtOAc:MeOH, 10:1) gave the purified selenonium, sulfonium, and ammonium salts 266-271.

Benzyl-2,3-O-[(2R,3R)-2,3-dimethoxybutane-2,3-diyl]-4-O-sulfooxy-6-deoxy-6-[1,4-dideoxy-2,3,5-tri-O-p-methoxybenzyl-1,4-episelenoniumylidene-D-arabinitol]-β-D-galactopyranoside Inner Salt (266)

Reaction of 256 (800 mg, 1.43 mmol) with the cyclic sulfate 259 (770 mg, 1.72 mmol) in HFIP (2.0 mL) for 12 h at 65-70° C. gave compound 266 as a colorless, amorphous foam (1.04 g, 72% based on 256). $[\alpha]^{22}_D$ −48.4 (c 1.0, $CH_2Cl_2$); $^1H$ NMR (($CD_3)_2O$) δ: 7.45-6.85 (m, 17H, Ar.), 4.95 and 4.68 (2 d, 2H, $J_{AB}$=12.7, $CH_2Ph$), 4.76 (m, 1H, H-3'), 4.72 (ddd, 1H, H-2), 4.68 (d, 1H, $J_{1',2'}$=7.4, H-1'), 4.64 and 4.60 (2 d, 2H, $J_{AB}$=11.7, $CH_2Ph$), 4.58 (m, 1H, H-3), 4.50 and 4.42 (2 d, 2H, $J_{AB}$=11.5, $CH_2Ph$), 4.42 (m, 1H, H-5'), 4.32 and 4.28 (2 d, 2H, $J_{AB}$=11.7, $CH_2Ph$), 4.20 (dd, 1H, $J_{5',6'a}$=6.2, H-6'a), 4.18 (m, 1H, H-4), 4.14 (dd, 1H, $J_{5',6'b}$=2.1, $J_{6'a,6'b}$=12.0, H-6'b), 3.96 (dd, 1H, $J_{1a,1b}$=12.4, $J_{1a,2}$=1.3, H-1a), 3.90-3.87 (m, 2H, H-2', H-4'), 3.79, 3.78, 3.75 (3 s, 9H, 3×$OCH_3$), 3.81-3.77 (m, 2H, H-5a, H-5b), 3.63 (dd, 1H, $J_{1b,2}$=3.2, H-1b), 3.23 and 3.20 (2 s, 6H, 2×$OCH_3$), 1.24 (s, 6H, 2×$CH_3$). $^{13}C$ NMR (($CD_3)_2O$) δ: 159.9, 159.8, 159.7, 138.6, 130.1, 130.0, 129.8, 129.7, 129.6, 129.5, 129.3, 128.4, 127.5, 127.0, 114.1, 114.0, and 113.9 ($C_{Ar}$), 101.3 (C-1'), 100.0, 99.4 (2×C(OR)$_2$(OMe)$_2$), 83.8 (C-3), 82.9 (C-2), 74.4 (C-3'), 72.7, 71.6, 71.1, and 70.6 (4×$CH_2Ph$), 70.7 (C-5'), 68.5 (C-4'), 67.0 (C-5), 66.9 (C-2'), 64.1 (C-4), 54.9, 54.8, and 54.7 (3×$OCH_3$), 47.9 (C-6'), 47.4, 47.2 (2×$OCH_3$), 44.7 (C-1), 17.45, 17.44 (2×$CH_3$). MALDI MS m/e 1027.22 ($M^+$+Na), 1005.34 ($M^+$+H), 925.23 ($M^+$+H−$SO_3$). Anal. Calcd. for $C_{48}H_{60}O_{16}SSe$: C, 57.42; H, 6.02; Found: C, 57.11; H, 6.14.

Benzyl-2,3-O-[(2R,3R)-2,3-dimethoxybutane-2,3-diyl]-4-O-sulfooxy-6-deoxy-6-[1,4-dideoxy-2,3,5-tri-O-p-methoxybenzyl-1,4-episulfoniumylidene-D-arabinitol]-β-D-galactopyranoside Inner Salt (267)

Reaction of 257 (800 mg, 1.57 mmol) with the cyclic sulfate 259 (840 mg, 1.88 mmol) in HFIP (2.0 mL) for 12 h at 75-80° C. gave compound 267 as a colorless, amorphous foam (1.12 g, 75% based on 257). $[\alpha]^{22}_D$ −47.2 (c 1.0, $CH_2Cl_2$); $^1H$ NMR (($CD_3)_2O$) δ: 7.60-6.80 (m, 17H, Ar.), 4.86 and 4.68 (2 d, 2H, $J_{AB}$=13.0, $CH_2Ph$), 4.67 and 4.59 (2 d, 2H, $J_{AB}$=13.0, $CH_2Ph$), 4.62 (m, 1H, H-2), 4.50 and 4.44 (2 d, 2H, $J_{AB}$=11.4, $CH_2Ph$), 4.48-4.42 (m, 2H, =H-1', H-3), 4.41 (s, 2H, $CH_2Ph$), 4.34 (ddd, 1H, H-5'), 4.29 (m, 1H, H-4'), 4.26 (dd, 1H, $J_{5',6'a}$=6.2, $J_{6'a,6'b}$=13.1, H-6'a), 4.14 (dd, 1H, $J_{5',6'b}$=4.3, H-6'b), 4.10 (m, 1H, H-4), 4.09 (dd, 1H, $J_{1a,1b}$=13.1, H-1a), 3.90 (dd, 1H, $J_{4,5a}$=3.4, $J_{5aa,5b}$=10.3, H-5a), 3.88-3.79 (m, 4H, H-5b, H-1b, H-2', H-3'), 3.78, 3.76 (2 s, 9H, 3×$OCH_3$), 3.26 and 3.19 (2 s, 6H, 2×$OCH_3$), 1.25 and 1.24 (2 s, 6H, 2×$CH_3$). $^{13}C$ NMR (($CD_3)_2O$) δ: 159.9, 159.8, 159.7, 138.6, 138.5, 132.8, 130.4, 130.1, 130.0, 129.8, 129.7, 129.6, 128.4, 127.5, 127.1,-112.6, 112.6, and 112.5 ($C_{Ar}$), 101.5 (C-1'), 100.0, 99.4 (2×C(OR)$_2$(OMe)$_2$), 82.8 (C-3), 82.4 (C-2), 73.7, 72.9, 71.3, and 70.9 (4×$CH_2Ph$), 71.9 (C-4), 71.6 (C-5'), 68.5 (C-3'), 67.1 (C-5), 67.0 (C-2'), 65.2 (C-4'), 54.9, 54.8 (3×$OCH_3$), 49.0 (C-6'), 47.7, 47.4 (2×$OCH_3$), 47.2 (C-1), 17.5, 17.4 (2×$CH_3$). MALDI MS m/e 979.39 ($M^+$+Na), 957.42 ($M^+$+H), 877.43 ($M^+$+H−$SO_3$). HRMS. Calcd. for $C_{48}H_{60}NaO_{16}S_2$: 979.3220. Found:

Benzyl-2,3-O-[(2R,3R)-2,3-dimethoxybutane-2,3-diyl]-4-O-sulfooxy-6-deoxy-6-[1,4-dideoxy-2,3,5-tri-O-p-methoxybenzyl-1,4-iminonium-D-arabinitol]-β-D-galactopyranoside Inner Salt (268)

Reaction of 258 (1.0 g, 2.02 mmol) with the cyclic sulfate 259 (1.09 g, 2.43 mmol) in dry acetone (3.0 mL) for 12 h at 55-60° C. gave compound 268 as a colorless, amorphous foam (1.69 g, 89% based on 13). $[\alpha]^{22}_D$ −38.5 (c 1.0, $CH_2Cl_2$); $^1H$ NMR ($CD_2Cl_2$) δ: 7.55-6.78 (m, 17H, Ar.), 4.85 and 4.58 (2 d, 2H, $J_{AB}$=12.4, $CH_2Ph$), 4.73 (m, 1H, H-4'), 4.52 and 4.35 (2 d, 2H, $J_{AB}$=11.7, $CH_2Ph$), 4.45 (m, 1H, H-1'), 4.62 (m, 1H, H-2), 4.50 and 4.44 (2 d, 2H, $J_{AB}$=11.4, $CH_2Ph$), 4.48-4.42 (m, 2H, =H-3), 4.41 and 4.34 (2 d, 2H, $J_{AB}$=11.8, $CH_2Ph$), 4.31 and 4.27 (2d, 2H, $J_{AB}$=11.5, $CH_2Ph$), 3.88-3.70 (m, 5H, H-2, H-3, H-2', H-3', H-5'), 3.76, 3.75, and 3.73 (3s, 9H, 3×OCH$_3$), 3.56 (dd, 1H, J$_{4,5a}$=5.1, J$_{5a,5b}$=9.9, H-5a), 3.44 (dd, 1H, J$_{4,5b}$=3.8, H-5b), 3.34-3.20 (m, 2H, H-6'b, H-1'b), 3.27 and 3.24 (2 s, 6H, 2×OCH$_3$), 3.00-2.62 (m, 3H, H-6'a, H-1a, H-4), 1.32 and 1.23 (2 s, 6H, 2×CH$_3$). $^{13}$C NMR (CD$_2$Cl$_2$) δ: 159.5, 159.4, 159.3, 137.8, 130.4, 130.1, 129.9, 129.8, 129.4, 128.4, 127.8, 127.7, 127.6, 113.9, 113.8, 113.7 (C$_{Ar}$), 112.0 (C-1'), 100.5, 100.0 (2×C(OR)$_2$(OMe)$_2$), 84.2 (C-2), 81.1 (C-5'), 75.8 (C-4'), 74.7 (C-3), 72.7, 71.1, 71.0, and 70.6 (4×CH$_2$Ph), 70.4 (C-4), 69.3 (C-3'), 68.6 (C-5), 67.5 (C-2'), 58.4 (C-1), 55.4, 55.3, and 55.2 (3×OCH$_3$), 55.0 (C-6'), 48.5, 48.2 (2×OCH$_3$), 17.6, 17.5 (2×CH$_3$). MALDI MS m/e 962.66 (M$^+$+Na), 939.63 (M$^+$+H), 860.78 (M$^+$+H–SO$_3$). HRMS. Calcd. for C$_{48}$H$_{61}$NNaO$_{16}$S: 962.3609. Found:

Benzyl-2,3-O-[(2R,3R)-2,3-dimethoxybutane-2,3-diyl]-4-O-sulfooxy-6-deoxy-6-[1,4-dideoxy-2,3,5-tri-O-p-methoxybenzyl-1,4-episelenoniumylidene-D-arabinitol]-β-D-glucopyranoside Inner Salt (269)

Reaction of 256 (800 mg, 1.43 mmol) with the cyclic sulfate 260 (770 mg, 1.72 mmol) in HFIP (2.0 mL) for 12 h at 65-70° C. gave compound 269 as a colorless, amorphous foam (1.01 g, 70% based on 256). [α]$^{22}_D$ –47.5 (c 1.0, CH$_2$Cl$_2$); $^1$H NMR ((CD$_3$)$_2$O) δ: 7.45-6.83 (m, 17H, Ar.), 4.90 and 4.72 (2 d, 2H, J$_{AB}$=12.4, CH$_2$Ph), 4.84 (m, 1H, H-2), 4.73 (d, 1H, J$_{1',2'}$=8.3, H-1'), 4.65 and 4.53 (2 d, 2H, J$_{AB}$=11.3, CH$_2$Ph), 4.66-4.62 (m, 2H, CH$_2$Ph), 4.59 (m, 1H, H-3), 4.46 and 4.42 (2 d, 2H, J$_{AB}$=11.9, CH$_2$Ph), 4.36 (dd, 1H, J$_{5',6'a}$=3.1, J$_{6'a,6'b}$=12.1, H-6'a), 4.33 (m, 1H, H-4), 4.30 (t, 1H, J$_{3',4}$=J$_{4',5}$=9.5, H-4'), 4.16 (dd, 1H, J$_{5',6'b}$=3.3, H-6'b), 4.08 (dd, 1H, J$_{1a,1b}$=12.4, H-1a), 4.08-4.02 (m, 1H, H-5'), 3.86-3.76 (m, 3H, H-3', H-5a, H-5b), 3.80, 3.79, 3.77 (3 s, 9H, 3×OCH$_3$), 3.75 (dd, 1H, J$_{1b,2}$=3.2, H-1b), 3.62 (dd, 1H, J$_{2,3}$=9.7, H-2'), 3.24 and 3.21 (2 s, 6H, 2×OCH$_3$), 1.26 and 1.25 (2 s, 6H, 2×CH$_3$). $^{13}$C NMR ((CD$_3$)$_2$O) δ: 164.5, 164.4, 164.3, 143.0, 134.7, 134.4, 134.3, 134.2, 134.0, 133.9, 133.0, 132.2, 132.0, 118.6, 118.5, and 118.4(C$_{Ar}$), 105.1 (C-1'), 104.1, 104.0(2× C(OR)$_2$(OMe)$_2$), 88.8 (C-3), 87.7 (C-2), 77.9 (C-4'), 77.2 (C-5'), 77.2, 76.3, 75.9, and 75.3 (4×CH$_2$Ph), 74.6 (C-2'), 74.5 (C-3'), 71.4 (C-5), 70.0 (C-4), 59.5, 59.4 (3×OCH$_3$), 52.5 (C-6'), 51.8, 51.7 (2×OCH$_3$), 50.0 (C-1), 21.9, 21.7 (2×CH$_3$). MALDI MS m/e 1027.19 (M$^+$+Na), 1005.13 (M$^+$+H), 925.24 (M$^+$+H–SO$_3$). Anal. Calcd. for C$_{48}$H$_{60}$O$_{16}$SSe: C, 57.42; H, 6.02; Found: C, 57.12; H, 6.09.

Benzyl-2,3-O-[(2R,3R)-2,3-dimethoxybutane-2,3-diyl]-4-O-sulfooxy-6-deoxy-6-[1,4-dideoxy-2,3,5-tri-O-p-methoxybenzyl-1,4-episulfoniumylidene-D-arabinitol]-β-D-glucopyranoside Inner Salt (270)

Reaction of 257 (800 mg, 1.57 mmol) with the cyclic sulfate 260 (840 mg, 1.88 mmol) in HFIP (2.0 mL) for 12 h at 75-80° C. gave compound 270 as a colorless, amorphous foam (1.17 g, 78% based on 257). [α]$^{22}_D$ –48.° (c 1.0, CH$_2$Cl$_2$); $^1$H NMR ((CD$_3$)$_2$O) δ: 7.45-6.85 (m, 17H, Ar.), 4.89 and 4.70 (2 d, 2H, J$_{AB}$=12.5, CH$_2$Ph), 4.75 (m, 1H, H-2), 4.67 and 4.53 (2 d, 2H, J$_{AB}$=11.2, CH$_2$Ph), 4.66-4.60 (m, 3H, H-1', CH$_2$Ph), 4.54 (m, 1H, H-3), 4.48 (m, 2H, CH$_2$Ph), 4.38 (dd, 1H, J$_{1a,2}$=3.4, J$_{1b,2}$=3.1, H-1b), 4.10 (m, 2H, H-5', H-6'a), 3.94-3.83 (m, 3H, H-5a, H-5b, H-6'b), 3.82-3.79 (m, 1H, H-3'), 3.80, 3.79 and 3.78 (3 s, 9H, 3×OCH$_3$), 3.62 (dd, 1H, J$_{1',2'}$=8.1, J$_{2',3}$=9.8, H-2'), 3.25 and 3.22 (2 s, 6H, 2×OCH$_3$), 1.25 and 1.24 (2 s, 6H, 2×CH$_3$). $^{13}$C NMR ((CD$_3$)$_2$O) δ: 164.6, 164.5, 142.9, 134.8, 134.7, 134.5, 134.3, 133.0, 132.2, 131.9, 118.7, 118.6, 118.5 (C$_{Ar}$), 105.3 (C-1'), 104.0 (2×C(OR)$_2$(OMe)$_2$), 88.1 (C-3), 87.0 (C-2), 77.4, 76.3, 76.1, and 75.5 (4×CH$_2$Ph), 76.9 (C-4'), 76.8 (C-5'), 74.5 (C-3'), 74.4 (C-2'), 71.3 (C-5), 70.2 (C-4), 59.5, 59.4 (3×OCH$_3$), 53.6 (C-1), 52.0 (C-6'), 51.9, 51.7 (2×OCH$_3$), 21.9, 21.8 (2×CH$_3$). MALDI MS m/e 979.47 (M$^+$+Na), 957.46 (M$^+$+H), 877.50 (M$^+$+H–SO$_3$). HRMS. Calcd. for C$_{48}$H$_{60}$NaO$_{16}$S$_2$: 979.3220. Found:

Benzyl-2,3-O-[(2R,3R)-2,3-dimethoxybutane-2,3-diyl]-4-O-sulfooxy-6-deoxy-6-[1,4-dideoxy-2,3,5-tri-O-p-methoxybenzyl-1,4-iminonium-D-arabinitol]-β-D-glucopyranoside Inner Salt (271) 1

Reaction of 258 (1.0 g, 2.02 mmol) with the cyclic sulfate 260 (1.09 g, 2.43 mmol) in dry acetone (3.0 mL) for 12 h at 55-60° C. gave compound 271 as a colorless, amorphous foam (1.71 g, 90% based on 258). [α]$^{22}_D$ –39.1 (c 1.0, CH$_2$Cl$_2$); $^1$H NMR (CD$_2$Cl$_2$) δ: 7.42-6.60 (m, 17H, Ar.), 4.72 and 4.47 (2 d, 2H, J$_{AB}$=12.2, CH$_2$Ph), 4.55-4.49 (m, 1H, H-1'), 4.49 and 4.24 (2 d, 2H, J$_{AB}$=11.9, CH$_2$Ph), 4.36 and 4.34 (2 d, 2H, J$_{AB}$=12.0, CH$_2$Ph), 4.18-4.14 (m, 1H, H-4'), 4.14 and 4.08 (2 d, 2H, J$_{AB}$=11.3, CH$_2$Ph), 3.87 (t, 1H, J$_{2',3}$=J$_{3,4}$=9.8, H-3'), 3.80-3.60 (m, 3H, H-2, H-3, H-5'), 3.68, 3.67, and 3.66 (3 s, 9H, 3×OCH$_3$), 3.53 (m, 1H, H-5a), 3.50 (dd, 1H, H-2'), 3.40-3.25 (m, 2H, H-6'a, H-5b), 3.23 (dd, 1H, H-1a), 3.16 and 3.13 (2 s, 6H, 2×OCH$_3$), 2.72-2.55 (m, 3H, H-1b, H-4, H-6'b), 1.19 and 1.18 (2 s, 6H, 2×CH$_3$). $^{13}$C NMR (CD$_2$Cl$_2$) δ: 159.5, 159.4, 159.3, 137.9, 137.8, 130.2, 130.1, 130.0, 129.8, 129.4, 128.2, 127.7, 127.5, 127.4, 114.0, 113.9, and 112.1 (C$_{Ar}$), 100.0 (C-1'), 99.8, 99.7 (2 2×C(OR)$_2$(OMe)$_2$), 84.7 (C-2), 79.9 (C-5'), 75.5 (C-4'), 74.8 (C-3), 72.8, 71.2, 70.9, and 70.8 (4×CH$_2$Ph), 70.8 (C-3'), 70.0 (C-4), 69.9 (C-2'), 67.6 (C-5), 58.4 (C-1), 55.4, 55.3, and 55.2 (3×OCH$_3$), 52.1 (C-6'), 48.4, 48.0 (2×OCH$_3$), 17.7, 17.6 (2×CH$_3$). MALDI MS m/e 962.97 (M$^+$+Na), 940.00 (M$^+$+H), 860.13 (M$^+$+H–SO$_3$). Anal. Calcd. for C$_{48}$H$_{60}$KNO$_{16}$S: C, 58.94; H, 6.18; N, 1.43; Found: C, 58.65; H, 6.03; N, 1.45.
General Procedure for the Preparation of the Sulfate Salts 272-277.

The protected coupled products 266-271 were dissolved in CH$_2$Cl$_2$ (2 mL), TFA (10 mL) was then added, and the mixture was stirred for 2 h at R.T. The progress of the reaction was followed by TLC analysis of aliquots (EtOAc:MeOH:H$_2$O, 7:3:1). When the starting material had been consumed, TFA and CH$_2$Cl$_2$ were removed under reduced pressure. The residue was rinsed with CH$_2$Cl$_2$ (4×2 mL) and the CH$_2$Cl$_2$ was decanted to remove the cleaved protecting groups. The remaining gum was dissolved in methanol and purified by column chromatography (EtOAc and EtOAc:MeOH, 2:1) to give the purified compounds 272-277 as colorless, amorphous, and hygroscopic solids.

Benzyl-4-O-sulfooxy-6-deoxy-6-[1,4-dideoxy-1,4-episelenoniumylidene-D-arabinitol]-β-D-galactopyranoside Inner Salt (272)

To a solution of 266 (900 mg, 0.90 mmol) in CH$_2$Cl$_2$ (2 mL) was added TFA (10 mL) to yield compound 272 as a colorless, amorphous, and hygroscopic solid (427 mg, 90%). [α]$^{22}_D$ +11.6 (c 1.0, H$_2$O); $^1$H NMR (CD$_3$OD) δ: 7.46-7.24 (m, 5H, Ar.), 4.92 and 4.70 (2 d, 2H, J$_{AB}$=11.9, CH$_2$Ph), 4.73-4.70 (m, 1H, H-2), 4.67-4.65 (m, 1H, H-4'), 4.49-4.44 (m, 2H, H-1', H-3), 4.24-4.20 (m, 1H, H-5'), 4.15-4.10 (m, 1H, H-4), 3.99 (dd, 1H, J$_{4,5a}$=5.7, J$_{5a,5b}$=11.7, H-5a), 3.94 (dd, 1H, J$_{5',6'a}$=5.3, J$_{6'a,6'b}$=11.5, H-6'a), 3.92 (dd, 1H, H-6'b), 3.91 (dd, 1H, J$_{4,5b}$=2.4, H-5b), 3.73 (dd, 1H, J$_{1a,2}$=2.0, J$_{1a,1b}$=11.9, H-1a), 3.70 (dd, 1H, J$_{1b,2}$=3.1, H-1b), 3.64 (dd, 1H, J$_{3,4}$=3.1, J$_{2',3}$=9.8, H-3'), 3.58 (dd, 1H, J$_{1',2'}$=7.7, H-2'). $^{13}$C NMR (CD$_3$OD) δ: 137.9, 128.2, 128.0, 127.6 (C$_{Ar}$), 103.2 (C-1'), 79.3 (C-3), 78.7 (C-2), 77.2 (C-4'), 72.4 (C-4), 72.3 (C-3'), 71.5 (CH$_2$Ph), 71.2 (C-2'), 69.6 (C-5'), 59.8 (C-6'), 47.3 (C-1), 44.5 (C-5). MALDI MS m/e 553.22 (M$^+$+Na), 531.23 (M$^+$+H), 451.33 (M$^+$+H—SO$_3$). HRMS. Calcd. for C$_{18}$H$_{26}$NaO$_{11}$SSe: 553.0259. Found:

Benzyl-4-O-sulfooxy-6-deoxy-6-[1,4-dideoxy-1,4-episulfoniumylidene-D-arabinitol]-β-D-galactopyranoside Inner Salt (273)

To a solution of 267 (900 mg, 0.94 mmol) in CH$_2$Cl$_2$ (2 mL) was added TFA (10 mL) to yield compound 273 as a colorless, amorphous, and hygroscopic solid (395 mg, 87%). [α]$^{22}_D$ +21.3 (c 1.0, H$_2$O); $^1$H NMR (CD$_3$OD) δ: 7.46-7.26 (m, 5H, Ar.), 4.92 and 4.72 (2 d, 2H, J$_{AB}$=12.0, CH$_2$Ph), 4.73 (m, 1H, H-4'), 4.63 (m, 1H, H-2), 4.50 (d, 1H, J$_{1,2}$=7.8, H-1'), 4.39 (m, 1H, H-3), 4.24 (m, 1H, H-5'), 4.14-4.06 (m, 2H, H-4, H-5a), 3.96 (dd, 1H, J$_{5',6'a}$=9.6, J$_{6'a,6'b}$=13.3, H-6'a), 3.91 (dd, 1H, J$_{4,5b}$=9.2, J$_{5a,5b}$=10.1, H-5b), 3.84 (dd, 1H, J$_{5',6'b}$=2.7, H-6'b), 3.80-3.73 (m, 2H, H-1a, H-1b), 3.73 (dd, 1H, J$_{3,4}$=3.0, H-3'), 3.59 (dd, 1H, J$_{2,3}$=9.7, H-2'). $^{13}$C NMR (CD$_3$OD) δ: 137.9, 128.2, 127.9, 127.7 (C$_{Ar}$), 103.3 (C-1'), 78.4 (C-3), 78.0 (C-2), 76.6 (C-4'), 72.2 (C-3'), 72.1 (C-4), 71.6 (CH$_2$Ph), 71.1 (C-2'), 69.6 (C-5'), 59.6 (C-5), 49.7 (C-1), 47.3 (C-6'). MALDI MS m/e 505.19 (M$^+$+Na), 483.16 (M$^+$+H), 403.28 (M$^+$+H–SO$_3$). HRMS. Calcd. for C$_{18}$H$_{26}$NaO$_{11}$S$_2$: 505.0814. Found:

Benzyl-4-O-sulfooxy-6-deoxy-6-[1,4-dideoxy-1,4-iminonium-D-arabinitol]-β-D-galactopyranoside Inner Salt (274)

To a solution of 268 (1.2 g, 1.28 mmol) in CH$_2$Cl$_2$ (2 mL) was added TFA (10 mL) to yield compound 274 as a colorless, amorphous, and hygroscopic solid (505 mg, 85%). [α]$^{22}_D$ −1.3 (c 1.0, H$_2$O); $^1$H NMR (D$_2$O) δ: 7.34-7.22 (m, 5H, Ar.), 4.76 and 4.60 (2 d, 2H, J$_{AB}$=11.7, CH$_2$Ph), 4.50 (m, 1H, H-4'), 4.37 (d, 1H, J$_{1',2}$=7.9, H-1'), 3.95 (ddd, 1H, H-2), 3.79-3.72 (m, 2H, H-3, H-5'), 3.58 (dd, 1H, J$_{3,4}$=3.2, H-3'), 3.58-3.55 (m, 2H, H-5a, H-5b), 3.40 (dd, 1H, J$_{2,3}$=10.0, H-2'), 3.04 (dd, 1H, J$_{5',6'a}$=2.2, J$_{6'a,6'b}$=14.1, H-6'a), 2.91 (dd, 1H, J$_{1a,2}$=1.2, J$_{1a,1b}$=11.1, H-1a), 2.68 (dd, 1H, J$_{1b,2}$=5.8, H-1b), 2.59 (dd, 1H, J$_{5',6'b}$=8.4, H-6'b), 2.45 (ddd, 1H, H-4). $^{13}$C NMR (D$_2$O) δ: 136.7, 128.8, 128.7, 128.6 (C$_{Ar}$), 101.8 (C-1'), 78.8 (C-4'), 78.7 (C-3), 75.7 (C-2), 73.5 (C-5'), 72.0 (C-4), 71.9 (C-3'), 71.8 (CH$_2$Ph), 70.9 (C-2'), 60.6 (C-5), 59.9 (C-1), 55.3 (C-6'). MALDI MS m/e 488.04 (M$^+$+Na), 466.11 (M$^+$+H), 386.19 (M$^+$+H–SO$_3$). HRMS. Calcd. for C$_{18}$H$_{27}$NNaO$_{11}$S: 488.1203. Found:

Benzyl-4-O-sulfooxy-6-deoxy-6-[1,4-dideoxy-1,4-episelenoniumylidene-D-arabinitol]-β-D-glucopyranoside Inner Salt (275)

To a solution of 269 (900 mg, 0.90 mmol) in CH$_2$Cl$_2$ (2 mL) was added TFA (10 mL) to yield compound 275 as a colorless, amorphous, and hygroscopic solid (389 mg, 82%). [α]$^{22}_D$ −7.2 (c 1.0, H$_2$O); $^1$H NMR (CD$_3$OD) δ: 7.46-7.24 (m, 5H, Ar.), 4.90 and 4.72 (2 d, 2H, J$_{AB}$=12.1, CH$_2$Ph), 4.70-4.68 (m, 1H, H-2), 4.54 (d, 1H, J$_{1',2}$=7.9, H-1'), 4.45 (m, 1H, H-3), 4.14 (t, 1H, J$_{3,4}$=J$_{4,5'}$=8.9, H-4'), 4.14-4.10 (m, 1H, H-4), 4.08 (dd, 1H, J$_{4,5a}$=2.8, H-5a), 3.98 (dd, 1H, J$_{5',6'a}$=5.7, J$_{6'a,6'b}$=12.0, H-6'a), 3.97-3.92 (m, 1H, H-5', H-6'b), 3.90 (dd, 1H, J$_{5a,5b}$=12.3, H-5b), 3.75-3.71 (m, 2H, H-1a, H-1b), 3.64 (dd, 1H, J$_{3',4'}$=8.9, H-3'), 3.40 (dd, 1H, J$_{1',2'}$=8.4, H-2'). $^{13}$C NMR (CD$_3$OD) δ: 137.8, 128.3, 128.0, 127.7 (C$_{Ar}$), 102.7 (C-1'), 79.3 (C-3), 78.7 (C-2), 78.5 (C-4'), 74.4 (C-3'), 73.6 (C-2'), 73.0 (C-4), 71.7 (CH$_2$Ph), 70.4 (C-5'), 59.7 (C-6'), 47.5 (C-1), 45.3 (C-5). MALDI MS m/e 553.25 (M$^+$+Na), 531.28 (M$^+$+H), 451.31 (M$^+$+H–SO$_3$). HRMS. Calcd. for C$_{18}$H$_{26}$NaO$_{11}$SSe: 553.0259. Found:

Benzyl-4-O-sulfooxy-6-deoxy-6-[1,4-dideoxy-1,4-episulfoniumylidene-D-arabinitol]-β-D-glucopyranoside Inner Salt (276)

To a solution of 270 (900 mg, 0.94 mmol) in CH$_2$Cl$_2$ (2 mL) was added TFA (10 mL) to yield compound 276 as a colorless, amorphous, and hygroscopic solid (408 mg, 90%). [α]$^{22}_D$ −8.2 (c 1.0, H$_2$O); $^1$H NMR (D$_2$O) δ: 7.36-7.26 (m, 5H, Ar.), 4.72 (s, 2H, CH$_2$Ph), 4.55 (ddd, 1H, H-2), 4.52 (d, 1H, J$_{1',2}$=8.1, H-1'), 4.28 (m, 1H, H-3), 4.07 (dd, 1H, J$_{4',5}$=9.2, H-4'), 3.96-3.90 (m, 2H, H-5', H-6'a), 3.86 (dd, 1H, J$_{4,5a}$=8.3, J$_{5a,5b}$=15.4, H-5a), 3.80-3.71 (m, 3H, H-4, H-5b, H-6'b), 3.62 (dd, 1H, J$_{1a,2}$=4.1, J$_{1a,1b}$=13.2, H-1a), 3.56 (t, 1H, J$_{2,3}$=J$_{3,4}$=9.4, H-3'), 3.53 (dd, 1H, J$_{1b,2}$=5.1, H-1b), 3.29 (dd, 1H, J$_{2,3}$=9.4, H-2'). $^{13}$C NMR (D$_2$O) δ: 136.9, 129.0, 128.8, 128.7 (C$_{Ar}$), 102.4 (C-1'), 77.8 (C-3), 77.5 (C-4'), 76.8 (C-2), 73.5 (C-3'), 73.0 (CH$_2$Ph), 72.7 (C-2'), 70.2 (C-5'), 70.1 (C-4), 58.7 (C-5), 47.6 (C-6'), 47.4 (C-1). MALDI MS m/e 505.41 (M$^+$+Na), 483.36 (M$^+$+H), 403.44 (M$^+$+H–SO$_3$). HRMS. Calcd. for C$_{18}$H$_{26}$NaO$_{11}$S$_2$: 505.0814. Found:

Benzyl-4-O-sulfooxy-6-deoxy-6-[1,4-dideoxy-1,4-iminonium-D-arabinitol]-β-D-glucopyranoside Inner Salt (277)

To a solution of 271 (1.2 mg, 1.28 mmol) in CH$_2$Cl$_2$ (2 mL) was added TFA (10 mL) to yield compound 277 as a colorless, amorphous, and hygroscopic solid (517 mg, 87%). [α]$^{22}_D$ −2.5 (c 1.0, H$_2$O); $^1$H NMR (D$_2$O) δ: 7.34-7.23 (m, 5H, Ar.), 4.74 and 4.62 (2 d, 2H, J$_{AB}$=11.7, CH$_2$Ph), 4.44 (d, 1H, J$_{1',2}$=8.0, H-1'), 3.95 (ddd, 1H, H-2), 3.85 (dd, 1H, J$_{4',5}$=9.5, H-4'), 3.77 (dd, 1H, J$_{2,3}$=2.9, J$_{3,4}$=5.2, H-3), 3.57 (d, 2H, H-5a, H-5b), 3.54 (m, 1H, H-5'), 3.53 (dd, 1H, J$_{3',4'}$=9.3, H-3'), 3.34 (dd, 1H, H-6'a), 3.24 (dd, 1H, J$_{2,3}$=9.4, H-2'), 2.94 (dd, 1H, J$_{1a,2}$=1.2, H-1a), 2.68 (dd, 1H, J$_{1b,2}$=58, J$_{1a,1b}$=11.3, H-1b), 2.46 (ddd, 1H, J$_{4,5a}$=J$_{4,5b}$=10.1, H-4), 2.38 (dd, 1H, J$_{5,6b}$=8.7, J$_{6'a,6'b}$=14.2, H-6'b),. $^{13}$C NMR (D$_2$O) δ: 136.7, 128.9, 128.6, 128.5 (C$_{Ar}$), 101.2 (C-1'), 78.8 (C-4'), 78.7 (C-3), 75.8 (C-2), 74.3 (C-3'), 74.2 (C-5'), 73.1 (C-2'), 72.1 (C-4), 72.0 (CH$_2$Ph), 60.5 (C-5), 60.2 (C-1), 54.8 (C-6'). MALDI MS m/e 488.05 (M$^+$+Na), 466.12 (M$^+$+H), 386.23 (M$^+$+H—SO$_3$). HRMS. Calcd. for C$_{18}$H$_{27}$NNaO$_{11}$S: 488.1203. Found:

General Procedure for the Preparation of the Final Compounds 250-255.

The partially deprotected compounds 272-277 were dissolved in 90% AcOH (10 mL), and Pd(OH)$_2$/C (20%, 300 mg-500 mg, depending on the amount of starting material) was added and the reaction mixture was subjected to hydrogenolysis for 24 h at R.T. After filtering the Pd(OH)$_2$/C, water (100 mL) was used to washed the Ph(OH)$_2$/C repeatedly. The combined filtrate and water was then evaporated under reduced pressure. The remaining gum was dissolved in water (20 mL), and the pH of the solution was carefully adjusted to 8 by addition of 2M NaOH solution. NaBH$_4$ (1.2 eq. of starting material) was slowly added to the reaction mixture. The progress of the reaction was followed by TLC (EtOAc: MeOH:H$_2$O, 7:3:1). When the starting material was essentially consumed, the pH of the reaction mixture was carefully adjusted to 4 by the addition of 2M HCl solution. After removal of the solvents under reduced pressure, the residue was purified by column chromatography (EtOAc and EtOAc:

MeOH:H$_2$O, 3:2:1) to give the purified compounds 250-255 as colorless, amorphous, hygroscopic solids.

1,4-Dideoxy-1,4-[[2S,3R,4R,5S-2,4,5,6-tetrahydroxy-3-(sulfooxy)hexyl]episelenoniumylidene]-D-arabinitol (250)

Compounds 272 (400 mg, 0.76 mmol) was dissolved in 90% AcOH (10 mL), Pd(OH)$_2$/C (20%, 400 mg) was added, and the reaction mixture was subjected to hydrogenolysis for 24 h at room temperature. The resulting hemiacetals were reduced with NaBH$_4$ (35 mg, 0.92 mmol) to give compound 250 (123 mg, 50%) as a colorless, amorphous, hygroscopic solid. $[\alpha]^{22}_D$ +43.3 (c 1.0, H$_2$O); $^1$H NMR (D$_2$O) δ: 4.68 (dt, 1H, H-2), 4.51 (ddd, 1H, H-2'), 4.38 (dd, 1H, $J_{2,3}$=3.6, H-3), 4.30 (dd, 1H, $J_{2',3'}$=1.3, $J_{3,4}$=9.1, H-3'), 4.05 (ddd, 1H, $J_{3,4}$=3.1, H-4), 3.97 (dd, 1H, $J_{4,5a}$=5.1, $J_{5a,5b}$=12.5, H-5a), 3.89 (dt, 1H, $J_{5',6'a}$=$J_{5',6'b}$=6.3, H-5'), 3.87-3.84 (m, 2H, H-1'a, H-1'b), 3.83 (dd, 1H, $J_{4,5b}$=3.8, H-5b), 3.72 (dd, 1H, $J_{4,5}$=0.9, H-4'), 3.69-3.64 (2d, 2H, H-1a, H-1b), 3.54 (d, 2H, H-6'a, H-6'a). $^{13}$C NMR (D$_2$O) δ: 78.8 (C-3'), 78.5 (C-3), 77.7 (C-2), 69.6 (C-4), 69.5 (C-5'), 68.7 (C-4'), 65.6 (C-2'), 62.8 (C-6'), 59.4 (C-5), 48.6 (C-1'), 44.8 (C-1). MALDI MS m/e 465.27 (M$^+$+Na), 363.36 (M$^+$+H–SO$_3$). HRMS. Calcd. for C$_{11}$H$_{22}$NaO$_{11}$SSe: 464.9946. Found:

1,4-Dideoxy-1,4-[[2S,3R,4R,5S-2,4,5,6-tetrahydroxy-3-(sulfooxy)hexyl]episulfoniumylidene]-D-arabinitol (251)

Compound 273 (300 mg, 0.62 mmol) was dissolved in 90% AcOH (10 mL), Pd(OH)$_2$/C (20%, 300 mg) was added, and the reaction mixture was subjected to hydrogenolysis for 24 h at room temperature. The resulting hemiacetals were reduced with NaBH$_4$ (29 mg, 0.77 mmol) to give compound 251 (127 mg, 52%) as a colorless, amorphous, hygroscopic solid. The $^1$H NMR and 13NMR data matched those reported in our previous publication.[14]

1,4-Dideoxy-1,4-[[2S,3R,4R,5S-2,4,5,6-tetrahydroxy-3-(sulfooxy)hexyl]iminonium]-D-arabinitol (252)

Compound 274 (500 mg, 1.07 mmol) was dissolved in 90% AcOH (10 mL), Pd(OH)$_2$/C (20%, 500 mg) was added, and the reaction mixture was subjected to hydrogenolysis for 24 h at room temperature. The resulting hemiacetals were reduced with NaBH$_4$ (50 mg, 1.32 mmol) to give compound 252 (275 mg, 68%) as a colorless, amorphous, hygroscopic solid. $[\alpha]^{22}_D$ +44.5 (c 1.0, H$_2$O); $^1$H NMR (D$_2$O) δ: 4.37-4.32 (m, 1H, H-2'), 4.24 (dd, 1H, $J_{2,3'}$=1.1, $J_{3,4}$=8.9, H-3'), 4.20-4.15 (m, 1H, H-2), 3.94 (dd, 1H, H-3), 3.85 (dt, 1H, H-5'), 3.81 (dd, 1H, $J_{4,5a}$=4.9, $J_{5a,5b}$=12.4, H-5a), 3.77 (dd, 1H, $J_{4,5b}$=6.9, H-5b), 3.70 (dd, 1H, $J_{4,5}$=0.8, H-4'), 3.55 (dd, 1H, $J_{1a,1b}$=11.1, H-1a), 3.52 (d, 2H, H-6'a, H-6'b), 3.46 (dd, 1H, $J_{1'a,1'b}$=12.4, H-1'a), 3.39(dd, 1H, $J_{1b,2}$=4.3, H-1b), 3.35-3.30 (m, 1H, H-4), 3.25 (dd, 1H, H-1'b). $^{13}$C NMR (D$_2$O) δ: 78.1 (C-3'), 76.5 (C-3), 75.3 (C-4), 74.4 (C-2), 69.5 (C-5'), 68.6 (C-4'), 66.5 (C-2'), 62.8 (C-6'), 60.8 (C-1), 60.0 (C-1'), 59.0 (C-5). MALDI MS m/e 400.09 (M$^+$+Na), 298.35 (M$^+$+H–SO$_3$). HRMS. Calcd. for C, H$_{23}$NNaO$_{11}$S: 400.0890. Found:

1,4-Dideoxy-1,4-[[2S,3S,4R,5S-2,4,5,6-tetrahydroxy-3-(sulfooxy)hexyl]episelenoniumylidene]-D-arabinitol (253)

Compound 275 (400 mg, 0.76 mmol) was dissolved in 90% AcOH (10 mL), Pd(OH)$_2$/C (20%, 400 mg) was added, and the reaction mixture was subjected to hydrogenolysis for 24 h at room temperature. The resulting hemiacetals were reduced with NaBH$_4$ (35 mg, 0.92 mmol) to give compound 253 (145 mg, 58%) as a colorless, amorphous, hygroscopic solid. $[\alpha]^{22}_D$ +39.8 (c 1.0, H$_2$O); $^1$H NMR (D$_2$O) δ: 4.68 (dd, 1H, $J_{1a,2}$=$J_{1b,2}$=7.8, $J_{2,3}$=3.5, H-2), 4.38 (dd, 1H, H-3), 4.33 (ddd, 1H, H-2'), 4.27 (dd, 1H, $J_{2,3}$=1.7, $J_{3,4}$=7.3, H-3'), 4.05 (ddd, 1H, $J_{3,4}$=3.0, H-4), 3.95 (dd, 1H, $J_{4,5a}$=5.1, $J_{5a,5b}$=12.5, H-5a), 3.94 (dd, 1H, $J_{1a,2}$=3.8, $J_{1'a,1'b}$=12.3, H-1'a), 3.84 (dd, 1H, $J_{1b,2}$=5.9, H-1'b), 3.82 (dd, 1H, $J_{4,5b}$=9.1, H-5b), 3.80-3.74 (m, 2H, H-4', H-5'), 3.67 (d, 2H, H-1a, H-1b), 3.62 (dd, 1H, $J_{5',6'a}$=3.4, $J_{6a,6b}$=8.5, H-6'a), 3.53 (dd, 1H, $J_{5',6'b}$=5.8, H-6'b). $^{13}$C NMR (D$_2$O) δ: 80.0 (C-3'), 78.6 (C-3), 77.7 (C-2), 71.7 (C-5'), 70.1 (C-4), 69.0 (C-4'), 66.6 (C-2'), 62.3 (C-6'), 59.5 (C-5), 48.5 (C-1'), 45.1 (C-1). MALDI MS m/e 465.13 (M$^+$+Na), 363.23 (M$^+$+H–SO$_3$). HRMS. Calcd. for C$_{11}$H$_{22}$NaO$_{11}$SSe: 464.9946. Found:

1,4-Dideoxy-1,4-[[2S,3S,4R,5S-2,4,5,6-tetrahydroxy-3-(sulfooxy)hexyl]episulfoniumylidene]-D-arabinitol (254)

Compound 276 (300 mg, 0.62 mmol) was dissolved in 90% AcOH (10 mL), Pd(OH)$_2$/C (20%, 300 mg) was added, and the reaction mixture was subjected to hydrogenolysis for 24 h at room temperature. The resulting hemiacetals were reduced with NaBH$_4$ (29 mg, 0.77 mmol) to give compound 254 (95 mg, 39%) as a colorless, amorphous, hygroscopic solid. The $^1$H NMR and $^{13}$NMR data matched those reported in our previous publication.[14]

1,4-Dideoxy-1,4-[[2S,3S,4R,5S-2,4,5,6-tetrahydroxy-3-(sulfooxy)hexyl]iminonium]-D-arabinitol (255)

Compound 277 (500 mg, 1.07 mmol) was dissolved in 90% AcOH (10 mL), Pd(OH)$_2$/C (20%, 500 mg) was added, and the reaction mixture was subjected to hydrogenolysis for 24 h at room temperature. The resulting hemiacetals were reduced with NaBH$_4$ (50 mg, 1.32 mmol) to give compound 255 (251 mg, 62%) as a colorless, amorphous, hygroscopic solid. $[\alpha]^{22}_D$ −2.7 (c 1.0, H$_2$O); $^1$H NMR (D$_2$O) δ: 4.23 (dd, 1H, $J_{2',3'}$=5.8, $J_{3,4}$=1.9, H-3'), 4.13-4.07 (m, 2H, H-2, H-2'), 3.87 (m, 1H, H-3), 3.78 (dd, 1H, $J_{4,5}$=6.5, H-4'), 3.85 (ddd, 1H, H-5'), 3.69 (2d, 2H, H-5a, H-5b), 3.60 (dd, 1H, $J_{5',6'a}$=3.5, $J_{6'a,6'b}$=12.0, H-6'a), 3.50 (dd, 1H, $J_{5',6'b}$=6.2, H-6'b), 3.42 (dd, 1H, $J_{1'a,1'b}$=12.1, H-1'a), 3.32 (dd, 1H, $J_{1a,2}$=10.5, $J_{1a,1b}$=12.0, H-1a), 3.10(dd, 1H, $J_{1b,2}$=10.3, H-1b), 3.02-2.94 (m, 1H, H-4), 2.82 (m, 1H, H-1'b). $^{13}$C NMR (D$_2$O) δ: 80.1 (C-3'), 77.4 (C-3), 74.9 (C-2), 74.2 (C-4), 71.7 (C-5'), 69.4 (C-4'), 68.7 (C-2'), 62.4 (C-6'), 60.4 (C-1), 59.7 (C-5), 58.2 (C-1'). MALDI MS m/e 400.03 (M$^+$+Na), 298.22 (M$^+$+H–SO$_3$). HRMS. Calcd. for C$_{11}$H$_{23}$NNaO$_{11}$S: 400.0890. Found:

5.3 Example 12

Enzyme Inhibition Assays

5.3.1 In Vitro Inhibition Assays of Non-Human Glycosidase Enzymes

Various isomers of Salacinol, Blintol, Ghavamiol, and Acarbose were tested for their inhibition of three glycosidase enzymes, namely glucoamylase G2,[19,20] porcine pancreatic α-amylase (PPA), and barley α-amylase (AMY1).[23] The results are summarized in Table 11. Glucoamylase G2 was weakly inhibited by Salacinol (1) (Ki=1.7 mM) whereas a stereoisomer of Blintol was a better inhibitor of this enzyme, with a Ki value of 0.72 mM. Salacinol (1) inhibited AMY1 and PPA, with $K_i$ values of 15±1 and 10±2 µM, respectively. Other compounds did not significantly inhibit either AMY1 or PPA. It would appear then that Salacinol (1) and analogues of Salacinol (1) show discrimination for certain glycosidase enzymes, and are promising candidates for selective inhibition of a wider panel of enzymes that includes human small intestinal maltase-glucoamylase[17] and human pancreatic α-amylase.[18]

The glucoamylase G2 form from *Aspergillus niger* was purified from a commercial enzyme (Novo Nordisk, Bagsvaerd, Denmark) as described.[19,20] The initial rates of glucoamylase G2-catalyzed hydrolysis of maltose was tested with 1 mM maltose as substrate in 0.1 M sodium acetate pH 4.5 at 45° C. using an enzyme concentration of $7.0 \times 10^{-8}$ M and five inhibitor concentrations in the range 1 µm-5 mM. The effect of the inhibition on rates of substrate hydrolysis were compared for the different compounds. The glucose released was analyzed in aliquots removed at appropriate time intervals using a glucose oxidase assay adapted to microtiter plate reading and using a total reaction volume for the enzyme reaction mixtures of 150 or 300 µL.[21] The $K_i$ values were calculated assuming competitive inhibition from $1/v = (1/Vmax) + [(K_m)/(Vmax[S]K_i)][I]$, where v is the rate measured in the presence or absence of inhibitor, [I] and [S] the concentrations of inhibitor and substrate, $K_m$ 1.6 mM and kcat 11.3 s$^{-1}$, using ENZFITTER.[22]

Porcine pancreatic α-amylase (PPA) and bovine serum albumin (BSA) were purchased from Sigma. Amylose EX-1 (DP17; average degree of polymerization 17) was purchased from Hayashibara Chemical Laboratories (Okayama, Japan). Recombinant barley α-amylase isozyme 1 (AMY1) was produced and purified as described.[23] An aliquot of the porcine pancreatic x-amylase (PPA) crystalline suspension (in ammonium sulfate) was dialyzed extensively against the assay buffer without BSA. The enzyme concentration was determined by aid of amino acid analysis as determined using an LKB model Alpha Plus amino acid analyzer. The inhibition of AMY1 ($3 \times 10^{-9}$ M) and PPA ($9 \times 10^{-9}$ M) activity towards DP17 amylose was measured at 37° C. in 20 mM sodium acetate, pH 5.5, 5 mM $CaCl_2$, 0.005% BSA (for AMY1) and 20 mM sodium phosphate, pH 6.9, 10 mM NaCl, 0.1 mM $CaCl_2$, 0.005% BSA (for PPA). Six different final inhibitor concentrations were used in the range 1 µM-5 mM. The inhibitor was pre-incubated with enzyme for 5 min at 37° C. before addition of substrate. Initial rates were determined by measuring reducing sugar by the copper-bicinchoninate method as described.[23,24] The $K_i$ values were calculated assuming competitive inhibition, as described above for the case of glucoamylase, and a $K_m$ of 0.57 mg/ml and kcat of 165 s$^{-1}$ for AMY1 and 1 mg/ml and 1200 s$^{-1}$ for PPA, as determined in the substrate concentration range 0.03-10 mg/ml using ENZFITTER.[22] For the $K_i$ determinations, [S]=0.7 mg/mL amylose DP 17 for the AMY1 binding and [S]=2.5 mg/mL amylose DP 17 for the PPA binding.

5.3.2 In Vitro Inhibition Assays of Human Glycosidase Enzymes

The in vitro inhibitory activities of Salacinol, Blintol, Ghavamiol, and Acarbose were tested against human glycosidase enzymes as described below.

5.3.2.1 Enzyme Assays with Maltase Glucoamylase (MGA)

Since recombinant MGA enzyme has not been expressed successfully, the assay for MGA activity measured effects on cell extracts. In the assays, COS cells transfected with MGA5' (maltase subunit clone 10) construct were used. Activity measurements were performed with cell extracts containing MGA. Maltose hydrolysis was monitored by measurement of the glucose released by a glucose oxidase colorimetric assay. Inhibition of this hydrolysis was measured as a reduction in OD reading. Since the assay deals with cell extracts, a standard inhibitor, e.g. Salacinol, is always included in each new assay of a putative inhibitor.

In practice, an OD reading in the absence of the inhibitor was recorded, followed by a reading in the presence of the inhibitor. The percent reduction in OD reading upon administering a candidate inhibitor (see Table 11) was then correlated with a percent inhibition for a given concentration. For example: 1) at 200 nM (0.2 µM), Blintol inhibits 50% of MGA activity whereas Salacinol inhibits 50% of MGA activity at 2500 nM (2.5 µM); 2) Whereas Salacinol at 5 µM concentration inhibits 60% of the breakdown of maltose, Acarbose only inhibits 4% of the activity.

5.3.2.2 Enzyme Assays with Human Pancreatic α-Amylase (HPA)

These assays were performed with purified enzyme. The ability of candidate inhibitors to inhibit the hydrolysis of 2,4-Dinitrophenyl maltotrioside was monitored by UV-visible spectroscopy of the released 2,4-dinitrophenol.

5.3.2.3 Summary of In Vitro Biological Activity

1) It appears that Acarbose acts principally by inhibiting human pancreatic α-amylase (HPA) and the breakdown of starch. Salacinol inhibits both HPA and MGA and Blintol appears to only MGA.

2) The selenium analogue of Salacinol, Blintol, shows inhibition of MGA at lower concentrations than Salacinol. More significantly, Blintol does not appear to inhibit HPA. Salacinol, on the other hand, inhibits both HPA and MGA, and Acarbose inhibits only HPA in these experimental assays.

3) Using similar monitoring of OD readings as in the MGA assay, the maltase activity in biopsies with live intestinal cells was monitored. At 5 µM concentration, Blintol inhibits 50% of maltase activity whereas Salacinol inhibits only 13% of the activity.

TABLE 11

Summary of Activity of Salacinol Derivatives Against Human Glycosidases

| Compound | Ki(mM) | | | | |
|---|---|---|---|---|---|
| | AMY1[a] | PPA[b] | HPA[c] | GA[d] | MGA[e] |
| 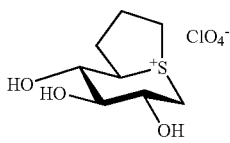 | >5 | >5 | — | 1.32 | — |

TABLE 11-continued

Summary of Activity of Salacinol Derivatives Against Human Glycosidases

| Compound | Ki(mM) | | | | |
|---|---|---|---|---|---|
| | AMY1[a] | PPA[b] | HPA[c] | GA[d] | MGA[e] |
| AG-1 | 0.015 | 0.01 | 0.075 | 1.71 | μM |
| AG-2 | >5 | >5 | n.a. | 2.17 | n.a. |
| AG-3 | >5 | >5 | n.a. | 1.06 | mM |
| AG-4 | >5 | >5 | n.a. | >2.5 | mM |
| AG-5 | >5 | >5 | 0.4 | >8 | n.a. |

TABLE 11-continued
Summary of Activity of Salacinol Derivatives Against Human Glycosidases
| Compound | Ki(mM) | | | | |
|---|---|---|---|---|---|
| | AMY1[a] | PPA[b] | HPA[c] | GA[d] | MGA[e] |
| 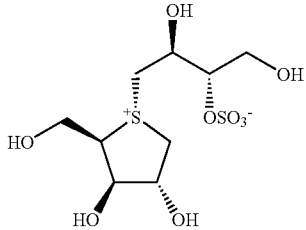<br>AG-6 | 0.109 | 0.052 | — | >5 | — |
| 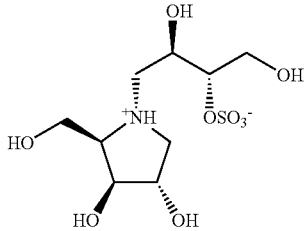<br>AG-7 | >5 | >5 | — | >30 | — |
| 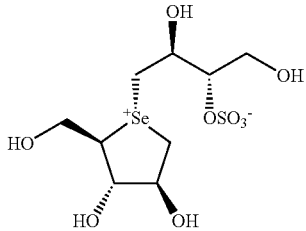<br>BJ-24-77-3, BJ-24-78-1, BJ-24-79-1 | >5 | >5 | >5 | 0.72 | nM |
| 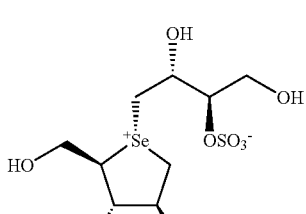<br>BJ-24-92-1 | >5 | >5 | n.a. | >9 | n.a. |
| 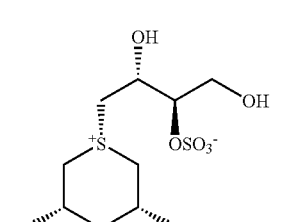<br>MS-02-159 | — | — | >5 | — | n.a. |

TABLE 11-continued

Summary of Activity of Salacinol Derivatives Against Human Glycosidases

| Compound | Ki(mM) | | | | |
|---|---|---|---|---|---|
| | AMY1[a] | PPA[b] | HPA[c] | GA[d] | MGA[e] |
| M S-02-153 | — | — | >5 | — | mM |
| M S-02-145 | — | — | >5 | — | n.a. |
| M S-03-119 | — | — | — | — | n.a. |
| M S-03-125 | — | — | — | — | n.a. |

TABLE 11-continued

Summary of Activity of Salacinol Derivatives Against Human Glycosidases

| Compound | Ki(mM) | | | | |
|---|---|---|---|---|---|
|  | AMY1[a] | PPA[b] | HPA[c] | GA[d] | MGA[e] |
| M S-03-163B | — | — | — | — | n.a. |
| M S-03-175 | — | — | — | — | n.a. |
| M S-03-171 | — | — | — | — | n.a. |

[a]AMY1 = Barley α-amylase
[b]PPA = Porcine pancreatic α-amylase
[c]HPA = Human pancreatic α-amylase
[d]GA = Glucoamylase
[e]MGA = Human intestinal maltase glucoamylase
n.a. = not active
— = not tested 5.3.3 In Vivo Inhibition Studies of Blintol and Salacinol In this Example the efficacy of Blintol in inhibiting glucose absorption and lowering post-prandial glucose levels in vivo was compared to Salacinol and Acarbose. Five week old Sprague-Dawley rats were housed singly under a 12:12-h light-dark photoperiod and given free access to water and rat chow (Purina rodent chow). After one week of acclimation, chronic indwelling catheters were implanted.

Animals were anesthetized with a combination of Ketamine-Xylazine-Butorphanol (0.1 ml/100 g im). Analgesic (Butorphenol, 1 mg/kg sc) was administered following recovery from anesthesia and the following morning. Antibiotic was administered by one dose sc and in the drinking water for 4 days post-operative (Baytril, 5 mg/kg sc, Bayer, Toronto, Canada; Baytril, 50 mg/ml: 0.36 ml solution in 250 ml drinking water). A sterile catheter (Intramedic PE-50 with ~3 cm beveled Silastic tip) was placed in the left carotid artery and the distal end of the catheter was tunneled subcutaneously, exteriorized, and anchored at the nape of the neck. The catheters were protected from chewing by a stainless steel tether connected to a swivel system which allowed free movement of the animal and easy access to the catheter by the investigator.

The animals were allowed to recover for 1 week. Experiments were performed on conscious, unrestrained animals that had been fasted overnight by removal of chow from the cage hoppers at 2100. At 0800 the following morning animals were weighed and Atropine (0.05 mg/kg sc) was administered as a muscle relaxant. At baseline, animals were administered a bolus of maltose by oral gavage (1000 mg/kg body weight) with or without drug (25 mg/kg body weight for all agents). Blood samples (0.1 mL) were taken via the implanted carotid line at -15 and -5 min for the baseline and at 7, 15, 30, 60, 90, 120, 210, 300 min.

Blood samples were kept on ice in microcentrifuge tubes and then were centrifuged. The plasma was stored at $-20°$ C. until it was assayed. Plasma volume was triple replaced with heparinized saline (10u/mL), but red blood cells were not reinfused. Plasma glucose was assayed with the glucose oxidase method (Trinder RAICHEM Division of Hemagen Diagnostics, Inc. San Diego, Calif.). Plasma insulin concentrations were measured by rat insulin ELISA (Crystal Chem INC, Downers Grove, Ill.). Six experiments were performed for each treatment (control, Blintol, Acarbose, Salacinol).

The AUC (Area Under the Curve) was calculated for glucose, glucose absorption, and insulin by applying the trapezoidal method over the 0 to 90 minute time points. For glucose the AUC was calculated for the excursion from each sample above the basal value (average of the -5 and -15 minute samples), and for insulin and glucose absorption for the excursion above 0.

All data are presented as means±SE. The significance of changes in plasma glucose and insulin were tested by two-way repeated-measures analysis of variance and were performed with the Statistical Analysis System for Windows (version 6.3, SAS Institute, Cary, N.C.). AUCs were compared using unpaired t-tests.

5.3.3.1 Plasma Glucose Concentrations

Figure 3:
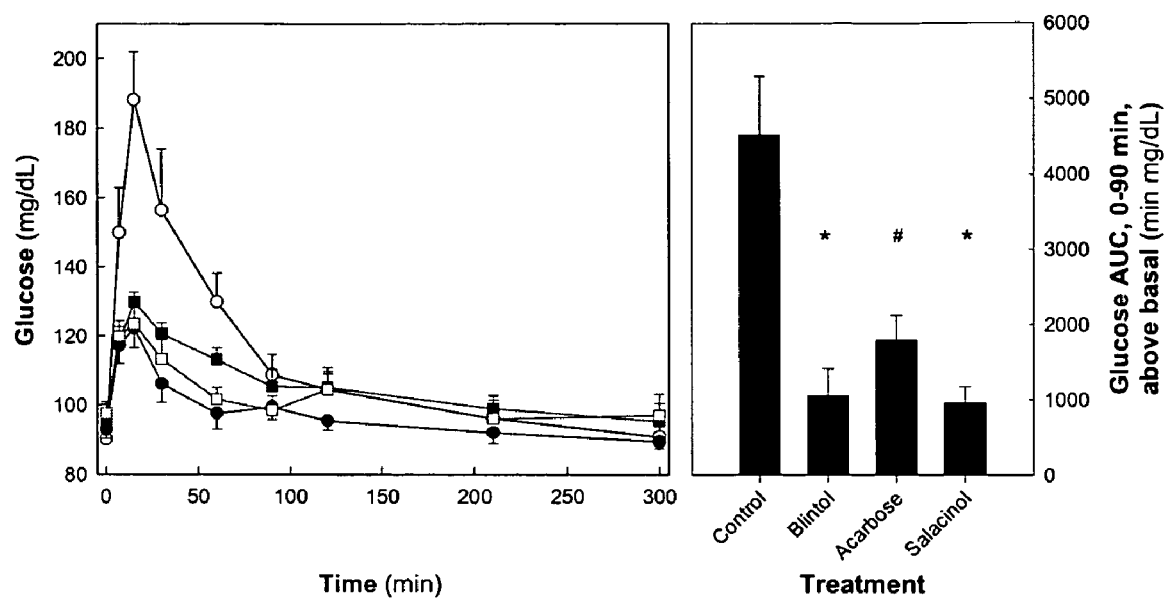
FIG. 3 depicts mean plasma glucose concentrations in rats after treatment with Acarbose, Blintol, and Salacinol. Panel a): Mean plasma glucose time course following a gavage of 1000 mg/kg body weight maltose without drug (Control: ○), or with 25 mg/kg of drug (Blintol: ●, Acarbose: ■, Salacinol: □) n=6 per group, ±standard error. The time zero (basal) sample for each animal was calculated as the mean of the -5 and -15 minute samples. Panel b): Mean Area Under the Curve of the glucose excursion above basal, 0-90 minutes (*: $P<0.005$, #: $P<0.05$ versus Control).

The plasma glucose profiles for all treatments were significantly lower than Control ($P<0.0001$; all treatments versus Control), and the Blintol group had a lower profile than Acarbose ($P<0.01$) but there was no difference between other treatments (see FIG. 3). Plasma glucose concentrations for all groups increased immediately following gavage ($P<0.01$), reaching a peak at 15 minutes. For the Control group, the 15 minute glucose excursion from basal was 98.0 i 12.4 mg/dL and this excursion was decreased with all treatments (Blintol: 29.3±6.5, Acarbose: 34.2±3.5, Salacinol: 26.0 i 5.1; $P<0.005$). All groups exhibited an exponential glucose decay following the 15 minute peak. For the control group glucose values did not return to basal values until 210 minutes ($P=0.46$). Blintol ($P=0.40$) and Salacinol ($P=0.43$) groups returned to basal at 60 minutes, and Acarbose at 90 minutes ($P=0.19$).

The Area Under the Curve was significantly decreased with all treatments. Blintol and Salacinol yielded slightly lower 90 minute AUC's than Acarbose, though the difference was not significant (Blintol: $P=0.16$, Salacinol: $P=0.6$; versus Acarbose).

5.3.3.2 Plasma Insulin Concentrations

Figure 4:
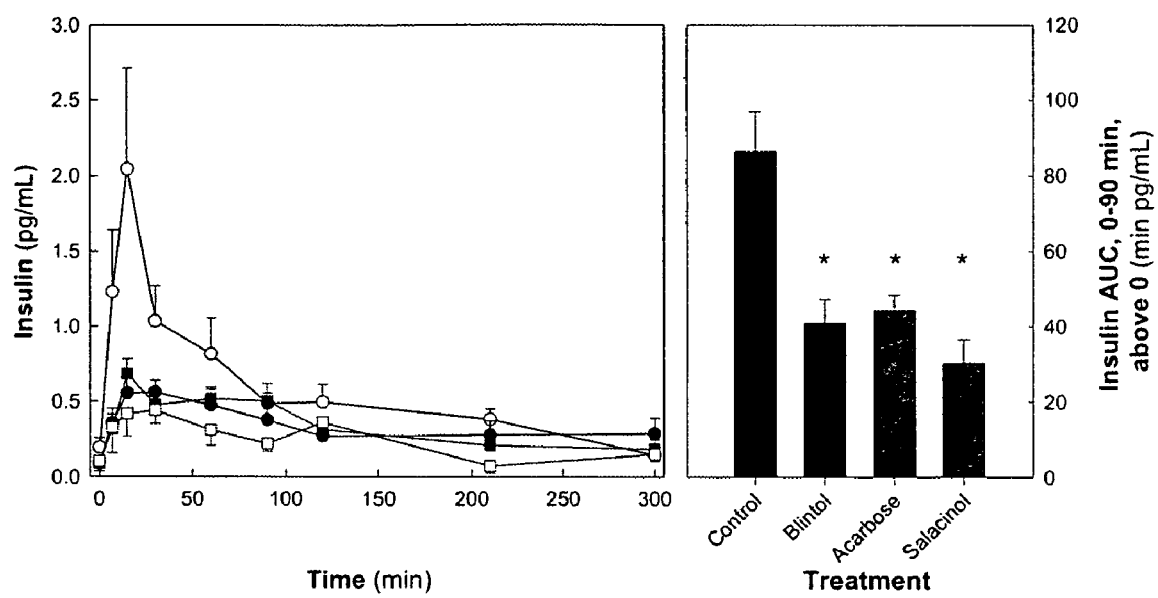
FIG. 4 depicts mean plasma insulin concentrations in rats after treatement with Acarbose, Blintol, and Salacinol. Panel a): Mean plasma insulin concentration (Control: ○, Blintol: ●, Acarbose: ■, Salacinol: □) n=6 per group, ±standard error. Panel b): Mean Area Under the Curve of the glucose absorption rate (*: $P<0.01$ versus Control).

Plasma insulin profiles were decreased with all treatments versus Control ($P<0.0001$) (FIG. 4). Consistent with the peak glucose at 15 minutes, the insulin for all groups was also peaked between 7 and 15 minutes; however the insulin profile was more rounded and did not show an exponential decay for any group. While the Control and Acarbose insulin values were different from basal for the 15 to 90 minute range, the Blintol and Salacinol insulin values were only different from basal at 15 minutes ($P<0.05$). The 90 minute insulin AUC was decreased with Blintol, Acarbose, and Salacinol treatments by 53%, 49%, and 65% respectively. There was no statistical difference between treatment groups.

The results of this experiment show that Blintol, Acarbose, and Salacinol, at a 25 mg/kg body weight dosage significantly lower post-prandial plasma glucose and insulin concentrations in normal, catheterized rats. Importantly, at this dosage, Blintol had a decreased glucose profile compared to Acarbose. The improvement in the glucose profile with all treatments seems to be directly attributable to an inhibited glucose absorption, consistent with the agents' expected mechanisms of action.

The inhibition of the post-prandial glucose peak observed with all treatments may contribute to a reduction in diabetic complications when these agents are used chronically. The reduced glucose levels decreased the demand on the insulin secreting $\beta$-cells and chronically may contribute to a preservation of $\beta$-cell mass and function. Moreover, the better controlled glucose levels may decrease a glucose-toxic effect which can kill or impair the function of the insulin-secreting. $\beta$-cells. Chronic administration of drug studies will help elucidate if these factors are able to slow or prevent the onset of diabetes in a diabetes-prone animal model.

As will be apparent to those skilled in the art in the light of the foregoing disclosure, many alterations and modifications are possible in the practice of this invention without departing from the spirit or scope thereof.

REFERENCES

1. Yoshikawa, M. et al. *Tetrahedron Lett.* 1997, 38(48), 8367-8370.
2. Yoshikawa, M. et al. *Chem. Pharm. Bull.* 1998, 46(8), 1339-1340.
3. Shimoda, H. et al. *Journal of the Food Hygienic Society of Japan.* 1999, 40(3), 198-205.
4. Goss, P. E. et al. *Clinical Cancer Res.* 1997, 3, 1077-1086.
5. Mohla, S. et al. *Anticancer Res.* 1990, 10, 1515-1522.
6. Goss, P. E. et al. *Cancer Res.* 1994, 54, 1450-1457.
7. Eames, J. et al. *Tetrahedron Lett.* 1998, 39(10), 1247-1250.
8. Calvo-Flores, F. G. et al. *J. Org. Chem.* 1997, 62, 3944-3961.
9. Foster, A. B. et al. *J. Chem. Soc.* 1961, 5005-5011.
10. MacDonald, D. L. et al. *J. Am. Chem. Soc.* 1956, 78, 3720-3722.
11. Yoshimura, Y. et al. *J. Org. Chem.* 1997, 62, 3140-3152.
12. Satoh, H. et al. *Bioorg. Med. Chem. Lett.* 1998, 8(9), 989-992.
13. Fleet, G. et al. *Tetrahedron.* 1986, 42, 5685-5692.
14. Reichardt, C. Solvents and Solvent Effects in Organic Chemistry, 2nd Ed.; VCH: Weinheim, 1996; pp 137-147, 359-384.
15. Yuasa, H.; Takada, J., Hashimoto, H. *Tetrahedron Lett.* 2000, 41, 6615-6618.
16. Ghavami, A.; Johnston, B. D.; Jensen, M. T.; Svensson, B.; Pinto, B. M. *J. Am. Chem. Soc.* 2001, 123, 6268-6271.
17. Nichols, B. L.; Eldering, J.; Avery, S.; Hahn, D.; Quaroni, A.; Sterchi, E. *J. Biol. Chem.* 1998, 273, 3076-3081.
18. Braun, C.; Brayer, G. D.; Withers, S. G. *J. Biol. Chem.* 1995, 270, 26778-26781.
19. Svensson, B.; Pedersen, T.; Svendsen, I.; Sakai, T.; Ottesen, M. *Carlsberg Res. Commun.* 1982, 47, 55-69.
20. Stoffer, B.; Frandsen, T. P.; Busk, P. K.; Schneider, P.; Svendsen, I.; Svensson, B. *Biochem J.* 1993, 292, 197-202.
21. Frandsen, T. P.; Dupont, C.; Lehmbeck, J.; Stoffer, B.; Sierks, M. R.; Honzatko, R. B.; Svensson, B. *Biochemistry* 1994, 33, 13808-13816.
22. Leatherbarrow, R. J. Enzfitter, a nonlinear regression data analysis program for IBM PC; Elsevier Science Publishers BV: Amsterdam, The Netherlands, 1987.
23. Juge, N.; Andersen, J. S.; Tull, D.; Roepstorff, P.; Svensson, B. *Protein Expression Purif.* 1996, 8, 204-214.
24. Fox, J. D.; Robyt, J. F. *Anal. Biochem.* 1991, 195, 93-96.

25. Ghavami, A. Johnston, B. D.; Pinto, B. M. *J. Org. Chem.* 2001, 66, 2312-2317.
26. Johnston, B. D.; Ghavami, A.; Jensen, M. T.; Svensson, B.; Pinto, B. M. *J. Am. Chem. Soc.* 2002, 124, 8245-8250.
27. Yoshikawa, M.; Morikawa, T.; Matsuda, H.; Tanabe, G.; Muraoka, O. *Bioorg. Med. Chem.*, 2002, 10, 1547-1554.
28. Svansson, L.; Johnston, B. D.; Gu, J.-H.; Patrick, B.; Pinto, B. M. *J. Am. Chem. Soc.*, 2000, 122, 10769-10775.
29. Ghavami, A.; Johnston, B. D.; Maddess, M. D.; Chinapoo, S. M.; Jensen, M. T.; Svensson, B.; Pinto, B. M. *Can. J. Chem.*, 2002, 80, 937-942.
30. Wakabayashi, T.; Mori, K.; Kobayashi, S. *J. Am. Chem. Soc.* 2001, 123, 1372-1375.
31. Crivello, J. V. *Advances in Polymer Science* 1984, 62, 1-48.
32. Trost, B. M.; Melvin, L. S., Jr. *Organic Chemistry, Vol. 31: Sulfur Ylides, Emerging Synthetic Intermediates*, 1975.
33. Fox, D. J.; House, D.; Warren, S. *Angew. Chem., Int. Ed.* 2002, 41, 2462-2482.
34. Stutz, A. E. *Iminosugars as Glycosidase Inhibitors: Nojirimycin and Beyond*, 1999.
35. Izquierdo, I.; Plaza, M. T.; Aragon, F. *Tetrahedron: Asymmetry* 1996, 7, 2567-2575.
36. Ulgar, V.; Femandez-Bolanos, J. G.; Bols, M. *J. Chem. Soc., Perkin Trans.* 1 2002, 1242-1246.
37. Bazin, H. G.; Linhardt, R. J. *Synthesis* 1999, 621-624.
38. Calvo-Asin, J. A.; Calvo-Flores, F. G.; Exposito-Lopez, J. M.; Hernandez-Mateo, F.; Garcia-Lopez, J. J.; Isac-Garcia, J.; Santoyo-Gonzalez, F.; Vargas-Berenguel, A. *J. Chem. Soc., Perkin Trans.* 1 1997, 1079-1081.
39. Bozo, E.; Boros, S.; Kuszmann, J.; Gacs-Baitz, E.; Parkanyi, L. *Carbohydr. Res.* 1998, 308, 297-310.
40. Dagron, F.; Lubineau, A. *J. Carbohydr. Chem.* 2000, 19, 311-321.
41. Bazin, H. G.; Wolff, M. W.; Linhardt, R. J. *J. Org. Chem.* 1999, 64, 144-152.
42. Yin, H.; D'Souza, F. W.; Lowary, T. L. *J Org Chem.* 2002, 67, 892-903.
43. Hatanaka, K.; Kuzuhara, H. *J Carbohydr. Chem.* 1985, 4, 333-345.
44. Ness, R. K.; Fletcher, H. G., Jr. *J. Am. Chem. Soc.* 1958, 80, 2007-2010.
45. Fukuyama, Y.; Ciancia, M.; Nonami, H.; Cerezo, A. S.; Erra-Balsells, R.; Matulewicz, M. C. *Carbohydr. Res.* 2002, 337, 1553-1562.
46. Harris, S. L, L. Craig, J. S. Mehroke, M. Rashed, M. B. Zwick, K. Kenar, E. J. Toone, N. Greenspan, F.-I. Auzanneau, J.-R. Marino-Albernas, B. M. Pinto, and J. K. Scott. Proc. Natl. Acad. Sci. USA, 94, 2434 (1997).
47. B. M. Pinto, J. K. Scott, S. L. Harris, M. A. Johnson, D. R. Bundle, M. C. Chervenak, M. N. Vyas, N. K. Vyas, F. A. Quiocho. XIX International Carbohydrate Symposium, San Diego, U.S.A., (August, 1998), Abstr. CP 132, CO 019; B. M. Pinto. Meeting on anti-idiotypes and mimotopes in vaccine development, Vibo Valentia, Italy, (May, 2000); B. M. Pinto. Glycobiology Symposium, Pacifichem 2000 Conference, Honolulu, Hi., U.S.A., (December, 2000) Abstr. 607.
48. (a) B. Belleau, U. Gulini, B. J. Gour-Salin, and F. R. Ahmed. Can. J. Chem. 63, 1268 (1985); (b) B. Belleau, U. Gulini, R. Camicioli, B. J. Gour-Salin, and G. Sauve. Can. J. Chem. 64, 110 (1986); (c) S. Lemaire, B. Belleau, and F. Jolicoeur. Adv. Biosci. 75, 105 (1989); (d) F. B. Jolicoeur, D. Menard, B. Belleau, and S. Lemaire. Int. Narcotics Res. Conf. 89, 49 (1990).
49. H. Yuasa, J. Takada, and H. Hashimoto. Bioorg. Med. Chem. Lett. 11, 1137 (2001).
50. O. Muraoka, S. Ying, K. Yoshikai, Y. Matsuura, E. Yamada, T. Minematsu, G. Tanabe, H. Matsuda, and M. Yoshikawa. Chem. Pharm. Bull. 49, 1503 (2001).
51. P. A. M. van der Klein, A. E. J. de Nooy, G. A. van der Marel, and J. H. van Boom. *Synthesis* 347, (1991).
52. P. A. M. van der Klein, W. Filemon, H. J. G. Broxterman, G. A. van der Marel, and J. H. van Boom. *Synth. Commun.* 22, 1763, (1992).
53. Ghavami, A.; Sadalapure, K. S.; Johnston, B. D.; Lobera, M.; Snider, B. B.; Pinto, B. M. *Synlett* 2003, 1259-1262.
54. Mootoo, D. R.; Date, V.; Fraser-Reid, B. *J. Chem. Soc., Chem. Commun.* 1987, 1462-1463.
55. Mootoo, D. R.; Date, V.; Fraser-Reid, B. *J. Am. Chem. Soc.* 1988, 110, 2662-2663.
56. Furneaux, R. H.; Rendle, P. M.; Sims, I. M. *J. Chem. Soc., Perkin, Trans.* 1, 2000, 2011-2014.
57. Gurjar, M. K.; Reddy, L. K.; Hotha, S. *J. Org. Chem.* 2001, 66, 4657-4660.
58. Varki, A.; Cummings, R.; Esko, J.; Freeze, H.; Hart, G.; Marth, J., Eds. *Essentials of Glycobiology*; Cold Spring Harbor Laboratory Press: Cold Spring Harbor, N.Y., 1999.
59. Taylor, M. E.; Drickamer, K. *Introduction to Glycobiology*; Oxford University Press: New York, N.Y., 2003.
60. Helenius, A.; Aebi, M. *Science.* 2001, 2364-2369.
61. (a) Dwek, R. A.; Butters, T. D. Platt, F. M.; Zitzmann, N. *Nature Rev. Drug Discovery,* 2002, 1, 65-75. (b) Dwek, R. A. *Chem. Rev.* 1996, 96, 683-720.
62. For leading references: (a) Elbein, A. D.; Molyneux, R. J. Ch. 7 in *Comprehensive Natural Products Chemistry*, Vol 3; Pinto, B. M., Ed.; Barton, D. H. R.; Nakanishi, K.; Meth-Cohn, O., Ser. Eds.; Elsevier: UK, 1999. (b) Asano, N,; Nash, R. J.; Molyneux, R. J.; Fleet, G. W. J. *Tetrahedron*: Asymmetry 2000, 11, 1645-1680. (c) McCarter, J. D.; Withers, S. G. *Curr. Opin. Struct. Biol.* 1994, 4, 885-892. (d) Ly, H. D.; Withers, S. G. *Annu. Rev. Biochem.* 1999, 68, 487-522.
63. Bock, K.; Sigurskjold, B. *Studies Nat. Prod. Chem.* 1990, 7, 29-86; Holman, R. R.; Cull, C. A.; Turner, R. C. *Diabetes Care,* 1999, 22, 960-964; Jacob, G. S. *Curr. Opin. Struct. Biol.* 1995, 5, 605-611. Sigurskjold, B. W.; Berland; C. R.; Svensson, B. *Biochemistry* 1994, 33, 10191-10199.
64. Kapit, W.; Macey, R. I.; Meisami, E. *The Physiology Coloring Book*; Harper Collins College Publishers: Menlo Park, Calif., 1987.
65. Cox, T.; Lachmann, R.; Hollak, C.; Aerts, J.; van Weely, S.; Hrebicek, M.; Platt, F.; Butters, T.; Dwek, R.; Moyses, C.; Gow, I.; Elstein, D.; Zimran, A. *Lancet* 2000, 355, 1481-1485.
66. (a) Koshland, D. E. *Biol. Rev.* 1953, 28, 416-436. (b) Zechel, D. L.; Withers, S. G. *Curr. Opin. Chem. Biol.* 2001, 5, 643-649.
67. Lillelund, V. H.; Jensen, H. H.; Liang, X; Bols, M. *Chemical Reviews* 2002, 102, 515-553.
68. Varrot, A.; Tarling, C. A.; MacDonald, J. M.; Stick, R. V.; Zechel, D. L.; Withers, S. G.; Davies, G. J. *J. Am. Chem. Soc.* 2003, 125, 7496-7497.
69. Varrot, A.; MacDonald, J.; Stick, R. V.; Pell, G.; Gilbert, H. J.; Davies, G. J. *Chem. Commun.* 2003, 946-947.
70. Zechel, D. L.; Boraston, A. B.; Gloster, T.; Boraston, C. M.; MacDonald, J. M.; Tilbrook, D. M. G.; Stick, R. V.; Davies, G. J. *J. Am. Chem. Soc.* 2003, 125, 14313-14323.
71. Johnson, M. A.; Jensen, M. T.; Svensson, B.; Pinto, B. M. *J. Am. Chem. Soc.* 2003, 125, 5663-5670.
72. Ghavami, A.; Chen, J. J-W.; Pinto, B. M. *Carbohydr. Res.* 2004, 339, 401-407.
73. van den Broek, L. A. G. M.; Vermaas, D. J.; Heskamp, B. M.; van Boeckel, C. A. A.; Tan, M. C. A. A.; Bolscher, J. G.

M.; Ploegh, H. L.; van Kemenade, F. J.; de Goede, R. E. Y.; Miedema, F. *Recl. Trav. Chim. Pays-Bas* 1993, 112, 82-94.
74. Asano, N.; Kizu, H.; Oseki, K.; Tomioka, E.; Matsui, K.; Okamoto, M.; Baba, M. *J. Med. Chem.* 1995, 38, 2349-56.
75. Hausler, H.; Rupitz, K.; Stutz, A. E.; Withers, S. G. Monatshefte fur Chem. 2002, 133, 555-560.
76. Halila, S.; Benazza, M.; Demailly, G. *Tetrahedron Lett.* 2001, 42, 3307-3310.
77. Klayman, D. L.; Griffin, T. S. *J. Am. Chem. Soc.* 1973, 95, 197-199.
78. Lucas, M. A. Nguyen, O. T. K.; Schiesser, C. H; Zheng, S.-L. *Tetrahedron* 2000, 56, 3995-4000.
79. Hashimoto, H.; Masashi, K.; Yuasa, H. *Carbohydr. Res.* 1996, 282, 207-222.
80. Svensson, B.; Sierks, M. R. *Carbohydr. Res.* 1992, 227, 29-44.
81. Gao, Y.; Sharpless, K. B. *J. Am. Chem. Soc.* 1988, 110, 7538-7539.
82. Siriwardena, A.; Strachan, H.; El-Dahar, S.; Way, G.; Winchester, B.; Glushka, J.; Moremen, K.; Boons, G.-*J. ChemBioChem* 2005, 6, 845-848.
83. Wolf, B. W.; Weisbrode, S. E. Food Chem. *Toxicol.* 2003, 41, 867-874.
84. Serasinghe, S.; Serasinghe, P.; Yamazaki, H.; Nishiguchi, K.; Hombhanje, F.; Nakanishi, S.; Sawa, K.; Hattori, M.; Namba, T. *Phytotherapy Res.* 1990, 4, 205-206
85. Szczepina, M. G.; Johnston, B. D.; Yuan, Y.; Svensson, B.; Pinto. B. M. *J. Am. Chem. Soc* 2004, 126, 12458-12469.
86. Wen, X.; Yuan Y.; Kuntz, D. A.; Rose, D. R.; Pinto B. M. *Biochemistry,* 2005. 44, 6729-6737.
87. Kuntz, D.; Ghavami, A.; Johnston, B. D.; Pinto, B. M.; Rose D. R. *Tetrahedron: Asymmetry* 2005, 16, 25-32.
88. Liu, H.; Pinto, B. *J. Org. Chem.* 2005, 70, 753-755.
89. Pinto, B. M.; Johnston, B. D.; Ghavami, A.; Szczepina, M. G.; Liu, H.; Sadalapure, K.; US Patent Publication No. 2005/0065139.
90. F. Garcia-Olmeda, G. Salcedo, R. Sanchez-Monge, L. Gomez, L. Royo, and P. Carbonero. *Oxford Surveys of Plant Molecular and Cell Biology* 1987, Oxford, 4, 275.
91. C. Bompard-Gilles, P. Rousseau, P. Rouge, and F. Payan, *Structure* 1996, 4, 1441.
92. F. Vallee, A. Kadziola, Y. Bourne, M. Juy, K. W. Rodenburg, B. Svensson, and R. Haser. *Structure* 1998, 6, 649.
93. S. Strobl, K. Maskos, G. Wiegand, R. Huber, F-X. Gomis Ruth, and R. Glockshuber. *Structure* 1998, 6, 911.
94. Y. Li, C. R. Scott, N. A. Chamoles, A. Chavami, B. M. Pinto, T. Frantisek, and M. H. Gelb. *Clin. Chem.* 2004, 50, 1785.
95. P. A. M. van der Klein, G. J. P. H. Boons, G. H. Veeneman, G. A. van der Marel, and J. H. van Boom. *Tetrahedron Lett.* 1989, 30, 5477.
96. J. Gelas, and D. Horton. *Carbohydr. Res.* 1978, 67, 371.
97. Holman, R. R.; Cull, C. A.; Turner, R. C. Diabetes Care 1999, 22, 960-964; Jacob, G. S. *Curr. Opin. Struct. Biol.* 1995, 5, 605-611.
98. Kuszmann, J.; Medgyes, G.; Boros, S. *Carbohydr. Res.* 2004, 339, 2407-2414.
99. Postema, M. H. D.; Calimente, D.; Liu, L.; Behrmann, T. L.; *J. Org Chem.* 2000, 65, 6061-6068.
100. Elie, C. J. J.; Hoogerhout, P.; Muntendam, H. J.; Van de Werken, G.; Van der Marel, G. A.; Van Boom, J. H. *Recueil des Travaux Chimiques des Pays-Bas* 1990, 109, 467-473.
101. Barker, R.; Fletcher, H. G. J. Org. Chem. 1961, 26, 4605-4609.
102. Naka, T.; Minakawa, N.; Abe, H.; Kaga, D.; Matsuda, A. *J. Am. Chem. Soc.* 2000, 122, 7233-7243.
103. Minakawa, N.; Kato, Y.; Uetake, K.; Kaga, D.; Matsuda, A. *Tetrahedron,* 2003, 59, 1699-1702.
104. Fleet, G. W. J.; Ramsden, N. G.; Witty, D. R. *Tetrahedron,* 1989, 45, 319-326.
105. Jeong, L. S.; Jin, D. Z.; Kim, H. O.; Shin, D. H.; Moon, H. R.; Gunaga, P.; Chun, M. W.; Kim, Y. C.; Melman, N.; Gao, Z. G.; Jacobson, K. A. *J. Med. Chem.* 2003, 46, 3775-3777.
106. Andrews, G. C.; Crawford, T. C.; Bacon, B. E. *J. Org. Chem.* 1981, 46, 2976-2977.
107. Gallienne, E.; Benazza, M.; Demailly, G.; Bolte, J.; Lemaire, M. *Tetrahedron,* 2005, 61, 4557-4568.
108. Rama Rao, A. V.; Ashok Reddy, K.; Srinivas, N. R.; Guiar, M. K.; Padmaja, N.; Ramakumar, S.; Viswamitra, M. A.; Swapna, G. V. T.; Jagannadh, B.; Kunwar, A. C. *J. Chem. Soc., Perkin Trans.* 1,1993,1255-1257.
109. Masaki, Y.; Oda, H.; Kazuta, K.; Usui, A.; Itoh, A.; Xu, F. *Tetrahedron Lett.,* 1992, 35, 5089-5092.
110. a) Sinnott, M. L. *Chem. Rev.* 1990, 90, 1171-1202. b) Heighman, T. D.; Vasella, A. T. *Angew. Chem. Int. Ed.* 1999, 38, 750. c) Zechel, D.; Withers, S. G. *Acc. Chem. Res.* 2000, 33, 11.
111. Baggert, N.; Stribblehill, P. *J. Chem. Soc., Perkin Trans* 1,1977, 1, 1123-1126.
112. Ley, S. V.; Baeschlin, D. K.; Dixon, D. J.; Foster, A. C.; Ince, S. J.; Priepke, H. W. M.; Reynolds, D. J. *Chem. Rev.* 2001, 101, 53-80 and the references within.
113. Hense, A.; Ley, S. V.; Osborn, H. M. I.; Owen, D. R.; Poisson, J.-F.; Warriner, S. L.; Wesson, K. E. *J. Chem. Soc., Perkin Trans.* 1, 1997, 2023-2031.
114. Xia, J.; Alderfer, J. L.; Piskorz, C. F.; Matta, K. L. *Chem. Eur. J.* 2001, 7, 356-367.
115. Smits, E.; Engberts, J. B. F. N.; Kellogg, R. M.; van Doren, H. A. *J. Chem. Soc., Perkin Trans.* 1, 1996, 2873-2877.

What is claimed is:

1. A non-naturally occurring compound selected from the group consisting of compounds represented by the general formula (I) and stereoisomers and pharmaceutically acceptable salts thereof:

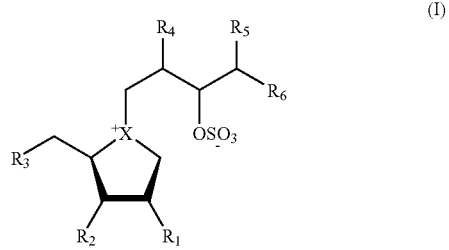

where X is selected from the group consisting of S, Se and NH; $R_1$, $R_2$, $R_3$, $R_4$ and $R_5$ are the same or different and are selected from the group consisting of H, OH, SH, $NH_2$ and halogens; and $R_6$ is selected from the group consisting of H, OH and optionally substituted straight chain, branched, or cyclic, saturated or unsaturated hydrocarbon radicals.

2. The compound as defined in claim 1, wherein X is S or Se, $R_1$, $R_2$, $R_3$, $R_4$ and $R_5$ is OH and $R_6$ is an alditol side-chain having between 1-3 carbon atoms.

3. The compound as defined in claim 1, wherein X is S or Se, $R_1$, $R_1$, $R_2$, $R_3$, $R_4$ and $R_5$ is OH and $R_6$ is a polyhydroxylated, acylic chain having between 1-3 carbon atoms.

4. The compound as defined in claim 3, wherein X=S and wherein said compound is a chain-extended homologue of Salacinol, wherein said homologue has a 1,4-anhydro-1,4-thio-D-arabinitol moiety and a polyhydroxylated acyclic side chain moiety.

5. The compound as defined in claim 1, wherein $R_1$, $R_2$, $R_3$, $R_4$ and $R_5$ are OH.

6. The compound as defined in claim 1, wherein said compound is 1,4-Dideoxy-1,4-[[2R,3R,4R,5S-2,4,5,6-tetrahydroxy-3-(sulfooxy)hexyl]episufonium-ylidene]-D-arabinitol.

7. A pharmaceutical composition comprising an effective amount of a compound according to claim 1 together with a pharmaceutically acceptable carrier.

8. A pharmaceutical comprising an effective amount of Salacinol and Blintol together with a pharmaceutically acceptable carrier.

9. The compound as defined in claim 1, selected from the group consisting of the following compounds:

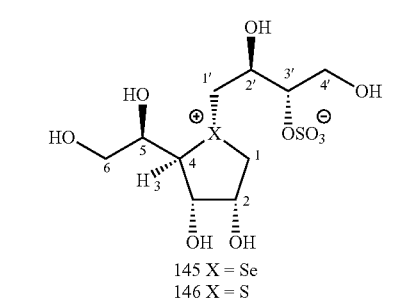

145 X = Se
146 X = S

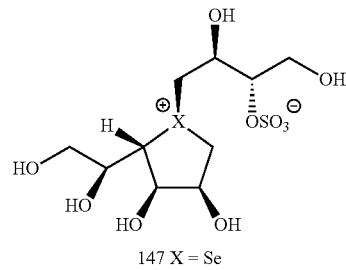

147 X = Se
148 X = S

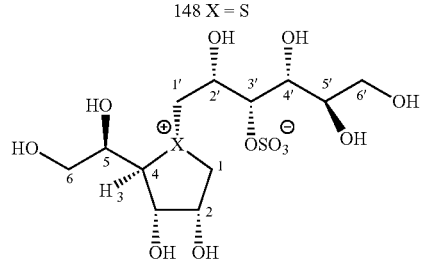

149 X = Se
150 X = S

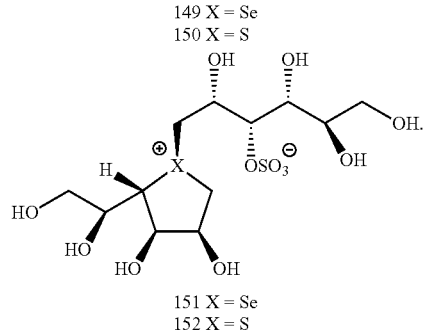

151 X = Se
152 X = S

10. A salacinol analaogue selected from the group consisting of the following compounds:

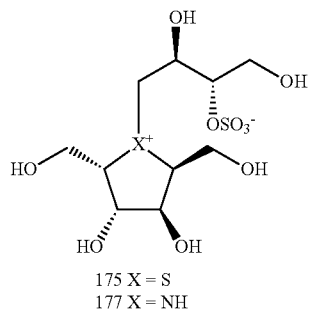

175 X = S
177 X = NH

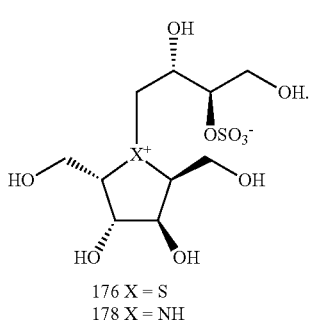

176 X = S
178 X = NH

11. The compound as defined in claim 1, wherein said compound is selected from the group consisting of the following compounds

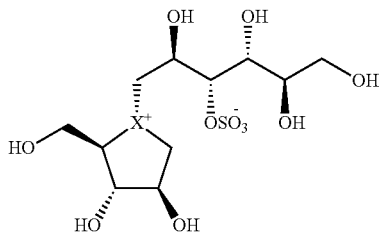

wherein X is S or Se.

12. The compound as defined in claim 1, wherein said compound has the structure

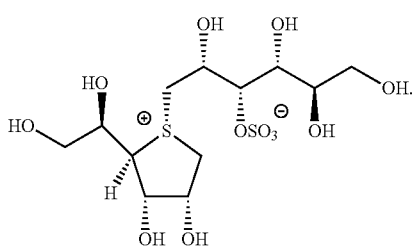

13. The compound as defined in claim 1, wherein said compound has the structure

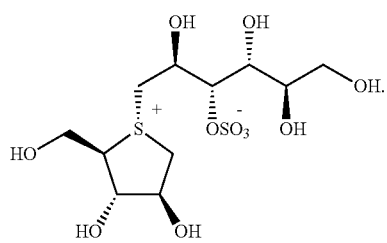

14. The compound as defined in claim 1, wherein said compound is selected from the group consisting of the following compounds

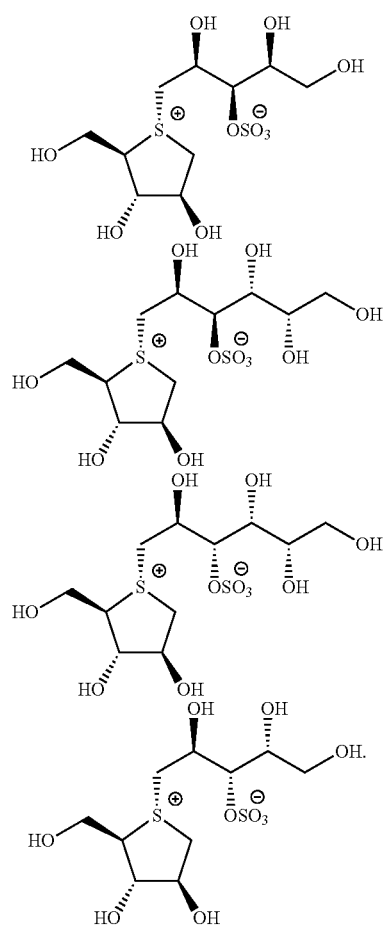

15. The compound as defined in claim 1, wherein said compound is selected from the group consisting of the following compounds

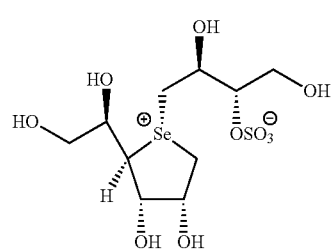

-continued

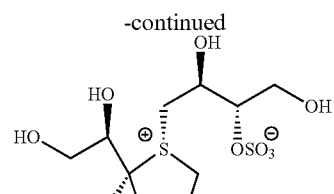
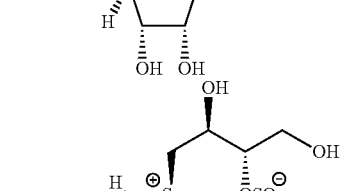
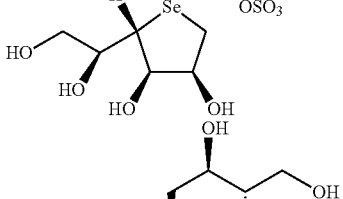
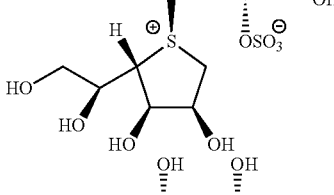
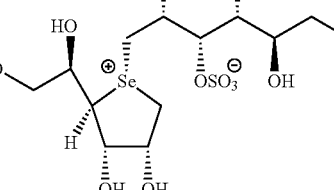
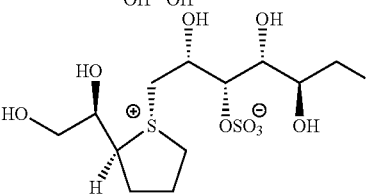
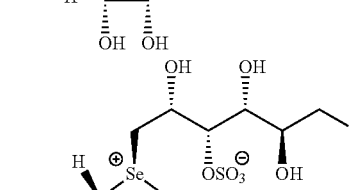
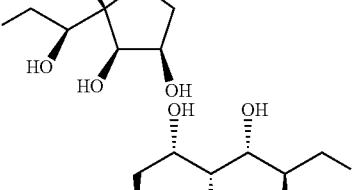
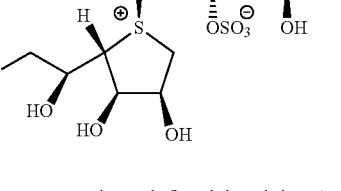

16. The compound as defined in claim 1, wherein said compound is selected from the group consisting of the following compounds

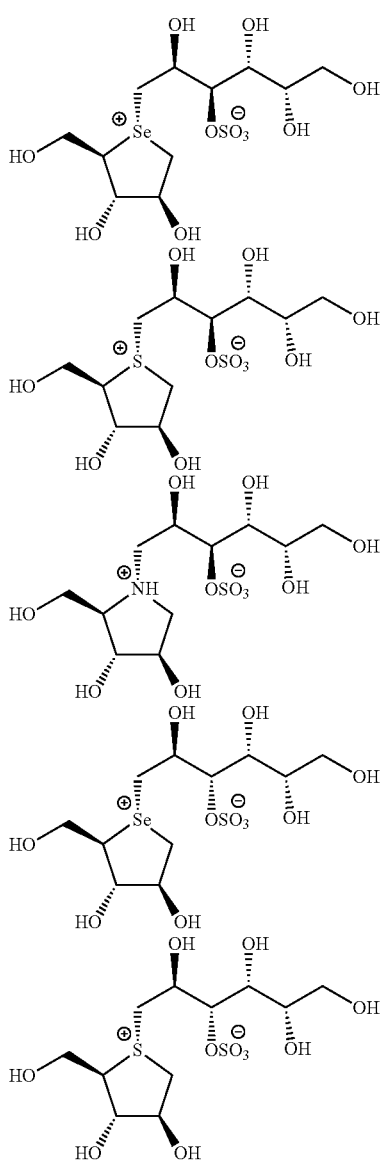

-continued

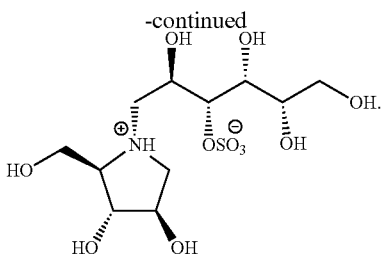

17. The compound as defined in claim 1, wherein said compound is selected from the group consisting of the following compounds

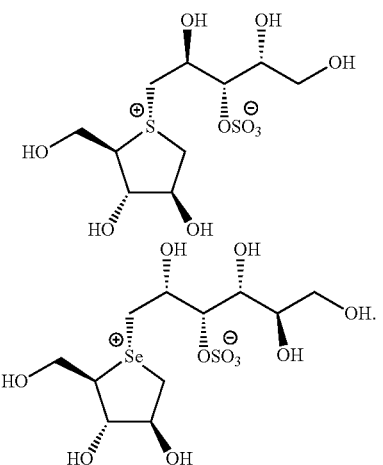

18. A pharmaceutical composition comprising an effective amount of a compound as defined in claim 12 together with a pharmaceutically acceptable carrier.

19. A pharmaceutical composition comprising an effective amount of a compound as defined in claim 13 together with a pharmaceutically acceptable carrier.

* * * * *